US011524064B2

(12) United States Patent
Barbero Calzado et al.

(10) Patent No.: US 11,524,064 B2
(45) **Date of Patent: *Dec. 13, 2022**

(54) ZIKA VIRUS PURIFICATION

(71) Applicant: Valneva Austria GmbH, Vienna (AT)

(72) Inventors: Jana Barbero Calzado, Vienna (AT); Mario Nebenführ, Vienna (AT); Robert Schiegl, Siegenfeld (AT); Michael Weber, Vienna (AT); Jürgen Heindl-Wruss, Vienna (AT)

(73) Assignee: Valneva Austria GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 16/927,086

(22) Filed: Jul. 13, 2020

(65) Prior Publication Data

US 2021/0093707 A1 Apr. 1, 2021

Related U.S. Application Data

(63) Continuation of application No. 15/781,825, filed as application No. PCT/EP2016/082667 on Dec. 23, 2016, now Pat. No. 10,744,194.

(30) Foreign Application Priority Data

| | | |
|---|---|---|
| Dec. 23, 2015 | (EP) | 15202585 |
| Mar. 18, 2016 | (EP) | 16161068 |
| Jun. 23, 2016 | (EP) | 16176025 |
| Jun. 23, 2016 | (EP) | 16176049 |
| Aug. 4, 2016 | (EP) | 16182845 |

(51) Int. Cl.

| | |
|---|---|
| ***A61K 39/12*** | (2006.01) |
| ***A61P 31/14*** | (2006.01) |
| ***C07K 14/18*** | (2006.01) |
| ***C12N 7/06*** | (2006.01) |
| ***A61K 39/39*** | (2006.01) |
| ***C12N 7/02*** | (2006.01) |
| ***C12N 7/00*** | (2006.01) |
| *A61K 39/00* | (2006.01) |

(52) U.S. Cl.

CPC .............. *A61K 39/12* (2013.01); *A61K 39/39* (2013.01); *A61P 31/14* (2018.01); *C07K 14/18* (2013.01); *C07K 14/1825* (2013.01); *C12N 7/00* (2013.01); *C12N 7/02* (2013.01); *C12N 7/06* (2013.01); *A61K 2039/5252* (2013.01); *A61K 2039/5254* (2013.01); *A61K 2039/5258* (2013.01); *A61K 2039/55505* (2013.01); *C12N 2770/24134* (2013.01); *C12N 2770/24151* (2013.01); *C12N 2770/24163* (2013.01); *Y02A 50/30* (2018.01)

(58) Field of Classification Search

CPC ...... C12N 15/8245; C12N 2710/10051; C12N 7/00; C12N 2750/14151; C12N 15/101; C12N 15/02; B01D 15/1807; B01D 15/1892; B01D 15/424

See application file for complete search history.

(56) References Cited

U.S. PATENT DOCUMENTS

| | | | |
|---|---|---|---|
| 6,309,650 | B1 | 10/2001 | Kim et al. |
| 8,765,148 | B2 | 7/2014 | Wizel et al. |
| 10,086,061 | B2 | 10/2018 | Thomas et al. |
| 10,537,630 | B2 | 1/2020 | Barbero Calzado et al. |
| 10,639,365 | B2 | 5/2020 | Barbero Calzado et al. |
| 10,744,194 | B2 * | 8/2020 | Barbero Calzado .... A61P 31/14 |
| 11,219,681 | B2 * | 1/2022 | Barbero Calzado ... A61K 39/12 |
| 11,331,382 | B2 | 5/2022 | Barbero Calzado et al. |
| 2013/0280295 | A1 | 10/2013 | Schlegl et al. |
| 2018/0362936 | A1 | 12/2018 | Barbero Calzado et al. |
| 2018/0362937 | A1 | 12/2018 | Barbero Calzado et al. |
| 2018/0369359 | A1 | 12/2018 | Barbero Calzado et al. |
| 2018/0371027 | A1 | 12/2018 | Barbero Calzado et al. |
| 2019/0008945 | A1 | 1/2019 | Barbero Calzado et al. |
| 2020/0017555 | A9 | 1/2020 | Barbero Calzado et al. |
| 2020/0384099 | A1 | 12/2020 | Barbero Calzado et al. |

FOREIGN PATENT DOCUMENTS

| | | | |
|---|---|---|---|
| CN | 105749268 | A | 7/2016 |
| WO | WO 1999/011762 | A1 | 3/1999 |
| WO | WO 2001/092552 | A2 | 12/2001 |
| WO | WO 2013/083726 | A1 | 6/2013 |
| WO | WO 2016/145149 | A1 | 9/2016 |
| WO | WO 2017/009873 | A1 | 1/2017 |

OTHER PUBLICATIONS

[No Author Listed] Centers for Disease Control and Prevention Ingredients of vaccines fact sheet. Retrieved from https://www.cdc.gov/vaccines/vac-gen/additives .htm.

[No Author Listed] Centers for Disease Control and Prevention. 2016. Japanese Encephalitis Vaccine. Retrieved from https://www.cdc.gov/japaneseencephalitis/vaccine/ on Jun. 16, 2016.

[No Author Listed] Genbank Accession No. AB154475. polyprotein [Zika virus]. Dec. 24, 2009. 4 pages.

[No Author Listed] Genbank Accession No. AY632535. Zika virus strain MR 766, complete genome. Nov. 23, 2010. 4 pages.

(Continued)

*Primary Examiner* — Bao Q Li

(74) *Attorney, Agent, or Firm* — Wolf, Greenfield & Sacks, P.C.

(57) ABSTRACT

Described herein are processes for purifying infectious Zika virus particles and uses of protamine in such processes.

18 Claims, 23 Drawing Sheets

Specification includes a Sequence Listing.

(56) References Cited

OTHER PUBLICATIONS

[No Author Listed] Media centre. Zika virus. World Health Organization, 2016. Zika Virus Fact Sheet. Downloaded Mar. 11, 2016 from http://www.who.int/en/news-room/fact-sheets/detail/zika-virus.
[No Author Listed] Pan-American Health Organization. 2015. Number of Reported Cases of Chikungunya Fever in the Americas, by Country or Territory 2013-2014, Cumulative Cases (Updated Oct. 23, 2015).
[No Author Listed] Valneva Announces Successful Generation of a Highly-purified Zika Vaccine Candidate Using its FDA-EMA Approved Japanese Encephalitis Platform. Press release Jul. 7, 2016.
[No Author Listed] Wikimedia Foundation, Inc., 2015. https://en.wikipedia.org/wiki/Protamine_sulfate; updated Sep. 30, 2015; downloaded Nov. 26, 2015.
[No Author Listed] World Health Organization, 2016. Zika Situation Report Feb. 5, 2016.
[No Author Listed] Zika virus, strain H/PF/2013. Nov. 28, 2013. European Virus Archive retrieved on Dec. 22, 2016 from http://www.who.int/mediacentre/factsheets/zika/en.
Abbink et al, Durability and correlates of vaccine protection against Zika virus in rhesus monkeys. Sci. Transl. Med. 2017;9:eaao4163.
Altschul et al., Basic Local Alignment Search Tool. J. Mol. Biol. 1990; 215: 403-410.
Altschul et al., Gapped BLAST and PSI-BLAST: a new generation of protein database search programs. Nuc. Acids Res. 1997 ;25: 3389-3402.
Athmaram et al., A two step purification strategy for Chikungunya virions purification using sucrose buoyant density gradient separation. J Virology Res. 2013;2(1):18-21.
Aubry et al., Inactivation of Zika virus in plasma with amotosalen and ultraviolet a illumination. Transfusion. Jan. 2016;56(1):33-40. doi: 10.1111/trf.13271. Epub Aug. 18, 2015.
Baronti et al., Complete Coding Sequence of Zika Virus from a French Polynesia Outbreak in 2013. Genome Announc. May-Jun. 2014; 2(3):e00500-14. Abstract.
Bender et al., Zika Virus Vaccine Candidate VLA1601: Cooperation VALNEVA & EMERGENT, Presentation at World Vaccine Congress Apr. 4, 2018.
Cohen, Infectious Disease. The race for a Zika vaccine is on. Science. Feb. 5, 2016;351(6273):543-4. doi: 10.1126/science.351.6273.543.
Cox et al., Predicting Zika virus structural biology:Challenges and opportunities for intervention. Antivir Chem Chemother. Aug. 2015;24(3-4): 118-26. doi: 10.1177/2040206616653873. Epub Jun. 13, 2016.
Dowall et al., A susceptible mouse model for Zika virus infection. PLOS Neglected Tropical Diseases; DOI:10.1371/journal.pntd.0004658. May 5, 2016.
Fritsche et al., Vaccine hypersensitivity—update and overview. Swiss Med Wkly. 2010;140(17-18):238-246.
Gardner et al., Deliberate Attenuation of Chikungunya Virus by Adaptation to Heparan Sulfate-Dependent Infectivity: A Model of Rational Arboviral Vaccine Design. PLoS Neglected Tropical Diseases. 2014;8(2):e2719.
Geradin et al., Chikungunya virus-associated encephalitis: A cohort study on La Réunion Island, 2005-2009. Neurology. 2016;86(1):94-102.
Haddow et al., Genetic Characterization of Zika Virus Strains: Geographic Expansion of the Asian Lineage. PLoS Negl Trop Dis. 2012;6(2): e1477. doi:10.1371/journal.pntd.0001477.
Hallengärd et al., Prime-Boost Immunization Strategies against Chikungunya Virus. J Virology. 2014;88(22):13333-13343.
Hallengärd et al., Novel Attenuated Chikungunya Vaccine Candidates Elicit Protective Immunity in C57BL/6 mice. J Virology. 2014;88(5):2858-2866.
Hombach et al., Report on a WHO consultation on immunological endpoints for evaluation of new Japanese encephalitis vaccines, WHO, Geneva, Sep. 2-3, 2004. Vaccine. 2005;23(45):5205-5211.
Hutornojs et al., Comparison of ultracentrifugation methods for concentration of recombinant alphaviruses: sucrose and iodixanol cushions, Environmental and Experimental Biology. 2012; 10: 117-123.
Katoh et al., Recent developments in the MAFFT multiple sequence alignment program. Briefings in Bioinformatics. 2008;9(4):286-298.
Kofler et al., Capsid protein C of tick-borne encephalitis virus tolerates large internal deletions and is a favorable target for attenuation of virulence. J Virol. Apr. 2002;76(7):3534-43.
Kuno et al., Full-length sequencing and genomic characterization of Bagaza, Kedougou, and Zika viruses. Arch Virol. 2007;152(4):687-696. doi:10.1007/s00705-006-0903-z.
Larkin et al., Clustal W and Clustal X version 2.0. Bioinformatics. 2007;23(21):2947-2948.
Larocca et al., Vaccine protection against Zika virus from Brazil. Nature. 2016;536:474-478. doi:10.1038/nature18952. Methods.
Malone et al., Zika Virus: Medical Countermeasure Development Challenges. PLoS Negl Trop Dis. 2016;10(3): e0004530. doi:10.1371/journal.pntd.0004530.
Modjarrad et al., Preliminary aggregate safety and immunogenicity results from three trials of a purified inactivated Zika virus vaccine candidate: phase 1, randomised, double-blind, placebo-controlled clinical trials, www.thelancet.com Published online Dec. 4, 2017 http://dx.doi.org/10.1016/80140-6736(17)33106-9.
Needleman et al., A general method applicable to the search for similarities in the amino acid sequence of two proteins. J. Mol. Biol. 1970;48(3):443-453.
Pearson et al., Improved tools for biological sequence comparison. Proc. Natl. Acad. Sci. USA. 1988;85(8):2444-8.
Pellerin, Walter Reed Scientists Test Zika Vaccine Candidate, U.S. Department of Defense News. Jun. 9, 2016.
Pinto et al., A Temporal Role of Type I Interferon Signaling in CD8+ T Cell Maturation during Acute West Nile Virus Infection. PLoS Pathog. 2011;7(12): e1002407. https://doi.org/10.1371/journal.ppat.1002407.
Plevka et al., Maturation of flaviviruses starts from one or more icosahedrally independent nucleation centres EMBO reports. 2011;12(6):602-606.
Putnak et al., Development of a purified, inactivated, dengue-2 virus vaccine prototype in Vero cells: immunogenicity and protection in mice and rhesus monkeys. J Infect Dis. Dec. 1996;174(6):1176-84.
Reed et al., A simple method of estimating fifty percent endpoints. American J Hygiene. 1938;27:493-497.
Rocha et al., Microcephaly: normality parameters and its determinants in northeastern Brazil: a multicentre prospective cohort study. Bull World Health Organ, E-pub: Feb. 8, 2016. doi:http://dx.doi.org/10.2471/BLT.16.171215.
Schlegl, Influence of elemental impurities in aluminum hydroxide adjuvant on the stability of inactivated Japanese Encephalitis vaccine, IXIARO®. Vaccine. 2015;33(44):5989-5996.
Smith et al., Comparison of Biosequences. Adv. Appl. Math. 1981;2: 482-489.
Srivastava et al., A purified inactivated Japanese encephalitis virus vaccine made in Vero cells. Vaccine. 2001;19:4557-4565.
Vega-Rua et al., Chikungunya Virus Transmission Potential by Local Aedes Mosquitoes in the Americas and Europe. PLOS Neglected Tropical Diseases. 2015;9(5): e0003780.
Waterhouse et al., Jalview Version 2—a multiple sequence alignment editor and analysis workbench. Bioinformatics. 2009;25(9):1189-1191.
Way et al., Comparative studies of some African arboviruses in cell culture and in mice. J Gen Virol. Jan. 1976;30(1):123-30.
Weaver, Arrival of Chikungunya Virus in the New World: Prospects for Spread and Impact on Public Health. PLoS Negl Trop Dis. 2014;8(6):e2921. doi:10.1371/journal.pntd.0002921.
Konishi et al., Studies on structural proteins of Chikungunya Virus. I. Separation of three species of proteins and their preliminary characterization. Microbiol Immunol. 1980;24(5):419-28. doi: 10.1111/j.1348-0421.1980.tb02846.x.

(56) References Cited

OTHER PUBLICATIONS

Third Party Observations filed in Opposition to EP 16828746.4, filed on Oct. 13, 2021. 6 pages.
Tiwari et al., Assessment of immunogenic potential of Vero adapted formalin inactivated vaccine derived from novel ECSA genotype of Chikungunya virus. Vaccine. Apr. 21, 2009;27(18):2513-22. doi: 10.1016/j.vaccine.2009.02.062. Epub Feb. 27, 2009.
U.S. Appl. No. 16/813,862, filed Mar. 10, 2020, Barbero Calzado et al.
PCT/EP2016/082667, Apr. 19, 2017, International Search Report and Written Opinion.
PCT/EP2016/082667, Jul. 8, 2018, International Preliminary Report on Patentability.
[No Author Listed] Genbank Accession No. KJ776791.2. Zika virus strain H/PF/2013, complete genome. Aug. 31, 2016. 5 pages.

* cited by examiner

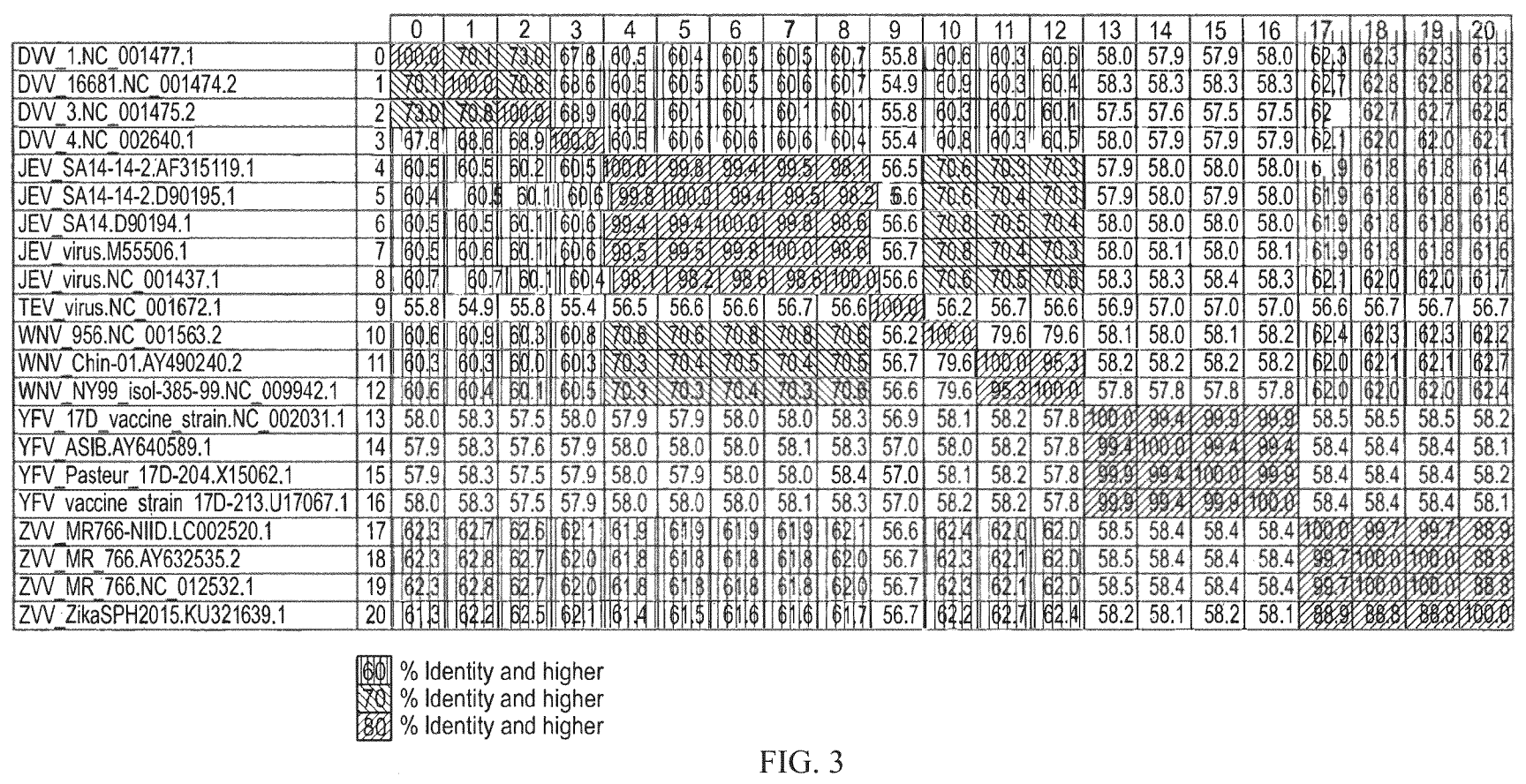

| | | 0 | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|---|
| DVV_1.NC_001477.1 | 0 | 100.0 | 70.1 | 73.0 | 67.8 | 60.5 | 60.4 | 60.5 | 60.5 | 60.7 | 55.8 | 60.6 | 60.3 | 60.6 | 58.0 | 57.9 | 57.9 | 58.0 | 62.3 | 62.3 | 62.3 | 61.3 |
| DVV_16681.NC_001474.2 | 1 | 70.1 | 100.0 | 70.8 | 68.6 | 60.5 | 60.5 | 60.5 | 60.6 | 60.7 | 54.9 | 60.9 | 60.3 | 60.4 | 58.3 | 58.3 | 58.3 | 58.3 | 62.7 | 62.8 | 62.8 | 62.2 |
| DVV_3.NC_001475.2 | 2 | 73.0 | 70.8 | 100.0 | 68.9 | 60.2 | 60.1 | 60.1 | 60.1 | 60.1 | 55.8 | 60.3 | 60.0 | 60.1 | 57.5 | 57.6 | 57.5 | 57.5 | 62 | 62.7 | 62.7 | 62.5 |
| DVV_4.NC_002640.1 | 3 | 67.8 | 68.6 | 68.9 | 100.0 | 60.5 | 60.6 | 60.6 | 60.6 | 60.4 | 55.4 | 60.8 | 60.3 | 60.5 | 58.0 | 57.9 | 57.9 | 57.9 | 62.1 | 62.0 | 62.0 | 62.1 |
| JEV_SA14-14-2.AF315119.1 | 4 | 60.5 | 60.5 | 60.2 | 60.5 | 100.0 | 99.8 | 99.4 | 99.5 | 98.1 | 56.5 | 70.6 | 70.3 | 70.3 | 57.9 | 58.0 | 58.0 | 58.0 | 6 .9 | 61.8 | 61.8 | 61.4 |
| JEV_SA14-14-2.D90195.1 | 5 | 60.4 | 60.5 | 60.1 | 60.6 | 99.8 | 100.0 | 99.4 | 99.5 | 98.2 | 56.6 | 70.6 | 70.4 | 70.3 | 57.9 | 58.0 | 57.9 | 58.0 | 61.9 | 61.8 | 61.8 | 61.5 |
| JEV_SA14.D90194.1 | 6 | 60.5 | 60.5 | 60.1 | 60.6 | 99.4 | 99.4 | 100.0 | 99.8 | 98.6 | 56.6 | 70.8 | 70.5 | 70.4 | 58.0 | 58.0 | 58.0 | 58.0 | 61.9 | 61.8 | 61.8 | 61.6 |
| JEV_virus.M55506.1 | 7 | 60.5 | 60.6 | 60.1 | 60.6 | 99.5 | 99.5 | 99.8 | 100.0 | 98.6 | 56.7 | 70.8 | 70.4 | 70.3 | 58.0 | 58.1 | 58.0 | 58.1 | 61.9 | 61.8 | 61.8 | 61.6 |
| JEV_virus.NC_001437.1 | 8 | 60.7 | 60.7 | 60.1 | 60.4 | 98.1 | 98.2 | 98.6 | 98.6 | 100.0 | 56.6 | 70.6 | 70.5 | 70.6 | 58.3 | 58.3 | 58.4 | 58.3 | 62.1 | 62.0 | 62.0 | 61.7 |
| TEV_virus.NC_001672.1 | 9 | 55.8 | 54.9 | 55.8 | 55.4 | 56.5 | 56.6 | 56.6 | 56.7 | 56.6 | 100.0 | 56.2 | 56.7 | 56.6 | 56.9 | 57.0 | 57.0 | 57.0 | 56.6 | 56.7 | 56.7 | 56.7 |
| WNV_956.NC_001563.2 | 10 | 60.6 | 60.9 | 60.3 | 60.8 | 70.6 | 70.6 | 70.8 | 70.8 | 70.6 | 56.2 | 100.0 | 79.6 | 79.6 | 58.1 | 58.0 | 58.1 | 58.2 | 62.4 | 62.3 | 62.3 | 62.2 |
| WNV_Chin-01.AY490240.2 | 11 | 60.3 | 60.3 | 60.0 | 60.3 | 70.3 | 70.4 | 70.5 | 70.4 | 70.5 | 56.7 | 79.6 | 100.0 | 95.3 | 58.2 | 58.2 | 58.2 | 58.2 | 62.0 | 62.1 | 62.1 | 62.7 |
| WNV_NY99_isol-385-99.NC_009942.1 | 12 | 60.6 | 60.4 | 60.1 | 60.5 | 70.3 | 70.3 | 70.4 | 70.3 | 70.6 | 56.6 | 79.6 | 95.3 | 100.0 | 57.8 | 57.8 | 57.8 | 57.8 | 62.0 | 62.0 | 62.0 | 62.4 |
| YFV_17D_vaccine_strain.NC_002031.1 | 13 | 58.0 | 58.3 | 57.5 | 58.0 | 57.9 | 57.9 | 58.0 | 58.0 | 58.3 | 56.9 | 58.1 | 58.2 | 57.8 | 100.0 | 99.4 | 99.9 | 99.9 | 58.5 | 58.5 | 58.5 | 58.2 |
| YFV_ASIB.AY640589.1 | 14 | 57.9 | 58.3 | 57.6 | 57.9 | 58.0 | 58.0 | 58.0 | 58.1 | 58.3 | 57.0 | 58.0 | 58.2 | 57.8 | 99.4 | 100.0 | 99.4 | 99.4 | 58.4 | 58.4 | 58.4 | 58.1 |
| YFV_Pasteur_17D-204.X15062.1 | 15 | 57.9 | 58.3 | 57.5 | 57.9 | 58.0 | 57.9 | 58.0 | 58.0 | 58.4 | 57.0 | 58.1 | 58.2 | 57.8 | 99.9 | 99.4 | 100.0 | 99.9 | 58.4 | 58.4 | 58.4 | 58.2 |
| YFV_vaccine_strain_17D-213.U17067.1 | 16 | 58.0 | 58.3 | 57.5 | 57.9 | 58.0 | 58.0 | 58.0 | 58.1 | 58.3 | 57.0 | 58.2 | 58.2 | 57.8 | 99.9 | 99.4 | 99.9 | 100.0 | 58.4 | 58.4 | 58.4 | 58.1 |
| ZVV_MR766-NIID.LC002520.1 | 17 | 62.3 | 62.7 | 62.6 | 62.1 | 61.9 | 61.9 | 61.9 | 61.9 | 62.1 | 56.6 | 62.4 | 62.0 | 62.0 | 58.5 | 58.4 | 58.4 | 58.4 | 100.0 | 99.7 | 99.7 | 88.9 |
| ZVV_MR_766.AY632535.2 | 18 | 62.3 | 62.8 | 62.7 | 62.0 | 61.8 | 61.8 | 61.8 | 61.8 | 62.0 | 56.7 | 62.3 | 62.1 | 62.0 | 58.5 | 58.4 | 58.4 | 58.4 | 99.7 | 100.0 | 100.0 | 88.8 |
| ZVV_MR_766.NC_012532.1 | 19 | 62.3 | 62.8 | 62.7 | 62.0 | 61.8 | 61.8 | 61.8 | 61.8 | 62.0 | 56.7 | 62.3 | 62.1 | 62.0 | 58.5 | 58.4 | 58.4 | 58.4 | 99.7 | 100.0 | 100.0 | 88.8 |
| ZVV_ZikaSPH2015.KU321639.1 | 20 | 61.3 | 62.2 | 62.5 | 62.1 | 61.4 | 61.5 | 61.6 | 61.6 | 61.7 | 56.7 | 62.2 | 62.7 | 62.4 | 58.2 | 58.1 | 58.2 | 58.1 | 88.9 | 88.8 | 88.8 | 100.0 |

60 % Identity and higher
70 % Identity and higher
80 % Identity and higher

FIG. 3

JEV_SA14.D90194.1
JEV_virus.NC_001437.1
JEV_virus.M55506.1
JEV_SA14-14-2.AF315119.1
JEV_SA14-14-2.D90195.1
WNV_956.NC_001563.2
WNV_NY99_isol-385-99.NC_009942.1
WNV_Chin-01.AY490240.2
DVV_1.NC_001477.1
DVV_3_isol-D3%H%IMTSSA-SRI%2000%1266.NC_001475.2
DVV_16681.NC_001474.2
DVV_4.NC_002640.1
ZVV_MR766-NIID.LC002520.1
ZVV_MR_766.NC_012532.1
ZVV_MR_766.AY632535.2
ZVV_ZikaSPH2015.KU321639.1
ZVV_BeH818995.KU365777.1
YFV_ASIBI.AY640589.1
YFV_17D_vaccine_strain.NC_002031.1
YFV_virus_isol-Pasteur_17D-204_yellow_fever_vaccine.X15062.1
YFV_vaccine_strain_17D-213.U17067.1
TEV_virus.NC_001672.1

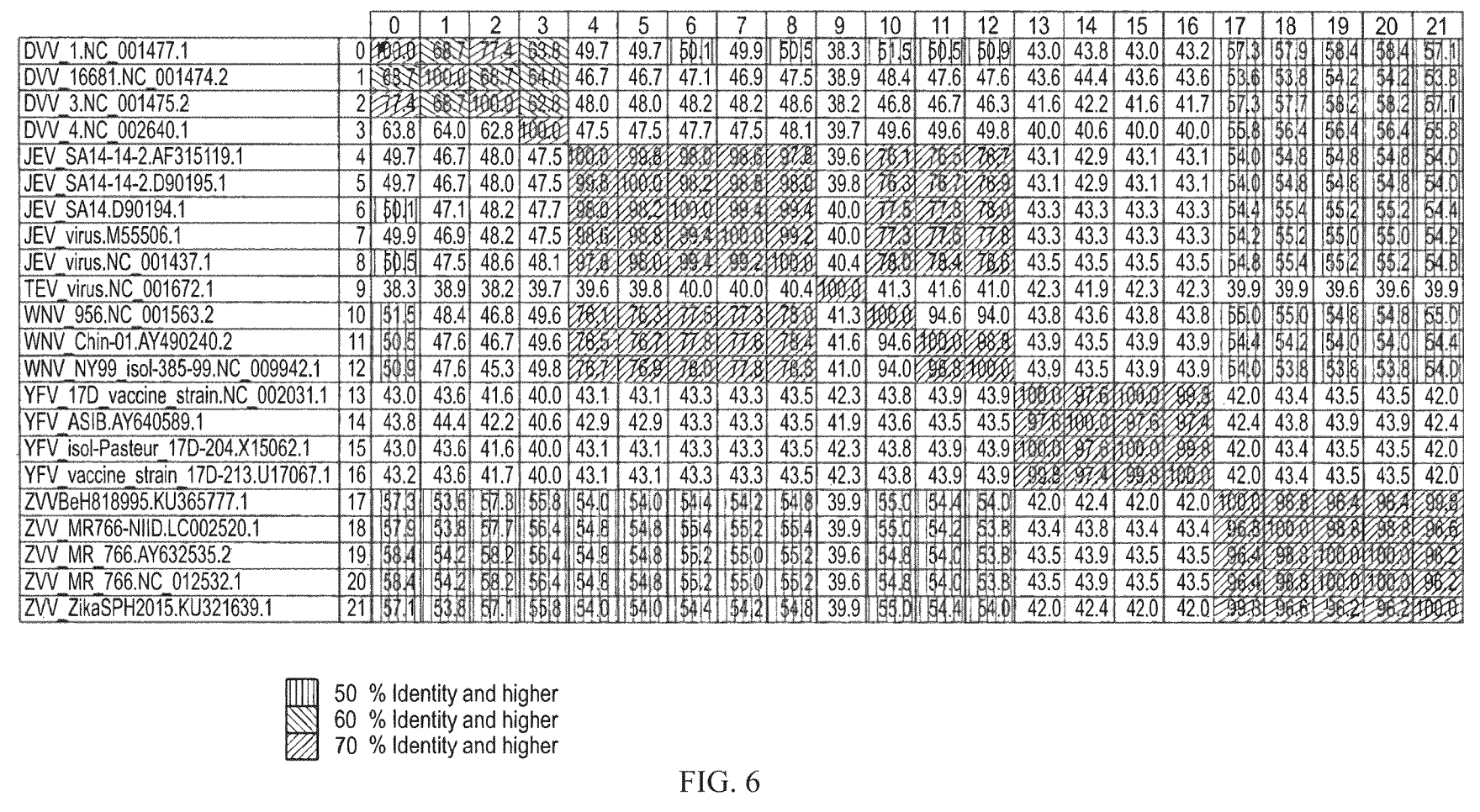

| | | 0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|---|
| DVV_1.NC_001477.1 | 0 | 100.0 | 68.7 | 77.4 | 63.8 | 49.7 | 49.7 | 50.1 | 49.9 | 50.5 | 38.3 | 51.5 | 50.5 | 50.9 | 43.0 | 43.8 | 43.0 | 43.2 | 57.3 | 57.9 | 58.4 | 58.4 | 57.1 |
| DVV_16681.NC_001474.2 | 1 | 68.7 | 100.0 | 68.7 | 64.0 | 46.7 | 46.7 | 47.1 | 46.9 | 47.5 | 38.9 | 48.4 | 47.6 | 47.6 | 43.6 | 44.4 | 43.6 | 43.6 | 53.6 | 53.8 | 54.2 | 54.2 | 53.8 |
| DVV_3.NC_001475.2 | 2 | 77.4 | 68.7 | 100.0 | 62.8 | 48.0 | 48.0 | 48.2 | 48.2 | 48.6 | 38.2 | 46.8 | 46.7 | 46.3 | 41.6 | 42.2 | 41.6 | 41.7 | 57.3 | 57.7 | 58.2 | 58.2 | 57.1 |
| DVV_4.NC_002640.1 | 3 | 63.8 | 64.0 | 62.8 | 100.0 | 47.5 | 47.5 | 47.7 | 47.5 | 48.1 | 39.7 | 49.6 | 49.6 | 49.8 | 40.0 | 40.6 | 40.0 | 40.0 | 55.8 | 56.4 | 56.4 | 56.4 | 55.8 |
| JEV_SA14-14-2.AF315119.1 | 4 | 49.7 | 46.7 | 48.0 | 47.5 | 100.0 | 99.8 | 98.0 | 98.6 | 97.8 | 39.6 | 76.1 | 76.5 | 76.7 | 43.1 | 42.9 | 43.1 | 43.1 | 54.0 | 54.8 | 54.8 | 54.8 | 54.0 |
| JEV_SA14-14-2.D90195.1 | 5 | 49.7 | 46.7 | 48.0 | 47.5 | 99.8 | 100.0 | 98.2 | 98.8 | 98.0 | 39.8 | 76.3 | 76.7 | 76.9 | 43.1 | 42.9 | 43.1 | 43.1 | 54.0 | 54.8 | 54.8 | 54.8 | 54.0 |
| JEV_SA14.D90194.1 | 6 | 50.1 | 47.1 | 48.2 | 47.7 | 98.0 | 98.2 | 100.0 | 99.4 | 99.4 | 40.0 | 77.5 | 77.8 | 78.0 | 43.3 | 43.3 | 43.3 | 43.3 | 54.4 | 55.4 | 55.2 | 55.2 | 54.4 |
| JEV_virus.M55506.1 | 7 | 49.9 | 46.9 | 48.2 | 47.5 | 98.6 | 98.8 | 99.4 | 100.0 | 99.2 | 40.0 | 77.3 | 77.6 | 77.8 | 43.3 | 43.3 | 43.3 | 43.3 | 54.2 | 55.2 | 55.0 | 55.0 | 54.2 |
| JEV_virus.NC_001437.1 | 8 | 50.5 | 47.5 | 48.6 | 48.1 | 97.8 | 98.0 | 99.4 | 99.2 | 100.0 | 40.4 | 78.0 | 78.4 | 78.6 | 43.5 | 43.5 | 43.5 | 43.5 | 54.8 | 55.4 | 55.2 | 55.2 | 54.8 |
| TEV_virus.NC_001672.1 | 9 | 38.3 | 38.9 | 38.2 | 39.7 | 39.6 | 39.8 | 40.0 | 40.0 | 40.4 | 100.0 | 41.3 | 41.6 | 41.0 | 42.3 | 41.9 | 42.3 | 42.3 | 39.9 | 39.9 | 39.6 | 39.6 | 39.9 |
| WNV_956.NC_001563.2 | 10 | 51.5 | 48.4 | 46.8 | 49.6 | 76.1 | 76.3 | 77.5 | 77.3 | 78.0 | 41.3 | 100.0 | 94.6 | 94.0 | 43.8 | 43.6 | 43.8 | 43.8 | 55.0 | 55.0 | 54.8 | 54.8 | 55.0 |
| WNV_Chin-01.AY490240.2 | 11 | 50.5 | 47.6 | 46.7 | 49.6 | 76.5 | 76.7 | 77.8 | 77.6 | 78.4 | 41.6 | 94.6 | 100.0 | 98.8 | 43.9 | 43.5 | 43.9 | 43.9 | 54.4 | 54.2 | 54.0 | 54.0 | 54.4 |
| WNV_NY99_isol-385-99.NC_009942.1 | 12 | 50.9 | 47.6 | 45.3 | 49.8 | 76.7 | 76.9 | 78.0 | 77.8 | 78.6 | 41.0 | 94.0 | 98.8 | 100.0 | 43.9 | 43.5 | 43.9 | 43.9 | 54.0 | 53.8 | 53.8 | 53.8 | 54.0 |
| YFV_17D_vaccine_strain.NC_002031.1 | 13 | 43.0 | 43.6 | 41.6 | 40.0 | 43.1 | 43.1 | 43.3 | 43.3 | 43.5 | 42.3 | 43.8 | 43.9 | 43.9 | 100.0 | 97.6 | 100.0 | 99.8 | 42.0 | 43.4 | 43.5 | 43.5 | 42.0 |
| YFV_ASIB.AY640589.1 | 14 | 43.8 | 44.4 | 42.2 | 40.6 | 42.9 | 42.9 | 43.3 | 43.3 | 43.5 | 41.9 | 43.6 | 43.5 | 43.5 | 97.6 | 100.0 | 97.6 | 97.4 | 42.4 | 43.8 | 43.9 | 43.9 | 42.4 |
| YFV_isol-Pasteur_17D-204.X15062.1 | 15 | 43.0 | 43.6 | 41.6 | 40.0 | 43.1 | 43.1 | 43.3 | 43.3 | 43.5 | 42.3 | 43.8 | 43.9 | 43.9 | 100.0 | 97.6 | 100.0 | 99.8 | 42.0 | 43.4 | 43.5 | 43.5 | 42.0 |
| YFV_vaccine_strain_17D-213.U17067.1 | 16 | 43.2 | 43.6 | 41.7 | 40.0 | 43.1 | 43.1 | 43.3 | 43.3 | 43.5 | 42.3 | 43.8 | 43.9 | 43.9 | 99.8 | 97.4 | 99.8 | 100.0 | 42.0 | 43.4 | 43.5 | 43.5 | 42.0 |
| ZVVBeH818995.KU365777.1 | 17 | 57.3 | 53.6 | 57.3 | 55.8 | 54.0 | 54.0 | 54.4 | 54.2 | 54.8 | 39.9 | 55.0 | 54.4 | 54.0 | 42.0 | 42.4 | 42.0 | 42.0 | 100.0 | 96.8 | 96.4 | 96.4 | 99.8 |
| ZVV_MR766-NIID.LC002520.1 | 18 | 57.9 | 53.8 | 57.7 | 56.4 | 54.8 | 54.8 | 55.4 | 55.2 | 55.4 | 39.9 | 55.0 | 54.2 | 53.8 | 43.4 | 43.8 | 43.4 | 43.4 | 96.8 | 100.0 | 98.8 | 98.8 | 96.6 |
| ZVV_MR_766.AY632535.2 | 19 | 58.4 | 54.2 | 58.2 | 56.4 | 54.8 | 54.8 | 55.2 | 55.0 | 55.2 | 39.6 | 54.8 | 54.0 | 53.8 | 43.5 | 43.9 | 43.5 | 43.5 | 96.4 | 98.8 | 100.0 | 100.0 | 96.2 |
| ZVV_MR_766.NC_012532.1 | 20 | 58.4 | 54.2 | 58.2 | 56.4 | 54.8 | 54.8 | 55.2 | 55.0 | 55.2 | 39.6 | 54.8 | 54.0 | 53.8 | 43.5 | 43.9 | 43.5 | 43.5 | 96.4 | 98.8 | 100.0 | 100.0 | 96.2 |
| ZVV_ZikaSPH2015.KU321639.1 | 21 | 57.1 | 53.8 | 57.1 | 55.8 | 54.0 | 54.0 | 54.4 | 54.2 | 54.8 | 39.9 | 55.0 | 54.4 | 54.0 | 42.0 | 42.4 | 42.0 | 42.0 | 99.8 | 96.6 | 96.2 | 96.2 | 100.0 |

50 % Identity and higher
60 % Identity and higher
70 % Identity and higher

FIG. 6

+ Similar virus concentration in harvests Day 2, Day3, Day 7; lower virus concentration in harvest Day 5

+ Day 2 and Day 3 harvests contained more HCP than Days 5/7 (correlates with observed CPE)

+ Minor amount of virus multimers observed

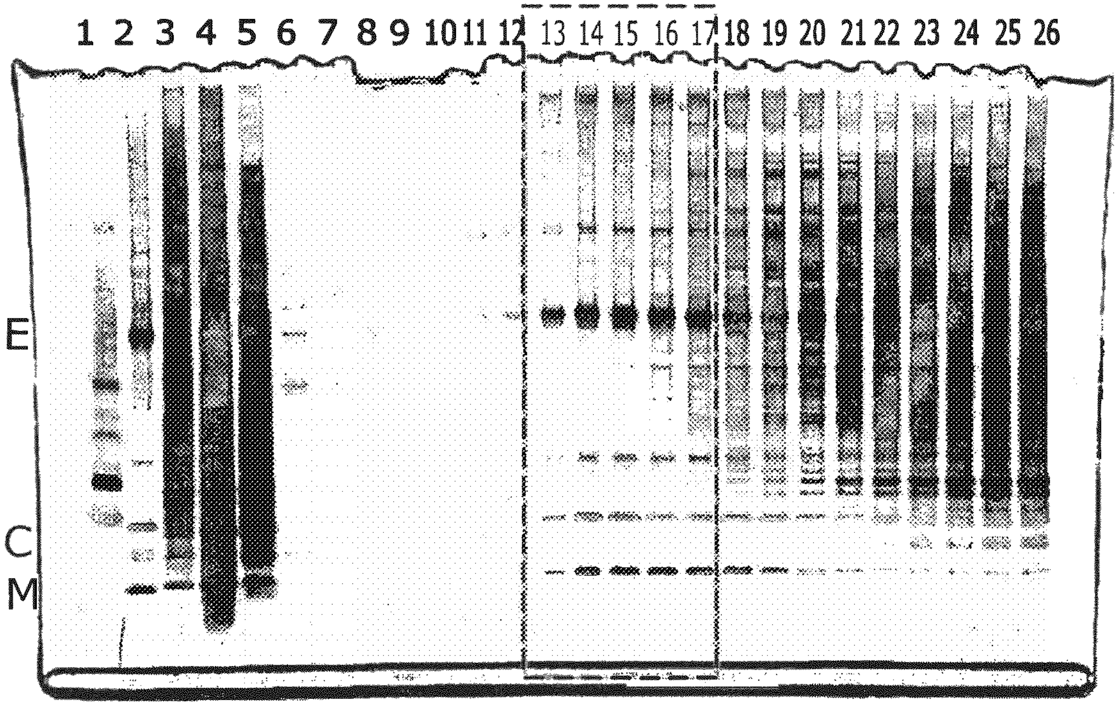

Pooled fractions F10-F14
(10mL total volume pere bottle)

| Lane | Sample |
|---|---|
| 1 | Molecular weight Marker |
| 2 | JEV Sucrose Gradient Pool (Reference) |
| 3 | Zika Harvest pool (day 2,3,5,7) |
| 4 | Zika Harvest pool (day 2,3,5,7)concentrated 300x |
| 5 | Zika Harvest pool (day 2,3,5,7)concentrated 300x + Protamine sulfate |
| 6 | Ultrafiltration Permeate |
| 7 | SGC Bottle 1, Fraction 4 |
| 8 | SGC Bottle 1, Fraction 5 |
| 9 | SGC Bottle 1, Fraction 6 |
| 10 | SGC Bottle 1, Fraction 7 |
| 11 | SGC Bottle 1, Fraction 8 |
| 12 | SGC Bottle 1, Fraction 9 |
| 13 | SGC Bottle 1, Fraction 10 |
| 14 | SGC Bottle 1, Fraction 11 |
| 15 | SGC Bottle 1, Fraction 12 |
| 16 | SGC Bottle 1, Fraction 13 |
| 17 | SGC Bottle 1, Fraction 14 |
| 18 | SGC Bottle 1, Fraction 15 |
| 19 | SGC Bottle 1, Fraction 16 |
| 20 | SGC Bottle 1, Fraction 17 |
| 21 | SGC Bottle 1, Fraction 18 |
| 22 | SGC Bottle 1, Fraction 19 |
| 23 | SGC Bottle 1, Fraction 20 |
| 24 | SGC Bottle 1, Fraction 21 |
| 25 | SGC Bottle 1, Fraction 22 |
| 26 | SGC Bottle 1, Fraction 23 |

FIG. 14

| | 12 µg | 3.0 µg | 1.0 µg | 0.33 µg | 0.11 µg | 0.037 µg |
|---|---|---|---|---|---|---|
| EC50 | 1371 | 807.6 | 380.7 | 456.1 | 179.9 | 142.0 |

| | 12 µg | 3.0 µg | 1.0 µg | 0.33 µg | 0.11 µg | 0.037 µg |
|---|---|---|---|---|---|---|
| EC50 | 1029 | 819.1 | 556.9 | 477.3 | 158.1 | 118.0 |

ZIKA VIRUS PURIFICATION

RELATED APPLICATION

This application is a continuation of U.S. application Ser. No. 15/781,825, filed Jun. 6, 2018, which is a national stage filing under 35 U.S.C. § 371 of International Patent Application Serial No. PCT/EP2016/082667, filed Dec. 23, 2016, the contents of each of which are incorporated by reference herein in its entirety.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Jul. 13, 2020, is named I042270127US01-SEQ-CEW and is 466,240 bytes in size.

FIELD OF THE INVENTION

The disclosure relates to methods for the purification of Zika viruses for use in vaccines.

BACKGROUND OF THE INVENTION

Regulatory agencies such as the World Health Organization establish standards and guidelines for the production of pharmaceutical compositions administered to humans, such as vaccines, that limit quantity and components of the compositions. Meeting these standards is particularly challenging with regard to production of vaccines containing biological agents, such as viruses, which must be propagated on cell substrates. Such vaccine preparations must be sterile (i.e., free from independently replicating organisms) and may contain no more than 10 ng of host cell DNA per human dose, among other requirements. These standards are in place in order to ensure safety of the composition for human administration, but may introduce challenges in the development of processes used to produce such compositions.

Protamine was originally isolated from the sperm of salmon and other species of fish but is now produced primarily through recombinant biotechnology. It is a highly cationic peptide that binds to negatively charged molecules such as nucleic acids to form a stable ion pair. Its use in removing host cell nucleic acid is well document.

SUMMARY

During the course of routine virus purification, it was observed that addition of protamine sulfate to a Zika virus harvest produced on a cell substrate removed not only contaminating DNA derived from host cells, as expected, but surprisingly also virtually eliminated immature and otherwise non-infectious virus particles from the preparation. This finding provides a streamlined, gentle and reproducible process for obtaining highly-purified infectious Zika virus particles for applications such as Zika vaccine preparation; furthermore, the process is not dependent on the charge of the Zika virus particle.

Disclosed herein are downstream processes for purifying Zika virus particles from a crude preparation. The downstream process can be applied to either a Zika virus which has not adapted for propagation on a particular cell substrate or for a partial/fully cell substrate adapted Zika virus particle.

Aspects of the invention provide processes for the purification of infectious Zika virus particles comprising the steps of (a) providing a crude harvest (a) comprising virus particles and impurities, wherein the impurities are generated from growing said virus particles on a cell substrate; (b) reducing impurities from the crude harvest (a) by precipitation with an agent comprising a protamine salt, preferably a protamine sulphate, to obtain a virus preparation (b); and further purifying the Zika virus preparation (b) by method or methods selecting for size of the Zika virus particles, such as e.g. a sucrose density gradient centrifugation to obtain a Zika virus preparation (c) comprising the infectious Zika virus particles.

In some embodiments, the concentration of protamine sulphate in step (b) is about 1 to 10 mg/ml, more preferably about 1 to 5 mg/ml, more preferably about 1 to 2 mg/ml. In one embodiment, the concentration of protamine sulphate in step (b) is about 2 mg/mL. In one embodiment, the concentration of protamine sulphate is 1.2 to 1.8 mg/ml, more preferably 1.4 to 1.6 mg/ml. In a preferred embodiment, the concentration of protamine sulphate in step (b) is about 1.6 mg/ml or about 2 mg/ml.

In some embodiments, the residual host cell DNA of the virus preparation (e) is less than 1 μg/mL, especially less than 900, 800, 700, 600, 500, 400, 300 or 200 ng/mL, preferably less than 100 ng/mL. In a preferred embodiment, the residual host cell DNA of the virus preparation (c) is less than 10 ng/mL. In some embodiments, the residual host cell protein of the final virus preparation (c) is less than 10 μg/mL, especially less than 9, 8, 7, 6, 5, 4, 3 or 2 μg/mL, preferably less than 1 μg/mL. In a preferred embodiment, the residual host cell protein of the virus preparation (c) is less than 100 ng/mL. In some embodiments, the residual non-infectious virus particles of the final virus preparation (c) is less than 10 μg/mL, especially less than 9, 8, 7, 6, 5, 4, 3 or 2 μg/mL, preferably less than 1 μg/mL. In a preferred embodiment, the residual non-infectious virus particles of the virus preparation (c) is less than 100 ng/mL.

In some embodiments, the residual protamine is less than 1 μg/mL, especially less than 900, 800, 700, 600, 500, 400, 300 or 200 ng/mL, preferably less than 100 ng/mL, more preferably is below the detection limit of HPLC, in particular below the detection limit in the final drug substance. In some embodiments, the PS content is tested by HPLC or size exclusion chromatography (SEC). For example, HPLC is validated for PS determination in JEV sucrose gradient pool samples as a routine release assay and is very sensitive (i.e., LOQ 3 μg/mL; LOD 1 μg/mL). In the current invention, PS content in in Zika virus DS samples was <LOD. In one embodiment, the HPLC assessment of PS content can be performed on a Superdex Peptide 10/300GL column (GE: 17-5176-01) using 30% Acetonitrile, 0.1% Trifluoroacetic acid as solvent with a flow rate of 0.6 ml/min at 25° C. and detection at 214 nm. A more sensitive method of measurement for residual protamine in a purified virus preparation is mass spectrometry (MS). In some embodiments, the residual PS levels in a Zika virus preparation are tested by MS or other such highly sensitive method, e.g., nuclear magnetic resonance (NMR). With this method, residual PS, as well as fragments and/or break-down products of PS, can be detected at trace amounts, such as levels as low as, for example, $10^6$, $10^7$ or $10^8$ molecules per typical sample load. In some embodiments, the PS levels are tested in the sucrose gradient pool. In some embodiments, the PS levels are tested in the drug product. In some embodiments, the PS levels are tested in the drug substance.

In some embodiments, the crude harvest (a) comprising the virus particles and impurities is subjected to one or more pre-purification step(s) prior to step (b). In some embodiments, the one or more pre-purification step(s) comprises digesting host cell genomic DNA in the crude harvest (a) comprising the virus particles and impurities by enzymatic treatment. In some embodiments, the one or more pre-purification step(s) comprises filtration, ultrafiltration, concentration, buffer exchange and/or diafiltration. In some embodiments, the one or more pre-purification steps is filtration using a filter having a pore size equal to or less than 1 μm. In some embodiments, the filter has a pore size equal to or less than 0.2 μm. In a preferred embodiment, the filter has a pore size of 0.2 μm. In some embodiments, the concentration and/or ultra/diafiltration and/or buffer exchange is performed by tangential flow filtration (TFF). In some embodiments, ultra/diafiltration of the crude harvest (a) comprising the virus particles and impurities is performed using a hollow fiber membrane having a cut-off of equal to or less than 300 kDa. In a preferred embodiment, the hollow fiber membrane has a cut-off of 100 kDa.

In some embodiments, the Zika virus particle is a live Zika virus, a chimeric virus, an attenuated live virus, a modified live virus, or a recombinant live virus. In a further step, the Zika virus particles of the invention may by optionally inactivated. In some embodiments, the Zika virus particle is an attenuated form of the virus particle. For example, the Zika virus may have reduced infectivity, virulence, and/or replication in a host, as compared to a wild-type Zika virus. In some embodiments, the Zika virus is a mutated or modified Zika virus, for example the nucleic acid of the Zika virus may contain at least one mutation relative to the wild-type Zika virus. In some embodiments, the Zika virus is a recombinant live Zika virus, meaning a Zika virus that is generated recombinantly and may contain nucleic acid from different sources.

In some embodiments, the Zika virus particle is a live virus, an attenuated live virus, a modified live virus, or a recombinant live virus. In a most preferred embodiment, the Zika virus is a Zika virus from the Asian lineage.

In some embodiments, the relative reduction of impurity of the final Zika virus preparation relative to the liquid medium (a) comprising the Zika virus particles and impurities is in a range from 60 to 95%. In some embodiments, the residual impurity of the final Zika virus preparation is less than 1%. We observed a decrease in the HCP peaks and the non-infectious aggregate peaks in the HPLC-SEC or SDS-PAGE. An exact quantification is difficult but one can measure the density of the SDS-PAGE bands and other methods.

In some embodiments, the Zika virus is propagated in a cell line selected from the group consisting of an EB66 cell line, a Vero cell line, a Vero-αHis cell line, a HeLa cell line, a HeLa—S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is EB66 cell line. In a preferred embodiment, said cell line is a Vero cell line.

Aspects of the invention provide a use of any of the processes described herein for manufacturing a composition for immunization against a Zika viral infection. In a preferred embodiment, the composition is a vaccine. In one embodiment, the composition or vaccine is directed against a Zika virus of the Asian lineage.

Other aspects provide compositions comprising the Zika virus particles obtainable by any of the processes described herein for treating and/or preventing a Zika viral infection. In one embodiment, the Zika virus infection is caused by a Zika virus of the Asian lineage.

In some embodiments, the Zika virus is derived from the Asian lineage. In some embodiments, the Zika virus is a Zika virus as described partially or fully in Sequence section of this application, i.e. any of sequences SEQ ID Nos 2 to 69 or 72, in particular all partly or fully described Zika viruses of the Asian lineages or an immunogenic variant thereof. The immunogenic variants of the Zika virus or Zika virus of the Asian lineages are herein defined as having at least 80% sequence identity to the nucleotide sequence of the sequences described in any of sequences SEQ ID Nos 2 to 69 or 72, especially at least 81%, 82%, 83%, 84%, 85%, 86%, 87%, 88% 89%, 90%, 91%, 92%, 93%, 94%, 95%, 96%, 97%, 98% or at least 99% sequence identity.

In some embodiments, the process of the invention results in an enrichment of infectious Zika virus particles from the crude harvest comprising infectious Zika virus particles and non-infectious Zika virus particles and other Zika virus products such that the enrichment of the infectious Zika virus particles is at least 50%, at least 60%, at least 70%, at least 80%, at least 90%, at least 95%, preferably at least 80%, especially 85% relative to the total virus particle content of the crude harvest (a) comprising the Zika virus particles and impurities.

In some embodiments, the residual impurity of the final Zika virus preparation with respect to all impurities in the crude harvest is less than 10%, 9%, 8%, 7%, 6%, 5%, 4%, 3%, 2%, 1%, preferably less than 5% as determined by SEC-HPLC (Size Exclusion Chromatography-HPLC).

In some embodiments, the filtration step of the Zika virus preparation (b) after contact with the solid-phase matrix is performed using a filter having a pore size equal to or greater than 1 μm. In some embodiments, the filter has a pore size equal to or greater than 0.2 μm. In a preferred embodiment, the filter has a pore size of about 0.2 μm, such as 0.22 μm.

In some embodiments, the Zika virus is propagated in a cell line selected from the group consisting of an EB66 cell line, a Vero cell line, a Vero-αHis cell line, a HeLa cell line, a HeLa—S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is EB66 cell line. In a preferred embodiment, said cell line is a Vero cell line.

Aspects of the invention provide a use of any of the processes described herein for manufacturing a composition for immunization against a Zika virus infection. In a preferred embodiment, the composition is a vaccine. In preferred embodiments, the vaccine is administered to the subject once, twice or three or more times. In a preferred embodiment, the vaccine is administered once or twice. In a preferred embodiment, the vaccine is administered only once.

The herein disclosed in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was unexpectedly higher than the recently reported inactivated Zika virus vaccine candidate (Larocca, et. al, 2016, Nature doi:10.1038/nature18952.).

Inactivated viruses are among the safest vaccines and especially preferred for delivery to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing, alignments were performed with the multi alignment package Jalview (Waterhouse et al., 2009, Bioinformatics 25 (9) 1189-1191). In the drawings:

FIG. 3: Pairwise alignment-Jalview (% identity, nt), complete genomes.

FIG. 6: Pairwise alignment-Jalview (% identity, aa), E-protein.

FIG. 14: Representative SDS-PAGE from the sucrose gradient harvest of a Zika virus purification is shown.

DETAILED DESCRIPTION OF THE INVENTION

Disclosed herein are processes for the purification of infectious Zika virus particles, i.e., mature, functional Zika virus particles. The processes disclosed are characterized by the removal of undesired by-products of Zika virus production on host cells, such as non-infectious Zika virus particles and aggregated and immature Zika virus by-products. The processes provided herein allow the production of highly-purified Zika virus preparations comprising mostly infectious Zika virus particles. During the course of the invention, it was observed that protamine sulphate (PS), added to remove contaminating DNA during Zika virus purification, resulted not only in removal of contaminating DNA, but also in the loss of a high percentage of total Zika virus particles present in the preparation. Surprisingly, however, quantification of total infectious Zika virus particles by TCID50 before and after PS treatment revealed that the absolute number of infectious Zika virus particles did not change following this loss of total Zika virus particles. This observation clearly shows that treatment with PS can facilitate selective removal of non-infectious, aggregated and immature viral by-products, leaving behind the infectious Zika virus particles. Because by-products produced during Zika virus growth on host cells may have different (and undesirable) immunological properties or other unwanted side-effects or safety issues, a simple and robust way to remove these by-products is of high importance for the quality and safety of the final product.

Protamines are small arginine-rich nuclear proteins, present in high amounts in the sperm of fish, which have an important role in DNA packaging during spermatogenesis. Protamine sulfate (or "protamine" or "PS") can form a stable ion pair with heparin and is thus commonly used during certain surgeries when the anti-coagulation effect of heparin is no longer needed. In large doses, protamine sulfate administered alone can also have a weak anticoagulant effect ("Protamine sulfate". Wikipedia: The Free Encyclopedia. Wikimedia Foundation, Inc. 30 Sep. 2015 Web. 26 Nov. 2015 <https://en.wikipedia.org/wiki/Protamine_sulfate>). Protamine Sulphate is additionally routinely used in biotechnology applications such as DNA precipitation (e.g., removal of host cell DNA from cell culture processes), purification of DNA binding proteins and retroviral-mediated gene transfer.

Protamine is obtained from salmon sperm or produced recombinantly and is used as a sulphate salt. The four major peptides, which constitute almost the entire nitrogen-containing material in salmon protamine, have been fully characterized and found to be polypeptides of 30-32 amino acids in length, of which 21-22 residues are arginine. The average molecular mass is in the range of 4250 Da for the following sequence: PRRRRSSSRP VRRRRRPRVS RRRRRRGGRR RR (SEQ ID NO: 1). Herein, protamine is also referred to as protamine salt, or preferably protamine sulphate.

Figure 1:
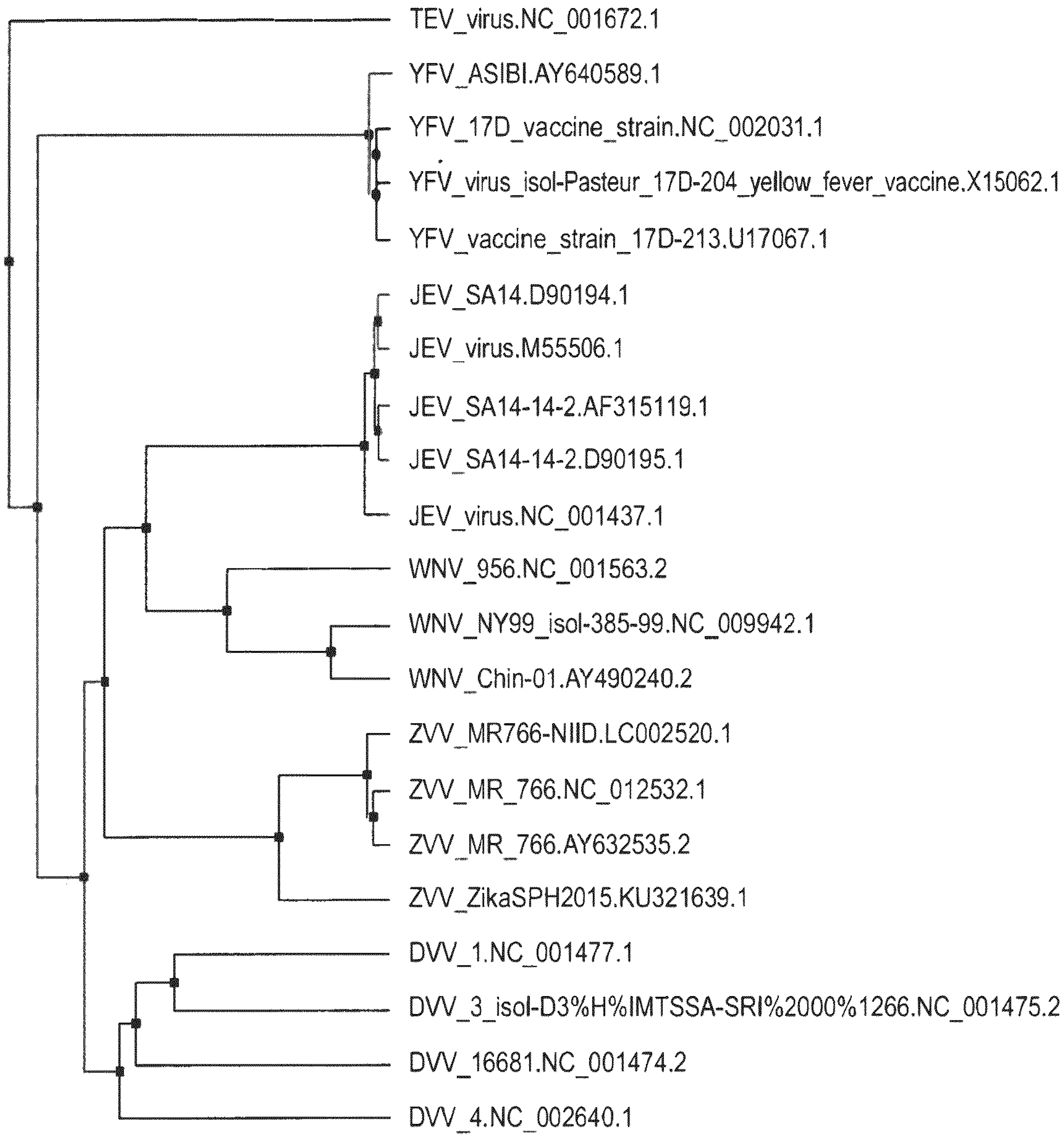
FIG. 1: Average distance tree (by % identity, nt), complete genomes.
Figure 2:
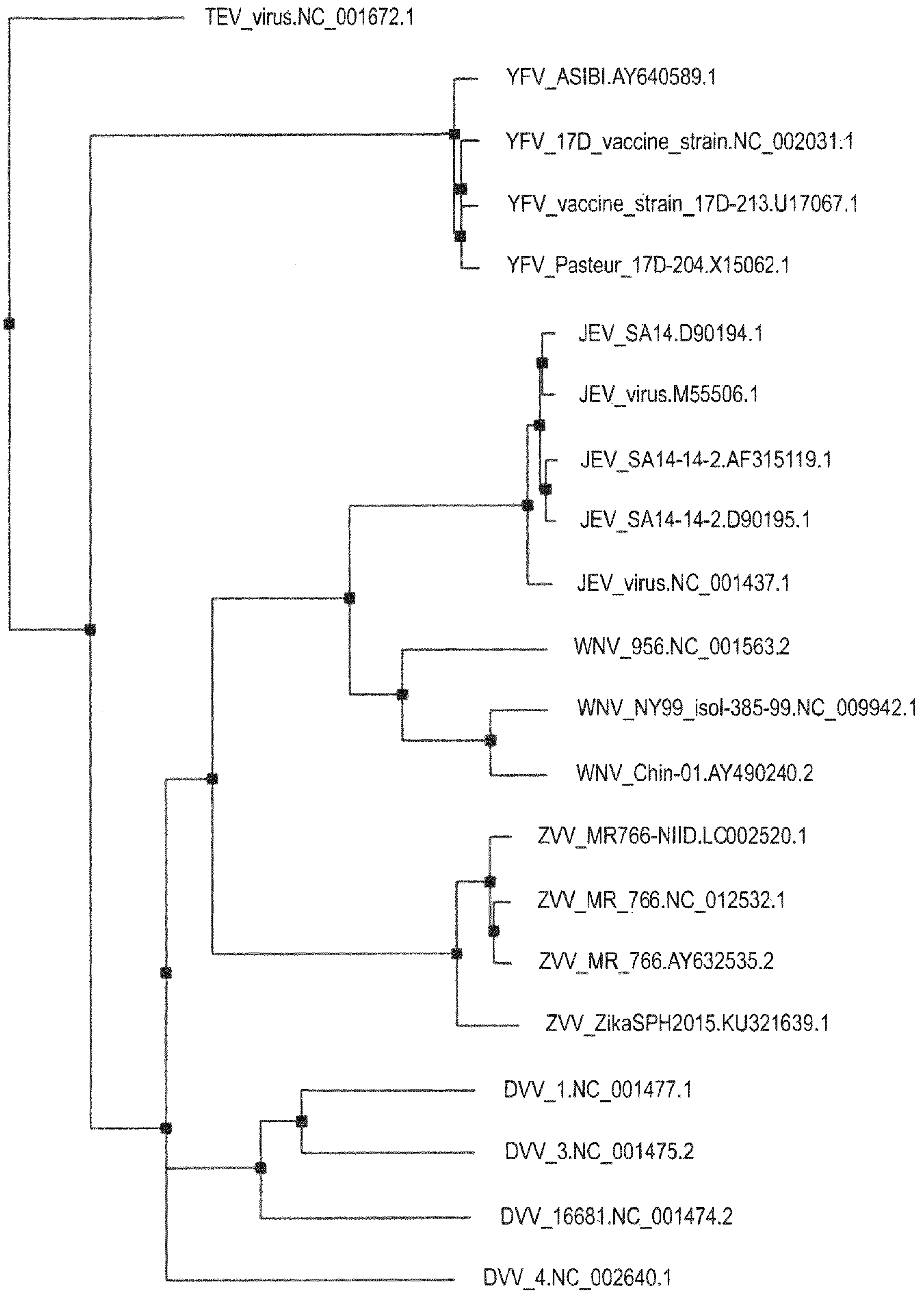
FIG. 2: Neighbor joining tree (by % identity, nt), complete genomes.
Figure 4:
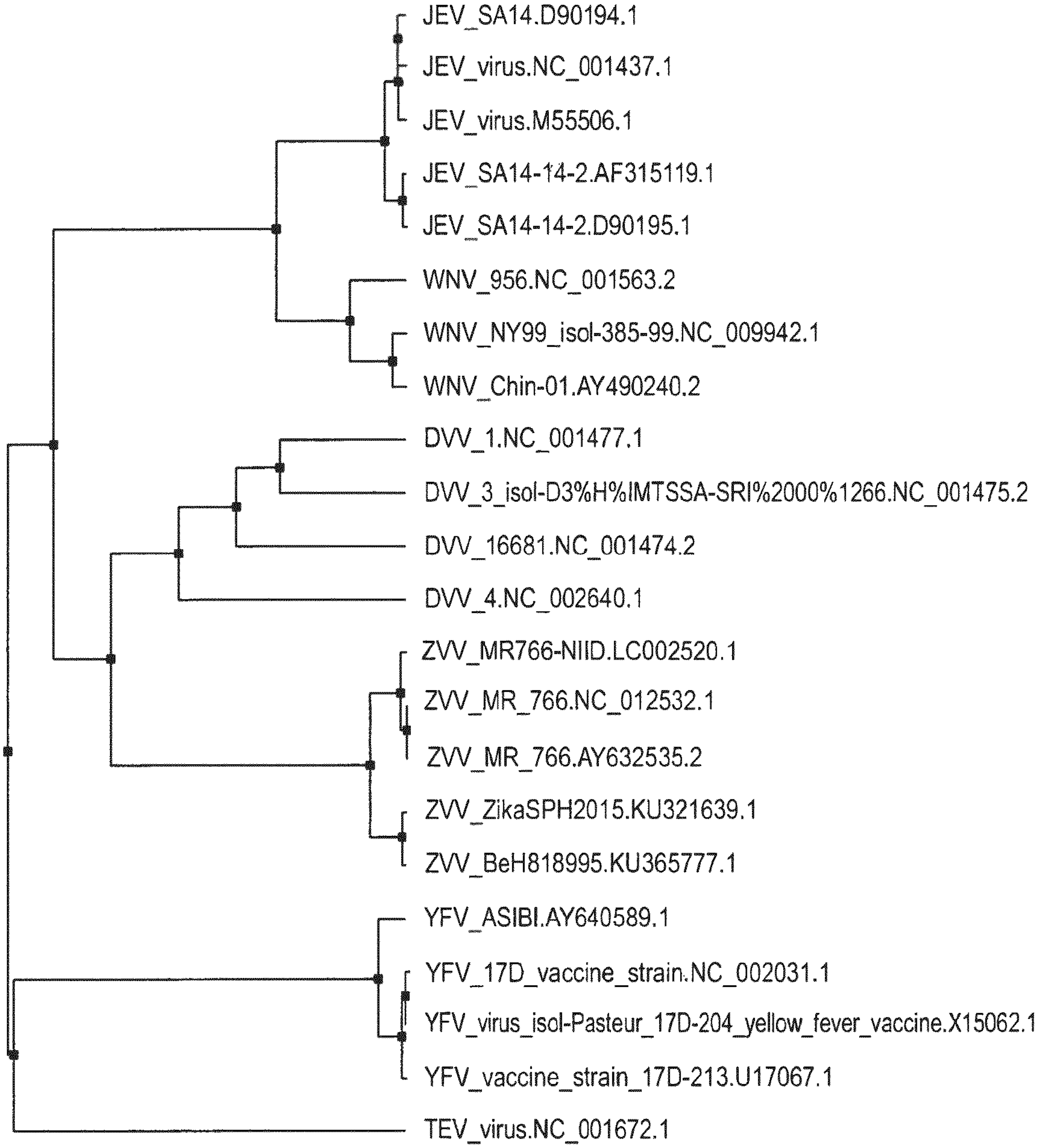
FIG. 4: Average distance tree (by % identity, aa), E-protein.
Figure 5:
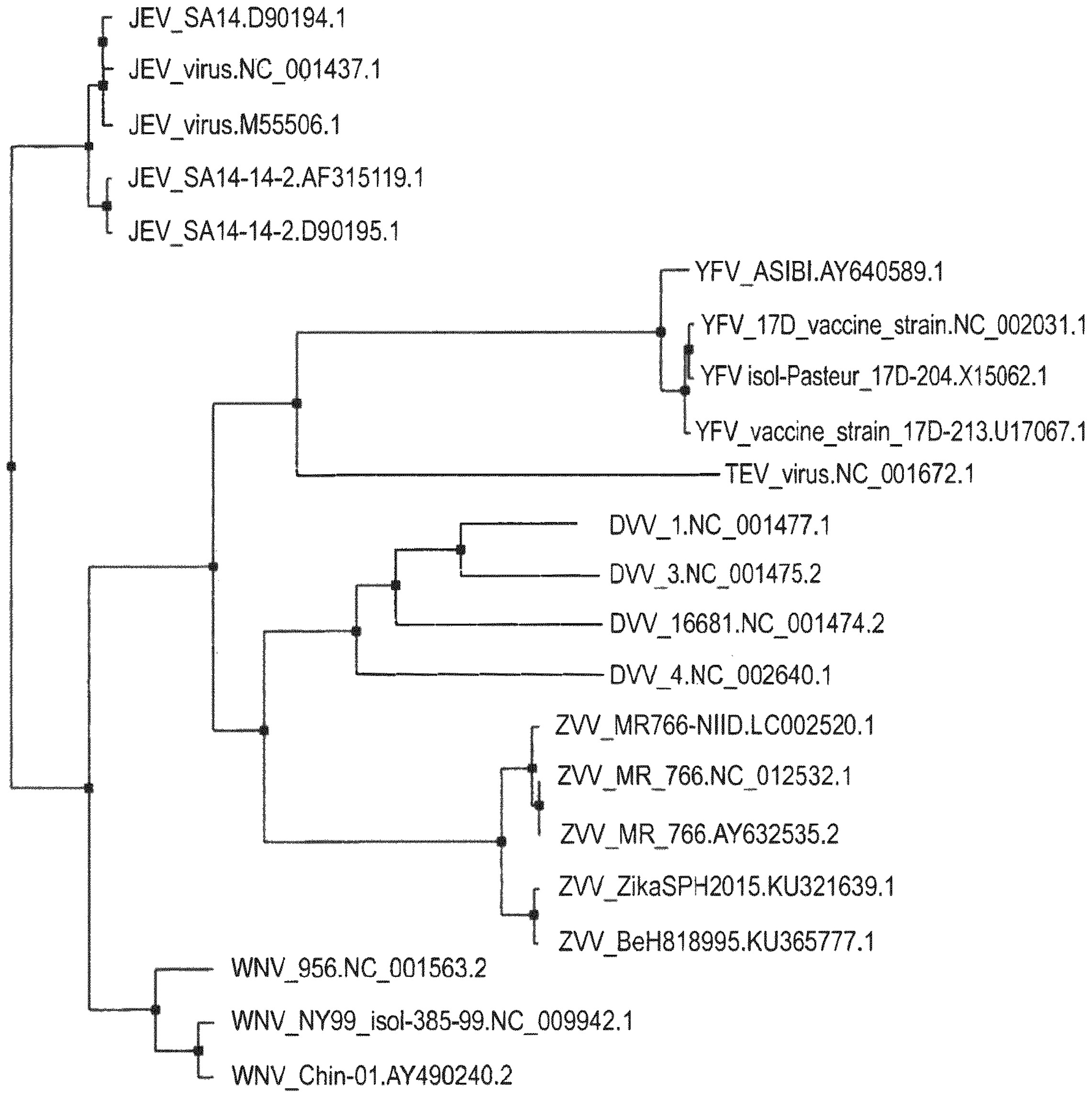
FIG. 5: Neighbor joining tree (by % identity. aa), E-protein.
Figure 7A:
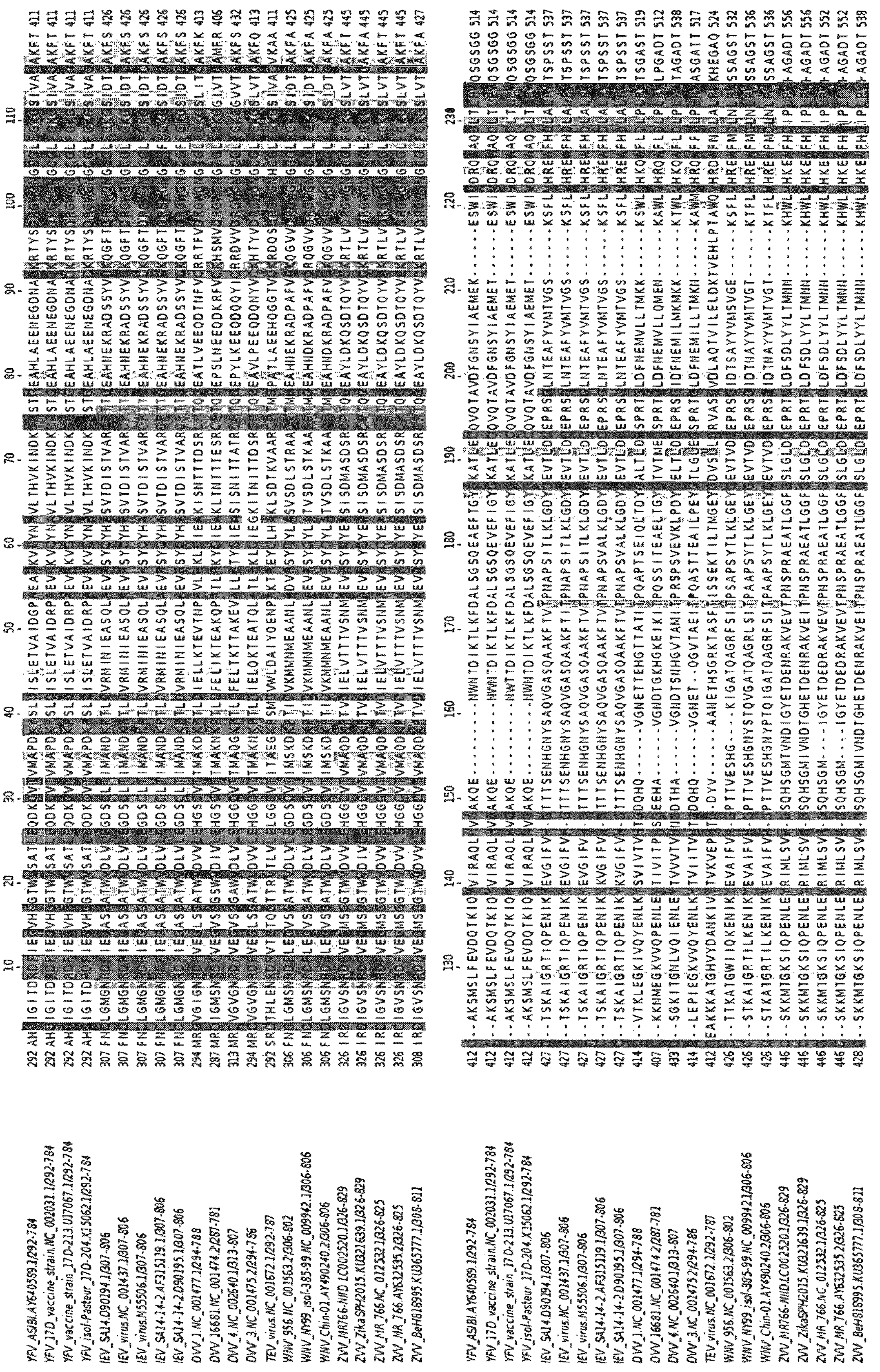
FIGS. 7A-7C: Alignment (shading: % identity, aa), E-protein.
Figure 7B:
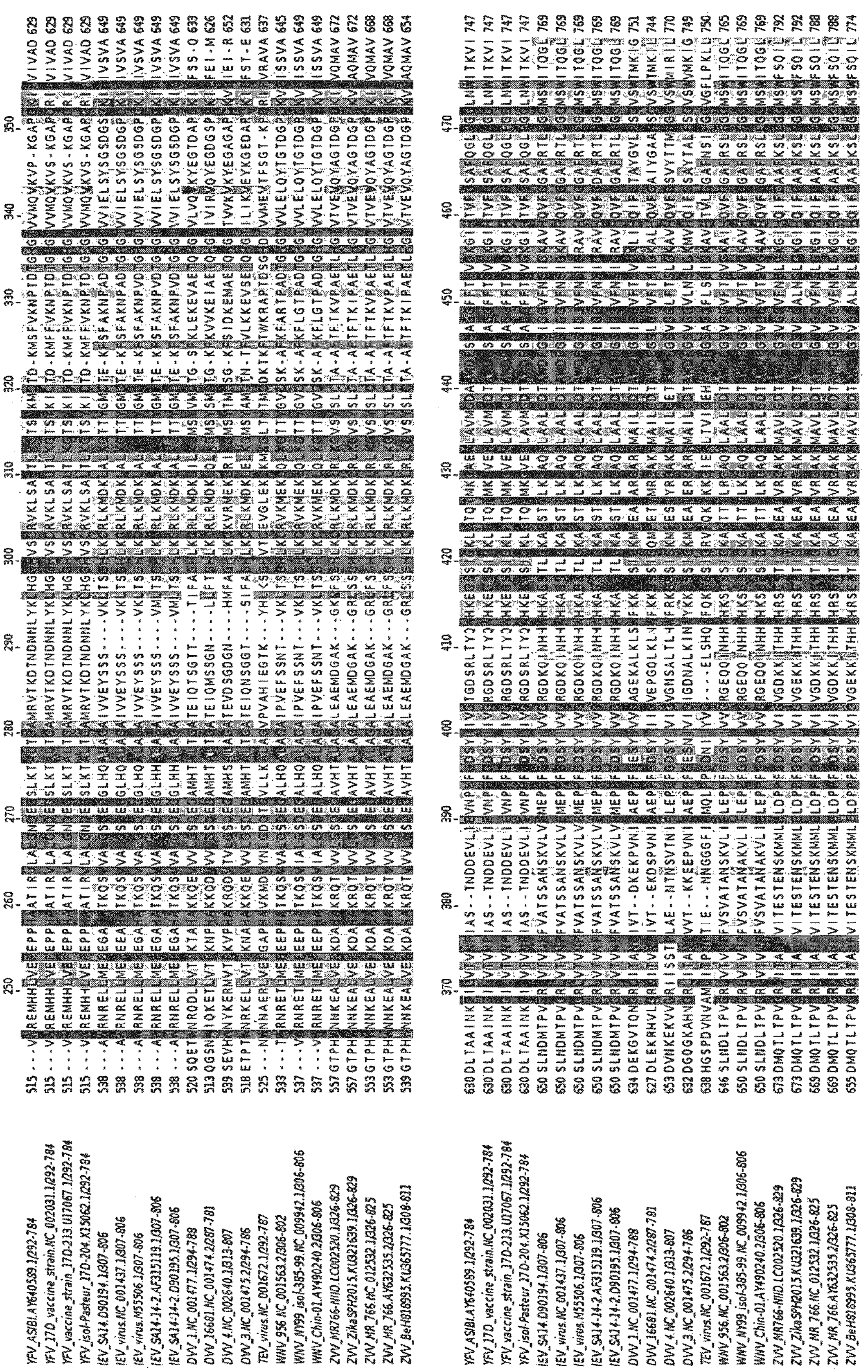
Figure 7C:
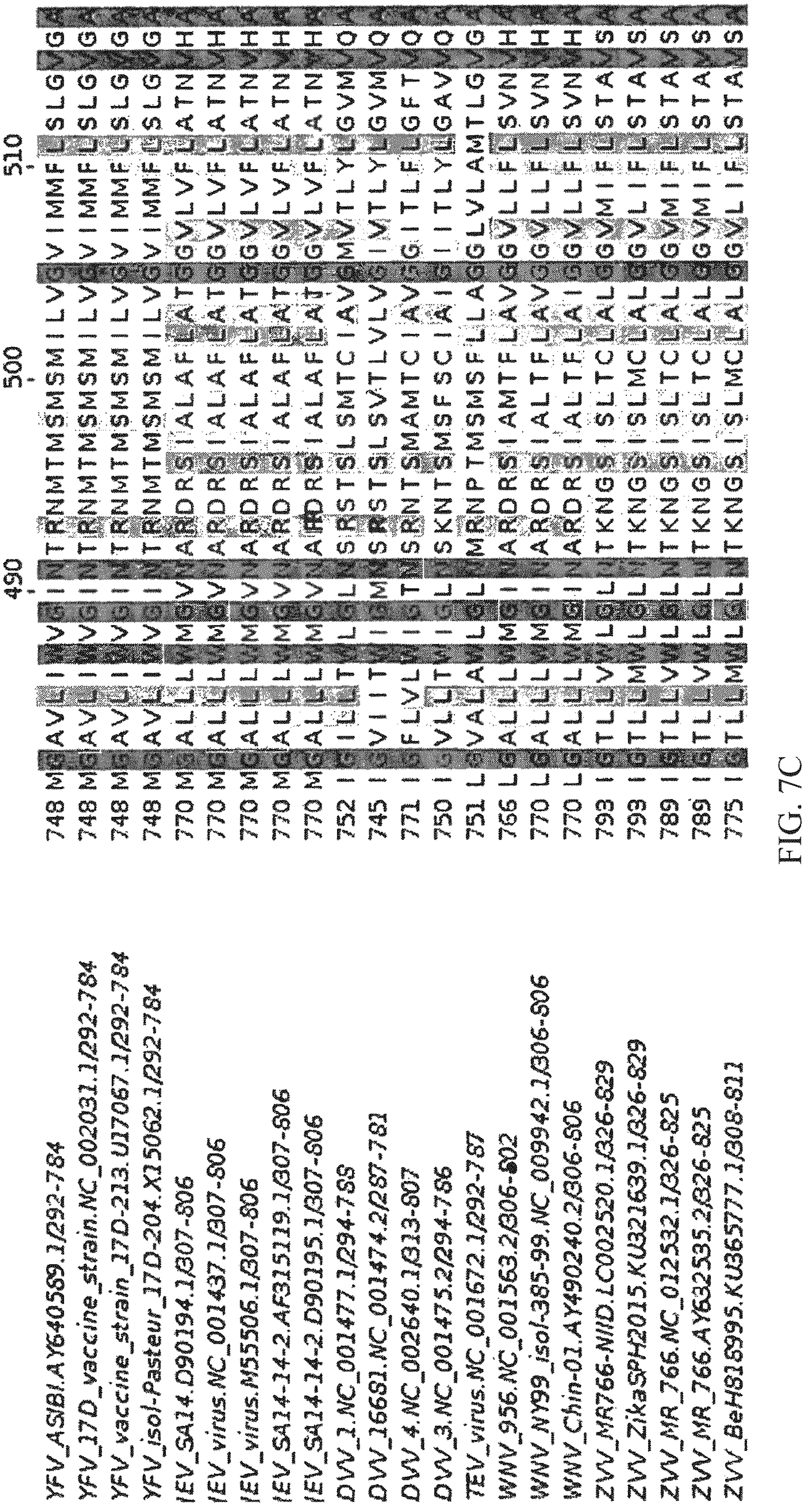
Figure 8:
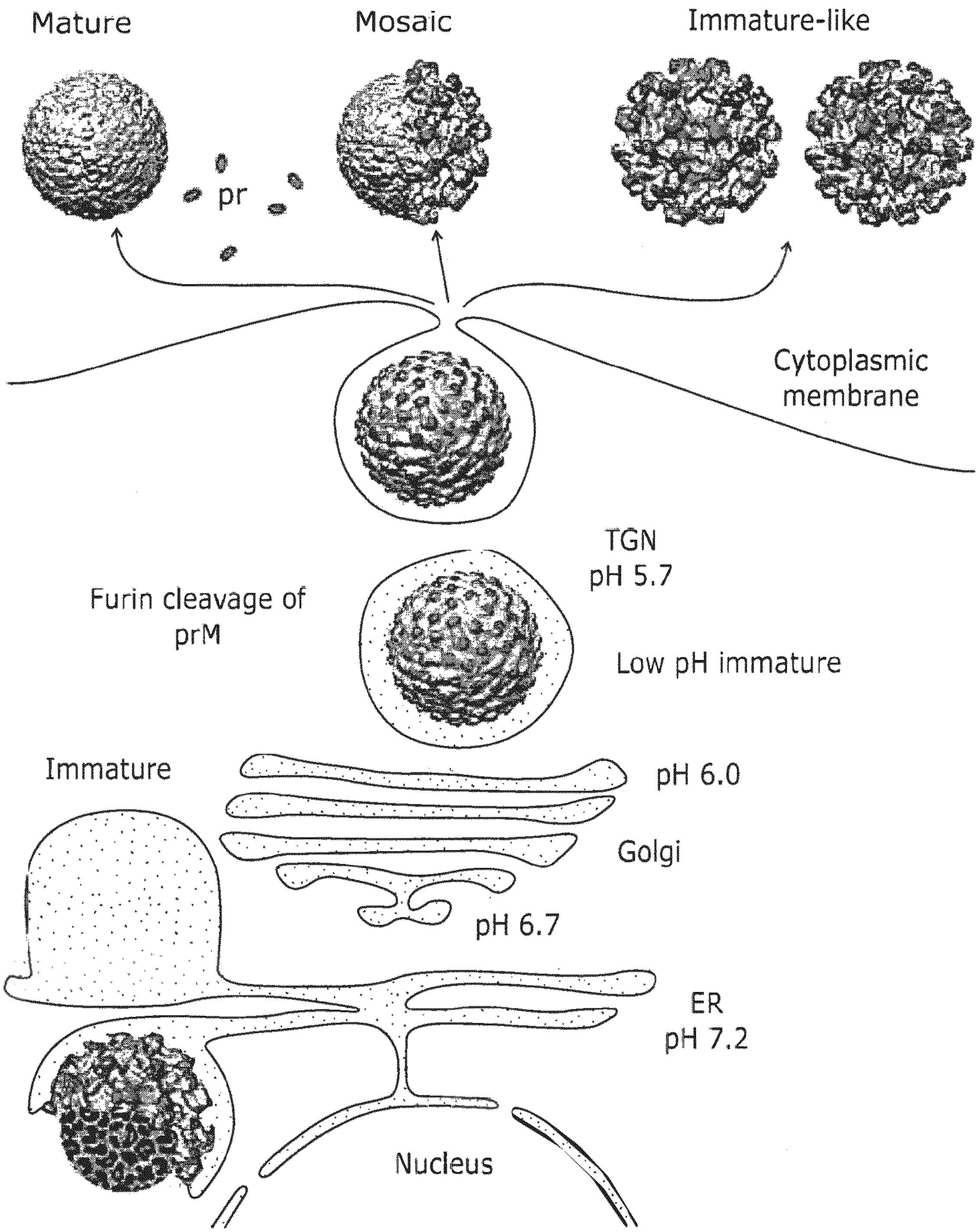
FIG. 8: An example of virus particle maturation in the host cell. As observed in flaviviruses, full maturation of the particles requires proteolytic cleavage of the precursor membrane glycoprotein (prM) by the host protease furin. Not all prM molecules are cleaved, resulting in the release of mature, mosaic or immature-like conformations from the cells. Mosaic and immature forms are generally not infectious—only mature virions are infective and have hemagglutinin (HA)/TCID50 activity. (Figure adapted from Plevka, et al., Maturation of flaviviruses starts from one or more icosahedrally independent nucleation centres, EMBO reports (2011) 12, 602-606).

The present invention relates to the use of protamine sulphate (PS) in a process of purification of a live Zika virus, wherein the protamine sulphate facilitates the removal of impurities from a crude virus harvest, including non-infectious virus particles and aggregates. As seen in FIG. 8 using flaviviruses as an example, virus production in the host cell can result in the release of virus products which are not mature, and non-infectious particles, which can also be considered impurities according to the present invention. As such, the present invention also relates to the enrichment of infectious virus particles from a crude harvest containing a mixture of virus particles and other viral products in various stages of maturation.

The use of protamine sulphate can follow crude cell lysis or any further step after cell lysis (e.g. including after a pre-purification with filtration, chromatography etc) wherein the Zika virus particles are further enriched or concentrated and/or other impurities are removed and/or buffer components are exchanged. The further steps may comprise filtration or concentration of the crude cell lysate.

The protamine sulphate may comprise the sequence PRRRRSSSRP VRRRRRPRVS RRRRRRGGRR RR (SEQ ID NO: 1) or a variant thereof wherein the amino acid sequence comprises from 28-35 amino acids, preferably 29-34, more preferably 30-33 amino acids, most preferably 31 or 32 amino acids. The protamine sulphate preferably comprises at least 19 arginine residues, more preferably at least 20 arginine residues, more preferably at least 21 arginine residues, even more preferably at least 22 residues, most preferably 20 or 21 arginine residues. Further, other protamine sulphate-like compounds or variants thereof may be used. Therefore, the use of the term "protamine salt" herein shall serve to encompass natural variations on SEQ ID NO: 1, preferably, but not limited to, the protamine sulphate forms.

The process comprising the use of protamine sulphate of the invention can be applied to purification of Zika virus for use in pharmaceutical compositions, for example, for a pharmaceutical composition such as a vaccine where it is important that the Zika virus is in its infectious form. The Zika virus to be purified may be a live virus, a live attenuated virus or a live chimeric virus, preferably a live wild type Zika virus, such as a Zika virus of the Asian lineage. In one embodiment, the Zika virus particle is also be later inactivated. In a preferred embodiment, the Zika virus is inactivated with formaldehyde.

The process according to the current invention may also comprise the use of a sucrose gradient, preferably an optimized sucrose gradient. The sucrose gradient is preferably optimized for the removal of protamine sulfate, also for the removal of immature viral particles or other viral particles which are non-infectious or host cell proteins or nucleic acids (DNA, RNA, mRNA, etc) or other host cell debris. In the current invention the optimized sucrose gradient comprises at least two, at least three, at least four layers of sucrose solutions with different densities. In one embodiment, the virus preparation to be purified is provided in a sucrose solution which has a density of about 8%, about 9%, about 10%, about 11%, about 12% sucrose (w/w), preferably about 10%. In one embodiment, one sucrose solution in the gradient has a density of about 45%, about 46%, about 47%, about 48%, about 49%, about 50%, about 51%, about 52%, about 53%, about 54%, about 55% sucrose (w/w), preferably about 50%. In one embodiment, one sucrose solution in the gradient has a density of about 30%, about 31%, about 32%, about 33%, about 34%, about 35%, about 36%, about 37%, about 38%, about 39%, about 40% sucrose (w/w), preferably about 35%. In one embodiment, one sucrose solution in the gradient has a density of about 10%, about 11%, about 12%, about 13%, about 14%, about 15%, about 16%, about 17%, about 18%, about 19%, about 20% sucrose (w/w), preferably about 15% sucrose. In a preferred embodiment, the sucrose gradient comprises three layers of sucrose solutions of about 50%, about 35% and about 15% (w/w) sucrose and the virus composition to be purified is contained in about 10% (w/w) sucrose. Because the invention provided for means to not only test for host cell DNA but also immature viral particles, the skilled person in the art is able to more precisely optimize the sucrose gradient for most efficient purification and include additional tools such as PRNT assay to monitor purification success.

In a preferred embodiment, the produced Zika virus is derived from the Asian lineage (which includes the strains found in South America and all strains derived from any Asian lineage). In some other embodiments, the produced Zika virus is a Zika virus as described in the Sequence section of this application (SEQ ID NO: 2 to 69). In a preferred embodiment, the Zika virus comprises the RNA corresponding to the DNA sequence provided by SEQ ID NO: 72 or variants thereof. In a preferred embodiment, the Zika virus encodes the entire polyprotein as provided by SEQ ID NO: 73.

TABLE 1

Overview of process buffers and stock solutions

| Buffer | Composition | Final pH | Final conductivity [mS/cm] |
|---|---|---|---|
| A | 0.5M NaOH | | n.a. |
| B | 0.1M NaOH | | n.a. |
| C | 25 mM Tris, 150 mM NaCl | 7.4 ± 0.2 | 16.5 |
| D | 1M Tris | 7.4 ± 0.2 | n.a. |
| E | 4.5M NaCl | n.a. | n.a. |
| F | 1M NaCl | n.a. | n.a. |
| G | 1% SDS | n.a. | n.a. |
| H | 50% (w/w) Sucrose in 25 mM Tris, 150 mM NaCl | 7.4 ± 0.2 | n.a. |
| I | 35% (w/w) Sucrose in 25 mM Tris, 150 mM NaCl | 7.4 ± 0.2 | n.a. |
| J | 15% (w/w) Sucrose in 25 mM Tris, 150 mM NaCl | 7.4 ± 0.2 | n.a. |
| K | 10 × PBS | 7.4 ± 0.2 | n.a. |
| L | 50 mg/mL Protamine sulphate | 7.4 ± 0.2 | n.a. |
| M | Drug substance formulation buffer (10 mM Tris (hydroxymethyl)-aminomethan, 5% Sucrose, 1% (10 mg/mL) rHSA) | 7.4 ± 0.2 | 1.3 |

TABLE 2

| Abbreviations | |
|---|---|
| ° Bx | Degrees Brix = sugar content (w/w) of an aqueous solution |

TABLE 2-continued

| Abbreviations | |
|---|---|
| BSA | Bovine serum albumin |
| CC700 | Capto ™ Core 700 |
| CPE | Cytopathic effect |
| EtOH | Ethanol |
| EU | Endotoxin units |
| DS | Drug Substance |
| DP | Drug Product |
| DSP | Downstream Process |
| HCP | Host cell protein |
| hcDNA | Host cell DNA |
| hpi | Hours post infection |
| HPLC | High Performance Liquid Chromatography |
| ID | Inner diameter |
| JEV | Japanese Encephalitis virus |
| LAL | Limulus amebocyte lysate |
| LDS buffer | Lithium dodecyl sulfate sample loading buffer |
| LOD | Limit of detection |
| LOQ | Limit of quantitation |
| MALLS | Multiangle light scattering |
| mAU | Milli absorbance units |
| MS | Mass spectroscopy |
| NIV | Neutralized inactivated virus |
| PBS | Phosphate buffered saline |
| PD | Process development |
| PFU | Plaque forming units |
| p.i. | Post-infection |
| PS | Protamine sulphate or protamine sulfate |
| rcf | Relative centrifugal force |
| rHSA | Recombinant human serum albumin |
| Rms radius | Root mean square radius |
| rMSB | Research master seed bank |
| RSD | Relative standard deviation |
| SEC | Size exclusion chromatography |
| SGC | Sucrose gradient centrifugation |
| SGP | Sucrose gradient purified |
| SDS | Sodium dodecyl sulphate |
| TBS | Tris buffered saline |
| TIM | Tangential flow filtration |
| TCID50 | Tissue culture infectious dose 50% |
| UF/DF | Ultrafiltration/diafiltration |
| WFI | Water for injection |
| ZikaV | Zika virus |

Brix:

Degrees Brix (° Bx) is the sugar content of an aqueous solution. One degree Brix is 1 gram of sucrose in 100 grams of solution and represents the strength of the solution as percentage by mass. ° Bx corresponds to the sucrose content in % (w/w), eg. 45° Bx equals 45% (w/w) sucrose.

TABLE A

Primers for Zika virus sequencing: lowercase letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 1 | 9320_Zika_PF_1F | SEQ ID NO: 74 ttaggatccGTTGTTGATCTGTGTGAAT | 69.9 | 74.6 | 707 |
| | 9321_Zika_PF_1R | SEQ ID NO: 75 taactcgagCGTACACAACCCAAGTT | 69.3 | 75.6 | |
| 2 | 9322_Zika_PF_2F | SEQ ID NO: 76 ttaggatccTCACTAGACGTGGGAGTG | 70 | 73.9 | 704 |
| | 9323_Zika_PF_2R | SEQ ID NO: 77 taactcgagAAGCCATGTCYGATATTGAT | 69.8 | 73.7 | |
| 3 | 9324_Zika_PF_3F | SEQ ID NO: 78 ttaggatccGCATACAGCATCAGGTG | 72.3 | 74.5 | 712 |
| | 9325_Zika_PF_3R | SEQ ID NO: 79 taactcgagTGTGGAGTTCCGGTGTCT | 72 | 76.4 | |
| 4 | 9326_Zika_PF_4F | SEQ ID NO: 80 ttaggatccGAATAGAGCGAARGTTGAGATA | 70.9 | 74 | 712 |
| | 9327_Zika_PF_4R | SEQ ID NO: 81 taactcgAGTGGTGGGTGATCTTCTTCT | 70.5 | 73.7 | |
| 5 | 9328_Zika_PF_5F | SEQ ID NO: 82 ttaggatcCAGTCACAGTGGAGGTACAGTAC | 70.3 | 75 | 704 |
| | 9329_Zika_PF_5R | SEQ ID NO: 83 taactcgagCRCAGATACCATCTTCCC | 71.5 | 77.3 | |
| 6 | 9330_Zika_PF_6F | SEQ ID NO: 84 ttaggatCCCTTATGTGCTTGGCCTTAG | 70.7 | 72.7 | 698 |
| | 9331_Zika_PF_6R | SEQ ID NO: 85 taactcgagTCTTCAGCCTCCATGTG | 70.4 | 76.9 | |
| 7 | 9332_Zika_PF_7F | SEQ ID NO: 86 ttaggatccAATGCCCACTCAAACATAGA | 71.9 | 75 | 716 |
| | 9333_Zika_PF_7R | SEQ ID NO: 87 taactcgagTCATTCTCTTCTTCAGCCCTT | 71 | 74 | |
| 8 | 9334_Zika_PF_8F | SEQ ID NO: 88 ttaggatccAAGGGTGATCGAGGAAT | 70.9 | 75.2 | 703 |
| | 9335_Zika_PF_8R | SEQ ID NO: 89 taactcgagTTCCCTTCAGAGAGAGGAGC | 71.9 | 73.4 | |

TABLE A-continued

Primers for Zika virus sequencing: lowercase letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 9 | 9336_Zika_PF_9F | SEQ ID NO: 90 ttaggatccTCTTTTGCAAACTGCGATC | 71.9 | 75 | 699 |
| | 9337_Zika_PF_9R | SEQ ID NO: 91 taactcgagTCCAGCTGCAAAGGGTAT | 71 | 74.9 | |
| 10 | 9338_Zika_PF_10F | SEQ ID NO: 92 ttaggatccGTGTGGACATGTACATTGA | 71.4 | 75.8 | 706 |
| | 9339_Zika_PF_10R | SEQ ID NO: 93 taactcgagCCCATTGCCATAAAGTC | 70.4 | 75.8 | |
| 11 | 9340_Zika_PF_11F | SEQ ID NO: 94 ttaggatccTCATACTGTGGTCCATGGA | 71.6 | 78.1 | 692 |
| | 9341_Zika_PF_11R | SEQ ID NO: 95 taactcgagGCCCATCTCAACCCTTG | 74 | 78 | |
| 12 | 9342_Zika_PF_12F | SEQ ID NO: 96 ttaggatccTAGAGGGCTTCCAGTGC | 70.9 | 74 | 707 |
| | 9343_Zika_PF_12R | SEQ ID NO: 97 taactcgAGATACTCATCTCCAGGTTTGTTG | 70.2 | 72.2 | |
| 13 | 9344_Zika_PF_13F | SEQ ID NO: 98 ttaggatccGAAAACAAAACATCAAGAGTG | 70.6 | 75.4 | 726 |
| | 9345_Zika_PF_13R | SEQ ID NO: 99 taactcgagGAATCTCTCTGTCATGTGTCCT | 71.9 | 75.6 | |
| 14 | 9346_Zika_PF_14F | SEQ ID NO: 100 ttaggatccTTGATGGCACGACCAAC | 73.1 | 75.6 | 715 |
| | 9347_Zika_PF_14R | SEQ ID NO: 101 ttaggatccGTTGTTGATCTGTGTGAAT | 70.8 | 77.9 | |
| 15 | 9348_Zika_PF_15F | SEQ ID NO: 102 taactcgagCAGGTCAATGTCCATTG | 71.9 | 75.4 | 719 |
| | 9349_Zika_PF_15R | SEQ ID NO: 103 ttaggatccTGTTGTGTTCCTATTGCTGGT | 73.9 | 77.2 | |
| 16 | 9350_Zika_PF_16F | SEQ ID NO: 104 taactcgaGTGATCAGRGCCCCAGC | 72.3 | 75.4 | 703 |
| | 9351_Zika_PF_16R | SEQ ID NO: 105 ttaggatccTGCTGCCCAGAAGAGAA | 72 | 76.3 | |
| 17 | 9352_Zika_PF_17F | SEQ ID NO: 106 taactcgaGCACCAACAYGGGTTCTT | 73.6 | 76 | 705 |
| | 9353_Zika_PF_17R | SEQ ID NO: 107 ttaggatcCTCAAGGACGGTGTGGC | 72 | 75.5 | |
| 18 | 9354_Zika_PF_18F | SEQ ID NO: 108 taactcgagCAATGATCTTCATGTTGGG | 71.7 | 75.8 | 699 |
| | 9355_Zika_PF_18R | SEQ ID NO: 109 ttaggatccTATGGGGGAGGACTGGT | 71 | 74.1 | |
| 19 | 9356_Zika_PF_19F | SEQ ID NO: 110 taactcGAGCCCAGAACCTTGGATC | 73.3 | 75.5 | 711 |
| | 9357_Zika_PF_19R | SEQ ID NO: 111 ttaggatcCAGACCCCCAAGAAGGC | 71.3 | 76.9 | |
| 20 | 9358_Zika_PF_20F | SEQ ID NO: 112 taactcgagCCCCTTTGGTCTTGTCT | 71.7 | 75 | 706 |
| | 9359_Zika_PF_20R | SEQ ID NO: 113 ttaggatccAGGAAGGATGTATGCAGATG | 71.9 | 73.9 | |
| 21 | 9360_Zika_PF_21F | SEQ ID NO: 114 taactcgagACATTTGCGCATATGATTTTG | 70.4 | 75.7 | 709 |
| | 9361_Zika_PF_21R | SEQ ID NO: 115 ttaggatccAGGAAGGACACACAAGAGT | 71.8 | 75 | |
| 22 | 9362_Zika_PF_22F | SEQ ID NO: 116 taactcgagACAGGCTGCACAGCTTT | 70 | 79.1 | 581 |
| | 9363_Zika_PF_22R | SEQ ID NO: 117 ttaggatccTCTCTCATAGGGCACAGAC | 74.8 | 81.1 | |

SEQUENCES

A typical form of protamine
SEQ ID NO: 1
PRRRRSSSRP VRRRRRPRVS RRRRRRGGRR RR

Provided below are examples of nucleic acid sequences of the genomes of Zika viruses that may be used in the methods, compositions, and/or vaccines described herein.

KU321639.1 Zika virus strain ZikaSPH2015, Brazil, complete genome
SEQ ID NO: 2

GTTGTTACTGTTGCTGACTCAGACTGCGACAGTTCGAGTTTGAAGCGAAAGCTAGCAACAGTATCAACAGGTTTTATTTGGATT

TGGAAACGAGAGTTTCTGGTCATGAAAAACCCAAAAAAGAAATCCGGAGGATTCCGGATTGTCAATATGCTAAAACGCGGAG

TAGCCCGTGTGAGCCCCTTTGGGGGCTTGAAGAGGCTGCCAGCCGGACTTCTGCTGGGTCATGGGCCCATCAGGATGGTCTTG

GCAATTCTAGCCTTTTTGAGATTCACGGCAATCAAGCCATCACTGGGTCTCATCAATAGATGGGGTTCAGTGGGGAAAAAAGA

GGCTATGGAAATAATAAAGAAGTTCAAGAAAGATCTGGCTGCCATGCTGAGAATAATCAATGCTAGGAAGGAGAAGAAGAG

ACGGGGCGCAGATACTAGTGTCGGAATTGTTGGCCTCCTGCTGACCACAGCTATGGCAGCGGAGGTCACTAGACGTGGGAGT

GCATACTATATGTACTTGGACAGAAACGATGCTGGGGAGGCCATATCTTTTCCAACCACATTGGGGATGAATAAGTGTTATAT

ACAGATCATGGATCTTGGACACATGTGTGATGCCACCATGAGCTATGAATGCCCTATGCTGGATGAGGGGGTGGAACCAGAT

GACGTCGATTGTTGGTGCAACACGACGTCAACTTGGGTTGTGTACGGAACCTGCCATCACAAAAAAGGTGAAGCACGGAGAT

CTAGAAGAGCTGTGACGCTCCCCTCCCATTCCACTAGGAAGCTGCAAACGCGGTCGCAAACCTGGTTGGAATCAAGAGAATAC

ACAAAGCACTTGATTAGAGTCGAAAATTGGATATTCAGGAACCCTGGCTTCGCGTTAGCAGCAGCTGCCATCGCTTGGCTTTTG

GGAAGCTCAACGAGCCAAAAAGTCATATACTTGGTCATGATACTGCTGATTGCCCCGGCATACAGCATCAGGTGCATAGGAGT

CAGCAATAGGGACTTTGTGGAAGGTATGTCAGGTGGGACTTGGGTTGATATTGTCTTGGAACATGGAGGTTGTGTCACCGTA

ATGGCACAGGACAAACCGACTGTCGACATAGAGCTGGTTACAACAACAGTCAGCAACATGGCGGAGGTAAGATCCTACTGCT

ATGAGGCATCAATATCAGACATGGCTTCGGACAGCCGCTGCCCAACACAAGGTGAAGCCTACCTTGACAAGCAATCAGACACT

CAATATGTCTGCAAAAGAACGTTAGTGGACAGAGGCTGGGGAAATGGATGTGGACTTTTTGGCAAAGGGAGTCTGGTGACAT

GCGCTAAGTTTGCATGCTCCAAGAAAATGACCGGGAAGAGCATCCAGCCAGAGAATCTGGAGTACCGGATAATGCTGTCAGT

TCATGGCTCCCAGCACAGTGGGATGATCGTTAATGACACAGGACATGAAACTGATGAGAATAGAGCGAAGGTTGAGATAACG

CCCAATTCACCAAGAGCCGAAGCCACCCTGGGGGGTTTTGGAAGCCTAGGACTTGATTGTGAACCGAGGACAGGCCTTGACTT

TTCAGATTTGTATTACTTGACTATGAATAACAAGCACTGGTTGGTTCACAAGGAGTGGTTCCACGACATTCCATTACCTTGGCAC

GCTGGGGCAGACACCGGAACTCCACACTGGAACAACAAAGAAGCACTGGTAGAGTTCAAGGACGCACATGCCAAAAGGCAA

ACTGTCGTGGTTCTAGGGAGTCAAGAAGGAGCAGTTCACACGGCCCTTGCTGGAGCTCTGGAGGCTGAGATGGATGGTGCAA

AGGGAAGGCTGTCCTCTGGCCACTTGAAATGTCGCCTGAAAATGGATAAACTTAGATTGAAGGGCGTGTCATACTCCTTGTGT

ACCGCAGCGTTCACATTCACCAAGATCCCGGCTGAAACACTGCACGGGACAGTCACAGTGGAGGTACAGTACGCAGGGACAG

ATGGACCTTGCAAGGTTCCAGCTCAGATGGCGGTGGACATGCAAACTCTGACCCCAGTTGGGAGGTTGATAACCGCTAACCCC

GTAATCACTGAAAGCACTGAGAACTCTAAGATGATGCTGGAACTTGATCCACCATTTGGGGACTCTTACATTGTCATAGGAGTC

GGGGAGAAGAAGATCACCCACCACTGGCACAGGAGTGGCAGCACCATTGGAAAAGCATTTGAAGCCACTGTGAGAGGTGCC

AAGAGAATGGCAGTCTTGGGAGACACAGCCTGGGACTTTGGATCAGTTGGAGGCGCTCTCAACTCATTGGGCAAGGGCATCC

ATCAAATTTTTGGAGCAGCTTTCAAATCATTGTTTGGAGGAATGTCCTGGTTCTCACAAATTCTCATTGGAACGTTGCTGATGTG

GTTGGGTCTGAACACAAAGAATGGATCTATTTCCCTTATGTGCTTGGCCTTAGGGGGAGTGTTGATCTTCTTATCCACAGCCGT

CTCTGCTGATGTGGGGTGCTCGGTGGACTTCTCAAAGAAGGAGACGAGATGCGGTACAGGGGTGTTCGTCTATAACGACGTT

GAAGCCTGGAGGGACAGGTACAAGTACCATCCTGACTCCCCCCGTAGATTGGCAGCAGCAGTCAAGCAAGCCTGGGAAGATG

GTATCTGCGGGATCTCCTCTGTTTCAAGAATGGAAAACATCATGTGGAGATCAGTAGAAGGGGAGCTCAACGCAATCCTGGAA

-continued

GAGAATGGAGTTCAACTGACGGTCGTTGTGGGATCTGTAAAAAACCCCATGTGGAGAGGTCCACAGAGATTGCCCGTGCCTG

TGAACGAGCTGCCCCACGGCTGGAAGGCTTGGGGGAAATCGCACTTCGTCAGAGCAGCAAAGACAAATAACAGCTTTGTCGT

GGATGGTGACACACTGAAGGAATGCCCACTCAAACATAGAGCATGGAACAGCTTTCTTGTGGAGGATCATGGGTTCGGGGTA

TTTCACACTAGTGTCTGGCTCAAGGTTAGAGAAGATTATTCATTAGAGTGTGATCCAGCCGTTATTGGAACAGCTGTTAAGGGA

AAGGAGGCTGTACACAGTGATCTAGGCTACTGGATTGAGAGTGAGAAGAATGACACATGGAGGCTGAAGAGGGCCCATCTG

ATCGAGATGAAAACATGTGAATGGCCAAAGTCCCACACATTGTGGACAGATGGAATAGAAGAGAGTGATCTGATCATACCCA

AGTCTTTAGCTGGGCCACTCAGCCATCACAATACCAGAGAGGGCTACAGGACCCAAATGAAAGGGCCATGGCACAGTGAAGA

GCTTGAAATTCGGTTTGAGGAATGCCCAGGCACTAAGGTCCACGTGGAGGAAACATGTGGAACAAGAGGACCATCTCTGAGA

TCAACCACTGCAAGCGGAAGGGTGATCGAGGAATGGTGCTGCAGGGAGTGCACAATGCCCCCACTGTCGTTCCGGGCTAAAG

ATGGCTGTTGGTATGGAATGGAGATAAGGCCCAGGAAAGAACCAGAAAGCAACTTAGTAAGGTCAATGGTGACTGCAGGATC

AACTGATCACATGGATCACTTCTCCCTTGGAGTGCTTGTGATTCTGCTCATGGTGCAGGAAGGGCTGAAGAAGAGAATGACCA

CAAAGATCATCATAAGCACATCAATGGCAGTGCTGGTAGCTATGATCCTGGGAGGATTTTCAATGAGTGACCTGGCTAAGCTT

GCAATTTTGATGGGTGCCACCTTCGCGGAAATGAACACTGGAGGAGATGTAGCTCATCTGGCGCTGATAGCGGCATTCAAAGT

CAGACCAGCGTTGCTGGTATCTTTCATCTTCAGAGCTAATTGGACACCCCGTGAAAGCATGCTGCTGGCCTTGGCCTCGTGTCT

TTTGCAAACTGCGATCTCCGCCTTGGAAGGCGACCTGATGGTTCTCATCAATGGTTTTGCTTTGGCCTGGTTGGCAATACGAGC

GATGGTTGTTCCACGCACTGATAACATCACCTTGGCAATCCTGGCTGCTCTGACACCACTGGCCCGGGGCACACTGCTTGTGGC

GTGGAGAGCAGGCCTTGCTACTTGCGGGGGGTTTATGCTCCTCTCTCTGAAGGGAAAAGGCAGTGTGAAGAAGAACTTACCA

TTTGTCATGGCCCTGGGACTAACCGCTGTGAGGCTGGTCGACCCCATCAACGTGGTGGGGCTGCTGTTGCTCACAAGGAGTGG

GAAGCGGAGCTGGCCCCCTAGCGAAGTACTCACAGCTGTTGGCCTGATATGCGCATTGGCTGGAGGGTTCGCCAAGGCAGAT

ATAGAGATGGCTGGGCCCATGGCCGCGGTCGGTCTGCTAATTGTCAGTTACGTGGTCTCAGGAAAGAGTGTGGACATGTACA

TTGAAAGAGCAGGTGACATCACATGGGAAAAAGATGCGGAAGTCACTGGAAACAGTCCCCGGCTCGATGTGGCGCTAGATGA

GAGTGGTGATTTCTCCCTGGTGGAGGATGACGGTCCCCCCATGAGAGAGATCATACTCAAGGTGGTCCTGATGACCATCTGTG

GCATGAACCCAATAGCCATACCCTTTGCAGCTGGAGCGTGGTACGTATACGTGAAGACTGGAAAAAGGAGTGGTGCTCTATG

GGATGTGCCTGCTCCCAAGGAAGTAAAAAAGGGGGAGACCACAGATGGAGTGTACAGAGTAATGACTCGTAGACTGCTAGG

TTCAACACAAGTTGGAGTGGGAGTTATGCAAGAGGGGGTCTTTCACACTATGTGGCACGTCACAAAAGGATCCGCGCTGAGA

AGCGGTGAAGGGAGACTTGATCCATACTGGGGAGATGTCAAGCAGGATCTGGTGTCATACTGTGGTCCATGGAAGCTAGATG

CCGCCTGGGACGGGCACAGCGAGGTGCAGCTCTTGGCCGTGCCCCCCGGAGAGAGAGCGAGGAACATCCAGACTCTGCCCG

GAATATTTAAGACAAAGGATGGGGACATTGGAGCGGTTGCGCTGGATTACCCAGCAGGAACTTCAGGATCTCCAATCCTAGA

CAAGTGTGGGAGAGTGATAGGACTTTATGGCAATGGGGTCGTGATCAAAAATGGGAGTTATGTTAGTGCCATCACCCAAGGG

AGGAGGGAGGAAGAGACTCCTGTTGAGTGCTTCGAGCCTTCGATGCTGAAGAAGAAGCAGCTAACTGTCTTAGACTTGCATC

CTGGAGCTGGGAAAACCAGGAGAGTTCTTCCTGAAATAGTCCGTGAAGCCATAAAAACAAGACTCCGTACTGTGATCTTAGCT

CCAACCAGGGTTGTCGCTGCTGAAATGGAGGAAGCCCTTAGAGGGCTTCCAGTGCGTTATATGACAACAGCAGTCAATGTCAC

CCACTCTGGAACAGAAATCGTCGACTTAATGTGCCATGCCACCTTCACTTCACGTCTACTACAGCCAATCAGAGTCCCCAACTAT

AATCTGTATATTATGGATGAGGCCCACTTCACAGATCCCTCAAGTATAGCAGCAAGAGGATACATTTCAACAAGGGTTGAGAT

GGGCGAGGCGGCTGCCATCTTCATGACCGCCACGCCACCAGGAACCCGTGACGCATTTCCGGACTCCAACTCACCAATTATGG

ACACCGAAGTGGAAGTCCCAGAGAGAGCCTGGAGCTCAGGCTTTGATTGGGTGACGGATTATTCTGGAAAAACAGTTTGGTT

TGTTCCAAGCGTGAGGAACGGCAATGAGATCGCAGCTTGTCTGACAAAGGCTGGAAAACGGGTCATACAGCTCAGCAGAAAG

ACTTTTGAGACAGAGTTCCAGAAAACAAAACATCAAGAGTGGGACTTTGTCGTGACAACTGACATTTCAGAGATGGGCGCCAA

CTTTAAAGCTGACCGTGTCATAGATTCCAGGAGATGCCTAAAGCCGGTCATACTTGATGGCGAGAGAGTCATTCTGGCTGGAC

CCATGCCTGTCACACATGCCAGCGCTGCCCAGAGGAGGGGGCGCATAGGCAGGAATCCCAACAAACCTGGAGATGAGTATCT

GTATGGAGGTGGGTGCGCAGAGACTGACGAAGACCATGCACACTGGCTTGAAGCAAGAATGCTCCTTGACAATATTTACCTCC

-continued

AAGATGGCCTCATAGCCTCGCTCTATCGACCTGAGGCCGACAAAGTAGCAGCCATTGAGGGAGAGTTCAAGCTTAGGACGGA

GCAAAGGAAGACCTTTGTGGAACTCATGAAAAGAGGAGATCTTCCTGTTTGGCTGGCCTATCAGGTTGCATCTGCCGGAATAA

CCTACACAGATAGAAGATGGTGCTTTGATGGCACGACCAACAACACCATAATGGAAGACAGTGTGCCGGCAGAGGTGTGGAC

CAGACACGGAGAGAAAAGAGTGCTCAAACCGAGGTGGATGGACGCCAGAGTTTGTTCAGATCATGCGGCCCTGAAGTCATTC

AAGGAGTTTGCCGCTGGGAAAAGAGGAGCGGCTTTTGGAGTGATGGAAGCCCTGGGAACACTGCCAGGACACATGACAGAG

AGATTCCAGGAAGCCATTGACAACCTCGCTGTGCTCATGCGGGCAGAGACTGGAAGCAGGCCTTACAAAGCCGCGGCGGCCC

AATTGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTGAGC

CAGCCAGAATTGCATGTGTCCTCATTGTTGTGTTCCTATTGCTGGTGGTGCTCATACCTGAGCCAGAAAAGCAAAGATCTCCCC

AGGACAACCAAATGGCAATCATCATCATGGTAGCAGTAGGTCTTCTGGGCTTGATTACCGCCAATGAACTCGGATGGTTGGAG

AGAACAAAGAGTGACCTAAGCCATCTAATGGGAAGGAGAGAGGAGGGGGCAACCATGGGATTCTCAATGGACATTGACCTG

CGGCCAGCCTCAGCTTGGGCCATCTATGCTGCCTTGACAACTTTCATTACCCCAGCCGTCCAACATGCAGTGACCACTTCATACA

ACAACTACTCCTTAATGGCGATGGCCACGCAAGCTGGAGTGTTGTTTGGTATGGGCAAAGGGATGCCATTCTACGCATGGGAC

TTTGGAGTCCCGCTGCTAATGATAGGTTGCTACTCACAATTAACGCCCCTGACCCTAATAGTGGCCATCATTTTGCTCGTGGCG

CACTACATGTACTTGATCCCAGGGCTGCAGGCAGCAGCTGCGCGTGCTGCCCAGAAGAGAACGGCAGCTGGCATCATGAAGA

ACCCTGTTGTGGATGGAATAGTGGTGACTGACATTGACACAATGACAATTGACCCCCAAGTGGAGAAAAAGATGGGACAGGT

GCTACTCATGGCAGTAGCCGTCTCCAGCGCCATACTGTCGCGGACCGCCTGGGGGTGGGGGGAGGCTGGGGCCCTGATCACA

GCCGCAACTTCCACTTTGTGGGAAGGCTCTCCGAACAAGTACTGGAACTCCTCTACAGCCACTTCACTGTGTAACATTTTTAGG

GGAAGTTACTTGGCTGGAGCTTCTCTAATCTACACAGTAACAAGAAACGCTGGCTTGGTCAAGAGACGTGGGGGTGGAACAG

GAGAGACCCTGGGAGAGAAATGGAAGGCCCGCTTGAACCAGATGTCGGCCCTGGAGTTCTACTCCTACAAAAAGTCAGGCAT

CACCGAGGTGTGCAGAGAAGAGGCCCGCCGCGCCCTCAAGGACGGTGTGGCAACGGGAGGCCATGCTGTGTCCCGAGGAAG

TGCAAAGCTGAGATGGTTGGTGGAGCGGGGATACCTGCAGCCCTATGGAAAGGTCATTGATCTTGGATGTGGCAGAGGGGG

CTGGAGTTACTACGCCGCCACCATCCGCAAAGTTCAAGAAGTGAAAGGATACACAAAAGGAGGCCCTGGTCATGAAGAACCC

GTGTTGGTGCAAAGCTATGGGTGGAACATAGTCCGTCTTAAGAGTGGGGTGGACGTCTTTCATATGGCGGCTGAGCCGTGTG

ACACGTTGCTGTGTGACATAGGTGAGTCATCATCTAGTCCTGAAGTGGAAGAAGCACGGACGCTCAGAGTCCTCTCCATGGTG

GGGGATTGGCTTGAAAAAAGACCAGGAGCCTTTTGTATAAAAGTGTTGTGCCCATACACCAGCACTATGATGGAAACCCTGGA

GCGACTGCAGCGTAGGTATGGGGGAGGACTGGTCAGAGTGCCACTCTCCCGCAACTCTACACATGAGATGTACTGGGTCTCT

GGAGCGAAAAGCAACACCATAAAAAGTGTGTCCACCACGAGCCAGCTCCTCTTGGGGCGCATGGACGGGCCTAGGAGGCCA

GTGAAATATGAGGAGGATGTGAATCTCGGCTCTGGCACGCGGGCTGTGGTAAGCTGCGCTGAAGCTCCCAACATGAAGATCA

TTGGTAACCGCATTGAAAGGATCCGCAGTGAGCACGCGGAAACGTGGTTCTTTGACGAGAACCACCCATATAGGACATGGGC

TTACCATGGAAGCTATGAGGCCCCCACACAAGGGTCAGCGTCCTCTCTAATAAACGGGGTTGTCAGGCTCCTGTCAAAACCCT

GGGATGTGGTGACTGGAGTCACAGGAATAGCCATGACCGACACCACACCGTATGGTCAGCAAAGAGTTTTCAAGGAAAAAGT

GGACACTAGGGTGCCAGACCCCCAAGAAGGTACTCGTCAGGTTATGAGCATGGTCTCTTCCTGGTTGTGGAAAGAGCTAGGC

AAACACAAACGGCCACGAGTCTGTACCAAAGAAGAGTTCATCAACAAGGTTCGTAGCAATGCAGCATTAGGGGCAATATTTGA

AGAGGAAAAAGAGTGGAAGACTGCAGTGGAAGCTGTGAACGATCCAAGGTTCTGGGCTCTAGTGGACAAGGAAAGAGAGCA

CCACCTGAGAGGAGAGTGCCAGAGTTGTGTGTACAACATGATGGGAAAAAGAGAAAAGAAACAAGGGGAATTTGGAAAGGC

CAAGGGCAGCCGCGCCATCTGGTATATGTGGCTAGGGGCTAGATTTCTAGAGTTCGAAGCCCTTGGATTCTTGAACGAGGATC

ACTGGATGGGGAGAGAGAACTCAGGAGGTGGTGTTGAAGGGCTGGGATTACAAAGACTCGGATATGTCCTAGAAGAGATGA

GTCGCATACCAGGAGGAAGGATGTATGCAGATGACACTGCTGGCTGGGACACCCGCATCAGCAGGTTTGATCTGGAGAATGA

AGCTCTAATCACCAACCAAATGGAGAAAGGGCACAGGGCCTTGGCATTGGCCATAATCAAGTACACATACCAAAACAAAGTG

-continued

GTAAAGGTCCTTAGACCAGCTGAAAAAGGGAAAACAGTTATGGACATTATTTCGAGACAAGACCAAAGGGGGAGCGGACAA

GTTGTCACTTACGCTCTTAACACATTTACCAACCTAGTGGTGCAACTCATTCGGAATATGGAGGCTGAGGAAGTCCTAGAGATG

CAAGACTTGTGGCTGCTGCGGAGGTCAGAGAAAGTGACCAACTGGTTGCAGAGCAACGGATGGGATAGGCTCAAACGAATG

GCAGTCAGTGGAGATGATTGCGTTGTGAAGCCAATTGATGATAGGTTTGCACATGCCCTCAGGTTCTTGAATGATATGGGAAA

AGTTAGGAAGGACACACAAGAGTGGAAACCCTCAACTGGATGGGACAACTGGGAAGAAGTTCCGTTTTGCTCCCACCACTTCA

ACAAGCTCCATCTCAAGGACGGGAGGTCCATTGTGGTTCCCTGCCGCCACCAAGATGAACTGATTGGCCGGGCCCGCGTCTCT

CCAGGGGCGGGATGGAGCATCCGGGAGACTGCTTGCCTAGCAAAATCATATGCGCAAATGTGGCAGCTCCTTTATTTCCACAG

AAGGGACCTCCGACTGATGGCCAATGCCATTTGTTCATCTGTGCCAGTTGACTGGGTTCCAACTGGGAGAACTACCTGGTCAAT

CCATGGAAAGGGAGAATGGATGACCACTGAAGACATGCTTGTGGTGTGGAACAGAGTGTGGATTGAGGAGAACGACCACAT

GGAAGACAAGACCCCAGTTACGAAATGGACAGACATTCCCTATTTGGGAAAAAGGGAAGACTTGTGGTGTGGATCTCTCATA

GGGCACAGACCGCGCACCACCTGGGCTGAGAACATTAAAAACACAGTCAACATGGTGCGCAGGATCATAGGTGATGAAGAAA

AGTACATGGACTACCTATCCACCCAAGTTCGCTACTTGGGTGAAGAAGGGTCTACACCTGGAGTGCTGTAAGCACCAATCTTA

ATGTTGTCAGGCCTGCTAGTCAGCCACAGCTTGGGGAAAGCTGTGCAGCCTGTGACCCCCCCAGGAGAAGCTGGGAAACCAA

GCCTATAGTCAGGCCGAGAACGCCATGGCACGGAAGAAGCCATGCTGCCTGTGAGCCCCTCAGAGGACACTGAGTCAAAAAA

CCCCACGCGCTTGGAGGCGCAGGATGGGAAAAGAAGGTGGCGACCTTCCCCACCCTTCAATCTGGGGCCTGAACTGGAGATC

AGCTGTGGATCTCCAGAAGAGGGACTAGTGGTTAGAGGAGA

KU497555.1 Zika virus isolate Brazil-ZKV2015, Brazil, complete genome

SEQ ID NO: 3

CCAATCTGTGAATCAGACTGCGACAGTTCGAGTTTGAAGCGAAAGCTAGCAACAGTATCAACAGGTTTTATTTTGGATTTGGA

AACGAGAGTTTCTGGTCATGAAAAACCCAAAAAAGAAATCCGGAGGATTCCGGATTGTCAATATGCTAAAACGCGGAGTAGC

CCGTGTGAGCCCCTTTGGGGGCTTGAAGAGGCTGCCAGCCGGACTTCTGCTGGGTCATGGGCCCATCAGGATGGTCTTGGCG

ATTCTAGCCTTTTTGAGATTCACGGCAATCAAGCCATCACTGGGTCTCATCAATAGATGGGGTTCAGTGGGGAAAAAAGAGGC

TATGGAAATAATAAAGAAGTTCAAGAAAGATCTGGCTGCCATGCTGAGAATAATCAATGCCAGGAAGGAGAAGAAGAGACG

AGGCGCAGATACTAGTGTCGGAATCGTTGGCCTCCTGCTGACCACAGCTATGGCAGCGGAGGTCACTAGACGTGGGAGTGCA

TACTATATGTACTTGGACAGAAACGATGCTGGGGAGGCCATATCTTTTCCAACCACATTGGGGATGAATAAGTGTTATATACA

GATCATGGATCTTGGACACATGTGTGATGCCACCATGAGCTATGAATGCCCTATGCTGGATGAGGGGGTGGAACCAGATGAC

GTCGATTGTTGGTGCAACACGACGTCAACTTGGGTTGTGTACGGAACCTGCCATCACAAAAAAGGTGAAGCACGGAGATCTA

GAAGAGCTGTGACGCTCCCCTCCCATTCCACTAGGAAGCTGCAAACGCGGTCGCAAACCTGGTTGGAATCAAGAGAATACACA

AAGCACTTGATTAGAGTCGAAAATTGGATATTCAGGAACCCTGGCTTCGCGTTAGCAGCAGCTGCCATCGCTTGGCTTTTGGG

AAGCTCAACGAGCCAAAAAGTCATATACTTGGTCATGATACTGCTGATTGCCCCGGCATACAGCATCAGGTGCATAGGAGTCA

GCAATAGGGACTTTGTGGAAGGTATGTCAGGTGGGACTTGGGTTGATGTTGTCTTGGAACATGGGGGTTGTGTCACCGTAAT

GGCACAGGACAAACCGACTGTCGACATAGAGCTGGTTACAACAACAGTCAGCAACATGGCGGAGGTAAGATCCTACTGCTAT

GAGGCATCAATATCAGACATGGCTTCGGACAGCCGCTGCCCAACACAAGGTGAAGCCTACCTTGACAAGCAATCAGACACTCA

ATATGTCTGCAAAAGAACGTTAGTGGACAGAGGCTGGGGAAATGGATGTGGACTTTTTGGCAAAGGGAGCCTGGTGACATGC

GCTAAGTTTGCATGCTCCAAGAAAATGACCGGGAAGAGCATCCAGCCAGAGAATCTGGAGTACCGGATAATGCTGTCAGTTC

ATGGCTCCCAGCACAGTGGGATGATCGTTAATGACACAGGACATGAAACTGATGAGAATAGAGCGAAGGTTGAGATAACGCC

CAATTCACCAAGAGCCGAAGCCACCCTGGGGGGTTTTGGAAGCTTAGGACTTGATTGTGAACCGAGGACAGGCCTTGACTTTT

CAGATTTGTATTACTTGACTATGAATAACAAGCACTGGTTGGTTCACAAGGAGTGGTTCCACGACATTCCATTACCTTGGCACG

CTGGGGCAGACACCGGAACTCCACACTGGAACAACAAAGAAGCACTGGTAGAGTTCAAGGACGCACATGCCAAAAGGCAAA

CTGTCGTGGTTCTAGGGACTCAAGAAGGAGCAGTTCACACGGCCCTTGCTGGAGCTCTGGAGGCTGAGATGGATGGTGCAAA

GGGAAGGCTGTCCTCTGGCCACTTGAAATGTCGCCTGAAAATGGATAAACTTAGATTGAAGGGCGTGTCATACTCCTTGTGTA

CCGCAGCGTTCACATTCACCAAGATCCCGGCTGAAACACTGCACGGGACAGTCACAGTGGAGGTACAGTACGCAGGGACAGA

-continued

TGGACCTTGCAAGGTTCCAGCTCAGATGGCGGTGGACATGCAAACTCTGACCCCAGTTGGGAGGTTGATAACCGCTAACCCCG

TAATCACTGAAAGCACTGAGAACTCTAAGATGATGCTGGAACTTGATCCACCATTTGGGGACTCTTACATTGTCATAGGAGTCG

GGGAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCATCCA

TCAAATTTTTGGAGCAGCTTTCAAATCATTGTTTGGAGGAATGTCCTGGTTCTCACAAATTCTCATTGGAACGTTGCTGATGTGG

TGGGTCTGAACACAAAGAATGGATCTATTTCCCTTATGTGCTTGGCCTTAGGGGGAGTGTTGATCTTCTTATCCACAGCCGTC

TCTGCTGATGTGGGGTGCTCGGTGGACTTCTCAAAGAAGGAGACGAGATGTGGTACAGGGGTGTTCGTCTATAACGACGTTG

AAGCCTGGAGGGACAGGTACAAGTACCATCCTGACTCTCCCCGTAGATTGGCAGCAGCAGTCAAGCAAGCCTGGGAAGATGG

TATCTGCGGGATCTCCTCTGTTTCAAGAATGGAAAACATCATGTGGAGATCAGTAGAAGGGGAGCTTAACGCAATCCTGGAAG

AGAATGGAGTTCAACTGACGGTCGTTGTGGGATCTGTAAAAAACCCCATGTGGAGAGGTCCACAGAGATTGCCCGTGCCTGT

GAACGAGCTGCCCCACGGCTGGAAGGCTTGGGGGAAATCGTACTTCGTCAGAGCAGCAAAGACAAATAACAGCTTTGTCGTG

GATGGTGACACACTGAAGGAATGCCCACTCAAACATAGAGCATGGAACAGCTTTCTTGTGGAGGATCATGGGTTCGGGGTAT

TTCACACTAGTGTCTGGCTCAAGGTTAGAGAAGATTATTCATTAGAGTGTGATCCAGCCGTTATTGGAACAGCTGTTAAGGGA

AAGGAGGCTGTACACAGTGATCTAGGCTACTGGATTGAGAGTGAGAAGAATGACACATGGAGGCTGAAGAGGGCCCATCTG

ATCGAGATGAAAACATGTGAATGGCCAAAGTCCCACACATTGTGGACAGATGGAATAGAAGAGAGTGATCTGATCATACCCA

AGTCTTTAGCTGGGCCACTCAGCCATCACAATACCAGAGAGGGCTACAGGACCCAAATGAAAGGGCCATGGCACAGTGAAGA

GCTTGAAATTCGGTTTGAGGAATGCCCAGGCACTAAGGTCCACGTGGAGGAAACATGTGGAACAAGAGGACCATCTCTGAGA

TCAACCACTGCAAGCGGAAGGGTGATCGAGGAATGGTGCTGCAGGGAGTGCACAATGCCCCCACTGTCGTTCCGGGCTAAAG

ATGGCTGTTGGTATGGAATGGAGATAAGGCCCAGGAAAGAACCAGAAAGCAACTTAGTAAGGTCAATGGTGACTGCAGGATC

AACTGATCACATGGATCACTTCTCCCTTGGAGTGCTTGTGATTCTGCTCATGGTGCAGGAAGGGCTGAAGAAGAGAATGACCA

CAAAGATCATCATAAGCACATCAATGGCAGTGCTGGTAGCTATGATCCTGGGAGGATTTTCAATGAGTGACCTGGCTAAGCTT

GCAATTTTGATGGGTGCCACCTTCGCGGAAATGAACACTGGAGGAGATGTAGCTCATCTGGCGCTGATAGCGGCATTCAAAGT

CAGACCAGCGTTGCTGGTATCTTTCATCTTCAGAGCTAATTGGACACCCCGTGAAAGCATGCTGCTGGCCTTGGCCTCGTGTTT

TTTGCAAACTGCGATCTCCGCCTTGGAAGGCGACCTGATGGTTCTCATCAATGGTTTTGCTTTGGCCTGGTTGGCAATACGAGC

GATGGTTGTTCCACGCACTGACAACATCACCTTGGCAATCCTGGCTGCTCTGACACCACTGGCCCGGGGCACACTGCTTGTGGC

GTGGAGAGCAGGCCTTGCTACTTGCGGGGGGTTTATGCTCCTCTCTCTGAAGGGAAAAGGCAGTGTGAAGAAGAACTTACCA

TTTGTCATGGCCCTGGGACTAACCGCTGTGAGGCTGGTCGACCCCATCAACGTGGTGGGACTGCTGTTGCTCACAAGGAGTGG

GAAGCGGAGCTGGCCCCCTAGCGAAGTACTCACAGCTGTTGGCCTGATATGCGCATTGGCTGGAGGGTTCGCCAAGGCAGAT

ATAGAGATGGCTGGGCCCATGGCCGCGGTCGGTCTGCTAATTGTCAGTTACGTGGTCTCAGGAAAGAGTGTGGACATGTACA

TTGAAAGAGCAGGTGACATCACATGGGAAAAAGATGCGGAAGTCACTGGAAACAGTCCCCGGCTCGATGTGGCGCTAGATGA

GAGTGGTGACTTCTCCCTGGTGGAGGATGACGGTCCCCCCATGAGAGAGATCATACTCAAGGTGGTCCTGATGACCATCTGTG

GCATGAACCCAATAGCCATACCCTTTGCAGCTGGAGCGTGGTACGTATACGTGAAGACTGGAAAAAGGAGTGGTGCTCTATG

GGATGTGCCTGCTCCCAAGGAAGTAAAAAAGGGGGAGACCACAGATGGAGTGTACAGAGTAATGACTCGTAGACTGCTAGG

TTCAACACAAGTTGGAGTGGGAGTTATGCAAGAGGGGGTCTTTCACACTATGTGGCACGTCACAAAAGGATCCGCGCTGAGA

AGCGGTGAAGGGAGACTTGATCCATACTGGGGAGATGTCAAGCAGGATCTGGTGTCATACTGTGGTCCATGGAAGCTAGATG

CCGCCTGGGACGGGCACAGCGAGGTGCAGCTCTTGGCCGTGCCCCCCGGAGAGAGAGCGAGGAACATCCAGACTCTGCCCG

GAATATTTAAGACAAAGGATGGGGACATTGGAGCGGTTGCGCTGGATTACCCAGCAGGAACTTCAGGATCTCCAATCCTAGA

CAAGTGTGGGAGAGTGATAGGACTTTATGGCAATGGGGTCGTGATAAAAAATGGGAGTTATGTTAGTGCCATCACCCAAGGG

AGGAGGGAGGAAGAGACTCCTGTTGAGTGCTTCGAGCCTTCGATGCTGAAGAAGAAGCAGCTAACTGTCTTAGACTTGCATC

CTGGAGCTGGGAAAACCAGGAGAGTTCTTCCTGAAATAGTCCGTGAAGCCATAAAAACAAGACTCCGTACTGTGATCTTAGCT

-continued

CCAACCAGGGTTGTCGCTGCTGAAATGGAGGAAGCCCTTAGAGGGCTTCCAGTGCGTTATATGACAACAGCAGTCAATGTCAC

CCACTCTGGAACAGAAATCGTCGACTTAATGTGCCATGCCACCTTCACTTCACGTCTACTACAGCCAATCAGAGTCCCCAACTAT

AATCTGTATATTATGGATGAGGCCCACTTCACAGATCCCTCAAGCATAGCAGCAAGAGGATACATTTCAACAAGGGTTGAGAT

GGGCGAGGCGGCTGCCATCTTCATGACCGCCACGCCACCAGGAACCCGTGACGCATTTCCGGACTCCAACTCACCAATTATGG

ACACCGAAGTGGAAGTCCCAGAGAGAGCCTGGAGCTCAGGCTTTGATTGGGTGACGGATCATTCTGGAAAAACAGTTTGGTT

TGTTCCAAGCGTGAGGAACGGCAATGAGATCGCAGCTTGTCTGACAAAGGCTGGAAAACGGGTCATACAGCTCAGCAGAAAG

ACTTTTGAGACAGAGTTCCAGAAAACAAAACATCAAGAGTGGGACTTTGTCGTGACAACTGACATTTCAGAGATGGGCGCCAA

CTTTAAAGCTGACCGTGTCATAGATTCCAGGAGATGCCTAAAGCCGGTCATACTTGATGGCGAGAGAGTCATTCTGGCTGGAC

CCATGCCTGTCACACATGCCAGCGCTGCCCAGAGGAGGGGGCGCATAGGCAGGAATCCCAACAAACCTGGAGATGAGTACCT

GTATGGAGGTGGGTGCGCAGAGACTGACGAAGACCATGCACACTGGCTTGAAGCAAGAATGCTCCTTGACAATATTTACCTCC

AAGATGGCCTCATAGCCTCGCTCTATCGACCTGAGGCCGACAAAGTAGCAGCCATTGAGGGAGAGTTCAAGCTTAGGACGGA

GCAAAGGAAGACCTTTGTGGAACTCATGAAAAGAGGAGATCTTCCTGTTTGGCTGGCCTATCAGGTTGCATCTGCCGGAATAA

CCTACACAGATAGAAGATGGTGCTTTGATGGCACGACCAACAACACCATAATGGAAGACAGTGTGCCGGCAGAGGTGTGGAC

CAGACACGGAGAGAAAAGAGTGCTCAAACCGAGGTGGATGGACGCCAGAGTTTGTTCAGATCATGCGGCCCTGAAGTCATTC

AAGGAGTTTGCCGCTGGGAAAAGAGGAGCGGCTTTTGGAGTGATGGAAGCCCTGGGAACACTGCCAGGACACATGACAGAG

AGATTCCAGGAAGCCATTGACAACCTCGCTGTGCTCATGCGGGCAGAGACTGGAAGCAGGCCTTACAAAGCCGCGGCGGCCC

AATTGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTGAGC

CAGCCAGAATTGCATGTGTCCTCATTGTTGTGTTCCTATTGCTGGTGGTGCTCATACCTGAGCCAGAAAAGCAAAGATCTCCCC

AGGACAACCAAATGGCAATCATCATCATGGTAGCAGTAGGTCTTCTGGGCTTGATTACCGCCAATGAACTCGGATGGTTGGAG

AGAACAAAGAGTGACCTAAGCCATCTAATGGGAAGGAGAGAGGAGGGGGCAACCATAGGATTCTCAATGGACATTGACCTG

CGGCCAGCCTCAGCTTGGGCCATCTATGCTGCCTTGACAACTTTCATTACCCCAGCCGTCCAACATGCAGTGACCACTTCATACA

ACAACTACTCCTTAATGGCGATGGCCACGCAAGCTGGAGTGTTGTTTGGTATGGGCAAAGGGATGCCATTCTACGCATGGGAC

TTTGGAGTCCCGCTGCTAATGATAGGTTGCTACTCACAATTAACACCCCTGACCCTAATAGTGGCCATCATTTTGCTCGTGGCGC

ACTACATGTACTTGATCCCAGGGCTGCAGGCAGCAGCTGCGCGTGCTGCCCAGAAGAGAACGGCAGCTGGCATCATGAAGAA

CCCTGTTGTGGATGGAATAGTGGTGACTGACATTGACACAATGACAATTGACCCCCAAGTGGAGAAAAAGATGGGACAGGTG

CTACTCATAGCAGTAGCCGTCTCCAGCGCCATACTGTCGCGGACCGCCTGGGGGTGGGGGGAGGCTGGGGCCCTGATCACAG

CCGCAACTTCCACTTTGTGGGAAGGCTCTCCGAACAAGTACTGGAACTCCTCTACAGCCACTTCACTGTGTAACATTTTTAGGG

GAAGTTACTTGGCTGGAGCTTCTCTAATCTACACAGTAACAAGAAACGCTGGCTTGGTCAAGAGACGTGGGGGTGGAACAGG

AGAGACCCTGGGAGAGAAATGGAAGGCCCGCTTGAACCAGATGTCGGCCCTGGAGTTCTACTCCTACAAAAAGTCAGGCATC

ACCGAGGTGTGCAGAGAAGAGGCCCGCCGCGCCCTCAAGGACGGTGTGGCAACGGGAGGCCATGCTGTGTCCCGAGGAAGT

GCAAAGCTGAGATGGTTGGTGGAGCGGGGATACCTGCAGCCCTATGGAAAGGTCATTGATCTTGGATGTGGCAGAGGGGGC

TGGAGTTACTACGCCGCCACCATCCGCAAAGTTCAAGAAGTGAAAGGATACACAAAAGGAGGCCCTGGTCATGAAGAACCCG

TGTTGGTGCAAAGCTATGGGTGGAACATAGTCCGTCTTAAGAGTGGGGTGGACGTCTTTCATATGGCGGCTGAGCCGTGTGA

CACGTTGCTGTGTGACATAGGTGAGTCATCATCTAGTCCTGAAGTGGAAGAAGCACGGACGCTCAGAGTCCTCTCCATGGTGG

GGGATTGGCTTGAAAAAAGACCAGGAGCCTTTTGCATAAAAGTGTTGTGCCCATACACCAGCACTATGATGGAAACCCTGGAG

CGACTGCAGCGTAGGTATGGGGGAGGACTGGTCAGAGTGCCACTCTCCCGCAACTCTACACATGAGATGTACTGGGTCTCTG

GAGCGAAAAGCAACACCATAAAAAGTGTGTCCACCACGAGCCAGCTCCTCTTGGGGCGCATGGACGGGCCTAGGAGGCCAGT

GAAATATGAGGAGGATGTGAATCTCGGCTCTGGCACGCGGGCTGTGGTAAGCTGCGCTGAAGCTCCCAACATGAAGATCATT

GGTAACCGCATTGAAAGGATCCGCAGTGAGCACGCGGAAACGTGGTTCTTTGACGAAAACCACCCATATAGGACATGGGCTT

ACCATGGAAGCTATGTGGCCCCCACACAAGGGTCAGCGTCCTCTCTAATAAACGGGGTTGTCAGGCTCCTGTCAAAACCCTGG

-continued

GATGTGGTGACTGGAGTCACAGGAATAGCCATGACCGACACCACACCGTATGGTCAGCAAAGAGTTTTCAAGGAAAAAGTGG

ACACTAGGGTGCCAGACCCCCAAGAAGGCACTCGTCAGGTTATGAGCATGGTCTCTTCCTGGTTGTGGAAAGAGCTAGGCAA

ACACAAACGACCACGAGTCTGTACCAAAGAAGAGTTCATCAACAAGGTTCGTAGCAATGCAGCATTAGGGGCAATATTTGAAG

AGGAAAAAGAGTGGAAGACTGCAGTGGAAGCTGTGAACGATCCAAGGTTCTGGGCTCTAGTGGACAAGGAAAGAGAGCACC

ACCTGAGAGGAGAGTGCCAGAGTTGTGTGTACAACATGATGGGAAAAAGAGAAAAGAAACAAGGGGAATTTGGAAAGGCCA

AGGGCAGCCGCGCCATCTGGTATATGTGGCTAGGGGCTAGATTTCTAGAGTTCGAAGCCCTTGGATTCTTGAACGAGGATCAC

TGGATGGGGAGAGAGAACTCAGGAGGTGGTGTTGAAGGGCTGGGATTACAAAGACTCGGATATGTCCTAGAAGAGATGAGT

CGCATACCAGGAGGAAGGATGTATGCAGATGACACTGCTGGCTGGGACACCCGCATCAGCAGGTTTGATCTGGAGAATGAAG

CTCTAATCACCAACCAAATGGAGAAAGGGCACAGGGCCTTGGCATTGGCCATAATCAAGTACACATACCAAAACAAAGTGGTA

AAGGTCCTTAGACCAGCTGAAAAAGGGAAAACAGTTATGGACATTATTTCGAGACAAGACCAAAGGGGGAGCGGACAAGTT

GTCACTTACGCTCTTAACACATTTACCAACCTAGTGGTGCAACTCATTCGGAATATGGAGGCTGAGGAAGTTCTAGAGATGCAA

GACTTGTGGCTGCTGCGGAGGTCAGAGAAAGTGACCAACTGGTTGCAGAGCAACGGATGGGATAGGCTCAAACGAATGGCA

GTCAGTGGAGATGATTGCGTTGTGAAGCCAATTGATGATAGGTTTGCACATGCCCTCAGGTTCTTGAATGATATGGGAAAAGT

TAGGAAGGACACACAAGAGTGGAAACCCTCAACTGGATGGGACAACTGGGAAGAAGTTCCGTTTTGCTCCCACCACTTCAACA

AGCTCCATCTCAAGGACGGGAGGTCCATTGTGGTTCCCTGCCGCCACCAAGATGAACTGATTGGCCGGGCCCGCGTCTCTCCA

GGGGCGGGATGGAGCATCCGGGAGACTGCTTGCCTAGCAAAATCATATGCGCAAATGTGGCAGCTCCTTTATTTCCACAGAA

GGGACCTCCGACTGATGGCCAATGCCATTTGTTCATCTGTGCCAGTTGACTGGGTTCCAACTGGGAGAACTACCTGGTCAATCC

ATGGAAAGGGAGAATGGATGACCACTGAAGACATGCTTGTGGTGTGGAACAGAGTGTGGATTGAGGAGAACGACCACATGG

AAGACAAGACCCCAGTTACGAAATGGACAGACATTCCCTATTTGGGAAAAAGGGAAGACTTGTGGTGTGGATCTCTCATAGG

GCACAGACCGCGCACCACCTGGGCTGAGAACATTAAAAATACAGTCAACATGGTGCGCAGGATCATAGGTGATGAAGAAAAG

TACATGGACTACCTATCCACCCAAGTTCGCTACTTGGGTGAAGAAGGGTCTACACCTGGAGTGCTGTGAGCACCAATCTTAATG

TTGTCAGGCCTGCTAGTCAGCCACAGCTTGGGGAAAGCTGTGCAGCCTGTGACCCCTCCAGGAGAAGCTGGGTAACCAAGCCT

ATAGTCAGGCCGAGAACGCCATGGCACGGAAGAAGCCATGCTGCCTGTGAGCCCCTCAGAGGACACTGAGTCAAAAAACCCC

ACGCGCTTGGAGGCGCAGGATGGGAAAAGAAGGTGGCGACCTTCCCCACCCTTCAATCTGGGGCCTGAACTGGAGATCAGCT

GTGGATCTCCAGAAGAGGGACTAGTGGTTAGAGGAGACCCCCCGGAAAACGCAAAACAGCATATTGACGCTGGGAAAGACC

AGAGACTCCATGAGTTTCCACCACGCTGGCCGCCAGGCACAGATCGCCGAATAGCGGCGGCCGGTGTGGGGAAATCCA

KU501215.1 Zika virus strain PRVABC59, Puerto Rico, complete genome

SEQ ID NO: 4

GTTGTTGATCTGTGTGAATCAGACTGCGACAGTTCGAGTTTGAAGCGAAAGCTAGCAACAGTATCAACAGGTTTTATTTTGGAT

TTGGAAACGAGAGTTTCTGGTCATGAAAAACCCAAAAAAGAAATCCGGAGGATTCCGGATTGTCAATATGCTAAAACGCGGA

GTAGCCCGTGTGAGCCCCTTTGGGGGCTTGAAGAGGCTGCCAGCCGGACTTCTGCTGGGTCATGGGCCCATCAGGATGGTCTT

GGCGATTCTAGCCTTTTTGAGATTCACGGCAATCAAGCCATCACTGGGTCTCATCAATAGATGGGGTTCAGTGGGGAAAAAAG

AGGCTATGGAAACAATAAAGAAGTTCAAGAAAGATCTGGCTGCCATGCTGAGAATAATCAATGCTAGGAAGGAGAAGAAGA

GACGAGGCGCAGATACTAGTGTCGGAATTGTTGGCCTCCTGCTGACCACAGCTATGGCAGCGGAGGTCACTAGACGTGGGAG

TGCATACTATATGTACTTGGACAGAAACGATGCTGGGGAGGCCATATCTTTTCCAACCACATTGGGGATGAATAAGTGTTATAT

ACAGATCATGGATCTTGGACACATGTGTGATGCCACCATGAGCTATGAATGCCCTATGCTGGATGAGGGGGTGGAACCAGAT

GACGTCGATTGTTGGTGCAACACGACGTCAACTTGGGTTGTGTACGGAACCTGCCATCACAAAAAAGGTGAAGCACGGAGAT

CTAGAAGAGCTGTGACGCTCCCCTCCCATTCCACCAGGAAGCTGCAAACGCGGTCGCAAACCTGGTTGGAATCAAGAGAATAC

ACAAAGCACTTGATTAGAGTCGAAAATTGGATATTCAGGAACCCTGGCTTCGCGTTAGCAGCAGCTGCCATCGCTTGGCTTTTG

GGAAGCTCAACGAGCCAAAAAGTCATATACTTGGTCATGATACTGCTGATTGCCCCGGCATACAGCATCAGGTGCATAGGAGT

CAGCAATAGGGACTTTGTGGAAGGTATGTCAGGTGGGACTTGGGTTGATGTTGTCTTGGAACATGGAGGTTGTGTCACCGTA

-continued

ATGGCACAGGACAAACCGACTGTCGACATAGAGCTGGTTACAACAACAGTCAGCAACATGGCGGAGGTAAGATCCTACTGCT

ATGAGGCATCAATATCAGACATGGCTTCTGACAGCCGCTGCCCAACACAAGGTGAAGCCTACCTTGACAAGCAATCAGACACT

CAATATGTCTGCAAAAGAACGTTAGTGGACAGAGGCTGGGGAAATGGATGTGGACTTTTTGGCAAAGGGAGCCTGGTGACAT

GCGCTAAGTTTGCATGCTCCAAGAAAATGACCGGGAAGAGCATCCAGCCAGAGAATCTGGAGTACCGGATAATGCTGTCAGT

TCATGGCTCCCAGCACAGTGGGATGATCGTTAATGACACAGGACATGAAACTGATGAGAATAGAGCGAAAGTTGAGATAACG

CCCAATTCACCGAGAGCCGAAGCCACCCTGGGGGGTTTTGGAAGCCTAGGACTTGATTGTGAACCGAGGACAGGCCTTGACTT

TTCAGATTTGTATTACTTGACTATGAATAACAAGCACTGGTTGGTTCACAAGGAGTGGTTCCACGACATTCCATTACCTTGGCAC

GCTGGGGCAGACACCGGAACTCCACACTGGAACAACAAAGAAGCACTGGTAGAGTTCAAGGACGCACATGCCAAAAGGCAA

ACTGTCGTGGTTCTAGGGAGTCAAGAAGGAGCAGTTCACACGGCCCTTGCTGGAGCTCTGGAGGCTGAGATGGATGGTGCAA

AGGGAAGGCTGTCCTCTGGCCACTTGAAATGTCGCCTGAAAATGGATAAACTTAGATTGAAGGGCGTGTCATACTCCTTGTGT

ACTGCAGCGTTCACATTCACCAAGATCCCGGCTGAAACACTGCACGGGACAGTCACAGTGGAGGTACAGTACGCAGGGACAG

ATGGACCTTGCAAGGTTCCAGCTCAGATGGCGGTGGACATGCAAACTCTGACCCCAGTTGGGAGGTTGATAACCGCTAACCCC

GTAATCACTGAAAGCACTGAGAACTCTAAGATGATGCTGGAACTTGATCCACCATTTGGGGACTCTTACATTGTCATAGGAGTC

GGGGAGAAGAAGATCACCCACCACTGGCACAGGAGTGGCAGCACCATTGGAAAAGCATTTGAAGCCACTGTGAGAGGTGCC

AAGAGAATGGCAGTCTTGGGAGACACAGCCTGGGACTTTGGATCAGTTGGAGGCGCTCTCAACTCATTGGGCAAGGGCATCC

ATCAAATTTTTGGAGCAGCTTTCAAATCATTGTTTGGAGGAATGTCCTGGTTCTCACAAATTCTCATTGGAACGTTGCTGATGTG

GTTGGGTCTGAACACAAAGAATGGATCTATTTCCCTTATGTGCTTGGCCTTAGGGGGAGTGTTGATCTTCTTATCCACAGCCGT

CTCTGCTGATGTGGGGTGCTCGGTGGACTTCTCAAAGAAGGAGACGAGATGCGGTACAGGGGTGTTCGTCTATAACGACGTT

GAAGCCTGGAGGGACAGGTACAAGTACCATCCTGACTCCCCCCGTAGATTGGCAGCAGCAGTCAAGCAAGCCTGGGAAGATG

GTATCTGCGGGATCTCCTCTGTTTCAAGAATGGAAAACATCATGTGGAGATCAGTAGAAGGGGAGCTCAACGCAATCCTGGAA

GAGAATGGAGTTCAACTGACGGTCGTTGTGGGATCTGTAAAAAACCCCATGTGGAGAGGTCCACAGAGATTGCCCGTGCCTG

TGAACGAGCTGCCCCACGGCTGGAAGGCTTGGGGGAAATCGTATTTCGTCAGAGCAGCAAAGACAAATAACAGCTTTGTCGT

GGATGGTGACACACTGAAGGAATGCCCACTCAAACATAGAGCATGGAACAGCTTTCTTGTGGAGGATCATGGGTTCGGGGTA

TTTCACACTAGTGTCTGGCTCAAGGTTAGAGAAGATTATTCATTAGAGTGTGATCCAGCCGTTATTGGAACAGCTGTTAAGGGA

AAGGAGGCTGTACACAGTGATCTAGGCTACTGGATTGAGAGTGAGAAGAATGACACATGGAGGCTGAAGAGGGCCCATCTG

ATCGAGATGAAAACATGTGAATGGCCAAAGTCCCACACATTGTGGACAGATGGAATAGAAGAGAGTGATCTGATCATACCCA

AGTCTTTAGCTGGGCCACTCAGCCATCACAATACCAGAGAGGGCTACAGGACCCAAATGAAAGGGCCATGGCACAGTGAAGA

GCTTGAAATTCGGTTTGAGGAATGCCCAGGCACTAAGGTCCACGTGGAGGAAACATGTGGAACAAGAGGACCATCTCTGAGA

TCAACCACTGCAAGCGGAAGGGTGATCGAGGAATGGTGCTGCAGGGAGTGCACAATGCCCCCACTGTCGTTCCGGGCTAAAG

ATGGCTGTTGGTATGGAATGGAGATAAGGCCCAGGAAAGAACCAGAAAGCAACTTAGTAAGGTCAATGGTGACTGCAGGATC

AACTGATCACATGGACCACTTCTCCCTTGGAGTGCTTGTGATCCTGCTCATGGTGCAGGAAGGGCTGAAGAAGAGAATGACCA

CAAAGATCATCATAAGCACATCAATGGCAGTGCTGGTAGCTATGATCCTGGGAGGATTTTCAATGAGTGACCTGGCTAAGCTT

GCAATTTTGATGGGTGCCACCTTCGCGGAAATGAACACTGGAGGAGATGTAGCTCATCTGGCGCTGATAGCGGCATTCAAAGT

CAGACCAGCGTTGCTGGTATCTTTCATCTTCAGAGCTAATTGGACACCCCGTGAAAGCATGCTGCTGGCCTTGGCCTCGTGTCT

TTTGCAAACTGCGATCTCCGCCTTGGAAGGCGACCTGATGGTTCTCATCAATGGTTTTGCTTTGGCCTGGTTGGCAATACGAGC

GATGGTTGTTCCACGCACTGATAACATCACCTTGGCAATCCTGGCTGCTCTGACACCACTGGCCCGGGGCACACTGCTTGTGGC

GTGGAGAGCAGGCCTTGCTACTTGCGGGGGGTTTATGCTCCTCTCTCTGAAGGGAAAAGGCAGTGTGAAGAAGAACTTACCA

TTTGTCATGGCCCTGGGACTAACCGCTGTGAGGCTGGTCGACCCCATCAACGTGGTGGGACTGCTGTTGCTCACAAGGAGTGG

GAAGCGGAGCTGGCCCCCTAGCGAAGTACTCACAGCTGTTGGCCTGATATGCGCATTGGCTGGAGGGTTCGCCAAGGCAGAT

ATAGAGATGGCTGGGCCCATGGCCGCGGTCGGTCTGCTAATTGTCAGTTACGTGGTCTCAGGAAAGAGTGTGGACATGTACA

TTGAAAGAGCAGGTGACATCACATGGGAAAAAGATGCGGAAGTCACTGGAAACAGTCCCCGGCTCGATGTGGCGCTAGATGA

-continued

GAGTGGTGATTTCTCCCTGGTGGAGGATGACGGTCCCCCCATGAGAGAGATCATACTCAAGGTGGTCCTGATGACCATCTGTG

GCATGAACCCAATAGCCATACCCTTTGCAGCTGGAGCGTGGTACGTATACGTGAAGACTGGAAAAAGGAGTGGTGCTCTATG

GGATGTGCCTGCTCCCAAGGAAGTAAAAAAGGGGGAGACCACAGATGGAGTGTACAGAGTAATGACTCGTAGACTGCTAGG

TTCAACACAAGTTGGAGTGGGAGTTATGCAAGAGGGGGTCTTTCACACTATGTGGCACGTCACAAAAGGATCCGCGCTGAGA

AGCGGTGAAGGGAGACTTGATCCATACTGGGGAGATGTCAAGCAGGATCTGGTGTCATACTGTGGTCCATGGAAGCTAGATG

CCGCCTGGGATGGGCACAGCGAGGTGCAGCTCTTGGCCGTGCCCCCCGGAGAGAGAGCGAGGAACATCCAGACTCTGCCCG

GAATATTTAAGACAAAGGATGGGGACATTGGAGCGGTTGCGCTGGATTACCCAGCAGGAACTTCAGGATCTCCAATCCTAGA

CAAGTGTGGGAGAGTGATAGGACTTTATGGCAATGGGGTCGTGATCAAAAACGGGAGTTATGTTAGTGCCATCACCCAAGGG

AGGAGGGAGGAAGAGACTCCTGTTGAGTGCTTCGAGCCCTCGATGCTGAAGAAGAAGCAGCTAACTGTCTTAGACTTGCATC

CTGGAGCTGGGAAAACCAGGAGAGTTCTTCCTGAAATAGTCCGTGAAGCCATAAAAACAAGACTCCGTACTGTGATCTTAGCT

CCAACCAGGGTTGTCGCTGCTGAAATGGAGGAGGCCCTTAGAGGGCTTCCAGTGCGTTATATGACAACAGCAGTCAATGTCAC

CCACTCTGGAACAGAAATCGTCGACTTAATGTGCCATGCCACCTTCACTTCACGTCTACTACAGCCAATCAGAGTCCCCAACTAT

AATCTGTATATTATGGATGAGGCCCACTTCACAGATCCCTCAAGTATAGCAGCAAGAGGATACATTTCAACAAGGGTTGAGAT

GGGCGAGGCGGCTGCCATCTTCATGACCGCCACGCCACCAGGAACCCGTGACGCATTTCCGGACTCCAACTCACCAATTATGG

ACACCGAAGTGGAAGTCCCAGAGAGAGCCTGGAGCTCAGGCTTTGATTGGGTGACGGATCATTCTGGAAAAACAGTTTGGTT

TGTTCCAAGCGTGAGGAACGGCAATGAGATCGCAGCTTGTCTGACAAAGGCTGGAAAACGGGTCATACAGCTCAGCAGAAAG

ACTTTTGAGACAGAGTTCCAGAAAACAAAACATCAAGAGTGGGACTTTGTCGTGACAACTGACATTTCAGAGATGGGCGCCAA

CTTTAAAGCTGACCGTGTCATAGATTCCAGGAGATGCCTAAAGCCGGTCATACTTGATGGCGAGAGAGTCATTCTGGCTGGAC

CCATGCCTGTCACACATGCCAGCGCTGCCCAGAGGAGGGGGCGCATAGGCAGGAATCCCAACAAACCTGGAGATGAGTATCT

GTATGGAGGTGGGTGCGCAGAGACTGACGAAGACCATGCACACTGGCTTGAAGCAAGAATGCTCCTTGACAATATTTACCTCC

AAGATGGCCTCATAGCCTCGCTCTATCGACCTGAGGCCGACAAAGTAGCAGCCATTGAGGGAGAGTTCAAGCTTAGGACGGA

GCAAAGGAAGACCTTTGTGGAACTCATGAAAAGAGGAGATCTTCCTGTTTGGCTGGCCTATCAGGTTGCATCTGCCGGAATAA

CCTACACAGATAGAAGATGGTGCTTTGATGGCACGACCAACAACACCATAATGGAAGACAGTGTGCCGGCAGAGGTGTGGAC

CAGACACGGAGAGAAAAGAGTGCTCAAACCGAGGTGGATGGACGCCAGAGTTTGTTCAGATCATGCGGCCCTGAAGTCATTC

AAGGAGTTTGCCGCTGGGAAAAGAGGAGCGGCTTTTGGAGTGATGGAAGCCCTGGGAACACTGCCAGGACACATGACAGAG

AGATTCCAGGAAGCCATTGACAACCTCGCTGTGCTCATGCGGGCAGAGACTGGAAGCAGGCCTTACAAAGCCGCGGCGGCCC

AATTGCCGGAGACCCTAGAGACCATAATGCTTTTGGGGTTGCTGGGAACAGTCTCGCTGGGAATCTTCTTCGTCTTGATGAGG

AACAAGGGCATAGGGAAGATGGGCTTTGGAATGGTGACTCTTGGGGCCAGCGCATGGCTCATGTGGCTCTCGGAAATTGAGC

CAGCCAGAATTGCATGTGTCCTCATTGTTGTGTTCCTATTGCTGGTGGTGCTCATACCTGAGCCAGAAAAGCAAAGATCTCCCC

AGGACAACCAAATGGCAATCATCATCATGGTAGCAGTAGGTCTTCTGGGCTTGATTACCGCCAATGAACTCGGATGGTTGGAG

AGAACAAAGAGTGACCTAAGCCATCTAATGGGAAGGAGAGAGGAGGGGGCAACCATAGGATTCTCAATGGACATTGACCTG

CGGCCAGCCTCAGCTTGGGCCATCTATGCTGCCTTGACAACTTTCATTACCCCAGCCGTCCAACATGCAGTGACCACCTCATACA

ACAACTACTCCTTAATGGCGATGGCCACGCAAGCTGGAGTGTTGTTTGGCATGGGCAAAGGGATGCCATTCTACGCATGGGAC

TTTGGAGTCCCGCTGCTAATGATAGGTTGCTACTCACAATTAACACCCCTGACCCTAATAGTGGCCATCATTTTGCTCGTGGCGC

ACTACATGTACTTGATCCCAGGGCTGCAGGCAGCAGCTGCGCGTGCTGCCCAGAAGAGAACGGCAGCTGGCATCATGAAGAA

CCCTGTTGTGGATGGAATAGTGGTGACTGACATTGACACAATGACAATTGACCCCCAAGTGGAGAAAAAGATGGGACAGGTG

CTACTCATAGCAGTAGCCGTCTCCAGCGCCATACTGTCGCGGACCGCCTGGGGGTGGGGGGAGGCTGGGGCTCTGATCACAG

CCGCAACTTCCACTTTGTGGGAAGGCTCTCCGAACAAGTACTGGAACTCCTCTACAGCCACTTCACTGTGTAACATTTTTAGGG

GAAGTTACTTGGCTGGAGCTTCTCTAATCTACACAGTAACAAGAAACGCTGGCTTGGTCAAGAGACGTGGGGGTGGAACAGG

AGAGACCCTGGGAGAGAAATGGAAGGCCCGCTTGAACCAGATGTCGGCCCTGGAGTTCTACTCCTACAAAAAGTCAGGCATC

-continued

ACCGAGGTGTGCAGAGAAGAGGCCCGCCGCGCCCTCAAGGACGGTGTGGCAACGGGAGGCCATGCTGTGTCCCGAGGAAGT

GCAAAGCTGAGATGGTTGGTGGAGCGGGGATACCTGCAGCCCTATGGAAAGGTCATTGATCTTGGATGTGGCAGAGGGGGC

TGGAGTTACTACGTCGCCACCATCCGCAAAGTTCAAGAAGTGAAAGGATACACAAAAGGAGGCCCTGGTCATGAAGAACCCG

TGTTGGTGCAAAGCTATGGGTGGAACATAGTCCGTCTTAAGAGTGGGGTGGACGTCTTTCATATGGCGGCTGAGCCGTGTGA

CACGTTGCTGTGTGACATAGGTGAGTCATCATCTAGTCCTGAAGTGGAAGAAGCACGGACGCTCAGAGTCCTCTCCATGGTGG

GGGATTGGCTTGAAAAAAGACCAGGAGCCTTTTGTATAAAAGTGTTGTGCCCATACACCAGCACTATGATGGAAACCCTGGAG

CGACTGCAGCGTAGGTATGGGGGAGGACTGGTCAGAGTGCCACTCTCCCGCAACTCTACACATGAGATGTACTGGGTCTCTG

GAGCGAAAAGCAACACCATAAAAAGTGTGTCCACCACGAGCCAGCTCCTCTTGGGGCGCATGGACGGGCCTAGGAGGCCAGT

GAAATATGAGGAGGATGTGAATCTCGGCTCTGGCACGCGGGCTGTGGTAAGCTGCGCTGAAGCTCCCAACATGAAGATCATT

GGTAACCGCATTGAAAGGATCCGCAGTGAGCACGCGGAAACGTGGTTCTTTGACGAGAACCACCCATATAGGACATGGGCTT

ACCATGGAAGCTATGAGGCCCCCACACAAGGGTCAGCGTCCTCTCTAATAAACGGGGTTGTCAGGCTCCTGTCAAAACCCTGG

GATGTGGTGACTGGAGTCACAGGAATAGCCATGACCGACACCACACCGTATGGTCAGCAAAGAGTTTTCAAGGAAAAAGTGG

ACACTAGGGTGCCAGACCCCCAAGAAGGCACTCGTCAGGTTATGAGCATGGTCTCTTCCTGGTTGTGGAAAGAGCTAGGCAA

ACACAAACGGCCACGAGTCTGCACCAAAGAAGAGTTCATCAACAAGGTTCGTAGCAATGCAGCATTAGGGGCAATATTTGAA

GAGGAAAAAGAGTGGAAGACTGCAGTGGAAGCTGTGAACGATCCAAGGTTCTGGGCTCTAGTGGACAAGGAAAGAGAGCAC

CACCTGAGAGGAGAGTGCCAGAGCTGTGTGTACAACATGATGGGAAAAAGAGAAAAGAAACAAGGGGAATTTGGAAAGGCC

AAGGGCAGCCGCGCCATCTGGTATATGTGGCTAGGGGCTAGATTTCTAGAGTTCGAAGCCCTTGGATTCTTGAACGAGGATCA

CTGGATGGGGAGAGAGAACTCAGGAGGTGGTGTTGAAGGGCTGGGATTACAAAGACTCGGATATGTCCTAGAAGAGATGAG

TCGTATACCAGGAGGAAGGATGTATGCAGATGACACTGCTGGCTGGGACACCCGCATTAGCAGGTTTGATCTGGAGAATGAA

GCTCTAATCACCAACCAAATGGAGAAAGGGCACAGGGCCTTGGCATTGGCCATAATCAAGTACACATACCAAAACAAAGTGGT

AAAGGTCCTTAGACCAGCTGAAAAAGGGAAAACAGTTATGGACATTATTTCGAGACAAGACCAAAGGGGGAGCGGACAAGTT

GTCACTTACGCTCTTAACACATTTACCAACCTAGTGGTGCAACTCATTCGGAATATGGAGGCTGAGGAAGTTCTAGAGATGCAA

GACTTGTGGCTGCTGCGGAGGTCAGAGAAAGTGACCAACTGGTTGCAGAGCAACGGATGGGATAGGCTCAAACGAATGGCA

GTCAGTGGAGATGATTGCGTTGTGAAGCCAATTGATGATAGGTTTGCACATGCCCTCAGGTTCTTGAATGATATGGGAAAAGT

TAGGAAGGACACACAAGAGTGGAAACCCTCAACTGGATGGGACAACTGGGAAGAAGTTCCGTTTTGCTCCCACCACTTCAACA

AGCTCCATCTCAAGGACGGGAGGTCCATTGTGGTTCCCTGCCGCCACCAAGATGAACTGATTGGCCGGGCCCGCGTCTCTCCA

GGGGCGGGATGGAGCATCCGGGAGACTGCTTGCCTAGCAAAATCATATGCGCAAATGTGGCAGCTCCTTTATTTCCACAGAA

GGGACCTCCGACTGATGGCCAATGCCATTTGTTCATCTGTGCCAGTTGACTGGGTTCCAACTGGGAGAACTACCTGGTCAATCC

ATGGAAAGGGAGAATGGATGACCACTGAAGACATGCTTGTGGTGTGGAACAGAGTGTGGATTGAGGAGAACGACCACATGG

AAGACAAGACCCCAGTTACGAAATGGACAGACATTCCCTATTTGGGAAAAAGGGAAGACTTGTGGTGTGGATCTCTCATAGG

GCACAGACCGCGCACCACCTGGGCTGAGAACATTAAAAACACAGTCAACATGGTGCGCAGGATCATAGGTGATGAAGAAAAG

TACATGGACTACCTATCCACCCAAGTTCGCTACTTGGGTGAAGAAGGGTCTACACCTGGAGTGCTGTAAGCACCAATCTTAATG

TTGTCAGGCCTGCTAGTCAGCCACAGCTTGGGGAAAGCTGTGCAGCCTGTGACCCCCCCAGGAGAAGCTGGGAAACCAAGCC

TATAGTCAGGCCGAGAACGCCATGGCACGGAAGAAGCCATGCTGCCTGTGAGCCCCTCAGAGGACACTGAGTCAAAAAACCC

CACGCGCTTGGAGGCGCAGGATGGGAAAAGAAGGTGGCGACCTTCCCCACCCTTCAATCTGGGGCCTGAACTGGAGATCAGC

TGTGGATCTCCAGAAGAGGGACTAGTGGTTAGAGGA

KU509998.1 Zika virus strain Haiti/1225/2014, Haiti, complete genome

SEQ ID NO: 5

GTTGTTACTGTTGCTGACTCAGACTGCGACAGTTCGAGTTTGAAGCGAAAGCTAGCAACAGTATCAACAGGTTTTATTTGGATT

TGGAAACGAGAGTTTCTGGTCATGAAAAACCCAAAAAAGAAATCCGGAGGATTCCGGATTGTCAATATGCTAAAACGCGGAG

TAGCCCGTGTGAGCCCCTTTGGGGGCTTGAAGAGGCTGCCAGCCGGACTTCTGCTGGGTCATGGGCCCATCAGGATGGTCTTG

GCAATTCTAGCCTTTTTGAGATTCACGGCAATCAAGCCATCACTGGGTCTCATCAATAGATGGGGTTCAGTGGGGAAAAAAGA

-continued

GGCTATGGAAATAATAAAGAAGTTCAAGAAAGATCTGGCTGCCATGCTGAGAATAATCAATGCTAGGAAGGAGAAGAAGAG

ACGAGGCGCAGATACTAGTGTCGGAATTGTTGGCCTCCTGCTGACCACAGCTATGGCAGCGGAGGTCACTAGACGTGGGAGT

GCATACTATATGTACTTGGACAGAAACGATGCTGGGGAGGCCATATCTTTTCCAACCACATTGGGGATGAATAAGTGTTATAT

ACAGATCATGGATCTTGGACACATGTGTGATGCCACCATGAGCTATGAATGCCCTATGCTGGATGAGGGGGTGGAACCAGAT

GACGTCGATTGTTGGTGCAACACGACGTCAACTTGGGTTGTGTACGGAACCTGCCATCACAAAAAAGGTGAAGCACGGAGAT

CTAGAAGAGCTGTGACGCTCCCCTCCCATTCCACTAGGAAGCTGCAAACGCGGTCGCAAACCTGGTTGGAATCAAGAGAATAC

ACAAAGCACTTGATTAGAGTCGAAAATTGGATATTCAGGAACCCTGGCTTCGCGTTAGCAGCAGCTGCCATCGCTTGGCTTTTG

GGAAGCTCAACGAGCCAAAAAGTCATATACTTGGTCATGATACTGCTGATTGCCCCGGCATACAGCATCAGGTGCATAGGAGT

CAGCAATAGGGACTTTGTGGAAGGTATGTCAGGTGGGACTTGGGTTGATGTTGTCTTGGAACATGGAGGTTGTGTCACCGTA

ATGGCACAGGACAAACCGACTGTCGACATAGAGCTGGTTACAACAACAGTCAGCAACATGGCGGAGGTAAGATCCTACTGCT

ATGAGGCATCAATATCAGACATGGCTTCGGACAGCCGCTGCCCAACACAAGGTGAAGCCTACCTTGACAAGCAATCAGACACT

CAATATGTCTGCAAAAGAACGTTAGTGGACAGAGGCTGGGGAAATGGATGTGGACTTTTTGGCAAAGGGAGTCTGGTGACAT

GCGCTAAGTTTGCATGCTCCAAGAAAATGACCGGGAAGAGCATCCAGCCAGAGAATCTGGAGTACCGGATAATGCTGTCAGT

TCATGGCTCCCAGCACAGTGGGATGATCGTTAATGACACAGGACATGAAACTGATGAGAATAGAGCGAAGGTTGAGATAACG

CCCAATTCACCAAGAGCCGAAGCCACCCTGGGGGGTTTTGGAAGCCTAGGACTTGATTGTGAACCGAGGACAGGCCTTGACTT

TTCAGATTTGTATTACTTGACTATGAATAACAAGCACTGGTTGGTTCACAAGGAGTGGTTCCACGACATTCCATTACCTTGGCAC

GCTGGGGCAGACACCGGAACTCCACACTGGAACAACAAAGAAGCACTGGTAGAGTTCAAGGACGCACATGCCAAAAGGCAA

ACTGTCGTGGTTCTAGGGAGTCAAGAAGGAGCAGTTCACACGGCCCTTGCTGGAGCTCTGGAGGCTGAGATGGATGGTGCAA

AGGGAAGGCTGTCCTCTGGCCACTTGAAATGTCGCCTGAAAATGGATAAACTTAGATTGAAGGGCGTGTCATACTCCTTGTGT

ACCGCAGCGTTCACATTCACCAAGATCCCGGCTGAAACACTGCACGGGACAGTCACAGTGGAGGTACAGTACGCAGGGACAG

ATGGACCTTGCAAGGTTCCAGCTCAGATGGCGGTGGACATGCAAACTCTGACCCCAGTTGGGAGGTTGATAACCGCTAACCCC

GTAATCACTGAAAGCACTGAGAACTCTAAGATGATGCTGGAACTTGATCCACCATTTGGGGACTCTTACATTGTCATAGGAGTC

GGGGAGAAGAAGATCACCCACCACTGGCACAGGAGTGGCAGCACCATTGGAAAAGCATTTGAAGCCACTGTGAGAGGTGCC

AAGAGAATGGCAGTCTTGGGAGACACAGCCTGGGACTTTGGATCAGTTGGAGGCGCTCTCAACTCATTGGGCAAGGGCATCC

ATCAAATTTTTGGAGCAGCTTTCAAATCATTGTTTGGAGGAATGTCCTGGTTCTCACAAATTCTCATTGGAACGTTGCTGATGTG

GTGGGTCTGAACACAAAGAATGGATCTATTTCCCTTATGTGCTTGGCCTTAGGGGGAGTGTTGATCTTCTTATCCACAGCCGT

CTCTGCTGATGTGGGGTGCTCGGTGGACTTCTCAAAGAAGGAGACGAGATGCGGTACAGGGGTGTTCGTCTATAACGACGTT

GAAGCCTGGAGGGACAGGTACAAGTACCATCCTGACTCCCCCCGTAGATTGGCAGCAGCAGTCAAGCAAGCCTGGGAAGATG

GTATCTGCGGGATCTCCTCTGTTTCAAGAATGGAAAACATCATGTGGAGATCAGTAGAAGGGGAGCTCAACGCAATCCTGGAA

GAGAATGGAGTTCAACTGACGGTCGTTGTGGGATCTGTAAAAAACCCCATGTGGAGAGGTCCACAGAGATTGCCCGTGCCTG

TGAACGAGCTGCCCCACGGCTGGAAGGCTTGGGGGAAATCGCACTTCGTCAGAGCAGCAAAGACAAATAACAGCTTTGTCGT

GGATGGTGACACACTGAAGGAATGCCCACTCAAACATAGAGCATGGAACAGCTTTCTTGTGGAGGATCATGGGTTCGGGGTA

TTTCACACTAGTGTCTGGCTCAAGGTTAGAGAAGATTATTCATTAGAGTGTGATCCAGCCGTTATTGGAACAGCTGTTAAGGGA

AAGGAGGCTGTACACAGTGATCTAGGCTACTGGATTGAGAGTGAGAAGAATGACACATGGAGGCTGAAGAGGGCCCATCTG

ATCGAGATGAAAACATGTGAATGGCCAAAGTCCCACACATTGTGGACAGATGGAATAGAAGAGAGTGATCTGATCATACCCA

AGTCTTTAGCTGGGCCACTCAGCCATCACAATACCAGAGAGGGCTACAGGACCCAAATGAAAGGGCCATGGCACAGTGAAGA

GCTTGAAATTCGGTTTGAGGAATGCCCAGGCACTAAGGTCCACGTGGAGGAAACATGTGGAACAAGAGGACCATCTCTGAGA

TCAACCACTGCAAGCGGAAGGGTGATCGAGGAATGGTGCTGCAGGGAGTGCACAATGCCCCCACTGTCGTTCCGGGCTAAAG

ATGGCTGTTGGTATGGAATGGAGATAAGGCCCAGGAAAGAACCAGAAAGCAACTTAGTAAGGTCAATGGTGACTGCAGGATC

AACTGATCACATGGATCACTTCTCCCTTGGAGTGCTTGTGATTCTGCTCATGGTGCAGGAAGGGCTGAAGAAGAGAATGACCA

-continued

CAAAGATCATCATAAGCACATCAATGGCAGTGCTGGTAGCTATGATCCTGGGAGGATTTTCAATGAGTGACCTGGCTAAGCTT

GCAATTTTGATGGGTGCCACCTTCGCGGAAATGAACACTGGAGGAGATGTAGCTCATCTGGCGCTGATAGCGGCATTCAAAGT

CAGACCAGCGTTGCTGGTATCTTTCATCTTCAGAGCTAATTGGACACCCCGTGAAAGCATGCTGCTGGCCTTGGCCTCGTGTCT

TTTGCAAACTGCGATCTCCGCCTTGGAAGGCGACCTGATGGTTCTCATCAATGGTTTTGCTTTGGCCTGGTTGGCAATACGAGC

GATGGTTGTTCCACGCACTGATAACATCACCTTGGCAATCCTGGCTGCTCTGACACCACTGGCCCGGGGCACACTGCTTGTGGC

GTGGAGAGCAGGCCTTGCTACTTGCGGGGGGTTTATGCTCCTCTCTCTGAAGGGAAAAGGCAGTGTGAAGAAGAACTTACCA

TTTGTCATGGCCCTGGGACTAACCGCTGTGAGGCTGGTCGACCCCATCAACGTGGTGGGGCTGCTGTTGCTCACAAGGAGTGG

GAAGCGGAGCTGGCCCCCTAGCGAAGTACTCACAGCTGTTGGCCTGATATGCGCATTGGCTGGAGGGTTCGCCAAGGCAGAT

ATAGAGATGGCTGGGCCCATGGCCGCGGTCGGTCTGCTAATTGTCAGTTACGTGGTCTCAGGAAAGAGTGTGGACATGTACA

TTGAAAGAGCAGGTGACATCACATGGGAAAAAGATGCGGAAGTCACTGGAAACAGTCCCCGGCTCGATGTGGCGCTAGATGA

GAGTGGTGATTTCTCCCTGGTGGAGGATGACGGTCCCCCCATGAGAGAGATCATACTCAAGGTGGTCCTGATGACCATCTGTG

GCATGAACCCAATAGCCATACCCTTTGCAGCTGGAGCGTGGTACGTATACGTGAAGACTGGAAAAAGGAGTGGTGCTCTATG

GGATGTGCCTGCTCCCAAGGAAGTAAAAAAGGGGGAGACCACAGATGGAGTGTACAGAGTAATGACTCGTAGACTGCTAGG

TTCAACACAAGTTGGAGTGGGAGTTATGCAAGAGGGGGTCTTTCACACTATGTGGCACGTCACAAAAGGATCCGCGCTGAGA

AGCGGTGAAGGGAGACTTGATCCATACTGGGGAGATGTCAAGCAGGATCTGGTGTCATACTGTGGTCCATGGAAGCTAGATG

CCGCCTGGGACGGGCACAGCGAGGTGCAGCTCTTGGCCGTGCCCCCCGGAGAGAGAGCGAGGAACATCCAGACTCTGCCCG

GAATATTTAAGACAAAGGATGGGGACATTGGAGCGGTTGCGCTGGATTACCCAGCAGGAACTTCAGGATCTCCAATCCTAGA

CAAGTGTGGGAGAGTGATAGGACTTTATGGCAATGGGGTCGTGATCAAAAATGGGAGTTATGTTAGTGCCATCACCCAAGGG

AGGAGGGAGGAAGAGACTCCTGTTGAGTGCTTCGAGCCTTCGATGCTGAAGAAGAAGCAGCTAACTGTCTTAGACTTGCATC

CTGGAGCTGGGAAAACCAGGAGAGTTCTTCCTGAAATAGTCCGTGAAGCCATAAAAACAAGACTCCGTACTGTGATCTTAGCT

CCAACCAGGGTTGTCGCTGCTGAAATGGAGGAAGCCCTTAGAGGGCTTCCAGTGCGTTATATGACAACAGCAGTCAATGTCAC

CCACTCTGGAACAGAAATCGTCGACTTAATGTGCCATGCCACCTTCACTTCACGTCTACTACAGCCAATCAGAGTCCCCAACTAT

AATCTGTATATTATGGATGAGGCCCACTTCACAGATCCCTCAAGTATAGCAGCAAGAGGATACATTTCAACAAGGGTTGAGAT

GGGCGAGGCGGCTGCCATCTTCATGACCGCCACGCCACCAGGAACCCGTGACGCATTTCCGGACTCCAACTCACCAATTATGG

ACACCGAAGTGGAAGTCCCAGAGAGAGCCTGGAGCTCAGGCTTTGATTGGGTGACGGATTATTCTGGAAAAACAGTTTGGTT

TGTTCCAAGCGTGAGGAACGGCAATGAGATCGCAGCTTGTCTGACAAAGGCTGGAAAACGGGTCATACAGCTCAGCAGAAAG

ACTTTTGAGACAGAGTTCCAGAAAACAAAACATCAAGAGTGGGACTTTGTCGTGACAACTGACATTTCAGAGATGGGCGCCAA

CTTTAAAGCTGACCGTGTCATAGATTCCAGGAGATGCCTAAAGCCGGTCATACTTGATGGCGAGAGAGTCATTCTGGCTGGAC

CCATGCCTGTCACACATGCCAGCGCTGCCCAGAGGAGGGGGCGCATAGGCAGGAATCCCAACAAACCTGGAGATGAGTATCT

GTATGGAGGTGGGTGCGCAGAGACTGACGAAGACCATGCACACTGGCTTGAAGCAAGAATGCTCCTTGACAATATTTACCTCC

AAGATGGCCTCATAGCCTCGCTCTATCGACCTGAGGCCGACAAAGTAGCAGCCATTGAGGGAGAGTTCAAGCTTAGGACGGA

GCAAAGGAAGACCTTTGTGGAACTCATGAAAAGAGGAGATCTTCCTGTTTGGCTGGCCTATCAGGTTGCATCTGCCGGAATAA

CCTACACAGATAGAAGATGGTGCTTTGATGGCACGACCAACAACACCATAATGGAAGACAGTGTGCCGGCAGAGGTGTGGAC

CAGACACGGAGAGAAAAGAGTGCTCAAACCGAGGTGGATGGACGCCAGAGTTTGTTCAGATCATGCGGCCCTGAAGTCATTC

AAGGAGTTTGCCGCTGGGAAAAGAGGAGCGGCTTTTGGAGTGATGGAAGCCCTGGGAACACTGCCAGGACACATGACAGAG

AGATTCCAGGAAGCCATTGACAACCTCGCTGTGCTCATGCGGGCAGAGACTGGAAGCAGGCCTTACAAAGCCGCGGCGGCCC

AATTGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTGAGC

CAGCCAGAATTGCATGTGTCCTCATTGTTGTGTTCCTATTGCTGGTGGTGCTCATACCTGAGCCAGAAAAGCAAAGATCTCCCC

AGGACAACCAAATGGCAATCATCATCATGGTAGCAGTAGGTCTTCTGGGCTTGATTACCGCCAATGAACTCGGATGGTTGGAG

AGAACAAAGAGTGACCTAAGCCATCTAATGGGAAGGAGAGAGGAGGGGGCAACCATGGGATTCTCAATGGACATTGACCTG

-continued

CGGCCAGCCTCAGCTTGGGCCATCTATGCTGCCTTGACAACTTTCATTACCCCAGCCGTCCAACATGCAGTGACCACTTCATACA

ACAACTACTCCTTAATGGCGATGGCCACGCAAGCTGGAGTGTTGTTTGGTATGGGCAAAGGGATGCCATTCTACGCATGGGAC

TTTGGAGTCCCGCTGCTAATGATAGGTTGCTACTCACAATTAACGCCCCTGACCCTAATAGTGGCCATCATTTTGCTCGTGGCG

CACTACATGTACTTGATCCCAGGGCTGCAGGCAGCAGCTGCGCGTGCTGCCCAGAAGAGAACGGCAGCTGGCATCATGAAGA

ACCCTGTTGTGGATGGAATAGTGGTGACTGACATTGACACAATGACAATTGACCCCCAAGTGGAGAAAAAGATGGGACAGGT

GCTACTCATGGCAGTAGCCGTCTCCAGCGCCATACTGTCGCGGACCGCCTGGGGGTGGGGGGAGGCTGGGGCCCTGATCACA

GCCGCAACTTCCACTTTGTGGGAAGGCTCTCCGAACAAGTACTGGAACTCCTCTACAGCCACTTCACTGTGTAACATTTTTAGG

GGAAGTTACTTGGCTGGAGCTTCTCTAATCTACACAGTAACAAGAAACGCTGGCTTGGTCAAGAGACGTGGGGGTGGAACAG

GAGAGACCCTGGGAGAGAAATGGAAGGCCCGCTTGAACCAGATGTCGGCCCTGGAGTTCTACTCCTACAAAAAGTCAGGCAT

CACCGAGGTGTGCAGAGAAGAGGCCCGCCGCGCCCTCAAGGACGGTGTGGCAACGGGAGGCCATGCTGTGTCCCGAGGAAG

TGCAAAGCTGAGATGGTTGGTGGAGCGGGGATACCTGCAGCCCTATGGAAAGGTCATTGATCTTGGATGTGGCAGAGGGGG

CTGGAGTTACTACGCCGCCACCATCCGCAAAGTTCAAGAAGTGAAAGGATACACAAAAGGAGGCCCTGGTCATGAAGAACCC

GTGTTGGTGCAAAGCTATGGGTGGAACATAGTCCGTCTTAAGAGTGGGGTGGACGTCTTTCATATGGCGGCTGAGCCGTGTG

ACACGTTGCTGTGTGACATAGGTGAGTCATCATCTAGTCCTGAAGTGGAAGAAGCACGGACGCTCAGAGTCCTCTCCATGGTG

GGGGATTGGCTTGAAAAAAGACCAGGAGCCTTTTGTATAAAAGTGTTGTGCCCATACACCAGCACTATGATGGAAACCCTGGA

GCGACTGCAGCGTAGGTATGGGGGAGGACTGGTCAGAGTGCCACTCTCCCGCAACTCTACACATGAGATGTACTGGGTCTCT

GGAGCGAAAAGCAACACCATAAAAAGTGTGTCCACCACGAGCCAGCTCCTCTTGGGGCGCATGGACGGGCCTAGGAGGCCA

GTGAAATATGAGGAGGATGTGAATCTCGGCTCTGGCACGCGGGCTGTGGTAAGCTGCGCTGAAGCTCCCAACATGAAGATCA

TTGGTAACCGCATTGAAAGGATCCGCAGTGAGCACGCGGAAACGTGGTTCTTTGACGAGAACCACCCATATAGGACATGGGC

TTACCATGGAAGCTATGAGGCCCCCACACAAGGGTCAGCGTCCTCTCTAATAAACGGGGTTGTCAGGCTCCTGTCAAAACCCT

GGGATGTGGTGACTGGAGTCACAGGAATAGCCATGACCGACACCACACCGTATGGTCAGCAAAGAGTTTTCAAGGAAAAAGT

GGACACTAGGGTGCCAGACCCCCAAGAAGGCACTCGTCAGGTTATGAGCATGGTCTCTTCCTGGTTGTGGAAAGAGCTAGGC

AAACACAAACGGCCACGAGTCTGTACCAAAGAAGAGTTCATCAACAAGGTTCGTAGCAATGCAGCATTAGGGGCAATATTTGA

AGAGGAAAAAGAGTGGAAGACTGCAGTGGAAGCTGTGAACGATCCAAGGTTCTGGGCTCTAGTGGACAAGGAAAGAGAGCA

CCACCTGAGAGGAGAGTGCCAGAGTTGTGTGTACAACATGATGGGAAAAAGAGAAAAGAAACAAGGGGAATTTGGAAAGGC

CAAGGGCAGCCGCGCCATCTGGTATATGTGGCTAGGGGCTAGATTTCTAGAGTTCGAAGCCCTTGGATTCTTGAACGAGGATC

ACTGGATGGGGAGAGAGAACTCAGGAGGTGGTGTTGAAGGGCTGGGATTACAAAGACTCGGATATGTCCTAGAAGAGATGA

GTCGCATACCAGGAGGAAGGATGTATGCAGATGACACTGCTGGCTGGGACACCCGCATCAGCAGGTTTGATCTGGAGAATGA

AGCTCTAATCACCAACCAAATGGAGAAAGGGCACAGGGCCTTGGCATTGGCCATAATCAAGTACACATACCAAAACAAAGTG

GTAAAGGTCCTTAGACCAGCTGAAAAAGGGAAGACAGTTATGGACATTATTTCGAGACAAGACCAAAGGGGGAGCGGACAA

GTTGTCACTTACGCTCTTAACACATTTACCAACCTAGTGGTGCAACTCATTCGGAATATGGAGGCTGAGGAAGTTCTAGAGATG

CAAGACTTGTGGCTGCTGCGGAGGTCAGAGAAAGTGACCAACTGGTTGCAGAGCAACGGATGGGATAGGCTCAAACGAATG

GCAGTCAGTGGAGATGATTGCGTTGTGAAGCCAATTGATGATAGGTTTGCACATGCCCTCAGGTTCTTGAATGATATGGGAAA

AGTTAGGAAGGACACACAAGAGTGGAAACCCTCAACTGGATGGGACAACTGGGAAGAAGTTCCGTTTTGCTCCCACCACTTCA

ACAAGCTCCATCTCAAGGACGGGAGGTCCATTGTGGTTCCCTGCCGCCACCAAGATGAACTGATTGGCCGGGCCCGCGTCTCT

CCAGGGGCGGGATGGAGCATCCGGGAGACTGCTTGCCTAGCAAAATCATATGCGCAAATGTGGCAGCTCCTTTATTTCCACAG

AAGGGACCTCCGACTGATGGCCAATGCCATTTGTTCATCTGTGCCAGTTGACTGGGTTCCAACTGGGAGAACTACCTGGTCAAT

CCATGGAAAGGGAGAATGGATGACCACTGAAGACATGCTTGTGGTGTGGAACAGAGTGTGGATTGAGGAGAACGACCACAT

GGAAGACAAGACCCCAGTTACGAAATGGACAGACATTCCCTATTTGGGAAAAAGGGAAGACTTGTGGTGTGGATCTCTCATA

GGGCACAGACCGCGCACCACCTGGGCTGAGAACATTAAAAACACAGTCAACATGGTGCGCAGGATCATAGGTGATGAAGAAA

-continued

AGTACATGGACTACCTATCCACCCAAGTTCGCTACTTGGGTGAAGAAGGGTCTACACCTGGAGTGCTGTAAGCACCAATCTTA

ATGTTGTCAGGCCTGCTAGTCAGCCACAGCTTGGGGAAAGCTGTGCAGCCTGTGACCCCCCCAGGAGAAGCTGGGAAACCAA

GCCTATAGTCAGGCCGAGAACGCCATGGCACGGAAGAAGCCATGCTGCCTGTGAGCCCCTCAGAGGACACTGAGTCAAAAAA

CCCCACGCGCTTGGAGGCGCAGGATGGGAAAAGAAGGTGGCGACCTTCCCCACCCTTCAATCTGGGGCCTGAACTGGAGATC

AGCTGTGGATCTCCAGAAGAGGGACTAGTGGTTAGAGGAGA

KU527068.1 Zika virus strain Natal RGN, Brazil: Rio Grande do Norte, Natal, complete genome

SEQ ID NO: 6

AGTTGTTGATCTGTGTGAATCAGACTGCGACAGTTCGAGTTTGAAGCGAAAGCTAGCAACAGTATCAACAGGTTTTATTTTGG

ATTTGGAAACGAGAGTTTCTGGTCATGAAAAACCCAAAAAAGAAATCCGGAGGATTCCGGATTGTCAATATGCTAAAACGCGG

AGTAGCCCGTGTGAGCCCCTTTGGGGGCTTGAAGAGGCTGCCAGCCGGACTTCTGCTGGGTCATGGGCCCATCAGGATGGTC

TGGCAATTCTAGCCTTTTTGAGATTCACGGCAATCAAGCCATCACTGGGTCTCATCAATAGATGGGGTTCAGTGGGGAAAAA

AGAGGCTATGGAAATAATAAAGAAGTTCAAGAAAGATCTGGCTGCCATGCTGAGAATAATCAATGCTAGGAAGGAGAAGAA

GAGACGAGGCGCAGATACTAGTGTCGGAATTGTTGGCCTCCTGCTGACCACAGCTATGGCAGCGGAGGTCACTAGACGTGGG

AGTGCATACTATATGTACTTGGACAGAAACGATGCTGGGGAGGCCATATCTTTTCCAACCACATTGGGGATGAATAAGTGTTA

TATACAGATCATGGATCTTGGACACATGTGTGATGCCACCATGAGCTATGAATGCCCTATGCTGGATGAGGGGGTGGAACCAG

ATGACGTCGATTGTTGGTGCAACACGACGTCAACTTGGGTTGTGTACGGAACCTGCCATCACAAAAAAGGTGAAGCACGGAG

ATCTAGAAGAGCTGTGACGCTCCCCTCCCATTCCACTAGGAAGCTGCAAACGCGGTCGCAAACCTGGTTGGAATCAAGAGAAT

ACACAAAGCACTTGATTAGAGTCGAAAATTGGATATTCAGGAACCCTGGCTTCGCGTTAGCAGCAGCTGCCATCGCTTGGCTTT

TGGGAAGCTCAACGAGCCAAAAAGTCATATACTTGGTCATGATACTGCTGATTGCCCCGGCATACAGCATCAGGTGCATAGGA

GTCAGCAATAGGGACTTTGTGGAAGGTATGTCAGGTGGGACTTGGGTTGATGTTGTCTTGGAACATGGAGGTTGTGTCACCG

TAATGGCACAGGACAAACCGACTGTCGACATAGAGCTGGTTACAACAACAGTCAGCAACATGGCGGAGGTAAGATCCTACTG

CTATGAGGCATCAATATCAGACATGGCTTCGGACAGCCGCTGCCCAACACAAGGTGAAGCCTACCTTGACAAGCAATCAGACA

CTCAATATGTCTGCAAAAGAACGTTAGTGGACAGAGGCTGGGGAAATGGATGTGGACTTTTTGGCAAAGGGAGCCTGGTGAC

ATGCGCTAAGTTTGCATGCTCCAAGAAAATGACCGGGAAGAGCATCCAGCCAGAGAATCTGGAGTACCGGATAATGCTGTCA

GTTCATGGCTCCCAGCACAGTGGGATGATCGTTAATGACACAGGACATGAAACTGATGAGAATAGAGCGAAGGTTGAGATAA

CGCCCAATTCACCAAGAGCCGAAGCCACCCTGGGGGGTTTTGGAAGCCTAGGACTTGATTGTGAACCGAGGACAGGCCTTGA

CTTTTCAGATTTGTATTACTTGACTATGAATAACAAGCACTGGTTGGTCCACAAGGAGTGGTTCCACGACATTCCATTACCTTGG

CACGCTGGGGCAGACACCGGAACTCCACACTGGAACAACAAAGAAGCACTGGTAGAGTTCAAGGACGCACATGCCAAAAGG

CAAACTGTCGTGGTTCTAGGGAGTCAAGAAGGAGCAGTTCACACGGCCCTTGCTGGAGCTCTGGAGGCTGAGATGGATGGTG

CAAAGGGAAGGCTGTCCTCTGGCCACTTGAAATGTCGCCTGAAAATGGATAAACTTAGATTGAAGGGCGTGTCATACTCCTTG

TGTACCGCAGCGTTCACATTCACCAAGATCCCGGCTGAAACACTGCACGGGACAGTCACAGTGGAGGTACAGTACGCAGGGA

CAGATGGACCTTGCAAGGTTCCAGCTCAGATGGCGGTGGACATGCAAACTCTGACCCCAGTTGGGAGGTTGATAACCGCTAAC

CCCGTAATCACTGAAAGCACTGAGAACTCTAAGATGATGCTGGAACTTGATCCACCATTTGGGGACTCTTACATTGTCATAGGA

GTCGGGGAGAAGAAGATCACCCACCACTGGCACAGGAGTGGCAGCACCATTGGAAAAGCATTTGAAGCCACTGTGAGAGGT

GCCAAGAGAATGGCAGTCTTGGGAGACACAGCCTGGGACTTTGGATCAGTTGGAGGCGCTCTCAACTCATTGGGCAAGGGCA

TCCATCAAATTTTTGGAGCAGCTTTCAAATCATTGTTTGGAGGAATGTCCTGGTTCTCACAAATCCTCATTGGAACGTTGCTGAT

GTGGTTGGGTCTGAACACAAAGAATGGATCTATTTCCCTTATGTGCTTGGCCTTAGGGGGAGTGTTGATCTTCTTATCCACAGC

CGTCTCTGCTGATGTGGGGTGCTCGGTGGACTTCTCAAAGAAGGAGACGAGATGCGGTACAGGGGTGTTCGTCTATAACGAC

GTTGAAGCCTGGAGGGACAGGTACAAGTACCATCCTGACTCCCCCCGTAGATTGGCAGCAGCAGTCAAGCAAGCCTGGGAAG

ATGGTATCTGCGGGATCTCCTCTGTTTCAAGAATGGAGAACATCATGTGGAGATCAGTAGAAGGGGAGCTCAACGCAATCTTG

GAAGAGAATGGAGTTCAACTGACGGTCGTTGTGGGATCTGTAAAAAACCCCATGTGGAGAGGTCCACAGAGATTGCCCGTGC

-continued

CTGTGAACGAGCTGCCCCACGGCTGGAAGGCTTGGGGGAAATCGTACTTCGTCAGAGCAGCAAAGACAAATAACAGCTTTGT

CGTGGATGGTGACACACTGAAGGAATGCCCACTCGAACATAGAGCATGGAACAGCTTTCTTGTGGAGGATCATGGGTTCGGG

GTATTTCACACTAGTGTCTGGCTCAAGGTTAGAGAAGATTATTCATTAGAGTGTGATCCAGCCGTTATTGGAACAGCTGTTAAG

GGGAAGGAGGCTGTACACAGTGATCTAGGCTACTGGATTGAGAGTGAGAAGAATGACACATGGAGGCTGAAGAGGGCCCAT

CTAATCGAGATGAAAACATGTGAATGGCCAAAGTCCCACACATTGTGGGCAGATGGAATAGAAGAGAGTGATCTGATCATTCC

CAAGTCTTTAGCTGGGCCACTCAGCCATCACAATACCAGAGAGGGCTACAGGACCCAAATGAAAGGGCCATGGCACAGTGAA

GAGCTTGAAATTCGGTTTGAGGAATGCCCGGGCACTAAGGTCCACGTGGAGGAAACATGTGGAACAAGAGGACCATCTCTGA

GATCAACCACTGCAAGCGGAAGGGTGATCGAGGAATGGTGCTGCAGGGAGTGCACAATGCCCCCACTGTCGTTCCGGGCTAA

AGATGGCTGTTGGTATGGAATGGAGATAAGGCCCAGGAAAGAACCAGAAAGCAACTTAGTAAGGTCAGTGGTGACTGCAGG

ATCAACTGATCACATGGATCACTTCTCCCTTGGAGTGCTTGTGATTCTGCTCATGGTGCAGGAAGGGCTGAAGAAGAGAATGA

CCACAAAGATCATCATAAGCACATCAATGGCAGTGCTGGTAGCTATGATCCTGGGAGGATTTTCAATGAGTGACCTGGCTAAG

CTTGCAATTTTGATGGGCGCCACCTTCGCGGAAATGAACACTGGAGGAGATGTAGCTCATCTGGCGCTGATAGCGGCATTCAA

AGTCAGACCAGCGTTGCTGGTATCTTTCATCTTCAGAGCTAATTGGACACCCCGTGAAAGCATGCTGCTGGCCTTGGCCTCGTG

TCTTTTGCAAACTGCGATCTCCGCCTTGGAAGGCGACCTGATGGTTCTCATCAATGGTTTTGCTTTGGCCTGGTTGGCAATACG

AGCGATGGTTGTTCCACGCACTGATAACATCACCTTGGCAATCCTGGCTGCTCTGACACCACTGGCCCGGGGCACACTGCTTGT

GGCGTGGAGAGCAGGCCTTGCTACTTGCGGGGGGTTTATGCTCCTCTCTCTGAAGGGAAAAGGCAGTGTGAAGAAGAACTTA

CCATTTGTCATGGCCCTGGGACTAACCGCTGTGAGGCTGGTCGACCCCATCAACGTGGTGGGACTGCTGTTGCTCACAAGGAG

TGGGAAGCGGAGCTGGCCCCCTAGCGAAGTACTCACAGCTGTTGGCCTGATATGCGCATTGGCTGGAGGGTTCGCCAAGGCA

GATATAGAGATGGCTGGGCCCATGGCCGCGGTCGGTCTGCTAATTGTCAGTTACGTGGTCTCAGGAAAGAGTGTGGACATGT

ACATTGAAAGAGCAGGTGACATCACATGGGAAAAAGATGCGGAAGTCACTGGAAACAGTCCCCGGCTCGATGTGGCGCTAGA

TGAGAGTGGTGATTTCTCCCTGGTGGAGGATGACGGTCCCCCCATGAGAGAGATCATACTCAAGGTGGTCCTGATGACCATCT

GTGGCATGAACCCAATAGCCATACCCTTTGCAGCTGGAGCGTGGTACGTATACGTGAAGACTGGAAAAAGGAGTGGTGCTCT

ATGGGATGTGCCTGCTCCCAAGGAAGTAAAAAAGGGGGAGACCACAGATGGAGTGTACAGAGTAATGACTCGTAGACTGCTA

GGTTCAACACAAGTTGGAGTGGGAGTTATGCAAGAGGGGGTCTTTCACACTATGTGGCACGTCACAAAAGGATCCGCGCTGA

GAAGCGGTGAAGGGAGACTTGATCCATACTGGGGAGATGTCAAGCAGGATCTGGTGTCATACTGTGGTCCATGGAAGCTAGA

TGCCGCCTGGGACGGGCACAGCGAGGTGCAGCTCTTGGCCGTGCCCCCCGGAGAGAGAGCGAGGAACATCCAGACTCTGCCC

GGAATATTTAAGACAAAGGATGGGGACATTGGAGCGGTTGCGCTGGATTACCCAGCAGGAACTTCAGGATCTCCAATCCTAG

ACAAGTGTGGGAGAGTGATAGGACTTTATGGCAATGGGGTCGTGATCAAAAATGGGAGTTATGTTAGTGCCATCACCCAAGG

GAGGAGGGAGGAAGAGACTCCTGTTGAGTGCTTCGAGCCTTCGATGCTGAAGAAGAAGCAGCTAACTGTCTTAGACTTGCAT

CCTGGAGCTGGGAAAACCAGGAGAGTTCTTCCTGAAATAGTCCGTGAAGCCATAAAAACAAGACTCCGTACTGTGATCTTAGC

TCCAACCAGGGTTGTCGCTGCTGAAATGGAGGAAGCCCTTAGAGGGCTTCCAGTGCGTTATATGACAACAGCAGTCAATGTCA

CCCACTCTGGAACAGAAATCGTCGACTTAATGTGCCATGCCACCTTCACTTCACGTCTACTACAGCCAATCAGAGTCCCCAACTA

TAATCTGTATATTATGGATGAGGCCCACTTCACAGATCCCTCAAGTATAGCAGCAAGAGGATACATTTCAACAAGGGTTGAGA

TGGGCGAGGCGGCTGCCATCTTCATGACCGCCACGCCACCAGGAACCCGTGACGCATTTCCGGACTCCAACTCACCAATTATG

GACACCGAAGTGGAAGTCCCAGAGAGAGCCTGGAGCTCAGGCTTTGATTGGGTGACGGATCATTCTGGAAAAACAGTTTGGT

TTGTTCCAAGCGTGAGGAACGGCAATGAGATCGCAGCTTGTCTGACAAAGGCTGGAAAACGGGTCATACAGCTCAGCAGAAA

GACTTTTGAGACAGAGTTCCAGAAAACAAAACATCAAGAGTGGGACTTTGTCGTGACAACTGACATTTCAGAGATGGGCGCCA

ACTTTAAAGCTGACCGTGTCATAGATTCCAGGAGATGCCTAAAGCCGGTCATACTTGATGGCGAGAGAGTCATTTTGGCTGGA

CCCATGCCTGTCACACATGCCAGCGCTGCCCAGAGGAGGGGGCGCATAGGCAGGAATCCCAACAAACCTGGAGATGAGTATC

TGTATGGAGGTGGGTGCGCAGAGACTGACGAAGACCATGCACACTGGCTTGAAGCAAGAATGCTCCTTGACAATATTTACCTC

CAAGATGGCCTCATAGCCTCGCTCTATCGACCTGAGGCCGACAAAGTAGCAGCCATTGAGGGAGAGTTCAAGCTTAGGACGG

-continued

AGCAAAGGAAGACCTTTGTGGAACTCATGAAAAGAGGAGATCTTCCTGTTTGGCTGGCCTATCAGGTTGCATCTGCCGGAATA

ACCTACACAGATAGAAGATGGTGCTTTGATGGCACGACCAACAACACCATAATGGAAGACAGTGTGCCGGCAGAGGTGTGGA

CCAGACACGGAGAGAAAAGAGTGCTCAAACCGAGGTGGATGGACGCCAGAGTTTGTTCAGATCATGCGGCCCTGAAGTCATT

CAAGGAGTTTGCCGCTGGGAAAAGAGGAGCGGCTTTTGGAGTGATGGAAGCCCTGGGAACACTGCCAGGACACATGACAGA

GAGATTCCAGGAAGCCATTGACAACCTCGCTGTGCTCATGCGGGCAGAGACTGGAAGCAGGCCTTACAAAGCCGCGGCGGCC

CAATTGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTGAGC

CAGCCAGAATTGCATGTGTCCTCATTGTTGTGTTCCTATTGCTGGTGGTGCTCATACCTGAGCCAGAAAAGCAAAGATCTCCCC

AGGACAACCAAATGGCAATCATCATCATGGTAGCAGTAGGTCTTCTGGGCTTGATTACCGCCAATGAACTCGGATGGTTGGAG

AGAACAAAGAGTGACCTAAGCCATCTAATGGGAAGGAGAGAGGAGGGAGCAACCATAGGATTCTCAATGGACATTGACCTG

CGGCCAGCCTCAGCTTGGGCCATCTATGCTGCCTTGACAACTTTCATTACCCCAGCCGTCCAACATGCAGTGACCACTTCATACA

ACAACTACTCCTTAATGGCGATGGCCACGCAAGCTGGAGTGTTGTTTGGTATGGGCAAAGGGATGCCATTCTACGCATGGGAC

TTTGGAGTCCCGCTGCTAATGATAGGTTGCTACTCACAATTAACACCCCTGACCCTAATAGTGGCCATCATTTTGCTCGTGGCGC

ACTACATGTACTTGATCCCAGGGCTGCAGGCAGCAGCTGCGCGTGCTGCCCAGAAGAGAACGGCAGCTGGCATCATGAAGAA

CCCTGTTGTGGATGGAATAGTGGTGACTGACATTGACACAATGACAATTGACCCCCAAGTGGAGAAAAAGATGGGACAGGTG

CTACTCATAGCAGTAGCAGTCTCCAGCGCCATACTGTCGCGGACCGCCTGGGGGTGGGGGGAGGCTGGGGCCCTGATCACAG

CCGCAACTTCCACTTTGTGGGAAGGCTCTCCGAACAAGTACTGGAACTCCTCTACAGCCACTTCACTGTGTAACATTTTTAGGG

GAAGTTACTTGGCTGGAGCTTCTCTAATCTACATAGTAACAAGAAACGCTGGCTTGGTCAAGAGACGTGGGGGTGGAACAGG

AGAGACCCTGGGAGAGAAATGGAAGGCCCGCTTGAACCAGATGTCGGCCCTGGAGTTCTACTCCTACAAAAAGTCAGGCATC

ACCGAGGTGTGCAGAGAAGAGGCCCGCCGCGCCCTCAAGGATGGTGTGGCAACGGGAGGCCATGCTGTGTCCCGAGGAAGT

GCAAAGCTGAGATGGTTGGTGGAGCGGGGATACCTGCAGCCCTATGGAAAGGTCATTGATCTTGGATGTGGCAGAGGGGGC

TGGAGTTACTACGCCGCCACCATCCGCAAAGTTCAAGAAGTGAAAGGATACACAAAAGGAGGCCCTGGTCATGAAGAACCCG

TGTTGGTGCAAAGCTATGGGTGGAACATAGTCCGTCTTAAGAGTGGGGTGGACGTCTTTCATATGGCGGCTGAGCCGTGTGA

CACGTTGCTGTGTGACATAGGTGAGTCATCATCTAGTCCTGAAGTGGAAGAAGCACGGACGCTCAGAGTCCTCTCCATGGTGG

GGGATTGGCTTGAAAAAAGACCAGGAGCCTTTTGTATAAAAGTGTTGTGCCCATACACCAGCACTATGATGGAAACCCTGGAG

CGACTGCAGCGTAGGTATGGGGGAGGACTGGTCAGAGTGCCACTCTCCCGCAACTCTACACATGAGATGTACTGGGTCTCTG

GAGCGAAAAGCAACACCATAAAAAGTGTGTCCACCACGAGCCAGCTCCTCTTGGGGCGCATGGACGGGCCTAGGAGGCCAGT

GAAATATGAGGAGGATGTGAATCTCGGCTCTGGCACGCGGGCTGTGGTAAGCTGCGCTGAAGCTCCCAACATGAAGATCATT

GGTAACCGCATTGAAAGGATCCGCAGTGAGCACGCGGAAACGTGGTTCTTTGACGAGAACCACCCATATAGGACATGGGCTT

ACCATGGAAGCTATGAGGCCCCCACACAAGGGTCAGCGTCCTCTCTAATAAACGGGGTTGTCAGGCTCCTGTCAAAACCCTGG

GATGTGGTGACTGGAGTCACAGGAATAGCCATGACCGACACCACACCGTATGGTCAGCAAAGAGTTTTCAAGGAAAAAGTGG

ACACTAGGGTGCCAGACCCCCAAGAAGGCACTCGTCAGGTTATGAGCATGGTCTCTTCCTGGTTGTGGAAAGAGCTAGGCAA

ACACAAACGGCCACGAGTCTGTACCAAAGAAGAGTTCATCAACAAGGTTCGTAGCAATGCAGCATTAGGGGCAATATTTGAA

GAGGAAAAAGAGTGGAAGACTGCAGTGGAAGCTGTGAACGATCCAAGGTTCTGGGCTCTAGTGGACAAGGAAAGAGAGCAC

CACCTGAGAGGAGAGTGCCAGAGTTGTGTGTACAACATGATGGGAAAAAGAGAAAAGAAACAAGGGGAATTTGGAAAGGCC

AAGGGCAGCCGCGCCATCTGGTATATGTGGCTAGGGGCTAGATTTCTAGAGTTCGAAGCCCTTGGATTCTTGAACGAGGATCA

CTGGATGGGGAGAGAGAACTCAGGAGGTGGTGTTGAAGGGCTGGGATTACAAAGACTCGGATATGTCCTAGAAGAGATGAG

TCGCATACCAGGAGGAAGGATGTATGCAGATGACACTGCTGGCTGGGACACCCGCATCAGCAGGTTCGATCTGGAGAATGAA

GCTCTAATCACCAACCAAATGGAGAAAGGGCATAGGGCCTTGGCATTGGCCATAATCAAGTACACATACCAAAACAAAGTGGT

AAAGGTCCTTAGACCAGCTGAAAAAGGGAAAACAGTTATGGACATTATTTCGAGACAAGACCAAAGGGGGAGCGGACAAGTT

-continued

GTCACTTACGCTCTTAACACATTTACCAACCTAGTGGTGCAACTCATTCGGAATATGGAGGCTGAGGAAGTTCTAGAGATGCAA

GACTTGTGGCTGCTGCGGAGGTCAGAGAAAGTGACCAACTGGTTGCAGAGCAACGGATGGGATAGGCTCAAACGAATGGCA

GTCAGTGGAGATGATTGCGTTGTGAAGCCAATTGATGATAGGTTTGCACATGCCCTCAGGTTCTTGAATGATATGGGAAAAGT

TAGGAAGGACACACAAGAGTGGAAACCCTCAACTGGATGGGACAACTGGGAAGAAGTTCCGTTTTGCTCCCACCACTTCAACA

AGCTCCATCTCAAGGACGGGAGGTCCATTGTGGTTCCCTGCCGCCACCAAGATGAACTGATTGGCCGGGCCCGCGTCTCTCCA

GGGGCGGGATGGAGCATCCGGGAGACTGCTTGCCTAGCAAAATCATATGCGCAAATGTGGCAGCTCCTTTATTTCCACAGAA

GGGACCTCCGACTGATGGCCAATGCCATTTGTTCATCTGTGCCAGTTGACTGGGTTCCAACTGGGAGAACTACCTGGTCAATCC

ATGGAAAGGGAGAATGGATGACCACTGAAGACATGCTTGTGGTGTGGAACAGAGTGTGGATTGAGGAGAACGACCACATGG

AAGACAAGACCCCAGTTACGAAATGGACAGACATTCCCTATTTGGGAAAAAGGGAAGACTTGTGGTGTGGATCTCTCATAGG

GCACAGACCGCGCACCACCTGGGCTGAGAACATTAAAAACACAGTCAACATGGTGCGCAGGATCATAGGTGATGAAGAAAAG

TACATGGACTACCTATCCACCCAAGTTCGCTACTTGGGTGAAGAAGGGTCTACACCTGGAGTGCTGTAAGCACCAATCTTAATG

TTGTCAGGCCTGCTAGTCAGCCACAGCTTGGGGAAAGCTGTGCAGCCTGTGACCCCCCCAGGAGAAGCTGGGAAACCAAGCC

TATAGTCAGGCCGAGAACGCCATGGCACGGAAGAAGCCATGCTGCCTGTGAGCCCCTCAGAGGACACTGAGTCAAAAAACCC

CATGCGCTTGGAGGCGCAGGATGGGAAAAGAAGGTGGCGACCTTCCCCACCCTTCAATCTGGGGCCTGAACTGGAGATCAGC

TGTGGATCTCCAGAAGAGGGACTAGTGGTTAGAGGAGACCCCCCGGAAAACGCAAAACAGCATATTGACGCTGGGAAAGAC

CAGAGACTCCATGAGTTTCCACCACGCTGGCCGCCAGGCACAGATCGCCGAATAGCGGCGGCCGGTGTGGGGAAATCCATGG

GTCTT

KU681081.3 Zika virus isolate Zika virus/*H.sapiens*-tc/THA/2014/SV0127-14, Thailand, complete genome

SEQ ID NO: 7

AGTTGTTGATCTGTGTGAATCAGACTGCGACAGTTCGAGTTTGAAGCGAAAGCTAGCAACAGTATCAACAGGTTTTATTTTGG

ATTTGGAAACGAGAGTTTCTGGTCATGAAAAACCCAAAAAAGAAATCCGGAGGATTCCGGATTGTCAATATGCTAAAACGCGG

AGTAGCCCGTGTGAGCCCCTTTGGGGGCTTGAAGAGGCTGCCAGCCGGACTTCTGCTGGGTCATGGGCCCATCAGGATGGTC

TGGCGATTCTAGCCTTTTTGAGATTCACGGCAATCAAGCCATCACTGGGTCTCATCAATAGATGGGGTTCAGTGGGAAAAAA

AGAGGCTATGGAAATAATAAAGAAGTTCAAGAAAGATCTGGCTGCCATGCTGAGAATAATCAATGCTAGGAAGGAGAAGAA

GAGACGAGGCACAGATACTAGTGTCGGAATTGTTGGCCTCCTGCTGACCACAGCTATGGCAGCGGAGGTCACTAGACGTGGG

AGTGCATACTATATGTACTTGGACAGAAGCGATGCTGGGGAGGCCATATCTTTTCCAACCACACTGGGGATGAATAAGTGTTA

TATACAGATCATGGATCTTGGACACATGTGTGATGCCACCATGAGCTATGAATGCCCTATGCTGGATGAGGGGGTAGAACCAG

ATGACGTCGATTGTTGGTGCAACACGACGTCAACTTGGGTTGTGTACGGAACCTGCCATCACAAAAAAGGTGAAGCACGGAG

ATCCAGAAGAGCTGTGACGCTCCCCTCCCATTCCACTAGGAAGCTGCAAACGCGGTCGCAGACCTGGTTGGAATCAAGAGAAT

ACACAAAGCACTTGATTAGAGTCGAAAATTGGATATTCAGGAACCCTGGCTTCGCGTTAGCAGCAGCTGCCATCGCTTGGCTTT

TGGGAAGCTCAACGAGCCAAAAAGTCATATACTTGGTCATGATACTGCTGATTGCCCCGGCATACAGCATCAGGTGCATAGGA

GTCAGTAATAGGGACTTTGTGGAAGGTATGTCAGGTGGGACTTGGGTTGATGTTGTCTTGGAACATGGAGGTTGTGTCACCGT

AATGGCACAGGACAAACCGACTGTCGACATAGAGCTGGTTACAACAACAGTCAGCAACATGGCGGAGGTAAGATCCTACTGC

TATGAGGCATCAATATCGGACATGGCTTCGGACAGCCGCTGCCCAACACAAGGTGAAGCCTACCTTGACAAGCAATCAGACAC

TCAATATGTCTGCAAAAGAACGTTAGTGGACAGAGGCTGGGGAAATGGATGTGGACTTTTTGGCAAAGGGAGCCTGGTGACA

TGCGCTAAGTTTGCATGCTCCAAGAAAATGACCGGGAAGAGCATCCAGCCAGAGAATCTGGAGTACCGGATAATGCTGTCAG

TTCATGGCTCCCAGCACAGTGGGATGATCGTTAATGACACAGGACATGAAACTGATGAGAATAGAGCGAAGGTTGAGATAAC

GCCCAATTCACCAAGAGCCGAAGCCACCCTGGGGGGTTTTGGAAGCCTAGGACTTGATTGTGAACCGAGGACAGGCCTTGAC

TTTTCAGATTTGTATTACTTGACTATGAACAACAAGCACTGGTTGGTTCACAAGGAGTGGTTCCACGACATTCCATTACCTTGGC

ACACTGGGGCAGACACCGGAACTCCACACTGGAACAACAAAGAAGCACTGGTAGAGTTCAAGGACGCACATGCCAAAAGGC

AAACTGTCGTGGTTCTAGGGAGTCAAGAAGGAGCAGTTCACACGGCCCTTGCTGGAGCTCTGGAGGCTGAGATGGATGGTGC

-continued

AAAGGGAAGGCTGTCCTCTGGCCACTTGAAATGTCGCCTGAAAATGGATAAACTTAGATTGAAGGGCGTGTCATACTCCTTGT

GTACCGCAGCGTTCACATTCACCAAGATCCCGGCTGAAACACTGCACGGGACAGTCACAGTGGAGGTACAGTACGCAGGGAC

AGATGGACCTTGCAAGGTTCCAGCTCAGATGGCGGTGGACATGCAAACTCTGACCCCAGTTGGGAGGTTGATAACCGCTAACC

CCGTAATCACTGAAGGCACTGAGAACTCTAAGATGATGCTGGAACTTGATCCACCATTTGGGGACTCTTACATTGTCATAGGA

GTCGGGGAGAAGAAGATCACCCACCACTGGCACAGGAGTGGCAGCACCATTGGAAAAGCATTTGAAGCCACTGTGAGAGGT

GCCAAGAGAATGGCAGTCTTGGGAGACACAGCCTGGGACTTTGGATCAGTTGGAGGCGTTCTTAACTCATTGGGCAAGGGCA

TCCATCAAATTTTTGGAGCAGCTTTCAAATCATTGTTTGGAGGAATGTCCTGGTTCTCACAAATTCTCATTGGAACGTTGCTGAT

GTGGTTGGGTCTGAATACAAAGAATGGATCTATTTCCCTTATGTGCTGGCCTTAGGGGGAGTGTTGATCTTCTTATCCACAGC

CGTCTCCGCTGATGTGGGGTGCTCGGTGGACTTCTCAAAGAAGGAAACGAGATGCGGTACAGGGGTGTTCGTCTATAACGAC

GTTGAAGCCTGGAGGGACAGGTACAAGTACCATCCTGACTCCCCTCGTAGATTGGCAGCAGTAGTCAAGCAAGCCTGGGAAG

ATGGTATCTGTGGGATCTCCTCTGTTTCAAGAATGGAAAACATCATGTGGAGATCAGTAGAAGGGGAGCTCAACGCAATCCTG

GAAGAGAATGGAGTTCAACTGACGGTCGTTGTGGGATCTGTAAAAAACCCCATGTGGAGAGGTCCACAGAGATTGCCCGTGC

CTGTGAACGAGCTGCCCCACGGCTGGAAGGCTTGGGGGAAATCGTACTTCGTCAGAGCAGCAAAGACAAATAACAGCTTTGT

CGTGGATGGTGACACACTGAAGGAATGCCCACTCAAACATAGAGCATGGAACAGCTTTCTTGTGGAGGATCATGGGTTCGGG

GTATTTCACACTAGTGTCTGGCTCAAGGTTAGAGAAGATTATTCACTAGAGTGTGATCCAGCCGTCATTGGAACAGCTGTTAAG

GGAAAGGAGGCTGTACACAGTGATCTAGGCTACTGGATTGAGAGTGAGAAGAACGACACATGGAGGCTGAGGAGGGCCCAC

CTGATCGAGATGAAAACATGTGAATGGCCAAAGTCCCACACATTGTGGACAGATGGAATAGAAGAGAGTGATCTGATCATAC

CCAAGTCTTTAGCTGGGCCACTCAGCCATCACAACACCAGAGAGGGCTACAGGACCCAAATGAAAGGGCCATGGCACAGTGA

AGAGCTTGAAATTCGGTTTGAGGAATGCCCAGGCACTAAGGTCCACGTGGAGGAAACATGTGGAACAAGAGGACCATCTCTG

AGATCAACCACTGCAAGCGGAAGGGTGATCGAGGAATGGTGCTGCAGGGAGTGCACAATGCCCCCACTGTCGTTCCGGGCTA

AAGATGGCTGTTGGTATGGAATGGAGATAAGGCCCAGGAAAGAACCAGAAAGTAACTTAGTAAGGTCAATGGTGACTGCAG

GATCAACTGATCACATGGATCACTTTTCCCTTGGAGTGCTTGTGATTCTGCTCATGGTGCAGGAAGGGCTGAAGAAGAGAATG

ACCACAAAGATCATCATAAGCACATCAATGGCAGTGCTGGTAGCTATGATCCTGGGAGGATTTTCAATGAGTGATCTGGCTAA

GCTTGCAATTTTGATGGGTGCCACCTTTGCGGAAATGAACACTGGAGGAGATGTAGCTCATCTGGCGCTGGTAGCGGCATTCA

AAGTCAGACCAGCGTTGCTGGTATCTTTCATCTTCAGAGCTAATTGGACACCCCGTGAAAGCATGCTGCTGGCCTTGGCCTCGT

GTCTTTTGCAAACTGCGATCTCCGCCTTGGAAGGCGACCTGATGGTTCTCATCAATGGTTTTGCTTTGGCCTGGTTGGCAATAC

GAGCGATGGTTGTTCCACGCACTGACAATATCACCTTGGCAATCCTGGCTGCTCTGACACCACTGGCCCGGGGCACACTGCTTG

TGGCGTGGAGAGCAGGCCTTGCTACTTGCGGGGGGTTCATGCTCCTCTCTCTGAAGGGGAAAGGCAGTGTGAAGAAGAACTT

ACCATTTGTCATGGCCCTGGGACTAACCGCTGTGAGGCTGGTCGACCCCATCAACGTGGTGGGACTGCTGTTGCTCACAAGGA

GTGGGAAGCGGAGCTGGCCCCCTAGCGAAGTACTCACAGCTGTTGGCCTGATATGCGCATTGGCTGGAGGGTTCGCCAAGGC

AGATATAGAGATGGCTGGGCCCATGGCCGCGGTCGGTCTGCTAATTGTCAGTTACGTGGTCTCAGGAAAGAGTGTGGACATG

TACATTGAAAGAGCAGGTGACATCACATGGGAAAAAGATGCGGAAGTTACTGGAAACAGTCCCCGGCTCGATGTGGCACTAG

ATGAGAGTGGTGATTTCTCCCTGGTGGAGGATGACGGTCCCCCCATGAGAGAGATCATACTCAAAGTGGTCCTGATGACCATC

TGTGGCATGAACCCAATAGCCATACCCTTTGCAGCTGGAGCGTGGTACGTATACGTGAAAACTGGAAAAAGGAGTGGTGCTCT

ATGGGATGTGCCTGCTCCCAAGGAAGTAAAAAAGGGGGAGACCACAGATGGAGTGTACAGAGTAATGACTCGTAGACTGCTA

GGTTCAACACAAGTTGGAGTGGGAGTTATGCAAGAGGGGGTCTTTCACACTATGTGGCATGTCACAAAAGGATCCGCGCTGA

GAAGCGGTGAAGGGAGACTTGATCCATACTGGGGAGATGTCAAGCAGGATCTGGTGTCATACTGTGGTCCATGGAAGCTAGA

TGCCGCCTGGGACGGGCACAGCGAGGTGCAGCTCTTGGCCGTGCCCCCCGGAGAGAGAGCGAGGAACATCCAGACTCTGCCC

GGAATATTTAAGACAAAGGATGGGGACATTGGAGCGGTTGCGCTGGACTATCCAGCAGGAACTTCAGGATCTCCAATCCTAG

ACAAGTGTGGGAGAGTGATAGGACTCTATGGCAATGGGGTCGTGATCAAGAATGGGAGTTATGTCAGTGCCATCACCCAAGG

GAGGAGGGAGGAAGAGACTCCTGTTGAGTGCTTCGAGCCTTCGATGCTGAAGAAGAAGCAGCTAACTGTCTTAGACTTGCAT

-continued

CCTGGAGCTGGGAAAACCAGGAGAGTTCTTCCTGAAATAGTCCGTGAAGCCATAAAAACGAGACTCCGTACTGTGATCTTAGC

TCCAACCAGGGTTGTCGCTGCTGAAATGGAGGAAGCCCTTAGAGGGCTTCCAGTGCGTTATATGACAACAGCAGTCAATGTCA

CCCATTCTGGGACAGAAATCGTTGACTTAATGTGCCATGCCACCTTCACTTCACGTCTACTACAGCCAATCAGAGTCCCCAACTA

TAATCTGTATATTATGGATGAGGCCCACTTCACAGATCCCTCAAGTATAGCAGCAAGAGGATACATTTCAACAAGGGTTGAGA

TGGGCGAGGCAGCTGCCATCTTCATGACCGCCACGCCACCAGGAACCCGTGACGCATTCCCGGACTCCAACTCACCAATTATG

GACACCGAAGTGGAAGTCCCAGAGAGAGCCTGGAGCTCAGGCTTTGATTGGGTGACGGATCATTCTGGAAAAACAGTTTGGT

TTGTCCCAAGCGTGAGGAACGGCAATGAGATCGCAGCTTGTCTGACAAAGGCTGGAAAACGGGTCATACAGCTCAGCAGAAA

GACTTTTGAGACAGAGTTCCAGAAAACAAAACATCAAGAGTGGGACTTCGTCGTGACAACTGACATTTCAGAGATGGGCGCCA

ACTTTAAAGCTGACCGTGTCATAGATTCCAGGAGATGCCTAAAGCCGGTCATACTTGATGGCGAGAGAGTCATTCTGGCTGGA

CCCATGCCTGTCACACATGCCAGCGCTGCCCAGAGGAGGGGGCGCATAGGCAGGAATCCCAACAAACCTGGAGATGAGTATC

TGTATGGAGGTGGGTGCGCAGAGACTGATGAAGACCATGCACACTGGCTTGAAGCAAGAATGCTCCTTGACAATATTTACCTC

CAAGATGGCCTCATAGCCTCGCTCTATCGACCTGAGGCCGACAAAGTAGCAGCCATTGAGGGAGAGTTCAAGCTTAGGACGG

AGCAAAGGAAGACCTTTGTGGAACTCATGAAAAGAGGAGATCTTCCTGTTTGGCTGGCCTATCAGGTTGCATCTGCCGGAATA

ACCTACACAGATAGAAGATGGTGCTTTGATGGCATGACCAACAACACCATAATGGAAGACAGTGTGCCGGCAGAGGTGTGGA

CCAGACACGGAGAGAAAAGAGTGCTCAAACCGAGGTGGATGGACGCCAGAGTTTGTTCAGATCATGCGGCCCTGAAGTCATT

CAAGGAGTTTGCCGCTGGGAAAAGAGGAGCGGCTTTTGGAGTGATGGAAGCCCTGGGAACACTGCCAGGACACATGACGGA

GAGATTCCAGGAAGCCATTGACAACCTCGCTGTGCTCATGCGGGCAGAGACTGGAAGCAGGCCTTACAAAGCCGCGGCGGCC

CAATTGCCGGAGACCCTAGAGACCATTATGCTTTTGGGGTTGCTGGGAACAGTCTCGCTGGGAATCTTTTTCGTCTTGATGCGG

AACAAGGGCATAGGGAAGATGGGCTTTGGAATGGTGACTCTTGGGGCCAGCGCATGGCTCATGTGGCTCTCGGAAATTGAGC

CAGCCAGAATTGCATGCGTCCTCATTGTTGTGTTCCTATTGCTGGTGGTGCTCATACCTGAGCCAGAAAAGCAAAGATCCCCCC

AGGACAACCAAATGGCAATCATCATCATGGTAGCAGTAGGTCTTCTGGGCTTGATTACCGCCAATGAACTCGGATGGTTGGAG

AGAACAAAGAGTGACCTAAGCCATCTAATGGGAAGGAGAGAGGAGGGGGCAACCATAGGATTCTCAATGGACATTGACCTG

CGGCCAGCCTCGGCCTGGGCCATCTATGCTGCCCTGACAACTTTCATTACCCCAGCCGTCCAACATGCAGTGACCACTTCATAC

AACAACTACTCCTTAATGGCGATGGCCACGCAAGCTGGAGTGTTGTTTGGTATGGGCAAAGGGATGCCATTCTACGCATGGGA

CTTTGGAGTCCCGCTGCTAATGATAGGTTGCTACTCACAATTAACACCCCTGACCCTAATAGTGGCTATCATTTTGCTCGTGGCG

CACTACATGTACTTGATCCCAGGGCTGCAGGCAGCAGCTGCGCGTGCTGCCCAGAAGAGAACGGCAGCTGGCATCATGAAGA

ACCCTGTTGTGGATGGAATAGTGGTGACTGACATTGACACAATGACTATTGACCCCCAAGTGGAGAAAAAGATGGGACAGGT

GCTACTCATAGCAGTAGCCGTCTCCAGCGCCATACTGTCGCGGACCGCCTGGGGGTGGGGGGAAGCTGGGGCCCTGATCACA

GCTGCAACTTCCACTTTGTGGGAAGGCTCTCCGAACAAGTACTGGAACTCCTCTACAGCCACTTCACTGTGCAACATTTTTAGG

GGAAGTTACTTGGCTGGAGCTTCTCTAATCTACACAGTAACAAGAAACGCTGGCTTGGTCAAGAGACGTGGGGGTGGAACAG

GAGAGACCCTGGGAGAGAAATGGAAGGCCCGCTTGAACCAGATGTCGGCCCTGGAGTTCTACTCCTACAAAAAGTCAGGCAT

CACCGAGGTGTGCAGAGAAGAGGCCCGCCGCGCCCTCAAGGACGGTGTGGCAACGGGAGGCCATGCTGTGTCCCGAGGAAG

TGCAAAGCTGAGATGGTTGGTGGAGCGGGGATACCTGCAGCCCTATGGAAAGGTCATTGATCTTGGATGTGGCAGAGGGGG

CTGGAGTTACTACGCCGCCACCATCCGCAAAGTTCAAGAAGTGAAAGGATACACAAAAGGAGGCCCTGGTCATGAAGAACCC

ATGTTGGTGCAAAGCTATGGGTGGAACATAGTCCGTCTTAAGAGTGGGGTGGACGTCTTTCATATGGCGGCTGAGCCGTGTG

ACACGTTGCTGTGTGACATAGGTGAGTCATCATCTAGTCCTGAAGTGGAAGAAGCACGGACGCTCAGAGTCCTCTCCATGGTG

GGGGATTGGCTTGAAAAAAGACCAGGAGCCTTTTGTGTAAAAGTGTTGTGCCCATACACCAGCACTATGATGGAAACCCTGGA

GCGACTGCAGCGTAGGTATGGGGGAGGACTGGTCAGAGTGCCACTCTCCCGCAACTCTACACATGAGATGTACTGGGTCTCT

GGAGCGAAAAGCAACACCATAAAAAGTGTGTCCACCACGAGCCAGCTCCTCTTGGGGCGCATGGACGGGCCCAGGAGGCCA

GTGAAATATGAGGAGGATGTGAATCTCGGCTCTGGCACGCGGGCTGTGGTAAGCTGCGCTGAAGCTCCCAACATGAAGATCA

-continued

TTGGTAACCGCATTGAAAGGATCCGCAGTGAGCACGCGGAAACGTGGTTCTTTGACGAGAACCACCCATATAGGACATGGGC

TTACCATGGAAGCTATGAGGCCCCTACACAAGGGTCAGCGTCCTCTCTAATAAACGGGGTTGTCAGGCTCCTGTCAAAACCCT

GGGATGTGGTGACTGGAGTCACAGGAATAGCCATGACCGACACCACACCGTATGGTCAGCAAAGAGTTTTCAAGGAAAAAGT

GGACACCAGGGTGCCAGACCCCCAAGAAGGCACTCGTCAGGTTATGAGCATGGTCTCTTCCTGGTTGTGGAAAGAGCTAGGC

AAACACAAACGGCCACGAGTCTGTACCAAAGAAGAGTTCATCAACAAGGTTCGTAGCAATGCAGCATTAGGGGCAATATTTGA

AGAGGAAAAAGAGTGGAAGACCGCAGTGGAAGCTGTGAACGATCCAAGGTTCTGGGCTCTAGTGGACAAGGAAAGAGAGC

ACCACCTGAGAGGAGAGTGCCAGAGCTGTGTGTACAACATGATGGGAAAAAGAGAAAAGAAACAAGGGGAATTTGGAAAG

GCCAAGGGCAGCCGCGCCATCTGGTATATGTGGCTAGGGGCTAGATTTCTAGAGTTCGAAGCCCTTGGATTCTTAAATGAGGA

TCACTGGATGGGGAGAGAGAACTCAGGAGGTGGTGTTGAAGGGCTGGGATTACAAAGACTCGGATATGTCCTAGAAGAGAT

GAGTCGCATACCAGGAGGAAGGATGTATGCAGATGACACTGCTGGCTGGGACACCCGCATCAGCAGGTTTGATCTGGAGAAT

GAAGCTTTAATCACCAACCAAATGGAGAAAGGGCACAGGGCCTTAGCATTGGCCATAATCAAGTACACATACCAAAACAAAGT

GGTAAAGGTCCTTAGACCAGCTGAAAAAGGGAAGACAGTTATGGACATTATTTCAAGACAAGACCAAAGGGGGAGCGGACA

AGTTGTCACTTACGCTCTTAACACATTTACCAACCTAGTGGTGCAACTCATTCGGAATATGGAGGCTGAGGAAGTTCTAGAGAT

GCAAGACTTGTGGCTGCTGCGGAGGTCAGAGAAAGTGACCAACTGGTTGCAGAGCAACGGATGGGATAGGCTCAAACGAAT

GGCAGTCAGTGGAGATGATTGCGTTGTGAAGCCAATTGATGATAGGTTTGCACATGCCCTCAGGTTCTTGAATGATATGGGAA

AAGTTAGGAAGGACACACAAGAGTGGAAACCCTCAACTGGATGGGACAACTGGGAAGAAGTTCCGTTTTGTTCCCACCACTTC

AACAAGCTCCATCTCAAGGACGGGAGGTCCATTGTGGTTCCCTGCCGCCACCAAGATGAACTGATTGGCCGGGCCCGTGTCTC

TCCAGGGGCGGGATGGAGCATCCGGGAGACTGCTTGCCTAGCAAAGTCATATGCGCAAATGTGGCAGCTCCTTTATTTCCACA

GAAGGGACCTCCGACTGATGGCCAATGCCATCTGTTCATCTGTGCCAGTTGACTGGGTTCCAACTGGGAGAACTACCTGGTCA

ATCCATGGAAAGGGAGAATGGATGACCACTGAAGACATGCTTGTGGTGTGGAACAGAGTGTGGATTGAGGAGAACGACCAC

ATGGAAGACAAGACCCCAGTTACGAAATGGACAGACATTCCCTATCTGGGAAAAAGGGAAGACTTGTGGTGTGGATCTCTCA

TAGGGCACAGACCGCGCACCACCTGGGCTGAGAACATTAAAAACACAGTCAACATGGTGCGCAGGATCATAGGTGATGAAGA

AAAGTACATGGACTACCTATCCACCCAAGTTCGCTACTTGGGTGAAGAAGGGTCTACACCTGGAGTGCTATAAGCACCAATCTT

AGTGTTGTCAGGCCTGCTAGTCAGCCACAGCTGGGGAAAGCTGTGCAGCCTGTGACCCCCCCAGGAGAGGCTGGGAAACCA

AGCCCATAGTCAGGCCGAGAACGCCATGGCACGGAAGAAGCCATGCTGCCTGTGAGCCCCTCAGAGGACACTGAGTCAAAAA

ACCCCACGCGCTGGAGGCGCAGGATGGGAAAAGAAGGTGGCGACCTTCCCCACCCTTCAATCTGGGGCCTGAACTGGAGAT

CAGCTGTGGATCTCCAGAAGAGGGACTAGTGGTTAGAGGAGACCCCCCGGAAAACGCAAAACAGCATATTGACGCTGGGAA

AGACCAGAGACTCCATGAGTTTCCACCACGCTGGCCGCCAGGCACAGATCGCCGAATAGCGGCGGCCGGTGTGGGGAAATCC

ATGGGTCT

KU681082.3 Zika virus isolate Zika virus/*H.sapiens*-tc/PHL/2012/CPC-0740, Philippines, complete genome

SEQ ID NO: 8

AGTTGTTGATCTGTGTGAATCAGACTGCGACAGTTCGAGTTTGAAGCGAAAGCTAGCAACAGTATCAACAGGTTTTATTTTGG

ATTTGGAAACGAGAGTTTCTGGTCATGAAAAACCCAAAAAAGAAATCCGGAGGATTCCGGATTGTCAATATGCTAAAACGCGG

AGTAGCCCGTGTGAGCCCCTTTGGGGGCTTGAAGAGGCTGCCAGCCGGACTTCTGCTGGGCCATGGGCCCATCAGGATGGTC

TGGCGATACTAGCCTTTTTGAGATTCACGGCAATCAAGCCATCACTGGGTCTCATCAATAGATGGGGTTCAGTGGGGAAAAA

AGAGGCTATGGAAATAATAAAGAAGTTCAAGAAAGATCTGGCTGCCATGCTGAGAATAATCAATGCTAGGAAGGAGAAGAA

GAGACGAGGCGCAGATACTAGCGTCGGAATTGTTGGCCTCCTCCTGACCACAGCCATGGCAGTAGAGGTCACTAGACGTGGG

AGTGCATACTATATGTACTTGGACAGAAGCGATGCTGGGGAGGCCATATCTTTTCCAACCACACTGGGGATGAATAAGTGTTA

CATACAAATCATGGATCTTGGACACATGTGTGATGCCACCATGAGCTATGAATGCCCTATGTTGGATGAGGGGGTAGAACCAG

ATGACGTCGATTGCTGGTGCAACACGACATCAACTTGGGTTGTGTATGGAACCTGCCACCACAAAAAAGGTGAAGCACGGAG

ATCTAGAAGAGCTGTGACGCTCCCCTCCCATTCCACTAGGAAGCTGCAAACGCGGTCGCAGACCTGGTTGGAATCAAGAGAAT

-continued

ACACAAAGCACCTGATTAGAGTTGAAAATTGGATATTCAGGAACCCTGGCTTCGCGTTAGCAGCAGCTGTCATCGCTTGGCTTT

TGGGAAGTTCAACGAGCCAAAAAGTCATATATCTGGTCATGATACTGCTGATTGCCCCGGCATACAGCATCAGGTGCATAGGA

GTCAGCAATAGGGACTTTGTGGAAGGTATGTCAGGTGGGACTTGGGTTGATGTTGTCTTGGAACATGGAGGTTGTGTTACCGT

AATGGCACAGGACAAACCGACTGTCGACATAGAGCTGGTTACAACAACAGTCAGCAACATGGCGGAGGTAAGATCCTACTGC

TATGAGGCATCAATATCGGATATGGCTTCGGACAGCCGCTGCCCAACACAAGGTGAGGCCTACCTTGACAAGCAGTCAGACAC

TCAATATGTCTGCAAAAGAACGTTAGTGGACAGAGGCTGGGGAAATGGATGTGGACTTTTTGGCAAAGGGAGCCTGGTGACA

TGCGCTAAGTTTGCATGCTCCAAGAAAATGACCGGGAAGAGCATCCAGCCAGAGAATCTGGAGTACCGGATAATGCTGTCAG

TTCATGGCTCCCAGCACAGTGGGATGATCGTTAATGACACAGGACATGAAACTGATGAGAATAGAGCGAAGGTTGAGATAAC

GCCCAATTCACCAAGAGCCGAAGCCACCCTGGGGGGTTTTGGGAGCCTAGGACTTGATTGTGAACCGAGGACAGGCCTTGAC

TTTTCAGATTTGTATTACCTGACTATGAATAACAAGCACTGGTTGGTTCACAAGGAGTGGTTCCACGACATTCCATTACCTTGGC

ATGCTGGGGCAGACACTGGAACTCCACATTGGAACAACAAAGAAGCACTGGTAGAGTTCAAGGACGCACATGCAAAAAGGCA

AACTGTCGTGGTTCTAGGGAGTCAAGAAGGAGCAGTTCACACGGCCCTTGCTGGAGCTCTGGAGGCTGAGATGGATGGAGCC

AAGGGAAGGCTGTCCTCTGGCCACTTGAAATGTCGCCTGAAAATGGATAAACTTAGATTGAAGGGCGTGTCATACTCCTTGTG

CACTGCAGCGTTCACATTCACCAAGATCCCGGCTGAAACACTGCACGGGACAGTCACAGTGGAGGTACAGTACGCAGGGACA

GATGGACCTTGCAAGGTTCCAGCTCAGATGGCGGTGGATATGCAAACTCTGACCCCAGTTGGGAGGTTGATAACCGCTAACCC

TGTAATCACTGAAAGCACCGAGAACTCTAAGATGATGCTGGAACTTGATCCACCATTTGGGGACTCTTACATTGTCATAGGAGT

CGGGGAGAAGAAGATCACCCATCACTGGCACAGGAGTGGCAGCACCATTGGAAAAGCATTTGAAGCCACTGTGAGAGGTGC

CAAGAGAATGGCAGTCTTGGGAGACACAGCCTGGGACTTTGGATCAGTTGGGGGTGCTCTCAACTCATTGGGCAAGGGCATC

CATCAAATTTTTGGAGCAGCTTTCAAATCATTGTTCGGAGGAATGTCCTGGTTCTCACAAATTCTCATTGGAACGTTGCTGGTGT

GGTTGGGTCTGAATACAAAGAATGGATCTATTTCCCTTACGTGCTTGGCCTTAGGGGGAGTGTTGATCTTCTTATCCACAGCCG

TTTCTGCTGATGTGGGGTGCTCGGTGGACTTCTCAAAGAAGGAAACGAGATGCGGTACAGGGGTGTTCGTCTATAACGACGTT

GAAGCCTGGAGGGACAGGTACAAGTACCATCCTGACTCCCCTCGTAGATTGGCAGCAGCAGTCAAGCAAGCCTGGGAAGATG

GGATCTGTGGGATCTCCTCTGTCTCAAGAATGGAAAACATCATGTGGAGATCAGTAGAAGGGGAGCTCAACGCAATCCTGGA

AGAGAATGGAGTTCAACTGACGGTCGTTGTGGGATCTGTAAAAAACCCCATGTGGAGAGGTCCACAGAGATTGCCCGTGCCT

GTGAACGAGCTGCCCCACGGCTGGAAGGCTTGGGGGAAATCGTACTTCGTCAGAGCAGCAAAGACAAATAACAGCTTTGTCG

TGGATGGTGACACACTGAAGGAATGCCCACTCAAACATAGAGCATGGAACAGCTTTCTTGTGGAGGATCATGGGTTTGGGGT

ATTTCACACTAGTGTCTGGCTCAAGGTTAGAGAAGATTATTCATTAGAGTGTGATCCAGCCGTCATTGGAACAGCTGCTAAGG

GAAAGGAGGCTGTGCACAGCGATCTAGGCTACTGGATTGAGAGTGAGAAGAACGACACATGGAGGCTGAAGAGGGCCCACC

TGATCGAGATGAAAACATGTGAATGGCCAAAGTCCCACACATTGTGGACAGATGGAGTAGAAGAAAGTGATCTGATCATACC

CAAGTCTTTAGCTGGGCCACTCAGCCATCACAACACCAGAGAGGGCTACAGGACTCAAATGAAAGGGCCATGGCACAGTGAA

GAGCTTGAAATTCGGTTTGAGGAATGCCCAGGCACTAAGGTCCACGTGGAGGAAACATGTGGGACAAGAGGACCATCCCTGA

GATCAACCACTGCAAGCGGAAGGGTGATCGAGGAATGGTGCTGCAGGGAATGCACAATGCCCCCACTGTCGTTCCGAGCTAA

AGATGGCTGTTGGTATGGAATGGAGATAAGGCCCAGGAAAGAACCAGAAAGTAACTTAGTAAGGTCAATGGTGACTGCAGG

ATCAACTGATCACATGGATCACTTCTCTCTTGGAGTGCTTGTGATTTTGCTCATGGTGCAGGAAGGGCTGAAGAAGAGAATGA

CCACAAAGATCATCATAAGCACATCAATGGCAGTGCTGGTAGCCATGATCCTGGGAGGATTTTCAATGAGTGACCTGGCTAAG

CTTGCAATTTTGATGGGTGCCACCTTCGCGGAAATGAACACTGGAGGAGATGTAGCTCATTTGGCGCTGATAGCGGCATTCAA

AGTCAGACCTGCGTTGCTGGTATCTTTCATCTTCAGAGCTAATTGGACACCCCGTGAGAGCATGCTGCTGGCCTTGGCCTCGTG

TCTTCTGCAAACTGCGATCTCCGCCTTGGAAGGCGACCTGATGGTTCTCATCAATGGTTTTGCTTTGGCCTGGTTGGCAATACG

AGCGATGGTTGTTCCACGCACTGACAACATCACCTTGGCAATCCTGGCTGCTCTGACACCACTGGCCCGGGGCACACTGCTTGT

GGCGTGGAGAGCAGGCCTTGCTACTTGCGGGGGGTTCATGCTCCTCTCTCTGAAGGGGAAAGGCAGTGTGAAGAAGAACCTA

CCATTTGTCATGGCCTTGGGACTAACTGCTGTGAGGCTGGTCGACCCCATCAACGTGGTGGGACTGCTGTTGCTCACAAGGAG

-continued

TGGGAAGCGGAGCTGGCCCCCTAGTGAAGTACTCACAGCTGTTGGCCTGATATGCGCATTGGCTGGAGGGTTCGCCAAGGCG

GATATAGAGATGGCTGGGCCCATGGCCGCGGTCGGTCTGCTAATTGTCAGTTACGTGGTCTCAGGAAAGAGTGTGGACATGT

ACATTGAAAGAGCAGGTGACATCACATGGGAAAAAGATGCGGAAATCACTGGAAACAGTCCCCGGCTCGATGTGGCACTAGA

TGAGAGTGGTGATTTCTCCCTAGTGGAGGATGATGGTCCACCCATGAGAGAGATCATACTCAAAGTGGTCCTGATGACCATCT

GCGGCATGAACCCAATAGCCATACCCTTTGCAGCTGGAGCGTGGTACGTGTATGTGAAGACTGGAAAAAGGAGTGGTGCTCT

ATGGGATGTGCCTGCTCCCAAGGAAGTAAAAAAGGGGGAGACCACAGATGGAGTGTACAGAGTAATGACTCGTAGACTGCTT

GGTTCAACACAAGTTGGAGTGGGAGTCATGCAAGAGGGGGTCTTCCACACTATGTGGCACGTCACAAAAGGATCCGCGCTGA

GAAGCGGTGAAGGGAGACTTGATCCATACTGGGGAGATGTCAAGCAGGATCTGGTGTCATACTGTGGTCCGTGGAAGCTAGA

CGCCGCCTGGGACGGGCACAGCGAGGTGCAGCTCTTGGCCGTGCCCCCCGGAGAGAGAGCGAGGAACATCCAGACTCTGCC

CGGAACATTTAAGACAAAGGATGGGGACATTGGAGCAGTTGCGCTGGACTACCCAGCAGGAACTTCAGGATCTCCAATCCTA

GACAAGTGTGGGAGAGTGATAGGACTCTATGGTAATGGGGTCGTGATAAAAAATGGGAGTTATGTTAGTGCCATCACCCAAG

GGAGGAGGGAGGAAGAGACTCCTGTTGAGTGCTTCGAGCCTTCGATGCTGAAGAAGAAGCAGCTAACTGTCTTAGACCTGCA

TCCTGGAGCCGGGAAAACCAGGAGAGTTCTTCCTGAAATAGTCCGTGAAGCCATAAAAACAAGACTCCGTACTGTGATCTTAG

CTCCAACCAGGGTCGTCGCTGCTGAAATGGAGGAAGCCCTTAGAGGGCTTCCAGTTCGTTATATGACAACAGCAGTCAATGTC

ACCCATTCTGGGACAGAAATCGTTGACTTAATGTGCCATGCTACCTTCACTTCACGCCTACTACAACCAATCAGAGTCCCCAACT

ATAATTTGTATATTATGGATGAGGCCCACTTCACAGATCCCTCAAGTATAGCAGCAAGAGGATACATTTCAACAAGGGTTGAG

ATGGGCGAGGCGGCTGCCATCTTCATGACCGCCACGCCACCAGGAACCCGTGACGCATTCCCGGACTCCAACTCACCAATTAT

GGACACCGAGGTGGAAGTCCCAGAGAGAGCCTGGAGCACAGGCTTTGATTGGGTGACGGATCATTCTGGGAAAACAGTCTG

GTTTGTTCCAAGCGTGAGGAACGGCAATGAGATCGCAGCTTGTCTGACAAAGGCTGGAAAACGGGTCATACAGCTCAGCAGA

AAGACTTTTGAGACAGAGTTCCAGAAAACGAAAAATCAAGAGTGGGACTTCGTCGTGACAACCGACATTTCAGAGATGGGCG

CCAACTTTAAAGCTGACCGTGTCATAGATTCCAGGAGATGCTTAAAGCCGGTCATACTTGATGGCGAGAGAGTCATTTTGGCT

GGACCCATGCCTGTCACACATGCCAGCGCTGCTCAGAGGAGGGGGCGCATAGGCAGGAATCCCAACAAACCTGGAGATGAGT

ATCTGTATGGAGGTGGGTGCGCAGAGACTGATGAAGATCACGCACACTGGCTTGAAGCAAGAATGCTTCTTGACAACATTTAC

CTCCAAGATGGCCTCATAGCTTCGCTCTATCGACCTGAGGCCGACAAAGTAGCAGCTATTGAGGGAGAGTTCAAGCTTAGGAC

GGAGCAAAGGAAGACCTTTGTGGAACTCATGAAAAGAGGAGATCTTCCGGTTTGGTTGGCCTATCAGGTTGCATCTGCCGGA

ATAACCTACACAGATAGAAGATGGTGCTTTGATGGCATGACCAACAACACCATAATGGAAGACAGTGTGCCGGCAGAGGTGT

GGACCAGATACGGAGAGAAAAGAGTGCTCAAACCGAGGTGGATGGACGCCAGAGTTTGTTCAGATCATGCGGCCCTGAAGT

CATTCAAAGAGTTTGCCGCTGGGAAAAGAGGAGCGGCCTTTGGAGTGATAGAAGCCCTGGGAACACTGCCAGGACACATGAC

AGAGAGATTCCAGGAAGCCATTGACAACCTCGCTGTGCTCATGCGGGCAGAGACTGGAAGCAGGCCTTACAAAGCCGCGGCG

GCCCAATTGCCGGAGACCCTAGAGACCATTATGCTTTTGGGGTTGCTGGGAACAGTCTCGCTGGGAATCTTTTTCGTCTTGATG

CGGAACAAGGGCATGGGGAAGATGGGCTTTGGAATGGTGACTCTTGGGGCCAGCGCATGGCTTATGTGGCTCTCGGAAATTG

AGCCAGCCAGAATTGCATGTGTCCTCATTGTCGTGTTCCTATTGCTGGTGGTGCTCATACCTGAGCCAGAAAAGCAAAGATCTC

CTCAGGACAACCAAATGGCAATCATCATCATGGTAGCAGTGGGTCTTCTGGGCTTGATTACCGCCAATGAACTCGGATGGTTG

GAGAGAACAAAAAGTGACCTAAGCCATCTAATGGGAAGGAGAGAGGAGGGGGCAACCACAGGATTCTCAATGGACATTGAC

CTGCGGCCAGCCTCAGCTTGGGCTATCTATGCTGCTCTGACAACTTTCATCACCCCAGCCGTCCAACATGCGGTGACCACTTCAT

ACAACAACTACTCCTTAATGGCGATGGCCACGCAAGCTGGGGTGTTGTTTGGTATGGGCAAAGGGATGCCATTCTACGCATGG

GACTTTGGAGTCCCGCTGCTAATGATGGGTTGCTACTCACAATTAACACCTCTGACCCTAATAGTGGCCATCATTTTGCTCGTG

GCGCACTACATGTACTTGATCCCAGGGCTGCAGGCAGCAGCTGCGCGGGCTGCCCAGAAGAGAACGGCAGCTGGCATCATGA

AGAACCCTGTTGTGGATGGAATAGTGGTGACTGACATTGACACAATGACAATTGACCCCCAAGTGGAAAAAAAGATGGGGCA

GGTGCTACTCATAGCAGTAGCCGTCTCCAGCGCCATACTGTCGCGGACCGCCTGGGGGTGGGGGGAGGCTGGGGCCCTGATC

-continued

ACAGCTGCAACTTCCACCTTGTGGGAAGGCTCTCCGAACAAGTACTGGAACTCCTCCACAGCCACTTCACTGTGTAACATTTTTA

GGGGAAGTTACTTGGCTGGAGCTTCTCTAATCTACACAGTAACAAGAAACGCTGGCTTGGTCAAGAGACGTGGGGGTGGAAC

GGGAGAGACCCTGGGAGAGAAATGGAAGGCCCGCCTGAACCAGATGTCGGCCCTGGAGUCTACTCCTACAAAAAGTCAGGC

ATCACCGAGGTGTGCAGAGAAGAGGCCCGCCGTGCCCTCAAGGACGGTGTGGCAACAGGAGGCCATGCTGTGTCCCGAGGA

AGTGCAAAGCTTAGATGGCTGGTGGAGAGAGGATACCTGCAGCCCTATGGAAAGGTCATTGATCTTGGATGTGGCAGAGGG

GGCTGGAGTTACTATGCCGCCACCATCCGCAAAGTTCAGGAAGTGAAAGGATACACAAAAGGAGGCCCTGGTCATGAAGAAC

CCATGTTGGTGCAAAGCTATGGGTGGAACATAGTCCGTCTTAAGAGTGGGGTGGACGTCTTTCACATGGCGGCTGAGCCGTG

TGACACTTTGCTGTGTGATATAGGTGAGTCATCATCTAGTCCTGAAGTGGAAGAAGCACGGACGCTCAGAGTCCTCTCCATGG

TGGGGGATTGGCTTGAAAAAAGACCAGGAGCCTTTTGTATAAAAGTGTTGTGCCCATACACCAGCACTATGATGGAAACCCTG

GAGCGACTGCAGCGTAGGTATGGGGGAGGACTGGTCAGGGTGCCACTCTCCCGCAACTCTACACATGAGATGTACTGGGTCT

CTGGAGCGAAAAGCAACACCATAAAAAGTGTGTCCACCACGAGCCAGCTCCTCTTGGGGCGCATGGACGGGCCCAGGAGGCC

AGTGAAATATGAGGAGGATGTGAATCTCGGCTCTGGCACGCGGGCTGTGGTAAGCTGCGCTGAAGCTCCCAACATGAAGATC

ATTGGTAACCGCATTGAGAGGATCCGCAGTGAGCACGCGGAAACGTGGTTCTTTGACGAGAACCACCCATATAGGACATGGG

CTTACCATGGAAGCTATGAGGCCCCTACACAAGGGTCAGCGTCCTCTCTAATAAACGGGGTTGTCAGGCTCCTGTCAAAACCCT

GGGATGTGGTGACTGGAGTCACAGGAATAGCCATGACTGACACCACACCGTATGGTCAGCAAAGAGTTTTCAAGGAAAAAGT

GGACACTAGGGTGCCAGACCCCCAAGAAGGCACTCGTCAGGTTATGAGCATGGTCTCTTCCTGGTTATGGAAGGAGCTAGGC

AAACACAAACGGCCACGAGTCTGTACCAAAGAAGAGTTCATCAACAAGGTTCGTAGCAATGCAGCATTAGGGGCAATATTTGA

AGAGGAAAAAGAGTGGAAGACTGCAGTGGAAGCTGTGAATGATCCAAGGTTCTGGGCTCTAGTGGACAAGGAAAGAGAGCA

TCACCTGAGAGGAGAGTGTCAGAGCTGTGTGTACAACATGATGGGAAAAAGAGAAAAGAAACAAGGGGAATTTGGAAAGGC

CAAGGGCAGCCGCGCCATCTGGTATATGTGGCTAGGGGCTAGATTCCTAGAGTTCGAAGCCCTTGGATTCTTGAATGAGGATC

ATTGGATGGGGAGAGAGAATTCAGGAGGTGGTGTTGAAGGACTGGGATTACAAAGACTCGGATATGTCCTAGAAGAGATGA

GTCGCATACCAGGAGGAAGGATGTATGCAGATGATACTGCTGGCTGGGACACCCGCATCAGCAGGTTTGATCTGGAGAATGA

AGCTCTAATCACCAACCAAATGGAGAAAGGGCACAGGGCCTTGGCATTGGCCATAATCAAGTACACATACCAAAACAAAGTG

GTAAAGGTCCTTAGACCAGCTGAAAAAGGGAAGACAGTTATGGACATTATTTCAAGACAAGACCAAAGGGGGAGCGGACAA

GTTGTCACTTACGCTCTTAATACATTCACCAACCTGGTGGTGCAGCTCATTCGGAATATGGAGGCTGAGGAAGTTCTAGAGATG

CAAGACTTGTGGCTGCTGCGGAGGCCAGAGAAAGTGACCAACTGGTTGCAAAGCAACGGATGGGATAGGCTCAAAAGAATG

GCAGTCAGTGGAGATGATTGCGTTGTGAAACCAATTGATGATAGGTTTGCACATGCCCTCAGGTTCTTGAATGATATGGGAAA

AGTTAGGAAGGACACACAAGAGTGGAAACCCTCAACTGGATGGGACAACTGGGAAGAAGTTCCGTTTTGCTCCCACCACTTCA

ACAAACTCCATCTTAAGGACGGGAGGTCCATTGTGGTTCCCTGCCGCCACCAAGATGAACTGATTGGCCGAGCCCGCGTATCA

CCAGGGGCGGGATGGAGCATCCGGGAGACTGCTTGCCTAGCAAAATCATATGCGCAAATGTGGCAGCTCCTTTATTTCCACAG

AAGGGACCTCCGACTGATGGCCAATGCCATTTGTTCATCTGTGCCAGTTGATTGGGTTCCAACTGGGAGAACTACCTGGTCAAT

CCATGGAAAGGGAGAATGGATGACCACTGAAGACATGCTTGTGGTATGGAACAGAGTGTGGATTGAGGAAAACGACCACAT

GGAAGACAAGACCCCAGTTACAAAATGGACAGACATTCCCTATTTGGGAAAAAGAGAAGACTTGTGGTGTGGATCTCTCATAG

GGCACAGACCGCGTACTACCTGGGCTGAGAACATCAAAAATACAGTCAACATGATGCGCAGGATCATAGGTGATGAAGAAAA

GTACATGGACTACCTATCCACCCAGGTTCGCTACTTGGGTGAAGAAGGGTCCACACCTGGAGTGCTGTAAGCACCAATCTTAG

TGTTGTCAGGCCTGCTAGTCAGCCACAGCTTGGGGAAAGCTGTGCAGCCTGTGACCCCCCCAGGAGAAGCTGGGAAACCAAG

CCTATAGTCAGGCCGAGAACGCCATGGCACGGAAGAAGCCATGCTGCCTGTGAGCCCCTCAGAGGACACTGAGTCAAAAAAC

CCCACGCGCTTGGAGGCGCAGGATGGGAAAAGAAGGTGGCGACCTTCCCCACCCTTCAATCTGGGGCCTGAACTGGAGATCA

GCTGTGGATCTCCAGAAGAGGGACTAGTGGTTAGAGGAGACCCCCCGGAAAACGCAAAACAGCATATTGACGCTGGGAAAG

ACCAGAGACTCCATGAGTTTCCACCACGCTGGCCGCCAGGCACAGATCGCCGAATAGCGGCGGCCGGTGTGGGGAAATCCAT

GGGTCT

-continued

KU707826.1 Zika virus isolate SSABR1, Brazil, complete genome

SEQ ID NO: 9

GACAGTTCGAGTTTGAAGCGAAAGCTAGCAACAGTATCAACAGGTTTTATTTGGATTTGGAAACGAGAGTTTCTGGTCATGAA

AAACCCAAAAAAGAAATCCGGAGGATTCCGGATTGTCAATATGCTAAAACGCGGAGTAGCCCGTGTGAGCCCCTTTGGGGGC

TTGAAGAGGCTGCCAGCCGGACTTCTGCTGGGTCATGGGCCCATCAGGATGGTCTTGGCGATTCTAGCCTTTTTGAGATTCAC

GGCAATCAAGCCATCACTGGGTCTCATCAATAGATGGGGTTCAGTGGGGAAAAAAGAGGCTATGGAAATAATAAAGAAGTTC

AAGAAAGATCTGGCTGCCATGCTGAGAATAATCAATGCTAGGAAGGAGAAGAAGAGACGAGGCGCAGATACTAGTGTCGGA

ATTGTTGGCCTCCTGCTGACCACAGCTATGGCAGCGGAGGTCACTAGACGTGGGAGTGCATACTATATGTACTTGGACAGAAA

CGATGCTGGGGAGGCCATATCTTTTCCAACCACATTGGGGATGAATAAGTGTTATATACAGATCATGGATCTTGGACACATGT

GTGATGCCACCATGAGCTATGAATGCCCTATGCTGGATGAGGGGGTGGAACCAGATGACGTCGATTGTTGGTGCAACACGAC

GTCAACTTGGGTTGTGTACGGAACCTGCCATCACAAAAAAGGTGAAGCACGGAGATCTAGAAGAGCTGTGACGCTCCCCTCCC

ATTCCACTAGGAAGCTGCAAACGCGGTCGCAAACCTGGTTGGAATCAAGAGAATACACAAAGCACTTGATTAGAGTCGAAAAT

TGGATATTCAGGAACCCTGGCTTCGCGTTAGCAGCAGCTGCCATCGCTTGGCTTTTGGGAAGCTCAACGAGCCAAAAAGTCAT

ATACTTGGTCATGATACTGCTGATTGCCCCGGCATACAGCATCAGGTGCATAGGAGTCAGCAATAGGGACTTTGTGGAAGGTA

TGTCAGGTGGGACCTGGGTTGATGTTGTCTTGGAACATGGAGGTTGTGTCACCGTAATGGCACAGGACAAACCGACTGTCGA

CATAGAGCTGGTTACAACAACAGTCAGCAACATGGCGGAGGTAAGATCCTACTGCTATGAGGCATCAATATCAGACATGGCTT

CGGACAGCCGCTGCCCAACACAAGGTGAAGCCTACCTTGACAAGCAATCAGACACTCAATATGTCTGCAAAAGAACGTTAGTG

GACAGAGGCTGGGGAAATGGATGTGGACTTTTTGGCAAAGGGAGCCTGGTGACATGCGCTAAGTTTGCATGCTCCAAGAAAA

TGACCGGGAAGAGCATCCAGCCAGAGAATCTGGAGTACCGGATAATGCTGTCAGTTCATGGCTCCCAGCACAGTGGGATGAT

TGTTAATGACACAGGACATGAAACTGATGAGAATAGAGCGAAAGTTGAGATAACGCCCAATTCACCAAGAGCCGAAGCCACC

CTGGGGGGTTTTGGAAGCCTAGGACTTGATTGTGAACCGAGGACAGGCCTTGACTTTTCAGATTTGTATTACTTGACTATGAAT

AACAAGCACTGGTTGGTTCACAAGGAGTGGTTCCACGACATTCCATTACCTTGGCACGCTGGGGCAGACACCGGAACTCCACA

CTGGAACAACAAAGAAGCACTGGTAGAGTTCAAGGACGCACATGCCAAAAGGCAAACTGTCGTGGTTCTAGGGAGTCAAGAA

GGAGCAGTTCACACGGCCCTTGCTGGAGCTCTGGAGGCTGAGATGGATGGTGCAAAGGGAAGGCTGTCCTCTGGCCACTTGA

AATGTCGCCTGAAAATGGATAAACTTAGATTGAAGGGCGTGTCATACTCCTTGTGTACTGCAGCGTTCACATTCACCAAGATCC

CGGCTGAAACACTGCACGGGACAGTCACAGTGGAGGTACAGTACGCAGGGACAGATGGACCTTGCAAGGTTCCAGCTCAGAT

GGCGGTGGACATGCAAACTCTGACCCCAGTTGGGAGGTTGATAACCGCTAACCCCGTAATCACTGAAAGCACTGAGAACTCTA

AGATGATGCTGGAACTTGATCCACCATTTGGGGACTCTTACATTGTCATAGGAGTCGGGGAGAAGAAGATCACCCACCACTGG

CACAGGAGTGGCAGCACCATTGGAAAAGCATTTGAAGCCACTGTGAGAGGTGCCAAGAGAATGGCAGTCTTGGGAGACACA

GCCTGGGACTTTGGATCAGTTGGAGGCGCTCTCAACTCATTGGGCAAGGGCATCCATCAAATTTTTGGAGCAGCTTTCAAATCA

TTGTTTGGAGGAATGTCCTGGTTCTCACAAATTCTCATTGGAACGTTGCTGATGTGGTTGGGTCTGAACACAAAGAATGGATCT

ATTTCCCTTATGTGCTTGGCCTTAGGGGGAGTGTTGATCTTCTTATCCACAGCCGTCTCTGCTGATGTGGGGTGCTCGGTGGAC

TTCTCAAAGAAGGAGACGAGATGCGGTACAGGGGTGTTCGTCTATAACGACGTTGAAGCCTGGAGGGACAGGTACAAGTACC

ATCCTGACTCCCCCCGTAGATTGGCAGCAGCAGTCAAGCAAGCCTGGGAAGATGGTATCTGCGGGATCTCCTCTGTTTCAAGA

ATGGAAAACATCATGTGGAGATCAGTAGAAGGGGAGCTCAACGCAATCCTGGAAGAGAATGGAGTTCAACTGACGGTCGTTG

TGGGATCTGTAAAAAACCCCATGTGGAGAGGTCCACAGAGATTGCCCGTGCCTGTGAACGAGCTGCCCCACGGCTGGAAGGC

TGGGGGAAATCGTACTTCGTCAGAGCAGCAAAGACAAATAACAGCTTTGTCGTGGATGGTGACACACTGAAGGAATGCCCA

CTCAAACATAGAGCATGGAACAGCTTTCTTGTGGAGGATCATGGGTTCGGGGTATTTCACACTAGTGTCTGGCTCAAGGTTAG

AGAAGATTATTCATTAGAGTGTGATCCAGCCGTTATTGGAACAGCTGTTAAGGGAAAGGAGGCTGTACACAGTGATCTAGGCT

ACTGGATTGAGAGTGAGAAGAATGACACATGGAGGCTGAAGAGGGCCCATCTGATCGAGATGAAAACATGTGAATGGCCAA

AGTCCCACACATTGTGGACAGATGGAATAGAAGAGAGTGATCTGATCATACCCAAGTCTTTAGCTGGGCCACTCAGCCATCAC

-continued

AATACCAGAGAGGGCTACAGGACCCAAATGAAAGGGCCATGGCACAGTGAAGAGCTTGAAATTCGGTTTGAGGAATGCCCA

GGCACTAAGGTCCACGTGGAGGAAACATGTGGAACAAGAGGACCATCTCTGAGATCAACCACTGCAAGCGGAAGGGTGATC

GAGGAATGGTGCTGCAGGGAGTGCACAATGCCCCCACTGTCGTTCCGGGCTAAAGATGGCTGTTGGTATGGAATGGAGATAA

GGCCCAGGAAAGAACCAGAAAGCAACTTAGTAAGGTCAATGGTGACTGCAGGATCAACTGATCACATGGACCACTTCTCCCTT

GGAGTGCTTGTGATTCTGCTCATGGTGCAGGAAGGGCTGAAGAAGAGAATGACCACAAAGATCATCATAAGCACATCAATGG

CAGTGCTGGTAGCTATGATCCTGGGAGGATTTTCAATGAGTGACCTGGCTAAGCTTGCAATTTTGATGGGTGCCACCTTCGCG

GAAATGAACACTGGAGGAGATGTAGCTCATCTGGCGCTGATAGCGGCATTCAAAGTCAGACCAGCGTTGCTGGTATCTTTCAT

CTTCAGAGCTAATTGGACACCCCGTGAAAGCATGCTGCTGGCCTTGGCCTCGTGTCTTTTGCAAACTGCGATCTCCGCCTTGGA

AGGCGACCTGATGGTTCTCATCAATGGTTTTGCTTTGGCCTGGTTGGCAATACGAGCGATGGTTGTTCCACGCACTGATAACAT

CACCTTGGCAATCCTGGCTGCTCTGACACCACTGGCCCGGGGCACACTGCTTGTGGCGTGGAGAGCAGGCCTTGCTACTTGCG

GGGGGTTTATGCTCCTCTCTCTGAAGGGAAAAGGCAGTGTGAAGAAGAACTTACCATTTGTCATGGCCCTGGGACTAACCGCT

GTGAGGCTGGTCGACCCCATCAACGTGGTGGGACTGCTGTTGCTCACAAGGAGTGGGAAGCGGAGCTGGCCCCCTAGCGAA

GTACTCACAGCTGTTGGCCTGATATGCGCATTGGCTGGAGGGTTCGCCAAGGCAGATATAGAGATGGCTGGGCCCATGGCCG

CGGTCGGTCTGCTAATTGTCAGTTACGTGGTCTCAGGAAAGAGTGTGGACATGTACATTGAAAGAGCAGGTGACATCACATG

GGAAAAAGATGCGGAAGTCACTGGAAACAGTCCCCGGCTCGATGTGGCGCTAGATGAGAGTGGTGATTTCTCCCTGGTGGAG

GATGACGGTCCCCCCATGAGAGAGATCATACTCAAGGTGGTCCTGATGACCATCTGTGGCATGAACCCAATAGCCATACCCTTT

GCAGCTGGAGCGTGGTACGTATACGTGAAGACTGGAAAAAGGAGTGGTGCTCTATGGGATGTGCCTGCTCCCAAGGAAGTAA

AAAAGGGGGAGACCACAGATGGAGTGTACAGAGTAATGACTCGTAGACTGCTAGGTTCAACACAAGTTGGAGTGGGAGTTA

TGCAAGAGGGGGTCTTTCACACTATGTGGCACGTCACAAAAGGATCCGCGCTGAGAAGCGGTGAAGGGAGACTTGATCCATA

CTGGGGAGATGTCAAGCAGGATCTGGTGTCATACTGTGGTCCATGGAAGCTAGATGCCGCCTGGGACGGGCACAGCGAGGT

GCAGCTCTTGGCCGTGCCCCCCGGAGAGAGAGCGAGGAACATCCAGACTCTGCCCGGAATATTTAAGACAAAGGATGGGGAC

AUGGAGCGGUGCGCTGGAUACCCAGCAGGAACUCAGGATCTCCAATCCTAGACAAGTGTGGGAGAGTGATAGGACTUA

TGGCAATGGGGTCGTGATCAAAAATGGGAGTTATGTTAGTGCCATCACCCAAGGGAGGAGGGAGGAAGAGACTCCTGTTGA

GTGCTTCGAGCCTTCGATGCTGAAGAAGAAGCAGCTAACTGTCTTAGACTTGCATCCTGGAGCTGGGAAAACCAGGAGAGTTC

TTCCTGAAATAGTCCGTGAAGCCATAAAAACAAGACTCCGTACTGTGATCTTAGCTCCAACCAGGGTTGTCGCTGCTGAAATGG

AGGAGGCCCTTAGAGGGCTTCCAGTGCGTTATATGACAACAGCAGTCAATGTCACCCACTCTGGAACAGAAATCGTCGACTTA

ATGTGCCATGCCACCTTCACTTCACGTCTACTACAGCCAATCAGAGTCCCCAACTATAATCTGTATATTATGGATGAGGCCCACT

TCACAGATCCCTCAAGTATAGCAGCAAGAGGATACATTTCAACAAGGGTTGAGATGGGCGAGGCGGCTGCCATCTTCATGACC

GCCACGCCACCAGGAACCCGTGACGCATTTCCGGACTCCAACTCACCAATTATGGACACCGAAGTGGAAGTCCCAGAGAGAGC

CTGGAGCTCAGGCTTTGATTGGGTGACGGATCATTCTGGAAAAACAGTTTGGTTTGTTCCAAGCGTGAGGAACGGCAATGAG

ATCGCAGCTTGTCTGACAAAGGCTGGAAAACGGGTCATACAGCTCAGCAGAAAGACTTTTGAGACAGAGTTCCAGAAAACAA

AACATCAAGAGTGGGACTTTGTCGTGACAACTGACATTTCAGAGATGGGCGCCAACTTTAAAGCTGACCGTGTCATAGATTCC

AGGAGATGCCTAAAGCCGGTCATACTTGATGGCGAGAGAGTCATTCTGGCTGGACCCATGCCTGTCACACATGCCAGCGCTGC

CCAGAGGAGGGGGCGCATAGGCAGGAATCCCAACAAACCTGGAGATGAGTATCTGTATGGAGGTGGGTGCGCAGAGACTGA

CGAAGACCATGCACACTGGCTTGAAGCAAGAATGCTCCTTGACAATATTTACCTCCAAGATGGCCTCATAGCCTCGCTCTATCG

ACCTGAGGCCGACAAAGTAGCAGCCATTGAGGGAGAGTTCAAGCTTAGGACGGAGCAAAGGAAGACCTTTGTGGAACTCATG

AAAAGAGGAGATCTTCCTGTTTGGCTGGCCTATCAGGTTGCATCTGCCGGAATAACCTACACAGATAGAAGATGGTGCTTTGA

TGGCACGACCAACAACACCATAATGGAAGACAGTGTGCCGGCAGAGGTGTGGACCAGACACGGAGAGAAAAGAGTGCTCAA

ACCGAGGTGGATGGACGCCAGAGTTTGTTCAGATCATGCGGCCCTGAAGTCATTCAAGGAGTTTGCCGCTGGGAAAAGAGGA

GCGGCTTTTGGAGTGATGGAAGCCCTGGGAACACTGCCAGGACACATGACAGAGAGATTCCAGGAAGCCATTGACAACCTCG

CTGTGCTCATGCGGGCAGAGACTGGAAGCAGGCCTTACAAAGCCGCGGCGGCCCAATTGCCGGAGACCCTAGAGACCATTAT

-continued

GCTTTTGGGGTTGCTGGGAACAGTCTCGCTGGGAATCTTCTTCGTCTTGATGAGGAACAAGGGCATAGGGAAGATGGGCTTT

GGAATGGTGACTCTTGGGGCCAGCGCATGGCTCATGTGGCTCTCGGAAATTGAGCCAGCCAGAATTGCATGTGTCCTCATTGT

TGTGTTTCTATTGCTGGTGGTGCTCATACCTGAGCCAGAAAAGCAAAGATCTCCCCAGGACAACCAAATGGCAATCATCATCAT

GGTAGCAGTAGGTCTTCTGGGCTTGATTACCGCCAATGAACTCGGATGGTTGGAGAGAACAAAGAGTGACCTAAGCCATCTA

ATGGGAAGGAGAGAGGAGGGGGCAACCATAGGATTCTCAATGGACATTGACCTGCGGCCAGCCTCAGCTTGGGCCATCTATG

CTGCCTTGACAACTTTCATTACCCCAGCCGTCCAACATGCAGTGACCACTTCATACAACAACTACTCCTTAATGGCGATGGCCAC

GCAAGCTGGAGTGTTGTTTGGTATGGGCAAAGGGATGCCATTCTACGCATGGGACTTTGGAGTCCCGCTGCTAATGATAGGTT

GCTACTCACAATTAACACCCCTGACCCTAATAGTGGCCATCATTTTGCTCGTGGCGCACTACATGTACTTGATCCCAGGGCTGCA

GGCAGCAGCTGCGCGTGCTGCCCAGAAGAGAACGGCAGCTGGCATCATGAAGAACCCTGTTGTGGATGGAATAGTGGTGACT

GACATTGACACAATGACAATTGACCCCCAAGTGGAGAAAAAGATGGGACAGGTGCTACTCATAGCAGTAGCCGTCTCCAGCG

CCATACTGTCGCGGACCGCCTGGGGGTGGGGGGAGGCTGGGGCCCTGATCACAGCCGCAACTTCCACTTTGTGGGAAGGCTC

TCCGAACAAGTACTGGAACTCCTCTACAGCCACTTCACTGTGTAACATTTTTAGGGGAAGTTACTTGGCTGGAGCTTCTCTAATC

TACACAGTAACAAGAAACGCTGGCTTGGTCAAGAGACGTGGGGGTGGAACAGGAGAGACCCTGGGAGAGAAATGGAAGGC

CCGCTTGAACCAGATGTCGGCCCTGGAGTTCTACTCCTACAAAAAGTCAGGCATCACCGAGGTGTGCAGAGAAGAGGCCCGC

CGCGCCCTCAAGGACGGTGTGGCAACGGGAGGCCATGCTGTGTCCCGAGGAAGTGCAAAGCTGAGATGGTTGGTGGAGCGG

GGATACCTGCAGCCCTATGGAAAGGTCATTGATCTTGGATGTGGCAGAGGGGGCTGGAGTTACTACGCCGCCACCATCCGCA

AAGTTCAAGAAGTGAAAGGATACACAAAAGGAGGCCCTGGTCATGAAGAACCCGTGTTGGTGCAAAGCTATGGGTGGAACAT

AGTCCGTCTTAAGAGTGGGGTGGACGTCTTTCATATGGCGGCTGAGCCGTGTGACACGTTGCTGTGTGACATAGGTGAGTCAT

CATCTAGTCCTGAAGTGGAAGAAGCACGGACGCTCAGAGTCCTCTCCATGGTGGGGGATTGGCTTGAAAAAAGACCAGGAGC

CTTTTGTATAAAGGTGTTGTGCCCATACACCAGCACTATGATGGAAACCCTGGAGCGACTGCAGCGTAGGTATGGGGGAGGA

CTGGTCAGAGTGCCACTCTCCCGCAACTCTACACATGAGATGTATTGGGTCTCTGGAGCGAAAAGCAACACCATAAAAAGTGT

GTCCACCACGAGCCAGCTCCTCTTGGGGCGCATGGACGGGCCTAGGAGGCCAGTGAAATATGAGGAGGATGTGAATCTCGGC

TCTGGCACGCGGGCTGTGGTAAGCTGCGCTGAAGCTCCCAACATGAAGATCATTGGTAACCGCATTGAAAGGATCCGCAGTG

AGCACGCGGAAACGTGGTTCTTTGACGAGAACCACCCATATAGGACATGGGCTTACCATGGAAGCTATGAGGCCCCCACACAA

GGGTCAGCGTCCTCTCTAATAAACGGGGTTGTCAGGCTCCTGTCAAAACCCTGGGATGTGGTGACTGGAGTCACAGGAATAGC

CATGACCGACACCACACCGTATGGTCAGCAAAGAGTTTTCAAGGAAAAAGTGGACACTAGGGTGCCAGACCCCCAAGAAGGC

ACTCGTCAGGTTATGAGCATGGTCTCTTCCTGGTTGTGGAAAGAGCTAGGCAAACACAAACGGCCACGAGTCTGTACCAAAGA

AGAGTTCATCAACAAGGTTCGTAGCAATGCAGCATTAGGGGCAATATTTGAAGAGGAAAAAGAGTGGAAGACTGCAGTGGA

AGCTGTGAACGATCCAAGGTTCTGGGCTCTAGTGGATAAGGAAAGAGAGCACCACCTGAGAGGAGAGTGCCAGAGTTGTGT

GTACAACATGATGGGAAAAAGAGAAAAGAAACAAGGGGAATTTGGAAAGGCCAAGGGCAGCCGCGCCATCTGGTATATGTG

GCTAGGGGCTAGATTTCTAGAGTTCGAAGCCCTTGGATTCTTGAACGAGGATCACTGGATGGGGAGAGAGAACTCAGGAGGT

GGTGTTGAAGGGCTGGGATTACAAAGACTCGGATATGTCCTAGAAGAGATGAGTCGTATACCAGGAGGAAGGATGTATGCA

GATGACACTGCTGGCTGGGACACCCGCATCAGCAGGTTTGATCTGGAGAATGAAGCTCTAATCACCAACCAAATGGAAAAAG

GGCACAGGGCCTTGGCATTGGCCATAATCAAGTACACATACCAAAACAAAGTGGTAAAGGTCCTTAGACCAGCTGAAAAAGG

GAAAACAGTTATGGACATTATTTCGAGACAAGACCAAAGGGGGAGCGGACAAGTTGTCACTTACGCTCTTAACACATTTACCA

ACCTAGTGGTGCAACTCATTCGGAATATGGAGGCTGAGGAAGTTCTAGAGATGCAAGACTTGTGGCTGCTGCGGAGGTCAGA

GAAAGTGACCAACTGGTTGCAGAGCAACGGATGGGATAGGCTCAAACGAATGGCAGTCAGTGGAGATGATTGCGTTGTGAA

GCCAATTGATGATAGGTTTGCACATGCCCTCAGGTTCTTGAATGATATGGGAAAAGTTAGGAAGGACACACAAGAGTGGAAA

CCCTCAACTGGATGGGACAACTGGGAAGAAGTTCCGTTTTGCTCCCACCACTTCAACAAGCTCCATCTCAAGGACGGGAGGTC

CATTGTGGTTCCCTGCCGCCACCAAGATGAACTGATTGGCCGGGCCCGCGTCTCTCCAGGGGCGGGATGGAGCATCCGGGAG

-continued

ACTGCTTGCCTAGCAAAATCATATGCGCAAATGTGGCAGCTCCTTTATTTCCACAGAAGGGACCTCCGACTGATGGCCAATGCC

ATTTGTTCATCTGTGCCAGTTGACTGGGTTCCAACTGGGAGAACTACCTGGTCAATCCATGGAAAGGGAGAATGGATGACCAC

TGAAGACATGCTTGTGGTGTGGAACAGAGTGTGGATTGAGGAGAACGACCACATGGAAGACAAGACCCCAGTTACGAAATG

GACAGACATCCCCTATTTGGGAAAAAGGGAAGACTTGTGGTGTGGATCTCTCATAGGGCACAGACCGCGCACCACCTGGGCT

GAGAACATTAAAAACACAGTCAACATGGTGCGCAGGATCATAGGTGATGAAGAAAAGTACATGGACTACCTATCCACCCAAG

TCGCTACTTGGGTGAAGAAGGGTCTACACCTGGAGTGCTGTAAGCACCAGTCTTAATGTTGTCAGGCCTGCTAGTCAGCCAC

AGCTTGGGGAAAGCTGTGCAGCCTGTGACCCCCCCAGGAGAAGCTGGGAAACCAAGCCTATAGTCAGGCCGAGAACGCCATG

GCACGGAAGAAGCCATGCTGCCTGTGAGCCCCTCAGAGGACACTGAGTCAAAAAACCCCACGCGCTTGGAGGCGCAGGATG

GGAAAAGAAGGTGGCGACCTTCCCCACCCTTCAATCTGGGGCCTGAACTGGAGATCAGCTGTGGATCTCCAGAAGAGGGACT

AGTGGTTAGAGGAG

KU744693.1 Zika virus isolate VE_Ganxian, China, complete genome

SEQ ID NO: 10

GTTGTTACTGTTGCTGACTCAGACTGCGACAGTTCGAGTTTGAAGCGAAAGCTAGCAACAGTATCAACAGGTTTTATTTGGATT

TGGAAACGAGAGTTTCTGGTCATGAAAAACCCAAAAAAGAAATCCGGAGGATTCCGGATTGTCAATATGCTAAAACGCGGAG

TAGCCCGTGTGAGCCCCTTTGGGGGCTTGAAGAGGCTGCCAGCCGGACTTCTGCTGGGTCATGGGCCCATCAGGATGGTCTTG

GCAATTCTAGCCTTTTTGAGATTCACGGCAATCAAGCCATCACTGGGTCTCATCAATAGATGGGGTTCAGTGGGGAAAAAAGA

TGCTATGGAAATAATAAAGAAGTTCAAGAAAGATCTGGCTGCCATGCTGAGAATAATCAATGCTAGGAAGGAGAAGAAGAGA

CGAGGCGCAGATACTAGTGTCGGAATTGTTGGCCTCCTGCTGACCACAGCTATGGCAGCGGAGGTCACTAGACGTGGGAGTG

CATACTATATGTACTTGGACAGAAACGATGCTGGGGAGGCCATATCTTTTCCAACCACATTGGGGATGAATAAGTGTTATATAC

AGATCATGGATCTTGGACACATGTGTGATGCCACCATGAGCTATGAATGCCCTATGCTGGATGAGGGGGTGGAACCAGATGA

CGTCGATTGTTGGTGCAACACGACGTCAACTTGGGTTGTGTACGGAACCTGCCATCACAAAAAAGGTGAAGCACGGAGATCTA

GAAGAGCTGTGACGCTCCCTTCCCATTCCACTAGGAAGCTGCAAACGCGGTCGCAAACCTGGTTGGAATCAAGAGAATACACA

AAGCACTTGATTAGAGTCGAAAATTGGATATTCAGGAACCCTGGCTTCGCGTTAGCAGCAGCTGCCATCGCTTGGCTTTTGGG

AAGCTCAACGAGCCAAAAAGTCATATACTTGGTCATGATACTGCTGATTGCCCCGGCATACAGCATCAGGTGCATAGGAGTCA

GCAATAGGGACTTTGTGGAAGGTATGTCAGGTGGGACTTGGGTTGATGTTGTCTTGGAACATGGAGGTTGTGTCACCGCAAT

GGCACAGGACAAACCGACTGTCGACATAGAGCTGGTTACAACAACAGTCAGCAACATGGCGGAGGTAAGATCCTACTGCTAT

GAGGCATCAATATCAGACATGGCTTCGGACAGCCGCTGCCCAACACAAGGTGAAGCCTACCTTGACAAGCAATCAGACACTCA

ATATGTTTGCAAAAGAACGTTAGTGGACAGAGGCTGGGGAAATGGATGTGGACTTTTTGGCAAAGGGAGTCTGGTGACATGC

GCTAAGTTTGCATGCTCCAAGAAAATGACCGGGAAGAGCATCCAGCCAGAGAATCTGGAGTACCGGATAATGCTGTCAGTTC

ATGGCTCCCAGCACAGTGGGATGCTCGTTAATGACACAGGACATGAAACTGATGAGAATAGAGCGAAGGTTGAGATAACGCC

CAATTCACCAAGAGCCGAAGCCACCCTGGGGGGTTTTGGAAGCCTAGGACTTGATTGTGAACCGAGGACAGGCCTTGACTTTT

CAGATTTGTATTACTTGACTATGAATAACAAGCACTGGTTGGCTCACAAGGAGTGGTTCCACGACATTCCATTACCTTGGCACG

CTGGGGCAGCCACCGGAACTCCACACTGGAACAACAAAGAAGCACTGGTAGAGTTCAAGGACGCACATGCCAAAAGGCAAAC

TGTCGTGGTTCTAGGGAGTCAAGAAGGAGCAGTTCACACGGCCCTTGCTGGAGCTCTGGAGGCTGAGATGGATGGTGCAAAG

GGAAGGCTGTCCTCTGGCCACTTGAAATGTCGCCTGAAAATGGATAAACTTAGATTGAAGGGCGTGTCATACTCCTTGTGTAC

CGCAGCGTTCACATTCACCAAGATCCCGGCTGAAACAGTGGACGGGACAGTCACAGTGGAGGGACAGTACGGAGGGACAGA

TGGACCTTGCAAGGTTCCAGCTCAGATGGCGGTGGACATGCAGACTCTGACCCCAGTTGGGAGGTTGATAACCGCTAACCCCG

TAATCACTGAAAGCACTGAGAACTCTAAGATGATGCTGGAACTTGATCCACCATTTGGGGACTCTTACATTGTCATAGGAGTCG

GGGAGAAGAAGATCACCCACCACTGGCACAGGAGTGGCAGCACCATTGGAAAAGCATTTGAAGCCACTGTGAGAGGTGCCA

AGAGAATGGCAGTCTTGGGAGACACAGCCTGGGACTTTGGATCAGTTGGAGGCGCTCTCAACTCATTGGGCAAGGGCATCCA

TCAAATTATTGGAGCAGCTTTCAAATCATTGTTTGGAGGAATGTCCTGGTTCTCACAAATTCTCATTGGGACGTTGCTGATGTG

GTTGGGTCTGAACACAAAGAATGGATCTATTTCCCTTATGTGCTTGGCCTTAGGGGGAGTGTTGATCTTCTTATCCACAGCCGT

-continued

CTCAGGTGGTGTGGGGTGCTCGGTGGACTTCTCAAAGAAGGAGACGAGATGCGGTACAGGGGTGTTCGTCTATAACGATGTT

GAAGCCTGGAGGGACAGGTACAAGTACCATCCTGACTCCCCCCGTAGATTGGCAGCAGCAGTCAAGCAAGCCTGGGAAGATG

GTATCTGCGGGATCTCCTCTGTTTCAAGAATGGAAAACATCATGTGGAGATCAGTAGAAGGGGAGCTCAACGCAATCCTGGAA

GAGAATGGAGTTCAACTGACGGTCGTTGTGGGATCTGTAAAAAACCCCATGTGGAGAGGTCCACAGAGATTGCCCGTGCCTG

TGAACGAGCTGCCCCACGGCTGGAAGGCTTGGGGGAAATCGTACTTCGTCAGAGCAGCAAAGACAAATAACAGCTTTGTCGT

GGATGGTGACACACTGAAGGAATGCCCACTCAAACATAGAGCATGGAACAGCTTTCTTGTGGAGGATCATGGGTTCGGGGTA

TTTCACACTAGTGTCTGGCTCAAGGTTAGAGAAGACTATTGGTTAGAGTGTGATCCAGCCGTTATTGGAACAGCTGTTAAGGG

AAAGGAGGCTGTACACAGTGATCTAGGCTACTGGATTGAGAGTGAGAAGAATGACACATGGTGGCTGAAGAGGGCCCATCT

GATCGAGATGAAAACATGTGAATGGCCAAAGTCCCACACATTGTGGACAGATGGAATAGAAGAGAGTGATCTGATCATACCC

AAGTCTTTAGCTGGGCCACTCAGCCATCACAATGCCAGAGAGGGCTACAGGACCCAAATGAAAGGGCCATGGCACAGTGAAG

AGCTTGAAATTCGGTTTGAGGAATGCCCAGGCACTAAGGTCCACGTGGAGGAAACATGTGGAACAAGAGGACCATCTCTGAG

ATCAACCACTGCAAGCGGAAGGGTGATCGAGGAATGGTGCTCCAGGGAGTGCACAATGCCCCCACTGTCCTTCCAGGCTAAA

GATGGCTGTTGGTATGGAATGGAGATAAGGCCCAGGAAAGAACCAGAAAGCAACTTAGTAAGGTCAATGGTGACTGCAGGA

TCAACTGATCACATGGATCACTTCTCCCTTGGAGTGCTTGTGATTCTGCTCATGGTGCAGGAAGGGCTGAAGAAGAGAATGAC

CACAAAGATCATCATAAGCACATCAATGGCAGTGCTGGTAGCTATGATCCTGGGAGGATTTTCAATGAGTGACCTGGCTAAGC

TTGCAATTTTGATGGGTGCCACCTTCGCGGAAATGAACACTGGAGGAGATGTAGCTCATCTGGCGCTGATAGCGGCATTCAAA

GTCAGACCAGCGTTGCTGGTATCTTTCATCTTCAGAGCTAATTGGACACCCCGTGAAAGCATGCTGCTGGCCTTGGCCTCGTGT

CTTTTGCAAACTGCGATCTCCGCCTTGGAAGGCGACCTGATGGTTCTCATCAATGGTTTTGCTTTGGCCTGGTTGGCAATACGA

GCGATGGTTGTTCCACGCACTGATAACATCACCTTAGCAATCCTGGCTGCTCTGACACCACTGGCCCGGGGCACACTGCTTGTG

GCGTGGAGAGCAGGCCTTGCTACTTGCGGGGGGTTTATGCTCCTCTCTCTGAAGGGAAAAGGCAGTGTGAAGAAGAACTTAC

CATTTGTCATGGCCCTGGGACTAACCGCTGTGAGGCTGGTCGACCCCATCAACGTGGTGGGACTGCTGTTGCTCACAAGGAGT

GGGAAGCGGAGCTGGCCCCCTAGCGAAGTACTCACAGCTGTTGGCCTGATATGCGCATTGGCTGGAGGGTTCGCCAAGGCAG

ATATAGAGATGGCTGGGCCCATGGCCGCGGTCGGTCTGCTAATTGTCAGTTACGTGGTCTCAGGAAAGAGTGTGGACATGTA

CATTGAAAGAGCAGGTGACATCACATGGGAAAAAGATGCGGAAGTCACTGGAAACAGTCCCCGGCTCGATGTGGCGCTAGAT

GAGAGTGGTGATTTCTCCCTGGTGGAGGATGACGGTCCCCCCATGAGAGAGATCATACTCAAGGTGGTCCTGATGACCATCTG

TGGCATGAACCCAATAGCCATACCCTTTGCAGCTGGAGCGTGGTACGTATACGTGAAGACTGGAAAAAGGAGTGGTGCTCTAT

GGGATGTGCCTGCTCCCAAGGAAGTAAAAAAGGGGGAGACCACAGATGGAGTGTACAGAGTAATGACTCGCAGACTGCTAG

GTTCAACACAAGTTGGAGTGGGAGTTATGCAAGAGGGGGTCTTTCACACTATGTGGCACGTCACAAAAGGATCCGCGCTGAG

AAGCGGTGAAGGGAGACTTGATCCATACTGGGGAGATGTCAAGCAGGATCTGGTGTCATACTGTGGTCCATGGAAGCTAGAT

GCCGCCTGGGACGGGCACAGCGAGGTGCAGCTCTTGGCCGTGCCCCCCGGAGAGAGAGCGAGGAACATCCAGACTCTGCCC

GGAATATTTAAGACAAAGGATGGGGACATTGGAGCGGTTGCACTGGATTACCCAGCAGGAACTTCAGGATCTCCAATCCTAG

ACAAGTGTGGGAGAGTGATAGGACTTTATGGCAATGGGGTCGTGATCAAAAATGGGAGTTATGTTAGTGCCATCACCCAAGG

GAGGAGGGAGGAAGAGACTCCTGTTGAGTGCTTCGAGCCTTCGATGCTGAAGAAGAAGCAGCTAACTGTCTTAGACTTGCAT

CCTGGAGCTGGGAAAACCAGGAGAGTTCTTCCTGAAATAGTCCGTGAAGCCATAAAAACAAGACTCCGTACTGTGATCTTGGC

TCCAACCAGGGTTGTCGCTGCTGAAATGGAGGAGGCCCTTAGAGGGCTTCCAGTGCGTTATATGACAACAGCAGTCAATGTCA

CCCACTCTGGAACAGAAATCGTCGACTTAATGTGCCATGCCACCTTCACTTCACGTCTACTACAGCCAATTAGAGTCCCCAACTA

TAATCTGTATATTATGGATGAGGCCCACTTCACAGATCCCTCAAGTATAGCAGCAAGAGGATACATTTCAACAAGGGTTGAGA

TGGGCGAGGCGGCTGCCATCTTCATGACCGCCACGCCACCAGGAACCCGTGACGCATTTCCGGACTCCAACTCACCAATTATG

GACACCGAAGTGGAAGTCCCAGAGAGAGCCTGGAGCTCAGGCTTTGATTGGGTGACGGAGTATTCTGGAAAAACAGTTTGGT

TTGTTCCACGCGTGAGGAACGGCAATGAGATCGCAGCTTGTCTGACAAAGGCTGGAAAACGGGTCATACAGCTCAGCAGAAA

-continued

GACTTTTGAGACAGAGTTCCAGAAAACAAAACATCAAGAGTGGGACTTTGTCGTGACAACTGACATTTCAGAGATGGGCGCCA

ACTTTAAAGCTGACCGTGTCATAGATTCCAGGAGATGCCTAAAGCCGGTCATACTTGGTGGCGAGAGAGTCATTCTGGCTGGA

CCCATGCCTGTCACACATGCCAGCGCTGCCCAGAGGAGGGGGCGCATAGGCAGGAATCCCAACAAACCTGGAGATGAGTATC

TGTATGGAGGTGGGTGCGCAGAGACTGACGAAGACCATGCACACTGGCTTGAAGCAAGAATGCTCCTTGACAATATTTACCTC

CAAGATGGCCTCATAGCCTCGCTCTATCGACCTGAGGCCGACAAAGTAGCAGCCATTGAGGGAGAGTTCAAGCTTAGGACGG

AGCAAAGGAAGACCTTTGTGGAACTCATGAAAAGAGGAGATCTTCCTGTTTGGCTGGCCTATCAGGTTGCATCTGCCGGAATA

ACCTACACAGATAGAAGATGGTGCTTTGATGGCACGACCAACAACACCATAATGGAAGACAGTGTGCCGGCAGAGGTGTGGA

CCAGACACGGAGAGAAAAGAGTGCTCAAACCGAGGTGGATGGACGCCAGAGTTTGTTCAGATCATGCGGCCCTGAAGTCATT

CAAGGAGTTTGCCGCTGGGAAAAGAGGAGCGGCTTTTGGAGTGATGGAAGCCCTGGGAACACTGCCAGGACACATGACAGA

GAGATTCCAGGAAGCCATTGACAACCTCGCTGTGCTCATGCGGGCAGAGACTGGAAGCAGGCCTTACAAAGCCGCGGCGGCC

CAATTGCCGGAGACCCTAGAGACCATTATGCTTTTGGGGTTGCTGGGAACAGTCTCGCTGGGAATCTTTTTCGTCTTGATGAGG

AACAAGGGCATAGGGAAGATGGGCTTTGGAATGGTGACTCTTGGGGCCAGCGCATGGCTCATGTGGCTCTCGGAAATTGAGC

CAGCCAGAATTGCATGTGTCCTCATTGTTGTGTTCCTATTGCTGGTGGTGCTCATACCTGAGCCAGAAAAGCAAAGATCTCCCC

AGGACAACCAAATGGCCATCATCATCATGGTAGCAGTAGGTCTTCTGGGCTTGATTACCGCCAATGAACTCGGATGGTTGGAG

AGAACAAAGAGTGACCTAAGCCATCTAATGGGAAGGAGAGAGGAGGGGGCAACCATGGGATTCTCAATGGACATTGACCTG

CGGCCAGCCTCAGCTTGGGCCATCTATCCTGCCTTGACATCTTTCATTACCCCAGCCGTCCAACATGCAGTGACCACTTCATACA

ACAACTACTCCTTAATGGCGATGGCCACGCAAGCTGGAGTGTTGTTTGGTATGGGCAAAGGGATGCCATTCTACGCATGGGAC

TTTGGAGTCCCGCTGCTAATGATAGGTTGCTACTCACAATTAACGCCCCTGACCCTAATAGTGGCCATCATTTTGCTCGTGGCG

CACTACATGTACTTGATCCCAGGGCTGCAGGCAGCAGCTGCGCGTGCTGCCCAGAAGAGAACGGCAGCTGGCATCATGAAGA

ACCCTGTTGTGGAGGGAATAGTGGTGACTGACATTGACACAATGACAATTGACCCCCAAGTGGAGAAAAAGATGGGACAGGT

GCTACTCATGGCAGTAGCCGTCTCCAGCGCCATACTGTCGAGGACCGCCTGGGGGTGGGGGGAGGCTGGGGCCCTGATCACA

GCCGCAACTTCCACTTTGTGGGAAGGCTCTCCGAACAAGTACTGGAACTCCTCTACAGCCACCTCACTGTGTAACATTTTTAGG

GGAAGTTACTTGGCTGGAGCTTCTCTAATCTACACAGTAACAAGAAACGCTGGCTTGGTCAAGAGACGTGGGGGTGGAACAG

GAGAGACCCTGGGAGAGAAATGGAAGGCCCGCTTGAACCAGATGTCGGCCCTGGAGTTCTACTCCTACAAAAAGTCAGGCAT

CACCGAGGTGTGCAGAGAAGAGGCCCGCCGCGCCCTCAAGGACGGTGTGGCAACGGGAGGCCATGCTGTGTCCCGAGGAAG

TGCAAAGCTGAGATGGTTGGTGGAGCGGGGATACCTGCAGCCCTATGGAAAGGTCATTGATCTTGGATGTGGCAGAGGGGG

CTGGAGTTACTACGCCGCCACCATCCGCAAAGTTCAAGAAGTGAAAGGATACACAAAAGGAGGCCCTGGTCATGAAGAACCC

GTGTTGGTGCAAAGCTATGGGTGGAACATAGTCCGTCTTAAGAGTGGGGTGGACGTCTTTCATATGGCGGCTGAGCCGTGTG

ACACGTTGCTGTGTGACATAGGTGAGTCATCATCTAGTCCTGAAGTGGAAGAAGCACGGACGCTCAGAGTCCTCTCCATGGTG

GGGGATTGGCTTGAAAAAAGACCAGGAGCCTTTTGTATAAAAGTGTTGTGCCCATACACCAGCACTATGATGGAAACCCTGGA

GCGACTGCAGCGTAGGTATGGGGGAGGACTGGTCAGAGTGCCACTCTCCCGCAACTCTACACATGAGATGTACTGGGTCTCT

GGAGCGAAAAGCAACACCATAAAAAGTGTGTCCACCACGAGCCAGCTCCTCTTGGGGCGCATGGACGGGCCTAGGAGGCCA

GTGAAATATGAGGAGGATGTGAATCTCGGCTCTGGCACGCGGGCTGTGGTAAGCTGCGCTGAAGCTCCCAACATGAAGATCA

TTGGTAACCGCATTGAAAGGATCCGCGCTGAGAAAGCGGAAACGTGGTTCTTTGACGAGAACCACCCATATAGGACATGGGC

TTACCATGGAAGCTATGATGCCGCCACACAAGGGTCAGCGTCCTCTCTAATAAACGGGGTTGTCAGGCTCCTGTCAAAACCCT

GGGATGTGGTGACTGGAGTCACAGGAATAGCCATGACCGACACCACACCGTATGGTCAGCAAAGAGTTTTCAAGGAAAAAGT

GGACACTAGGGTGCCAGACCCCCAAGAAGGCACTCGTCAGGTTATGAGCATGGTCTCTTCCTGGTTGTGGAAAGAGCTAGGC

AAACACAAACGGCCACGAGTCTGTACCAAAGAAGAGTTCATCAACAAGGTTCGTAGCAATGCAGCATTAGGGGCAATATTTGA

AGAGGAAAAAGAGTGGAAGACTGCAGTGGAAGCTGTGAACGATCCAAGGTTCTGGGCTCTAGTGGACAAGGAAAGAGAGCA

CCACCTGAGAGGAGAGTGCCAGAGTTGTGTGTACATCACAATGGGAAAAAGAGAAAAGAAACAAGGGGAATTTGGAAAGGC

CAAGGGCAGCCGCGCCATCTGGTATATGTGGCTAGGGGCTAGATTTCTAGAGTTCGAAGCCCTTGGATTCTTGAACGAGGATC

-continued

ACTGGATGGGGAGAGAGAACTCAGGAGGTGGTGTTGAAGGGCTGGGATTACAAAGACTCGGATATGTCCTAGAAGAGATGA

GTCGCATACCAGGAGGAAGGATGTATGCAGATGACACTGCTGGCTGGGACACCCGCATCAGCAGGTTTGATCTGGAGAATGA

AGCTCTAATCACCAACCAAATGGAGAAAGGGCACAGGGCCTTGGCATTGGCCATAATCAAGTACACATACCAAAACAAAGTG

GTAAAGGTCCTTAGACCAGCTGAAAAAGGGAAGACAGTTATGGACATTATTTCGAGACAAGACCAAAGGGGGAGCGGACAA

GTTGTCACTTACGCTCTCAACACATTTACCAACCTAGTGGTGCAACTCATTCGGAATATGGAGGCTGAGGAAGTTCTAGAGATG

CAAGACTTGTGGCTGCTGCGGAGGTCAGAGAAAGTGACCAACTGGTTGCAGAGCAACGGATGGGATAGGCTCAAACGAATG

GCGGTCAGTGGAGATGATTGCGTTGTGAAACCAATTGATGATAGGTTTGCACATGCCCTCAGGTTCTTGAATGATATGGGAAA

AGTTAGGAAGGACACACAAGAGTGGAAACCCTCAACTGGATGGGACAACTGGGAAGAAGTTCCCTTCTGCTCCCACCACTTCA

ACAAGCTCCATCTCAAGGACGGGAGGTCCATTGTGGTTCCCTGCCGCCACCAAGATGAACTGATTGGCCGGGCCCGCGTCTCT

CCAGGGGCGGGATGGAGCATCCGGGAGACTGCTTGCCTAGCAAAATCATATGCGCAAATGTGGCAGCTCCTTTATTTCCACAG

AAGGGACCTCCGACTGATGGCCAATGCCATTTGTTCATCTGTGCCAGTTGACTGGGTTCCAACTGGGAGAACTACCTGGTCAAT

CCATGGAAAGGGAGAATGGATGACCACTGAAGACATGCTTGTGGCGTGGAACAGAGTGTGGATTGAGGAGAACGACCACAT

GGAAGACAAGACCCCAGTCACGAAATGGACAGACATTCCCTATTTGGGAAAAAGGGAAGACTTGTGGTGTGGATCTCTCATA

GGGCACAGACCGCGCACCACCTGGGCTGAGAACATTAAAAACACAGTCAACATGGTGCGCAGGATCATAGGTGATGAAGAAA

AGTACATGGACTACCTATCCACCCAAGTTCGCTACTTGGGTGAAGAAGGGTCTACACCTGGAGTGCTGTAAGCACCAATCTTA

ATGTTGTCAGGCCTGCTAGTCAGCCACAGCTTGGGGAAAGCTGTGCAGCCTGTGACCCCCCCAGGAGAAGCTGGGAAACCAA

GCCTATAGTCAGGCCGAGAACGCCATGGCACGGAAGAAGCCATGCTGCCTGTGAGCCCCTCAGAGGACACTGAGTCAAAAAA

CCCCACGCGCTTGGAGGCGCAGGATGGGAAAAGAAGGTGGCGACCTTCCCCACCCTTCAATCTGGGGCCTGAACTGGAGATC

AGCTGTGGATCTCCAGAAGAGGGACTAGTGGTTAGAGGAGA

LC002520.1 Zika virus genomic RNA, strain: MR766-NIID, Uganda, complete genome
SEQ ID NO: 11

AGTTGTTGATCTGTGTGAGTCAGACTGCGACAGTTCGAGTCTGAAGCGAGAGCTAACAACAGTATCAACAGGTTTAATTTGGA

TTTGGAAACGAGAGTTTCTGGTCATGAAAAACCCAAAGAAGAAATCCGGAGGATTCCGGATTGTCAATATGCTAAAACGCGG

AGTAGCCCGTGTAAACCCCTTGGGAGGTTTGAAGAGGTTGCCAGCCGGACTTCTGCTGGGTCATGGACCCATCAGAATGGTTT

TGGCGATACTAGCCTTTTTGAGATTTACAGCAATCAAGCCATCACTGGGCCTTATCAACAGATGGGGTTCCGTGGGGAAAAAA

GAGGCTATGGAAATAATAAAGAAGTTCAAGAAAGATCTTGCTGCCATGTTGAGAATAATCAATGCTAGGAAAGAGAGGAAGA

GACGTGGCGCAGACACCAGCATCGGAATCATTGGCCTCCTGCTGACTACAGCCATGGCAGCAGAGATCACTAGACGCGGGAG

TGCATACTACATGTACTTGGATAGGAGCGATGCCGGGAAGGCCATTTCGTTTGCTACCACATTGGGAGTGAACAAGTGCCACG

TACAGATCATGGACCTCGGGCACATGTGTGACGCCACCATGAGTTATGAGTGCCCTATGCTGGATGAGGGAGTGGAACCAGA

TGATGTCGATTGCTGGTGCAACACGACATCAACTTGGGTTGTGTACGGAACCTGTCATCACAAAAAAGGTGAGGCACGGCGAT

CTAGAAGAGCCGTGACGCTCCCTTCTCACTCTACAAGGAAGTTGCAAACGCGGTCGCAGACCTGGTTAGAATCAAGAGAATAC

ACGAAGCACTTGATCAAGGTTGAAAACTGGATATTCAGGAACCCCGGGTTTGCGCTAGTGGCCGTTGCCATTGCCTGGCTTTT

GGGAAGCTCGACGAGCCAAAAAGTCATATACTTGGTCATGATACTGCTGATTGCCCCGGCATACAGTATCAGGTGCATTGGAG

TCAGCAATAGAGACTTCGTGGAGGGCATGTCAGGTGGGACCTGGGTTGATGTTGTCTTGGAACATGGAGGCTGCGTTACCGT

GATGGCACAGGACAAGCCAACAGTTGACATAGAGTTGGTCACGACGACGGTTAGTAACATGGCCGAGGTAAGATCCTATTGC

TACGAGGCATCGATATCGGACATGGCTTCGGACAGTCGTTGCCCAACACAAGGTGAAGCCTACCTTGACAAGCAATCAGACAC

TCAATATGTCTGCAAAAGAACATTAGTGGACAGAGGTTGGGGAAACGGTTGTGGACTTTTTGGCAAAGGGAGCTTGGTGACA

TGTGCCAAGTTTACGTGTTCTAAGAAGATGACCGGGAAGAGCATTCAACCGGAAAATCTGGAGTATCGGATAATGCTATCAGT

GCATGGCTCCCAGCATAGCGGGATGACTGTCAATGATATAGGATATGAAACTGACGAAAATAGAGCGAAAGTCGAGGTTACG

CCTAATTCACCAAGAGCGGAAGCAACCTTGGGAGGCTTTGGAAGCTTAGGACTTGACTGTGAACCAAGGACAGGCCTTGACTT

TTCAGATCTGTATTACCTGACCATGAACAATAAGCATTGGTTGGTGCACAAAGAGTGGTTTCATGACATCCCATTGCCTTGGCA

-continued

TGCTGGGGCAGACACTGGAACTCCACACTGGAACAACAAAGAGGCATTGGTAGAATTCAAGGATGCCCACGCCAAGAGGCAA

ACCGTCGTCGTTCTGGGGAGCCAGGAAGGAGCCGTTCACACGGCTCTCGCTGGAGCTCTAGAGGCTGAGATGGATGGTGCAA

AGGGAAAGCTGTTCTCTGGCCATTTGAAATGCCGCCTAAAAATGGACAAGCTTAGATTGAAGGGCGTGTCATATTCCTTGTGC

ACTGCGGCATTCACATTCACCAAGGTCCCAGCTGAAACACTGCATGGAACAGTCACAGTGGAGGTGCAGTATGCAGGGACAG

ATGGACCCTGCAAGATCCCAGTCCAGATGGCGGTGGACATGCAGACCCTGACCCCAGTTGGAAGGCTGATAACCGCCAACCC

CGTGATTACTGAAAGCACTGAGAACTCAAAGATGATGTTGGAGCTTGACCCACCATTTGGGGATTCTTACATTGTCATAGGAG

TGGGGACAAGAAAATCACCCACCACTGGCATAGGAGTGGTAGCACCATCGGAAAGGCATTTGAGGCCACTGTGAGAGGCGC

CAAGAGAATGGCAGTCCTGGGGGATACAGCCTGGGACTTCGGATCAGTCGGGGGTGTGTTCAACTCACTGGGTAAGGGCATT

CACCAGATTTTTGGAGCAGCCTTCAAATCACTGTTTGGAGGAATGTCCTGGTTCTCACAGATCCTCATAGGCACGCTGCTAGTG

TGGTTAGGTTTGAACACAAAGAATGGATCTATCTCCCTCACATGCTTGGCCCTGGGGGGAGTGATGATCTTCCTCTCCACGGCT

GTTTCTGCTGACGTGGGGTGCTCAGTGGACTTCTCAAAAAAGGAAACGAGATGTGGCACGGGGGTATTCATCTATAATGATGT

TGAAGCCTGGAGGGACCGGTACAAGTACCATCCTGACTCCCCCCGCAGATTGGCAGCAGCAGTCAAGCAGGCCTGGGAAGAG

GGGATCTGTGGGATCTCATCCGTTTCAAGAATGGAAAACATCATGTGGAAATCAGTAGAAGGGGAGCTCAATGCTATCCTAGA

GGAGAATGGAGTTCAACTGACAGTTGTTGTGGGATCTGTAAAAAACCCCATGTGGAGAGGTCCACAAAGATTGCCAGTGCCT

GTGAATGAGCTGCCCCATGGCTGGAAAGCCTGGGGGAAATCGTATTTTGTTAGGGCGGCAAAGACCAACAACAGTTTTGTTGT

CGACGGTGACACACTGAAGGAATGTCCGCTTGAGCACAGAGCATGGAATAGTTTTCTTGTGGAGGATCACGGGTTTGGAGTC

TTCCACACCAGTGTCTGGCTTAAGGTCAGAGAAGATTACTCATTAGAATGTGACCCAGCCGTCATAGGAACAGCTGTTAAGGG

AAGGGAGGCCGCGCACAGTGATCTGGGCTATTGGATTGAAAGTGAAAAGAATGACACATGGAGGCTGAAGAGGGCCCACCT

GATTGAGATGAAAACATGTGAATGGCCAAAGTCTCACACATTGTGGACAGATGGAGTAGAAGAAAGTGATCTTATCATACCCA

AGTCTTTAGCTGGTCCACTCAGCCACCACAACACCAGAGAGGGTTACAGAACCCAAGTGAAAGGGCCATGGCACAGTGAAGA

GCTTGAAATCCGGTTTGAGGAATGTCCAGGCACCAAGGTTTACGTGGAGGAGACATGCGGAACTAGAGGACCATCTCTGAGA

TCAACTACTGCAAGTGGAAGGGTCATTGAGGAATGGTGCTGTAGGGAATGCACAATGCCCCCACTATCGTTTCGAGCAAAAG

ACGGCTGCTGGTATGGAATGGAGATAAGGCCCAGGAAAGAACCAGAGAGCAACTTAGTGAGGTCAATGGTGACAGCGGGGT

CAACCGATCATATGGACCACTTCTCTCTTGGAGTGCTTGTGATTCTACTCATGGTGCAGGAGGGGTTGAAGAAGAGAATGACC

ACAAAGATCATCATGAGCACATCAATGGCAGTGCTGGTAGTCATGATCTTGGGAGGATTTTCAATGAGTGACCTGGCCAAGCT

TGTGATCCTGATGGGTGCTACTTTCGCAGAAATGAACACTGGAGGAGATGTAGCTCACTTGGCATTGGTAGCGGCATTTAAAG

TCAGACCAGCCTTGCTGGTCTCCTTCATTTTCAGAGCCAATTGGACACCCCGTGAGAGCATGCTGCTAGCCCTGGCTTCGTGTC

TTCTGCAAACTGCGATCTCTGCTCTTGAAGGTGACTTGATGGTCCTCATTAATGGATTTGCTTTGGCCTGGTTGGCAATTCGAGC

AATGGCCGTGCCACGCACTGACAACATCGCTCTACCAATCTTGGCTGCTCTAACACCACTAGCTCGAGGCACACTGCTCGTGGC

ATGGAGAGCGGGCCTGGCTACTTGTGGAGGGATCATGCTCCTCTCCCTGAAAGGGAAAGGTAGTGTGAAGAAGAACCTGCCA

TTTGTCATGGCCCTGGGATTGACAGCTGTGAGGGTAGTAGACCCTATTAATGTGGTAGGACTACTGTTACTCACAAGGAGTGG

GAAGCGGAGCTGGCCCCCTAGTGAAGTTCTCACAGCCGTTGGCCTGATATGTGCACTGGCCGGAGGGTTTGCCAAGGCAGAC

ATTGAGATGGCTGGACCCATGGCTGCAGTAGGCTTGCTAATTGTCAGCTATGTGGTCTCGGGAAAGAGTGTGGACATGTACAT

TGAAAGAGCAGGTGACATCACATGGGAAAAGGACGCGGAAGTCACTGGAAACAGTCCTCGGCTTGACGTGGCACTGGATGA

GAGTGGTGATTTCTCCTTGGTAGAGGAAGATGGTCCACCCATGAGAGAGATCATACTTAAGGTGGTCCTGATGGCCATCTGTG

GCATGAACCCAATAGCTATACCTTTTGCTGCAGGAGCGTGGTATGTGTATGTGAAGACTGGGAAAAGGAGTGGCGCCCTCTG

GGACGTGCCTGCTCCCAAAGAAGTGAAGAAAGGAGAGACCACAGATGGAGTGTACAGAGTGATGACTCGCAGACTGCTAGG

TTCAACACAGGTTGGAGTGGGAGTCATGCAAGAGGGAGTCTTCCACACCATGTGGCACGTTACAAAAGGAGCCGCACTGAGG

AGCGGTGAGGGAAGACTTGATCCATACTGGGGGGATGTCAAGCAGGACTTGGTGTCATACTGTGGGCCTTGGAAGTTGGATG

CAGCTTGGGATGGACTCAGCGAGGTACAGCTTTTGGCCGTACCTCCCGGAGAGAGGGCCAGAAACATTCAGACCCTGCCTGG

AATATTCAAGACAAAGGACGGGGACATCGGAGCAGTTGCTCTGGACTACCCTGCAGGGACCTCAGGATCTCCGATCCTAGAC

-continued

AAATGTGGAAGAGTGATAGGACTCTATGGCAATGGGGTTGTGATCAAGAATGGAAGCTATGTTAGTGCTATAACCCAGGGAA

AGAGGGAGGAGGAGACTCCGGTTGAATGTTTCGAACCCTCGATGCTGAAGAAGAAGCAGCTAACTGTCTTGGATCTGCATCC

AGGAGCCGGAAAAACCAGGAGAGTTCTTCCTGAAATAGTCCGTGAAGCCATAAAAAAGAGACTCCGGACAGTGATCTTGGCA

CCAACTAGGGTTGTCGCTGCTGAGATGGAGGAGGCCTTGAGAGGACTTCCGGTGCGTTACATGACAACAGCAGTCAACGTCA

CCCATTCTGGGACAGAAATCGTTGATTTGATGTGCCATGCCACTTTCACTTCACGCTTACTACAACCCATCAGAGTCCCTAATTA

CAATCTCTACATCATGGATGAAGCCCACTTCACAGACCCCTCAAGTATAGCTGCAAGAGGATATATATCAACAAGGGTTGAAAT

GGGCGAGGCGGCTGCCATTTTTATGACTGCCACACCACCAGGAACCCGTGATGCGTTTCCTGACTCTAACTCACCAATCATGGA

CACAGAAGTGGAAGTCCCAGAGAGAGCCTGGAGCTCAGGCTTTGATTGGGTGACAGACCATTCTGGGAAAACAGTTTGGTTC

GTTCCAAGCGTGAGAAACGGAAATGAAATCGCAGCCTGTCTGACAAAGGCTGGAAAGCGGGTCATACAGCTCAGCAGGAAG

ACTTTTGAGACAGAATTTCAGAAAACAAAAAATCAAGAGTGGGACTTTGTCATAACAACTGACATCTCAGAGATGGGCGCCAA

CTTCAAGGCTGACCGGGTCATAGACTCTAGGAGATGCCTAAAACCAGTCATACTTGATGGTGAGAGAGTCATCTTGGCTGGGC

CCATGCCTGTCACGCATGCTAGTGCTGCTCAGAGGAGAGGACGTATAGGCAGGAACCCTAACAAACCTGGAGATGAGTACAT

GTATGGAGGTGGGTGTGCAGAGACTGATGAAGGCCATGCACACTGGCTTGAAGCAAGAATGCTTCTTGACAACATCTACCTCC

AGGATGGCCTCATAGCCTCGCTCTATCGGCCTGAGGCCGATAAGGTAGCCGCCATTGAGGGAGAGTTTAAGCTGAGGACAGA

GCAAAGGAAGACCTTCGTGGAACTCATGAAGAGAGGAGACCTTCCCGTCTGGCTAGCCTATCAGGTTGCATCTGCCGGAATAA

CTTACACAGACAGAAGATGGTGCTTTGATGGCACAACCAACAACACCATAATGGAAGACAGCGTACCAGCAGAGGTGTGGAC

AAAGTATGGAGAGAAGAGAGTGCTCAAACCGAGATGGATGGATGCTAGGGTCTGTTCAGACCATGCGGCCCTGAAGTCGTTC

AAAGAATTCGCCGCTGGAAAAAGAGGAGCGGCTTTGGGAGTAATGGAGGCCCTGGGAACACTGCCAGGACACATGACAGAG

AGGTTTCAGGAAGCCATTGACAACCTCGCCGTGCTCATGCGAGCAGAGACTGGAAGCAGGCCTTATAAGGCAGCGGCAGCCC

AACTGCCGGAGACCCTAGAGACCATTATGCTCTTAGGTTTGCTGGGAACAGTTTCACTGGGGATCTTCTTCGTCTTGATGCGGA

ATAAGGGCATCGGGAAGATGGGCTTTGGAATGGTAACCCTTGGGGCCAGTGCATGGCTCATGTGGCTTTCGGAAATTGAACC

AGCCAGAATTGCATGTGTCCTCATTGTTGTGTTTTTATTACTGGTGGTGCTCATACCCGAGCCAGAGAAGCAAAGATCTCCCCA

AGATAACCAGATGGCAATTATCATCATGGTGGCAGTGGGCCTTCTAGGTTTGATAACTGCAAACGAACTTGGATGGCTGGAAA

GAACAAAAAATGACATAGCTCATCTAATGGGAAGGAGAGAAGAAGGAGCAACCATGGGATTCTCAATGGACATTGATCTGCG

GCCAGCCTCCGCCTGGGCTATCTATGCCGCATTGACAACTCTCATCACCCCAGCTGTCCAACATGCGGTAACCACTTCATACAAC

AACTACTCCTTAATGGCGATGGCCACACAAGCTGGAGTGCTGTTTGGCATGGGCAAAGGGATGCCATTTTATGCATGGGACCT

TGGAGTCCCGCTGCTAATGATGGGTTGCTATTCACAATTAACACCCCTGACTCTGATAGTAGCTATCATTCTGCTTGTGGCGCA

CTACATGTACTTGATCCCAGGCCTACAAGCGGCAGCAGCGCGTGCTGCCCAGAAAAGGACAGCAGCTGGCATCATGAAGAAT

CCCGTTGTGGATGGAATAGTGGTAACTGACATTGACACAATGACAATAGACCCCCAGGTGGAGAAGAAGATGGGACAAGTGT

TACTCATAGCAGTAGCCATCTCCAGTGCTGTGCTGCTGCGGACCGCCTGGGGATGGGGGGAGGCTGGAGCTCTGATCACAGC

AGCGACCTCCACCTTGTGGGAAGGCTCTCCAAACAAATACTGGAACTCCTCTACAGCCACCTCACTGTGCAACATCTTCAGAGG

AAGCTATCTGGCAGGAGCTTCCCTTATCTATACAGTGACGAGAAACGCTGGCCTGGTTAAGAGACGTGGAGGTGGGACGGGA

GAGACTCTGGGAGAGAAGTGGAAAGCTCGTCTGAATCAGATGTCGGCCCTGGAGTTCTACTCTTATAAAAAGTCAGGTATCAC

TGAAGTGTGTAGAGAGGAGGCTCGCCGTGCCCTCAAGGATGGAGTGGCCACAGGAGGACATGCCGTATCCCGGGGAAGTGC

AAAGCTCAGATGGTTGGTGGAGAGAGGATATCTGCAGCCCTATGGGAAGGTTGTTGACCTCGGATGTGGCAGAGGGGGCTG

GAGCTATTATGCCGCCACCATCCGCAAAGTGCAGGAGGTGAGAGGATACACAAAGGGAGGTCCCGGTCATGAAGAACCCATG

CTGGTGCAAAGCTATGGGTGGAACATAGTTCGTCTCAAGAGTGGAGTGGACGTCTTCCACATGGCGGCTGAGCCGTGTGACA

CTCTGCTGTGTGACATAGGTGAGTCATCATCTAGTCCTGAAGTGGAAGAGACACGAACACTCAGAGTGCTCTCTATGGTGGGG

GACTGGCTTGAAAAAAGACCAGGGGCCTTCTGTATAAAGGTGCTGTGCCCATACACCAGCACTATGATGGAAACCATGGAGC

GACTGCAACGTAGGCATGGGGGAGGATTAGTCAGAGTGCCATTGTCTCGCAACTCCACACATGAGATGTACTGGGTCTCTGG

-continued

GGCAAAGAGCAACATCATAAAAAGTGTGTCCACCACAAGTCAGCTCCTCCTGGGACGCATGGATGGCCCCAGGAGGCCAGTG

AAATATGAGGAGGATGTGAACCTCGGCTCGGGTACACGAGCTGTGGCAAGCTGTGCTGAGGCTCCTAACATGAAAATCATCG

GCAGGCGCATTGAGAGAATCCGCAATGAACATGCAGAAACATGGTTTCTTGATGAAAACCACCCATACAGGACATGGGCCTAC

CATGGGAGCTACGAAGCCCCCACGCAAGGATCAGCGTCTTCCCTCGTGAACGGGGTTGTTAGACTCCTGTCAAAGCCTTGGGA

CGTGGTGACTGGAGTTACAGGAATAGCCATGACTGACACCACACCATACGGCCAACAAAGAGTCTTCAAAGAAAAAGTGGAC

ACCAGGGTGCCAGATCCCCAAGAAGGCACTCGCCAGGTAATGAACATAGTCTCTTCCTGGCTGTGGAAGGAGCTGGGGAAAC

GCAAGCGGCCACGCGTCTGCACCAAAGAAGAGTTTATCAACAAGGTGCGCAGCAATGCAGCACTGGGAGCAATATTTGAAGA

GGAAAAAGAATGGAAGACGGCTGTGGAAGCTGTGAATGATCCAAGGTTTTGGGCCCTAGTGGATAGGGAGAGAGAACACCA

CCTGAGAGGAGAGTGTCACAGCTGTGTGTACAACATGATGGGAAAAAGAGAAAAGAAGCAAGGAGAGTTCGGGAAAGCAA

AAGGTAGCCGCGCCATCTGGTACATGTGGTTGGGAGCCAGATTCTTGGAGTTTGAAGCCCTTGGATTCTTGAACGAGGACCAT

TGGATGGGAAGAGAAAACTCAGGAGGTGGAGTCGAAGGGTTAGGATTGCAAAGACTTGGATACATTCTAGAAGAAATGAAT

CGGGCACCAGGAGGAAAGATGTACGCAGATGACACTGCTGGCTGGGACACCCGCATTAGTAAGTTTGATCTGGAGAATGAAG

CTCTGATTACCAACCAAATGGAGGAAGGGCACAGAACTCTGGCGTTGGCCGTGATTAAATACACATACCAAAACAAAGTGGTG

AAGGTTCTCAGACCAGCTGAAGGAGGAAAAACAGTTATGGACATCATTTCAAGACAAGACCAGAGAGGGAGTGGACAAGTT

GTCACTTATGCTCTCAACACATTCACCAACTTGGTGGTGCAGCTTATCCGGAACATGGAAGCTGAGGAAGTGTTAGAGATGCA

AGACTTATGGTTGTTGAGGAAGCCAGAGAAAGTGACCAGATGGTTGCAGAGCAATGGATGGGATAGACTCAAACGAATGGC

GGTCAGTGGAGATGACTGCGTTGTGAAGCCAATCGATGATAGGTTTGCACATGCCCTCAGGTTCTTGAATGACATGGGAAAA

GTTAGGAAAGACACACAGGAGTGGAAACCCTCGACTGGATGGAGCAATTGGGAAGAAGTCCCGTTCTGCTCCCACCACTTCA

ACAAGCTGTACCTCAAGGATGGGAGATCCATTGTGGTCCCTTGCCGCCACCAAGATGAACTGATTGGCCGAGCTCGCGTCTCA

CCAGGGGCAGGATGGAGCATCCGGGAGACTGCCTGTCTTGCAAAATCATATGCGCAGATGTGGCAGCTCCTTTATTTCCACAG

AAGAGACCTTCGACTGATGGCTAATGCCATTTGCTCGGCTGTGCCAGTTGACTGGGTACCAACTGGGAGAACCACCTGGTCAA

TCCATGGAAAGGGAGAATGGATGACCACTGAGGACATGCTCATGGTGTGGAATAGAGTGTGGATTGAGGAGAACGACCATA

TGGAGGACAAGACTCCTGTAACAAAATGGACAGACATTCCCTATCTAGGAAAAAGGGAGGACTTATGGTGTGGATCCCTTATA

GGGCACAGACCCCGCACCACTTGGGCTGAAAACATCAAAGACACAGTCAACATGGTGCGCAGGATCATAGGTGATGAAGAAA

AGTACATGGACTATCTATCCACCCAAGTCCGCTACTTGGGTGAGGAAGGGTCCACACCCGGAGTGTTGTAAGCACCAATTTTA

GTGTTGTCAGGCCTGCTAGTCAGCCACAGTTTGGGGAAAGCTGTGCAGCCTGTAACCCCCCCAGGAGAAGCTGGGAAACCAA

GCTCATAGTCAGGCCGAGAACGCCATGGCACGGAAGAAGCCATGCTGCCTGTGAGCCCCTCAGAGGACACTGAGTCAAAAAA

CCCCACGCGCTTGGAAGCGCAGGATGGGAAAAGAAGGTGGCGACCTTCCCCACCCTTCAATCTGGGGCCTGAACTGGAGACT

AGCTGTGAATCTCCAGCAGAGGGACTAGTGGTTAGAGGAGACCCCCCGGAAAACGCAAAACAGCATATTGACGCTGGGAAA

GACCAGAGACTCCATGAGTTTCCACCACGCTGGCCGCCAGGCACAGATCGCCGAACAGCGGCGGCCGGTGTGGGGAAATCCA

TGGTTTCT

AY632535.2 NC_012532.1 Zika virus strain MR 766, Uganda, complete genome

SEQ ID NO: 12

AGTTGTTGATCTGTGTGAGTCAGACTGCGACAGTTCGAGTCTGAAGCGAGAGCTAACAACAGTATCAACAGGTTTAATTTGGA

TTTGGAAACGAGAGTTTCTGGTCATGAAAAACCCCAAAGAAGAAATCCGGAGGATCCGGATTGTCAATATGCTAAAACGCGG

AGTAGCCCGTGTAAACCCCTTGGGAGGTTTGAAGAGGTTGCCAGCCGGACTTCTGCTGGGTCATGGACCCATCAGAATGGTTT

TGGCGATACTAGCCTTTTTGAGATTTACAGCAATCAAGCCATCACTGGGCCTTATCAACAGATGGGGTTCCGTGGGGAAAAAA

GAGGCTATGGAAATAATAAAGAAGTTCAAGAAAGATCTTGCTGCCATGTTGAGAATAATCAATGCTAGGAAAGAGAGGAAGA

GACGTGGCGCAGACACCAGCATCGGAATCATTGGCCTCCTGCTGACTACAGCCATGGCAGCAGAGATCACTAGACGCGGGAG

TGCATACTACATGTACTTGGATAGGAGCGATGCCGGGAAGGCCATTTCGTTTGCTACCACATTGGGAGTGAACAAGTGCCACG

TACAGATCATGGACCTCGGGCACATGTGTGACGCCACCATGAGTTATGAGTGCCCTATGCTGGATGAGGGAGTGGAACCAGA

TGATGTCGATTGCTGGTGCAACACGACATCAACTTGGGTTGTGTACGGAACCTGTCATCACAAAAAAGGTGAGGCACGGCGAT

-continued

CTAGAAGAGCCGTGACGCTCCCTTCTCACTCTACAAGGAAGTTGCAAACGCGGTCGCAGACCTGGTTAGAATCAAGAGAATAC

ACGAAGCACTTGATCAAGGTTGAAAACTGGATATTCAGGAACCCCGGGTTTGCGCTAGTGGCCGTTGCCATTGCCTGGCTTTT

GGGAAGCTCGACGAGCCAAAAAGTCATATACTTGGTCATGATACTGCTGATTGCCCCGGCATACAGTATCAGGTGCATTGGAG

TCAGCAATAGAGACTTCGTGGAGGGCATGTCAGGTGGGACCTGGGTTGATGTTGTCTTGGAACATGGAGGCTGCGTTACCGT

GATGGCACAGGACAAGCCAACAGTCGACATAGAGTTGGTCACGACGACGGTTAGTAACATGGCCGAGGTAAGATCCTATTGC

TACGAGGCATCGATATCGGACATGGCTTCGGACAGTCGTTGCCCAACACAAGGTGAAGCCTACCTTGACAAGCAATCAGACAC

TCAATATGTCTGCAAAAGAACATTAGTGGACAGAGGTTGGGGAAACGGTTGTGGACTTTTTGGCAAAGGGAGCTTGGTGACA

TGTGCCAAGTTTACGTGTTCTAAGAAGATGACCGGGAAGAGCATTCAACCGGAAAATCTGGAGTATCGGATAATGCTATCAGT

GCATGGCTCCCAGCATAGCGGGATGATTGGATATGAAACTGACGAAGATAGAGCGAAAGTCGAGGTTACGCCTAATTCACCA

AGAGCGGAAGCAACCTTGGGAGGCTTTGGAAGCTTAGGACTTGACTGTGAACCAAGGACAGGCCTTGACTTTTCAGATCTGTA

TTACCTGACCATGAACAATAAGCATTGGTTGGTGCACAAAGAGTGGTTTCATGACATCCCATTGCCTTGGCATGCTGGGGCAG

ACACCGGAACTCCACACTGGAACAACAAAGAGGCATTGGTAGAATTCAAGGATGCCCACGCCAAGAGGCAAACCGTCGTCGT

TCTGGGGAGCCAGGAAGGAGCCGTTCACACGGCTCTCGCTGGAGCTCTAGAGGCTGAGATGGATGGTGCAAAGGGAAGGCT

GTTCTCTGGCCATTTGAAATGCCGCCTAAAAATGGACAAGCTTAGATTGAAGGGCGTGTCATATTCCTTGTGCACTGCGGCATT

CACATTCACCAAGGTCCCAGCTGAAACACTGCATGGAACAGTCACAGTGGAGGTGCAGTATGCAGGGACAGATGGACCCTGC

AAGATCCCAGTCCAGATGGCGGTGGACATGCAGACCCTGACCCCAGTTGGAAGGCTGATAACCGCCAACCCCGTGATTACTGA

AAGCACTGAGAACTCAAAGATGATGTTGGAGCTTGACCCACCATTTGGGGATTCTTACATTGTCATAGGAGTTGGGGACAAGA

AAATCACCCACCACTGGCATAGGAGTGGTAGCACCATCGGAAAGGCATTTGAGGCCACTGTGAGAGGCGCCAAGAGAATGGC

AGTCCTGGGGGATACAGCCTGGGACTTCGGATCAGTCGGGGGTGTGTTCAACTCACTGGGTAAGGGCATTCACCAGATTTTTG

GAGCAGCCTTCAAATCACTGTTTGGAGGAATGTCCTGGTTCTCACAGATCCTCATAGGCACGCTGCTAGTGTGGTTAGGTTTGA

ACACAAAGAATGGATCTATCTCCCTCACATGCTTGGCCCTGGGGGGAGTGATGATCTTCCTCTCCACGGCTGTTTCTGCTGACG

TGGGGTGCTCAGTGGACTTCTCAAAAAAGGAAACGAGATGTGGCACGGGGGTATTCATCTATAATGATGTTGAAGCCTGGAG

GGACCGGTACAAGTACCATCCTGACTCCCCCCGCAGATTGGCAGCAGCAGTCAAGCAGGCCTGGGAAGAGGGGATCTGTGGG

ATCTCATCCGTTTCAAGAATGGAAAACATCATGTGGAAATCAGTAGAAGGGGAGCTCAATGCTATCCTAGAGGAGAATGGAG

TTCAACTGACAGTTGTTGTGGGATCTGTAAAAAACCCCATGTGGAGAGGTCCACAAAGATTGCCAGTGCCTGTGAATGAGCTG

CCCCATGGCTGGAAAGCCTGGGGGAAATCGTATTTTGTTAGGGCGGCAAAGACCAACAACAGTTTTGTTGTCGACGGTGACAC

ACTGAAGGAATGTCCGCTTGAGCACAGAGCATGGAATAGTTTTCTTGTGGAGGATCACGGGTTTGGAGTCTTCCACACCAGTG

TCTGGCTTAAGGTCAGAGAAGATTACTCATTAGAATGTGACCCAGCCGTCATAGGAACAGCTGTTAAGGGAAGGGAGGCCGC

GCACAGTGATCTGGGCTATTGGATTGAAAGTGAAAAGAATGACACATGGAGGCTGAAGAGGGCCCACCTGATTGAGATGAAA

ACATGTGAATGGCCAAAGTCTCACACATTGTGGACAGATGGAGTAGAAGAAAGTGATCTTATCATACCCAAGTCTTTAGCTGG

TCCACTCAGCCACCACAACACCAGAGAGGGTTACAGAACCCAAGTGAAAGGGCCATGGCACAGTGAAGAGCTTGAAATCCGG

TTTGAGGAATGTCCAGGCACCAAGGTTTACGTGGAGGAGACATGCGGAACTAGAGGACCATCTCTGAGATCAACTACTGCAA

GTGGAAGGGTCATTGAGGAATGGTGCTGTAGGGAATGCACAATGCCCCCACTATCGTTTCGAGCAAAAGACGGCTGCTGGTA

TGGAATGGAGATAAGGCCCAGGAAAGAACCAGAGAGCAACTTAGTGAGGTCAATGGTGACAGCGGGGTCAACCGATCATAT

GGACCACTTCTCTCTTGGAGTGCTTGTGATTCTACTCATGGTGCAGGAGGGGTTGAAGAAGAGAATGACCACAAAGATCATCA

TGAGCACATCAATGGCAGTGCTGGTAGTCATGATCTTGGGAGGATTTTCAATGAGTGACCTGGCCAAGCTTGTGATCCTGATG

GGTGCTACTTTCGCAGAAATGAACACTGGAGGAGATGTAGCTCACTTGGCATTGGTAGCGGCATTTAAAGTCAGACCAGCCTT

GCTGGTCTCCTTCATTTTCAGAGCCAATTGGACACCCCGTGAGAGCATGCTGCTAGCCCTGGCTTCGTGTCTTCTGCAAACTGC

GATCTCTGCTCTTGAAGGTGACTTGATGGTCCTCATTAATGGATTTGCTTTGGCCTGGTTGGCAATTCGAGCAATGGCCGTGCC

ACGCACTGACAACATCGCTCTACCAATCTTGGCTGCTCTAACACCACTAGCTCGAGGCACACTGCTCGTGGCATGGAGAGCGG

-continued

GCCTGGCTACTTGTGGAGGGATCATGCTCCTCTCCCTGAAAGGGAAAGGTAGTGTGAAGAAGAACCTGCCATTTGTCATGGCC

CTGGGATTGACAGCTGTGAGGGTAGTAGACCCTATTAATGTGGTAGGACTACTGTTACTCACAAGGAGTGGGAAGCGGAGCT

GGCCCCCTAGTGAAGTTCTCACAGCCGTTGGCCTGATATGTGCACTGGCCGGAGGGTTTGCCAAGGCAGACATTGAGATGGCT

GGACCCATGGCTGCAGTAGGCTTGCTAATTGTCAGCTATGTGGTCTCGGGAAAGAGTGTGGACATGTACATTGAAAGAGCAG

GTGACATCACATGGGAAAAGGACGCGGAAGTCACTGGAAACAGTCCTCGGCTTGACGTGGCACTGGATGAGAGTGGTGACTT

CTCCTTGGTAGAGGAAGATGGTCCACCCATGAGAGAGATCATACTCAAGGTGGTCCTGATGGCCATCTGTGGCATGAACCCAA

TAGCTATACCTTTTGCTGCAGGAGCGTGGTATGTGTATGTGAAGACTGGGAAAAGGAGTGGCGCCCTCTGGGACGTGCCTGC

TCCCAAAGAAGTGAAGAAAGGAGAGACCACAGATGGAGTGTACAGAGTGATGACTCGCAGACTGCTAGGTTCAACACAGGTT

GGAGTGGGAGTCATGCAAGAGGGAGTCTTCCACACCATGTGGCACGTTACAAAAGGAGCCGCACTGAGGAGCGGTGAGGGA

AGACTTGATCCATACTGGGGGGATGTCAAGCAGGACTTGGTGTCATACTGTGGGCCTTGGAAGTTGGATGCAGCTTGGGATG

GACTCAGCGAGGTACAGCTTTTGGCCGTACCTCCCGGAGAGAGGGCCAGAAACATTCAGACCCTGCCTGGAATATTCAAGACA

AAGGACGGGGACATCGGAGCAGTTGCTCTGGACTACCCTGCAGGGACCTCAGGATCTCCGATCCTAGACAAATGTGGAAGAG

TGATAGGACTCTATGGCAATGGGGTTGTGATCAAGAATGGAAGCTATGTTAGTGCTATAACCCAGGGAAAGAGGGAGGAGG

AGACTCCGGTTGAATGTTTCGAACCCTCGATGCTGAAGAAGAAGCAGCTAACTGTCTTGGATCTGCATCCAGGAGCCGGAAAA

ACCAGGAGAGTTCTTCCTGAAATAGTCCGTGAAGCCATAAAAAAGAGACTCCGGACAGTGATCTTGGCACCAACTAGGGTTGT

CGCTGCTGAGATGGAGGAGGCCTTGAGAGGACTTCCGGTGCGTTACATGACAACAGCAGTCAACGTCACCCATTCTGGGACA

GAAATCGTTGATTTGATGTGCCATGCCACTTTCACTTCACGCTTACTACAACCCATCAGAGTCCCTAATTACAATCTCAACATCAT

GGATGAAGCCCACTTCACAGACCCCTCAAGTATAGCTGCAAGAGGATACATATCAACAAGGGTTGAAATGGGCGAGGCGGCT

GCCATTTTTATGACTGCCACACCACCAGGAACCCGTGATGCGTTTCCTGACTCTAACTCACCAATCATGGACACAGAAGTGGAA

GTCCCAGAGAGAGCCTGGAGCTCAGGCTTTGATTGGGTGACAGACCATTCTGGGAAAACAGTTTGGTTCGTTCCAAGCGTGA

GAAACGGAAATGAAATCGCAGCCTGTCTGACAAAGGCTGGAAAGCGGGTCATACAGCTCAGCAGGAAGACTTTTGAGACAGA

ATTTCAGAAAACAAAAAATCAAGAGTGGGACTTTGTCATAACAACTGACATCTCAGAGATGGGCGCCAACTTCAAGGCTGACC

GGGTCATAGACTCTAGGAGATGCCTAAAACCAGTCATACTTGATGGTGAGAGAGTCATCTTGGCTGGGCCCATGCCTGTCACG

CATGCTAGTGCTGCTCAGAGGAGAGGACGTATAGGCAGGAACCCTAACAAACCTGGAGATGAGTACATGTATGGAGGTGGG

TGTGCAGAGACTGATGAAGGCCATGCACACTGGCTTGAAGCAAGAATGCTTCTTGACAACATCTACCTCCAGGATGGCCTCAT

AGCCTCGCTCTATCGGCCTGAGGCCGATAAGGTAGCCGCCATTGAGGGAGAGTTTAAGCTGAGGACAGAGCAAAGGAAGAC

CTTCGTGGAACTCATGAAGAGAGGAGACCTTCCCGTCTGGCTAGCCTATCAGGTTGCATCTGCCGGAATAACTTACACAGACA

GAAGATGGTGCTTTGATGGCACAACCAACAACACCATAATGGAAGACAGTGTACCAGCAGAGGTTTGGACAAAGTATGGAGA

GAAGAGAGTGCTCAAACCGAGATGGATGGATGCTAGGGTCTGTTCAGACCATGCGGCCCTGAAGTCGTTCAAAGAATTCGCC

GCTGGAAAAAGAGGAGCGGCTTTGGGAGTAATGGAGGCCCTGGGAACACTGCCAGGACACATGACAGAGAGGTTTCAGGAA

GCCATTGACAACCTCGCCGTGCTCATGCGAGCAGAGACTGGAAGCAGGCCTTATAAGGCAGCGGCAGCCCAACTGCCGGAGA

CCCTAGAGACCATTATGCTCTTAGGTTTGCTGGGAACAGTTTCACTGGGGATCTTCTTCGTCTTGATGCGGAATAAGGGCATCG

GGAAGATGGGCTTTGGAATGGTAACCCTTGGGGCCAGTGCATGGCTCATGTGGCTTTCGGAAATTGAACCAGCCAGAATTGC

ATGTGTCCTCATTGTTGTGTTTTTATTACTGGTGGTGCTCATACCCGAGCCAGAGAAGCAAAGATCTCCCCAAGATAACCAGAT

GGCAATTATCATCATGGTGGCAGTGGGCCTTCTAGGTTTGATAACTGCAAACGAACTTGGATGGCTGGAAAGAACAAAAAAT

GACATAGCTCATCTAATGGGAAGGAGAGAAGAAGGAGCAACCATGGGATTCTCAATGGACATTGATCTGCGGCCAGCCTCCG

CCTGGGCTATCTATGCCGCATTGACAACTCTCATCACCCCAGCTGTCCAACATGCGGTAACCACTTCATACAACAACTACTCCTT

AATGGCGATGGCCACACAAGCTGGAGTGCTGTTTGGCATGGGCAAAGGGATGCCATTTATGCATGGGGACCTTGGAGTCCCG

CTGCTAATGATGGGTTGCTATTCACAATTAACACCCCTGACTCTGATAGTAGCTATCATTCTGCTTGTGGCGCACTACATGTACT

TGATCCCAGGCCTACAAGCGGCAGCAGCGCGTGCTGCCCAGAAAAGGACAGCAGCTGGCATCATGAAGAATCCCGTTGTGGA

TGGAATAGTGGTAACTGACATTGACACAATGACAATAGACCCCCAGGTGGAGAAGAAGATGGGACAAGTGTTACTCATAGCA

-continued

GTAGCCATCTCCAGTGCTGTGCTGCTGCGGACCGCCTGGGGATGGGGGGAGGCTGGAGCTCTGATCACAGCAGCGACCTCCA

CCTTGTGGGAAGGCTCTCCAAACAAATACTGGAACTCCTCTACAGCCACCTCACTGTGCAACATCTTCAGAGGAAGCTATCTGG

CAGGAGCTTCCCTTATCTATACAGTGACGAGAAACGCTGGCCTGGTTAAGAGACGTGGAGGTGGGACGGGAGAGACTCTGG

GAGAGAAGTGGAAAGCTCGTCTGAATCAGATGTCGGCCCTGGAGTTCTACTCTTATAAAAAGTCAGGTATCACTGAAGTGTGT

AGAGAGGAGGCTCGCCGTGCCCTCAAGGATGGAGTGGCCACAGGAGGACATGCCGTATCCCGGGGAAGTGCAAAGATCAGA

TGGTTGGAGGAGAGAGGATATCTGCAGCCCTATGGGAAGGTTGTTGACCTCGGATGTGGCAGAGGGGGCTGGAGCTATTAT

GCCGCCACCATCCGCAAAGTGCAGGAGGTGAGAGGATACACAAAGGGAGGTCCCGGTCATGAAGAACCCATGCTGGTGCAA

AGCTATGGGTGGAACATAGTTCGTCTCAAGAGTGGAGTGGACGTCTTCCACATGGCGGCTGAGCCGTGTGACACTCTGCTGTG

TGACATAGGTGAGTCATCATCTAGTCCTGAAGTGGAAGAGACACGAACACTCAGAGTGCTCTCTATGGTGGGGGACTGGCTT

GAAAAAAGACCAGGGGCCTTCTGTATAAAGGTGCTGTGCCCATACACCAGCACTATGATGGAAACCATGGAGCGACTGCAAC

GTAGGCATGGGGGAGGATTAGTCAGAGTGCCATTGTGTCGCAACTCCACACATGAGATGTACTGGGTCTCTGGGGCAAAGAG

CAACATCATAAAAAGTGTGTCCACCACAAGTCAGCTCCTCCTGGGACGCATGGATGGCCCCAGGAGGCCAGTGAAATATGAG

GAGGATGTGAACCTCGGCTCGGGTACACGAGCTGTGGCAAGCTGTGCTGAGGCTCCTAACATGAAAATCATCGGCAGGCGCA

TTGAGAGAATCCGCAATGAACATGCAGAAACATGGTTTCTTGATGAAAACCACCCATACAGGACATGGGCCTACCATGGGAGC

TACGAAGCCCCCACGCAAGGATCAGCGTCTTCCCTCGTGAACGGGGTTGTTAGACTCCTGTCAAAGCCTTGGGACGTGGTGAC

TGGAGTTACAGGAATAGCCATGACTGACACCACACCATACGGCCAACAAAGAGTCTTCAAAGAAAAAGTGGACACCAGGGTG

CCAGATCCCCAAGAAGGCACTCGCCAGGTAATGAACATAGTCTCTTCCTGGCTGTGGAAGGAGCTGGGGAAACGCAAGCGGC

CACGCGTCTGCACCAAAGAAGAGTTTATCAACAAGGTGCGCAGCAATGCAGCACTGGGAGCAATATTTGAAGAGGAAAAAGA

ATGGAAGACGGCTGTGGAAGCTGTGAATGATCCAAGGTTTTGGGCCCTAGTGGATAGGGAGAGAGAACACCACCTGAGAGG

AGAGTGTCACAGCTGTGTGTACAACATGATGGGAAAAAGAGAAAAGAAGCAAGGAGAGTTCGGGAAAGCAAAAGGTAGCC

GCGCCATCTGGTACATGTGGTTGGGAGCCAGATTCTTGGAGTTTGAAGCCCTTGGATTCTTGAACGAGGACCATTGGATGGGA

AGAGAAAACTCAGGAGGTGGAGTCGAAGGGTTAGGATTGCAAAGACTTGGATACATTCTAGAAGAAATGAATCGGGCACCA

GGAGGAAAGATGTACGCAGATGACACTGCTGGCTGGGACACCCGCATTAGTAAGTTTGATCTGGAGAATGAAGCTCTGATTA

CCAACCAAATGGAGGAAGGGCACAGAACTCTGGCGTTGGCCGTGATTAAATACACATACCAAAACAAAGTGGTGAAGGTTCT

CAGACCAGCTGAAGGAGGAAAAACAGTTATGGACATCATTTCAAGACAAGACCAGAGAGGGAGTGGACAAGTTGTCACTTAT

GCTCTCAACACATTCACCAACTTGGTGGTGCAGCTTATCCGGAACATGGAAGCTGAGGAAGTGTTAGAGATGCAAGACTTATG

GTTGTTGAGGAAGCCAGAGAAAGTGACCAGATGGTTGCAGAGCAATGGATGGGATAGACTCAAACGAATGGCGGTCAGTGG

AGATGACTGCGTTGTGAAGCCAATCGATGATAGGTTTGCACATGCCCTCAGGTTCTTGAATGACATGGGAAAAGTTAGGAAAG

ACACACAGGAGTGGAAACCCTCGACTGGATGGAGCAATTGGGAAGAAGTCCCGTTCTGCTCCCACCACTTCAACAAGCTGTAC

CTCAAGGATGGGAGATCCATTGTGGTCCCTTGCCGCCACCAAGATGAACTGATTGGCCGAGCTCGCGTCTCACCAGGGGCAG

GATGGAGCATCCGGGAGACTGCCTGTCTTGCAAAATCATATGCGCAGATGTGGCAGCTCCTTTATTTCCACAGAAGAGACCTT

CGACTGATGGCTAATGCCATTTGCTCGGCTGTGCCAGTTGACTGGGTACCAACTGGGAGAACCACCTGGTCAATCCATGGAAA

GGGAGAATGGATGACCACTGAGGACATGCTCATGGTGTGGAATAGAGTGTGGATTGAGGAGAACGACCATATGGAGGACAA

GACTCCTGTAACAAAATGGACAGACATTCCCTATCTAGGAAAAAGGGAGGACTTATGGTGTGGATCCCTTATAGGGCACAGAC

CCCGCACCACTTGGGCTGAAAACATCAAAGACACAGTCAACATGGTGCGCAGGATCATAGGTGATGAAGAAAAGTACATGGA

CTATCTATCCACCCAAGTCCGCTACTTGGGTGAGGAAGGGTCCACACCCGGAGTGTTGTAAGCACCAATTTTAGTGTTGTCAGG

CCTGCTAGTCAGCCACAGTTTGGGGAAAGCTGTGCAGCCTGTAACCCCCCCAGGAGAAGCTGGGAAACCAAGCTCATAGTCA

GGCCGAGAACGCCATGGCACGGAAGAAGCCATGCTGCCTGTGAGCCCCTCAGAGGACACTGAGTCAAAAAACCCCACGCGCT

-continued

TGGAAGCGCAGGATGGGAAAAGAAGGTGGCGACCTTCCCCACCCTTCAATCTGGGGCCTGAACTGGAGACTAGCTGTGAATC

TCCAGCAGAGGGACTAGTGGTTAGAGGAGACCCCCCGGAAAACGCAAAACAGCATATTGACGTGGGAAAGACCAGAGACTC

CATGAGTTTCCACCACGCTGGCCGCCAGGCACAGATCGCCGAACTTCGGCGGCCGGTGTGGGGAAATCCATGGTTTCT

KJ776791.1, Zika virus strain H/PF/2013 polyprotein gene, complete cds

SEQ ID NO: 13

AGTATCAACAGGTTTTATTTTGGATTTGGAAACGAGAGTTTCTGGTCATGAAAAACCCAAAAAAGAAATCCGGAGGATTCCGG

ATTGTCAATATGCTAAAACGCGGAGTAGCCCGTGTGAGCCCCTTTGGGGGCTTGAAGAGGCTGCCAGCCGGACTTCTGCTGG

GTCATGGGCCCATCAGGATGGTCTTGGCGATTCTAGCCTTTTTGAGATTCACGGCAATCAAGCCATCACTGGGTCTCATCAATA

GATGGGGTTCAGTGGGGAAAAAAGAGGCTATGGAAATAATAAAGAAGTTCAAGAAAGATCTGGCTGCCATGCTGAGAATAA

TCAATGCTAGGAAGGAGAAGAAGAGACGAGGCGCAGATACTAGTGTCGGAATTGTTGGCCTCCTGCTGACCACAGCTATGGC

AGCGGAGGTCACTAGACGTGGGAGTGCATACTATATGTACTTGGACAGAAACGACGCTGGGGAGGCCATATCTTTTCCAACC

ACATTGGGGATGAATAAGTGTTATATACAGATCATGGATCTTGGACACATGTGTGATGCCACCATGAGCTATGAATGCCCTAT

GCTGGATGAGGGGGTGGAACCAGATGACGTCGATTGTTGGTGCAACACGACGTCAACTTGGGTTGTGTACGGAACCTGCCAT

CACAAAAAAGGTGAAGCACGGAGATCTAGAAGAGCTGTGACGCTCCCCTCCCATTCCACTAGGAAGCTGCAAACGCGGTCGC

AAACCTGGTTGGAATCAAGAGAATACACAAAGCACTTGATTAGAGTCGAAAATTGGATATTCAGGAACCCTGGCTTCGCGTTA

GCAGCAGCTGCCATCGCTTGGCTTTTGGGAAGCTCAACGAGCCAAAAAGTCATATACTTGGTCATGATACTGCTGATTGCCCCG

GCATACAGCATCAGGTGCATAGGAGTCAGCAATAGGGACTTTGTGGAAGGTATGTCAGGTGGGACTTGGGTTGATGTTGTCT

TGGAACATGGAGGTTGTGTCACCGTAATGGCACAGGACAAACCGACTGTCGACATAGAGCTGGTTACAACAACAGTCAGCAA

CATGGCGGAGGTAAGATCCTACTGCTATGAGGCATCAATATCGGACATGGCTTCGGACAGCCGCTGCCCAACACAAGGTGAA

GCCTACCTTGACAAGCAATCAGACACTCAATATGTCTGCAAAAGAACGTTAGTGGACAGAGGCTGGGGAAATGGATGTGGAC

TTTTTGGCAAAGGGAGCCTGGTGACATGCGCTAAGTTTGCATGCTCCAAGAAAATGACCGGGAAGAGCATCCAGCCAGAGAA

TCTGGAGTACCGGATAATGCTGTCAGTTCATGGCTCCCAGCACAGTGGGATGATCGTTAATGACACAGGACATGAAACTGATG

AGAATAGAGCGAAGGTTGAGATAACGCCCAATTCACCAAGAGCCGAAGCCACCCTGGGGGGTTTTGGAAGCCTAGGACTTGA

TTGTGAACCGAGGACAGGCCTTGACTTTTCAGATTTGTATTACTTGACTATGAATAACAAGCACTGGTTGGTTCACAAGGAGTG

GTTCCACGACATTCCATTACCTTGGCACGCTGGGGCAGACACCGGAACTCCACACTGGAACAACAAAGAAGCACTGGTAGAGT

TCAAGGACGCACATGCCAAAAGGCAAACTGTCGTGGTTCTAGGGAGTCAAGAAGGAGCAGTTCACACGGCCCTTGCTGGAGC

TCTGGAGGCTGAGATGGATGGTGCAAAGGGAAGGCTGTCCTCTGGCCACTTGAAATGTCGCCTGAAAATGGATAAACTTAGA

TTGAAGGGCGTGTCATACTCCTTGTGTACCGCAGCGTTCACATTCACCAAGATCCCGGCTGAAACACTGCACGGGACAGTCAC

AGTGGAGGTACAGTACGCAGGGACAGATGGACCTTGCAAGGTTCCAGCTCAGATGGCGGTGGACATGCAAACTCTGACCCCA

GTTGGGAGGTTGATAACCGCTAACCCCGTAATCACTGAAAGCACTGAGAACTCTAAGATGATGCTGGAACTTGATCCACCATT

TGGGGACTCTTACATTGTCATAGGAGTCGGGGAGAAGAAGATCACCCACCACTGGCACAGGAGTGGCAGCACCATTGGAAAA

GCATTTGAAGCCACTGTGAGAGGTGCCAAGAGAATGGCAGTCTTGGGAGACACAGCCTGGGACTTTGGATCAGTTGGAGGCG

CTCTCAACTCATTGGGCAAGGGCATCCATCAAATTTTTGGAGCAGCTTTCAAATCATTGTTTGGAGGAATGTCCTGGTTCTCACA

AATTCTCATTGGAACGTTGCTGATGTGGTTGGGTCTGAACACAAAGAATGGATCTATTTCCCTTATGTGCTTGGCCTTAGGGGG

AGTGTTGATCTTCTTATCCACAGCTGTCTCTGCTGATGTGGGGTGCTCGGTGGACTTCTCAAAGAAGGAGACGAGATGCGGTA

CAGGGGTGTTCGTCTATAACGACGTTGAAGCCTGGAGGGACAGGTACAAGTACCATCCTGACTCCCCCCGTAGATTGGCAGCA

GCAGTCAAGCAAGCCTGGGAAGATGGTATCTGTGGGATCTCCTCTGTTTCAAGAATGGAAAACATCATGTGGAGATCAGTAG

AAGGGGAGCTCAACGCAATCCTGGAAGAGAATGGAGTTCAACTGACGGTCGTTGTGGGATCTGTAAAAAACCCCATGTGGAG

AGGTCCACAGAGATTGCCCGTGCCTGTGAACGAGCTGCCCCACGGCTGGAAGGCTTGGGGGAAATCGTACTTCGTCAGAGCA

GCAAAGACAAATAACAGCTTTGTCGTGGATGGTGACACACTGAAGGAATGCCCACTCAAACATAGAGCATGGAACAGCTTTCT

TGTGGAGGATCATGGGTTCGGGGTATTTCACACTAGTGTCTGGCTCAAGGTTAGAGAAGATTATTCATTAGAGTGTGATCCAG

-continued

CCGTTATTGGAACAGCTGTTAAGGGAAAGGAGGCTGTACACAGTGATCTAGGCTACTGGATTGAGAGTGAGAAGAATGACAC

ATGGAGGCTGAAGAGGGCCCATCTGATCGAGATGAAAACATGTGAATGGCCAAAGTCCCACACATTGTGGACAGATGGAATA

GAAGAGAGTGATCTGATCATACCCAAGTCTTTAGCTGGGCCACTCAGCCATCACAATACCAGAGAGGGCTACAGGACCCAAAT

GAAAGGGCCATGGCACAGTGAAGAGCTTGAAATTCGGTTTGAGGAATGCCCAGGCACTAAGGTCCACGTGGAGGAAACATG

TGGAACAAGAGGACCATCTCTGAGATCAACCACTGCAAGCGGAAGGGTGATCGAGGAATGGTGCTGCAGGGAGTGCACAAT

GCCCCCACTGTCGTTCCGGGCTAAAGATGGCTGTTGGTATGGAATGGAGATAAGGCCCAGGAAAGAACCAGAAAGTAACTTA

GTAAGGTCAATGGTGACTGCAGGATCAACTGATCACATGGATCACTTCTCCCTTGGAGTGCTTGTGATTCTGCTCATGGTGCAG

GAAGGGCTGAAGAAGAGAATGACCACAAAGATCATCATAAGCACATCGATGGCAGTGCTGGTAGCTATGATCCTGGGAGGAT

TTTCAATGAGTGACCTGGCTAAGCTTGCAATTTTGATGGGTGCCACCTTCGCGGAAATGAACACTGGAGGAGATGTAGCTCAT

CTGGCGCTGATAGCGGCATTCAAAGTCAGACCAGCGTTGCTGGTATCTTTCATCTTCAGAGCTAATTGGACACCCCGTGAAAGC

ATGCTGCTGGCCTTGGCCTCGTGTCTTTTGCAAACTGCGATCTCCGCCTTGGAAGGCGACCTGATGGTTCTCATCAATGGTTTT

GCTTTGGCCTGGTTGGCAATACGAGCGATGGTTGTTCCACGCACTGATAACATCACCTTGGCAATCCTGGCTGCTCTGACACCA

CTGGCCCGGGGCACACTGCTTGTGGCGTGGAGAGCAGGCCTTGCTACTTGCGGGGGGTTTATGCTCCTCTCTCTGAAGGGAA

AAGGCAGTGTGAAGAAGAACTTACCATTTGTCATGGCCCTGGGACTAACCGCTGTGAGGCTGGTCGACCCCATCAACGTGGTG

GGACTGCTGTTGCTCACAAGGAGTGGGAAGCGGAGCTGGCCCCCTAGCGAAGTACTCACAGCTGTTGGCCTGATATGCGCAT

TGGCTGGAGGGTTCGCCAAGGCAGATATAGAGATGGCTGGGCCCATGGCCGCGGTCGGTCTGCTAATTGTCAGTTACGTGGT

CTCAGGAAAGAGTGTGGACATGTACATTGAAAGAGCAGGTGACATCACATGGGAAAAAGATGCGGAAGTCACTGGAAACAG

TCCCCGGCTCGATGTGGCGCTAGATGAGAGTGGTGATTTCTCCCTGGTGGAGGATGACGGTCCCCCCATGAGAGAGATCATAC

TCAAGGTGGTCCTGATGACCATCTGTGGCATGAACCCAATAGCCATACCCTTTGCAGCTGGAGCGTGGTACGTATACGTGAAG

ACTGGAAAAAGGAGTGGTGCTCTATGGGATGTGCCTGCTCCCAAGGAAGTAAAAAAGGGGGAGACCACAGATGGAGTGTAC

AGAGTAATGACTCGTAGACTGCTAGGTTCAACACAAGTTGGAGTGGGAGTTATGCAAGAGGGGGTCTTTCACACTATGTGGC

ACGTCACAAAAGGATCCGCGCTGAGAAGCGGTGAAGGGAGACTTGATCCATACTGGGGAGATGTCAAGCAGGATCTGGTGT

CATACTGTGGTCCATGGAAGCTAGATGCCGCCTGGGACGGGCACAGCGAGGTGCAGCTCTTGGCCGTGCCCCCCGGAGAGAG

AGCGAGGAACATCCAGACTCTGCCCGGAATATTTAAGACAAAGGATGGGGACATTGGAGCGGTTGCGCTGGATTACCCAGCA

GGAACTTCAGGATCTCCAATCCTAGACAAGTGTGGGAGAGTGATAGGACTTTATGGCAATGGGGTCGTGATCAAAAATGGGA

GTTATGTTAGTGCCATCACCCAAGGGAGGAGGGAGGAAGAGACTCCTGTTGAGTGCTTCGAGCCTTCGATGCTGAAGAAGAA

GCAGCTAACTGTCTTAGACTTGCATCCTGGAGCTGGGAAAACCAGGAGAGTTCTTCCTGAAATAGTCCGTGAAGCCATAAAAA

CAAGACTCCGTACTGTGATCTTAGCTCCAACCAGGGTTGTCGCTGCTGAAATGGAGGAAGCCCTTAGAGGGCTTCCAGTGCGT

TATATGACAACAGCAGTCAATGTCACCCACTCTGGAACAGAAATCGTCGACTTAATGTGCCATGCCACCTTCACTTCACGTCTAC

TACAGCCAATCAGAGTCCCCAACTATAATCTGTATATTATGGATGAGGCCCACTTCACAGATCCCTCAAGTATAGCAGCAAGAG

GATACATTTCAACAAGGGTTGAGATGGGCGAGGCGGCTGCCATCTTCATGACCGCCACGCCACCAGGAACCCGTGACGCATTT

CCGGACTCCAACTCACCAATTATGGACACCGAAGTGGAAGTCCCAGAGAGAGCCTGGAGCTCAGGCTTTGATTGGGTGACGG

ATCATTCTGGAAAAACAGTTTGGTTTGTTCCAAGCGTGAGGAACGGCAATGAGATCGCAGCTTGTCTGACAAAGGCTGGAAAA

CGGGTCATACAGCTCAGCAGAAAGACTTTTGAGACAGAGTTCCAGAAAACAAAACATCAAGAGTGGGACTTTGTCGTGACAA

CTGACATTTCAGAGATGGGCGCCAACTTTAAAGCTGACCGTGTCATAGATTCCAGGAGATGCCTAAAGCCGGTCATACTTGAT

GGCGAGAGAGTCATTCTGGCTGGACCCATGCCTGTCACACATGCCAGCGCTGCCCAGAGGAGGGGGCGCATAGGCAGGAAT

CCCAACAAACCTGGAGATGAGTATCTGTATGGAGGTGGGTGCGCAGAGACTGACGAAGACCATGCACACTGGCTTGAAGCAA

GAATGCTCCTTGACAATATTTACCTCCAAGATGGCCTCATAGCCTCGCTCTATCGACCTGAGGCCGACAAAGTAGCAGCCATTG

AGGGAGAGTTCAAGCTTAGGACGGAGCAAAGGAAGACCTTTGTGGAACTCATGAAAAGAGGAGATCTTCCTGTTTGGCTGGC

CTATCAGGTTGCATCTGCCGGAATAACCTACACAGATAGAAGATGGTGCTTTGATGGCACGACCAACAACACCATAATGGAAG

ACAGTGTGCCGGCAGAGGTGTGGACCAGACACGGAGAGAAAAGAGTGCTCAAACCGAGGTGGATGGACGCCAGAGTTTGTT

-continued

CAGATCATGCGGCCCTGAAGTCATTCAAGGAGTTTGCCGCTGGGAAAAGAGGAGCGGCTTTTGGAGTGATGGAAGCCCTGGG

AACACTGCCAGGACACATGACAGAGAGATTCCAGGAAGCCATTGACAACCTCGCTGTGCTCATGCGGGCAGAGACTGGAAGC

AGGCCTTACAAAGCCGCGGCGGCCCAATTGCCGGAGACCCTAGAGACCATTATGCTTTTGGGGTTGCTGGGAACAGTCTCGCT

GGGAATCTTTTTCGTCTTGATGAGGAACAAGGGCATAGGGAAGATGGGCTTTGGAATGGTGACTCTTGGGGCCAGCGCATGG

CTCATGTGGCTCTCGGAAATTGAGCCAGCCAGAATTGCATGTGTCCTCATTGTTGTGTTCCTATTGCTGGTGGTGCTCATACCTG

AGCCAGAAAAGCAAAGATCTCCCCAGGACAACCAAATGGCAATCATCATCATGGTAGCAGTAGGTCTTCTGGGCTTGATTACC

GCCAATGAACTCGGATGGTTGGAGAGAACAAAGAGTGACCTAAGCCATCTAATGGGAAGGAGAGAGGAGGGGGCAACCATA

GGATTCTCAATGGACATTGACCTGCGGCCAGCCTCAGCTTGGGCCATCTATGCTGCCTTGACAACTTTCATTACCCCAGCCGTCC

AACATGCAGTGACCACTTCATACAACAACTACTCCTTAATGGCGATGGCCACGCAAGCTGGAGTGTTGTTTGGTATGGGCAAA

GGGATGCCATTCTACGCATGGGACTTTGGAGTCCCGCTGCTAATGATAGGTTGCTACTCACAATTAACACCCCTGACCCTAATA

GTGGCCATCATTTTGCTCGTGGCGCACTACATGTACTTGATCCCAGGGCTGCAGGCAGCAGCTGCGCGTGCTGCCCAGAAGAG

AACGGCAGCTGGCATCATGAAGAACCCTGTTGTGGATGGAATAGTGGTGACTGACATTGACACAATGACAATTGACCCCCAA

GTGGAGAAAAAGATGGGACAGGTGCTACTCATAGCAGTAGCCGTCTCCAGCGCCATACTGTCGCGGACCGCCTGGGGGTGG

GGGGAGGCTGGGGCCCTGATCACAGCGGCAACTTCCACTTTGTGGGAAGGCTCTCCGAACAAGTACTGGAACTCCTCTACAGC

CACTTCACTGTGTAACATTTTTAGGGGAAGTTACTTGGCTGGAGCTTCTCTAATCTACACAGTAACAAGAAACGCTGGCTTGGT

CAAGAGACGTGGGGGTGGAACAGGAGAGACCCTGGGAGAGAAATGGAAGGCCCGCTTGAACCAGATGTCGGCCCTGGAGT

TCTACTCCTACAAAAAGTCAGGCATCACCGAGGTGTGCAGAGAAGAGGCCCGCCGCGCCCTCAAGGACGGTGTGGCAACGGG

AGGCCATGCTGTGTCCCGAGGAAGTGCAAAGCTGAGATGGTTGGTGGAGCGGGGATACCTGCAGCCCTATGGAAAGGTCATT

GATCTTGGATGTGGCAGAGGGGGCTGGAGTTACTACGCCGCCACCATCCGCAAAGTTCAAGAAGTGAAAGGATACACAAAAG

GAGGCCCTGGTCATGAAGAACCCATGTTGGTGCAAAGCTATGGGTGGAACATAGTCCGTCTTAAGAGTGGGGTGGACGTCTT

TCATATGGCGGCTGAGCCGTGTGACACGTTGCTGTGTGACATAGGTGAGTCATCATCTAGTCCTGAAGTGGAAGAAGCACGG

ACGCTCAGAGTCCTCTCCATGGTGGGGGATTGGCTTGAAAAAAGACCAGGAGCCTTTTGTATAAAAGTGTTGTGCCCATACAC

CAGCACTATGATGGAAACCCTGGAGCGACTGCAGCGTAGGTATGGGGGAGGACTGGTCAGAGTGCCACTCTCCCGCAACTCT

ACACATGAGATGTACTGGGTCTCTGGAGCGAAAAGCAACACCATAAAAAGTGTGTCCACCACGAGCCAGCTCCTCTTGGGGC

GCATGGACGGGCCCAGGAGGCCAGTGAAATATGAGGAGGATGTGAATCTCGGCTCTGGCACGCGGGCTGTGGTAAGCTGCG

CTGAAGCTCCCAACATGAAGATCATTGGTAACCGCATTGAAAGGATCCGCAGTGAGCACGCGGAAACGTGGTTCTTTGACGA

GAACCACCCATATAGGACATGGGCTTACCATGGAAGCTATGAGGCCCCCACACAAGGGTCAGCGTCCTCTCTAATAAACGGGG

TTGTCAGGCTCCTGTCAAAACCCTGGGATGTGGTGACTGGAGTCACAGGAATAGCCATGACCGACACCACACCGTATGGTCAG

CAAAGAGTTTTCAAGGAAAAAGTGGACACTAGGGTGCCAGACCCCCAAGAAGGCACTCGTCAGGTTATGAGCATGGTCTCTTC

CTGGTTGTGGAAAGAGCTAGGCAAACACAAACGGCCACGAGTCTGTACCAAAGAAGAGTTCATCAACAAGGTTCGTAGCAAT

GCAGCATTAGGGGCAATATTTGAAGAGGAAAAAGAGTGGAAGACTGCAGTGGAAGCTGTGAACGATCCAAGGTTCTGGGCT

CTAGTGGACAAGGAAAGAGAGCACCACCTGAGAGGAGAGTGCCAGAGTTGTGTGTACAACATGATGGGAAAAAGAGAAAAG

AAACAAGGGGAATTTGGAAAGGCCAAGGGCAGCCGCGCCATCTGGTATATGTGGCTAGGGGCTAGATTTCTAGAGTTCGAAG

CCCTTGGATTCTTGAACGAGGATCACTGGATGGGGAGAGAGAACTCAGGAGGTGGTGTTGAAGGGCTGGGATTACAAAGAC

TCGGATATGTCCTAGAAGAGATGAGTCGCATACCAGGAGGAAGGATGTATGCAGATGACACTGCTGGCTGGGACACCCGCAT

CAGCAGGTTTGATCTGGAGAATGAAGCTCTAATCACCAACCAAATGGAGAAAGGGCACAGGGCCTTGGCATTGGCCATAATC

AAGTACACATACCAAAACAAAGTGGTAAAGGTCCTTAGACCAGCTGAAAAAGGGAAGACAGTTATGGACATTATTTCGAGAC

AAGACCAAAGGGGGAGCGGACAAGTTGTCACTTACGCTCTTAACACATTTACCAACCTAGTGGTGCAACTCATTCGGAATATG

GAGGCTGAGGAAGTTCTAGAGATGCAAGACTTGTGGCTGCTGCGGAGGTCAGAGAAAGTGACCAACTGGTTGCAGAGCAAC

GGATGGGATAGGCTCAAACGAATGGCAGTCAGTGGAGATGATTGCGTTGTGAAGCCAATTGATGATAGGTTTGCACATGCCC

-continued

TCAGGTTCTTGAATGATATGGGAAAAGTTAGGAAGGACACACAAGAGTGGAAACCCTCAACTGGATGGGACAACTGGGAAG

AAGTTCCGTTTTGCTCCCACCACTTCAACAAGCTCCATCTCAAGGACGGGAGGTCCATTGTGGTTCCCTGCCGCCACCAAGATG

AACTGATTGGCCGGGCCCGCGTCTCTCCAGGGGCGGGATGGAGCATCCGGGAGACTGCTTGCCTAGCAAAATCATATGCGCA

AATGTGGCAGCTCCTTTATTTCCACAGAAGGGACCTCCGACTGATGGCCAATGCCATTTGTTCATCTGTGCCAGTTGACTGGGT

TCCAACTGGGAGAACTACCTGGTCAATCCATGGAAAGGGAGAATGGATGACCACTGAAGACATGCTTGTGGTGTGGAACAGA

GTGTGGATTGAGGAGAACGACCACATGGAAGACAAGACCCCAGTTACGAAATGGACAGACATTCCCTATTTGGGAAAAAGGG

AAGACTTGTGGTGTGGATCTCTCATAGGGCACAGACCGCGCACCACCTGGGCTGAGAACATTAAAAACACAGTCAACATGGT

GCGCAGGATCATAGGTGATGAAGAAAAGTACATGGACTACCTATCCACCCAAGTTCGCTACTTGGGTGAAGAAGGGTCTACA

CCTGGAGTGCTGTAAGCACCAATCTTAGTGTTGTCAGGCCTGCTAGTCAGCCACAGCTTGGGGAAAGCTGTGCAGCCTGTGAC

CCCCCCAGGAGAAGCTGGGAAACCAAGCCTATAGTCAGGCCGAGAACGCCATGGCACGGAAGAAGCCATGCTGCCTGTGAGC

CCCTCAGAGGACACTGAGTCAAAAAACCCCACGCGCTTGGAGGCGCAGGATGGGAAAAGAAGGTGGCGACCTTCCCCACCCT

TCAATCTGGGGCCTGAACTGGAGATCAGCTGTGGATCTCCAGAAGAGGGACTAGTGGTTAGAGGAG

In some embodiments, the Zika virus has a RNA genome corresponding to the DNA sequence provided by the nucleic acid sequence of any one of SEQ ID NOs: 2-13 or 72. In some embodiments, the Zika virus has a variant genome that is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-13 or 72.

Provided below are amino acid sequences of the E-proteins of Zika strains that may be used in the methods, compositions, and/or vaccines described herein.

isol-ARB15076.AHF49784.1.Central_African_Republic/291-788 Flavivirus envelope glycoprotein E.

SEQ ID NO: 14

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDENRAKVEVTPNSPRA

EATLGGFGSLGLDCEPRTGLDFSDLYYLTMNNKHWLVHKEWFHDIPLPWHAGADTGTPHWNNKEALVEFKDAHAKRQTVVVLGS

QEGAVHTALAGALEAEMDGAKGRLFSGHLKCRLKMDKLRLKGVSYSLCTAAFTFTKVPAETLHGTVTVEVQYAGTDGPCKVPAQM

AVDMQTLTPVGRLITANPVITESTENSKMMLELDPPFGDSYIVIGVGDKKITHHWHRSGSTIGKAFEATVRGAKRMAVLGDTAWDF

GSVGGVFNSLGKGIHQIFGAAFKSLFGGMSWFSQILIGTLLVWLGLNTKNGSISLTCLALGGVMIFLSTAVSA isol-IbH_30656.AEN75265.1.Nigeria/291-788 Flavivirus envelope glycoprotein E.

SEQ ID NO: 15

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDENRAKVEVTPNSPRA

EATLGGFGSLGLDCEPRTGLDFSDLYYLTMNNKHWLVHKEWFHDIPLPWHSGADTETPHWNNKEALVEFKDAHAKRQTVVVLGS

QEGAVHTALAGALEAEMDGAKGRLSSGHLKCRLKMDKLRLKGVSYSLCTAAFTFTKVPAETLHGTVTVEVQYAGRDGPCKVPAQM

AVDMQTLTPVGRLITANPVITESTENSKMMLELDPPFGDSYIVIGVGDKKITHHWHRSGSIIGKAFEATVRGAKRMAVLGDTAWDF

GSVGGVFNSLGKGIHQIFGAAFKSLFGGMSWFSQILIGTLLVWLGLNTKNGSISLTCLALGGVMIFLSTAVSA

ArB1362.AHL43500.1.-/291-794 Flavivirus envelope glycoprotein E.

SEQ ID NO: 16

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDXXXXXXXNRAEVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

-continued

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA

ArD128000.AHL43502.1.-/291-794 Flavivirus envelope glycoprotein E.

SEQ ID NO: 17

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMXXXXXGHETDENRAKVEVT

PNSPRAEATLGGFGSLGLDCEPRTGLDFSDLYYLTMNNKHRLVRKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWLKKGSSIGKAFEATVRGAKRMAVLGD

TAWDFGSVGGVFNSLGKGVHQIFGAAFKSLFGGMSWFSQILIGTLLVWLGLNTKNGSISLTCLALGGVMIFLSTAVSA

ArD158095.AHL43505.1.-/291-794 Flavivirus envelope glycoprotein E.

SEQ ID NO: 18

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDIGHETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA

ArD158084.AHL43504.1.-/291-794 Flavivirus envelope glycoprotein E.

SEQ ID NO: 19

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDIGHETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA isol-ARB13565.AHF49783.1.Central_African_Republic/291-794 Flavivirus envelope glycoprotein E.

SEQ ID NO: 20

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDIGHETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGVHQIFGAAFKSLFGGMSWFSQILIGTLLVWLGLNTKNGSISLTCLALGGVMIFLSTAVSA isol-ARB7701.AHF49785.1.Central_African_Republic/291-794 Flavivirus envelope glycoprotein E.

SEQ ID NO: 21

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDIGHETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGVHQIFGAAFKSLFGGMSWFSQILIGTLLVWLGLNTKNGSISLTCLALGGVMIFLSTAVSA isol-ArD_41519.AEN75266.1.Senegal/291-794 Flavivirus envelope glycoprotein E.

-continued

SEQ ID NO: 22

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDTGHETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAAFTFTKVPAETLHGTVTVEVQYAGTDGPCK

VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA

MR766-NIID.BAP47441.1.Uganda/291-794 Flavivirus envelope glycoprotein E.

SEQ ID NO: 23

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMTVNDIGYETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGKLFSGHLKCRLKMDKLRLKGVSYSLCTAAFTFTKVPAETLHGTVTVEVQYAGTDGPCK

IPVQMAVDMQTLTPVGRLITANPVITESTENSKMMLELDPPFGDSYIVIGVGDKKITHHWHRSGSTIGKAFEATVRGAKRMAVLGD

TAWDFGSVGGVFNSLGKGIHQIFGAAFKSLFGGMSWFSQILIGTLLVWLGLNTKNGSISLTCLALGGVMIFLSTAVSA

LC002520.1/326-829 Zika virus genomic RNA, strain: MR766-NIID, Uganda, Flavivirus envelope glycoprotein E.

SEQ ID NO: 24

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMTVNDIGYETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGKLFSGHLKCRLKMDKLRLKGVSYSLCTAAFTFTKVPAETLHGTVTVEVQYAGTDGPCK

IPVQMAVDMQTLTPVGRLITANPVITESTENSKMMLELDPPFGDSYIVIGVGDKKITHHWHRSGSTIGKAFEATVRGAKRMAVLGD

TAWDFGSVGGVFNSLGKGIHQIFGAAFKSLFGGMSWFSQILIGTLLVWLGLNTKNGSISLTCLALGGVMIFLSTAVSA isol-MR_766.AEN75263.1.Uganda/291-794 Flavivirus envelope glycoprotein E.

SEQ ID NO: 25

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDTGYETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGKLFSGHLKCRLKMDKLRLKGVSYSLCTAAFTFTKVPAETLHGTVTVEVQYAGTDGPCK

IPVQMAVDMQTLTPVGRLITANPVITESTENSKMMLELDPPFGDSYIVIGVGDKKITHHWHRSGSTIGKAFEATVRGAKRMAVLGD

TAWDFGSVGGVFNSLGKGIHQIFGAAFKSLFGGMSWFSQILIGTLLVWLGLNTKNGSISLTCLALGGVMIFLSTAVSA

ArD7117.AHL43501.1.1291-794 Flavivirus envelope glycoprotein E.

SEQ ID NO: 26

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDIGHETDENRAKVEVT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVSYSLCTAVCTAAKVPAETLHGTVTVEVQYAGTDGPC

KVPAQMAVDMQTLTPVGRLITANPVITESTENSKMMLELDPPFGDSYIVIGVGDKKITHHWHRSGSTIGKAFEATVRGAKRMAVL

GDTAWDFGSVGGVFNSLGKGIHQIFGAAFKSLFGGMSWFSQILIGTLLVWLGLNTKNGSISLTCLALGGVMIFLSTAVSA

AY632535.2/326-825 NC_012532.1 Zika virus strain MR 766, Uganda, Flavivirus envelope glycoprotein E.

SEQ ID NO: 27

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIGYETDEDRAKVEVTPNSPR

AEATLGGFGSLGLDCEPRTGLDFSDLYYLTMNNKHWLVHKEWFHDIPLPWHAGADTGTPHWNNKEALVEFKDAHAKRQTVVVL

GSQEGAVHTALAGALEAEMDGAKGRLFSGHLKCRLKMDKLRLKGVSYSLCTAAFTFTKVPAETLHGTVTVEVQYAGTDGPCKIPVQ

-continued

MAVDMQTLTPVGRLITANPVITESTENSKMMLELDPPFGDSYIVIGVGDKKITHHWHRSGSTIGKAFEATVRGAKRMAVLGDTAW

DFGSVGGVFNSLGKGIHQIFGAAFKSLFGGMSWFSQILIGTLLVWLGLNTKNGSISLTCLALGGVMIFLSTAVSA

MR_766.AAV34151.1.Uganda/291-790 Flavivirus envelope glycoprotein E. |Q32ZE1|Q32ZE1_9FL

SEQ ID NO: 28

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIGYETDEDRAKVEVTPNSPR

AEATLGGFGSLGLDCEPRTGLDFSDLYYLTMNNKHWLVHKEWFHDIPLPWHAGADTGTPHWNNKEALVEFKDAHAKRQTVVVL

GSQEGAVHTALAGALEAEMDGAKGRLFSGHLKCRLKMDKLRLKGVSYSLCTAAFTFTKVPAETLHGTVTVEVQYAGTDGPCKIPVQ

MAVDMQTLTPVGRLITANPVITESTENSKMMLELDPPFGDSYIVIGVGDKKITHHWHRSGSTIGKAFEATVRGAKRMAVLGDTAW

DFGSVGGVFNSLGKGIHQIFGAAFKSLFGGMSWFSQILIGTLLVWLGLNTKNGSISLTCLALGGVMIFLSTAVSA

MR_766.YP_009227198.1.Uganda/1-500 envelope protein E [Zika virus]

SEQ ID NO: 29

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIGYETDEDRAKVEVTPNSPR

AEATLGGFGSLGLDCEPRTGLDFSDLYYLTMNNKHWLVHKEWFHDIPLPWHAGADTGTPHWNNKEALVEFKDAHAKRQTVVVL

GSQEGAVHTALAGALEAEMDGAKGRLFSGHLKCRLKMDKLRLKGVSYSLCTAAFTFTKVPAETLHGTVTVEVQYAGTDGPCKIPVQ

MAVDMQTLTPVGRLITANPVITESTENSKMMLELDPPFGDSYIVIGVGDKKITHHWHRSGSTIGKAFEATVRGAKRMAVLGDTAW

DFGSVGGVFNSLGKGIHQIFGAAFKSLFGGMSWFSQILIGTLLVWLGLNTKNGSISLTCLALGGVMIFLSTAVSA

KU681081.3/308-811 Zika virus isolate Zika virus/*H. sapiens*-tc/THA/2014/SV0127-14, Thailand, Flavivirus envelope glycoprotein E.

SEQ ID NO: 30

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHTGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITEGTENSKMMLELDPPFGDSYIVIGVGEKKITHHWHRSGSTIGKAFEATVRGAKRMAVLG

DTAWDFGSVGGVLNSLGKGIHQIFGAAFKSLFGGMSWFSQILIGTLLMWLGLNTKNGSISLMCLALGGVLIFLSTAVSA isol-Zika_virus % *H. sapiens*-tc % THA % 2014% SV0127-_14.AMD61710.1.Thailand/291-794 Flavivirus envelope glycoprotein E.

SEQ ID NO: 31

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHTGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITEGTENSKMMLELDPPFGDSYIVIGVGEKKITHHWHRSGSTIGKAFEATVRGAKRMAVLG

DTAWDFGSVGGVLNSLGKGIHQIFGAAFKSLFGGMSWFSQILIGTLLMWLGLNTKNGSISLMCLALGGVLIFLSTAVSA

CK-ISL_2014.AIC06934.1.Cook_Islands/1-504 Flavivirus envelope glycoprotein E. (Fragment) OS = Zika virus GN = E PE = 4 SV = 1

SEQ ID NO: 32

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

Natal_RGN.AMB18850.1.Brazil:_Rio_Grande_do_Norte,_Natal/291-794 Flavivirus envelope glycoprotein E.]

-continued

SEQ ID NO: 33
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Si323.AMC37200.1.Colombia/1-504 Flavivirus envelope glycoprotein E.

SEQ ID NO: 34
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU707826.1/317-820 Zika virus isolate SSABR1, Brazil, Flavivirus envelope glycoprotein E.

SEQ ID NO: 35
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU509998.1/326-829 Zika virus strain Haiti/1225/2014, Haiti, Flavivirus envelope glycoprotein E.

SEQ ID NO: 36
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-GDZ16001.AML82110.1.China/291-794 Flavivirus envelope glycoprotein E.

SEQ ID NO: 37
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

BeH819015.AMA12085.1.Brazil/291-794 Flavivirus envelope glycoprotein E.]

SEQ ID NO: 38
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

-continued

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

MRS_OPY_Martinique_PaRi_2015.AMC33116.1.Martinique/291-794 Flavivirus envelope glycoprotein E.

SEQ ID NO: 39

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU501215.1/308-811 Zika virus strain PRVABC59, Puerto Rico, Flavivirus envelope glycoprotein E.

SEQ ID NO: 40

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

Haiti % 1225% 2014.AMB37295.1.Haiti/291-794 Flavivirus envelope glycoprotein E.

SEQ ID NO: 41

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU527068.1/308-811 Zika virus strain Natal RGN, Brazil: Rio Grande do Norte, Natal, Flavivirus envelope glycoprotein E.

SEQ ID NO: 42

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Z1106027.ALX35662.1.Suriname/5-508 Flavivirus envelope glycoprotein E.

SEQ ID NO: 43

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-FLR.AMM39804.1.Colombia:_Barranquilla/291-794 Flavivirus envelope glycoprotein E.

-continued

SEQ ID NO: 44
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

PLCal_ZV_isol-From_Vero_E6_cells.AHL37808.1.Canada/254-757 Flavivirus envelope glycoprotein E.

SEQ ID NO: 45
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

BeH818995.AMA12084.1.Brazil/291-794 Flavivirus envelope glycoprotein E. [Zika virus].

SEQ ID NO: 46
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

H/PF/2013.AHZ13508.1.French_Polynesia/291-794 Flavivirus envelope glycoprotein E.

SEQ ID NO: 47
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

PRVABC59.AMC13911.1.Puerto_Rico/291-794 Flavivirus envelope glycoprotein E.

SEQ ID NO: 48
IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU321639.1/326-829 Zika virus strain ZikaSPH2015, Brazil, Flavivirus envelope glycoprotein E.

SEQ ID NO: 49
IRCIGVSNRDFVEGMSGGTWVDIVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

-continued

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

ZikaSPH2015.ALU33341.1.Brazil/291-794 Flavivirus envelope glycoprotein E.

SEQ ID NO: 50

IRCIGVSNRDFVEGMSGGTWVDIVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

103344.AMC13912.1.Guatemala/291-794 polyprotein [Zika virus]. 103344.AMC13912.1.Guatemala Flavivirus envelope glycoprotein E.

SEQ ID NO: 51

IRCIGVSNRDFVEGMSGGTWVDVVLEHGGCVTVMAQDKPTVDIELVTTTVSNMAEIRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Brazil-ZKV2015.AMD16557.1.Brazil/291-794 Flavivirus envelope glycoprotein E.

SEQ ID NO: 52

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGTQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU497555.1/308-811 Zika virus isolate Brazil-ZKV2015, Flavivirus envelope glycoprotein E.

SEQ ID NO: 53

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGTQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-ZJ03.AMM39806.1.China/291-794 Flavivirus envelope glycoprotein E.

SEQ ID NO: 54

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGARRMAVLG

DTAWDFGSVGGALNSLGKGIHQIFGAAFKSLFGGMSWFSQILIGTLLMWLGLNTKNGSISLMCLALGGVLIFLSTAVSA isol-F5513025.AFD30972.1.Cambodia/291-794 Flavivirus envelope glycoprotein E.

SEQ ID NO: 55

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

-continued

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLVWLGLNTKNGSISLMCLALGGVLIFLSTAVSA isol-Z1106032.ALX35660.1.Suriname/291-794 Flavivirus envelope glycoprotein E. [Zika virus]
SEQ ID NO: 56

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNAKNGSISLMCLALGGVLIFLSTAVSA isol-Z1106033.ALX35659.1.Suriname/291-794 Flavivirus envelope glycoprotein E. [Zika virus]
SEQ ID NO: 57

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNAKNGSISLMCLALGGVLIFLSTAVSA isol-BeH828305.AMK49165.1.Brazil/291-794 Flavivirus envelope glycoprotein E.
SEQ ID NO: 58

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDTQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-GD01.AMK79468.1.China/291-794 Flavivirus envelope glycoprotein E.
SEQ ID NO: 59

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNGTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Z1106031.ALX35661.1.Suriname/291-794 Flavivirus envelope glycoprotein E.
SEQ ID NO: 60

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

-continued

VLAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

ACD75819.1.Micronesia/291-794 Flavivirus envelope glycoprotein E.

SEQ ID NO: 61

IRCIGVSNRDFVEGMSGGTWVDVVLEHGGCVTVMAQDKPAVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLVWLGLNTKNGSISLTCLALGGVLIFLSTAVSA

KU681082.3/308-811 Zika virus isolate Zika virus/*H. sapiens*-tc/PHL/2012/CPC-0740, Philippines, Flavivirus envelope glycoprotein E.

SEQ ID NO: 62

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLVWLGLNTKNGSISLTCLALGGVLIFLSTAVSA isol-Zika_virus % *H. sapiens*-tc % PHL % 2012% CPC-0740.AMD61711.1.Philippines/ 291-794 Flavivirus envelope glycoprotein E.

SEQ ID NO: 63

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLVWLGLNTKNGSISLTCLALGGVLIFLSTAVSA isol-BeH823339.AMK49164.2.Brazil/291-794 Flavivirus envelope glycoprotein E.

SEQ ID NO: 64

IRCIGVSNRDFVEGMSGGTWVDVVLEHGGCVTVMAQDKPTVDIELVSTTVSNMAEVRSYCYEATISDIASDSRCPTQGEAYLDKQS

DTQYVCKRTLVDRGWGNGCGLFGKGSLVTCAKFACSKKMTGKSIQPENLEYRIMLSVHGSQHSGMIVNDTGHETDENRAKVEITP

NSPRAEATLGGFGSLGLDCEPRTGLDFSDLYYLTMNNKHWLVHKEWFHDIPLPWHAGADTGTPHWNNKEALVEFKDAHAKRQT

AVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-P6-740.AEN75264.1.Malaysia/291-794 Flavivirus envelope glycoprotein E.

SEQ ID NO: 65

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDXGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGDKKITHHWXRSGSTIGKAFEATVRGAKRMAVLG

DTAWDFGSVGGALNSLGKGIHQIFGAAFKSLFGGMSWFSQILIGTLLVWLGLNTKNGSISLTCLALGGVLIFLSTAVSA

KU744693.1/326-829 Zika virus isolate VE_Ganxian, China, Flavivirus envelope glycoprotein E.

-continued

SEQ ID NO: 66
IRCIGVSNRDFVEGMSGGTWVDVVLEHGGCVTAMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMLVNDTGHETDENRAKVEIT
PNSPRAEATLGGFGSLGLDCEPRTGLDFSDLYYLTMNNKHWLAHKEWFHDIPLPWHAGAATGTPHWNNKEALVEFKDAHAKRQT
VVVLGSQEGAVHTALAGALEAEMDGAKGRLSSGHLKCRLKMDKLRLKGVSYSLCTAAFTFTKIPAETVDGTVTVEGQYGGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIIGAAFKSLFGGMSWFSQILIGTLLMWLGLNTKNGSISLMCLALGGVLIFLSTAVSG isol-VE_Ganxian.AMK79469.1.China/291-794 Flavivirus envelope glycoprotein E.

SEQ ID NO: 67
IRCIGVSNRDFVEGMSGGTWVDVVLEHGGCVTAMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMLVNDTGHETDENRAKVEIT
PNSPRAEATLGGFGSLGLDCEPRTGLDFSDLYYLTMNNKHWLAHKEWFHDIPLPWHAGAATGTPHWNNKEALVEFKDAHAKRQT
VVVLGSQEGAVHTALAGALEAEMDGAKGRLSSGHLKCRLKMDKLRLKGVSYSLCTAAFTFTKIPAETVDGTVTVEGQYGGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIIGAAFKSLFGGMSWFSQILIGTLLMWLGLNTKNGSISLMCLALGGVLIFLSTAVSG

ArD157995.AHL43503.1.1291-794 Flavivirus envelope glycoprotein E.

SEQ ID NO: 68
ISCIGVSNRDLVEGMSGGTWVDVVLEHGGCVTEMAQDKPTVDIELVTMTVSNMAEVRSYCYEASLSDMASASRCPTQGEPSLDK
QSDTQSVCKRTLGDRGWGNGCGIFGKGSLVTCSKFTCCKKMPGKSIQPENLEYRIMLPVHGSQHSGMIVNDIGHETDENRAKVEV
TPNSPRAEATLGGFGSLGLDCEPRTGLDFSDLYYLTMNNKHWLVHKEWFHDIPLPWHAGADTGTPHWNNKEALVEFKDAHAKRQ
TVVVLGSQEGAVHTALAGALEAEMDGAKGRLFSGHLKCRLKMDKLRLKGVSYSLCTAAFTFTKVPAETLHGTVTVEVQSAGTDGPC
KVPAQMAVDMQTLTPVGRLITANPVITESTENSKMMLELDPPFGDSYIVIGVGDKKITHHWHRSGSTIGKAFEATVRGAKRMAVL
GDTAWDFGSVGGVFNSLGKGIHQIFGAAFKSLFGGMSWFSQILIGTLLVWLGLNTKNGSISLTCLALGGVMIFLSTAVSA

MR_766.ABI54475.1.Uganda/291-788 Flavivirus envelope glycoprotein E.

SEQ ID NO: 69
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFTCSKKMTGKSIQPENLEYRIMLSVHGSQHSGMIVNDENRAKVEVTPNSPRA
EATLGGFGSLGLDCEPRTGLDFSDLYYLTMNNKHWLVHKEWFHDIPLPWHAGADTGTPHWNNKEALVEFKDAHAKRQTVVVLGS
QEGAVHTALAGALEAEMDGAKGRLFSGHLKCRLKMDKLRLKGVSYSLCTAAFTFTKVPAETLHGTVTVEVQYAGTDGPCKVPAQM
AVDMQTLTPVGRLITANPVITESTENSKMMLELDPPFGDSYIVIGVGDKKITHHWHRSGSTIGKAFEATVRGAKRMAVLGDTAWDF
GSVGGVFNSLGKGIHQIFGAAFKSLFGGMSWFSQILIGTLLVWLGLNTKNGSISLTCLALGGVMIFLSTAVSA

5'-$(dIdC)_{13}$-3'

SEQ ID NO: 70
dIdC dIdC dIdC dIdC dIdC dIdC dIdC dIdC dIdC dIdC dIdC dIdC dIdC

KLK peptide

SEQ ID NO: 71
KLKLLLLLKLK

ZIKV Sequence H/PF/2013 as sequenced

SEQ ID NO: 72
CAGACTGCGACAGTTCGAGTTTGAAGCGAAAGCTAGCAACAGTATCAACAGGTTTTATTTTGGATTTGGAAACGAGAGTTTCT
GGTCATGAAAAACCCAAAAAAGAAATCCGGAGGATTCCGGATTGTCAATATGCTAAAACGCGGAGTAGCCCGTGTGAGCCCC
TTTGGGGGCTTGAAGAGGCTGCCAGCCGGACTTCTGCTGGGTCATGGGCCCATCAGGATGGTCTTGGCGATTCTAGCCTTTTT
GAGATTCACGGCAATCAAGCCATCACTGGGTCTCATCAATAGATGGGGTTCAGTGGGGAAAAAAGAGGCTATGGAAATAATA
AAGAAGTTCAAGAAAGATCTGGCTGCCATGCTGAGAATAATCAATGCTAGGAAGGAGAAGAAGAGACGAGGCGCAGATACT
AGTGTCGGAATTGTTGGCCTCCTGCTGACCACAGCTATGGCAGCGGAGGTCACTAGACGTGGGAGTGCATACTATATGTACTT
GGACAGAAACGACGCTGGGGAGGCCATATCTTTTCCAACCACATTGGGGATGAATAAGTGTTATATACAGATCATGGATCTTG
GACACATGTGTGATGCCACCATGAGCTATGAATGCCCTATGCTGGATGAGGGGGTGGAACCAGATGACGTCGATTGTTGGTG

-continued

CAACACGACGTCAACTTGGGTTGTGTACGGAACCTGCCATCACAAAAAAGGTGAAGCACGGAGATCTAGAAGAGCTGTGACG

CTCCCCTCCCATTCCACTAGGAAGCTGCAAACGCGGTCGCAAACCTGGTTGGAATCAAGAGAATACACAAAGCACTTGATTAG

AGTCGAAAATTGGATATTCAGGAACCCTGGCTTCGCGTTAGCAGCAGCTGCCATCGCTTGGCTTTTGGGAAGCTCAACGAGCC

AAAAAGTCATATACTTGGTCATGATACTGCTGATTGCCCCGGCATACAGCATCAGGTGCATAGGAGTCAGCAATAGGGACTTT

GTGGAAGGTATGTCAGGTGGGACTTGGGTTGATGTTGTCTTGGAACATGGAGGTTGTGTCACCGTAATGGCACAGGACAAAC

CGACTGTCGACATAGAGCTGGTTACAACAACAGTCAGCAACATGGCGGAGGTAAGATCCTACTGCTATGAGGCATCAATATCG

GACATGGCTTCGGACAGCCGCTGCCCAACACAAGGTGAAGCCTACCTTGACAAGCAATCAGACACTCAATATGTCTGCAAAAG

AACGTTAGTGGACAGAGGCTGGGGAAATGGATGTGGACTTTTTGGCAAAGGGAGCCTGGTGACATGCGCTAAGTTTGCATGC

TCCAAGAAAATGACCGGGAAGAGCATCCAGCCAGAGAATCTGGAGTACCGGATAATGCTGTCAGTTCATGGCTCCCAGCACA

GTGGGATGATCGTTAATGACACAGGACATGAAACTGATGAGAATAGAGCGAAGGTTGAGATAACGCCCAATTCACCAAGAGC

CGAAGCCACCCTGGGGGGTTTTGGAAGCCTAGGACTTGATTGTGAACCGAGGACAGGCCTTGACTTTTCAGATTTGTATTACT

TGACTATGAATAACAAGCACTGGTTGGTTCACAAGGAGTGGTTCCACGACATTCCATTACCTTGGCACGCTGGGGCAGACACC

GGAACTCCACACTGGAACAACAAAGAAGCACTGGTAGAGTTCAAGGACGCACATGCCAAAAGGCAAACTGTCGTGGTTCTAG

GGAGTCAAGAAGGAGCAGTTCACACGGCCCTTGCTGGAGCTCTGGAGGCTGAGATGGATGGTGCAAAGGGAAGGCTGTCCT

CTGGCCACTTGAAATGTCGCCTGAAAATGGATAAACTTAGATTGAAGGGCGTGTCATACTCCTTGTGTACCGCAGCGTTCACAT

TCACCAAGATCCCGGCTGAAACACTGCACGGGACAGTCACAGTGGAGGTACAGTACGCAGGGACAGATGGACCTTGCAAGGT

TCCAGCTCAGATGGCGGTGGACATGCAAACTCTGACCCCAGTTGGGAGGTTGATAACCGCTAACCCCGTAATCACTGAAAGCA

CTGAGAACTCTAAGATGATGCTGGAACTTGATCCACCATTTGGGGACTCTTACATTGTCATAGGAGTCGGGGAGAAGAAGATC

ACCCACCACTGGCACAGGAGTGGCAGCACCATTGGAAAAGCATTTGAAGCCACTGTGAGAGGTGCCAAGAGAATGGCAGTCT

TGGGAGACACAGCCTGGGACTTTGGATCAGTTGGAGGCGCTCTCAACTCATTGGGCAAGGGCATCCATCAAATTTTTGGAGCA

GCTTTCAAATCATTGTTTGGAGGAATGTCCTGGTTCTCACAAATTCTCATTGGAACGTTGCTGATGTGGTTGGGTCTGAACACA

AAGAATGGATCTATTTCCCTTATGTGCTTGGCCTTAGGGGGAGTGTTGATCTTCTTATCCACAGCTGTCTCTGCTGATGTGGGG

TGCTCGGTGGACTTCTCAAAGAAGGAGACGAGATGCGGTACAGGGGTGTTCGTCTATAACGACGTTGAAGCCTGGAGGGACA

GGTACAAGTACCATCCTGACTCCCCCCGTAGATTGGCAGCAGCAGTCAAGCAAGCCTGGGAAGATGGTATCTGTGGGATCTCC

TCTGTTTCAAGAATGGAAAACATCATGTGGAGATCAGTAGAAGGGGAGCTCAACGCAATCCTGGAAGAGAATGGAGTTCAAC

TGACGGTCGTTGTGGGATCTGTAAAAAACCCCATGTGGAGAGGTCCACAGAGATTGCCCGTGCCTGTGAACGAGCTGCCCCAC

GGCTGGAAGGCTTGGGGGAAATCGTACTTCGTCAGAGCAGCAAAGACAAATAACAGCTTTGTCGTGGATGGTGACACACTGA

AGGAATGCCCACTCAAACATAGAGCATGGAACAGCTTTCTTGTGGAGGATCATGGGTTCGGGGTATTTCACACTAGTGTCTGG

CTCAAGGTTAGAGAAGATTATTCATTAGAGTGTGATCCAGCCGTTATTGGAACAGCTGTTAAGGGAAAGGAGGCTGTACACA

GTGATCTAGGCTACTGGATTGAGAGTGAGAAGAATGACACATGGAGGCTGAAGAGGGCCCATCTGATCGAGATGAAAACAT

GTGAATGGCCAAAGTCCCACACATTGTGGACAGATGGAATAGAAGAGAGTGATCTGATCATACCCAAGTCTTTAGCTGGGCCA

CTCAGCCATCACAATACCAGAGAGGGCTACAGGACCCAAATGAAAGGGCCATGGCACAGTGAAGAGCTTGAAATTCGGTTTG

AGGAATGCCCAGGCACTAAGGTCCACGTGGAGGAAACATGTGGAACAAGAGGACCATCTCTGAGATCAACCACTGCAAGCGG

AAGGGTGATCGAGGAATGGTGCTGCAGGGAGTGCACAATGCCCCCACTGTCGTTCCGGGCTAAAGATGGCTGTTGGTATGGA

ATGGAGATAAGGCCCAGGAAAGAACCAGAAAGTAACTTAGTAAGGTCAATGGTGACTGCAGGATCAACTGATCACATGGATC

ACTTCTCCCTTGGAGTGCTTGTGATTCTGCTCATGGTGCAGGAAGGGCTGAAGAAGAGAATGACCACAAAGATCATCATAAGC

ACATCGATGGCAGTGCTGGTAGCTATGATCCTGGGAGGATTTTCAATGAGTGACCTGGCTAAGCTTGCAATTTTGATGGGTGC

CACCTTCGCGGAAATGAACACTGGAGGAGATGTAGCTCATCTGGCGCTGATAGCGGCATTCAAAGTCAGACCAGCGTTGCTG

GTATCTTTCATCTTCAGAGCTAATTGGACACCCCGTGAAAGCATGCTGCTGGCCTTGGCCTCGTGTCTTTTGCAAACTGCGATCT

CCGCCTTGGAAGGCGACCTGATGGTTCTCATCAATGGTTTTGCTTTGGCCTGGTTGGCAATACGAGCGATGGTTGTTCCACGCA

CTGATAACATCACCTTGGCAATCCTGGCTGCTCTGACACCACTGGCCCGGGGCACACTGCTTGTGGCGTGGAGAGCAGGCCTT

-continued

GCTACTTGCGGGGGGTTTATGCTCCTCTCTCTGAAGGGAAAAGGCAGTGTGAAGAAGAACTTACCATTTGTCATGGCCCTGGG

ACTAACCGCTGTGAGGCTGGTCGACCCCATCAACGTGGTGGGACTGCTGTTGCTCACAAGGAGTGGGAAGCGGAGCTGGCCC

CCTAGCGAAGTACTCACAGCTGTTGGCCTGATATGCGCATTGGCTGGAGGGTTCGCCAAGGCAGATATAGAGATGGCTGGGC

CCATGGCCGCGGTCGGTCTGCTAATTGTCAGTTACGTGGTCTCAGGAAAGAGTGTGGACATGTACATTGAAAGAGCAGGTGA

CATCACATGGGAAAAAGATGCGGAAGTCACTGGAAACAGTCCCCGGCTCGATGTGGCGCTAGATGAGAGTGGTGATTTCTCC

CTGGTGGAGGATGACGGTCCCCCCATGAGAGAGATCATACTCAAGGTGGTCCTGATGACCATCTGTGGCATGAACCCAATAGC

CATACCCTTTGCAGCTGGAGCGTGGTACGTATACGTGAAGACTGGAAAAAGGAGTGGTGCTCTATGGGATGTGCCTGCTCCCA

AGGAAGTAAAAAAGGGGGAGACCACAGATGGAGTGTACAGAGTAATGACTCGTAGACTGCTAGGTTCAACACAAGTTGGAG

TGGGAGTTATGCAAGAGGGGGTCTTTCACACTATGTGGCACGTCACAAAAGGATCCGCGCTGAGAAGCGGTGAAGGGAGAC

TTGATCCATACTGGGGAGATGTCAAGCAGGATCTGGTGTCATACTGTGGTCCATGGAAGCTAGATGCCGCCTGGGACGGGCA

CAGCGAGGTGCAGCTCTTGGCCGTGCCCCCCGGAGAGAGAGCGAGGAACATCCAGACTCTGCCCGGAATATTTAAGACAAAG

GATGGGGACATTGGAGCGGTTGCGCTGGATTACCCAGCAGGAACTTCAGGATCTCCAATCCTAGACAAGTGTGGGAGAGTGA

TAGGACTTTATGGCAATGGGGTCGTGATCAAAAATGGGAGTTATGTTAGTGCCATCACCCAAGGGAGGAGGGAGGAAGAGA

CTCCTGTTGAGTGCTTCGAGCCTTCGATGCTGAAGAAGAAGCAGCTAACTGTCTTAGACTTGCATCCTGGAGCTGGGAAAACC

AGGAGAGTTCTTCCTGAAATAGTCCGTGAAGCCATAAAAACAAGACTCCGTACTGTGATCTTAGCTCCAACCAGGGTTGTCGCT

GCTGAAATGGAGGAAGCCCTTAGAGGGCTTCCAGTGCGTTATATGACAACAGCAGTCAATGTCACCCACTCTGGAACAGAAAT

CGTCGACTTAATGTGCCATGCCACCTTCACTTCACGTCTACTACAGCCAATCAGAGTCCCCAACTATAATCTGTATATTATGGAT

GAGGCCCACTTCACAGATCCCTCAAGTATAGCAGCAAGAGGATACATTTCAACAAGGGTTGAGATGGGCGAGGCGGCTGCCA

TCTTCATGACCGCCACGCCACCAGGAACCCGTGACGCATTTCCGGACTCCAACTCACCAATTATGGACACCGAAGTGGAAGTCC

CAGAGAGAGCCTGGAGCTCAGGCTTTGATTGGGTGACGGATCATTCTGGAAAAACAGTTTGGTTTGTTCCAAGCGTGAGGAA

CGGCAATGAGATCGCAGCTTGTCTGACAAAGGCTGGAAAACGGGTCATACAGCTCAGCAGAAAGACTTTTGAGACAGAGTTC

CAGAAAACAAAACATCAAGAGTGGGACTTTGTCGTGACAACTGACATTTCAGAGATGGGCGCCAACTTTAAAGCTGACCGTGT

CATAGATTCCAGGAGATGCCTAAAGCCGGTCATACTTGATGGCGAGAGAGTCATTCTGGCTGGACCCATGCCTGTCACACATG

CCAGCGCTGCCCAGAGGAGGGGGCGCATAGGCAGGAATCCCAACAAACCTGGAGATGAGTATCTGTATGGAGGTGGGTGCG

CAGAGACTGACGAAGACCATGCACACTGGCTTGAAGCAAGAATGCTCCTTGACAATATTTACCTCCAAGATGGCCTCATAGCC

TCGCTCTATCGACCTGAGGCCGACAAAGTAGCAGCCATTGAGGGAGAGTTCAAGCTTAGGACGGAGCAAAGGAAGACCTTTG

TGGAACTCATGAAAAGAGGAGATCTTCCTGTTTGGCTGGCCTATCAGGTTGCATCTGCCGGAATAACCTACACAGATAGAAGA

TGGTGCTTTGATGGCACGACCAACAACACCATAATGGAAGACAGTGTGCCGGCAGAGGTGTGGACCAGACACGGAGAGAAA

AGAGTGCTCAAACCGAGGTGGATGGACGCCAGAGTTTGTTCAGATCATGCGGCCCTGAAGTCATTCAAGGAGTTTGCCGCTG

GGAAAAGAGGAGCGGCTTTTGGAGTGATGGAAGCCCTGGGAACACTGCCAGGACACATGACAGAGAGATTCCAGGAAGCCA

TTGACAACCTCGCTGTGCTCATGCGGGCAGAGACTGGAAGCAGGCCTTACAAAGCCGCGGCGGCCCAATTGCCGGAGACCCT

AGAGACCATTATGCTTTTGGGGTTGCTGGGAACAGTCTCGCTGGGAATCTTTTTCGTCTTGATGAGGAACAAGGGCATAGGGA

AGATGGGCTTTGGAATGGTGACTCTTGGGGCCAGCGCATGGCTCATGTGGCTCTCGGAAATTGAGCCAGCCAGAATTGCATGT

GTCCTCATTGTTGTGTTCCTATTGCTGGTGGTGCTCATACCTGAGCCAGAAAAGCAAAGATCTCCCCAGGACAACCAAATGGCA

ATCATCATCATGGTAGCAGTAGGTCTTCTGGGCTTGATTACCGCCAATGAACTCGGATGGTTGGAGAGAACAAAGAGTGACCT

AAGCCATCTAATGGGAAGGAGAGAGGAGGGGGCAACCATAGGATTCTCAATGGACATTGACCTGCGGCCAGCCTCAGCTTGG

GCCATCTATGCTGCCTTGACAACTTTCATTACCCCAGCCGTCCAACATGCAGTGACCACTTCATACAACAACTACTCCTTAATGG

CGATGGCCACGCAAGCTGGAGTGTTGTTTGGTATGGGCAAAGGGATGCCATTCTACGCATGGGACTTTGGAGTCCCGCTGCTA

ATGATAGGTTGCTACTCACAATTAACACCCCTGACCCTAATAGTGGCCATCATTTTGCTCGTGGCGCACTACATGTACTTGATCC

CAGGGCTGCAGGCAGCAGCTGCGCGTGCTGCCCAGAAGAGAACGGCAGCTGGCATCATGAAGAACCCTGTTGTGGATGGAA

-continued

TAGTGGTGACTGACATTGACACAATGACAATTGACCCCCAAGTGGAGAAAAAGATGGGACAGGTGCTACTCATAGCAGTAGC

CGTCTCCAGCGCCATACTGTCGCGGACCGCCTGGGGGTGGGGGGAGGCTGGGGCCCTGATCACAGCGGCAACTTCCACTTTG

TGGGAAGGCTCTCCGAACAAGTACTGGAACTCCTCTACAGCCACTTCACTGTGTAACATTTTTAGGGGAAGTTACTTGGCTGGA

GCTTCTCTAATCTACACAGTAACAAGAAACGCTGGCTTGGTCAAGAGACGTGGGGGTGGAACAGGAGAGACCCTGGGAGAG

AAATGGAAGGCCCGCTTGAACCAGATGTCGGCCCTGGAGTTCTACTCCTACAAAAAGTCAGGCATCACCGAGGTGTGCAGAG

AAGAGGCCCGCCGCGCCCTCAAGGACGGTGTGGCAACGGGAGGCCATGCTGTGTCCCGAGGAAGTGCAAAGCTGAGATGGT

TGGTGGAGCGGGGATACCTGCAGCCCTATGGAAAGGTCATTGATCTTGGATGTGGCAGAGGGGGCTGGAGTTACTACGCCGC

CACCATCCGCAAAGTTCAAGAAGTGAAAGGATACACAAAAGGAGGCCCTGGTCATGAAGAACCCATGTTGGTGCAAAGCTAT

GGGTGGAACATAGTCCGTCTTAAGAGTGGGGTGGACGTCTTTCATATGGCGGCTGAGCCGTGTGACACGTTGCTGTGTGACA

TAGGTGAGTCATCATCTAGTCCTGAAGTGGAAGAAGCACGGACGCTCAGAGTCCTCTCCATGGTGGGGGATTGGCTTGAAAA

AAGACCAGGAGCCTTTTGTATAAAAGTGTTGTGCCCATACACCAGCACTATGATGGAAACCCTGGAGCGACTGCAGCGTAGGT

ATGGGGGAGGACTGGTCAGAGTGCCACTCTCCCGCAACTCTACACATGAGATGTACTGGGTCTCTGGAGCGAAAAGCAACAC

CATAAAAAGTGTGTCCACCACGAGCCAGCTCCTCTTGGGGCGCATGGACGGGCCCAGGAGGCCAGTGAAATATGAGGAGGAT

GTGAATCTCGGCTCTGGCACGCGGGCTGTGGTAAGCTGCGCTGAAGCTCCCAACATGAAGATCATTGGTAACCGCATTGAAAG

GATCCGCAGTGAGCACGCGGAAACGTGGTTCTTTGACGAGAACCACCCATATAGGACATGGGCTTACCATGGAAGCTATGAG

GCCCCCACACAAGGGTCAGCGTCCTCTCTAATAAACGGGGTTGTCAGGCTCCTGTCAAAACCCTGGGATGTGGTGACTGGAGT

CACAGGAATAGCCATGACCGACACCACACCGTATGGTCAGCAAAGAGTTTTCAAGGAAAAAGTGGACACTAGGGTGCCAGAC

CCCCAAGAAGGCACTCGTCAGGTTATGAGCATGGTCTCTTCCTGGTTGTGGAAAGAGCTAGGCAAACACAAACGGCCACGAG

TCTGTACCAAAGAAGAGTTCATCAACAAGGTTCGTAGCAATGCAGCATTAGGGGCAATATTTGAAGAGGAAAAAGAGTGGAA

GACTGCAGTGGAAGCTGTGAACGATCCAAGGTTCTGGGCTCTAGTGGACAAGGAAAGAGAGCACCACCTGAGAGGAGAGTG

CCAGAGTTGTGTGTACAACATGATGGGAAAAAGAGAAAAGAAACAAGGGGAATTTGGAAAGGCCAAGGGCAGCCGCGCCAT

CTGGTATATGTGGCTAGGGGCTAGATTTCTAGAGTTCGAAGCCCTTGGATTCTTGAACGAGGATCACTGGATGGGGAGAGAG

AACTCAGGAGGTGGTGTTGAAGGGCTGGGATTACAAAGACTCGGATATGTCCTAGAAGAGATGAGTCGCATACCAGGAGGA

AGGATGTATGCAGATGACACTGCTGGCTGGGACACCCGCATCAGCAGGTTTGATCTGGAGAATGAAGCTCTAATCACCAACCA

AATGGAGAAAGGGCACAGGGCCTTGGCATTGGCCATAATCAAGTACACATACCAAAACAAAGTGGTAAAGGTCCTTAGACCA

GCTGAAAAAGGGAAGACAGTTATGGACATTATTTCGAGACAAGACCAAAGGGGGAGCGGACAAGTTGTCACTTACGCTCTTA

ACACATTTACCAACCTAGTGGTGCAACTCATTCGGAATATGGAGGCTGAGGAAGTTCTAGAGATGCAAGACTTGTGGCTGCTG

CGGAGGTCAGAGAAAGTGACCAACTGGTTGCAGAGCAACGGATGGGATAGGCTCAAACGAATGGCAGTCAGTGGAGATGAT

TGCGTTGTGAAGCCAATTGATGATAGGTTTGCACATGCCCTCAGGTTCTTGAATGATATGGGAAAAGTTAGGAAGGACACACA

AGAGTGGAAACCCTCAACTGGATGGGACAACTGGGAAGAAGTTCCGTTTTGCTCCCACCACTTCAACAAGCTCCATCTCAAGG

ACGGGAGGTCCATTGTGGTTCCCTGCCGCCACCAAGATGAACTGATTGGCCGGGCCCGCGTCTCTCCAGGGGCGGGATGGAG

CATCCGGGAGACTGCTTGCCTAGCAAAATCATATGCGCAAATGTGGCAGCTCCTTTATTTCCACAGAAGGGACCTCCGACTGAT

GGCCAATGCCATTTGTTCATCTGTGCCAGTTGACTGGGTTCCAACTGGGAGAACTACCTGGTCAATCCATGGAAAGGGAGAAT

GGATGACCACTGAAGACATGCTTGTGGTGTGGAACAGAGTGTGGATTGAGGAGAACGACCACATGGAAGACAAGACCCCAG

TTACGAAATGGACAGACATTCCCTATTTGGGAAAAAGGGAAGACTTGTGGTGTGGATCTCTCATAGGGCACAGACCGCGCACC

ACCTGGGCTGAGAACATTAAAAACACAGTCAACATGGTGCGCAGGATCATAGGTGATGAAGAAAAGTACATGGACTACCTAT

CCACCCAAGTTCGCTACTTGGGTGAAGAAGGGTCTACACCTGGAGTGCTGTAAGCACCAATCTTAGTGTTGTCAGGCCTGCTA

GTCAGCCACAGCTTGGGGAAAGCTGTGCAGCCTGTGACCCCCCCAGGAGAAGCTGGGAAACCAAGCCTATAGTCAGGCCGAG

AACGCCATGGCACGGAAGAAGCCATGCTGCCTGTGAGCCCCTCAGAGGACACTGAGTCAAAAAACCCCACGCGCTTGGAGGC

GCAGGATGGGAAAAGAAGGTGGCGACCTTCCCCACCCTTCAATCTGGGGCCTGAACTGGAGATCAGCTGTGGATCTCCAGAA

-continued

GAGGGACTAGTGGTTAGAGGAGACCCCCCGGAAAACGCAAAACAGCATATTGACGCTGGGAAAGACCAGAGACTCCATGAG

TTTCCACCACGCTGGCCGCCAGGCACAGATCGCCGAATAGCGGCGGCCGGTGTGGGG

AHZ13508.1, Zika virus polyprotein from Polynesian outbreak (H/PF/2013)

SEQ ID NO: 73

MKNPKKKSGGFRIVNMLKRGVARVSPFGGLKRLPAGLLLGHGPIRMVLAILAFLRFTAIKPSLGLINRWGSVGKKEAMEIIKKFKKDLA

AMLRIINARKEKKRRGADTSVGIVGLLLTTAMAAEVTRRGSAYYMYLDRNDAGEAISFPTTLGMNKCYIQIMDLGHMCDATMSYEC

PMLDEGVEPDDVDCWCNTTSTWVVYGTCHHKKGEARRSRRAVTLPSHSTRKLQTRSQTWLESREYTKHLIRVENWIFRNPGFALA

AAAIAWLLGSSTSQKVIYLVMILLIAPAYSIRCIGVSNRDFVEGMSGGTWVDVVLEHGGCVTVMAQDKPTVDIELVTTTVSNMAEVR

SYCYEASISDMASDSRCPTQGEAYLDKQSDTQYVCKRTLVDRGWGNGCGLFGKGSLVTCAKFACSKKMTGKSIQPENLEYRIMLSV

HGSQHSGMIVNDTGHETDENRAKVEITPNSPRAEATLGGFGSLGLDCEPRTGLDFSDLYYLTMNNKHWLVHKEWFHDIPLPWHA

GADTGTPHWNNKEALVEFKDAHAKRQTVVVLGSQEGAVHTALAGALEAEMDGAKGRLSSGHLKCRLKMDKLRLKGVSYSLCTAAF

TFTKIPAETLHGTVTVEVQYAGTDGPCKVPAQMAVDMQTLTPVGRLITANPVITESTENSKMMLELDPPFGDSYIVIGVGEKKITHH

WHRSGSTIGKAFEATVRGAKRMAVLGDTAWDFGSVGGALNSLGKGIHQIFGAAFKSLFGGMSWFSQILIGTLLMWLGLNTKNGSI

SLMCLALGGVLIFLSTAVSADVGCSVDFSKKETRCGTGVFVYNDVEAWRDRYKYHPDSPRRLAAAVKQAWEDGICGISSVSRMENI

MWRSVEGELNAILEENGVQLTVVVGSVKNPMWRGPQRLPVPVNELPHGWKAWGKSYFVRAAKTNNSFVVDGDTLKECPLKHRA

WNSFLVEDHGFGVFHTSVWLKVREDYSLECDPAVIGTAVKGKEAVHSDLGYWIESEKNDTWRLKRAHLIEMKTCEWPKSHTLWTD

GIEESDLIIPKSLAGPLSHHNTREGYRTQMKGPWHSEELEIRFEECPGTKVHVEETCGTRGPSLRSTTASGRVIEEWCCRECTMPPLSF

RAKDGCWYGMEIRPRKEPESNLVRSMVTAGSTDHMDHFSLGVLVILLMVQEGLKKRMTTKIIISTSMAVLVAMILGGFSMSDLAKL

AILMGATFAEMNTGGDVAHLALIAAFKVRPALLVSFIFRANWTPRESMLLALASCLLQTAISALEGDLMVLINGFALAWLAIRAMVV

PRTDNITLAILAALTPLARGTLLVAWRAGLATCGGFMLLSLKGKGSVKKNLPFVMALGLTAVRLVDPINVVGLLLLTRSGKRSWPPSE

VLTAVGLICALAGGFAKADIEMAGPMAAVGLLIVSYVVSGKSVDMYIERAGDITWEKDAEVTGNSPRLDVALDESGDFSLVEDDGPP

MREIILKVVLMTICGMNPIAIPFAAGAWYVYVKTGKRSGALWDVPAPKEVKKGETTDGVYRVMTRRLLGSTQVGVGVMQEGVFH

TMWHVTKGSALRSGEGRLDPYWGDVKQDLVSYCGPWKLDAAWDGHSEVQLLAVPPGERARNIQTLPGIFKTKDGDIGAVALDYP

AGTSGSPILDKCGRVIGLYGNGVVIKNGSYVSAITQGRREEETPVECFEPSMLKKKQLTVLDLHPGAGKTRRVLPEIVREAIKTRLRTVIL

APTRVVAAEMEEALRGLPVRYMTTAVNVTHSGTEIVDLMCHATFTSRLLQPIRVPNYNLYIMDEANFTDPSSIAARGYISTRVEMGE

AAAIFMTATPPGTRDAFPDSNSPIMDTEVEVPERAWSSGFDWVTDHSGKTVWFVPSVRNGNEIAACLTKAGKRVIQLSRKTFETEF

QKTKHQEWDFVVTTDISEMGANFKADRVIDSRRCLKPVILDGERVILAGPMPVTHASAAQRRGRIGRNPNKPGDEYLYGGGCAETD

EDHAHWLEARMLLDNIYLQDGLIASLYRPEADKVAAIEGEFKLRTEQRKTFVELMKRGDLPVWLAYQVASAGITYTDRRWCFDGTT

NNTIMEDSVPAEVWTRHGEKRVLKPRWMDARVCSDHAALKSFKEFAAGKRGAAFGVMEALGTLPGHMTERFQEAIDNLAVLMR

AETGSRPYKAAAAQLPETLETIMLLGLLGTVSLGIFFVLMRNKGIGKMGFGMVTLGASAWLMWLSEIEPARIACVLIVVFLLLVVLIPE

PEKQRSPQDNQMAIIIMVAVGLLGLITANELGWLERTKSDLSHLMGRREEGATIGFSMDIDLRPASAWAIYAALTTFITPAVQHAVT

TSYNNYSLMAMATQAGVLFGMGKGMPFYAWDFGVPLLMIGCYSQLTPLTLIVAIILLVAHYMYLIPGLQAAAARAAQKRTAAGIM

KNPVVDGIVVTDIDTMTIDPQVEKKMGQVLLIAVAVSSAILSRTAWGWGEAGALITAATSTLWEGSPNKYWNSSTATSLCNIFRGSY

LAGASLIYTVTRNAGLVKRRGGGTGETLGEKWKARLNQMSALEFYSYKKSGITEVCREEARRALKDGVATGGHAVSRGSAKLRWLV

ERGYLQPYGKVIDLGCGRGGWSYYAATIRKVQEVKGYTKGGPGHEEPMLVQSYGWNIVRLKSGVDVFHMAAEPCDTLLCDIGESSS

SPEVEEARTLRVLSMVGDWLEKRPGAFCIKVLCPYTSTMMETLERLQRRYGGGLVRVPLSRNSTHEMYWVSGAKSNTIKSVSTTSQL

LLGRMDGPRRPVKYEEDVNLGSGTRAVVSCAEAPNMKIIGNRIERIRSEHAETWFFDENHPYRTWAYHGSYEAPTQGSASSLINGV

VRLLSKPWDVVTGVTGIAMTDTTPYGQQRVFKEKVDTRVPDPQEGTRQVMSMVSSWLWKELGKHKRPRVCTKEEFINKVRSNAA

LGAIFEEEKEWKTAVEAVNDPRFWALVDKEREHHLRGECQSCVYNMMGKREKKQGEFGKAKGSRAIWYMWLGARFLEFEALGFL

NEDHWMGRENSGGGVEGLGLQRLGYVLEEMSRIPGGRMYADDTAGWDTRISRFDLENEALITNQMEKGHRALALAIIKYTYQNK

VVKVLRPAEKGKTVMDIISRQDQRGSGQVVTYALNTFTNLVVQLIRNMEAEEVLEMQDLWLLRRSEKVTNWLQSNGWDRLKRMA

-continued

VSGDDCVVKPIDDRFAHALRFLNDMGKVRKDTQEWKPSTGWDNWEEVPFCSHHFNKLHLKDGRSIVVPCRHQDELIGRARVSPG

AGWSIRETACLAKSYAQMWQLLYFHRRDLRLMANAICSSVPVDWVPTGRTTWSIHGKGEWMTTEDMLVVWNRVWIEENDHM

EDKTPVTKWTDIPYLGKREDLWCGSLIGHRPRTTWAENIKNTVNMVRRIIGDEEKYMDYLSTQVRYLGEEGSTPGVL

9320_Zika_PF_1F  SEQ ID NO: 74 ttaggatccGTTGTTGATCTGTGTGAAT

9321_Zika_PF_1R  SEQ ID NO: 75 taactcgagCGTACACAACCCAAGTT

9322_Zika_PF_2F  SEQ ID NO: 76 ttaggatccTCACTAGACGTGGGAGTG

9323_Zika_PF_2R  SEQ ID NO: 77 taactcgagAAGCCATGTCYGATATTGAT

9324_Zika_PF_3F  SEQ ID NO: 78 ttaggatccGCATACAGCATCAGGTG

9325_Zika_PF_3R  SEQ ID NO: 79 taactcgagTGTGGAGTTCCGGTGTCT

9326_Zika_PF_4F  SEQ ID NO: 80 ttaggatccGAATAGAGCGAARGTTGAGATA

9327_Zika_PF_4R  SEQ ID NO: 81 taactcgAGTGGTGGGTGATCTTCTTCT

9328_Zika_PF_5F  SEQ ID NO: 82 ttaggatcCAGTCACAGTGGAGGTACAGTAC

9329_Zika_PF_5R  SEQ ID NO: 83 taactcgagCRCAGATACCATCTTCCC

9330_Zika_PF_6F  SEQ ID NO: 84 ttaggatCCCTTATGTGCTTGGCCTTAG

9331_Zika_PF_6R  SEQ ID NO: 85 taactcgagTCTTCAGCCTCCATGTG

9332_Zika_PF_7F  SEQ ID NO: 86 ttaggatccAATGCCCACTCAAACATAGA

9333_Zika_PF_7R  SEQ ID NO: 87 taactcgagTCATTCTCTTCTTCAGCCCTT

9334_Zika_PF_8F  SEQ ID NO: 88 ttaggatccAAGGGTGATCGAGGAAT

9335_Zika_PF_8R  SEQ ID NO: 89 taactcgagTTCCCTTCAGAGAGAGGAGC

9336_Zika_PF_9F  SEQ ID NO: 90 ttaggatccTCTTTTGCAAACTGCGATC

9337_Zika_PF_9R  SEQ ID NO: 91 taactcgagTCCAGCTGCAAAGGGTAT

9338_Zika_PF_10F  SEQ ID NO: 92 ttaggatccGTGTGGACATGTACATTGA

-continued

9339_Zika_PF_10R SEQ ID NO: 93
taactcgagCCCATTGCCATAAAGTC

9340_Zika_PF_11F SEQ ID NO: 94
ttaggatccTCATACTGTGGTCCATGGA

9341_Zika_PF_11R SEQ ID NO: 95
taactcgagGCCCATCTCAACCCTTG

9342_Zika_PF_12F SEQ ID NO: 96
ttaggatccTAGAGGGCTTCCAGTGC

9343_Zika_PF_12R SEQ ID NO: 97
taactcgAGATACTCATCTCCAGGTTTGTTG

9344_Zika_PF_13F SEQ ID NO: 98
ttaggatccGAAAACAAAACATCAAGAGTG

9345_Zika_PF_13R SEQ ID NO: 99
taactcgagGAATCTCTCTGTCATGTGTCCT

9346_Zika_PF_14F SEQ ID NO: 100
ttaggatccTTGATGGCACGACCAAC

9347_Zika_PF_14R SEQ ID NO: 101
ttaggatccGTTGTTGATCTGTGTGAAT

9348_Zika_PF_15F SEQ ID NO: 102
taactcgagCAGGTCAATGTCCATTG

9349_Zika_PF_15R SEQ ID NO: 103
ttaggatccTGTTGTGTTCCTATTGCTGGT

9350_Zika_PF_16F SEQ ID NO: 104
taactcgaGTGATCAGRGCCCCAGC

9351_Zika_PF_16R SEQ ID NO: 105
ttaggatccTGCTGCCCAGAAGAGAA

9352_Zika_PF_17F SEQ ID NO: 106
taactcgaGCACCAACAYGGGTTCTT

9353_Zika_PF_17R SEQ ID NO: 107
ttaggatccCTCAAGGACGGTGTGGC

9354_Zika_PF_18F SEQ ID NO: 108
taactcgagCAATGATCTTCATGTTGGG

9355_Zika_PF_18R SEQ ID NO: 109
ttaggatccTATGGGGGAGGACTGGT

9356_Zika_PF_19F SEQ ID NO: 110
taactcGAGCCCAGAACCTTGGATC

9357_Zika_PF_19R SEQ ID NO: 111
ttaggatcCAGACCCCCAAGAAGGC

9358_Zika_PF_20F SEQ ID NO: 112
taactcgagCCCCTTTGGTCTTGTCT

-continued

9359_Zika_PF_20R

SEQ ID NO: 113 ttaggatccAGGAAGGATGTATGCAGATG

9360_Zika_PF_21F

SEQ ID NO: 114 taactcgagACATTTGCGCATATGATTTTG

9361_Zika_PF_21R

SEQ ID NO: 115 ttaggatccAGGAAGGACACACAAGAGT

9362_Zika_PF_22F

SEQ ID NO: 116 taactcgagACAGGCTGCACAGCTTT

9363_Zika_PF_22R

SEQ ID NO: 117 ttaggatccTCTCTCATAGGGCACAGAC

In some embodiments, the Zika virus has a polyprotein, including an envelope (E) protein, with an amino acid sequence provided by any one of SEQ ID NO: 14-69. In some embodiments, the polyprotein or E protein sequence is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-69 or 72.

The terms "identical" or percent "identity" in the context of two or more nucleic acids or amino acid sequences refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, or 99% identity) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. In some embodiments, the identity exists over the length of a protein, such as the E protein.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman. Proc. Natl. Acad. Sci. USA 85:2444, 1988, by computerized implementations of these algorithms (GAP, BESTFIT, FASTA, Jalview and TFASTA in the Wisconsin Genetics Software Package, Genetics Computer Group. 575 Science Dr., Madison, Wis.), by multi sequence alignment implementation using e.g. CLUSTALW (Larkin et al., (2007). Bioinformatics, 23, 2947-2948.) or MAFFT (Katoh & Toh 2008 Briefings in Bioinformatics 9:286-298), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977 and Altschul et al., J. Mol. Biol. 215:403-410, 1990, respectively.

EXAMPLES

Figure 9A:
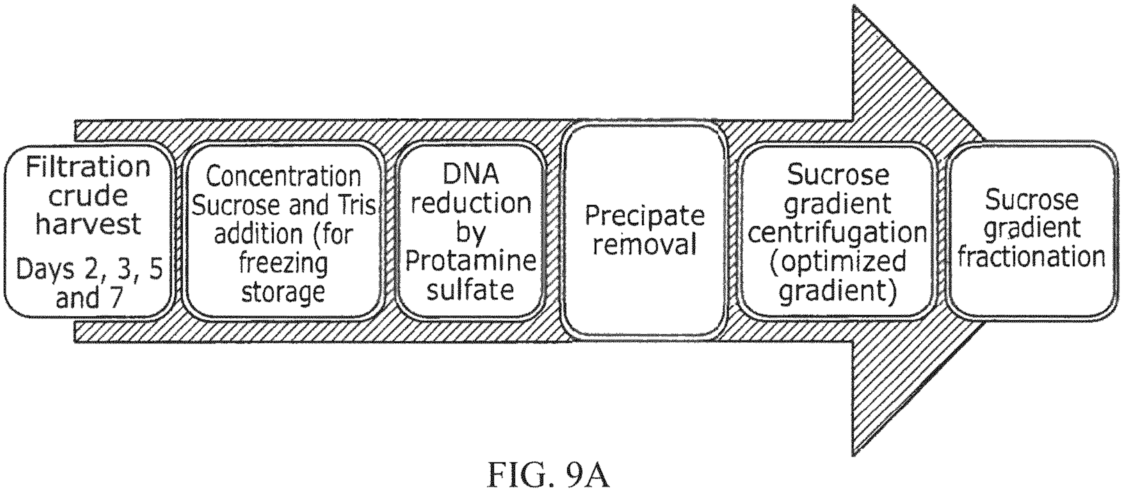
FIGS. 9A-9B: An exemplary downstream Zika virus purification process from the crude harvest to formulation of the drug substance (vaccine), a preferred embodiment of the process of the invention (FIG. 9A). A flow-chart of an exemplary Zika virus inactivation process is shown in (FIG. 9B).
Figure 9B:
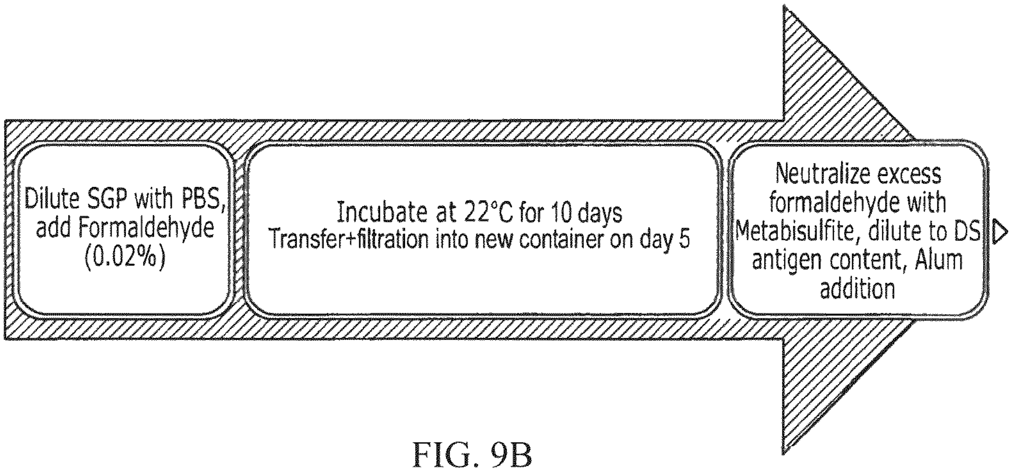
Figure 10:
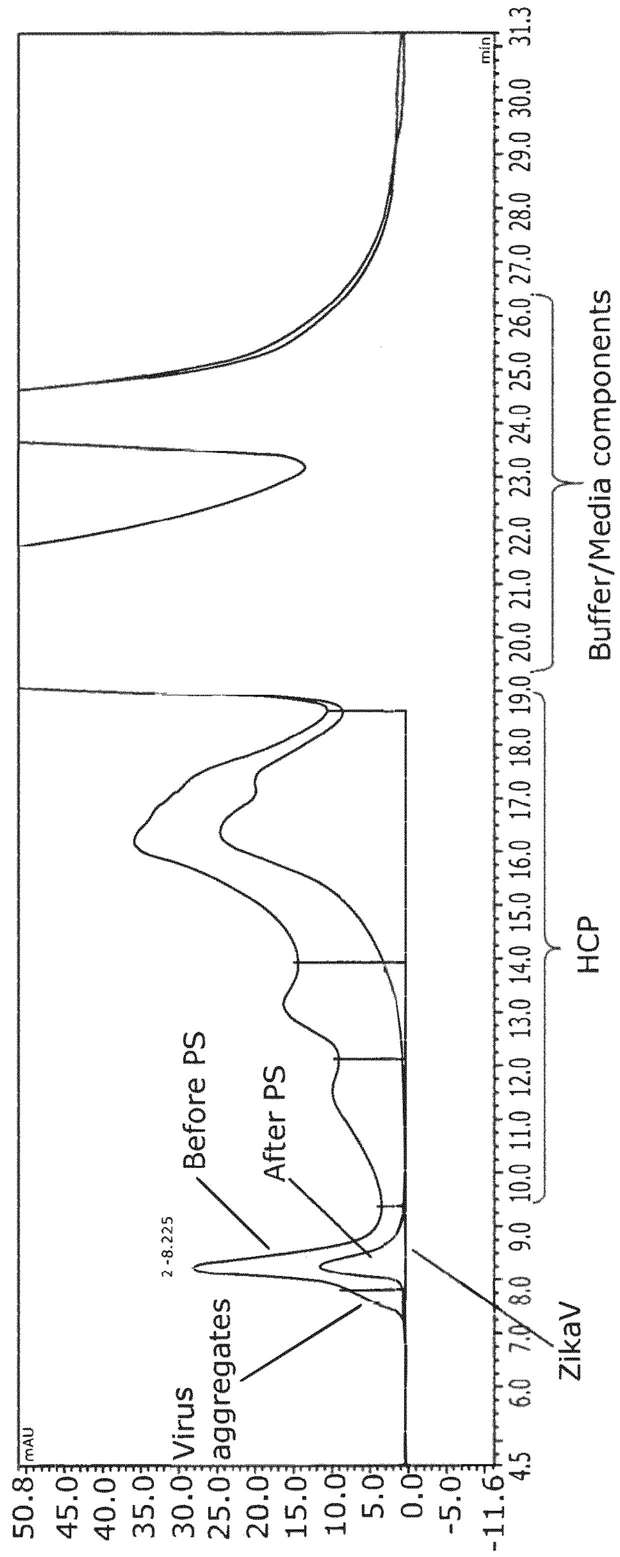
FIG. 10: PS treatment results in selective removal of Zika virus aggregates and Vero HCP and LMW impurities (SEC-HPLC of 30× concentrated Zika Virus harvest day 5).

Example 1: Production of a Zika Drug Substance Suitable for Application as a Vaccine in Humans and Animals Materials and Methods:

For the production of ZikaV the JEV process platform (Srivastava et al., Vaccine 19 (2001) 4557-4565; U.S. Pat. No. 6,309,650B1) was used as a basis Small changes of certain process steps were adapted to ZikaV properties and to improve purity. A short summary of the process steps is outlined below (see also FIGS. 9A and 9B). Briefly, the unexpected and novel purification properties of protamine sulphate (PS) were evaluated in purification processes for Zika Virus. As shown in FIG. 10, non-infectious virus particle aggregates, HCP and other LMW impurities were removed by PS precipitation as shown by removal of aggregate shoulder in SEC-HPLC and no loss of infectious virus titer by PS treatment. Further optimization of the Zika purification protocol is provided below.

Upstream:

- Roller Bottle based Vero cell expansion (25×850 cm2 CellBind):
- 5% $CO_2$, 35° C., MEM+2 mM L-Glutamine+10% FBS
- Infection with ZikaV research Master Seed Bank (rMSB) at MOI 0.01
- Virus Production without serum
- 5% $CO_2$, 35° C., MEM+2 mM L-Glutamine
- Multiple harvests (days 2, 3, 5 and 7) with re-feed
- Sterile filtration of harvests and storage at 2-8° C. until further processing Downstream:

- Pooling of harvests and concentration by ultrafiltration (100 kDa)
- Stabilization of concentrated harvest (Tris/10% sucrose) for storage if required (−80° C.)
- Removal of hcDNA by Protamine Sulphate (2 mg/mL)
- Sucrose Gradient Purification (optimized three layered gradient)
- Formaldehyde Inactivation (0.02%, 22° C., 10 days), neutralization with Na-metabisulfite
- Dilution to DS antigen target content and formulation with Aluminium hydroxide (0.5 mg Al/mL)

Zika Virus Strain H/PF/2013 was originally isolated from a 51-year-old woman (accession number KJ776791.1, also SEQ ID NO: 13 herein) from French Polynesia. A sample was obtained from the European Virus Archive (EVAg; Ref-SKU: 001v-EVA1545). Based on this material, a research master seed bank (rMSB) was prepared on Vero cells as the cell substrate and the genomic sequence was checked by sequencing. Because the genomic sequence at the 5' and 3'flanking sequences of Zika virus strain H/PF/2013 was unknown, primers for sequencing were designed in those regions based on other Zika virus strains whereas the internal primers were designed from the published sequence (SEQ ID NOs: 74 to 117, see also Table A). The sequence obtained from the rMSB by use of these primers is provided by SEQ ID NO: 72. There was 100% overlap of the sequence with the published sequence of Zika Virus Strain H/PF/2013 (SEQ ID NO: 13). However, we sequenced additional regions 5' (an additional 40 bp) and 3' (an additional 160 bp) represented in SEQ ID NO: 72. In a preferred embodiment, the Zika virus of the invention comprises SEQ ID NO: 72. The genomic RNA is somewhat longer than the sequence according to SEQ ID NO: 72 (perhaps an additional 200 bp). Additionally, a Zika virus adapted to a host cell such as e.g. Vero cells may be expected to contain one or more mutations. For these reasons, the Zika virus of the current invention comprises the sequence of SEQ ID NO: 72 or, preferably, a sequence with at least 95%, 96%, 97%, 98%, or at least 99% sequence identity to the sequence provided by SEQ ID NO: 72. Furthermore, because the viral genome is likely to contain even further flanking regions to SEQ ID NO: 72; in one embodiment, the Zika virus of the invention contains the sequence of SEQ ID NO: 72 and optionally further comprises extensions at the 5' and/or 3' ends of at least 10, at least 20, at least 30, at least 40, at least 50, at least 60, at least 70, at least 80, at least 90, at least 100, at least 110, at least 120 or at least 130 nucleotides. In a preferred embodiment, the Zika virus comprises at least the coding sequence for the entire polyprotein of Zika Virus Strain H/PF/2013 of the invention i.e. the amino acid sequence of SEQ ID NO: 73 or a polyprotein with at least 95%, 96%, 97%, 98%, or at least 99% sequence identity to the sequence provided by SEQ ID NO: 73. Furthermore, the Zika virus comprises at least the coding sequence for the E-protein of Zika Virus Strain H/PF/2013 of the invention SEQ ID NO: 47 or an E-protein thereof with at least 95%, 96%, 97%, 98%, or at least 99% sequence identity to the sequence provided by SEQ ID NO: 47.

Virus Growth on Vero Cells

Vero cells were grown in Eagle's minimal essential medium (EMEM) containing 10% fetal bovine serum (FBS). Roller bottle cultures of Vero cell monolayers were infected with Zika Virus Strain H/PF/2013 at a multiplicity of infection (moi) of 0.01 plaque forming units (pfu) per cell. After 2 hours of virus adsorption, the cultures were washed 3 μmes with PBS and fed with EMEM without FBS and incubated at +35° C. with 5% $CO_2$. Infected Vero cell cultures were incubated until the virus titer reaches a desired level.

The culture medium was harvested at days 2, 3, 5 and 7 and were pooled from those harvest days and then centrifuged in a standard centrifuge. The supernatants were then filtered. Virus culture supernatants were concentrated by TFF ultrafiltration to remove cell culture media components and to reduce batch volume.

Evaluation of Harvest Procedure

The current JEV harvest process has scheduled harvests on days 3, 5, 7 and 9 post infection. To mimic the JEV process roller bottles were infected with ZIKV bank P4-FBS at an MOI of 0.01 in infection medium (MEM with 2% FBS+2 mM L-glutamine) for 2 hours. After removing the inoculum the cells were washed twice with PBS and 200 mL production medium (MEM+ 2 mM L-glutamine) was added.

After taking a sample on day 2 the first virus harvest was conducted on day 3 after infection. At this point significantly higher CPE could be observed compared to cells where virus was removed on day 2. Plaque assay analysis showed that the viral titers on day 2 were in the same range as for the standard harvesting schedule. However, starting with the day 3 harvest, the observed titers were significantly lower correlating with the increased CPE observed compared to the standard harvest schedule. On day 5 post infection no more living cells could be observed at all and the experiment was terminated with a final day 5 harvest.

TABLE 3

The calculated titers per plaque assay are summarized in the list below.

| | Log 10 PFU/mL |
|---|---|
| sample day2 | 7.02 |
| harvest day 3 | 6.66 |
| harvest day 5 | 6.26 |

Figure 15:
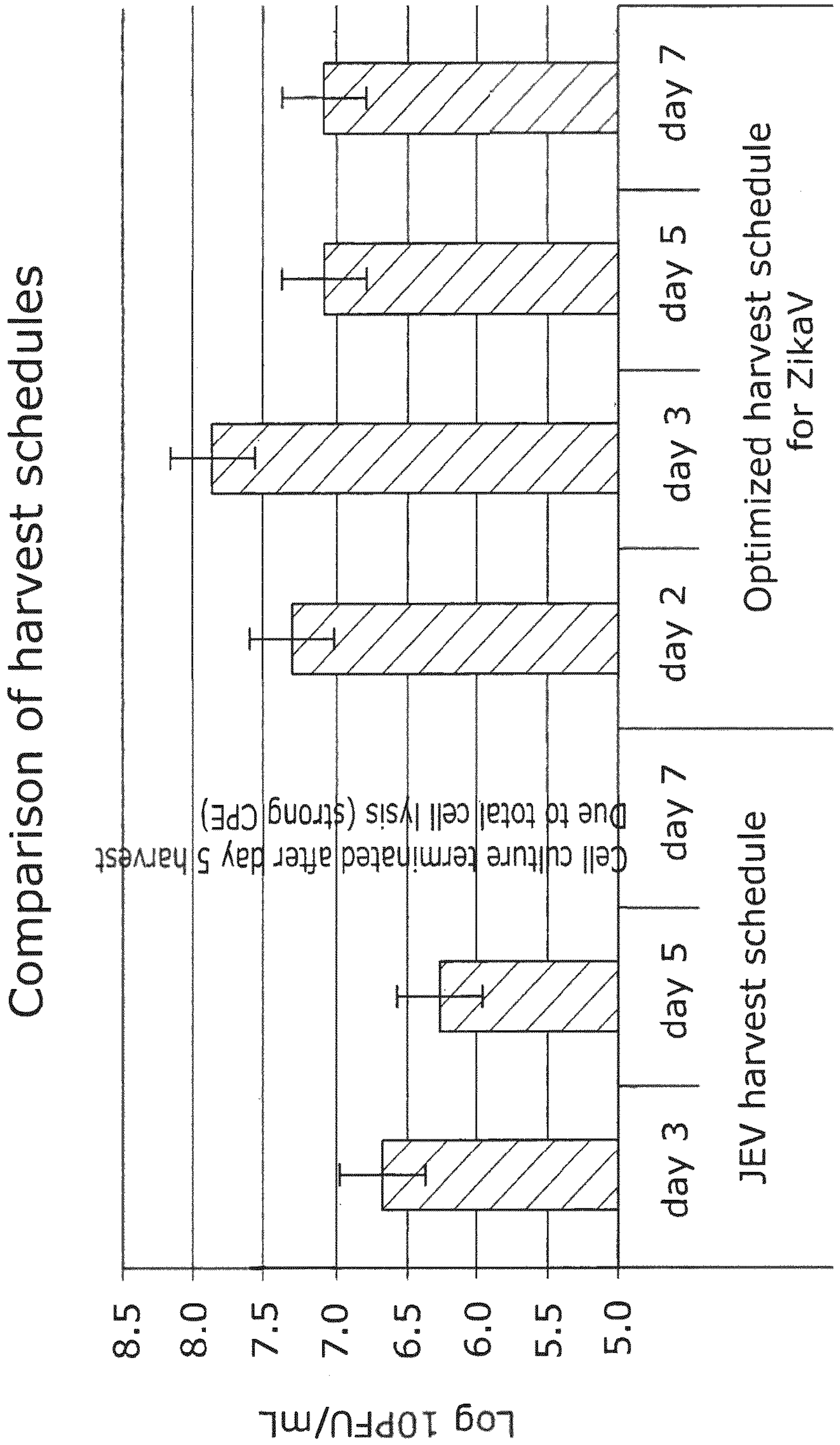
FIG. 15: Comparison of JEV and ZikaV harvest schedules/yields.

This finding led to an optimized harvest schedule to better control of CPE and allow additional harvest day 5 and 7, see FIG. 15. For both harvest days the optimized ZikaV protocol yield significant higher virus titers compared to the modified protocol showing that the time of the first harvest is crucial for production yields. Additionally first harvesting at day 3 results in maximum 2 harvest points whereas first harvesting at day 2 allows for 4 harvest points further increasing the yield gain.

Downstream Purification of Zika Virus

Figure 11:
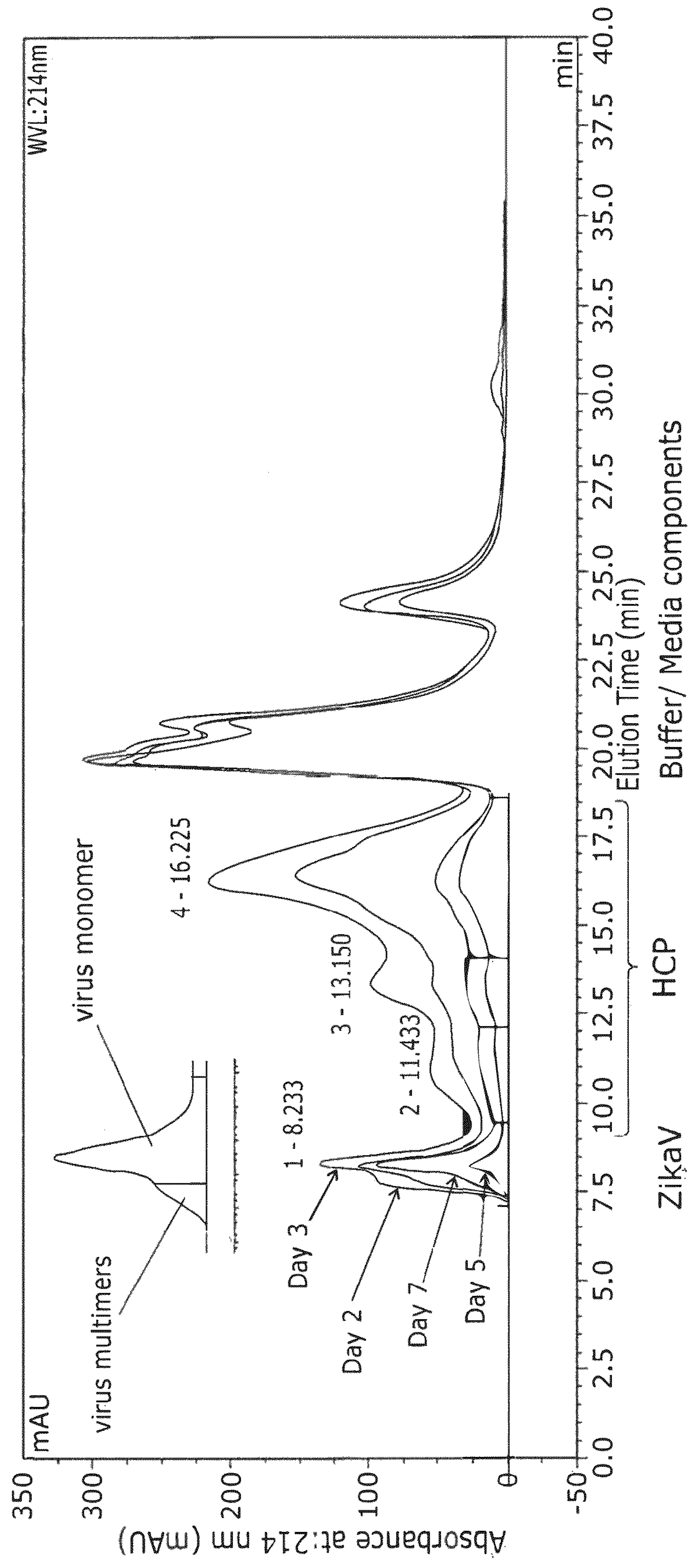
FIG. 11: SEC-HPLC of individual 30× concentrated Zika harvest prior to PS treatment at different time points.

The purification process was carried out at room temperature (18-22° C.) unless stated otherwise. Virus purification started with concentration of filtered combined harvest using 100 kDa cut-off TFF ultrafiltration modules to remove cell culture media components and reduce batch volume. After concentration, the pooled filtered harvest material was adjusted to a final concentration of 25 mM Tris pH 7.5 and 10% sucrose (w/w) using stock solution of both components (see FIG. 11 for SEC-HPLC of different harvests prior to PS treatment). This allowed for freezing the concentrated harvest at <−65° C. if required.

Figure 20:
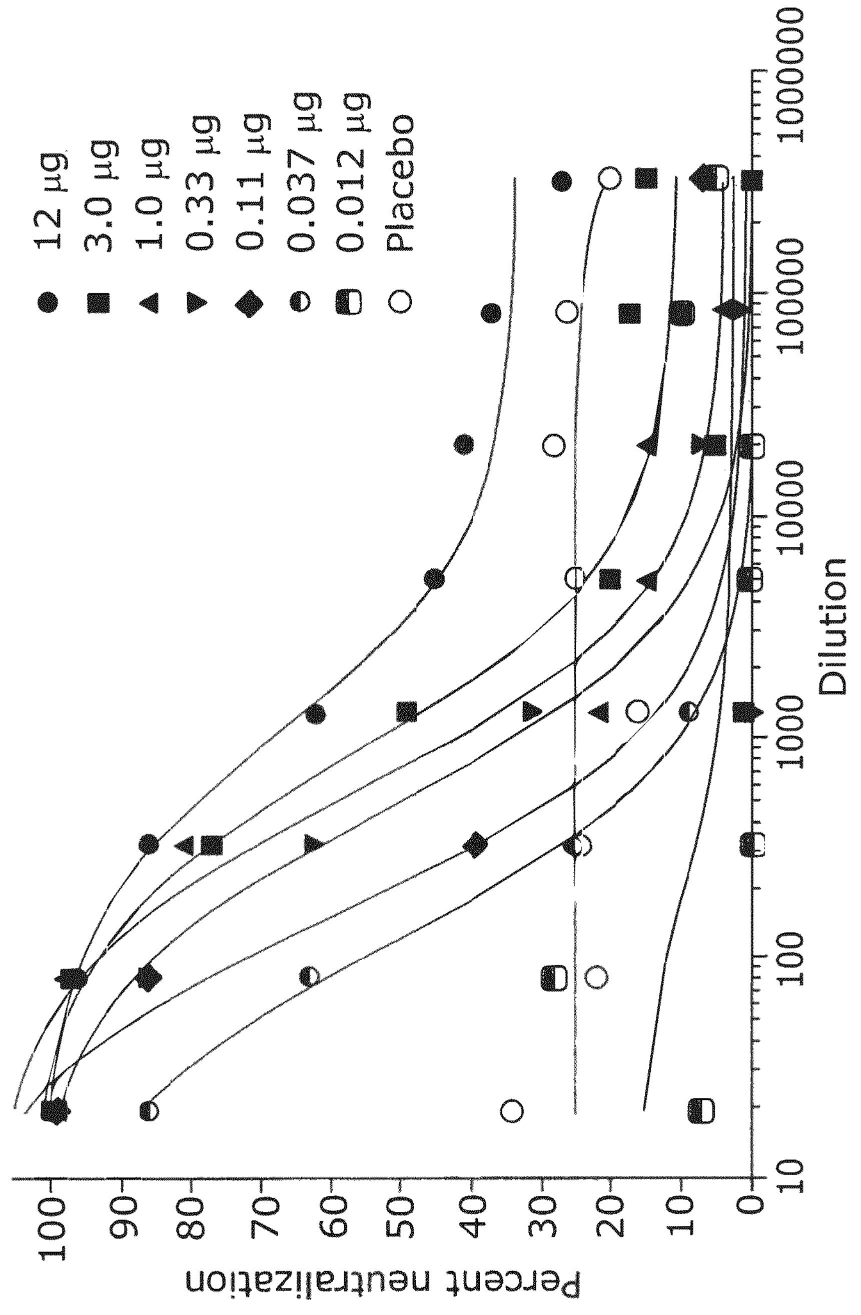
FIG. 20: Graphical representation of the neutralization of the Zika virus MR766 with pooled mouse sera. The number of plaques without serum was set to 100%. The EC50 was calculated using the 3-parameter method.
Figure 21:
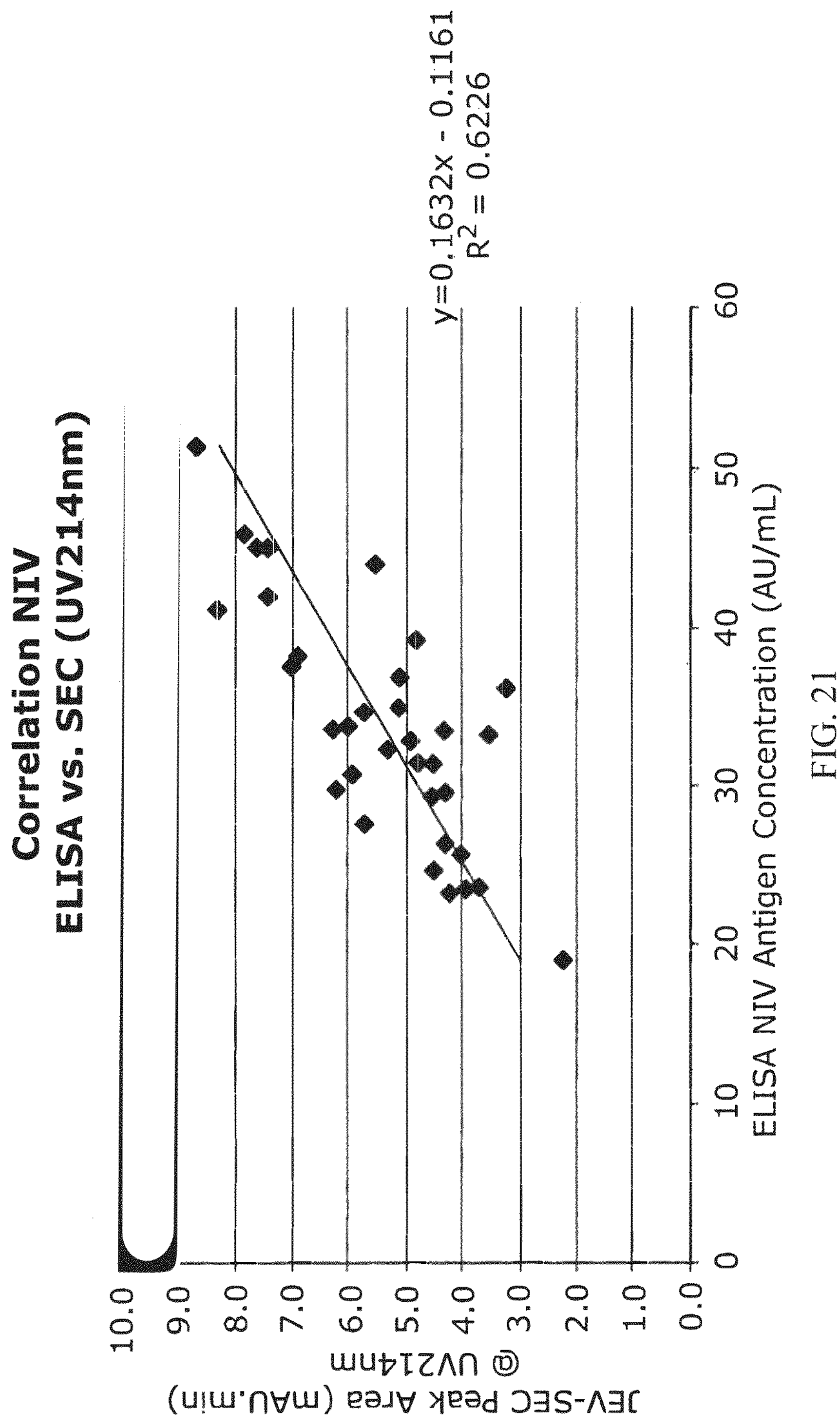
FIG. 21: Correlation between JEV antigen content in neutralized inactivated virus (NIV) analysed by ELISA and SEC-HPLC (Dionex Ultimate 3000, Superose 6 column).

Host cell DNA and protein reduction as well reduction of non-infectious virus aggregates in the concentrated material was achieved by precipitation with protamine sulphate (2 mg/mL) followed by sucrose density centrifugation (2-8° C.) as final polishing step (see FIG. 20 for SEC-HPLC of different harvests post PS treatment). The purification process was designed to be completed within 2 working days with SGC starting on end of day 1 followed by fractionation and SDS-PAGE analysis on day 2. The sucrose gradient fractions were stored at 2-8° C. during the SDS-PAGE analysis (Silver staining) to identify the pure fractions containing ZikaV (see FIG. 21). After pooling the relevant fractions, the pool was diluted and inactivated by Formalin After pooling the relevant fractions of sucrose gradient centrifugation, the pool was diluted 1:3 in PBS and inactivated by Formalin (0.02% v/v, 200 ppm). Fractions were subjected to analysis by SDS-PAGE.

Effect of PS Treatment on Virus Recovery

Figure 12:
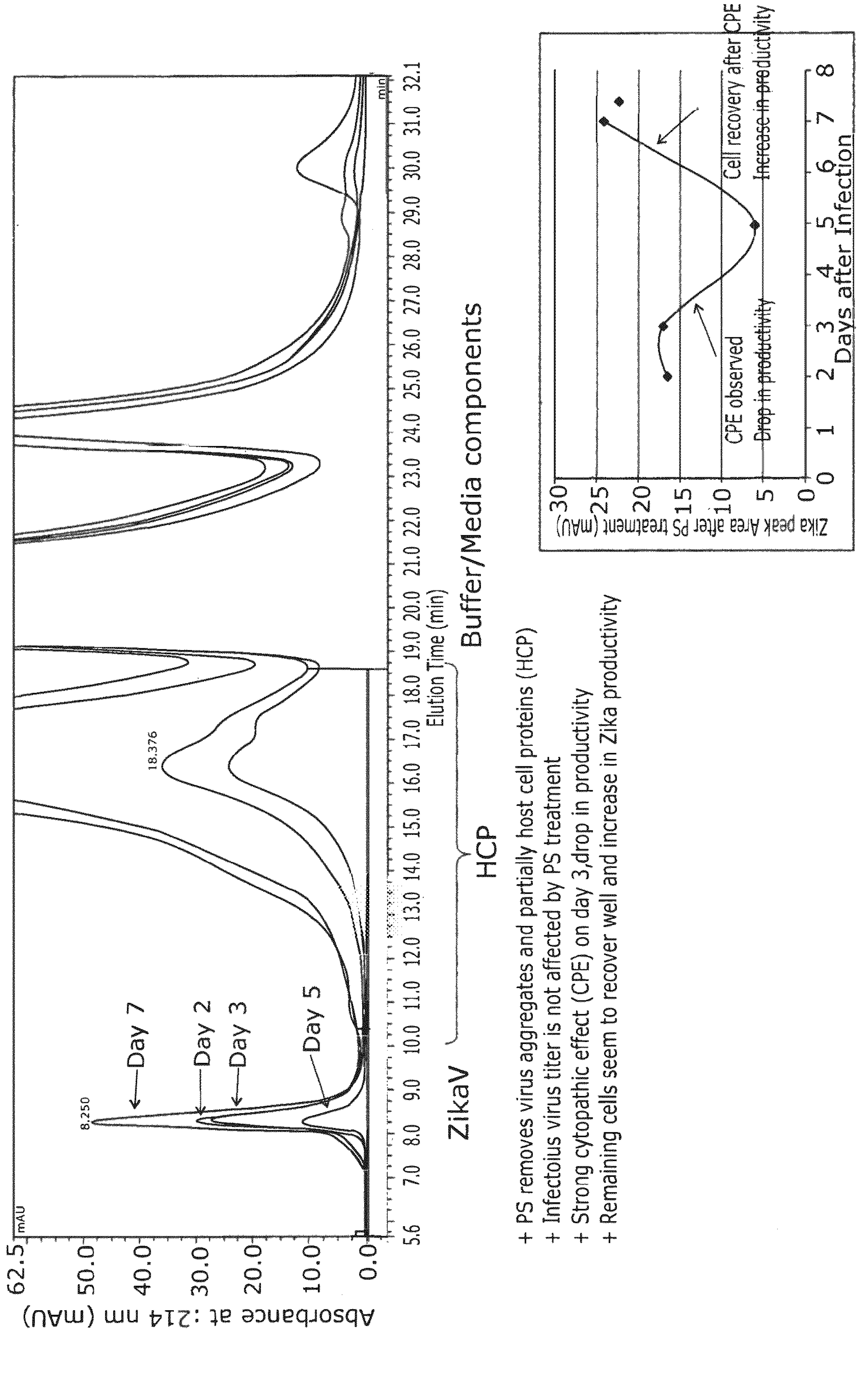
FIG. 12: SEC-HPLC of individual 30× concentrated Zika harvest post PS treatment at different time points. The smaller graph indicates the observed cytopathic effect (CPE) over time.
Figure 13:
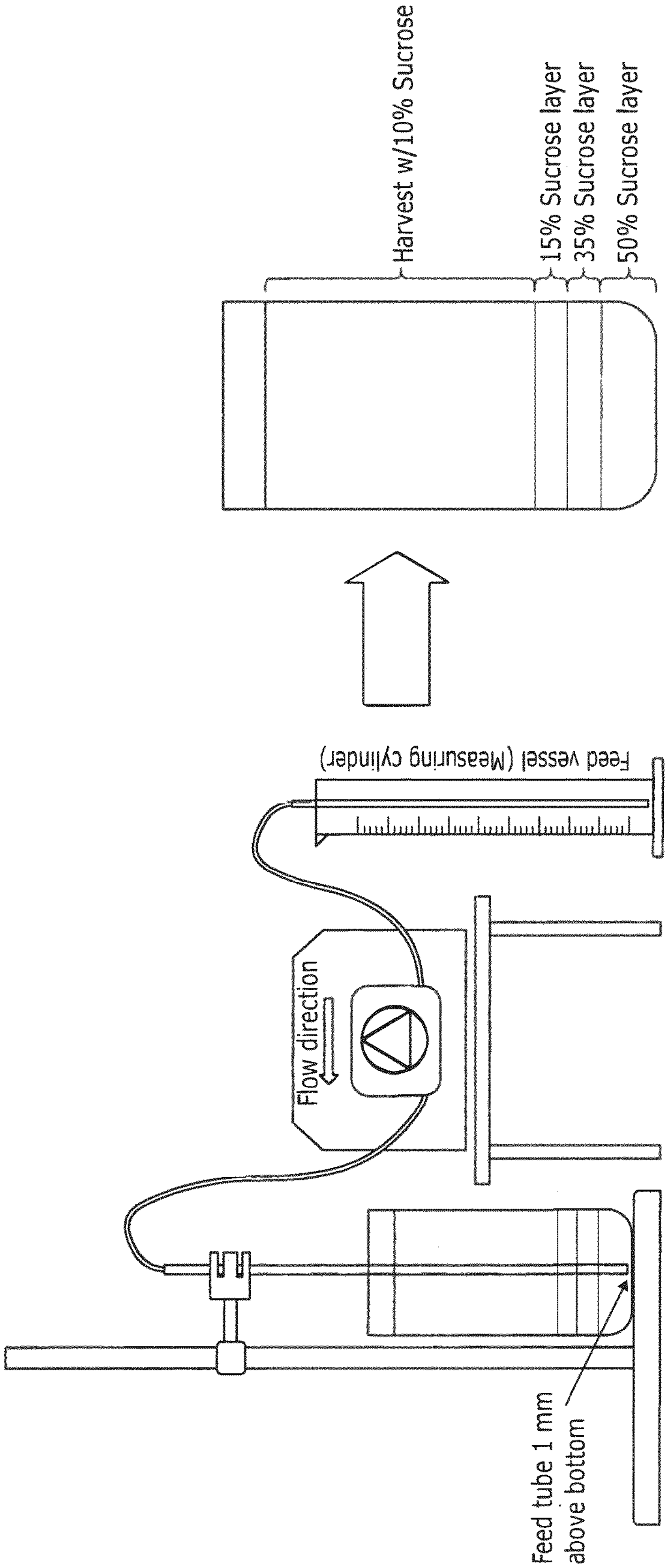
FIG. 13: Preparation of the sucrose gradient for Zika virus purification.

Samples of individual 30× concentrated harvests days 2, 3, 5 and 7 were analysed before (FIG. 11) and after PS (FIG. 12) treatment by SEC-HPLC and plaque assay. SEC-HPLC was used for determination of relative total ZikaV content (active+inactive) expressed as peak area, whereas the rd. ZikaV peak purity is given as relative content of virus monomer population to total virus peak. Plaque assay states the content of total active virus particles in each sample. Experimental results are summarized in Table 4. The virus peak recovery by SEC-HPLC was only between 12 to 36% with peak purity after PS treatment in the range of >90% (no virus aggregates detected). The recovery of active virus particles by plaque assay was all >100% (130-700%, range within the variability of the assay) showing that no active virus particles were lost during PS treatment. These results show that during PS treatment only non-infective (immature and/or aggregated virus) particles were removed.

TABLE 4

ZikaV recovery by SEC-HPLC and plaque assay before and after PS treatment.

SEC-HPLC

| Harvest day | Peak area mAU*min 30× conc | 30× + PS | SEC Recovery (%) | rel. virus monomer content after PS (%) |
|---|---|---|---|---|
| Day 2 | 101.36 | 18.63 | 18 | 89% |
| Day 3 | 144.51 | 17.48 | 12 | 90% |
| Day 5 | 19.97 | 5.92 | 30 | 96% |
| Day 7 | 68.80 | 24.43 | 36 | 99% |

Plaque Assay

| Harvest day | PFU/mL 30× conc | 30× + PS | Plaque Recovery (%) |
|---|---|---|---|
| Day 2 | 3E+08 | 5E+08 | 179 |
| Day 3 | 2E+08 | 4E+08 | 193 |
| Day 5 | 1E+08 | 9E+08 | 700 |
| Day 7 | 3E+08 | 4E+08 | 132 |

Sucrose Gradient Centrifugation

The PS treated harvest was split in two parts and loaded on two centrifuge bottles. Sucrose density gradient centrifugation (SGC) was used for final concentration and polishing of the ZikaV material. The ZikaV PS treated concentrated harvest was loaded on top of a solution consisting of three layers of sucrose with different densities. The three sucrose layers were selected based on a preliminary study which showed the formation of a linear sucrose gradient and complete separation of the virus particles from residual contaminants as demonstrated for ChikV (FIG. 15D). The optimal volumes of the sucrose solutions were determined empirically. The volumes of individual layers for a centrifugation in 100 mL bottle scale are shown in Table 5.

TABLE 5

Individual layers/volumes for a centrifugation in bottle.

| Solution | Volume (mL) |
|---|---|
| PS treated harvest in 10% sucrose (L) | 40 |
| 15% sucrose (J) | 15 |
| 35% sucrose (I) | 15 |
| 50% sucrose (H) | 20 |
| Total volume | 90 |

The sucrose gradient bottles were prepared by stratifying the individual sucrose layers. A plastic tube was attached to peristaltic pump tubing. The plastic tube was mounted on a laboratory stand using a clamp and placed into the centrifuge bottle. The nozzle of the plastic tube was touching the bottom of the bottle. Using a peristaltic pump the ZikaV material and the sucrose solutions were pumped into the cylinder. A measuring cylinder was used as feed vessel. The first solution pumped was the ZikaV material as it represented the solution of lowest density (10% sucrose (w/w)). After the ZikaV material the sucrose solutions were pumped in ascending order starting with the 15 (w/w) solution J, followed by 35% sucrose solution I and finishing with the highest density sucrose solution H (50% (w/w)). The described setup is shown in FIG. 14. After all sucrose solutions were transferred the plastic tubing was carefully removed in order not to disturb the layers.

Prior to centrifugation the centrifuge was pre-cooled to 4° C. The prepared SG bottles were carefully transferred into the pre-cooled rotor. (Note: Sudden movement of the bottles during transfer to the rotor must be avoided in order not to disturb the sucrose layers.) The bottles were centrifuged at ~11.000 RCF max at 4° C. for at least 20 hours, no brake/deceleration activated. In case a different centrifuge system with a different rotor is used the necessary speed and centrifugation times need to be calculated based on the k-factor in order to achieve comparable centrifugation efficiency.

Harvesting of the sucrose gradient was done manually using a peristaltic pump. A plastic tube attached to peristaltic pump tubing was used for harvesting the sucrose gradient. The bottle containing the gradient was mounted onto a laboratory stand in a tilted position (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14).

Using a peristaltic pump set to a flow rate of 30 mL per minute the gradient was harvested and manually split into 2 mL fractions. A total number of 32 fractions per bottle were harvested (~64 mL) and the remaining volume was discarded. The fractions were immediately tested by SDS-PAGE/silver stain to identify the virus containing fractions with sufficient high purity. Representative SDS-PAGE is shown in FIG. 14. Fraction 10-14 were pooled and further processed.

The purified viral solution was inactivated by incubation with 0.02% formaldehyde over a period of ten days in a 22° C. controlled-temperature incubator. The formaldehyde is neutralized by addition of sodium metabisulphite on the tenth day.

The sucrose gradient pool (~17 mL after sampling) was further diluted 3-fold with PBS to a final volume of 51 mL in a PETG container. A volume of 1% formaldehyde (10,000 ppm) solution equivalent to 1/50 of the final volume of the pre-formaldehyde pool was added to this pool resulting in an effective concentration of 200 ppm. The formaldehyde-treated solution was mixed on a magnetic stirrer for 10 minutes. After sampling, the formaldehyde-treated viral solution was placed within a cooled incubator at 22° C.±2° C. On Day 5 post addition of formaldehyde, the formaldehyde-treated viral solution was filtered through a 0.2 μm filter and then placed in the incubator at 22° C.±2° C. again. On Day 10, after removing the 10-Day inactivation final sample, a volume of 1% (of the weight of the final formaldehyde-treated viral solution) of 200 mM-sodium metabisulphite solution (2 mM final concentration) was aseptically transferred into the PETG container containing the formaldehyde-treated viral solution. After mixing for 5 minutes on a magnetic stirrer, the neutralized inactivated viral solution is held at room temperature (20 to 25° C.) for a minimum of 30 minutes. After sampling, the neutralized inactivated viral solution is stored at 5° C.±3° C. until further processing.

Inactivation by Formaldehyde

Critical parameters for this step are final formalin concentration, temperature, mixing and transfer into a new container. A preliminary acceptance criterion for maximum pfu/mL (determined by plaque assay) has been set on the diluted pool pre formaldehyde treatment.

The quality of the neutralized inactivated viral solution was monitored by the following parameters: Plaque assay on Day 10, SEC-HPLC, SDS-PAGE/Western Blot.

Interestingly, SEC-HPLC analysis of samples taken during the inactivation period followed by neutralization with bisulfite showed more or less constant peak area throughout the inactivation period. This is in contrast to JEV where losses of viral particles up to 60% are observed using the process disclosed by Srivastava et al. Vaccine 19 (2001) 4557-4565. In a scale-down model the viral losses were even much higher due to surface/area ratio at smaller scale and high losses due to unspecific adsorption. Differences of the ZikaV inactivation experiment and JEV inactivation were noticed as follows:

A) Much higher purity of ZikaV SGP pool with regard to residual PS (<2 μg/mL) compared to JEV. The 3-fold ZikaV inactivated sample contained therefore <<1 μg/mL of residual PS. Commercial JEV SGP pool contains on average ~120 μg/mL (up to 152 μg/mL possible). The average dilution to inactivation solution of ~14-fold results in a residual PS content up to ~11 μg/mL. It may be that higher amount of residual PS could cause virus precipitation due to cross-linking/reaction with formalin.

B) ZikaV inactivation sample contained ~10% sucrose (3-fold dilution of SGP pool containing ~30-35% sucrose). Sucrose might have stabilizing effect of viral ZikaV particles during treatment with formalin.

Dilution to DS and Formulation with Aluminium Hydroxide (DP)

For preparation of ZikaV drug substance used in mouse potency assay an antigen content (expressed as total viral particles or SEC peak area) of 5 μmes higher compared to Ixiaro was targeted. The basis for determination of antigen content was SEC-HPLC. Briefly, a Superose 6 10/300 Increase column (GE Healthcare) equilibrated with PBS+250 mM NaCl, pH 7.4 at 1 ml/min and 25° C., was used to detect ZikaV at 214 nm detection wavelength in harvest samples and throughout the downstream process. In the current JEV process the antigen content in NIV is determined by a specific ELISA. A good correlation was observed between antigen content determined by ELISA and SEC-HPLC. On average, the antigen content in commercial NIV samples is in the range of 33 AU/mL corresponding to ~5.2 mAU JEV peak area, see FIG. 21.

ZikaV NIV day10 (Zika peak ~36 mAU, analysed on Waters HPLC/Superose6 Increase column) was diluted with PBS to a target of 6.3 (~5.7× dilution). Aluminium hydroxide was added to a final concentration of 0.5 mg/mL Aluminium (1/20 v/v Alum 2% stock solution added) to prepare ZikaV Drug Product (DP). The DP was gently mixed for 5 min. An aliquot of the DP was removed, Alum sedimented by centrifugation and the clear supernatant analysed by SEC-HPLC. No ZikaV peak was detected in the supernatant indicating complete adsorption (estimated as >95%) of viral particles on the mineral adjuvant. Formulated ZikaV DP was stored at 2-8° C.

The impurity profile of the inactivated Zika virus DS is comparable to the profile of JEV DS with the exception of a lower PS content (Table 6).

TABLE 6

Determination of impurity profile in Zika and JEV DS samples:

| | Specification (JEV DS) | JEV | Zika |
|---|---|---|---|
| HCP (ng/mL) | <100<br>LOQ 12 ng/mL | <LOQ | <LOQ |
| DNA (pg/mL) | <200<br>LOQ 40 pg/mL | <40 | <40 |
| Aggregates by SEC-MALLS (%) | Not specified, part of characterization<br>LOQ 5% | <LOQ | <LOQ |
| PS (μg/mL) | Specification only at SGP pool to demonstrate consistent process performance (19-152 μg/mL), *PS content in DS calculated based on PS content in SGP pool (~100 μg/mL) and average dilution factor (~28×) to DS;<br>LOQ 2 μg/mL | ~4* | <<LOQ |

*Typical PS impurity in a JEV sample produced in accordance with protocol disclosed in Srivastava et al. Vaccine 19 (2001) 4557-4565.

SEC-MALLS Results

Figure 16:
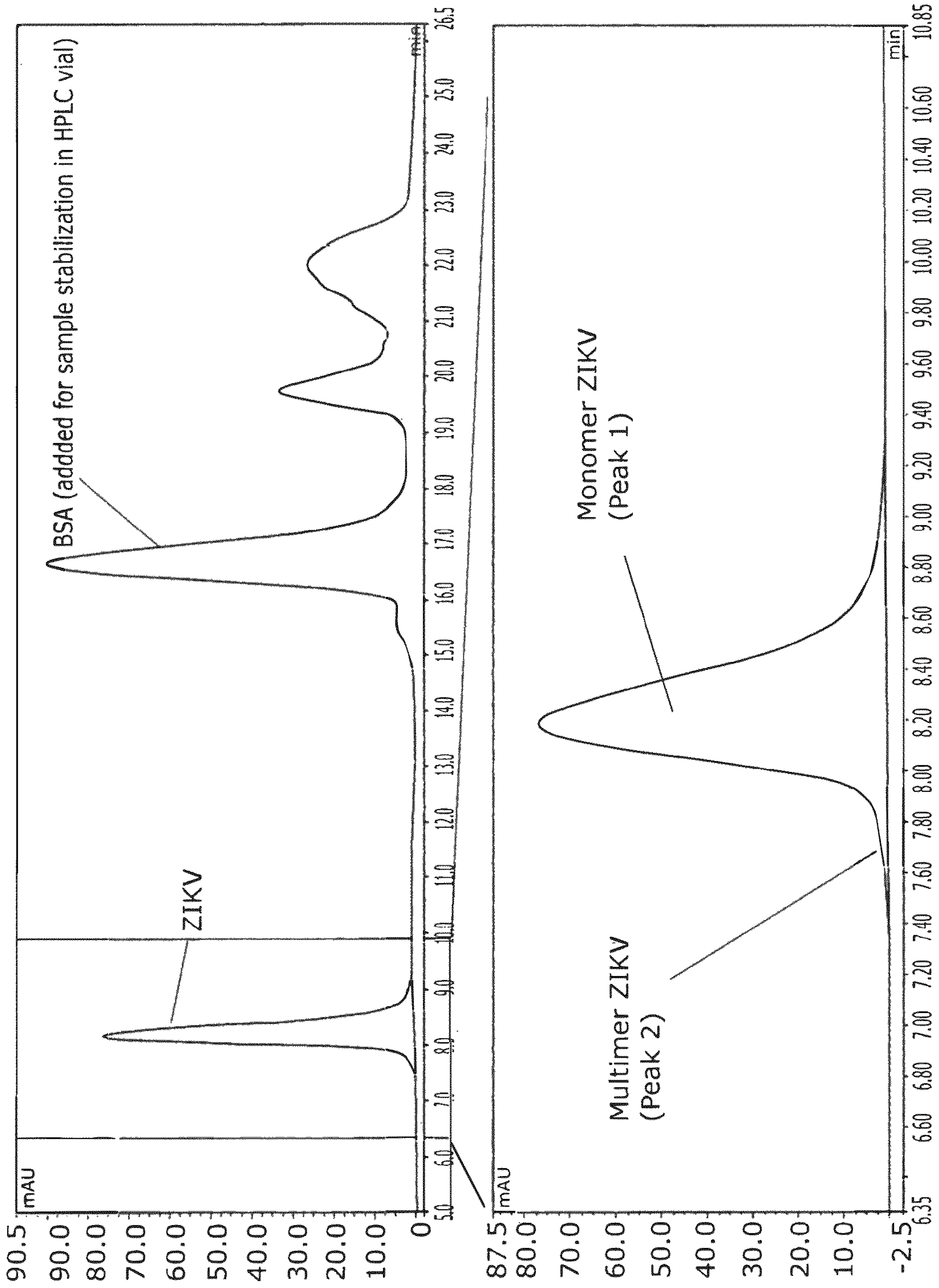
FIG. 16: SEC-HPLC elution profile of ZikaV neutralized inactivated virus (NIV). Data were processed on Dionex Ultimate 3000/Superose 6 Increase column. Both panels are from the same chromatogram. The upper graph is the complete elution profile; the lower graph is an enlargement of the ZikaV elution peak.

A representative SEC-HPLC elution profile of ZikaV NIV at 214 nm detection wave length is shown in FIG. 16. Note that BSA (50 μg/mL) was added to the sample to minimize losses in HPLC glass vial due to unspecific surface adsorption. ZikaV monomer content was estimated as ~98% with a multimer content of ~2%.

Figure 17:
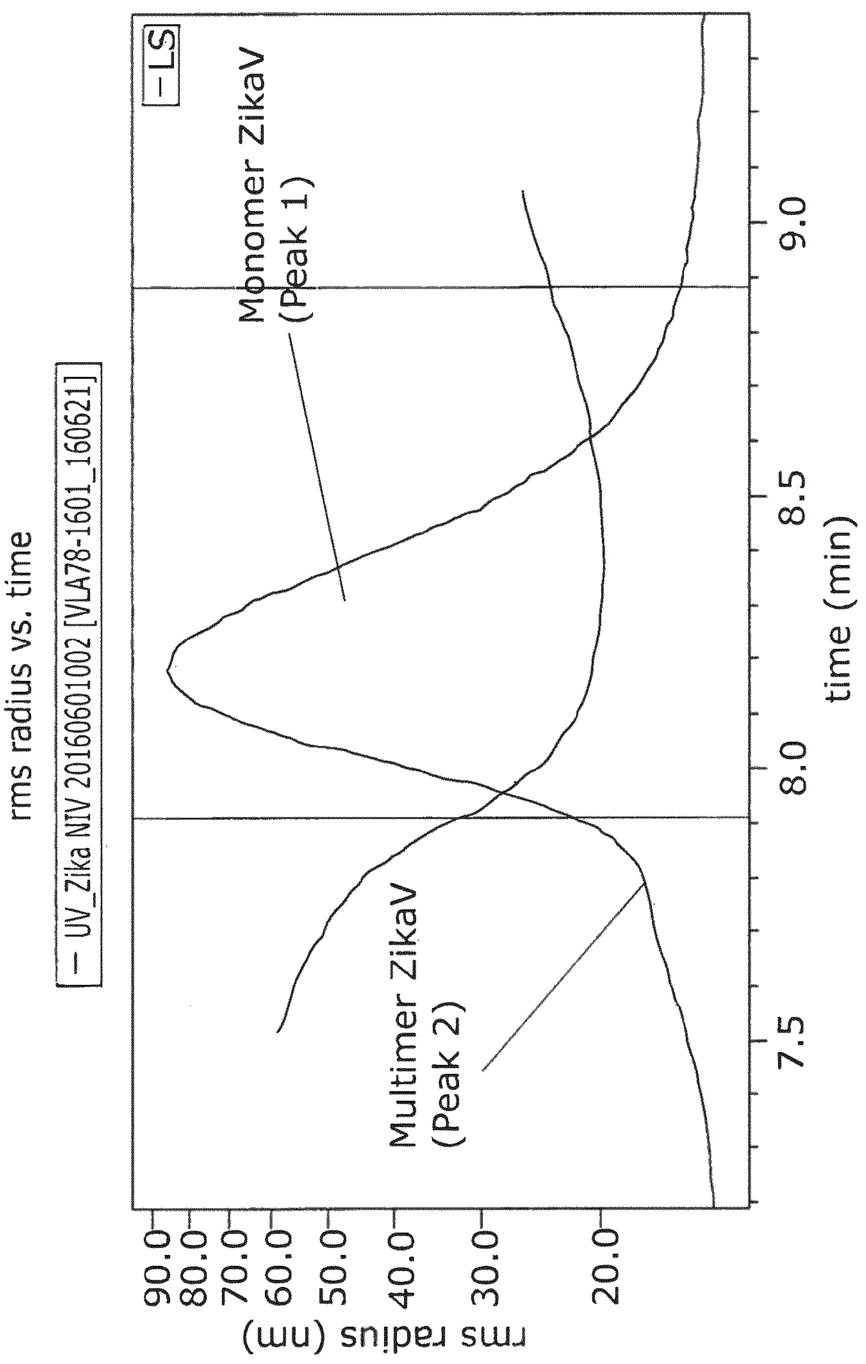
FIG. 17: SEC-MALLS analysis of inactivated ZikaV.
Figure 18:
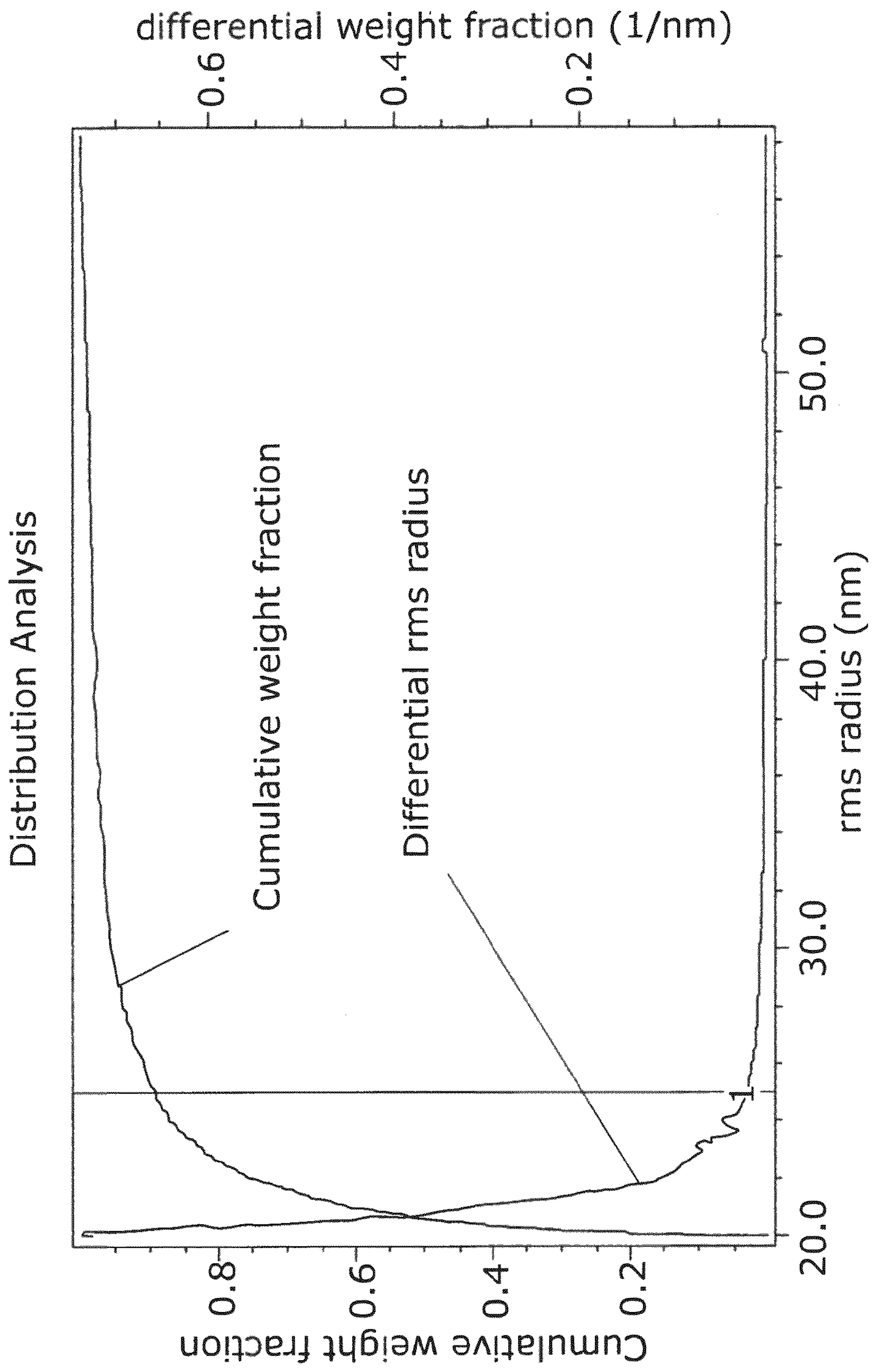
FIG. 18: Cumulative particle size distribution of Zika NIV.

SEC-MALLS analysis (FIG. 17) of the sample confirmed the radius Rz of the monomer ZikaV population peak 1 as 21.6 nm and ~49 nm for the multimer peak 2. Cumulative particle size distribution showed that 89% of all viral particles are within a radius range between 18 to 25 nm (FIG. 18).

Results confirm purity and homogeneity of ZikaV NIV.

Viral Titer by Plaque Assay

TABLE 7

Active ZikaV pfus were quantified by plaque assay throughout the process.

| Sample | Pfu/mL |
|---|---|
| Harvest day 2 (filtered) | $6.4 \times 10^7$ |
| Harvest day 3 (filtered) | $1.0 \times 10^8$ |
| Harvest day 5 (filtered) | $1.5 \times 10^8$ |
| Harvest day 7 (filtered) | $1.1 \times 10^8$ |
| PS treated harvest 300× concentrate (=SGP load) | $9.0 \times 10^8$ |
| SGP pool | $8.9 \times 10^8$ |

TABLE 7-continued

| Active ZikaV pfus were quantified by plaque assay throughout the process. | |
|---|---|
| Sample | Pfu/mL |
| Inactivation start (SGP pool 1:3 diluted) | $3.4 \times 10^8$ |
| Inactivation day 5 | <LOD |
| Inactivation day 10 | <LOD |

Comparison of PS and Benzonase on Process Performance

A direct comparison of DNA removal method of concentrated ZikaV harvest pool was done. One aliquot was treated with PS (2 mg/mL, 15 min at room temperature), the other aliquot was treated with Benzonase (50 U/mL, 2 mM MgCl2, 4 h RT, 48 h 2-8° C.). Both samples were further purified by sucrose gradient as described in this report. Interestingly, the Benzonase treated samples did not yield any pure fractions after sucrose gradient centrifugation of the treated ZikaV harvest. In those fractions where the specific virus bands were detected, a high amount of host cell protein was detected throughout the collected fractions. The PS treated material resulted in pure ZikaV containing fractions as expected. This finding may suggest that PS is not only effective for DNA removal by precipitation; in addition it improves the recovery of virus particles in the gradient by disrupting interaction of DNA (fragments) and virus particles. Benzonase treatment does not remove DNA, it only results in its fragmentation. Residual DNA fragments might still interact with virus particles and residual HCPs resulting in cross-contamination and co-purification in the sucrose gradient. Pooled SGP fractions were also analysed by SEC-HPLC. Although a large peak was detected, SDS-PAGE confirmed that this sample was highly contaminated with HCPs. A large peak might be detected at UV214 and 280 nm after SEC-HPLC analysis due to possible interaction of HCPs with large virus particles, changing the UV absorbance.

Immunogenicity of Vero Grown Zika Virus

Immunization of Mice

Prior to immunization, groups of ten 6-week-old female CD1 mice were bled via vena facialis and pre-immune sera were prepared. One intraperitoneal immunizations of 200 μL were administered. A dose titration (12 μg, 3 μg, 1 μg, 0.33 μg, 0.11 μg, 0.037 μg and 0.012 μg, equivalent to the protein amount in IXIARO) of inactivated Zika virus formulated with aluminium hydroxide (Al(OH)3) at a final concentration of 0.7%. Three weeks after immunization, blood was collected and immune sera were prepared. All animal experiments were conducted in accordance with Austrian law (BGB1 Nr. 501/1989) and approved by "Magistratsabteilung 58".

Plaque Reduction Neutralization Test (PRNT)

Twelve well plates were used for PRNT. Each well was seeded with 1 mL medium containing $4\times10^5$ Vero cells and incubated 35° C. with 5% $CO_2$ overnight. Pools of heat inactivated sera from each dose group were tested in triplicate. The target viruses (H/PF/2013 (SEQ ID NO: 13) or MR766 (SEQ ID NO: 11)) were diluted to 100 pfu/165 μL. Equal volumes of target virus and serum dilution were incubated at 35° C. with 5% $CO_2$ for 1 hour. The cell culture medium was aspirated from the Vero cells and 330 μL of the mixture target virus/serum dilution were added to each well and the plates were rocked back and forth 5 times before incubating for 2 hours at 35° C. with 5% $CO_2$. To each well 1 mL of a 2% methylcellulose solution containing EMEM and nutrients was added, the plates were then incubated for 5 days at 35° C. with 5% $CO_2$ before staining the cells for 1 hour with crystal violet/5% formaldehyde and subsequently washed 3 μmes with deionized water. The plates were air dried and the numbers of plaques in each well were manually counted.

Results

Figure 19:
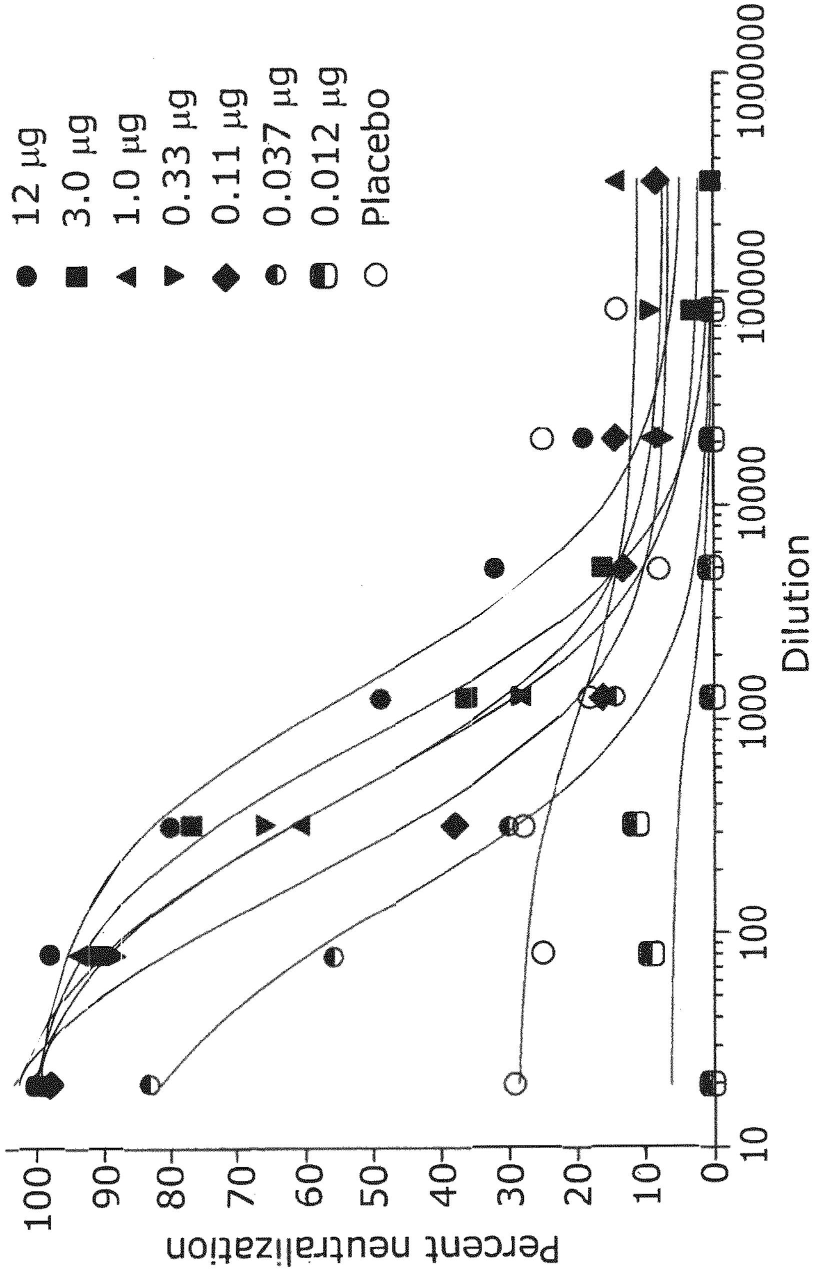
FIG. 19: Graphical representation of the neutralization of the Zika virus H/PF/2013 with pooled mouse sera. The number of plaques without serum was set to 100%. The EC50 was calculated using the 3-parameter method.

Neutralization was observed with serum pools from mice immunized with inactivated Zika virus vaccine (H/PF/2013) down to 37 ng (dosing equivalent to the amount protein in IXIARO®) against Zika viruses of both the Asian (H/PF/2013) and African (MR766) lineages (FIGS. 19 and 20, respectively). Complete inhibition was seen at the 1:20 serum dilution with an immunization dose down to 110 ng (dosing equivalent to the amount protein in IXIARO®). The neutralization of both the Asian (H/PF/2013) and African (MR766) lineages of the Zika virus was equivalent, which indicates high cross-neutralization between different Zika virus strains of the inactivated Zika virus vaccine (H/PF/2013).

Another neutralization assay was performed using the microneutralization assay as described by Larocca, et al. (2016, Nature doi:10.1038/nature18952). It was found that the inactivated Zika virus of the current invention had an MN50 (microneutralization) titer of 90 at 1 μg of inactivated purified virus.

Further methods: The immunogenicity of inactivated Zika virus preparations is assessed using a mouse model of Zika infection. Groups of adult mice are immunized subcutaneously (s.c.) with 500, 50, or 5 ng of inactivated Zika virus with adjuvant (e.g. aluminium hydroxide with or without IC31®), or without adjuvant. An additional group of mice receive PBS as a negative control. Each group is administered the indicated inoculum at t=0 and in some cases also at three to four weeks later (t=¾). Beginning approximately three weeks after administration of the last immunization, serum samples are obtained from each of the mice at regular intervals. The serum samples are tested for the presence of neutralizing antibodies using PRNT.

The in vivo protective efficacy of the inactivated Zika virus preparations is also assessed using a mouse model of Zika infection, i.e. IFN-alpha/beta receptor knock-out mice (A129) (see e.g. Dowall et al., 4. Mar. 2016, http://dx-.doi.org/10.1101/042358) or blocking of the IFN-alpha/beta receptor by administration of anti-IFN-alpha/beta receptor monoclonal antibodies to C57BL/6 or BALB/c mice (see e.g. Pinto et al., 7. Dec. 2011, DOI: 10.1371/journal.p-pat.1002407). For protection assays, groups of 10 three- to eight-weeks-old A129, C57BL/6 of BALB/c mice are inoculated subcutaneously in the hindquarters with inactivated Zika virus with adjuvant (aluminium hydroxide) or without adjuvant at t=0. Age-matched controls are inoculated with PBS or non-specific antigens in alum. Mice are optionally boosted with a second administration of the indicated inoculation three to four weeks later. The mice are then challenged subcutaneously at three to eight weeks post immunization by inoculation with a deadly dose of live Zika virus. One day prior to challenge of C57BL/6 and BALB/c mice, they are passively administered (intraperitoneally) anti-IFN-alpha/beta receptor monoclonal antibodies. Challenged mice are monitored daily for morbidity and mortality for up to twenty-one days. Another alternative is to challenge intracranially adult vaccinated/non-vaccinated adult mice and observe protection.

It is expected that the Zika virus produced by the process of the invention will provide very similar functional read-outs in in vitro, in vivo and finally human trials as the currently licensed JEV vaccine in the EU and US and elsewhere, IXIARO®. The dosage may alter but due to the very similar impurity profile and almost identical manufacture, a very similar efficacy and safety result will be expected as was determined for the currently licensed JEV vaccine (licensed in the EU and US and elsewhere).

DISCUSSION & CONCLUSION

The existing manufacturing platform for production of inactivated JEV vaccine IXIARO® was used as a basis for a manufacturing feasibility study of inactivated ZikaV vaccine candidate (Asian strain H/PF/2013). The virus was produced on Vero cells cultivated in roller bottles. The virus was purified by PS treatment followed by an optimized sucrose gradient. Inactivation was done by formalin treat (0.02%, 10 days at 22° C.). For exploratory immunization studies in mice, a DP formulated with Alum was prepared with an estimated 5-fold higher virus particle content compared to IXIARO®, the commercial JEV Vaccine. The impurity profile of the DS met all criteria as defined in the specification for IXIARO®, the commercial JEV vaccine. The neutralization of both the Asian (H/PF/2013) and African (MR766) lineages of the Zika virus was equivalent, which indicates high cross-neutralization between different Zika virus strains of the inactivated Zika virus vaccine (H/PF/2013).

The in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was higher than the recently reported inactivated Zika virus vaccine candidate (Larocca, et. al, 2016, supra.). Inactivated viruses are among the safest vaccines and especially preferred for deliver to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Further more detailed aspects of the invention:

A1. A Zika virus vaccine comprising an optimally inactivated Zika virus particle, wherein the Zika virus particle is able to seroconvert a subject that is administered the Zika virus vaccine with at least a 70% probability.

A2. The Zika virus vaccine of A1, wherein the Zika virus particle is able to seroconvert the subject that is administered the Zika virus vaccine with at least a 80%, 85%, 90%, or 95% probability.

A3. The vaccine of A1 or A2, wherein the Zika virus particle has a RNA genome corresponding to the DNA sequence provided by any one of the nucleic acid sequences of SEQ ID NOs: 2-13 or 72, or a variant nucleic acid sequence that is at least 88% identical to any one of SEQ ID NOs: 2-13 or 72 and able to pack a virulent Zika virus.

A4. The vaccine of any one of A1-A3, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

A5. The vaccine of any one of A1-A4, wherein the Zika virus is inactivated by chemical inactivation, thermal inactivation, pH inactivation, or UV inactivation.

A6. The vaccine of A5, wherein the chemical inactivation comprises contacting the Zika virus with a chemical inactivation agent to completely inactivate the Zika virus as measured by plaque assay.

A7. The vaccine of A6, wherein the chemical inactivation comprises contacting the Zika virus with formaldehyde.

A8. The vaccine of A7, wherein the formaldehyde inactivation comprises contacting the Zika virus with formaldehyde for between 2-10 days.

A9. The vaccine of any one of A5-A8, wherein the chemical activation is performed at about +4° C. or about +22° C.

A10. The vaccine of any one of A1-A9, further comprising an adjuvant.

A11. The vaccine of A10, wherein the adjuvant is an aluminum salt adjuvant.

A12. The vaccine of A11, wherein the aluminum salt adjuvant is aluminium hydroxide or aluminium phosphate salt.

A13. The vaccine of any one of A10-A12, wherein the vaccine comprises or further comprises an adjuvant comprising a peptide and a deoxyinosine-containing immunostimulatory oligodeoxynucleic acid molecule (I-ODN).

A14. The vaccine of A13, wherein the peptide comprises the sequence KLKL5KLK (SEQ ID NO: 71) and the I-ODN comprises oligo-d(IC)13 (SEQ ID NO: 70).

A15. The vaccine of any one of A1-A14, further comprising one or more pharmaceutically acceptable excipient.

B1. A kit comprising a Zika virus vaccine of any one of A1-A15.

B2. The kit of B1, further comprising a second vaccine.

B3. The kit of B2, wherein the second vaccine is a West Nile virus vaccine, a Japanese Encephalitis virus vaccine, a yellow fever virus vaccine, a Dengue virus vaccine or a Chikungunya virus vaccine.

C1. A method, comprising administering a first dose of a therapeutically effective amount of the Zika virus vaccine of any one of A1-A15 to a subject in need thereof.

C2. The method of C1, further comprising administering a second dose of a therapeutically effective amount of the Zika virus vaccine.

C3. The method of C1 or C2, wherein the second dose of the Zika virus vaccine is administered about 7 days after the first dose of the Zika virus vaccine.

C4. The method of C1 or C2, wherein the second dose of the Zika virus vaccine is administered about 14 days after the first dose of the Zika virus vaccine.

C5. The method of C1 or C2, wherein the second dose of the Zika virus vaccine is administered about 28 days after the first dose of the Zika virus vaccine.

C6. The method of any one of C1-05, wherein the administering results in production of Zika virus neutralizing antibodies.

D1. A method of producing a Zika virus vaccine, comprising (i) passaging a Zika virus on Vero cells, thereby producing a culture supernatant comprising the Zika virus;

(ii) harvesting the culture medium of (i);

(iii) precipitating the harvested culture medium of (ii), thereby producing a Zika virus supernatant; and (iv) optimally inactivating the Zika virus in the Zika virus supernatant of (iii) thereby producing an inactivated Zika virus.

D2. The method of D1, further comprising concentrating the culture medium of (ii) prior to step (iii).

D3. The method of D1 or D2, wherein the precipitating of (iii) comprises contacting the culture medium of (ii) with protamine sulfate or benzonase.

D4. The method of any one of D1-D3, further comprising (v) dialyzing the inactivated Zika virus of (iv), thereby producing a dialyzed Zika virus.

D5. The method of D4, further comprising (vi) filtering the dialyzed Zika virus of (v).

D6. The method of any one of D1-D5, wherein the inactivating is by chemical inactivation, thermal inactivation, pH inactivation, or UV inactivation.

D7. The method of D6, wherein the chemical inactivation comprises contacting the Zika virus with a chemical inactivation agent for at least 4 days.

D8. The method of D6 or D7, wherein the chemical inactivation agent comprises formaldehyde.

D9. The method of any one of D6-D8, wherein the chemical activation is performed at about +4° C. or about +22° C.

D10. The method of D8 or D9, further comprising neutralizing the formaldehyde.

D11. The method of D10, wherein the neutralizing is performed with sodium metabisulfite.

E1. The use of the optimally inactivated Zika virus vaccine of any one of A1-A15 for the treatment and prevention of a Zika virus infection.

E2. The use of E1, wherein the inactivated Zika virus vaccine is administered in a first dose of a therapeutically effective amount to a subject in need thereof.

E3. The use of E2, wherein the inactivated Zika virus vaccine is administered in a second dose of a therapeutically effective amount to the subject.

E4. The use of E3, wherein the second dose of the inactivated Zika virus vaccine is administered about 7 days after the first dose of the Zika virus vaccine.

E5. The use of E3, wherein the second dose of the Zika virus vaccine is administered about 14 days after the first dose of the Zika virus vaccine.

E6. The use of E3, wherein the second dose of the Zika virus vaccine is administered about 28 days after the first dose of the Zika virus vaccine.

E7. The use of any one of E1-E6, wherein the vaccine administration results in production of Zika virus neutralizing antibodies.

F1. A pharmaceutical composition for use in the treatment and prevention of a Zika virus infection, wherein said pharmaceutical composition comprises the optimally inactivated Zika virus vaccine of any one of A1-A15.

F2. The pharmaceutical composition of F1, wherein the inactivated Zika virus vaccine is administered in a first dose of a therapeutically effective amount to a subject in need thereof.

F3. The use of F2, wherein the inactivated Zika virus vaccine is administered in a second dose of a therapeutically effective amount to the subject.

F4. The use of F3, wherein the second dose of the inactivated Zika virus vaccine is administered about 7 days after the first dose of the Zika virus vaccine.

F5. The use of F3, wherein the second dose of the Zika virus vaccine is administered about 14 days after the first dose of the Zika virus vaccine.

F6. The use of F3, wherein the second dose of the Zika virus vaccine is administered about 28 days after the first dose of the Zika virus vaccine.

F7. The use of any one of F1-F6, wherein the vaccine administration results in production of Zika virus neutralizing antibodies.

G1. A Zika virus vaccine comprising an inactivated Zika virus particle, wherein the Zika virus vaccine is able to confer seroprotection on at least 70% of subjects that are administered the Zika virus vaccine.

G2. The Zika virus vaccine of G1, wherein the Zika virus particle is able to confer seroprotection on at least 75%, 80%, 90%, 95%, 96%, 97%, 98%, or at least 99% of vaccinated subjects that are administered the Zika virus vaccine, preferably on at least 80% of subjects.

G3. The vaccine of G1 or G2, wherein the Zika virus particle has a RNA genome corresponding to the DNA sequence provided by any one of the nucleic acid sequences of SEQ ID NOs: 2-13 or 72, or a variant nucleic acid sequence that is at least 88% identical to any one of SEQ ID NOs: 2-13 or 72 and able to pack a virulent Zika virus.

G4. The vaccine of any one of G1 to G3, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

G5. The vaccine of any one of G1 to G4, wherein the Zika virus is inactivated by chemical inactivation, thermal inactivation, pH inactivation, or UV inactivation.

G6. The vaccine of G5, wherein the chemical inactivation comprises contacting the Zika virus with a chemical inactivation agent for longer than is required to completely inactivate the Zika virus as measured by plaque assay.

G7. The vaccine of G6, wherein the chemical inactivation comprises contacting the Zika virus with formaldehyde.

G8. The vaccine of G7, wherein the formaldehyde inactivation comprises contacting the Zika virus with formaldehyde for between 2-10 days.

G9. The vaccine of any one of G5 to G8, wherein the chemical activation is performed at about +4° C. or about +22° C.

G10. The vaccine of any one of G1 to G9, further comprising an adjuvant.

G11. The vaccine of G10, wherein the adjuvant is an aluminum salt adjuvant.

G12. The vaccine of G11, wherein the aluminum salt adjuvant is aluminium hydroxide or aluminium phosphate salt.

G13. The vaccine of any one of G10 to G12, wherein the vaccine comprises or further comprises an adjuvant comprising a peptide and a deoxyinosine-containing immunostimulatory oligodeoxynucleic acid molecule (I-ODN).

G14. The vaccine of G13, wherein the peptide comprises the sequence KLKL5KLK (SEQ ID NO: 71) and the I-ODN comprises oligo-d(IC)13 (SEQ ID NO: 70).

G15. The vaccine of any one of G1 to G14, further comprising one or more pharmaceutically acceptable excipients.

G16. The vaccine of any one of G1 to G15, wherein the vaccine contains protamine sulphate or fragments or break-down products of PS at amounts too low to detect by HPLC, i.e., below 1 μg/mL, especially below 100 ng/mL.

G17. The vaccine of G16, wherein said protamine sulphate or fragments or break-down products of PS can be detected by mass spectroscopy or another sensitive method.

Q1. A process of purification of infectious Zika virus particles, comprising the steps of:

(a) providing a crude harvest (a) comprising Zika virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b);

(c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 μg/ml, preferably below 0.5 μg/mL, more preferably below 0.1 μg/mL, most preferably below 0.05 μg/mL.

Q2. The process of Q2, wherein the virus particles are from Zika virus.

Q3. The process of Q1 or Q2, additionally comprising the step of:

(d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

Q4. The process of any of Q1 to 3, wherein the residual host cell DNA of the Zika virus preparation (c) is less than 10 ng/mL and the residual host cell protein of the final Zika virus preparation (c) is less than 100 ng/mL.

Q5. The process of any of Q1 to 4, wherein the crude harvest (a) comprising Zika virus particles and impurities is subjected to one or more pre-purification step(s) prior to step (b).

Q6. The process of Q5, wherein the one or more pre-purification step(s) comprises (a) filtration using a filter having a pore size equal to or less than 0.2 μm; and/or (b) digestion of host cell genomic DNA by enzymatic treatment; and/or (c) ultra/diafiltration using a hollow fiber membrane having a pore size equal to or greater than 300 kDa, preferably equal to or greater than 100 kDa.

Q7. The process of any one of Q1 to 6, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

Q8. The process of any one of Q1 to 7, wherein the enrichment of infectious Zika virus particles in the virus preparation (c) or any final virus preparation relative to total Zika virus products in the crude harvest (a) is in the range from at least 50% to 95%, preferably at least 80%.

Q9. The process of any one of Q5 to 8, wherein the one or more pre-purification step(s) prior to step (b) of any of Q5 to 8 is performed using a filter having a pore size equal to or less than 1 μm, preferably 0.2 μm.

Q10. The process of any one of Q1 to 9, wherein the residual impurity of the Zika virus preparation (c) is less than 10%.

Q11. The process of any one of Q1 to 10, wherein the Zika virus is propagated in a cell line selected from the group consisting of an EB66 cell line, a Vero cell line, a Vero-αHis cell line, a HeLa cell line, a HeLa—S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

Q12. The process of Q11, wherein said cell line is a Vero cell line.

Q13. The process of any one of Q1 to 12, wherein the infectious Zika virus particle is a live virus, an attenuated live virus, a chimeric virus, a modified live virus, or a recombinant live virus.

Q14. The process of any one of Q1 to 13, wherein the Zika virus is a Zika virus strain of the Asian lineage or an immunogenic variant thereof.

Q15. The process of any one of Q1 to 14, wherein said process resulting in final Zika virus preparation (c) or (d) is followed by an inactivation step, wherein the virus is inactivated preferably by formaldehyde.

Q16. Use of the process according to any one of Q1 to 15 for manufacturing a composition for immunization against a Zika virus infection.

Q17. The use according to Q16, wherein the composition for immunization against a virus infection is an infection caused by Zika virus.

Q18. A composition comprising the Zika virus particles obtainable or obtained by the process of any one of Q1 to 17 for treating and/or preventing an infection, such as e.g. a Zika virus infection.

Q19. A Zika virus vaccine comprising an inactivated Zika virus particle grown on vero cells, wherein the Zika virus particle is able to seroconvert a subject that is administered the Zika virus vaccine with at least a 70% probability and comprises minor amounts of protamine sulphate, preferably below the detection limit.

Q20. The Zika virus vaccine of Q19, wherein the Zika virus particle is able to seroconvert the subject that is administered the Zika virus vaccine with at least a 80%, 85%, 90%, or 95% probability, preferably a 80% probability.

Q21. The vaccine of Q19 or 20, wherein the Zika virus particle has a RNA genome corresponding to the DNA sequence provided by any one of the nucleic acid sequences of SEQ ID NOs: 2-13 or 72, or a variant nucleic acid sequence that is at least 88% identical to any one of SEQ ID NOs: 2-13 or 72 and able to pack a virulent Zika virus.

Q22. The vaccine of any one of Q19, 20 and 21, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

Q23. The vaccine of any one of Q19, 20 to 22, wherein the Zika virus obtained by culturing on Vero cells is purified by protamine sulfate precipitation and sucrose gradient centrifugation.

Q24. The vaccine of Q23, wherein the sucrose gradient centrifugation is an optimized sucrose gradient centrifugation.

Q25. The vaccine of Q24, wherein the optimized sucrose gradient centrifugation comprises a virus comprising fraction in a 10% (w/w) sucrose solution and three layers of sucrose with different densities, i.e. a first sucrose solution with 15% (w/w) sucrose solution, a second sucrose solution with 35% (w/w) sucrose solution, and a third sucrose solution with a 50% (w/w) sucrose solution.

Q26. The vaccine of any one of Q19, 20 to 25, wherein the Zika virus is inactivated by chemical inactivation, thermal inactivation, pH inactivation, or UV inactivation.

Q27. The vaccine of Q26, wherein the chemical inactivation comprises contacting the Zika virus with a chemical inactivation agent for longer than is required to completely inactivate the Zika virus as measured by plaque assay.

Q28. The vaccine of Q27, wherein the chemical inactivation comprises contacting the Zika virus with formaldehyde.

Q29. The vaccine of Q28, wherein the formaldehyde inactivation comprises contacting the Zika virus with formaldehyde for between 2-10 days.

Q30. The vaccine of any one of Q27-29, wherein the chemical activation is performed at about +4° C. or about +22° C.

Q31. The vaccine of any one of Q19 to 30, further comprising an adjuvant.

Q32. The vaccine of Q31, wherein the adjuvant is an aluminum salt adjuvant.

Q33. The vaccine of Q32, wherein the aluminum salt adjuvant is aluminium hydroxide or aluminium phosphate salt.

Q34. The vaccine of Q32, wherein the aluminum salt adjuvant is aluminium hydroxide with less than 1.25 ppb Cu based on the final pharmaceutical composition comprising the Zika virus, preferably the inactivated Zika virus.

Q35. The vaccine of any one of Q19 to 34, further comprising one or more pharmaceutically acceptable excipient(s).

R1. Use of protamine, preferably a protamine salt, to separate infectious and non-infectious Zika virus particles, host cell proteins and/or undefined low molecular weight materials.

R2. A process of purification of infectious Zika virus particles, comprising the steps of:

(a) providing a crude harvest (a) comprising Zika virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b), wherein the enrichment of infectious virus particles in the virus preparation (b) relative to total virus products in the crude harvest (a) is in the range from at least 50% to 95%, preferably at least 80%.

R3. The use of R1 or the process of R2, wherein the virus particles are from Zika virus.

R4. A process of purification of infectious Zika virus particles, comprising the steps of:

(a) providing a crude harvest (a) comprising Zika virus particles and impurities, wherein the impurities are generated from growing said virus particles on a cell substrate;

(b) reducing impurities from the crude harvest (a) by precipitation with an agent comprising protamine, preferably a protamine salt, more preferably a protamine sulphate, even more preferably a recombinant protamine sulphate, to obtain a virus preparation (b);

(c) further purifying the virus preparation (b) by one or more size exclusion methods such as (i) a sucrose density gradient centrifugation, (ii) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles, and/or (iii) size exclusion chromatography to obtain a virus preparation (c) comprising the infectious virus particles, wherein the residual host cell DNA of the virus preparation (c) is less than 100 ng/mL and the residual host cell protein and the residual aggregates of infectious virus particles of the final virus preparation (c) is less than 1 m/mL.

R5. The process of R4, wherein the residual host cell DNA of the Zika virus preparation (c) is less than 10 ng/mL and the residual host cell protein of the final virus preparation (c) is less than 100 ng/mL.

R6. The process of any of R2 to 5, wherein the crude harvest (a) comprising virus particles and impurities is subjected to one or more pre-purification step(s) prior to step (b).

R7. The process of R6, wherein the one or more pre-purification step(s) comprises (a) filtration using a filter having a pore size equal to or less than 0.2 μm; and/or (b) digestion of host cell genomic DNA by enzymatic treatment; and/or (c) ultra/diafiltration using a hollow fiber membrane having a pore size equal to or greater than 300 kDa, preferably equal to or greater than 100 kDa.

R8. The process of any one of R2 to 7, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml.

R9. The process of any one of R2 to 8, wherein the enrichment of infectious virus particles in the virus preparation (c) or any final virus preparation relative to total virus products in the crude harvest (a) is in the range from at least 50% to 95%, preferably at least 80%.

R10. The process of any one of R6 to 9, wherein the one or more pre-purification step(s) prior to step (b) of any of R6 to 9 is performed using a filter having a pore size equal to or less than 1 μm, preferably 0.2 μm.

R11. The process of any one of R2 to 10, wherein the residual impurity of the Zika virus preparation (c) is less than 10%.

R12. The process of any one of R2 to 11, wherein the Zika virus is propagated in a cell line selected from the group consisting of an EB66 cell line, a Vero cell line, a Vero-αHis cell line, a HeLa cell line, a HeLa—S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

R13. The process of R12, wherein said cell line is a Vero cell line.

R14. The process of any one of R2 to 13, wherein the Zika virus is a live virus, an attenuated live virus, a chimeric virus, a modified live virus, or a recombinant live virus.

R15. The process of any one of R2 to 14, wherein the Zika virus is a Zika virus strain of the Asian lineage or an immunogenic variant thereof.

R16. The process of any one of R2 to 15, wherein said process resulting in final virus preparation (c) is followed by an inactivation step, wherein the virus is inactivated preferably by formaldehyde.

R17. Use of the process according to any one of R1 to 16 for manufacturing a composition for immunization against a virus infection.

R18. The use according to R17, wherein the composition for immunization against a virus infection is an infection caused by a Zika virus.

R19. A composition comprising the virus particles obtainable or obtained by the process of any one of R2 to 16 for treating and/or preventing an infection.

What is claimed is:

1. A process for purifying infectious Zika virus particles, wherein said process comprises the steps of:

(i) providing a crude harvest (a) comprising infectious Zika virus particles, non-infectious Zika virus particles, and impurities, wherein the impurities are generated from growing Zika virus particles on a cell substrate;

(ii) contacting said crude harvest (a) with an agent comprising protamine to obtain a Zika virus preparation (b) comprising infectious Zika virus particles, wherein said agent facilitates separation of infectious Zika virus particles from non-infectious Zika virus particles; and (iii) further purifying said Zika virus preparation (b) by sucrose density gradient centrifugation;

to obtain a final Zika virus preparation (c) comprising infectious Zika virus particles, less than 100 ng/mL residual host cell DNA, less than 1 μg/mL residual host cell protein, and less than 1 μg/mL residual aggregates of Zika virus particles.

2. The process according to claim 1, wherein said agent comprising protamine also facilitates the separation of infectious Zika virus particles from host cell proteins and/or low molecular weight materials.

3. The process according to claim 1, wherein the final Zika virus preparation (c) comprises less than 10 ng/mL residual host cell DNA, less than 100 ng/mL residual host cell protein, and less than 100 ng/mL residual aggregates of Zika virus particles.

4. The process according to claim 1, wherein said crude harvest (a) is subjected to a concentration step prior to step (ii), wherein said concentration step comprises ultra/diafiltration using a hollow-fiber membrane having a pore size equal to or greater than 100 kDa.

5. The process according to claim 1, wherein said agent comprising protamine comprises a protamine salt.

6. The process according to claim 5, wherein said protamine salt is protamine sulphate.

7. The process according to claim 6, wherein the concentration of protamine sulphate is between 0.5 and 3 mg/mL.

8. The process according to claim 7, wherein the concentration of protamine sulphate is 2 mg/mL.

9. The process according to claim 1, wherein the infectious Zika virus particles in said final Zika virus preparation (c) are enriched by at least 50% to 95% relative to total Zika virus particles in said crude harvest (a).

10. The process according to claim 1, wherein said final Zika virus preparation (c) comprises less than 10% residual impurities relative to impurities in said crude harvest (a).

11. The process according to claim 1, wherein said cell line is a Vero cell line.

12. The process according to claim 1, wherein said Zika virus is a Zika virus strain of the Asian lineage or an immunogenic variant thereof.

13. The process according to claim 12, wherein said Zika virus strain of the Asian lineage is H/PF/2013 comprising an RNA genome corresponding to the DNA sequence provided by SEQ ID NOs: 13 or 72.

14. The process according to claim 1, wherein said process resulting in final Zika virus preparation (c) is followed by an inactivation step, wherein the Zika virus is inactivated with formaldehyde.

15. The process according to claim 14, wherein said formaldehyde inactivation comprises contacting final Zika virus preparation (c) with 0.02% (w/v) formaldehyde at 22° C. for 10 days, followed by neutralization with sodium-metabisulphite.

16. The process according to claim 1, for manufacturing a composition for immunization against a Zika virus infection.

17. The process according to claim 1, wherein said sucrose gradient centrifugation is an optimized sucrose gradient centrifugation, comprising a Zika virus fraction provided in a 10%±1% (w/w) sucrose solution and three further layers of sucrose solutions with different densities.

18. The process according to claim 17, wherein the three further layers of sucrose solutions comprise a first sucrose solution with 15%±1% (w/w) sucrose, a second sucrose solution with 35%±1% (w/w) sucrose, and a third sucrose solution with 50%±1% (w/w) sucrose.

* * * * *

UNITED STATES PATENT AND TRADEMARK OFFICE

CERTIFICATE OF CORRECTION

PATENT NO. : 11,524,064 B2
APPLICATION NO. : 16/927086
DATED : December 13, 2022
INVENTOR(S) : Jana Barbero Calzado et al.

It is certified that error appears in the above-identified patent and that said Letters Patent is hereby corrected as shown below:

On the Title Page

Item (72) should read:
(72) Inventors: Jana Barbero Calzado, Vienna (AT); Mario Nebenführ, Vienna (AT); Robert Schlegl, Siegenfeld (AT); Michael Weber, Vienna (AT); Jürgen Heindl-Wruss, Vienna (AT)

Signed and Sealed this
Nineteenth Day of December, 2023

Katherine Kelly Vidal
*Director of the United States Patent and Trademark Office*

SEQUENCE LISTING

<160> NUMBER OF SEQ ID NOS: 117

<210> SEQ ID NO 1
<211> LENGTH: 32
<212> TYPE: PRT
<213> ORGANISM: Artificial Sequence
<220> FEATURE:
<223> OTHER INFORMATION: synthetic peptide

<400> SEQUENCE: 1

```
Pro Arg Arg Arg Arg Ser Ser Ser Arg Pro Val Arg Arg Arg Arg Arg
1               5                   10                  15

Pro Arg Val Ser Arg Arg Arg Arg Arg Arg Gly Gly Arg Arg Arg Arg
            20                  25                  30
```

<210> SEQ ID NO 2
<211> LENGTH: 10676
<212> TYPE: DNA
<213> ORGANISM: Zika virus

<400> SEQUENCE: 2

```
gttgttactg ttgctgactc agactgcgac agttcgagtt tgaagcgaaa gctagcaaca     60

gtatcaacag gttttatttg gatttggaaa cgagagtttc tggtcatgaa aaacccaaaa    120

aagaaatccg gaggattccg gattgtcaat atgctaaaac gcggagtagc ccgtgtgagc    180

ccctttgggg gcttgaagag gctgccagcc ggacttctgc tgggtcatgg gcccatcagg    240

atggtcttgg caattctagc ctttttgaga ttcacggcaa tcaagccatc actgggtctc    300

atcaatagat ggggttcagt ggggaaaaaa gaggctatgg aaataataaa gaagttcaag    360

aaagatctgg ctgccatgct gagaataatc aatgctagga aggagaagaa gagacggggc    420

gcagatacta gtgtcggaat tgttggcctc ctgctgacca cagctatggc agcggaggtc    480

actagacgtg ggagtgcata ctatatgtac ttggacagaa acgatgctgg ggaggccata    540

tcttttccaa ccacattggg gatgaataag tgttatatac agatcatgga tcttggacac    600

atgtgtgatg ccaccatgag ctatgaatgc cctatgctgg atgagggggt ggaaccagat    660

gacgtcgatt gttggtgcaa cacgacgtca acttgggttg tgtacggaac ctgccatcac    720

aaaaaaggtg aagcacggag atctagaaga gctgtgacgc tcccctccca ttccactagg    780

aagctgcaaa cgcggtcgca aacctggttg gaatcaagag aatacacaaa gcacttgatt    840

agagtcgaaa attggatatt caggaaccct ggcttcgcgt tagcagcagc tgccatcgct    900

tggcttttgg gaagctcaac gagccaaaaa gtcatatact tggtcatgat actgctgatt    960

gccccggcat acagcatcag gtgcatagga gtcagcaata gggactttgt ggaaggtatg   1020

tcaggtggga cttgggttga tattgtcttg gaacatggag gttgtgtcac cgtaatggca   1080

caggacaaac cgactgtcga catagagctg gttacaacaa cagtcagcaa catggcggag   1140

gtaagatcct actgctatga ggcatcaata tcagacatgg cttcggacag ccgctgccca   1200

acacaaggtg aagcctacct tgacaagcaa tcagacactc aatatgtctg caaaagaacg   1260

ttagtggaca gaggctgggg aaatggatgt ggactttttg gcaaagggag tctggtgaca   1320

tgcgctaagt ttgcatgctc caagaaaatg accgggaaga gcatccagcc agagaatctg   1380

gagtaccgga taatgctgtc agttcatggc tcccagcaca gtgggatgat cgttaatgac   1440
```

-continued acaggacatg aaactgatga gaatagagcg aaggttgaga taacgcccaa ttcaccaaga 1500
gccgaagcca ccctgggggg ttttggaagc ctaggacttg attgtgaacc gaggacaggc 1560
cttgactttt cagatttgta ttacttgact atgaataaca agcactggtt ggttcacaag 1620
gagtggttcc acgacattcc attaccttgg cacgctgggg cagacaccgg aactccacac 1680
tggaacaaca aagaagcact ggtagagttc aaggacgcac atgccaaaag gcaaactgtc 1740
gtggttctag ggagtcaaga aggagcagtt cacacggccc ttgctggagc tctggaggct 1800
gagatggatg gtgcaaaggg aaggctgtcc tctggccact tgaaatgtcg cctgaaaatg 1860
gataaactta gattgaaggg cgtgtcatac tccttgtgta ccgcagcgtt cacattcacc 1920
aagatcccgg ctgaaacact gcacgggaca gtcacagtgg aggtacagta cgcagggaca 1980
gatggacctt gcaaggttcc agctcagatg gcggtggaca tgcaaactct gaccccagtt 2040
gggaggttga taaccgctaa ccccgtaatc actgaaagca ctgagaactc taagatgatg 2100
ctggaacttg atccaccatt tggggactct tacattgtca taggagtcgg ggagaagaag 2160
atcacccacc actggcacag gagtggcagc accattggaa aagcatttga agccactgtg 2220
agaggtgcca agagaatggc agtcttggga gacacagcct gggactttgg atcagttgga 2280
ggcgctctca actcattggg caagggcatc catcaaattt ttggagcagc tttcaaatca 2340
ttgtttggag gaatgtcctg gttctcacaa attctcattg gaacgttgct gatgtggttg 2400
ggtctgaaca caaagaatgg atctatttcc cttatgtgct tggccttagg gggagtgttg 2460
atcttcttat ccacagccgt ctctgctgat gtggggtgct cggtggactt ctcaaagaag 2520
gagacgagat gcggtacagg ggtgttcgtc tataacgacg ttgaagcctg gagggacagg 2580
tacaagtacc atcctgactc cccccgtaga ttggcagcag cagtcaagca agcctgggaa 2640
gatggtatct gcgggatctc ctctgtttca agaatggaaa acatcatgtg gagatcagta 2700
gaaggggagc tcaacgcaat cctggaagag aatggagttc aactgacggt cgttgtggga 2760
tctgtaaaaa accccatgtg gagaggtcca cagagattgc ccgtgcctgt gaacgagctg 2820
ccccacggct ggaaggcttg gggggaaatcg cacttcgtca gagcagcaaa gacaaataac 2880
agctttgtcg tggatggtga cacactgaag gaatgcccac tcaaacatag agcatggaac 2940
agctttcttg tggaggatca tgggttcggg gtatttcaca ctagtgtctg gctcaaggtt 3000
agagaagatt attcattaga gtgtgatcca gccgttattg gaacagctgt taagggaaag 3060
gaggctgtac acagtgatct aggctactgg attgagagtg agaagaatga cacatggagg 3120
ctgaagaggg cccatctgat cgagatgaaa acatgtgaat ggccaaagtc ccacacattg 3180
tggacagatg gaatagaaga gagtgatctg atcataccca agtctttagc tgggccactc 3240
agccatcaca ataccagaga gggctacagg acccaaatga aagggccatg gcacagtgaa 3300
gagcttgaaa ttcggtttga ggaatgccca ggcactaagg tccacgtgga ggaaacatgt 3360
ggaacaagag gaccatctct gagatcaacc actgcaagcg gaagggtgat cgaggaatgg 3420
tgctgcaggg agtgcacaat gcccccactg tcgttccggg ctaaagatgg ctgttggtat 3480
ggaatggaga taaggcccag gaaagaacca gaaagcaact tagtaaggtc aatggtgact 3540
gcaggatcaa ctgatcacat ggatcacttc tcccttggag tgcttgtgat tctgctcatg 3600
gtgcaggaag ggctgaagaa gagaatgacc acaaagatca tcataagcac atcaatggca 3660
gtgctggtag ctatgatcct gggaggattt tcaatgagtg acctggctaa gcttgcaatt 3720
ttgatgggtg ccaccttcgc ggaaatgaac actggaggag atgtagctca tctggcgctg 3780
atagcggcat tcaaagtcag accagcgttg ctggtatctt tcatcttcag agctaattgg 3840
acaccccgtg aaagcatgct gctggccttg gcctcgtgtc ttttgcaaac tgcgatctcc 3900
gccttggaag gcgacctgat ggttctcatc aatggttttg ctttggcctg gttggcaata 3960
cgagcgatgg ttgttccacg cactgataac atcaccttgg caatcctggc tgctctgaca 4020
ccactggccc ggggcacact gcttgtggcg tggagagcag gccttgctac ttgcgggggg 4080
tttatgctcc tctctctgaa gggaaaaggc agtgtgaaga agaacttacc atttgtcatg 4140
gccctgggac taaccgctgt gaggctggtc gaccccatca acgtggtggg gctgctgttg 4200
ctcacaagga gtgggaagcg gagctggccc cctagcgaag tactcacagc tgttggcctg 4260
atatgcgcat tggctggagg gttcgccaag gcagatatag agatggctgg gcccatggcc 4320
gcggtcggtc tgctaattgt cagttacgtg gtctcaggaa agagtgtgga catgtacatt 4380
gaaagagcag gtgacatcac atgggaaaaa gatgcggaag tcactggaaa cagtccccgg 4440
ctcgatgtgg cgctagatga gagtggtgat ttctccctgg tggaggatga cggtccccc 4500
atgagagaga tcatactcaa ggtggtcctg atgaccatct gtggcatgaa cccaatagcc 4560
ataccctttg cagctggagc gtggtacgta tacgtgaaga ctggaaaaag gagtggtgct 4620
ctatgggatg tgcctgctcc caaggaagta aaaaaggggg agaccacaga tggagtgtac 4680
agagtaatga ctcgtagact gctaggttca acacaagttg gagtgggagt tatgcaagag 4740
ggggtctttc acactatgtg gcacgtcaca aaaggatccg cgctgagaag cggtgaaggg 4800
agacttgatc catactgggg agatgtcaag caggatctgg tgtcatactg tggtccatgg 4860
aagctagatg ccgcctggga cgggcacagc gaggtgcagc tcttggccgt gccccccgga 4920
gagagagcga ggaacatcca gactctgccc ggaatattta agacaaagga tggggacatt 4980
ggagcggttg cgctggatta cccagcagga acttcaggat ctccaatcct agacaagtgt 5040
gggagagtga taggacttta tggcaatggg gtcgtgatca aaaatgggag ttatgttagt 5100
gccatcaccc aagggaggag ggaggaagag actcctgttg agtgcttcga gccttcgatg 5160
ctgaagaaga agcagctaac tgtcttagac ttgcatcctg gagctgggaa aaccaggaga 5220
gttcttcctg aaatagtccg tgaagccata aaaacaagac tccgtactgt gatcttagct 5280
ccaaccaggg ttgtcgctgc tgaaatggag gaagccctta gagggcttcc agtgcgttat 5340
atgacaacag cagtcaatgt cacccactct ggaacagaaa tcgtcgactt aatgtgccat 5400
gccaccttca cttcacgtct actacagcca atcagagtcc ccaactataa tctgtatatt 5460
atggatgagg cccacttcac agatccctca agtatagcag caagaggata catttcaaca 5520
agggttgaga tgggcgaggc ggctgccatc ttcatgaccg ccacgccacc aggaacccgt 5580
gacgcatttc cggactccaa ctcaccaatt atggacaccg aagtggaagt cccagagaga 5640
gcctggagct caggctttga ttgggtgacg gattattctg gaaaaacagt ttggtttgtt 5700
ccaagcgtga ggaacggcaa tgagatcgca gcttgtctga caaaggctgg aaaacgggtc 5760
atacagctca gcagaaagac ttttgagaca gagttccaga aacaaaaca tcaagagtgg 5820
gactttgtcg tgacaactga catttcagag atgggcgcca actttaaagc tgaccgtgtc 5880
atagattcca ggagatgcct aaagccggtc atacttgatg gcgagagagt cattctggct 5940
ggacccatgc ctgtcacaca tgccagcgct gcccagagga gggggcgcat aggcaggaat 6000
cccaacaaac ctggagatga gtatctgtat ggaggtgggt gcgcagagac tgacgaagac 6060
catgcacact ggcttgaagc aagaatgctc cttgacaata tttacctcca agatggcctc 6120
atagcctcgc tctatcgacc tgaggccgac aaagtagcag ccattgaggg agagttcaag 6180

-continued

```
cttaggacgg agcaaaggaa gacctttgtg gaactcatga aaagaggaga tcttcctgtt   6240
tggctggcct atcaggttgc atctgccgga ataacctaca cagatagaag atggtgcttt   6300
gatggcacga ccaacaacac cataatggaa gacagtgtgc cggcagaggt gtggaccaga   6360
cacggagaga aaagagtgct caaaccgagg tggatggacg ccagagtttg ttcagatcat   6420
gcggccctga agtcattcaa ggagtttgcc gctgggaaaa gaggagcggc ttttggagtg   6480
atggaagccc tgggaacact gccaggacac atgacagaga gattccagga agccattgac   6540
aacctcgctg tgctcatgcg ggcagagact ggaagcaggc cttacaaagc cgcggcggcc   6600
caattgccgg agaccctaga gaccattatg cttttggggt tgctgggaac agtctcgctg   6660
ggaatctttt tcgtcttgat gaggaacaag ggcataggga agatgggctt tggaatggtg   6720
actcttgggg ccagcgcatg gctcatgtgg ctctcggaaa ttgagccagc cagaattgca   6780
tgtgtcctca ttgttgtgtt cctattgctg gtggtgctca tacctgagcc agaaaagcaa   6840
agatctcccc aggacaacca aatggcaatc atcatcatgg tagcagtagg tcttctgggc   6900
ttgattaccg ccaatgaact cggatggttg gagagaacaa agagtgacct aagccatcta   6960
atgggaagga gagaggaggg ggcaaccatg ggattctcaa tggacattga cctgcggcca   7020
gcctcagctt gggccatcta tgctgccttg acaactttca ttaccccagc cgtccaacat   7080
gcagtgacca cttcatacaa caactactcc ttaatggcga tggccacgca agctggagtg   7140
ttgtttggta tgggcaaagg gatgccattc tacgcatggg actttggagt cccgctgcta   7200
atgataggtt gctactcaca attaacgccc ctgaccctaa tagtggccat cattttgctc   7260
gtggcgcact acatgtactt gatcccaggg ctgcaggcag cagctgcgcg tgctgcccag   7320
aagagaacgg cagctggcat catgaagaac cctgttgtgg atggaatagt ggtgactgac   7380
attgacacaa tgacaattga cccccaagtg gagaaaaaga tgggacaggt gctactcatg   7440
gcagtagccg tctccagcgc catactgtcg cggaccgcct gggggtgggg ggaggctggg   7500
gccctgatca cagccgcaac ttccactttg tgggaaggct ctccgaacaa gtactggaac   7560
tcctctacag ccacttcact gtgtaacatt tttaggggaa gttacttggc tggagcttct   7620
ctaatctaca cagtaacaag aaacgctggc ttggtcaaga gacgtggggg tggaacagga   7680
gagaccctgg gagagaaatg gaaggcccgc ttgaaccaga tgtcggccct ggagttctac   7740
tcctacaaaa agtcaggcat caccgaggtg tgcagagaag aggcccgccg cgccctcaag   7800
gacggtgtgg caacgggagg ccatgctgtg tcccgaggaa gtgcaaagct gagatggttg   7860
gtggagcggg gatacctgca gccctatgga aaggtcattg atcttggatg tggcagaggg   7920
ggctggagtt actacgccgc caccatccgc aaagttcaag aagtgaaagg atacacaaaa   7980
ggaggccctg gtcatgaaga acccgtgttg gtgcaaagct atgggtggaa catagtccgt   8040
cttaagagtg ggggtggacgt ctttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaaaga ccaggagcct tttgtataaa agtgttgtgc   8220
ccatacacca gcactatgat ggaaaccctg gagcgactgc agcgtaggta tgggggagga   8280
ctggtcagag tgccactctc ccgcaactct acacatgaga tgtactgggt ctctggagcg   8340
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcagtgagc acgcggaaac gtggttcttt gacgagaacc acccatatag gacatgggct   8580
```

```
taccatggaa gctatgaggc ccccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aaggtactcg tcaggttatg agcatggtct cttcctggtt gtggaaagag   8820
ctaggcaaac acaaacggcc acgagtctgt accaaagaag agttcatcaa caaggttcgt   8880
agcaatgcag cattaggggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacaacatg atggaaaaaa gagaaaagaa acaaggggaa   9060
tttggaaagg ccaagggcag ccgcgccatc tggtatatgt ggctaggggc tagatttcta   9120
gagttcgaag cccttggatt cttgaacgag gatcactgga tggggagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
tttgatctgg agaatgaagc tctaatcacc aaccaaatgg agaaagggca cagggccttg   9360
gcattggcca taatcaagta cacataccaa aacaaagtgg taaaggtcct tagaccagct   9420
gaaaaaggga aaacagttat ggacattatt tcgagacaag accaaagggg gagcggacaa   9480
gttgtcactt acgctcttaa cacatttacc aacctagtgg tgcaactcat tcggaatatg   9540
gaggctgagg aagtcctaga gatgcaagac ttgtggctgc tgcggaggtc agagaaagtg   9600
accaactggt tgcagagcaa cggatgggat aggctcaaac gaatggcagt cagtggagat   9660
gattgcgttg tgaagccaat tgatgatagg tttgcacatg ccctcaggtt cttgaatgat   9720
atgggaaaag ttaggaagga cacacaagag tggaaaccct caactggatg ggacaactgg   9780
gaagaagttc cgttttgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc ctagcaaaat catatgcgca aatgtggcag   9960
ctcctttatt tccacagaag ggacctccga ctgatggcca atgccatttg ttcatctgtg  10020
ccagttgact gggttccaac tgggagaact acctggtcaa tccatggaaa gggagaatgg  10080
atgaccactg aagacatgct tgtggtgtgg aacagagtgt ggattgagga gaacgaccac  10140
atggaagaca agaccccagt tacgaaatgg acagacattc cctatttggg aaaaagggaa  10200
gacttgtggt gtggatctct catagggcac agaccgcgca ccacctgggc tgagaacatt  10260
aaaaacacag tcaacatggt gcgcaggatc ataggtgatg aagaaaagta catggactac  10320
ctatccaccc aagttcgcta cttgggtgaa gaagggtcta cacctggagt gctgtaagca  10380
ccaatcttaa tgttgtcagg cctgctagtc agccacagct tggggaaagc tgtgcagcct  10440
gtgacccccc caggagaagc tgggaaacca agcctatagt caggccgaga acgccatggc  10500
acggaagaag ccatgctgcc tgtgagcccc tcagaggaca ctgagtcaaa aaaccccacg  10560
cgcttggagg cgcaggatgg gaaaagaagg tggcgacctt ccccaccctt caatctgggg  10620
cctgaactgg agatcagctg tggatctcca gaagagggac tagtggttag aggaga      10676
```

<210> SEQ ID NO 3
<211> LENGTH: 10793
<212> TYPE: DNA
<213> ORGANISM: Zika virus

<400> SEQUENCE: 3

-continued

```
ccaatctgtg aatcagactg cgacagttcg agtttgaagc gaaagctagc aacagtatca     60
acaggtttta ttttggattt ggaaacgaga gtttctggtc atgaaaaacc caaaaaagaa    120
atccggagga ttccggattg tcaatatgct aaaacgcgga gtagcccgtg tgagcccctt    180
tgggggcttg aagaggctgc cagccggact tctgctgggt catgggccca tcaggatggt    240
cttggcgatt ctagcctttt tgagattcac ggcaatcaag ccatcactgg gtctcatcaa    300
tagatggggt tcagtgggga aaaaagaggc tatggaaata ataaagaagt tcaagaaaga    360
tctggctgcc atgctgagaa taatcaatgc caggaaggag aagaagagac gaggcgcaga    420
tactagtgtc ggaatcgttg gcctcctgct gaccacagct atggcagcgg aggtcactag    480
acgtgggagt gcatactata tgtacttgga cagaaacgat gctggggagg ccatatcttt    540
tccaaccaca ttggggatga ataagtgtta tatacagatc atggatcttg gacacatgtg    600
tgatgccacc atgagctatg aatgccctat gctggatgag ggggtggaac cagatgacgt    660
cgattgttgg tgcaacacga cgtcaacttg ggttgtgtac ggaacctgcc atcacaaaaa    720
aggtgaagca cggagatcta gaagagctgt gacgctcccc tcccattcca ctaggaagct    780
gcaaacgcgg tcgcaaacct ggttggaatc aagagaatac acaaagcact tgattagagt    840
cgaaaattgg atattcagga accctggctt cgcgttagca gcagctgcca tcgcttggct    900
tttgggaagc tcaacgagcc aaaaagtcat atacttggtc atgatactgc tgattgcccc    960
ggcatacagc atcaggtgca taggagtcag caatagggac tttgtggaag gtatgtcagg   1020
tgggacttgg gttgatgttg tcttggaaca tgggggttgt gtcaccgtaa tggcacagga   1080
caaaccgact gtcgacatag agctggttac aacaacagtc agcaacatgg cggaggtaag   1140
atcctactgc tatgaggcat caatatcaga catggcttcg gacagccgct gcccaacaca   1200
aggtgaagcc taccttgaca agcaatcaga cactcaatat gtctgcaaaa gaacgttagt   1260
ggacagaggc tggggaaatg gatgtggact tttggcaaa gggagcctgg tgacatgcgc   1320
taagtttgca tgctccaaga aaatgaccgg gaagagcatc cagccagaga atctggagta   1380
ccggataatg ctgtcagttc atggctccca gcacagtggg atgatcgtta atgacacagg   1440
acatgaaact gatgagaata gagcgaaggt tgagataacg cccaattcac caagagccga   1500
agccaccctg gggggtttg gaagcttagg acttgattgt gaaccgagga caggccttga   1560
cttttcagat ttgtattact tgactatgaa taacaagcac tggttggttc acaaggagtg   1620
gttccacgac attccattac cttggcacgc tggggcagac accggaactc cacactggaa   1680
caacaaagaa gcactggtag agttcaagga cgcacatgcc aaaaggcaaa ctgtcgtggt   1740
tctagggact caagaaggag cagttcacac ggcccttgct ggagctctgg aggctgagat   1800
ggatggtgca aagggaaggc tgtcctctgg ccacttgaaa tgtcgcctga aaatggataa   1860
acttagattg aagggcgtgt catactcctt gtgtaccgca gcgttcacat tcaccaagat   1920
cccggctgaa acactgcacg ggacagtcac agtggaggta cagtacgcag ggacagatgg   1980
accttgcaag gttccagctc agatggcggt ggacatgcaa actctgaccc cagttgggag   2040
gttgataacc gctaaccccg taatcactga aagcactgag aactctaaga tgatgctgga   2100
acttgatcca ccatttgggg actcttacat tgtcatagga gtcggggaga agaagatcac   2160
ccaccactgg cacaggagtg gcagcaccat tggaaaagca tttgaagcca ctgtgagagg   2220
tgccaagaga atggcagtct tgggagacac agcctgggac tttggatcag ttggaggcgc   2280
tctcaactca ttgggcaagg gcatccatca aatttttgga gcagctttca aatcattgtt   2340
tggaggaatg tcctggttct cacaaattct cattggaacg ttgctgatgt ggttgggtct   2400
```

```
gaacacaaag aatggatcta tttcccttat gtgcttggcc ttagggggag tgttgatctt   2460
cttatccaca gccgtctctg ctgatgtggg gtgctcggtg gacttctcaa agaaggagac   2520
gagatgtggt acaggggtgt tcgtctataa cgacgttgaa gcctggaggg acaggtacaa   2580
gtaccatcct gactctcccc gtagattggc agcagcagtc aagcaagcct gggaagatgg   2640
tatctgcggg atctcctctg tttcaagaat ggaaaacatc atgtggagat cagtagaagg   2700
ggagcttaac gcaatcctgg aagagaatgg agttcaactg acggtcgttg tgggatctgt   2760
aaaaaacccc atgtggagag gtccacagag attgcccgtg cctgtgaacg agctgcccca   2820
cggctggaag gcttggggga aatcgtactt cgtcagagca gcaaagacaa ataacagctt   2880
tgtcgtggat ggtgacacac tgaaggaatg cccactcaaa catagagcat ggaacagctt   2940
tcttgtggag gatcatgggt tcggggtatt tcacactagt gtctggctca aggttagaga   3000
agattattca ttagagtgtg atccagccgt tattggaaca gctgttaagg gaaaggaggc   3060
tgtacacagt gatctaggct actggattga gagtgagaag aatgacacat ggaggctgaa   3120
gagggcccat ctgatcgaga tgaaaacatg tgaatggcca aagtcccaca cattgtggac   3180
agatggaata gaagagagtg atctgatcat acccaagtct ttagctgggc cactcagcca   3240
tcacaatacc agagagggct acaggaccca aatgaaaggg ccatggcaca gtgaagagct   3300
tgaaattcgg tttgaggaat gcccaggcac taaggtccac gtggaggaaa catgtggaac   3360
aagaggacca tctctgagat caaccactgc aagcggaagg gtgatcgagg aatggtgctg   3420
cagggagtgc acaatgcccc cactgtcgtt ccgggctaaa gatggctgtt ggtatggaat   3480
ggagataagg cccaggaaag aaccagaaag caacttagta aggtcaatgg tgactgcagg   3540
atcaactgat cacatggatc acttctccct tggagtgctt gtgattctgc tcatggtgca   3600
ggaagggctg aagaagagaa tgaccacaaa gatcatcata agcacatcaa tggcagtgct   3660
ggtagctatg atcctgggag gattttcaat gagtgacctg gctaagcttg caattttgat   3720
gggtgccacc ttcgcggaaa tgaacactgg aggagatgta gctcatctgg cgctgatagc   3780
ggcattcaaa gtcagaccag cgttgctggt atctttcatc ttcagagcta attggacacc   3840
ccgtgaaagc atgctgctgg ccttggcctc gtgtttttg caaactgcga tctccgcctt   3900
ggaaggcgac ctgatggttc tcatcaatgg ttttgctttg gcctggttgg caatacgagc   3960
gatggttgtt ccacgcactg acaacatcac cttggcaatc ctggctgctc tgacaccact   4020
ggcccggggc acactgcttg tggcgtggag agcaggcctt gctacttgcg gggggtttat   4080
gctcctctct ctgaagggaa aaggcagtgt gaagaagaac ttaccatttg tcatggccct   4140
gggactaacc gctgtgaggc tggtcgaccc catcaacgtg gtgggactgc tgttgctcac   4200
aaggagtggg aagcggagct ggccccctag cgaagtactc acagctgttg gcctgatatg   4260
cgcattggct ggagggttcg ccaaggcaga tatagagatg gctgggccca tggccgcggt   4320
cggtctgcta attgtcagtt acgtggtctc aggaaagagt gtggacatgt acattgaaag   4380
agcaggtgac atcacatggg aaaaagatgc ggaagtcact ggaaacagtc cccggctcga   4440
tgtggcgcta gatgagagtg gtgacttctc cctggtggag gatgacggtc cccccatgag   4500
agagatcata ctcaaggtgg tcctgatgac catctgtggc atgaacccaa tagccatacc   4560
ctttgcagct ggagcgtggt acgtatacgt gaagactgga aaaaggagtg gtgctctatg   4620
ggatgtgcct gctcccaagg aagtaaaaaa gggggagacc acagatggag tgtacagagt   4680
aatgactcgt agactgctag gttcaacaca agttggagtg ggagttatgc aagagggggt   4740
```

-continued

```
ctttcacact atgtggcacg tcacaaaagg atccgcgctg agaagcggtg aagggagact   4800
tgatccatac tggggagatg tcaagcagga tctggtgtca tactgtggtc catggaagct   4860
agatgccgcc tgggacgggc acagcgaggt gcagctcttg gccgtgcccc ccggagagag   4920
agcgaggaac atccagactc tgcccggaat atttaagaca aaggatgggg acattggagc   4980
ggttgcgctg gattacccag caggaacttc aggatctcca atcctagaca agtgtgggag   5040
agtgatagga ctttatggca atggggtcgt gataaaaaat gggagttatg ttagtgccat   5100
cacccaaggg aggagggagg aagagactcc tgttgagtgc ttcgagcctt cgatgctgaa   5160
gaagaagcag ctaactgtct tagacttgca tcctggagct gggaaaacca ggagagttct   5220
tcctgaaata gtccgtgaag ccataaaaac aagactccgt actgtgatct tagctccaac   5280
cagggttgtc gctgctgaaa tggaggaagc ccttagaggg cttccagtgc gttatatgac   5340
aacagcagtc aatgtcaccc actctggaac agaaatcgtc gacttaatgt gccatgccac   5400
cttcacttca cgtctactac agccaatcag agtccccaac tataatctgt atattatgga   5460
tgaggcccac ttcacagatc cctcaagcat agcagcaaga ggatacattt caacaagggt   5520
tgagatgggc gaggcggctg ccatcttcat gaccgccacg ccaccaggaa cccgtgacgc   5580
atttccggac tccaactcac caattatgga caccgaagtg gaagtcccag agagagcctg   5640
gagctcaggc tttgattggg tgacggatca ttctggaaaa acagtttggt ttgttccaag   5700
cgtgaggaac ggcaatgaga tcgcagcttg tctgacaaag gctggaaaac gggtcataca   5760
gctcagcaga aagacttttg agacagagtt ccagaaaaca aaacatcaag agtgggactt   5820
tgtcgtgaca actgacattt cagagatggg cgccaacttt aaagctgacc gtgtcataga   5880
ttccaggaga tgcctaaagc cggtcatact tgatggcgag agagtcattc tggctggacc   5940
catgcctgtc acacatgcca gcgctgccca gaggaggggg cgcataggca ggaatcccaa   6000
caaacctgga gatgagtacc tgtatggagg tgggtgcgca gagactgacg aagaccatgc   6060
acactggctt gaagcaagaa tgctccttga caatatttac ctccaagatg gcctcatagc   6120
ctcgctctat cgacctgagg ccgacaaagt agcagccatt gagggagagt tcaagcttag   6180
gacggagcaa aggaagacct ttgtggaact catgaaaaga ggagatcttc ctgtttggct   6240
ggcctatcag gttgcatctg ccggaataac ctacacagat agaagatggt gctttgatgg   6300
cacgaccaac aacaccataa tggaagacag tgtgccggca gaggtgtgga ccagacacgg   6360
agagaaaaga gtgctcaaac cgaggtggat ggacgccaga gtttgttcag atcatgcggc   6420
cctgaagtca ttcaaggagt ttgccgctgg gaaaagagga gcggcttttg gagtgatgga   6480
agccctggga acactgccag gacacatgac agagagattc caggaagcca ttgacaacct   6540
cgctgtgctc atgcgggcag agactggaag caggccttac aaagccgcgg cggcccaatt   6600
gccggagacc ctagagacca ttatgctttt ggggttgctg ggaacagtct cgctgggaat   6660
ctttttcgtc ttgatgagga acaagggcat agggaagatg ggctttggaa tggtgactct   6720
tggggccagc gcatggctca tgtggctctc ggaaattgag ccagccagaa ttgcatgtgt   6780
cctcattgtt gtgttcctat tgctggtggt gctcatacct gagccagaaa agcaaagatc   6840
tccccaggac aaccaaatgg caatcatcat catggtagca gtaggtcttc tgggcttgat   6900
taccgccaat gaactcggat ggttggagag aacaaagagt gacctaagcc atctaatggg   6960
aaggagagag gagggggcaa ccataggatt ctcaatggac attgacctgc ggccagcctc   7020
agcttgggcc atctatgctg ccttgacaac tttcattacc ccagccgtcc aacatgcagt   7080
gaccacttca tacaacaact actccttaat ggcgatggcc acgcaagctg gagtgttgtt   7140
```

tggtatgggc aaagggatgc cattctacgc atgggacttt ggagtcccgc tgctaatgat 7200
aggttgctac tcacaattaa cacccctgac cctaatagtg gccatcattt tgctcgtggc 7260
gcactacatg tacttgatcc cagggctgca ggcagcagct gcgcgtgctg cccagaagag 7320
aacggcagct ggcatcatga agaaccctgt tgtggatgga atagtggtga ctgacattga 7380
cacaatgaca attgaccccc aagtggagaa aaagatggga caggtgctac tcatagcagt 7440
agccgtctcc agcgccatac tgtcgcggac cgcctggggg tggggggagg ctggggccct 7500
gatcacagcc gcaacttcca ctttgtggga aggctctccg aacaagtact ggaactcctc 7560
tacagccact tcactgtgta acatttttag ggaagttac ttggctggag cttctctaat 7620
ctacacagta acaagaaacg ctggcttggt caagagacgt gggggtggaa caggagagac 7680
cctgggagag aaatggaagg cccgcttgaa ccagatgtcg gccctggagt tctactccta 7740
caaaaagtca ggcatcaccg aggtgtgcag agaagaggcc cgccgcgccc tcaaggacgg 7800
tgtggcaacg ggaggccatg ctgtgtcccg aggaagtgca aagctgagat ggttggtgga 7860
gcggggatac ctgcagccct atggaaaggt cattgatctt ggatgtggca gagggggctg 7920
gagttactac gccgccacca tccgcaaagt tcaagaagtg aaaggataca caaaaggagg 7980
ccctggtcat gaagaacccg tgttggtgca aagctatggg tggaacatag tccgtcttaa 8040
gagtggggtg gacgtctttc atatggcggc tgagccgtgt gacacgttgc tgtgtgacat 8100
aggtgagtca tcatctagtc ctgaagtgga agaagcacgg acgctcagag tcctctccat 8160
ggtgggggat tggcttgaaa aaagaccagg agccttttgc ataaaagtgt tgtgcccata 8220
caccagcact atgatggaaa ccctggagcg actgcagcgt aggtatgggg gaggactggt 8280
cagagtgcca ctctcccgca actctacaca tgagatgtac tgggtctctg gagcgaaaag 8340
caacaccata aaaagtgtgt ccaccacgag ccagctcctc ttggggcgca tggacgggcc 8400
taggaggcca gtgaaatatg aggaggatgt gaatctcggc tctggcacgc gggctgtggt 8460
aagctgcgct gaagctccca acatgaagat cattggtaac cgcattgaaa ggatccgcag 8520
tgagcacgcg gaaacgtggt tctttgacga aaaccaccca tataggacat gggcttacca 8580
tggaagctat gtggccccca cacaagggtc agcgtcctct ctaataaacg gggttgtcag 8640
gctcctgtca aaaccctggg atgtggtgac tggagtcaca ggaatagcca tgaccgacac 8700
cacaccgtat ggtcagcaaa gagttttcaa ggaaaaagtg gacactaggg tgccagaccc 8760
ccaagaaggc actcgtcagg ttatgagcat ggtctcttcc tggttgtgga aagagctagg 8820
caaacacaaa cgaccacgag tctgtaccaa agaagagttc atcaacaagg ttcgtagcaa 8880
tgcagcatta ggggcaatat ttgaagagga aaaagagtgg aagactgcag tggaagctgt 8940
gaacgatcca aggttctggg ctctagtgga caaggaaaga gagcaccacc tgagaggaga 9000
gtgccagagt tgtgtgtaca acatgatggg aaaaagagaa aagaaacaag gggaatttgg 9060
aaaggccaag ggcagccgcg ccatctggta tatgtggcta ggggctagat ttctagagtt 9120
cgaagccctt ggattcttga acgaggatca ctggatgggg agagagaact caggaggtgg 9180
tgttgaaggg ctgggattac aaagactcgg atatgtccta gaagagatga gtcgcatacc 9240
aggaggaagg atgtatgcag atgacactgc tggctgggac acccgcatca gcaggtttga 9300
tctggagaat gaagctctaa tcaccaacca aatggagaaa gggcacaggg ccttggcatt 9360
ggccataatc aagtacacat accaaaacaa agtggtaaag gtccttagac cagctgaaaa 9420
agggaaaaca gttatggaca ttatttcgag acaagaccaa agggggagcg gacaagttgt 9480

```
cacttacgct cttaacacat ttaccaacct agtggtgcaa ctcattcgga atatggaggc   9540
tgaggaagtt ctagagatgc aagacttgtg gctgctgcgg aggtcagaga aagtgaccaa   9600
ctggttgcag agcaacggat gggataggct caaacgaatg gcagtcagtg gagatgattg   9660
cgttgtgaag ccaattgatg ataggtttgc acatgccctc aggttcttga atgatatggg   9720
aaaagttagg aaggacacac aagagtggaa accctcaact ggatgggaca actgggaaga   9780
agttccgttt tgctcccacc acttcaacaa gctccatctc aaggacggga ggtccattgt   9840
ggttccctgc cgccaccaag atgaactgat tggccgggcc cgcgtctctc caggggcggg   9900
atggagcatc cgggagactg cttgcctagc aaaatcatat gcgcaaatgt ggcagctcct   9960
ttatttccac agaagggacc tccgactgat ggccaatgcc atttgttcat ctgtgccagt  10020
tgactgggtt ccaactggga gaactacctg gtcaatccat ggaaagggag aatggatgac  10080
cactgaagac atgcttgtgg tgtggaacag agtgtggatt gaggagaacg accacatgga  10140
agacaagacc ccagttacga aatggacaga cattccctat ttgggaaaaa gggaagactt  10200
gtggtgtgga tctctcatag ggcacagacc gcgcaccacc tggggctgaga acattaaaaa  10260
tacagtcaac atggtgcgca ggatcatagg tgatgaagaa aagtacatgg actacctatc  10320
cacccaagtt cgctacttgg gtgaagaagg gtctacacct ggagtgctgt gagcaccaat  10380
cttaatgttg tcaggcctgc tagtcagcca cagcttgggg aaagctgtgc agcctgtgac  10440
ccctccagga gaagctgggt aaccaagcct atagtcaggc cgagaacgcc atggcacgga  10500
agaagccatg ctgcctgtga gcccctcaga ggacactgag tcaaaaaacc ccacgcgctt  10560
ggaggcgcag gatgggaaaa gaaggtggcg accttcccca cccttcaatc tggggcctga  10620
actggagatc agctgtggat ctccagaaga gggactagtg gttagaggag accccccgga  10680
aaacgcaaaa cagcatattg acgctgggaa agaccagaga ctccatgagt ttccaccacg  10740
ctggccgcca ggcacagatc gccgaatagc ggcggccggt gtggggaaat cca         10793
```

<210> SEQ ID NO 4
<211> LENGTH: 10675
<212> TYPE: DNA
<213> ORGANISM: Zika virus

<400> SEQUENCE: 4

```
gttgttgatc tgtgtgaatc agactgcgac agttcgagtt tgaagcgaaa gctagcaaca     60
gtatcaacag gttttatttt ggatttggaa acgagagttt ctggtcatga aaaacccaaa    120
aaagaaatcc ggaggattcc ggattgtcaa tatgctaaaa cgcggagtag cccgtgtgag    180
ccccttttggg ggcttgaaga ggctgccagc cggacttctg ctgggtcatg ggcccatcag    240
gatggtcttg gcgattctag cctttttgag attcacggca atcaagccat cactgggtct    300
catcaataga tggggttcag tggggaaaaa agaggctatg gaaacaataa agaagttcaa    360
gaaagatctg gctgccatgc tgagaataat caatgctagg aaggagaaga agagacgagg    420
cgcagatact agtgtcggaa ttgttggcct cctgctgacc acagctatgg cagcggaggt    480
cactagacgt gggagtgcat actatatgta cttggacaga aacgatgctg gggaggccat    540
atcttttcca accacattgg ggatgaataa gtgttatata cagatcatgg atcttggaca    600
catgtgtgat gccaccatga gctatgaatg ccctatgctg gatgaggggg tggaaccaga    660
tgacgtcgat tgttggtgca acacgacgtc aacttgggtt gtgtacggaa cctgccatca    720
caaaaaaggt gaagcacgga gatctagaag agctgtgacg ctcccctccc attccaccag    780
gaagctgcaa acgcggtcgc aaacctggtt ggaatcaaga gaatacacaa agcacttgat    840
```

```
tagagtcgaa aattggatat tcaggaaccc tggcttcgcg ttagcagcag ctgccatcgc    900
ttggcttttg ggaagctcaa cgagccaaaa agtcatatac ttggtcatga tactgctgat    960
tgccccggca tacagcatca ggtgcatagg agtcagcaat agggactttg tggaaggtat   1020
gtcaggtggg acttgggttg atgttgtctt ggaacatgga ggttgtgtca ccgtaatggc   1080
acaggacaaa ccgactgtcg acatagagct ggttacaaca acagtcagca acatggcgga   1140
ggtaagatcc tactgctatg aggcatcaat atcagacatg gcttctgaca gccgctgccc   1200
aacacaaggt gaagcctacc ttgacaagca atcagacact caatatgtct gcaaaagaac   1260
gttagtggac agaggctggg gaaatggatg tggacttttt ggcaaaggga gcctggtgac   1320
atgcgctaag tttgcatgct ccaagaaaat gaccgggaag agcatccagc cagagaatct   1380
ggagtaccgg ataatgctgt cagttcatgg ctcccagcac agtgggatga tcgttaatga   1440
cacaggacat gaaactgatg agaatagagc gaaagttgag ataacgccca attcaccgag   1500
agccgaagcc accctggggg gttttggaag cctaggactt gattgtgaac cgaggacagg   1560
ccttgacttt tcagatttgt attacttgac tatgaataac aagcactggt tggttcacaa   1620
ggagtggttc cacgacattc cattaccttg gcacgctggg gcagacaccg gaactccaca   1680
ctggaacaac aaagaagcac tggtagagtt caaggacgca catgccaaaa ggcaaactgt   1740
cgtggttcta gggagtcaag aaggagcagt tcacacggcc cttgctggag ctctggaggc   1800
tgagatggat ggtgcaaagg gaaggctgtc ctctggccac ttgaaatgtc gcctgaaaat   1860
ggataaactt agattgaagg gcgtgtcata ctccttgtgt actgcagcgt tcacattcac   1920
caagatcccg gctgaaacac tgcacgggac agtcacagtg gaggtacagt acgcagggac   1980
agatggacct tgcaaggttc cagctcagat ggcggtggac atgcaaactc tgaccccagt   2040
tgggaggttg ataaccgcta accccgtaat cactgaaagc actgagaact ctaagatgat   2100
gctggaactt gatccaccat ttggggactc ttacattgtc ataggagtcg gggagaagaa   2160
gatcacccac cactggcaca ggagtggcag caccattgga aaagcatttg aagccactgt   2220
gagaggtgcc aagagaatgg cagtcttggg agacacagcc tgggactttg gatcagttgg   2280
aggcgctctc aactcattgg gcaagggcat ccatcaaatt tttggagcag ctttcaaatc   2340
attgtttgga ggaatgtcct ggttctcaca aattctcatt ggaacgttgc tgatgtggtt   2400
gggtctgaac acaaagaatg gatctatttc ccttatgtgc ttggccttag ggggagtgtt   2460
gatcttctta tccacagccg tctctgctga tgtggggtgc tcggtggact tctcaaagaa   2520
ggagacgaga tgcggtacag gggtgttcgt ctataacgac gttgaagcct ggagggacag   2580
gtacaagtac catcctgact ccccccgtag attggcagca gcagtcaagc aagcctggga   2640
agatggtatc tgcgggatct cctctgtttc aagaatggaa aacatcatgt ggagatcagt   2700
agaaggggag ctcaacgcaa tcctggaaga gaatggagtt caactgacgg tcgttgtggg   2760
atctgtaaaa aaccccatgt ggagaggtcc acagagattg cccgtgcctg tgaacgagct   2820
gccccacggc tggaaggctt gggggaaatc gtatttcgtc agagcagcaa agacaaataa   2880
cagctttgtc gtggatggtg acacactgaa ggaatgccca ctcaaacata gagcatggaa   2940
cagctttctt gtggaggatc atgggttcgg ggtatttcac actagtgtct ggctcaaggt   3000
tagagaagat tattcattag agtgtgatcc agccgttatt ggaacagctg ttaagggaaa   3060
ggaggctgta cacagtgatc taggctactg gattgagagt gagaagaatg acacatggag   3120
gctgaagagg gcccatctga tcgagatgaa aacatgtgaa tggccaaagt cccacacatt   3180
```

-continued

```
gtggacagat ggaatagaag agagtgatct gatcataccc aagtctttag ctgggccact   3240
cagccatcac aataccagag agggctacag gacccaaatg aaagggccat ggcacagtga   3300
agagcttgaa attcggtttg aggaatgccc aggcactaag gtccacgtgg aggaaacatg   3360
tggaacaaga ggaccatctc tgagatcaac cactgcaagc ggaagggtga tcgaggaatg   3420
gtgctgcagg gagtgcacaa tgcccccact gtcgttccgg gctaaagatg gctgttggta   3480
tggaatggag ataaggccca ggaaagaacc agaaagcaac ttagtaaggt caatggtgac   3540
tgcaggatca actgatcaca tggaccactt ctcccttgga gtgcttgtga tcctgctcat   3600
ggtgcaggaa gggctgaaga agagaatgac cacaaagatc atcataagca catcaatggc   3660
agtgctggta gctatgatcc tgggaggatt ttcaatgagt gacctggcta agcttgcaat   3720
tttgatgggt gccaccttcg cggaaatgaa cactggagga gatgtagctc atctggcgct   3780
gatagcggca ttcaaagtca gaccagcgtt gctggtatct ttcatcttca gagctaattg   3840
gacaccccgt gaaagcatgc tgctggcctt ggcctcgtgt cttttgcaaa ctgcgatctc   3900
cgccttggaa ggcgacctga tggttctcat caatggtttt gctttggcct ggttggcaat   3960
acgagcgatg gttgttccac gcactgataa catcaccttg gcaatcctgg ctgctctgac   4020
accactggcc cggggcacac tgcttgtggc gtggagagca ggccttgcta cttgcggggg   4080
gtttatgctc ctctctctga agggaaaagg cagtgtgaag aagaacttac catttgtcat   4140
ggccctggga ctaaccgctg tgaggctggt cgaccccatc aacgtggtgg gactgctgtt   4200
gctcacaagg agtgggaagc ggagctggcc ccctagcgaa gtactcacag ctgttggcct   4260
gatatgcgca ttggctggag ggttcgccaa ggcagatata gagatggctg ggcccatggc   4320
cgcggtcggt ctgctaattg tcagttacgt ggtctcagga aagagtgtgg acatgtacat   4380
tgaaagagca ggtgacatca catgggaaaa agatgcggaa gtcactggaa acagtccccg   4440
gctcgatgtg gcgctagatg agagtggtga tttctccctg gtggaggatg acggtccccc   4500
catgagagag atcatactca aggtggtcct gatgaccatc tgtggcatga acccaatagc   4560
cataccettt gcagctggag cgtggtacgt atacgtgaag actggaaaaa ggagtggtgc   4620
tctatgggat gtgcctgctc ccaaggaagt aaaaaagggg gagaccacag atggagtgta   4680
cagagtaatg actcgtagac tgctaggttc aacacaagtt ggagtgggag ttatgcaaga   4740
gggggtcttt cacactatgt ggcacgtcac aaaaggatcc gcgctgagaa gcggtgaagg   4800
gagacttgat ccatactggg gagatgtcaa gcaggatctg gtgtcatact gtggtccatg   4860
gaagctagat gccgcctggg atgggcacag cgaggtgcag ctcttggccg tgccccccgg   4920
agagagagcg aggaacatcc agactctgcc cggaatattt aagacaaagg atggggacat   4980
tggagcggtt gcgctggatt acccagcagg aacttcagga tctccaatcc tagacaagtg   5040
tgggagagtg ataggacttt atggcaatgg ggtcgtgatc aaaaacggga gttatgttag   5100
tgccatcacc caagggagga gggaggaaga gactcctgtt gagtgcttcg agccctcgat   5160
gctgaagaag aagcagctaa ctgtcttaga cttgcatcct ggagctggga aaaccaggag   5220
agttcttcct gaaatagtcc gtgaagccat aaaaacaaga ctccgtactg tgatcttagc   5280
tccaaccagg gttgtcgctg ctgaaatgga ggaggccctt agagggcttc cagtgcgtta   5340
tatgacaaca gcagtcaatg tcacccactc tggaacagaa atcgtcgact taatgtgcca   5400
tgccaccttc acttcacgtc tactacagcc aatcagagtc cccaactata atctgtatat   5460
tatggatgag gcccacttca cagatccctc aagtatagca gcaagaggat acatttcaac   5520
aagggttgag atgggcgagg cggctgccat cttcatgacc gccacgccac caggaacccg   5580
```

tgacgcattt ccggactcca actcaccaat tatggacacc gaagtggaag tcccagagag 5640
agcctggagc tcaggctttg attgggtgac ggatcattct ggaaaaacag tttggtttgt 5700
tccaagcgtg aggaacggca atgagatcgc agcttgtctg acaaaggctg gaaaacgggt 5760
catacagctc agcagaaaga cttttgagac agagttccag aaaacaaaac atcaagagtg 5820
ggactttgtc gtgacaactg acatttcaga gatgggcgcc aactttaaag ctgaccgtgt 5880
catagattcc aggagatgcc taaagccggt catacttgat ggcgagagag tcattctggc 5940
tggacccatg cctgtcacac atgccagcgc tgcccagagg agggggcgca taggcaggaa 6000
tcccaacaaa cctggagatg agtatctgta tggaggtggg tgcgcagaga ctgacgaaga 6060
ccatgcacac tggcttgaag caagaatgct ccttgacaat atttacctcc aagatggcct 6120
catagcctcg ctctatcgac ctgaggccga caaagtagca gccattgagg gagagttcaa 6180
gcttaggacg gagcaaagga agacctttgt ggaactcatg aaaagaggag atcttcctgt 6240
ttggctggcc tatcaggttg catctgccgg aataacctac acagatagaa gatggtgctt 6300
tgatggcacg accaacaaca ccataatgga agacagtgtg ccggcagagg tgtggaccag 6360
acacggagag aaaagagtgc tcaaaccgag gtggatggac gccagagttt gttcagatca 6420
tgcggccctg aagtcattca aggagtttgc cgctgggaaa agaggagcgg cttttggagt 6480
gatggaagcc ctgggaacac tgccaggaca catgacagag agattccagg aagccattga 6540
caacctcgct gtgctcatgc gggcagagac tggaagcagg ccttacaaag ccgcggcggc 6600
ccaattgccg gagaccctag agaccataat gcttttgggg ttgctgggaa cagtctcgct 6660
gggaatcttc ttcgtcttga tgaggaacaa gggcataggg aagatgggct ttggaatggt 6720
gactcttggg gccagcgcat ggctcatgtg gctctcggaa attgagccag ccagaattgc 6780
atgtgtcctc attgttgtgt tcctattgct ggtggtgctc atacctgagc cagaaaagca 6840
aagatctccc caggacaacc aaatggcaat catcatcatg gtagcagtag gtcttctggg 6900
cttgattacc gccaatgaac tcggatggtt ggagagaaca aagagtgacc taagccatct 6960
aatgggaagg agagaggagg gggcaaccat aggattctca atggacattg acctgcggcc 7020
agcctcagct tgggccatct atgctgcctt gacaactttc attaccccag ccgtccaaca 7080
tgcagtgacc acctcataca acaactactc cttaatggcg atggccacgc aagctggagt 7140
gttgtttggc atgggcaaag ggatgccatt ctacgcatgg gactttggag tcccgctgct 7200
aatgataggt tgctactcac aattaacacc cctgacccta atagtggcca tcattttgct 7260
cgtggcgcac tacatgtact tgatcccagg gctgcaggca gcagctgcgc gtgctgccca 7320
gaagagaacg gcagctggca tcatgaagaa ccctgttgtg gatggaatag tggtgactga 7380
cattgacaca atgacaattg acccccaagt ggagaaaaag atgggacagg tgctactcat 7440
agcagtagcc gtctccagcg ccatactgtc gcggaccgcc tgggggtggg gggaggctgg 7500
ggctctgatc acagccgcaa cttccacttt gtgggaaggc tctccgaaca agtactggaa 7560
ctcctctaca gccacttcac tgtgtaacat ttttagggga agttacttgg ctggagcttc 7620
tctaatctac acagtaacaa gaaacgctgg cttggtcaag agacgtgggg gtggaacagg 7680
agagaccctg ggagagaaat ggaaggcccg cttgaaccag atgtcggccc tggagttcta 7740
ctcctacaaa aagtcaggca tcaccgaggt gtgcagagaa gaggcccgcc gcgccctcaa 7800
ggacggtgtg gcaacgggag gccatgctgt gtcccgagga agtgcaaagc tgagatggtt 7860
ggtggagcgg ggatacctgc agccctatgg aaaggtcatt gatcttggat gtggcagagg 7920

-continued

```
gggctggagt tactacgtcg ccaccatccg caaagttcaa gaagtgaaag gatacacaaa   7980
aggaggccct ggtcatgaag aacccgtgtt ggtgcaaagc tatgggtgga acatagtccg   8040
tcttaagagt ggggtggacg tctttcatat ggcggctgag ccgtgtgaca cgttgctgtg   8100
tgacataggt gagtcatcat ctagtcctga agtggaagaa gcacggacgc tcagagtcct   8160
ctccatggtg gggggattggc ttgaaaaaag accaggagcc ttttgtataa aagtgttgtg  8220
cccatacacc agcactatga tggaaaccct ggagcgactg cagcgtaggt atgggggagg   8280
actggtcaga gtgccactct cccgcaactc tacacatgag atgtactggg tctctggagc   8340
gaaaagcaac accataaaaa gtgtgtccac cacgagccag ctcctcttgg ggcgcatgga   8400
cgggcctagg aggccagtga aatatgagga ggatgtgaat ctcggctctg gcacgcgggc   8460
tgtggtaagc tgcgctgaag ctcccaacat gaagatcatt ggtaaccgca ttgaaaggat   8520
ccgcagtgag cacgcggaaa cgtggttctt tgacgagaac cacccatata ggacatgggc   8580
ttaccatgga agctatgagg cccccacaca agggtcagcg tcctctctaa taaacggggt   8640
tgtcaggctc ctgtcaaaac cctgggatgt ggtgactgga gtcacaggaa tagccatgac   8700
cgacaccaca ccgtatggtc agcaaagagt tttcaaggaa aaagtggaca ctagggtgcc   8760
agacccccaa gaaggcactc gtcaggttat gagcatggtc tcttcctggt tgtggaaaga   8820
gctaggcaaa cacaaacggc cacgagtctg caccaaagaa gagttcatca acaaggttcg   8880
tagcaatgca gcattagggg caatatttga agaggaaaaa gagtggaaga ctgcagtgga   8940
agctgtgaac gatccaaggt tctgggctct agtggacaag gaaagagagc accacctgag   9000
aggagagtgc cagagctgtg tgtacaacat gatgggaaaa agagaaaaga aacaagggga   9060
atttggaaag gccaagggca gccgcgccat ctggtatatg tggctagggg ctagatttct   9120
agagttcgaa gcccttggat tcttgaacga ggatcactgg atggggagag agaactcagg   9180
aggtggtgtt gaagggctgg gattacaaag actcggatat gtcctagaag agatgagtcg   9240
tataccagga ggaaggatgt atgcagatga cactgctggc tgggacaccc gcattagcag   9300
gtttgatctg gagaatgaag ctctaatcac caaccaaatg gagaaagggc acagggcctt   9360
ggcattggcc ataatcaagt acacatacca aaacaaagtg gtaaaggtcc ttagaccagc   9420
tgaaaaaggg aaaacagtta tggacattat ttcgagacaa gaccaaaggg ggagcggaca   9480
agttgtcact tacgctctta acacatttac caacctagtg gtgcaactca ttcggaatat   9540
ggaggctgag gaagttctag agatgcaaga cttgtggctg ctgcggaggt cagagaaagt   9600
gaccaactgg ttgcagagca acggatggga taggctcaaa cgaatggcag tcagtggaga   9660
tgattgcgtt gtgaagccaa ttgatgatag gtttgcacat gccctcaggt tcttgaatga   9720
tatgggaaaa gttaggaagg acacacaaga gtggaaaccc tcaactggat gggacaactg   9780
ggaagaagtt ccgttttgct cccaccactt caacaagctc catctcaagg acgggaggtc   9840
cattgtggtt ccctgccgcc accaagatga actgattggc cgggcccgcg tctctccagg   9900
ggcgggatgg agcatccggg agactgcttg cctagcaaaa tcatatgcgc aaatgtggca   9960
gctcctttat ttccacagaa gggacctccg actgatggcc aatgccattt gttcatctgt  10020
gccagttgac tgggttccaa ctgggagaac tacctggtca atccatggaa agggagaatg  10080
gatgaccact gaagacatgc ttgtggtgtg gaacagagtg tggattgagg agaacgacca  10140
catggaagac aagaccccag ttacgaaatg gacagacatt ccctatttgg gaaaaaggga  10200
agacttgtgg tgtggatctc tcatagggca cagaccgcgc accacctggg ctgagaacat  10260
taaaaacaca gtcaacatgg tgcgcaggat cataggtgat gaagaaaagt acatggacta  10320
```

cctatccacc caagttcgct acttgggtga agaagggtct acacctggag tgctgtaagc 10380
accaatctta atgttgtcag gcctgctagt cagccacagc ttggggaaag ctgtgcagcc 10440
tgtgaccccc ccaggagaag ctgggaaacc aagcctatag tcaggccgag aacgccatgg 10500
cacggaagaa gccatgctgc ctgtgagccc ctcagaggac actgagtcaa aaaaccccac 10560
gcgcttggag gcgcaggatg ggaaaagaag gtggcgacct tccccaccct tcaatctggg 10620
gcctgaactg gagatcagct gtggatctcc agaagaggga ctagtggtta gagga 10675

<210> SEQ ID NO 5
<211> LENGTH: 10676
<212> TYPE: DNA
<213> ORGANISM: Zika virus

<400> SEQUENCE: 5
gttgttactg ttgctgactc agactgcgac agttcgagtt tgaagcgaaa gctagcaaca 60
gtatcaacag gttttatttg gatttggaaa cgagagtttc tggtcatgaa aaacccaaaa 120
aagaaatccg gaggattccg gattgtcaat atgctaaaac gcggagtagc ccgtgtgagc 180
ccctttgggg gcttgaagag gctgccagcc ggacttctgc tgggtcatgg gcccatcagg 240
atggtcttgg caattctagc ctttttgaga ttcacggcaa tcaagccatc actgggtctc 300
atcaatagat ggggttcagt ggggaaaaaa gaggctatgg aaataataaa gaagttcaag 360
aaagatctgg ctgccatgct gagaataatc aatgctagga aggagaagaa gagacgaggc 420
gcagatacta gtgtcggaat tgttggcctc ctgctgacca cagctatggc agcggaggtc 480
actagacgtg ggagtgcata ctatatgtac ttggacagaa acgatgctgg ggaggccata 540
tcttttccaa ccacattggg gatgaataag tgttatatac agatcatgga tcttggacac 600
atgtgtgatg ccaccatgag ctatgaatgc cctatgctgg atgagggggt ggaaccagat 660
gacgtcgatt gttggtgcaa cacgacgtca acttgggttg tgtacggaac ctgccatcac 720
aaaaaaggtg aagcacggag atctagaaga gctgtgacgc tcccctccca ttccactagg 780
aagctgcaaa cgcggtcgca aacctggttg gaatcaagag aatacacaaa gcacttgatt 840
agagtcgaaa attggatatt caggaaccct ggcttcgcgt tagcagcagc tgccatcgct 900
tggcttttgg gaagctcaac gagccaaaaa gtcatatact tggtcatgat actgctgatt 960
gccccggcat acagcatcag gtgcatagga gtcagcaata gggactttgt ggaaggtatg 1020
tcaggtggga cttgggttga tgttgtcttg gaacatggag gttgtgtcac cgtaatggca 1080
caggacaaac cgactgtcga catagagctg gttacaacaa cagtcagcaa catggcggag 1140
gtaagatcct actgctatga ggcatcaata tcagacatgg cttcggacag ccgctgccca 1200
acacaaggtg aagcctacct tgacaagcaa tcagacactc aatatgtctg caaaagaacg 1260
ttagtggaca gaggctgggg aaatggatgt ggactttttg gcaaagggag tctggtgaca 1320
tgcgctaagt ttgcatgctc caagaaaatg accgggaaga gcatccagcc agagaatctg 1380
gagtaccgga taatgctgtc agttcatggc tcccagcaca gtgggatgat cgttaatgac 1440
acaggacatg aaactgatga gaatagagcg aaggttgaga taacgcccaa ttcaccaaga 1500
gccgaagcca ccctgggggg ttttggaagc ctaggacttg attgtgaacc gaggacaggc 1560
cttgactttt cagatttgta ttacttgact atgaataaca agcactggtt ggttcacaag 1620
gagtggttcc acgacattcc attaccttgg cacgctgggg cagacaccgg aactccacac 1680
tggaacaaca aagaagcact ggtagagttc aaggacgcac atgccaaaag gcaaactgtc 1740

-continued

```
gtggttctag ggagtcaaga aggagcagtt cacacggccc ttgctggagc tctggaggct   1800
gagatggatg gtgcaaaggg aaggctgtcc tctggccact tgaaatgtcg cctgaaaatg   1860
gataaactta gattgaaggg cgtgtcatac tccttgtgta ccgcagcgtt cacattcacc   1920
aagatcccgg ctgaaacact gcacgggaca gtcacagtgg aggtacagta cgcagggaca   1980
gatggacctt gcaaggttcc agctcagatg gcggtggaca tgcaaactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaattt ttggagcagc tttcaaatca   2340
ttgtttggag gaatgtcctg gttctcacaa attctcattg gaacgttgct gatgtggttg   2400
ggtctgaaca caaagaatgg atctatttcc cttatgtgct tggccttagg gggagtgttg   2460
atcttcttat ccacagccgt ctctgctgat gtggggtgct cggtggactt ctcaaagaag   2520
gagacgagat gcggtacagg ggtgttcgtc tataacgacg ttgaagcctg gagggacagg   2580
tacaagtacc atcctgactc cccccgtaga ttggcagcag cagtcaagca agcctgggaa   2640
gatggtatct gcgggatctc ctctgtttca agaatggaaa acatcatgtg gagatcagta   2700
gaaggggagc tcaacgcaat cctggaagag aatggagttc aactgacggt cgttgtggga   2760
tctgtaaaaa accccatgtg gagaggtcca cagagattgc ccgtgcctgt gaacgagctg   2820
ccccacggct ggaaggcttg gggggaaatcg cacttcgtca gagcagcaaa gacaaataac   2880
agctttgtcg tggatggtga cacactgaag gaatgcccac tcaaacatag agcatggaac   2940
agctttcttg tggaggatca tgggttcggg gtatttcaca ctagtgtctg gctcaaggtt   3000
agagaagatt attcattaga gtgtgatcca gccgttattg gaacagctgt taagggaaag   3060
gaggctgtac acagtgatct aggctactgg attgagagtg agaagaatga cacatggagg   3120
ctgaagaggg cccatctgat cgagatgaaa acatgtgaat ggccaaagtc ccacacattg   3180
tggacagatg gaatagaaga gagtgatctg atcataccca agtctttagc tgggccactc   3240
agccatcaca ataccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg gaagggtgat cgaggaatgg   3420
tgctgcaggg agtgcacaat gcccccactg tcgttccggg ctaaagatgg ctgttggtat   3480
ggaatggaga taaggcccag gaaagaacca gaaagcaact tagtaaggtc aatggtgact   3540
gcaggatcaa ctgatcacat ggatcacttc tcccttggag tgcttgtgat tctgctcatg   3600
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatgggtg ccaccttcgc ggaaatgaac actggaggag atgtagctca tctggcgctg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggttttg ctttggcctg gttggcaata   3960
cgagcgatgg ttgttccacg cactgataac atcaccttgg caatcctggc tgctctgaca   4020
ccactggccc ggggcacact gcttgtggcg tggagagcag gccttgctac ttgcgggggg   4080
tttatgctcc tctctctgaa gggaaaaggc agtgtgaaga agaacttacc atttgtcatg   4140
```

-continued

```
gccctgggac taaccgctgt gaggctggtc gaccccatca acgtggtggg gctgctgttg   4200
ctcacaagga gtgggaagcg gagctggccc cctagcgaag tactcacagc tgttggcctg   4260
atatgcgcat tggctggagg gttcgccaag gcagatatag agatggctgg gcccatggcc   4320
gcggtcggtc tgctaattgt cagttacgtg gtctcaggaa agagtgtgga catgtacatt   4380
gaaagagcag gtgacatcac atgggaaaaa gatgcggaag tcactggaaa cagtccccgg   4440
ctcgatgtgg cgctagatga gagtggtgat ttctccctgg tggaggatga cggtcccccc   4500
atgagagaga tcatactcaa ggtggtcctg atgaccatct gtggcatgaa cccaatagcc   4560
atacccttg cagctggagc gtggtacgta tacgtgaaga ctggaaaaag gagtggtgct   4620
ctatgggatg tgcctgctcc caaggaagta aaaaaggggg agaccacaga tggagtgtac   4680
agagtaatga ctcgtagact gctaggttca acacaagttg gagtgggagt tatgcaagag   4740
ggggtctttc acactatgtg gcacgtcaca aaaggatccg cgctgagaag cggtgaaggg   4800
agacttgatc catactgggg agatgtcaag caggatctgg tgtcatactg tggtccatgg   4860
aagctagatg ccgcctggga cgggcacagc gaggtgcagc tcttggccgt gccccccgga   4920
gagagagcga ggaacatcca gactctgccc ggaatattta agacaaagga tggggacatt   4980
ggagcggttg cgctggatta cccagcagga acttcaggat ctccaatcct agacaagtgt   5040
gggagagtga taggacttta tggcaatggg gtcgtgatca aaaatgggag ttatgttagt   5100
gccatcaccc aagggaggag ggaggaagag actcctgttg agtgcttcga gccttcgatg   5160
ctgaagaaga agcagctaac tgtcttagac ttgcatcctg gagctgggaa aaccaggaga   5220
gttcttcctg aaatagtccg tgaagccata aaaacaagac tccgtactgt gatcttagct   5280
ccaaccaggg ttgtcgctgc tgaaatggag gaagccctta gagggcttcc agtgcgttat   5340
atgacaacag cagtcaatgt cacccactct ggaacagaaa tcgtcgactt aatgtgccat   5400
gccaccttca cttcacgtct actacagcca atcagagtcc ccaactataa tctgtatatt   5460
atggatgagg cccacttcac agatccctca agtatagcag caagaggata catttcaaca   5520
agggttgaga tgggcgaggc ggctgccatc ttcatgaccg ccacgccacc aggaacccgt   5580
gacgcatttc cggactccaa ctcaccaatt atggacaccg aagtggaagt cccagagaga   5640
gcctggagct caggctttga ttgggtgacg gattattctg gaaaaacagt ttggtttgtt   5700
ccaagcgtga ggaacggcaa tgagatcgca gcttgtctga caaaggctgg aaaacgggtc   5760
atacagctca gcagaaagac ttttgagaca gagttccaga aacaaaaaca tcaagagtgg   5820
gactttgtcg tgacaactga catttcagag atgggcgcca actttaaagc tgaccgtgtc   5880
atagattcca ggagatgcct aaagccggtc atacttgatg gcgagagagt cattctggct   5940
ggacccatgc ctgtcacaca tgccagcgct gcccagagga gggggcgcat aggcaggaat   6000
cccaacaaac ctggagatga gtatctgtat ggaggtgggt gcgcagagac tgacgaagac   6060
catgcacact ggcttgaagc aagaatgctc cttgacaata tttacctcca agatggcctc   6120
atagcctcgc tctatcgacc tgaggccgac aaagtagcag ccattgaggg agagttcaag   6180
cttaggacgg agcaaaggaa gacctttgtg gaactcatga aaagaggaga tcttcctgtt   6240
tggctggcct atcaggttgc atctgccgga ataacctaca cagatagaag atggtgcttt   6300
gatggcacga ccaacaacac cataatggaa gacagtgtgc cggcagaggt gtggaccaga   6360
cacggagaga aaagagtgct caaaccgagg tggatggacg ccagagtttg ttcagatcat   6420
gcggccctga agtcattcaa ggagtttgcc gctgggaaaa gaggagcggc ttttggagtg   6480
```

-continued

```
atggaagccc tgggaacact gccaggacac atgacagaga gattccagga agccattgac   6540
aacctcgctg tgctcatgcg ggcagagact ggaagcaggc cttacaaagc cgcggcggcc   6600
caattgccgg agaccctaga gaccattatg cttttggggt tgctgggaac agtctcgctg   6660
ggaatctttt tcgtcttgat gaggaacaag ggcataggga agatgggctt tggaatggtg   6720
actcttgggg ccagcgcatg gctcatgtgg ctctcggaaa ttgagccagc cagaattgca   6780
tgtgtcctca ttgttgtgtt cctattgctg gtggtgctca tacctgagcc agaaaagcaa   6840
agatctcccc aggacaacca aatggcaatc atcatcatgg tagcagtagg tcttctgggc   6900
ttgattaccg ccaatgaact cggatggttg gagagaacaa agagtgacct aagccatcta   6960
atgggaagga gagaggaggg ggcaaccatg ggattctcaa tggacattga cctgcggcca   7020
gcctcagctt gggccatcta tgctgccttg acaactttca ttaccccagc cgtccaacat   7080
gcagtgacca cttcatacaa caactactcc ttaatggcga tggccacgca agctggagtg   7140
ttgtttggta tgggcaaagg gatgccattc tacgcatggg actttggagt cccgctgcta   7200
atgataggtt gctactcaca attaacgccc ctgaccctaa tagtggccat catttttgctc   7260
gtggcgcact acatgtactt gatcccaggg ctgcaggcag cagctgcgcg tgctgcccag   7320
aagagaacgg cagctggcat catgaagaac cctgttgtgg atggaatagt ggtgactgac   7380
attgacacaa tgacaattga cccccaagtg gagaaaaaga tgggacaggt gctactcatg   7440
gcagtagccg tctccagcgc catactgtcg cggaccgcct gggggtgggg ggaggctggg   7500
gccctgatca cagccgcaac ttccactttg tgggaaggct ctccgaacaa gtactggaac   7560
tcctctacag ccacttcact gtgtaacatt tttaggggaa gttacttggc tggagcttct   7620
ctaatctaca cagtaacaag aaacgctggc ttggtcaaga gacgtggggg tggaacagga   7680
gagaccctgg gagagaaatg gaaggcccgc ttgaaccaga tgtcggccct ggagttctac   7740
tcctacaaaa agtcaggcat caccgaggtg tgcagagaag aggcccgccg cgccctcaag   7800
gacggtgtgg caacgggagg ccatgctgtg tcccgaggaa gtgcaaagct gagatggttg   7860
gtggagcggg gatacctgca gccctatgga aaggtcattg atcttggatg tggcagaggg   7920
ggctggagtt actacgccgc caccatccgc aaagttcaag aagtgaaagg atacacaaaa   7980
ggaggccctg gtcatgaaga acccgtgttg gtgcaaagct atgggtggaa catagtccgt   8040
cttaagagtg ggggtggacgt ctttcatatg gcggctgagc cgtgtgacac gttgctgtgt   8100
gacataggtg agtcatcatc tagtcctgaa gtggaagaag cacggacgct cagagtcctc   8160
tccatggtgg gggattggct tgaaaaaaga ccaggagcct tttgtataaa agtgttgtgc   8220
ccatacacca gcactatgat ggaaaccctg gagcgactgc agcgtaggta tgggggagga   8280
ctggtcagag tgccactctc ccgcaactct acacatgaga tgtactgggt ctctggagcg   8340
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcagtgagc acgcggaaac gtggttcttt gacgagaacc acccatatag gacatgggct   8580
taccatggaa gctatgaggc cccccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aaggcactcg tcaggttatg agcatggtct cttcctggtt gtggaaagag   8820
ctaggcaaac acaaacggcc acgagtctgt accaaagaag agttcatcaa caaggttcgt   8880
```

```
agcaatgcag cattaggggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacaacatg atgggaaaaa gagaaaagaa acaaggggaa   9060
tttggaaagg ccaagggcag ccgcgccatc tggtatatgt ggctaggggc tagatttcta   9120
gagttcgaag cccttggatt cttgaacgag gatcactgga tggggagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
tttgatctgg agaatgaagc tctaatcacc aaccaaatgg agaaagggca cagggccttg   9360
gcattggcca taatcaagta cacataccaa aacaaagtgg taaaggtcct tagaccagct   9420
gaaaaaggga agacagttat ggacattatt tcgagacaag accaaagggg gagcggacaa   9480
gttgtcactt acgctcttaa cacatttacc aacctagtgg tgcaactcat tcggaatatg   9540
gaggctgagg aagttctaga gatgcaagac ttgtggctgc tgcggaggtc agagaaagtg   9600
accaactggt tgcagagcaa cggatgggat aggctcaaac gaatggcagt cagtggagat   9660
gattgcgttg tgaagccaat tgatgatagg tttgcacatg ccctcaggtt cttgaatgat   9720
atgggaaaag ttaggaagga cacacaagag tggaaaccct caactggatg ggacaactgg   9780
gaagaagttc cgttttgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc ctagcaaaat catatgcgca aatgtggcag   9960
ctcctttatt tccacagaag ggacctccga ctgatggcca atgccatttg ttcatctgtg  10020
ccagttgact gggttccaac tgggagaact acctggtcaa tccatggaaa gggagaatgg  10080
atgaccactg aagacatgct tgtggtgtgg aacagagtgt ggattgagga gaacgaccac  10140
atggaagaca agaccccagt tacgaaatgg acagacattc cctatttggg aaaaagggaa  10200
gacttgtggt gtggatctct catagggcac agaccgcgca ccacctgggc tgagaacatt  10260
aaaaacacag tcaacatggt gcgcaggatc ataggtgatg aagaaaagta catggactac  10320
ctatccaccc aagttcgcta cttgggtgaa gaagggtcta cacctggagt gctgtaagca  10380
ccaatcttaa tgttgtcagg cctgctagtc agccacagct tggggaaagc tgtgcagcct  10440
gtgacccccc caggagaagc tgggaaacca agcctatagt caggccgaga acgccatggc  10500
acggaagaag ccatgctgcc tgtgagcccc tcagaggaca ctgagtcaaa aaaccccacg  10560
cgcttggagg cgcaggatgg gaaaagaagg tggcgacctt ccccaccctt caatctgggg  10620
cctgaactgg agatcagctg tggatctcca gaagagggac tagtggttag aggaga      10676
```

<210> SEQ ID NO 6
<211> LENGTH: 10808
<212> TYPE: DNA
<213> ORGANISM: Zika virus

<400> SEQUENCE: 6

```
agttgttgat ctgtgtgaat cagactgcga cagttcgagt ttgaagcgaa agctagcaac     60
agtatcaaca ggttttattt tggatttgga aacgagagtt tctggtcatg aaaaacccaa    120
aaaagaaatc cggaggattc cggattgtca atatgctaaa acgcggagta gcccgtgtga    180
gcccctttgg gggcttgaag aggctgccag ccggacttct gctgggtcat gggcccatca    240
ggatggtctt ggcaattcta gcctttttga gattcacggc aatcaagcca tcactgggtc    300
```

-continued

```
tcatcaatag atggggttca gtggggaaaa aagaggctat ggaaataata aagaagttca    360
agaaagatct ggctgccatg ctgagaataa tcaatgctag gaaggagaag aagagacgag    420
gcgcagatac tagtgtcgga attgttggcc tcctgctgac cacagctatg gcagcggagg    480
tcactagacg tgggagtgca tactatatgt acttggacag aaacgatgct ggggaggcca    540
tatcttttcc aaccacattg ggatgaata agtgttatat acagatcatg gatcttggac     600
acatgtgtga tgccaccatg agctatgaat gccctatgct ggatgagggg gtggaaccag    660
atgacgtcga ttgttggtgc aacacgacgt caacttgggt tgtgtacgga acctgccatc    720
acaaaaaagg tgaagcacgg agatctagaa gagctgtgac gctcccctcc cattccacta    780
ggaagctgca aacgcggtcg caaacctggt tggaatcaag agaatacaca aagcacttga    840
ttagagtcga aaattggata ttcaggaacc ctggcttcgc gttagcagca gctgccatcg    900
cttggctttt gggaagctca acgagccaaa aagtcatata cttggtcatg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtc accgtaatgg   1080
cacaggacaa accgactgtc gacatagagc tggttacaac aacagtcagc aacatggcgg   1140
aggtaagatc ctactgctat gaggcatcaa tatcagacat ggcttcggac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc caccctgggg ggttttggaa gcctaggact tgattgtgaa ccgaggacag   1560
gccttgactt ttcagatttg tattacttga ctatgaataa caagcactgg ttggtccaca   1620
aggagtggtt ccacgacatt ccattacctt ggcacgctgg ggcagacacc ggaactccac   1680
actggaacaa caaagaagca ctggtagagt tcaaggacgc acatgccaaa aggcaaactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggataaact tagattgaag ggcgtgtcat actccttgtg taccgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccccgtaa tcactgaaag cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
gaggcgctct caactcattg ggcaagggca tccatcaaat ttttggagca gctttcaaat   2340
cattgtttgg aggaatgtcc tggttctcac aaatcctcat tggaacgttg ctgatgtggt   2400
tgggtctgaa cacaaagaat ggatctattt cccttatgtg cttggcctta gggggagtgt   2460
tgatcttctt atccacagcc gtctctgctg atgtggggtg ctcggtggac ttctcaaaga   2520
aggagacgag atgcggtaca ggggtgttcg tctataacga cgttgaagcc tggagggaca   2580
ggtacaagta ccatcctgac tccccccgta gattggcagc agcagtcaag caagcctggg   2640
aagatggtat ctgcgggatc tcctctgttt caagaatgga gaacatcatg tggagatcag   2700
```

tagaaggga gctcaacgca atcttggaag agaatggagt tcaactgacg gtcgttgtgg 2760
gatctgtaaa aaaccccatg tggagaggtc cacagagatt gcccgtgcct gtgaacgagc 2820
tgccccacgg ctggaaggct tgggggaaat cgtacttcgt cagagcagca aagacaaata 2880
acagctttgt cgtggatggt gacacactga aggaatgccc actcgaacat agagcatgga 2940
acagctttct tgtggaggat catgggttcg gggtatttca cactagtgtc tggctcaagg 3000
ttagagaaga ttattcatta gagtgtgatc cagccgttat tggaacagct gttaagggga 3060
aggaggctgt acacagtgat ctaggctact ggattgagag tgagaagaat gacacatgga 3120
ggctgaagag ggcccatcta atcgagatga aaacatgtga atggccaaag tcccacacat 3180
tgtgggcaga tggaatagaa gagagtgatc tgatcattcc caagtcttta gctgggccac 3240
tcagccatca caataccaga gagggctaca ggacccaaat gaaagggcca tggcacagtg 3300
aagagcttga aattcggttt gaggaatgcc cgggcactaa ggtccacgtg gaggaaacat 3360
gtggaacaag aggaccatct ctgagatcaa ccactgcaag cggaagggtg atcgaggaat 3420
ggtgctgcag ggagtgcaca atgcccccac tgtcgttccg ggctaaagat ggctgttggt 3480
atggaatgga gataaggccc aggaaagaac cagaaagcaa cttagtaagg tcagtggtga 3540
ctgcaggatc aactgatcac atggatcact tctcccttgg agtgcttgtg attctgctca 3600
tggtgcagga agggctgaag aagagaatga ccacaaagat catcataagc acatcaatgg 3660
cagtgctggt agctatgatc ctgggaggat tttcaatgag tgacctggct aagcttgcaa 3720
ttttgatggg cgccaccttc gcggaaatga acactggagg agatgtagct catctggcgc 3780
tgatagcggc attcaaagtc agaccagcgt tgctggtatc tttcatcttc agagctaatt 3840
ggacaccccg tgaaagcatg ctgctggcct tggcctcgtg tcttttgcaa actgcgatct 3900
ccgccttgga aggcgacctg atggttctca tcaatggttt tgctttggcc tggttggcaa 3960
tacgagcgat ggttgttcca cgcactgata acatcacctt ggcaatcctg gctgctctga 4020
caccactggc ccggggcaca ctgcttgtgg cgtggagagc aggccttgct acttgcgggg 4080
ggtttatgct cctctctctg aagggaaaag gcagtgtgaa gaagaactta ccatttgtca 4140
tggccctggg actaaccgct gtgaggctgg tcgaccccat caacgtggtg ggactgctgt 4200
tgctcacaag gagtgggaag cggagctggc cccctagcga agtactcaca gctgttggcc 4260
tgatatgcgc attggctgga gggttcgcca aggcagatat agagatggct gggcccatgg 4320
ccgcggtcgg tctgctaatt gtcagttacg tggtctcagg aaagagtgtg gacatgtaca 4380
ttgaaagagc aggtgacatc acatgggaaa aagatgcgga agtcactgga aacagtcccc 4440
ggctcgatgt ggcgctagat gagagtggtg atttctccct ggtggaggat gacggtcccc 4500
ccatgagaga gatcatactc aaggtggtcc tgatgaccat ctgtggcatg aacccaatag 4560
ccataccctt tgcagctgga gcgtggtacg tatacgtgaa gactggaaaa aggagtggtg 4620
ctctatggga tgtgcctgct cccaaggaag taaaaaaggg ggagaccaca gatggagtgt 4680
acagagtaat gactcgtaga ctgctaggtt caacacaagt tggagtggga gttatgcaag 4740
agggggtctt tcacactatg tggcacgtca caaaaggatc cgcgctgaga agcggtgaag 4800
ggagacttga tccatactgg ggagatgtca agcaggatct ggtgtcatac tgtggtccat 4860
ggaagctaga tgccgcctgg gacgggcaca gcgaggtgca gctcttggcc gtgccccccg 4920
gagagagagc gaggaacatc cagactctgc ccggaatatt taagacaaag gatggggaca 4980
ttggagcggt tgcgctggat tacccagcag gaacttcagg atctccaatc ctagacaagt 5040

-continued gtgggagagt gataggactt tatggcaatg gggtcgtgat caaaaatggg agttatgtta 5100
gtgccatcac ccaagggagg agggaggaag agactcctgt tgagtgcttc gagccttcga 5160
tgctgaagaa gaagcagcta actgtcttag acttgcatcc tggagctggg aaaaccagga 5220
gagttcttcc tgaaatagtc cgtgaagcca taaaaacaag actccgtact gtgatcttag 5280
ctccaaccag ggttgtcgct gctgaaatgg aggaagccct tagagggctt ccagtgcgtt 5340
atatgacaac agcagtcaat gtcacccact ctggaacaga aatcgtcgac ttaatgtgcc 5400
atgccacctt cacttcacgt ctactacagc caatcagagt ccccaactat aatctgtata 5460
ttatggatga ggcccacttc acagatccct caagtatagc agcaagagga tacatttcaa 5520
caagggttga gatgggcgag gcggctgcca tcttcatgac cgccacgcca ccaggaaccc 5580
gtgacgcatt tccggactcc aactcaccaa ttatggacac cgaagtggaa gtcccagaga 5640
gagcctggag ctcaggcttt gattgggtga cggatcattc tggaaaaaca gtttggtttg 5700
ttccaagcgt gaggaacggc aatgagatcg cagcttgtct gacaaaggct ggaaaacggg 5760
tcatacagct cagcagaaag acttttgaga cagagttcca gaaaacaaaa catcaagagt 5820
gggactttgt cgtgacaact gacatttcag agatgggcgc caactttaaa gctgaccgtg 5880
tcatagattc caggagatgc ctaaagccgg tcatacttga tggcgagaga gtcattttgg 5940
ctggacccat gcctgtcaca catgccagcg ctgcccagag gagggggcgc ataggcagga 6000
atcccaacaa acctggagat gagtatctgt atggaggtgg gtgcgcagag actgacgaag 6060
accatgcaca ctggcttgaa gcaagaatgc tccttgacaa tatttacctc caagatggcc 6120
tcatagcctc gctctatcga cctgaggccg acaaagtagc agccattgag ggagagttca 6180
agcttaggac ggagcaaagg aagacctttg tggaactcat gaaaagagga gatcttcctg 6240
tttggctggc ctatcaggtt gcatctgccg gaataaccta cacagataga agatggtgct 6300
ttgatggcac gaccaacaac accataatgg aagacagtgt gccggcagag gtgtggacca 6360
gacacggaga gaaaagagtg ctcaaaccga ggtggatgga cgccagagtt tgttcagatc 6420
atgcggccct gaagtcattc aaggagtttg ccgctgggaa aagaggagcg gcttttggag 6480
tgatggaagc cctgggaaca ctgccaggac acatgacaga gagattccag gaagccattg 6540
acaacctcgc tgtgctcatg cgggcagaga ctggaagcag gccttacaaa gccgcggcgg 6600
cccaattgcc ggagacccta gagaccatta tgcttttggg gttgctggga acagtctcgc 6660
tgggaatctt tttcgtcttg atgaggaaca agggcatagg gaagatgggc tttggaatgg 6720
tgactcttgg ggccagcgca tggctcatgt ggctctcgga aattgagcca gccagaattg 6780
catgtgtcct cattgttgtg ttcctattgc tggtggtgct catacctgag ccagaaaagc 6840
aaagatctcc ccaggacaac caaatggcaa tcatcatcat ggtagcagta ggtcttctgg 6900
gcttgattac cgccaatgaa ctcggatggt tggagagaac aaagagtgac ctaagccatc 6960
taatgggaag gagagaggag ggagcaacca taggattctc aatggacatt gacctgcggc 7020
cagcctcagc ttgggccatc tatgctgcct tgacaacttt cattacccca gccgtccaac 7080
atgcagtgac cacttcatac aacaactact ccttaatggc gatggccacg caagctggag 7140
tgttgtttgg tatgggcaaa gggatgccat tctacgcatg ggactttgga gtcccgctgc 7200
taatgatagg ttgctactca caattaacac ccctgaccct aatagtggcc atcattttgc 7260
tcgtggcgca ctacatgtac ttgatcccag ggctgcaggc agcagctgcg cgtgctgccc 7320
agaagagaac ggcagctggc atcatgaaga accctgttgt ggatggaata gtggtgactg 7380
acattgacac aatgacaatt gacccccaag tggagaaaaa gatgggacag gtgctactca 7440

-continued tagcagtagc agtctccagc gccatactgt cgcggaccgc ctgggggtgg ggggaggctg 7500
gggccctgat cacagccgca acttccactt tgtgggaagg ctctccgaac aagtactgga 7560
actcctctac agccacttca ctgtgtaaca tttttagggg aagttacttg gctggagctt 7620
ctctaatcta catagtaaca agaaacgctg gcttggtcaa gagacgtggg ggtggaacag 7680
gagagaccct gggagagaaa tggaaggccc gcttgaacca gatgtcggcc ctggagttct 7740
actcctacaa aaagtcaggc atcaccgagg tgtgcagaga agaggcccgc cgcgccctca 7800
aggatggtgt ggcaacggga ggccatgctg tgtcccgagg aagtgcaaag ctgagatggt 7860
tggtggagcg gggatacctg cagccctatg gaaaggtcat tgatcttgga tgtggcagag 7920
ggggctggag ttactacgcc gccaccatcc gcaaagttca agaagtgaaa ggatacacaa 7980
aaggaggccc tggtcatgaa gaacccgtgt tggtgcaaag ctatgggtgg aacatagtcc 8040
gtcttaagag tggggtggac gtctttcata tggcggctga gccgtgtgac acgttgctgt 8100
gtgacatagg tgagtcatca tctagtcctg aagtggaaga agcacggacg ctcagagtcc 8160
tctccatggt gggggattgg cttgaaaaaa gaccaggagc cttttgtata aaagtgttgt 8220
gcccatacac cagcactatg atggaaaccc tggagcgact gcagcgtagg tatgggggag 8280
gactggtcag agtgccactc tcccgcaact ctacacatga gatgtactgg gtctctggag 8340
cgaaaagcaa caccataaaa agtgtgtcca ccacgagcca gctcctcttg ggcgcatgg 8400 acgggcctag gaggccagtg aaatatgagg aggatgtgaa tctcggctct ggcacgcggg 8460
ctgtggtaag ctgcgctgaa gctcccaaca tgaagatcat tggtaaccgc attgaaagga 8520
tccgcagtga gcacgcggaa acgtggttct ttgacgagaa ccacccatat aggacatggg 8580
cttaccatgg aagctatgag gcccccacac aagggtcagc gtcctctcta ataaacgggg 8640
ttgtcaggct cctgtcaaaa ccctgggatg tggtgactgg agtcacagga atagccatga 8700
ccgacaccac accgtatggt cagcaaagag ttttcaagga aaaagtggac actagggtgc 8760
cagaccccca agaaggcact cgtcaggtta tgagcatggt ctcttcctgg ttgtggaaag 8820
agctaggcaa acacaaacgg ccacgagtct gtaccaaaga agagttcatc aacaaggttc 8880
gtagcaatgc agcattaggg gcaatatttg aagaggaaaa agagtggaag actgcagtgg 8940
aagctgtgaa cgatccaagg ttctgggctc tagtggacaa ggaaagagag caccacctga 9000
gaggagagtg ccagagttgt gtgtacaaca tgatgggaaa aagagaaaag aaacaagggg 9060
aatttggaaa ggccaagggc agccgcgcca tctggtatat gtggctaggg gctagatttc 9120
tagagttcga agcccttgga ttcttgaacg aggatcactg gatggggaga gagaactcag 9180
gaggtggtgt tgaagggctg ggattacaaa gactcggata tgtcctagaa gagatgagtc 9240
gcataccagg aggaaggatg tatgcagatg acactgctgg ctgggacacc cgcatcagca 9300
ggttcgatct ggagaatgaa gctctaatca ccaaccaaat ggagaaaggg catagggcct 9360
tggcattggc cataatcaag tacacatacc aaaacaaagt ggtaaaggtc cttagaccag 9420
ctgaaaaagg gaaaacagtt atggacatta tttcgagaca agaccaaagg gggagcggac 9480
aagttgtcac ttacgctctt aacacattta ccaacctagt ggtgcaactc attcggaata 9540
tggaggctga ggaagttcta gagatgcaag acttgtggct gctgcggagg tcagagaaag 9600
tgaccaactg gttgcagagc aacggatggg ataggctcaa acgaatggca gtcagtggag 9660
atgattgcgt tgtgaagcca attgatgata ggtttgcaca tgccctcagg ttcttgaatg 9720
atatgggaaa agttaggaag gacacacaag agtggaaacc ctcaactgga tgggacaact 9780

```
gggaagaagt tccgttttgc tcccaccact tcaacaagct ccatctcaag gacgggaggt   9840

ccattgtggt tccctgccgc caccaagatg aactgattgg ccgggcccgc gtctctccag   9900

gggcgggatg gagcatccgg gagactgctt gcctagcaaa atcatatgcg caaatgtggc   9960

agctccttta tttccacaga agggacctcc gactgatggc caatgccatt tgttcatctg  10020

tgccagttga ctgggttcca actgggagaa ctacctggtc aatccatgga aagggagaat  10080

ggatgaccac tgaagacatg cttgtggtgt ggaacagagt gtggattgag gagaacgacc  10140

acatggaaga caagacccca gttacgaaat ggacagacat tccctatttg ggaaaaaggg  10200

aagacttgtg gtgtggatct ctcatagggc acagaccgcg caccacctgg gctgagaaca  10260

ttaaaaacac agtcaacatg gtgcgcagga tcataggtga tgaagaaaag tacatggact  10320

acctatccac ccaagttcgc tacttgggtg aagaagggtc tacacctgga gtgctgtaag  10380

caccaatctt aatgttgtca ggcctgctag tcagccacag cttggggaaa gctgtgcagc  10440

ctgtgacccc cccaggagaa gctgggaaac caagcctata gtcaggccga gaacgccatg  10500

gcacggaaga agccatgctg cctgtgagcc cctcagagga cactgagtca aaaaacccca  10560

tgcgcttgga ggcgcaggat gggaaaagaa ggtggcgacc ttccccaccc ttcaatctgg  10620

ggcctgaact ggagatcagc tgtggatctc cagaagaggg actagtggtt agaggagacc  10680

ccccggaaaa cgcaaaacag catattgacg ctgggaaaga ccagagactc catgagtttc  10740

caccacgctg gccgccaggc acagatcgcc gaatagcggc ggccggtgtg gggaaatcca  10800

tgggtctt                                                           10808
```

<210> SEQ ID NO 7
<211> LENGTH: 10807
<212> TYPE: DNA
<213> ORGANISM: Zika virus

<400> SEQUENCE: 7

```
agttgttgat ctgtgtgaat cagactgcga cagttcgagt ttgaagcgaa agctagcaac     60

agtatcaaca ggttttattt tggatttgga aacgagagtt tctggtcatg aaaaacccaa    120

aaaagaaatc cggaggattc cggattgtca atatgctaaa acgcggagta gcccgtgtga    180

gcccctttgg gggcttgaag aggctgccag ccggacttct gctgggtcat gggcccatca    240

ggatggtctt ggcgattcta gcctttttga gattcacggc aatcaagcca tcactgggtc    300

tcatcaatag atggggttca gtgggaaaaa aagaggctat ggaaataata aagaagttca    360

agaaagatct ggctgccatg ctgagaataa tcaatgctag gaaggagaag aagagacgag    420

gcacagatac tagtgtcgga attgttggcc tcctgctgac cacagctatg gcagcggagg    480

tcactagacg tgggagtgca tactatatgt acttggacag aagcgatgct ggggaggcca    540

tatcttttcc aaccacactg gggatgaata agtgttatat acagatcatg gatcttggac    600

acatgtgtga tgccaccatg agctatgaat gccctatgct ggatgagggg gtagaaccag    660

atgacgtcga ttgttggtgc aacacgacgt caacttgggt tgtgtacgga acctgccatc    720

acaaaaaagg tgaagcacgg agatccagaa gagctgtgac gctcccctcc cattccacta    780

ggaagctgca aacgcggtcg cagacctggt tggaatcaag agaatacaca aagcacttga    840

ttagagtcga aaattggata ttcaggaacc ctggcttcgc gttagcagca gctgccatcg    900

cttggctttt gggaagctca acgagccaaa aagtcatata cttggtcatg atactgctga    960

ttgccccggc atacagcatc aggtgcatag gagtcagtaa tagggacttt gtggaaggta   1020

tgtcaggtgg gacttgggtt gatgttgtct tggaacatgg aggttgtgtc accgtaatgg   1080
```

-continued cacaggacaa accgactgtc gacatagagc tggttacaac aacagtcagc aacatggcgg 1140
aggtaagatc ctactgctat gaggcatcaa tatcggacat ggcttcggac agccgctgcc 1200
caacacaagg tgaagcctac cttgacaagc aatcagacac tcaatatgtc tgcaaaagaa 1260
cgttagtgga cagaggctgg ggaaatggat gtggactttt tggcaaaggg agcctggtga 1320
catgcgctaa gtttgcatgc tccaagaaaa tgaccgggaa gagcatccag ccagagaatc 1380
tggagtaccg gataatgctg tcagttcatg gctcccagca cagtgggatg atcgttaatg 1440
acacaggaca tgaaactgat gagaatagag cgaaggttga gataacgccc aattcaccaa 1500
gagccgaagc caccctgggg ggttttggaa gcctaggact tgattgtgaa ccgaggacag 1560
gccttgactt ttcagatttg tattacttga ctatgaacaa caagcactgg ttggttcaca 1620
aggagtggtt ccacgacatt ccattacctt ggcacactgg ggcagacacc ggaactccac 1680
actggaacaa caaagaagca ctggtagagt tcaaggacgc acatgccaaa aggcaaactg 1740
tcgtggttct agggagtcaa gaaggagcag ttcacacggc ccttgctgga gctctggagg 1800
ctgagatgga tggtgcaaag ggaaggctgt cctctggcca cttgaaatgt cgcctgaaaa 1860
tggataaact tagattgaag ggcgtgtcat actccttgtg taccgcagcg ttcacattca 1920
ccaagatccc ggctgaaaca ctgcacggga cagtcacagt ggaggtacag tacgcaggga 1980
cagatggacc ttgcaaggtt ccagctcaga tggcggtgga catgcaaact ctgaccccag 2040
ttgggaggtt gataaccgct aaccccgtaa tcactgaagg cactgagaac tctaagatga 2100
tgctggaact tgatccacca tttggggact cttacattgt cataggagtc ggggagaaga 2160
agatcaccca ccactggcac aggagtggca gcaccattgg aaaagcattt gaagccactg 2220
tgagaggtgc caagagaatg gcagtcttgg gagacacagc ctgggacttt ggatcagttg 2280
gaggcgttct taactcattg ggcaagggca tccatcaaat ttttggagca gctttcaaat 2340
cattgtttgg aggaatgtcc tggttctcac aaattctcat tggaacgttg ctgatgtggt 2400
tgggtctgaa tacaaagaat ggatctattt cccttatgtg cttggcctta gggggagtgt 2460
tgatcttctt atccacagcc gtctccgctg atgtggggtg ctcggtggac ttctcaaaga 2520
aggaaacgag atgcggtaca ggggtgttcg tctataacga cgttgaagcc tggagggaca 2580
ggtacaagta ccatcctgac tcccctcgta gattggcagc agtagtcaag caagcctggg 2640
aagatggtat ctgtgggatc tcctctgttt caagaatgga aaacatcatg tggagatcag 2700
tagaagggga gctcaacgca atcctggaag agaatggagt tcaactgacg gtcgttgtgg 2760
gatctgtaaa aaaccccatg tggagaggtc cacagagatt gcccgtgcct gtgaacgagc 2820
tgccccacgg ctggaaggct tgggggaaat cgtacttcgt cagagcagca aagacaaata 2880
acagctttgt cgtggatggt gacacactga aggaatgccc actcaaacat agagcatgga 2940
acagctttct tgtggaggat catgggttcg ggtatttca cactagtgtc tggctcaagg 3000
ttagagaaga ttattcacta gagtgtgatc cagccgtcat tggaacagct gttaagggaa 3060
aggaggctgt acacagtgat ctaggctact ggattgagag tgagaagaac gacacatgga 3120
ggctgaggag ggcccacctg atcgagatga aaacatgtga atggccaaag tcccacacat 3180
tgtggacaga tggaatagaa gagagtgatc tgatcatacc caagtcttta gctgggccac 3240
tcagccatca caacaccaga gagggctaca ggacccaaat gaaagggcca tggcacagtg 3300
aagagcttga aattcggttt gaggaatgcc caggcactaa ggtccacgtg gaggaaacat 3360
gtggaacaag aggaccatct ctgagatcaa ccactgcaag cggaagggtg atcgaggaat 3420

-continued

```
ggtgctgcag ggagtgcaca atgcccccac tgtcgttccg ggctaaagat ggctgttggt   3480
atggaatgga gataaggccc aggaaagaac cagaaagtaa cttagtaagg tcaatggtga   3540
ctgcaggatc aactgatcac atggatcact tttcccttgg agtgcttgtg attctgctca   3600
tggtgcagga agggctgaag aagagaatga ccacaaagat catcataagc acatcaatgg   3660
cagtgctggt agctatgatc ctgggaggat tttcaatgag tgatctggct aagcttgcaa   3720
ttttgatggg tgccaccttt gcggaaatga acactggagg agatgtagct catctggcgc   3780
tggtagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgaca atatcacctt ggcaatcctg gctgctctga   4020
caccactggc ccggggcaca ctgcttgtgg cgtggagagc aggccttgct acttgcgggg   4080
ggttcatgct cctctctctg aaggggaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agagatggct gggcccatgg   4320
ccgcggtcgg tctgctaatt gtcagttacg tggtctcagg aaagagtgtg gacatgtaca   4380
ttgaaagagc aggtgacatc acatgggaaa aagatgcgga agttactgga aacagtcccc   4440
ggctcgatgt ggcactagat gagagtggtg atttctccct ggtggaggat gacggtcccc   4500
ccatgagaga gatcatactc aaagtggtcc tgatgaccat ctgtggcatg aacccaatag   4560
ccatacccttt tgcagctgga gcgtggtacg tatacgtgaa aactggaaaa aggagtggtg   4620
ctctatggga tgtgcctgct cccaaggaag taaaaaaggg ggagaccaca gatggagtgt   4680
acagagtaat gactcgtaga ctgctaggtt caacacaagt tggagtggga gttatgcaag   4740
agggggtctt tcacactatg tggcatgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggac tatccagcag gaacttcagg atctccaatc ctagacaagt   5040
gtgggagagt gataggactc tatggcaatg gggtcgtgat caagaatggg agttatgtca   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaaacgag actccgtact gtgatcttag   5280
ctccaaccag ggttgtcgct gctgaaatgg aggaagccct tagagggctt ccagtgcgtt   5340
atatgacaac agcagtcaat gtcacccatt ctgggacaga aatcgttgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcagctgcca tcttcatgac cgccacgcca ccaggaaccc   5580
gtgacgcatt cccggactcc aactcaccaa ttatggacac cgaagtggaa gtcccagaga   5640
gagcctggag ctcaggcttt gattgggtga cggatcattc tggaaaaaca gtttggtttg   5700
tcccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
```

gggacttcgt cgtgacaact gacatttcag agatgggcgc caactttaaa gctgaccgtg 5880
tcatagattc caggagatgc ctaaagccgg tcatacttga tggcgagaga gtcattctgg 5940
ctggacccat gcctgtcaca catgccagcg ctgcccagag gagggggcgc ataggcagga 6000
atcccaacaa acctggagat gagtatctgt atggaggtgg gtgcgcagag actgatgaag 6060
accatgcaca ctggcttgaa gcaagaatgc tccttgacaa tatttacctc caagatggcc 6120
tcatagcctc gctctatcga cctgaggccg acaaagtagc agccattgag ggagagttca 6180
agcttaggac ggagcaaagg aagacctttg tggaactcat gaaaagagga gatcttcctg 6240
tttggctggc ctatcaggtt gcatctgccg gaataaccta cacagataga agatggtgct 6300
ttgatggcat gaccaacaac accataatgg aagacagtgt gccggcagag gtgtggacca 6360
gacacggaga gaaaagagtg ctcaaaccga ggtggatgga cgccagagtt tgttcagatc 6420
atgcggccct gaagtcattc aaggagtttg ccgctgggaa aagaggagcg gcttttggag 6480
tgatggaagc cctgggaaca ctgccaggac acatgacgga gagattccag gaagccattg 6540
acaacctcgc tgtgctcatg cgggcagaga ctggaagcag gccttacaaa gccgcggcgg 6600
cccaattgcc ggagaccct a gagaccatta tgcttttggg gttgctggga acagtctcgc 6660
tgggaatctt tttcgtcttg atgcggaaca agggcatagg gaagatgggc tttggaatgg 6720
tgactcttgg ggccagcgca tggctcatgt ggctctcgga aattgagcca gccagaattg 6780
catgcgtcct cattgttgtg ttcctattgc tggtggtgct catacctgag ccagaaaagc 6840
aaagatcccc ccaggacaac caaatggcaa tcatcatcat ggtagcagta ggtcttctgg 6900
gcttgattac cgccaatgaa ctcggatggt tggagagaac aaagagtgac ctaagccatc 6960
taatgggaag gagagaggag ggggcaacca taggattctc aatggacatt gacctgcggc 7020
cagcctcggc ctgggccatc tatgctgccc tgacaacttt cattacccca gccgtccaac 7080
atgcagtgac cacttcatac aacaactact ccttaatggc gatggccacg caagctggag 7140
tgttgtttgg tatgggcaaa gggatgccat tctacgcatg ggactttgga gtcccgctgc 7200
taatgatagg ttgctactca caattaacac ccctgaccct aatagtggct atcattttgc 7260
tcgtggcgca ctacatgtac ttgatcccag ggctgcaggc agcagctgcg cgtgctgccc 7320
agaagagaac ggcagctggc atcatgaaga accctgttgt ggatggaata gtggtgactg 7380
acattgacac aatgactatt gacccccaag tggagaaaaa gatgggacag gtgctactca 7440
tagcagtagc cgtctccagc gccatactgt cgcggaccgc ctgggggtgg ggggaagctg 7500
gggccctgat cacagctgca acttccactt tgtgggaagg ctctccgaac aagtactgga 7560
actcctctac agccacttca ctgtgcaaca tttttagggg aagttacttg gctggagctt 7620
ctctaatcta cacagtaaca agaaacgctg gcttggtcaa gagacgtggg ggtggaacag 7680
gagagaccct gggagagaaa tggaaggccc gcttgaacca gatgtcggcc ctggagttct 7740
actcctacaa aaagtcaggc atcaccgagg tgtgcagaga agaggcccgc cgcgccctca 7800
aggacggtgt ggcaacggga ggccatgctg tgtcccgagg aagtgcaaag ctgagatggt 7860
tggtggagcg gggatacctg cagccctatg gaaaggtcat tgatcttgga tgtggcagag 7920
gggctggag ttactacgcc gccaccatcc gcaaagttca agaagtgaaa ggatacacaa 7980
aaggaggccc tggtcatgaa gaacccatgt tggtgcaaag ctatgggtgg aacatagtcc 8040
gtcttaagag tggggtggac gtctttcata tggcggctga gccgtgtgac acgttgctgt 8100
gtgacatagg tgagtcatca tctagtcctg aagtggaaga agcacggacg ctcagagtcc 8160

-continued

```
tctccatggt gggggattgg cttgaaaaaa gaccaggagc cttttgtgta aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg gggcgcatgg   8400
acgggcccag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccctacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac accagggtgc   8760
cagaccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag accgcagtgg   8940
aagctgtgaa cgatccaagg ttctgggctc tagtggacaa ggaaagagag caccacctga   9000
gaggagagtg ccagagctgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttaaatg aggatcactg gatggggaga gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
ggtttgatct ggagaatgaa gctttaatca ccaaccaaat ggagaaaggg cacagggcct   9360
tagcattggc cataatcaag tacacatacc aaaacaaagt ggtaaaggtc cttagaccag   9420
ctgaaaaagg gaagacagtt atggacatta tttcaagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgt tcccaccact tcaacaagct ccatctcaag gacgggaggt   9840
ccattgtggt tccctgccgc caccaagatg aactgattgg ccgggcccgt gtctctccag   9900
gggcgggatg gagcatccgg gagactgctt gcctagcaaa gtcatatgcg caaatgtggc   9960
agctccttta tttccacaga agggacctcc gactgatggc caatgccatc tgttcatctg  10020
tgccagttga ctgggttcca actgggagaa ctacctggtc aatccatgga aagggagaat  10080
ggatgaccac tgaagacatg cttgtggtgt ggaacagagt gtggattgag gagaacgacc  10140
acatggaaga caagacccca gttacgaaat ggacagacat tccctatctg ggaaaaaggg  10200
aagacttgtg gtgtggatct ctcatagggc acagaccgcg caccacctgg gctgagaaca  10260
ttaaaaacac agtcaacatg gtgcgcagga tcataggtga tgaagaaaag tacatggact  10320
acctatccac ccaagttcgc tacttgggtg aagaagggtc tacacctgga gtgctataag  10380
caccaatctt agtgttgtca ggcctgctag tcagccacag cttggggaaa gctgtgcagc  10440
ctgtgacccc cccaggagag gctgggaaac caagcccata gtcaggccga gaacgccatg  10500
gcacggaaga agccatgctg cctgtgagcc cctcagagga cactgagtca aaaaacccca  10560
```

```
cgcgcttgga ggcgcaggat gggaaaagaa ggtggcgacc ttccccaccc ttcaatctgg  10620
ggcctgaact ggagatcagc tgtggatctc cagaagaggg actagtggtt agaggagacc  10680
ccccggaaaa cgcaaaacag catattgacg ctgggaaaga ccagagactc catgagtttc  10740
caccacgctg gccgccaggc acagatcgcc gaatagcggc ggccggtgtg gggaaatcca  10800
tgggtct                                                            10807
```

<210> SEQ ID NO 8
<211> LENGTH: 10807
<212> TYPE: DNA
<213> ORGANISM: Zika virus

<400> SEQUENCE: 8

```
agttgttgat ctgtgtgaat cagactgcga cagttcgagt ttgaagcgaa agctagcaac     60
agtatcaaca ggttttattt tggatttgga aacgagagtt tctggtcatg aaaaacccaa    120
aaaagaaatc cggaggattc cggattgtca atatgctaaa acgcggagta gcccgtgtga    180
gcccctttgg gggcttgaag aggctgccag ccggacttct gctgggccat gggcccatca    240
ggatggtctt ggcgatacta gcctttttga gattcacggc aatcaagcca tcactgggtc    300
tcatcaatag atggggttca gtggggaaaa aagaggctat ggaaataata aagaagttca    360
agaaagatct ggctgccatg ctgagaataa tcaatgctag gaaggagaag aagagacgag    420
gcgcagatac tagcgtcgga attgttggcc tcctcctgac cacagccatg gcagtagagg    480
tcactagacg tgggagtgca tactatatgt acttggacag aagcgatgct ggggaggcca    540
tatcttttcc aaccacactg gggatgaata agtgttacat acaaatcatg gatcttggac    600
acatgtgtga tgccaccatg agctatgaat gccctatgtt ggatgagggg gtagaaccag    660
atgacgtcga ttgctggtgc aacacgacat caacttgggt tgtgtatgga acctgccacc    720
acaaaaaagg tgaagcacgg agatctagaa gagctgtgac gctcccctcc cattccacta    780
ggaagctgca aacgcggtcg cagacctggt tggaatcaag agaatacaca aagcacctga    840
ttagagttga aaattggata ttcaggaacc ctggcttcgc gttagcagca gctgtcatcg    900
cttggctttt gggaagttca acgagccaaa aagtcatata tctggtcatg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtt accgtaatgg   1080
cacaggacaa accgactgtc gacatagagc tggttacaac aacagtcagc aacatggcgg   1140
aggtaagatc ctactgctat gaggcatcaa tatcggatat ggcttcggac agccgctgcc   1200
caacacaagg tgaggcctac cttgacaagc agtcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc caccctgggg ggttttggga gcctaggact tgattgtgaa ccgaggacag   1560
gccttgactt ttcagatttg tattacctga ctatgaataa caagcactgg ttggttcaca   1620
aggagtggtt ccacgacatt ccattacctt ggcatgctgg ggcagacact ggaactccac   1680
attggaacaa caaagaagca ctggtagagt tcaaggacgc acatgcaaaa aggcaaactg   1740
tcgtggttct agggagtcaa gaaggagcag ttcacacggc ccttgctgga gctctggagg   1800
```

-continued

```
ctgagatgga tggagccaag ggaaggctgt cctctggcca cttgaaatgt cgcctgaaaa   1860
tggataaact tagattgaag ggcgtgtcat actccttgtg cactgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga tatgcaaact ctgaccccag   2040
ttgggaggtt gataaccgct aaccctgtaa tcactgaaag caccgagaac tctaagatga   2100
tgctggaact tgatccacca tttggggact cttacattgt cataggagtc ggggagaaga   2160
agatcaccca tcactggcac aggagtggca gcaccattgg aaaagcattt gaagccactg   2220
tgagaggtgc caagagaatg gcagtcttgg gagacacagc ctgggacttt ggatcagttg   2280
ggggtgctct caactcattg ggcaagggca tccatcaaat ttttggagca gctttcaaat   2340
cattgttcgg aggaatgtcc tggttctcac aaattctcat tggaacgttg ctggtgtggt   2400
tgggtctgaa tacaaagaat ggatctattt cccttacgtg cttggcctta gggggagtgt   2460
tgatcttctt atccacagcc gtttctgctg atgtggggtg ctcggtggac ttctcaaaga   2520
aggaaacgag atgcggtaca ggggtgttcg tctataacga cgttgaagcc tggagggaca   2580
ggtacaagta ccatcctgac tcccctcgta gattggcagc agcagtcaag caagcctggg   2640
aagatgggat ctgtgggatc tcctctgtct caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtacttcgt cagagcagca aagacaaata   2880
acagctttgt cgtggatggt gacacactga aggaatgccc actcaaacat agagcatgga   2940
acagctttct tgtggaggat catgggtttg ggggtatttca cactagtgtc tggctcaagg   3000
ttagagaaga ttattcatta gagtgtgatc cagccgtcat tggaacagct gctaagggaa   3060
aggaggctgt gcacagcgat ctaggctact ggattgagag tgagaagaac gacacatgga   3120
ggctgaagag ggcccacctg atcgagatga aaacatgtga atggccaaag tcccacacat   3180
tgtggacaga tggagtagaa gaaagtgatc tgatcatacc caagtcttta gctgggccac   3240
tcagccatca caacaccaga gagggctaca ggactcaaat gaaagggcca tggcacagtg   3300
aagagcttga aattcggttt gaggaatgcc caggcactaa ggtccacgtg gaggaaacat   3360
gtgggacaag aggaccatcc ctgagatcaa ccactgcaag cggaagggtg atcgaggaat   3420
ggtgctgcag ggaatgcaca atgcccccac tgtcgttccg agctaaagat ggctgttggt   3480
atggaatgga gataaggccc aggaaagaac cagaaagtaa cttagtaagg tcaatggtga   3540
ctgcaggatc aactgatcac atggatcact tctctcttgg agtgcttgtg attttgctca   3600
tggtgcagga agggctgaag aagagaatga ccacaaagat catcataagc acatcaatgg   3660
cagtgctggt agccatgatc ctgggaggat tttcaatgag tgacctggct aagcttgcaa   3720
ttttgatggg tgccaccttc gcggaaatga acactggagg agatgtagct catttggcgc   3780
tgatagcggc attcaaagtc agacctgcgt tgctggtatc tttcatcttc agagctaatt   3840
ggacaccccg tgagagcatg ctgctggcct tggcctcgtg tcttctgcaa actgcgatct   3900
ccgccttgga aggcgacctg atggttctca tcaatggttt tgctttggcc tggttggcaa   3960
tacgagcgat ggttgttcca cgcactgaca acatcacctt ggcaatcctg gctgctctga   4020
caccactggc ccggggcaca ctgcttgtgg cgtggagagc aggccttgct acttgcgggg   4080
ggttcatgct cctctctctg aaggggaaag gcagtgtgaa gaagaaccta ccatttgtca   4140
tggccttggg actaactgct gtgaggctgg tcgaccccat caacgtggtg ggactgctgt   4200
```

-continued

```
tgctcacaag gagtgggaag cggagctggc cccctagtga agtactcaca gctgttggcc   4260
tgatatgcgc attggctgga gggttcgcca aggcggatat agagatggct gggcccatgg   4320
ccgcggtcgg tctgctaatt gtcagttacg tggtctcagg aaagagtgtg gacatgtaca   4380
ttgaaagagc aggtgacatc acatgggaaa aagatgcgga aatcactgga aacagtcccc   4440
ggctcgatgt ggcactagat gagagtggtg atttctccct agtggaggat gatggtccac   4500
ccatgagaga gatcatactc aaagtggtcc tgatgaccat ctgcggcatg aacccaatag   4560
ccataccctt tgcagctgga gcgtggtacg tgtatgtgaa gactggaaaa aggagtggtg   4620
ctctatggga tgtgcctgct cccaaggaag taaaaaaggg ggagaccaca gatggagtgt   4680
acagagtaat gactcgtaga ctgcttggtt caacacaagt tggagtggga gtcatgcaag   4740
agggggtctt ccacactatg tggcacgtca caaaaggatc cgcgctgaga agcggtgaag   4800
ggagacttga tccatactgg ggagatgtca agcaggatct ggtgtcatac tgtggtccgt   4860
ggaagctaga cgccgcctgg gacgggcaca gcgaggtgca gctcttggcc gtgccccccg   4920
gagagagagc gaggaacatc cagactctgc ccggaacatt taagacaaag gatggggaca   4980
ttggagcagt tgcgctggac tacccagcag gaacttcagg atctccaatc ctagacaagt   5040
gtgggagagt gataggactc tatggtaatg gggtcgtgat aaaaaatggg agttatgtta   5100
gtgccatcac ccaagggagg agggaggaag agactcctgt tgagtgcttc gagccttcga   5160
tgctgaagaa gaagcagcta actgtcttag acctgcatcc tggagccggg aaaaccagga   5220
gagttcttcc tgaaatagtc cgtgaagcca taaaaacaag actccgtact gtgatcttag   5280
ctccaaccag ggtcgtcgct gctgaaatgg aggaagccct tagagggctt ccagttcgtt   5340
atatgacaac agcagtcaat gtcacccatt ctgggacaga aatcgttgac ttaatgtgcc   5400
atgctacctt cacttcacgc ctactacaac caatcagagt ccccaactat aatttgtata   5460
ttatggatga ggcccacttc acagatccct caagtatagc agcaagagga tacatttcaa   5520
caagggttga gatgggcgag gcggctgcca tcttcatgac cgccacgcca ccaggaaccc   5580
gtgacgcatt cccggactcc aactcaccaa ttatggacac cgaggtggaa gtcccagaga   5640
gagcctggag cacaggcttt gattgggtga cggatcattc tgggaaaaca gtctggtttg   5700
ttccaagcgt gaggaacggc aatgagatcg cagcttgtct gacaaaggct ggaaaacggg   5760
tcatacagct cagcagaaag acttttgaga cagagttcca gaaaacgaaa aatcaagagt   5820
gggacttcgt cgtgacaacc gacatttcag agatgggcgc caactttaaa gctgaccgtg   5880
tcatagattc caggagatgc ttaaagccgg tcatacttga tggcgagaga gtcattttgg   5940
ctggacccat gcctgtcaca catgccagcg ctgctcagag gagggggcgc ataggcagga   6000
atcccaacaa acctggagat gagtatctgt atggaggtgg gtgcgcagag actgatgaag   6060
atcacgcaca ctggcttgaa gcaagaatgc ttcttgacaa catttacctc caagatggcc   6120
tcatagcttc gctctatcga cctgaggccg acaaagtagc agctattgag ggagagttca   6180
agcttaggac ggagcaaagg aagacctttg tggaactcat gaaaagagga gatcttccgg   6240
tttggttggc ctatcaggtt gcatctgccg gaataaccta cacagataga agatggtgct   6300
ttgatggcat gaccaacaac accataatgg aagacagtgt gccggcagag gtgtggacca   6360
gatacggaga gaaaagagtg ctcaaaccga ggtggatgga cgccagagtt tgttcagatc   6420
atgcggccct gaagtcattc aaagagtttg ccgctgggaa aagaggagcg gcctttggag   6480
tgatagaagc cctgggaaca ctgccaggac acatgacaga gagattccag gaagccattg   6540
```

-continued

```
acaacctcgc tgtgctcatg cgggcagaga ctggaagcag gccttacaaa gccgcggcgg   6600
cccaattgcc ggagacccta gagaccatta tgcttttggg gttgctggga acagtctcgc   6660
tgggaatctt tttcgtcttg atgcggaaca agggcatggg gaagatgggc tttggaatgg   6720
tgactcttgg ggccagcgca tggcttatgt ggctctcgga aattgagcca gccagaattg   6780
catgtgtcct cattgtcgtg ttcctattgc tggtggtgct catacctgag ccagaaaagc   6840
aaagatctcc tcaggacaac caaatggcaa tcatcatcat ggtagcagtg ggtcttctgg   6900
gcttgattac cgccaatgaa ctcggatggt tggagagaac aaaaagtgac ctaagccatc   6960
taatgggaag gagagaggag gggcaacca caggattctc aatggacatt gacctgcggc    7020
cagcctcagc ttgggctatc tatgctgctc tgacaacttt catcacccca gccgtccaac   7080
atgcggtgac cacttcatac aacaactact ccttaatggc gatggccacg caagctgggg   7140
tgttgtttgg tatgggcaaa gggatgccat tctacgcatg ggactttgga gtcccgctgc   7200
taatgatggg ttgctactca caattaacac ctctgaccct aatagtggcc atcattttgc   7260
tcgtggcgca ctacatgtac ttgatcccag ggctgcaggc agcagctgcg cgggctgccc   7320
agaagagaac ggcagctggc atcatgaaga accctgttgt ggatggaata gtggtgactg   7380
acattgacac aatgacaatt gacccccaag tggaaaaaaa gatggggcag gtgctactca   7440
tagcagtagc cgtctccagc gccatactgt cgcggaccgc ctgggggtgg ggggaggctg   7500
gggccctgat cacagctgca acttccacct tgtgggaagg ctctccgaac aagtactgga   7560
actcctccac agccacttca ctgtgtaaca tttttagggg aagttacttg gctggagctt   7620
ctctaatcta cacagtaaca agaaacgctg gcttggtcaa gagacgtggg ggtggaacgg   7680
gagagaccct gggagagaaa tggaaggccc gcctgaacca gatgtcggcc ctggagttct   7740
actcctacaa aaagtcaggc atcaccgagg tgtgcagaga agaggcccgc cgtgccctca   7800
aggacggtgt ggcaacagga ggccatgctg tgtcccgagg aagtgcaaag cttagatggc   7860
tggtggagag aggatacctg cagccctatg gaaaggtcat tgatcttgga tgtggcagag   7920
ggggctggag ttactatgcc gccaccatcc gcaaagttca ggaagtgaaa ggatacacaa   7980
aaggaggccc tggtcatgaa gaacccatgt tggtgcaaag ctatgggtgg aacatagtcc   8040
gtcttaagag tggggtggac gtctttcaca tggcggctga gccgtgtgac actttgctgt   8100
gtgatatagg tgagtcatca tctagtcctg aagtggaaga agcacggacg ctcagagtcc   8160
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag ggtgccactc tcccgcaact ctacacatga gatgtactgg gtctctggag   8340
cgaaaagcaa caccataaaa agtgtgtcca ccacgagcca gctcctcttg ggcgcatgg    8400
acgggcccag gaggccagtg aaatatgagg aggatgtgaa tctcggctct ggcacgcggg   8460
ctgtggtaag ctgcgctgaa gctcccaaca tgaagatcat tggtaaccgc attgagagga   8520
tccgcagtga gcacgcggaa acgtggttct ttgacgagaa ccacccatat aggacatggg   8580
cttaccatgg aagctatgag gcccctacac aagggtcagc gtcctctcta ataaacgggg   8640
ttgtcaggct cctgtcaaaa ccctgggatg tggtgactgg agtcacagga atagccatga   8700
ctgacaccac accgtatggt cagcaaagag ttttcaagga aaaagtggac actagggtgc   8760
cagaccccca agaaggcact cgtcaggtta tgagcatggt ctcttcctgg ttatggaagg   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
```

aagctgtgaa tgatccaagg ttctgggctc tagtggacaa ggaaagagag catcacctga 9000
gaggagagtg tcagagctgt gtgtacaaca tgatgggaaa aagagaaaag aaacaagggg 9060
aatttggaaa ggccaagggc agccgcgcca tctggtatat gtggctaggg gctagattcc 9120
tagagttcga agcccttgga ttcttgaatg aggatcattg gatggggaga gagaattcag 9180
gaggtggtgt tgaaggactg ggattacaaa gactcggata tgtcctagaa gagatgagtc 9240
gcataccagg aggaaggatg tatgcagatg atactgctgg ctgggacacc cgcatcagca 9300
ggtttgatct ggagaatgaa gctctaatca ccaaccaaat ggagaaaggg cacagggcct 9360
tggcattggc cataatcaag tacacatacc aaaacaaagt ggtaaaggtc cttagaccag 9420
ctgaaaaagg gaagacagtt atggacatta tttcaagaca agaccaaagg gggagcggac 9480
aagttgtcac ttacgctctt aatacattca ccaacctggt ggtgcagctc attcggaata 9540
tggaggctga ggaagttcta gagatgcaag acttgtggct gctgcggagg ccagagaaag 9600
tgaccaactg gttgcaaagc aacggatggg ataggctcaa aagaatggca gtcagtggag 9660
atgattgcgt tgtgaaacca attgatgata ggtttgcaca tgccctcagg ttcttgaatg 9720
atatgggaaa agttaggaag gacacacaag agtggaaacc ctcaactgga tgggacaact 9780
gggaagaagt tccgttttgc tcccaccact tcaacaaact ccatcttaag gacgggaggt 9840
ccattgtggt tccctgccgc caccaagatg aactgattgg ccgagcccgc gtatcaccag 9900
gggcgggatg gagcatccgg gagactgctt gcctagcaaa atcatatgcg caaatgtggc 9960
agctccttta tttccacaga agggacctcc gactgatggc caatgccatt tgttcatctg 10020
tgccagttga ttgggttcca actgggagaa ctacctggtc aatccatgga aagggagaat 10080
ggatgaccac tgaagacatg cttgtggtat ggaacagagt gtggattgag gaaaacgacc 10140
acatggaaga caagacccca gttacaaaat ggacagacat tccctatttg ggaaaaagag 10200
aagacttgtg gtgtggatct ctcatagggc acagaccgcg tactacctgg gctgagaaca 10260
tcaaaaatac agtcaacatg atgcgcagga tcataggtga tgaagaaaag tacatggact 10320
acctatccac ccaggttcgc tacttgggtg aagaagggtc cacacctgga gtgctgtaag 10380
caccaatctt agtgttgtca ggcctgctag tcagccacag cttggggaaa gctgtgcagc 10440
ctgtgacccc cccaggagaa gctgggaaac caagcctata gtcaggccga gaacgccatg 10500
gcacggaaga agccatgctg cctgtgagcc cctcagagga cactgagtca aaaaacccca 10560
cgcgcttgga ggcgcaggat gggaaaagaa ggtggcgacc ttccccaccc ttcaatctgg 10620
ggcctgaact ggagatcagc tgtggatctc cagaagaggg actagtggtt agaggagacc 10680
ccccggaaaa cgcaaaacag catattgacg ctgggaaaga ccagagactc catgagtttc 10740
caccacgctg gccgccaggc acagatcgcc gaatagcggc ggccggtgtg gggaaatcca 10800
tgggtct 10807

<210> SEQ ID NO 9
<211> LENGTH: 10648
<212> TYPE: DNA
<213> ORGANISM: Zika virus

<400> SEQUENCE: 9
gacagttcga gtttgaagcg aaagctagca acagtatcaa caggttttat ttggatttgg 60
aaacgagagt ttctggtcat gaaaaaccca aaaaagaaat ccggaggatt ccggattgtc 120
aatatgctaa aacgcggagt agcccgtgtg agcccctttg ggggcttgaa gaggctgcca 180

-continued

```
gccggacttc tgctgggtca tgggcccatc aggatggtct tggcgattct agcctttttg    240
agattcacgg caatcaagcc atcactgggt ctcatcaata gatggggttc agtggggaaa    300
aaagaggcta tggaaataat aaagaagttc aagaaagatc tggctgccat gctgagaata    360
atcaatgcta ggaaggagaa gaagagacga ggcgcagata ctagtgtcgg aattgttggc    420
ctcctgctga ccacagctat ggcagcggag gtcactagac gtgggagtgc atactatatg    480
tacttggaca gaaacgatgc tggggaggcc atatcttttc caaccacatt ggggatgaat    540
aagtgttata tacagatcat ggatcttgga cacatgtgtg atgccaccat gagctatgaa    600
tgccctatgc tggatgaggg ggtggaacca gatgacgtcg attgttggtg caacacgacg    660
tcaacttggg ttgtgtacgg aacctgccat cacaaaaaag gtgaagcacg gagatctaga    720
agagctgtga cgctcccctc ccattccact aggaagctgc aaacgcggtc gcaaacctgg    780
ttggaatcaa gagaatacac aaagcacttg attagagtcg aaaattggat attcaggaac    840
cctggcttcg cgttagcagc agctgccatc gcttggcttt tgggaagctc aacgagccaa    900
aaagtcatat acttggtcat gatactgctg attgccccgg catacagcat caggtgcata    960
ggagtcagca atagggactt tgtggaaggt atgtcaggtg ggacctgggt tgatgttgtc   1020
ttggaacatg gaggttgtgt caccgtaatg gcacaggaca aaccgactgt cgacatagag   1080
ctggttacaa caacagtcag caacatggcg gaggtaagat cctactgcta tgaggcatca   1140
atatcagaca tggcttcgga cagccgctgc ccaacacaag gtgaagccta ccttgacaag   1200
caatcagaca ctcaatatgt ctgcaaaaga acgttagtgg acagaggctg gggaaatgga   1260
tgtggacttt ttggcaaagg gagcctggtg acatgcgcta agtttgcatg ctccaagaaa   1320
atgaccggga agagcatcca gccagagaat ctggagtacc ggataatgct gtcagttcat   1380
ggctcccagc acagtgggat gattgttaat gacacaggac atgaaactga tgagaataga   1440
gcgaaagttg agataacgcc caattcacca agagccgaag ccaccctggg gggttttgga   1500
agcctaggac ttgattgtga accgaggaca ggccttgact tttcagattt gtattacttg   1560
actatgaata acaagcactg gttggttcac aaggagtggt tccacgacat tccattacct   1620
tggcacgctg gggcagacac cggaactcca cactggaaca acaaagaagc actggtagag   1680
ttcaaggacg cacatgccaa aaggcaaact gtcgtggttc tagggagtca agaaggagca   1740
gttcacacgg cccttgctgg agctctggag gctgagatgg atggtgcaaa gggaaggctg   1800
tcctctggcc acttgaaatg tcgcctgaaa atggataaac ttagattgaa gggcgtgtca   1860
tactccttgt gtactgcagc gttcacattc accaagatcc cggctgaaac actgcacggg   1920
acagtcacag tggaggtaca gtacgcaggg acagatggac cttgcaaggt tccagctcag   1980
atggcggtgg acatgcaaac tctgacccca gttgggaggt tgataaccgc taaccccgta   2040
atcactgaaa gcactgagaa ctctaagatg atgctggaac ttgatccacc atttggggac   2100
tcttacattg tcataggagt cggggagaag aagatcaccc accactggca caggagtggc   2160
agcaccattg gaaaagcatt tgaagccact gtgagaggtg ccaagagaat ggcagtcttg   2220
ggagacacag cctgggactt tggatcagtt ggaggcgctc tcaactcatt gggcaagggc   2280
atccatcaaa tttttggagc agctttcaaa tcattgtttg gaggaatgtc ctggttctca   2340
caaattctca ttggaacgtt gctgatgtgg ttgggtctga acacaaagaa tggatctatt   2400
tcccttatgt gcttggcctt agggggagtg ttgatcttct tatccacagc cgtctctgct   2460
gatgtggggt gctcggtgga cttctcaaag aaggagacga gatgcggtac aggggtgttc   2520
gtctataacg acgttgaagc ctggagggac aggtacaagt accatcctga ctccccccgt   2580
```

-continued agattggcag cagcagtcaa gcaagcctgg gaagatggta tctgcgggat ctcctctgtt 2640
tcaagaatgg aaaacatcat gtggagatca gtagaagggg agctcaacgc aatcctggaa 2700
gagaatggag ttcaactgac ggtcgttgtg ggatctgtaa aaaaccccat gtggagaggt 2760
ccacagagat tgcccgtgcc tgtgaacgag ctgccccacg gctggaaggc ttgggggaaa 2820
tcgtacttcg tcagagcagc aaagacaaat aacagctttg tcgtggatgg tgacacactg 2880
aaggaatgcc cactcaaaca tagagcatgg aacagctttc ttgtggagga tcatgggttc 2940
ggggtatttc acactagtgt ctggctcaag gttagagaag attattcatt agagtgtgat 3000
ccagccgtta ttggaacagc tgttaaggga aaggaggctg tacacagtga tctaggctac 3060
tggattgaga gtgagaagaa tgacacatgg aggctgaaga gggcccatct gatcgagatg 3120
aaaacatgtg aatggccaaa gtcccacaca ttgtggacag atggaataga agagagtgat 3180
ctgatcatac ccaagtcttt agctgggcca ctcagccatc acaataccag agagggctac 3240
aggacccaaa tgaaagggcc atggcacagt gaagagcttg aaattcggtt tgaggaatgc 3300
ccaggcacta aggtccacgt ggaggaaaca tgtggaacaa gaggaccatc tctgagatca 3360
accactgcaa gcggaagggt gatcgaggaa tggtgctgca gggagtgcac aatgccccca 3420
ctgtcgttcc gggctaaaga tggctgttgg tatggaatgg agataaggcc caggaaagaa 3480
ccagaaagca acttagtaag gtcaatggtg actgcaggat caactgatca catggaccac 3540
ttctcccttg gagtgcttgt gattctgctc atggtgcagg aagggctgaa gaagagaatg 3600
accacaaaga tcatcataag cacatcaatg gcagtgctgg tagctatgat cctgggagga 3660
ttttcaatga gtgacctggc taagcttgca attttgatgg gtgccacctt cgcggaaatg 3720
aacactggag gagatgtagc tcatctggcg ctgatagcgg cattcaaagt cagaccagcg 3780
ttgctggtat ctttcatctt cagagctaat tggacacccc gtgaaagcat gctgctggcc 3840
ttggcctcgt gtcttttgca aactgcgatc tccgccttgg aaggcgacct gatggttctc 3900
atcaatggtt ttgctttggc ctggttggca atacgagcga tggttgttcc acgcactgat 3960
aacatcacct tggcaatcct ggctgctctg acaccactgg cccggggcac actgcttgtg 4020
gcgtggagag caggccttgc tacttgcggg gggtttatgc tcctctctct gaagggaaaa 4080
ggcagtgtga agaagaactt accatttgtc atggccctgg gactaaccgc tgtgaggctg 4140
gtcgacccca tcaacgtggt gggactgctg ttgctcacaa ggagtgggaa gcggagctgg 4200
ccccctagcg aagtactcac agctgttggc ctgatatgcg cattggctgg agggttcgcc 4260
aaggcagata tagagatggc tgggcccatg gccgcggtcg gtctgctaat tgtcagttac 4320
gtggtctcag gaaagagtgt ggacatgtac attgaaagag caggtgacat cacatgggaa 4380
aaagatgcgg aagtcactgg aaacagtccc cggctcgatg tggcgctaga tgagagtggt 4440
gatttctccc tggtggagga tgacggtccc cccatgagag agatcatact caaggtggtc 4500
ctgatgacca tctgtggcat gaacccaata gccataccct ttgcagctgg agcgtggtac 4560
gtatacgtga agactggaaa aaggagtggt gctctatggg atgtgcctgc tcccaaggaa 4620
gtaaaaaagg gggagaccac agatggagtg tacagagtaa tgactcgtag actgctaggt 4680
tcaacacaag ttggagtggg agttatgcaa gagggggtct ttcacactat gtggcacgtc 4740
acaaaaggat ccgcgctgag aagcggtgaa gggagacttg atccatactg gggagatgtc 4800
aagcaggatc tggtgtcata ctgtggtcca tggaagctag atgccgcctg ggacgggcac 4860
agcgaggtgc agctcttggc cgtgcccccc ggagagagag cgaggaacat ccagactctg 4920

-continued

```
cccggaatat ttaagacaaa ggatggggac attggagcgg ttgcgctgga ttacccagca   4980
ggaacttcag gatctccaat cctagacaag tgtgggagag tgataggact ttatggcaat   5040
ggggtcgtga tcaaaaatgg gagttatgtt agtgccatca cccaagggag gagggaggaa   5100
gagactcctg ttgagtgctt cgagccttcg atgctgaaga agaagcagct aactgtctta   5160
gacttgcatc ctggagctgg gaaaaccagg agagttcttc ctgaaatagt ccgtgaagcc   5220
ataaaaacaa gactccgtac tgtgatctta gctccaacca gggttgtcgc tgctgaaatg   5280
gaggaggccc ttagagggct tccagtgcgt tatatgacaa cagcagtcaa tgtcacccac   5340
tctggaacag aaatcgtcga cttaatgtgc catgccacct tcacttcacg tctactacag   5400
ccaatcagag tccccaacta taatctgtat attatggatg aggcccactt cacagatccc   5460
tcaagtatag cagcaagagg atacatttca acaagggttg agatgggcga ggcggctgcc   5520
atcttcatga ccgccacgcc accaggaacc cgtgacgcat ttccggactc caactcacca   5580
attatggaca ccgaagtgga agtcccagag agagcctgga gctcaggctt tgattgggtg   5640
acggatcatt ctggaaaaac agtttggttt gttccaagcg tgaggaacgg caatgagatc   5700
gcagcttgtc tgacaaaggc tggaaaacgg gtcatacagc tcagcagaaa gacttttgag   5760
acagagttcc agaaaacaaa acatcaagag tgggactttg tcgtgacaac tgacatttca   5820
gagatgggcg ccaactttaa agctgaccgt gtcatagatt ccaggagatg cctaaagccg   5880
gtcatacttg atggcgagag agtcattctg gctggaccca tgcctgtcac acatgccagc   5940
gctgcccaga ggagggggcg cataggcagg aatcccaaca aacctggaga tgagtatctg   6000
tatggaggtg ggtgcgcaga gactgacgaa gaccatgcac actggcttga agcaagaatg   6060
ctccttgaca atatttacct ccaagatggc ctcatagcct cgctctatcg acctgaggcc   6120
gacaaagtag cagccattga gggagagttc aagcttagga cggagcaaag gaagaccttt   6180
gtggaactca tgaaaagagg agatcttcct gtttggctgg cctatcaggt tgcatctgcc   6240
ggaataacct acacagatag aagatggtgc tttgatggca cgaccaacaa caccataatg   6300
gaagacagtg tgccggcaga ggtgtggacc agacacggag agaaaagagt gctcaaaccg   6360
aggtggatgg acgccagagt ttgttcagat catgcggccc tgaagtcatt caaggagttt   6420
gccgctggga aaagaggagc ggcttttgga gtgatggaag ccctgggaac actgccagga   6480
cacatgacag agagattcca ggaagccatt gacaacctcg ctgtgctcat gcgggcagag   6540
actggaagca ggccttacaa agccgcggcg gcccaattgc cggagaccct agagaccatt   6600
atgcttttgg ggttgctggg aacagtctcg ctgggaatct tcttcgtctt gatgaggaac   6660
aagggcatag ggaagatggg ctttggaatg gtgactcttg gggccagcgc atggctcatg   6720
tggctctcgg aaattgagcc agccagaatt gcatgtgtcc tcattgttgt gtttctattg   6780
ctggtggtgc tcatacctga gccagaaaag caaagatctc cccaggacaa ccaaatggca   6840
atcatcatca tggtagcagt aggtcttctg ggcttgatta ccgccaatga actcggatgg   6900
ttggagagaa caaagagtga cctaagccat ctaatgggaa ggagagagga gggggcaacc   6960
ataggattct caatggacat tgacctgcgg ccagcctcag cttgggccat ctatgctgcc   7020
ttgacaactt tcattacccc agccgtccaa catgcagtga ccacttcata caacaactac   7080
tccttaatgg cgatggccac gcaagctgga gtgttgtttg gtatgggcaa agggatgcca   7140
ttctacgcat gggactttgg agtcccgctg ctaatgatag gttgctactc acaattaaca   7200
cccctgaccc taatagtggc catcattttg ctcgtggcgc actacatgta cttgatccca   7260
gggctgcagg cagcagctgc gcgtgctgcc cagaagagaa cggcagctgg catcatgaag   7320
```

-continued aaccctgttg tggatggaat agtggtgact gacattgaca caatgacaat tgacccccaa 7380
gtggagaaaa agatgggaca ggtgctactc atagcagtag ccgtctccag cgccatactg 7440
tcgcggaccg cctgggggtg gggggaggct ggggccctga tcacagccgc aacttccact 7500
ttgtgggaag gctctccgaa caagtactgg aactcctcta cagccacttc actgtgtaac 7560
atttttaggg gaagttactt ggctggagct tctctaatct acacagtaac aagaaacgct 7620
ggcttggtca agagacgtgg gggtggaaca ggagagaccc tgggagagaa atggaaggcc 7680
cgcttgaacc agatgtcggc cctggagttc tactcctaca aaaagtcagg catcaccgag 7740
gtgtgcagag aagaggcccg ccgcgccctc aaggacggtg tggcaacggg aggccatgct 7800
gtgtcccgag gaagtgcaaa gctgagatgg ttggtggagc ggggatacct gcagccctat 7860
ggaaaggtca ttgatcttgg atgtggcaga gggggctgga gttactacgc cgccaccatc 7920
cgcaaagttc aagaagtgaa aggatacaca aaaggaggcc ctggtcatga agaacccgtg 7980
ttggtgcaaa gctatgggtg gaacatagtc cgtcttaaga gtggggtgga cgtctttcat 8040
atggcggctg agccgtgtga cacgttgctg tgtgacatag gtgagtcatc atctagtcct 8100
gaagtggaag aagcacggac gctcagagtc ctctccatgg tgggggattg gcttgaaaaa 8160
agaccaggag ccttttgtat aaaggtgttg tgcccataca ccagcactat gatggaaacc 8220
ctggagcgac tgcagcgtag gtatgggggga ggactggtca gagtgccact ctcccgcaac 8280
tctacacatg agatgtattg ggtctctgga gcgaaaagca acaccataaa aagtgtgtcc 8340
accacgagcc agctcctctt ggggcgcatg gacgggccta ggaggccagt gaaatatgag 8400
gaggatgtga atctcggctc tggcacgcgg gctgtggtaa gctgcgctga agctcccaac 8460
atgaagatca ttggtaaccg cattgaaagg atccgcagtg agcacgcgga aacgtggttc 8520
tttgacgaga accacccata taggacatgg gcttaccatg gaagctatga ggcccccaca 8580
caagggtcag cgtcctctct aataaacggg gttgtcaggc tcctgtcaaa accctgggat 8640
gtggtgactg gagtcacagg aatagccatg accgacacca caccgtatgg tcagcaaaga 8700
gttttcaagg aaaaagtgga cactagggtg ccagaccccc aagaaggcac tcgtcaggtt 8760
atgagcatgg tctcttcctg gttgtggaaa gagctaggca aacacaaacg gccacgagtc 8820
tgtaccaaag aagagttcat caacaaggtt cgtagcaatg cagcattagg ggcaatattt 8880
gaagaggaaa aagagtggaa gactgcagtg gaagctgtga acgatccaag gttctgggct 8940
ctagtggata aggaaagaga gcaccacctg agaggagagt gccagagttg tgtgtacaac 9000
atgatgggaa aaagagaaaa gaaacaaggg gaatttggaa aggccaaggg cagccgcgcc 9060
atctggtata tgtggctagg ggctagattt ctagagttcg aagcccttgg attcttgaac 9120
gaggatcact ggatggggag agagaactca ggaggtggtg ttgaagggct gggattacaa 9180
agactcggat atgtcctaga agagatgagt cgtataccag gaggaaggat gtatgcagat 9240
gacactgctg gctgggacac ccgcatcagc aggtttgatc tggagaatga agctctaatc 9300
accaaccaaa tggaaaaagg gcacagggcc ttggcattgg ccataatcaa gtacacatac 9360
caaaacaaag tggtaaaggt ccttagacca gctgaaaaag ggaaaacagt tatggacatt 9420
atttcgagac aagaccaaag gggggagcgga caagttgtca cttacgctct taacacattt 9480
accaacctag tggtgcaact cattcggaat atggaggctg aggaagttct agagatgcaa 9540
gacttgtggc tgctgcggag gtcagagaaa gtgaccaact ggttgcagag caacggatgg 9600
gataggctca aacgaatggc agtcagtgga gatgattgcg ttgtgaagcc aattgatgat 9660

-continued

```
aggtttgcac atgccctcag gttcttgaat gatatgggaa aagttaggaa ggacacacaa   9720
gagtggaaac cctcaactgg atgggacaac tgggaagaag ttccgttttg ctcccaccac   9780
ttcaacaagc tccatctcaa ggacgggagg tccattgtgg ttccctgccg ccaccaagat   9840
gaactgattg gccgggcccg cgtctctcca ggggcgggat ggagcatccg ggagactgct   9900
tgcctagcaa aatcatatgc gcaaatgtgg cagctccttt atttccacag aagggacctc   9960
cgactgatgg ccaatgccat ttgttcatct gtgccagttg actgggttcc aactgggaga  10020
actacctggt caatccatgg aaagggagaa tggatgacca ctgaagacat gcttgtggtg  10080
tggaacagag tgtggattga ggagaacgac cacatggaag acaagacccc agttacgaaa  10140
tggacagaca tcccctattt gggaaaaagg gaagacttgt ggtgtggatc tctcataggg  10200
cacagaccgc gcaccacctg ggctgagaac attaaaaaca cagtcaacat ggtgcgcagg  10260
atcataggtg atgaagaaaa gtacatggac tacctatcca cccaagttcg ctacttgggt  10320
gaagaagggt ctacacctgg agtgctgtaa gcaccagtct taatgttgtc aggcctgcta  10380
gtcagccaca gcttggggaa agctgtgcag cctgtgaccc ccccaggaga agctgggaaa  10440
ccaagcctat agtcaggccg agaacgccat ggcacggaag aagccatgct gcctgtgagc  10500
ccctcagagg acactgagtc aaaaaacccc acgcgcttgg aggcgcagga tgggaaaaga  10560
aggtggcgac cttccccacc cttcaatctg gggcctgaac tggagatcag ctgtggatct  10620
ccagaagagg gactagtggt tagaggag                                     10648
```

```
<210> SEQ ID NO 10
<211> LENGTH: 10676
<212> TYPE: DNA
<213> ORGANISM: Zika virus

<400> SEQUENCE: 10

gttgttactg ttgctgactc agactgcgac agttcgagtt tgaagcgaaa gctagcaaca     60
gtatcaacag gttttatttg gatttggaaa cgagagtttc tggtcatgaa aaacccaaaa    120
aagaaatccg gaggattccg gattgtcaat atgctaaaac gcggagtagc ccgtgtgagc    180
ccctttgggg gcttgaagag gctgccagcc ggacttctgc tgggtcatgg gcccatcagg    240
atggtcttgg caattctagc ctttttgaga ttcacggcaa tcaagccatc actgggtctc    300
atcaatagat ggggttcagt ggggaaaaaa gatgctatgg aaataataaa gaagttcaag    360
aaagatctgg ctgccatgct gagaataatc aatgctagga aggagaagaa gagacgaggc    420
gcagatacta gtgtcggaat tgttggcctc ctgctgacca cagctatggc agcggaggtc    480
actagacgtg ggagtgcata ctatatgtac ttggacagaa acgatgctgg ggaggccata    540
tcttttccaa ccacattggg gatgaataag tgttatatac agatcatgga tcttggacac    600
atgtgtgatg ccaccatgag ctatgaatgc cctatgctgg atgagggggt ggaaccagat    660
gacgtcgatt gttggtgcaa cacgacgtca acttgggttg tgtacggaac ctgccatcac    720
aaaaaaggtg aagcacggag atctagaaga gctgtgacgc tcccttccca ttccactagg    780
aagctgcaaa cgcggtcgca aacctggttg gaatcaagag aatacacaaa gcacttgatt    840
agagtcgaaa attggatatt caggaaccct ggcttcgcgt tagcagcagc tgccatcgct    900
tggcttttgg gaagctcaac gagccaaaaa gtcatatact tggtcatgat actgctgatt    960
gccccggcat acagcatcag gtgcatagga gtcagcaata gggactttgt ggaaggtatg   1020
tcaggtggga cttgggttga tgttgtcttg gaacatggag gttgtgtcac cgcaatggca   1080
caggacaaac cgactgtcga catagagctg gttacaacaa cagtcagcaa catggcggag   1140
```

-continued

```
gtaagatcct actgctatga ggcatcaata tcagacatgg cttcggacag ccgctgccca   1200
acacaaggtg aagcctacct tgacaagcaa tcagacactc aatatgtttg caaaagaacg   1260
ttagtggaca gaggctgggg aaatggatgt ggactttttg gcaaagggag tctggtgaca   1320
tgcgctaagt ttgcatgctc caagaaaatg accgggaaga gcatccagcc agagaatctg   1380
gagtaccgga taatgctgtc agttcatggc tcccagcaca gtgggatgct cgttaatgac   1440
acaggacatg aaactgatga gaatagagcg aaggttgaga taacgcccaa ttcaccaaga   1500
gccgaagcca ccctgggggg ttttggaagc ctaggacttg attgtgaacc gaggacaggc   1560
cttgactttt cagatttgta ttacttgact atgaataaca agcactggtt ggctcacaag   1620
gagtggttcc acgacattcc attaccttgg cacgctgggg cagccaccgg aactccacac   1680
tggaacaaca aagaagcact ggtagagttc aaggacgcac atgccaaaag gcaaactgtc   1740
gtggttctag ggagtcaaga aggagcagtt cacacggccc ttgctggagc tctggaggct   1800
gagatggatg gtgcaaaggg aaggctgtcc tctggccact tgaaatgtcg cctgaaaatg   1860
gataaactta gattgaaggg cgtgtcatac tccttgtgta ccgcagcgtt cacattcacc   1920
aagatcccgg ctgaaacagt ggacgggaca gtcacagtgg agggacagta cggagggaca   1980
gatggacctt gcaaggttcc agctcagatg gcggtggaca tgcagactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaatta ttggagcagc tttcaaatca   2340
ttgtttggag gaatgtcctg gttctcacaa attctcattg ggacgttgct gatgtggttg   2400
ggtctgaaca caaagaatgg atctatttcc cttatgtgct tggccttagg gggagtgttg   2460
atcttcttat ccacagccgt ctcaggtggt gtggggtgct cggtggactt ctcaaagaag   2520
gagacgagat gcggtacagg ggtgttcgtc tataacgatg ttgaagcctg gagggacagg   2580
tacaagtacc atcctgactc cccccgtaga ttggcagcag cagtcaagca agcctgggaa   2640
gatggtatct gcgggatctc ctctgtttca agaatggaaa acatcatgtg gagatcagta   2700
gaaggggagc tcaacgcaat cctggaagag aatggagttc aactgacggt cgttgtggga   2760
tctgtaaaaa accccatgtg gagaggtcca cagagattgc ccgtgcctgt gaacgagctg   2820
ccccacggct ggaaggcttg gggggaaatcg tacttcgtca gagcagcaaa gacaaataac   2880
agctttgtcg tggatggtga cacactgaag gaatgcccac tcaaacatag agcatggaac   2940
agctttcttg tggaggatca tgggttcggg gtatttcaca ctagtgtctg gctcaaggtt   3000
agagaagact attggttaga gtgtgatcca gccgttattg gaacagctgt taagggaaag   3060
gaggctgtac acagtgatct aggctactgg attgagagtg agaagaatga cacatggtgg   3120
ctgaagaggg cccatctgat cgagatgaaa acatgtgaat ggccaaagtc ccacacattg   3180
tggacagatg gaatagaaga gagtgatctg atcataccca agtctttagc tgggccactc   3240
agccatcaca atgccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg gaagggtgat cgaggaatgg   3420
tgctccaggg agtgcacaat gcccccactg tccttccagg ctaaagatgg ctgttggtat   3480
```

-continued

```
ggaatggaga taaggcccag gaaagaacca gaaagcaact tagtaaggtc aatggtgact   3540
gcaggatcaa ctgatcacat ggatcacttc tcccttggag tgcttgtgat tctgctcatg   3600
gtgcaggaag ggctgaagaa gagaatgacc acaaagatca tcataagcac atcaatggca   3660
gtgctggtag ctatgatcct gggaggattt tcaatgagtg acctggctaa gcttgcaatt   3720
ttgatgggtg ccaccttcgc ggaaatgaac actggaggag atgtagctca tctggcgctg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggttttg ctttggcctg gttggcaata   3960
cgagcgatgg ttgttccacg cactgataac atcaccttag caatcctggc tgctctgaca   4020
ccactggccc ggggcacact gcttgtggcg tggagagcag gccttgctac ttgcgggggg   4080
tttatgctcc tctctctgaa gggaaaaggc agtgtgaaga agaacttacc atttgtcatg   4140
gccctgggac taaccgctgt gaggctggtc gaccccatca acgtggtggg actgctgttg   4200
ctcacaagga gtgggaagcg gagctggccc cctagcgaag tactcacagc tgttggcctg   4260
atatgcgcat tggctggagg gttcgccaag gcagatatag agatggctgg gcccatggcc   4320
gcggtcggtc tgctaattgt cagttacgtg gtctcaggaa agagtgtgga catgtacatt   4380
gaaagagcag gtgacatcac atgggaaaaa gatgcggaag tcactggaaa cagtccccgg   4440
ctcgatgtgg cgctagatga gagtggtgat ttctccctgg tggaggatga cggtcccccc   4500
atgagagaga tcatactcaa ggtggtcctg atgaccatct gtggcatgaa cccaatagcc   4560
atacccttttg cagctggagc gtggtacgta tacgtgaaga ctggaaaaag gagtggtgct   4620
ctatgggatg tgcctgctcc caaggaagta aaaaaggggg agaccacaga tggagtgtac   4680
agagtaatga ctcgcagact gctaggttca acacaagttg gagtgggagt tatgcaagag   4740
ggggtctttc acactatgtg gcacgtcaca aaaggatccg cgctgagaag cggtgaaggg   4800
agacttgatc catactgggg agatgtcaag caggatctgg tgtcatactg tggtccatgg   4860
aagctagatg ccgcctggga cgggcacagc gaggtgcagc tcttggccgt gcccccccgga   4920
gagagagcga ggaacatcca gactctgccc ggaatattta agacaaagga tggggacatt   4980
ggagcggttg cactggatta cccagcagga acttcaggat ctccaatcct agacaagtgt   5040
gggagagtga taggacttta tggcaatggg gtcgtgatca aaaatgggag ttatgttagt   5100
gccatcaccc aagggaggag ggaggaagag actcctgttg agtgcttcga gccttcgatg   5160
ctgaagaaga agcagctaac tgtcttagac ttgcatcctg gagctgggaa aaccaggaga   5220
gttcttcctg aaatagtccg tgaagccata aaaacaagac tccgtactgt gatcttggct   5280
ccaaccaggg ttgtcgctgc tgaaatggag gaggccctta gagggcttcc agtgcgttat   5340
atgacaacag cagtcaatgt cacccactct ggaacagaaa tcgtcgactt aatgtgccat   5400
gccaccttca cttcacgtct actacagcca attagagtcc ccaactataa tctgtatatt   5460
atggatgagg cccacttcac agatccctca agtatagcag caagaggata catttcaaca   5520
agggttgaga tgggcgaggc ggctgccatc ttcatgaccg ccacgccacc aggaacccgt   5580
gacgcatttc cggactccaa ctcaccaatt atggacaccg aagtggaagt cccagagaga   5640
gcctggagct caggctttga ttgggtgacg gagtattctg gaaaaacagt ttggtttgtt   5700
ccacgcgtga ggaacggcaa tgagatcgca gcttgtctga caaaggctgg aaaacgggtc   5760
atacagctca gcagaaagac ttttgagaca gagttccaga aaacaaaaca tcaagagtgg   5820
gactttgtcg tgacaactga catttcagag atgggcgcca actttaaagc tgaccgtgtc   5880
```

-continued atagattcca ggagatgcct aaagccggtc atacttggtg gcgagagagt cattctggct 5940
ggacccatgc ctgtcacaca tgccagcgct gcccagagga gggggcgcat aggcaggaat 6000
cccaacaaac ctggagatga gtatctgtat ggaggtgggt gcgcagagac tgacgaagac 6060
catgcacact ggcttgaagc aagaatgctc cttgacaata tttacctcca agatggcctc 6120
atagcctcgc tctatcgacc tgaggccgac aaagtagcag ccattgaggg agagttcaag 6180
cttaggacgg agcaaaggaa gacctttgtg gaactcatga aaagaggaga tcttcctgtt 6240
tggctggcct atcaggttgc atctgccgga ataacctaca cagatagaag atggtgcttt 6300
gatggcacga ccaacaacac cataatggaa gacagtgtgc cggcagaggt gtggaccaga 6360
cacggagaga aaagagtgct caaaccgagg tggatggacg ccagagtttg ttcagatcat 6420
gcggccctga agtcattcaa ggagtttgcc gctgggaaaa gaggagcggc ttttggagtg 6480
atggaagccc tgggaacact gccaggacac atgacagaga gattccagga agccattgac 6540
aacctcgctg tgctcatgcg ggcagagact ggaagcaggc cttacaaagc cgcggcggcc 6600
caattgccgg agaccctaga gaccattatg cttttggggt tgctgggaac agtctcgctg 6660
ggaatctttt tcgtcttgat gaggaacaag ggcataggga agatgggctt tggaatggtg 6720
actcttgggg ccagcgcatg gctcatgtgg ctctcggaaa ttgagccagc cagaattgca 6780
tgtgtcctca ttgttgtgtt cctattgctg gtggtgctca tacctgagcc agaaaagcaa 6840
agatctcccc aggacaacca aatggccatc atcatcatgg tagcagtagg tcttctgggc 6900
ttgattaccg ccaatgaact cggatggttg gagagaacaa agagtgacct aagccatcta 6960
atgggaagga gagaggaggg ggcaaccatg ggattctcaa tggacattga cctgcggcca 7020
gcctcagctt gggccatcta tcctgccttg acatctttca ttaccccagc cgtccaacat 7080
gcagtgacca cttcatacaa caactactcc ttaatggcga tggccacgca agctggagtg 7140
ttgtttggta tgggcaaagg gatgccattc tacgcatggg actttggagt cccgctgcta 7200
atgataggtt gctactcaca attaacgccc ctgaccctaa tagtggccat cattttgctc 7260
gtggcgcact acatgtactt gatcccaggg ctgcaggcag cagctgcgcg tgctgcccag 7320
aagagaacgg cagctggcat catgaagaac cctgttgtgg agggaatagt ggtgactgac 7380
attgacacaa tgacaattga cccccaagtg gagaaaaaga tgggacaggt gctactcatg 7440
gcagtagccg tctccagcgc catactgtcg aggaccgcct gggggtgggg ggaggctggg 7500
gccctgatca cagccgcaac ttccactttg tgggaaggct ctccgaacaa gtactggaac 7560
tcctctacag ccacctcact gtgtaacatt tttaggggaa gttacttggc tggagcttct 7620
ctaatctaca cagtaacaag aaacgctggc ttggtcaaga gacgtggggg tggaacagga 7680
gagaccctgg gagagaaatg gaaggcccgc ttgaaccaga tgtcggccct ggagttctac 7740
tcctacaaaa agtcaggcat caccgaggtg tgcagagaag aggcccgccg cgccctcaag 7800
gacggtgtgg caacgggagg ccatgctgtg tcccgaggaa gtgcaaagct gagatggttg 7860
gtggagcggg gatacctgca gccctatgga aaggtcattg atcttggatg tggcagaggg 7920
ggctggagtt actacgccgc caccatccgc aaagttcaag aagtgaaagg atacacaaaa 7980
ggaggccctg gtcatgaaga acccgtgttg gtgcaaagct atgggtggaa catagtccgt 8040
cttaagagtg gggtggacgt ctttcatatg gcggctgagc cgtgtgacac gttgctgtgt 8100
gacataggtg agtcatcatc tagtcctgaa gtggaagaag cacggacgct cagagtcctc 8160
tccatggtgg gggattggct tgaaaaaaga ccaggagcct tttgtataaa agtgttgtgc 8220

-continued

```
ccatacacca gcactatgat ggaaaccctg gagcgactgc agcgtaggta tgggggagga   8280
ctggtcagag tgccactctc ccgcaactct acacatgaga tgtactgggt ctctggagcg   8340
aaaagcaaca ccataaaaag tgtgtccacc acgagccagc tcctcttggg gcgcatggac   8400
gggcctagga ggccagtgaa atatgaggag gatgtgaatc tcggctctgg cacgcgggct   8460
gtggtaagct gcgctgaagc tcccaacatg aagatcattg gtaaccgcat tgaaaggatc   8520
cgcgctgaga aagcggaaac gtggttcttt gacgagaacc acccatatag gacatgggct   8580
taccatggaa gctatgatgc cgccacacaa gggtcagcgt cctctctaat aaacggggtt   8640
gtcaggctcc tgtcaaaacc ctgggatgtg gtgactggag tcacaggaat agccatgacc   8700
gacaccacac cgtatggtca gcaaagagtt ttcaaggaaa aagtggacac tagggtgcca   8760
gacccccaag aaggcactcg tcaggttatg agcatggtct cttcctggtt gtggaaagag   8820
ctaggcaaac acaaacggcc acgagtctgt accaaagaag agttcatcaa caaggttcgt   8880
agcaatgcag cattaggggc aatatttgaa gaggaaaaag agtggaagac tgcagtggaa   8940
gctgtgaacg atccaaggtt ctgggctcta gtggacaagg aaagagagca ccacctgaga   9000
ggagagtgcc agagttgtgt gtacatcaca atgggaaaaa gagaaaagaa acaaggggaa   9060
tttggaaagg ccaagggcag ccgcgccatc tggtatatgt ggctaggggc tagatttcta   9120
gagttcgaag cccttggatt cttgaacgag gatcactgga tggggagaga gaactcagga   9180
ggtggtgttg aagggctggg attacaaaga ctcggatatg tcctagaaga gatgagtcgc   9240
ataccaggag gaaggatgta tgcagatgac actgctggct gggacacccg catcagcagg   9300
tttgatctgg agaatgaagc tctaatcacc aaccaaatgg agaaagggca cagggccttg   9360
gcattggcca taatcaagta cacataccaa aacaaagtgg taaaggtcct tagaccagct   9420
gaaaaaggga agacagttat ggacattatt tcgagacaag accaaagggg gagcggacaa   9480
gttgtcactt acgctctcaa cacatttacc aacctagtgg tgcaactcat tcggaatatg   9540
gaggctgagg aagttctaga gatgcaagac ttgtggctgc tgcggaggtc agagaaagtg   9600
accaactggt tgcagagcaa cggatgggat aggctcaaac gaatggcggt cagtggagat   9660
gattgcgttg tgaaaccaat tgatgatagg tttgcacatg ccctcaggtt cttgaatgat   9720
atgggaaaag ttaggaagga cacacaagag tggaaaccct caactggatg ggacaactgg   9780
gaagaagttc ccttctgctc ccaccacttc aacaagctcc atctcaagga cgggaggtcc   9840
attgtggttc cctgccgcca ccaagatgaa ctgattggcc gggcccgcgt ctctccaggg   9900
gcgggatgga gcatccggga gactgcttgc ctagcaaaat catatgcgca aatgtggcag   9960
ctcctttatt tccacagaag ggacctccga ctgatggcca atgccatttg ttcatctgtg  10020
ccagttgact gggttccaac tggagaagact acctggtcaa tccatggaaa gggagaatgg  10080
atgaccactg aagacatgct tgtggcgtgg aacagagtgt ggattgagga gaacgaccac  10140
atggaagaca agaccccagt cacgaaatgg acagacattc cctatttggg aaaaagggaa  10200
gacttgtggt gtggatctct catagggcac agaccgcgca ccacctgggc tgagaacatt  10260
aaaaacacag tcaacatggt gcgcaggatc ataggtgatg aagaaaagta catggactac  10320
ctatccaccc aagttcgcta cttgggtgaa gaagggtcta cacctggagt gctgtaagca  10380
ccaatcttaa tgttgtcagg cctgctagtc agccacagct tggggaaagc tgtgcagcct  10440
gtgacccccc caggagaagc tgggaaacca agcctatagt caggccgaga acgccatggc  10500
acggaagaag ccatgctgcc tgtgagcccc tcagaggaca ctgagtcaaa aaaccccacg  10560
cgcttggagg cgcaggatgg gaaaagaagg tggcgacctt ccccaccctt caatctgggg  10620
```

cctgaactgg agatcagctg tggatctcca gaagagggac tagtggttag aggaga 10676

<210> SEQ ID NO 11
<211> LENGTH: 10807
<212> TYPE: DNA
<213> ORGANISM: Zika virus

<400> SEQUENCE: 11
agttgttgat ctgtgtgagt cagactgcga cagttcgagt ctgaagcgag agctaacaac 60
agtatcaaca ggtttaattt ggatttggaa acgagagttt ctggtcatga aaaacccaaa 120
gaagaaatcc ggaggattcc ggattgtcaa tatgctaaaa cgcggagtag cccgtgtaaa 180
ccccttggga ggtttgaaga ggttgccagc cggacttctg ctgggtcatg gacccatcag 240
aatggttttg gcgatactag ccttttttgag atttacagca atcaagccat cactgggcct 300
tatcaacaga tggggttccg tggggaaaaa agaggctatg gaaataataa agaagttcaa 360
gaaagatctt gctgccatgt tgagaataat caatgctagg aaagagagga agagacgtgg 420
cgcagacacc agcatcggaa tcattggcct cctgctgact acagccatgg cagcagagat 480
cactagacgc gggagtgcat actacatgta cttggatagg agcgatgccg ggaaggccat 540
ttcgtttgct accacattgg gagtgaacaa gtgccacgta cagatcatgg acctcgggca 600
catgtgtgac gccaccatga gttatgagtg ccctatgctg gatgagggag tggaaccaga 660
tgatgtcgat tgctggtgca acacgacatc aacttgggtt gtgtacggaa cctgtcatca 720
caaaaaaggt gaggcacggc gatctagaag agccgtgacg ctcccttctc actctacaag 780
gaagttgcaa acgcggtcgc agacctggtt agaatcaaga gaatacacga agcacttgat 840
caaggttgaa aactggatat tcaggaaccc cgggtttgcg ctagtggccg ttgccattgc 900
ctggcttttg ggaagctcga cgagccaaaa agtcatatac ttggtcatga tactgctgat 960
tgccccggca tacagtatca ggtgcattgg agtcagcaat agagacttcg tggagggcat 1020
gtcaggtggg acctgggttg atgttgtctt ggaacatgga ggctgcgtta ccgtgatggc 1080
acaggacaag ccaacagttg acatagagtt ggtcacgacg acggttagta acatggccga 1140
ggtaagatcc tattgctacg aggcatcgat atcggacatg gcttcggaca gtcgttgccc 1200
aacacaaggt gaagcctacc ttgacaagca atcagacact caatatgtct gcaaaagaac 1260
attagtggac agaggttggg gaaacggttg tggacttttt ggcaaaggga gcttggtgac 1320
atgtgccaag tttacgtgtt ctaagaagat gaccgggaag agcattcaac cggaaaatct 1380
ggagtatcgg ataatgctat cagtgcatgg ctcccagcat agcgggatga ctgtcaatga 1440
tataggatat gaaactgacg aaaatagagc gaaagtcgag gttacgccta attcaccaag 1500
agcggaagca accttgggag gctttggaag cttaggactt gactgtgaac caaggacagg 1560
ccttgacttt tcagatctgt attacctgac catgaacaat aagcattggt tggtgcacaa 1620
agagtggttt catgacatcc cattgccttg gcatgctggg gcagacactg gaactccaca 1680
ctggaacaac aaagaggcat tggtagaatt caaggatgcc cacgccaaga ggcaaaccgt 1740
cgtcgttctg gggagccagg aaggagccgt tcacacggct ctcgctggag ctctagaggc 1800
tgagatggat ggtgcaaagg gaaagctgtt ctctggccat ttgaaatgcc gcctaaaaat 1860
ggacaagctt agattgaagg gcgtgtcata ttccttgtgc actgcggcat tcacattcac 1920
caaggtccca gctgaaacac tgcatggaac agtcacagtg gaggtgcagt atgcagggac 1980
agatggaccc tgcaagatcc cagtccagat ggcggtggac atgcagaccc tgaccccagt 2040
tggaaggctg ataaccgcca accccgtgat tactgaaagc actgagaact caaagatgat 2100
gttggagctt gacccaccat ttggggattc ttacattgtc ataggagttg gggacaagaa 2160
aatcacccac cactggcata ggagtggtag caccatcgga aaggcatttg aggccactgt 2220
gagaggcgcc aagagaatgg cagtcctggg ggatacagcc tgggacttcg gatcagtcgg 2280
gggtgtgttc aactcactgg gtaagggcat tcaccagatt tttggagcag ccttcaaatc 2340
actgtttgga ggaatgtcct ggttctcaca gatcctcata ggcacgctgc tagtgtggtt 2400
aggtttgaac acaaagaatg gatctatctc cctcacatgc ttggccctgg ggggagtgat 2460
gatcttcctc tccacggctg tttctgctga cgtggggtgc tcagtggact tctcaaaaaa 2520
ggaaacgaga tgtggcacgg gggtattcat ctataatgat gttgaagcct ggagggaccg 2580
gtacaagtac catcctgact ccccccgcag attggcagca gcagtcaagc aggcctggga 2640
agaggggatc tgtgggatct catccgtttc aagaatggaa aacatcatgt ggaaatcagt 2700
agaaggggag ctcaatgcta tcctagagga gaatggagtt caactgacag ttgttgtggg 2760
atctgtaaaa aaccccatgt ggagaggtcc acaaagattg ccagtgcctg tgaatgagct 2820
gccccatggc tggaaagcct gggggaaatc gtattttgtt agggcggcaa agaccaacaa 2880
cagttttgtt gtcgacggtg acacactgaa ggaatgtccg cttgagcaca gagcatggaa 2940
tagttttctt gtggaggatc acgggtttgg agtcttccac accagtgtct ggcttaaggt 3000
cagagaagat tactcattag aatgtgaccc agccgtcata ggaacagctg ttaagggaag 3060
ggaggccgcg cacagtgatc tgggctattg gattgaaagt gaaaagaatg acacatggag 3120
gctgaagagg gcccacctga ttgagatgaa aacatgtgaa tggccaaagt ctcacacatt 3180
gtggacagat ggagtagaag aaagtgatct tatcataccc aagtctttag ctggtccact 3240
cagccaccac aacaccagag agggttacag aacccaagtg aaagggccat ggcacagtga 3300
agagcttgaa atccggtttg aggaatgtcc aggcaccaag gtttacgtgg aggagacatg 3360
cggaactaga ggaccatctc tgagatcaac tactgcaagt ggaagggtca ttgaggaatg 3420
gtgctgtagg gaatgcacaa tgcccccact atcgtttcga gcaaaagacg gctgctggta 3480
tggaatggag ataaggccca ggaaagaacc agagagcaac ttagtgaggt caatggtgac 3540
agcggggtca accgatcata tggaccactt ctctcttgga gtgcttgtga ttctactcat 3600
ggtgcaggag gggttgaaga agagaatgac cacaaagatc atcatgagca catcaatggc 3660
agtgctggta gtcatgatct tgggaggatt ttcaatgagt gacctggcca agcttgtgat 3720
cctgatgggt gctactttcg cagaaatgaa cactggagga gatgtagctc acttggcatt 3780
ggtagcggca tttaaagtca gaccagcctt gctggtctcc ttcattttca gagccaattg 3840
gacaccccgt gagagcatgc tgctagccct ggcttcgtgt cttctgcaaa ctgcgatctc 3900
tgctcttgaa ggtgacttga tggtcctcat taatggattt gctttggcct ggttggcaat 3960
tcgagcaatg gccgtgccac gcactgacaa catcgctcta ccaatcttgg ctgctctaac 4020
accactagct cgaggcacac tgctcgtggc atggagagcg ggcctggcta cttgtggagg 4080
gatcatgctc ctctccctga aagggaaagg tagtgtgaag aagaacctgc catttgtcat 4140
ggccctggga ttgacagctg tgagggtagt agaccctatt aatgtggtag gactactgtt 4200
actcacaagg agtgggaagc ggagctggcc ccctagtgaa gttctcacag ccgttggcct 4260
gatatgtgca ctggccggag ggtttgccaa ggcagacatt gagatggctg gacccatggc 4320
tgcagtaggc ttgctaattg tcagctatgt ggtctcggga aagagtgtgg acatgtacat 4380
tgaaagagca ggtgacatca catgggaaaa ggacgcggaa gtcactggaa acagtcctcg 4440

```
gcttgacgtg gcactggatg agagtggtga tttctccttg gtagaggaag atggtccacc   4500
catgagagag atcatactta aggtggtcct gatggccatc tgtggcatga acccaatagc   4560
tatacctttt gctgcaggag cgtggtatgt gtatgtgaag actgggaaaa ggagtggcgc   4620
cctctgggac gtgcctgctc ccaaagaagt gaagaaagga gagaccacag atggagtgta   4680
cagagtgatg actcgcagac tgctaggttc aacacaggtt ggagtgggag tcatgcaaga   4740
gggagtcttc cacaccatgt ggcacgttac aaaaggagcc gcactgagga gcggtgaggg   4800
aagacttgat ccatactggg gggatgtcaa gcaggacttg gtgtcatact gtgggccttg   4860
gaagttggat gcagcttggg atggactcag cgaggtacag cttttggccg tacctcccgg   4920
agagagggcc agaaacattc agaccctgcc tggaatattc aagacaaagg acggggacat   4980
cggagcagtt gctctggact accctgcagg gacctcagga tctccgatcc tagacaaatg   5040
tggaagagtg ataggactct atggcaatgg ggttgtgatc aagaatggaa gctatgttag   5100
tgctataacc cagggaaaga gggaggagga gactccggtt gaatgtttcg aaccctcgat   5160
gctgaagaag aagcagctaa ctgtcttgga tctgcatcca ggagccggaa aaaccaggag   5220
agttcttcct gaaatagtcc gtgaagccat aaaaaagaga ctccggacag tgatcttggc   5280
accaactagg gttgtcgctg ctgagatgga ggaggccttg agaggacttc cggtgcgtta   5340
catgacaaca gcagtcaacg tcacccattc tgggacagaa atcgttgatt tgatgtgcca   5400
tgccactttc acttcacgct tactacaacc catcagagtc cctaattaca atctctacat   5460
catggatgaa gcccacttca cagacccctc aagtatagct gcaagaggat atatatcaac   5520
aagggttgaa atgggcgagg cggctgccat tttatgact gccacaccac caggaacccg    5580
tgatgcgttt cctgactcta actcaccaat catggacaca gaagtggaag tcccagagag   5640
agcctggagc tcaggctttg attgggtgac agaccattct gggaaaacag tttggttcgt   5700
tccaagcgtg agaaacggaa atgaaatcgc agcctgtctg acaaaggctg gaaagcgggt   5760
catacagctc agcaggaaga cttttgagac agaatttcag aaaacaaaaa atcaagagtg   5820
ggactttgtc ataacaactg acatctcaga gatgggcgcc aacttcaagg ctgaccgggt   5880
catagactct aggagatgcc taaaaccagt catacttgat ggtgagagag tcatcttggc   5940
tgggcccatg cctgtcacgc atgctagtgc tgctcagagg agaggacgta taggcaggaa   6000
ccctaacaaa cctggagatg agtacatgta tggaggtggg tgtgcagaga ctgatgaagg   6060
ccatgcacac tggcttgaag caagaatgct tcttgacaac atctacctcc aggatggcct   6120
catagcctcg ctctatcggc ctgaggccga taaggtagcc gccattgagg gagagtttaa   6180
gctgaggaca gagcaaagga agaccttcgt ggaactcatg aagagaggag accttcccgt   6240
ctggctagcc tatcaggttg catctgccgg aataacttac acagacagaa gatggtgctt   6300
tgatggcaca accaacaaca ccataatgga agacagcgta ccagcagagg tgtggacaaa   6360
gtatggagag aagagagtgc tcaaaccgag atggatggat gctagggtct gttcagacca   6420
tgcggccctg aagtcgttca aagaattcgc cgctggaaaa agaggagcgg ctttgggagt   6480
aatggaggcc ctgggaacac tgccaggaca catgacagag aggtttcagg aagccattga   6540
caacctcgcc gtgctcatgc gagcagagac tggaagcagg ccttataagg cagcggcagc   6600
ccaactgccg gagaccctag agaccattat gctcttaggt ttgctgggaa cagtttcact   6660
ggggatcttc ttcgtcttga tgcggaataa gggcatcggg aagatgggct ttggaatggt   6720
aacccttggg gccagtgcat ggctcatgtg gctttcggaa attgaaccag ccagaattgc   6780
```

atgtgtcctc attgttgtgt ttttattact ggtggtgctc atacccgagc cagagaagca 6840
aagatctccc caagataacc agatggcaat tatcatcatg gtggcagtgg gccttctagg 6900
tttgataact gcaaacgaac ttggatggct ggaaagaaca aaaaatgaca tagctcatct 6960
aatgggaagg agagaagaag gagcaaccat gggattctca atggacattg atctgcggcc 7020
agcctccgcc tgggctatct atgccgcatt gacaactctc atcaccccag ctgtccaaca 7080
tgcggtaacc acttcataca acaactactc cttaatggcg atggccacac aagctggagt 7140
gctgtttggc atgggcaaag ggatgccatt ttatgcatgg gaccttggag tcccgctgct 7200
aatgatgggt tgctattcac aattaacacc cctgactctg atagtagcta tcattctgct 7260
tgtggcgcac tacatgtact tgatcccagg cctacaagcg gcagcagcgc gtgctgccca 7320
gaaaaggaca gcagctggca tcatgaagaa tcccgttgtg gatggaatag tggtaactga 7380
cattgacaca atgacaatag acccccaggt ggagaagaag atgggacaag tgttactcat 7440
agcagtagcc atctccagtg ctgtgctgct gcggaccgcc tggggatggg gggaggctgg 7500
agctctgatc acagcagcga cctccacctt gtgggaaggc tctccaaaca aatactggaa 7560
ctcctctaca gccacctcac tgtgcaacat cttcagagga agctatctgg caggagcttc 7620
ccttatctat acagtgacga gaaacgctgg cctggttaag agacgtggag gtgggacggg 7680
agagactctg ggagagaagt ggaaagctcg tctgaatcag atgtcggccc tggagttcta 7740
ctcttataaa aagtcaggta tcactgaagt gtgtagagag gaggctcgcc gtgccctcaa 7800
ggatggagtg gccacaggag gacatgccgt atcccgggga agtgcaaagc tcagatggtt 7860
ggtggagaga ggatatctgc agccctatgg gaaggttgtt gacctcggat gtggcagagg 7920
gggctggagc tattatgccg ccaccatccg caaagtgcag gaggtgagag gatacacaaa 7980
gggaggtccc ggtcatgaag aacccatgct ggtgcaaagc tatgggtgga acatagttcg 8040
tctcaagagt ggagtggacg tcttccacat ggcggctgag ccgtgtgaca ctctgctgtg 8100
tgacataggt gagtcatcat ctagtcctga agtggaagag acacgaacac tcagagtgct 8160
ctctatggtg ggggactggc ttgaaaaaag accaggggcc ttctgtataa aggtgctgtg 8220
cccatacacc agcactatga tggaaaccat ggagcgactg caacgtaggc atgggggagg 8280
attagtcaga gtgccattgt ctcgcaactc cacacatgag atgtactggg tctctggggc 8340
aaagagcaac atcataaaaa gtgtgtccac cacaagtcag ctcctcctgg gacgcatgga 8400
tggccccagg aggccagtga aatatgagga ggatgtgaac ctcggctcgg gtacacgagc 8460
tgtggcaagc tgtgctgagg ctcctaacat gaaaatcatc ggcaggcgca ttgagagaat 8520
ccgcaatgaa catgcagaaa catggtttct tgatgaaaac cacccataca ggacatgggc 8580
ctaccatggg agctacgaag cccccacgca aggatcagcg tcttccctcg tgaacggggt 8640
tgttagactc ctgtcaaagc cttgggacgt ggtgactgga gttacaggaa tagccatgac 8700
tgacaccaca ccatacggcc aacaaagagt cttcaaagaa aaagtggaca ccagggtgcc 8760
agatccccaa gaaggcactc gccaggtaat gaacatagtc tcttcctggc tgtggaagga 8820
gctggggaaa cgcaagcggc cacgcgtctg caccaaagaa gagtttatca acaaggtgcg 8880
cagcaatgca gcactgggag caatatttga agaggaaaaa gaatggaaga cggctgtgga 8940
agctgtgaat gatccaaggt tttgggccct agtggatagg gagagagaac accacctgag 9000
aggagagtgt cacagctgtg tgtacaacat gatgggaaaa agagaaaaga agcaaggaga 9060
gttcgggaaa gcaaaaggta gccgcgccat ctggtacatg tggttgggag ccagattctt 9120
ggagtttgaa gcccttggat tcttgaacga ggaccattgg atgggaagag aaaactcagg 9180

-continued aggtggagtc gaagggttag gattgcaaag acttggatac attctagaag aaatgaatcg 9240
ggcaccagga ggaaagatgt acgcagatga cactgctggc tgggacaccc gcattagtaa 9300
gtttgatctg gagaatgaag ctctgattac caaccaaatg gaggaagggc acagaactct 9360
ggcgttggcc gtgattaaat acacatacca aaacaaagtg gtgaaggttc tcagaccagc 9420
tgaaggagga aaaacagtta tggacatcat ttcaagacaa gaccagagag ggagtggaca 9480
agttgtcact tatgctctca acacattcac caacttggtg gtgcagctta tccggaacat 9540
ggaagctgag gaagtgttag agatgcaaga cttatggttg ttgaggaagc cagagaaagt 9600
gaccagatgg ttgcagagca atggatggga tagactcaaa cgaatggcgg tcagtggaga 9660
tgactgcgtt gtgaagccaa tcgatgatag gtttgcacat gccctcaggt tcttgaatga 9720
catgggaaaa gttaggaaag acacacagga gtggaaaccc tcgactggat ggagcaattg 9780
ggaagaagtc ccgttctgct cccaccactt caacaagctg tacctcaagg atgggagatc 9840
cattgtggtc ccttgccgcc accaagatga actgattggc cgagctcgcg tctcaccagg 9900
ggcaggatgg agcatccggg agactgcctg tcttgcaaaa tcatatgcgc agatgtggca 9960
gctcctttat ttccacagaa gagaccttcg actgatggct aatgccattt gctcggctgt 10020
gccagttgac tgggtaccaa ctgggagaac cacctggtca atccatggaa agggagaatg 10080
gatgaccact gaggacatgc tcatggtgtg gaatagagtg tggattgagg agaacgacca 10140
tatggaggac aagactcctg taacaaaatg gacagacatt ccctatctag gaaaaaggga 10200
ggacttatgg tgtggatccc ttatagggca cagaccccgc accacttggg ctgaaaacat 10260
caaagacaca gtcaacatgg tgcgcaggat cataggtgat gaagaaaagt acatggacta 10320
tctatccacc caagtccgct acttgggtga ggaagggtcc acacccggag tgttgtaagc 10380
accaatttta gtgttgtcag gcctgctagt cagccacagt ttggggaaag ctgtgcagcc 10440
tgtaaccccc ccaggagaag ctgggaaacc aagctcatag tcaggccgag aacgccatgg 10500
cacggaagaa gccatgctgc ctgtgagccc ctcagaggac actgagtcaa aaaaccccac 10560
gcgcttggaa gcgcaggatg ggaaaagaag gtggcgacct tccccaccct tcaatctggg 10620
gcctgaactg gagactagct gtgaatctcc agcagaggga ctagtggtta gaggagaccc 10680
cccggaaaac gcaaaacagc atattgacgc tgggaaagac cagagactcc atgagtttcc 10740
accacgctgg ccgccaggca cagatcgccg aacagcggcg gccggtgtgg ggaaatccat 10800
ggtttct 10807

<210> SEQ ID NO 12
<211> LENGTH: 10794
<212> TYPE: DNA
<213> ORGANISM: Zika virus

<400> SEQUENCE: 12
agttgttgat ctgtgtgagt cagactgcga cagttcgagt ctgaagcgag agctaacaac 60
agtatcaaca ggtttaattt ggatttggaa acgagagttt ctggtcatga aaaaccccaa 120
agaagaaatc cggaggatcc ggattgtcaa tatgctaaaa cgcggagtag cccgtgtaaa 180
ccccttggga ggtttgaaga ggttgccagc cggacttctg ctgggtcatg gacccatcag 240
aatggttttg gcgatactag cctttttgag atttacagca atcaagccat cactgggcct 300
tatcaacaga tggggttccg tggggaaaaa agaggctatg gaaataataa agaagttcaa 360
gaaagatctt gctgccatgt tgagaataat caatgctagg aaagagagga agagacgtgg 420

-continued

```
cgcagacacc agcatcggaa tcattggcct cctgctgact acagccatgg cagcagagat    480
cactagacgc gggagtgcat actacatgta cttggatagg agcgatgccg ggaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720
caaaaaaggt gaggcacggc gatctagaag agccgtgacg ctcccttctc actctacaag    780
gaagttgcaa acgcggtcgc agacctggtt agaatcaaga gaatacacga agcacttgat    840
caaggttgaa aactggatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctgggttg atgttgtctt ggaacatgga ggctgcgtta ccgtgatggc   1080
acaggacaag ccaacagtcg acatagagtt ggtcacgacg acggttagta acatggccga   1140
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaaacggttg tggacttttt ggcaaaggga gcttggtgac   1320
atgtgccaag tttacgtgtt ctaagaagat gaccgggaag agcattcaac cggaaaatct   1380
ggagtatcgg ataatgctat cagtgcatgg ctcccagcat agcgggatga ttggatatga   1440
aactgacgaa gatagagcga aagtcgaggt tacgcctaat tcaccaagag cggaagcaac   1500
cttgggaggc tttggaagct taggacttga ctgtgaacca aggacaggcc ttgacttttc   1560
agatctgtat tacctgacca tgaacaataa gcattggttg gtgcacaaag agtggtttca   1620
tgacatccca ttgccttggc atgctggggc agacaccgga actccacact ggaacaacaa   1680
agaggcattg gtagaattca aggatgccca cgccaagagg caaaccgtcg tcgttctggg   1740
gagccaggaa ggagccgttc acacggctct cgctggagct ctagaggctg agatggatgg   1800
tgcaaaggga aggctgttct ctggccattt gaaatgccgc ctaaaaatgg acaagcttag   1860
attgaagggc gtgtcatatt ccttgtgcac tgcggcattc acattcacca aggtcccagc   1920
tgaaacactg catggaacag tcacagtgga ggtgcagtat gcagggacag atggaccctg   1980
caagatccca gtccagatgg cggtggacat gcagaccctg accccagttg gaaggctgat   2040
aaccgccaac cccgtgatta ctgaaagcac tgagaactca aagatgatgt tggagcttga   2100
cccaccattt ggggattctt acattgtcat aggagttggg gacaagaaaa tcacccacca   2160
ctggcatagg agtggtagca ccatcggaaa ggcatttgag gccactgtga gaggcgccaa   2220
gagaatggca gtcctggggg atacagcctg ggacttcgga tcagtcgggg gtgtgttcaa   2280
ctcactgggt aagggcattc accagatttt tggagcagcc ttcaaatcac tgtttggagg   2340
aatgtcctgg ttctcacaga tcctcatagg cacgctgcta gtgtggttag gtttgaacac   2400
aaagaatgga tctatctccc tcacatgctt ggccctgggg ggagtgatga tcttcctctc   2460
cacggctgtt tctgctgacg tggggtgctc agtggacttc tcaaaaaagg aaacgagatg   2520
tggcacgggg gtattcatct ataatgatgt tgaagcctgg agggaccggt acaagtacca   2580
tcctgactcc ccccgcagat tggcagcagc agtcaagcag gcctgggaag aggggatctg   2640
tgggatctca tccgtttcaa gaatggaaaa catcatgtgg aaatcagtag aaggggagct   2700
caatgctatc ctagaggaga atggagttca actgacagtt gttgtgggat ctgtaaaaaa   2760
ccccatgtgg agaggtccac aaagattgcc agtgcctgtg aatgagctgc cccatggctg   2820
```

```
gaaagcctgg gggaaatcgt attttgttag ggcggcaaag accaacaaca gttttgttgt   2880
cgacggtgac acactgaagg aatgtccgct tgagcacaga gcatggaata gttttcttgt   2940
ggaggatcac gggtttggag tcttccacac cagtgtctgg cttaaggtca gagaagatta   3000
ctcattagaa tgtgacccag ccgtcatagg aacagctgtt aagggaaggg aggccgcgca   3060
cagtgatctg ggctattgga ttgaaagtga aaagaatgac acatggaggc tgaagagggc   3120
ccacctgatt gagatgaaaa catgtgaatg gccaaagtct cacacattgt ggacagatgg   3180
agtagaagaa agtgatctta tcatacccaa gtctttagct ggtccactca gccaccacaa   3240
caccagagag ggttacagaa cccaagtgaa agggccatgg cacagtgaag agcttgaaat   3300
ccggtttgag gaatgtccag gcaccaaggt ttacgtggag gagacatgcg gaactagagg   3360
accatctctg agatcaacta ctgcaagtgg aagggtcatt gaggaatggt gctgtaggga   3420
atgcacaatg cccccactat cgtttcgagc aaaagacggc tgctggtatg gaatggagat   3480
aaggcccagg aaagaaccag agagcaactt agtgaggtca atggtgacag cggggtcaac   3540
cgatcatatg gaccacttct ctcttggagt gcttgtgatt ctactcatgg tgcaggaggg   3600
gttgaagaag agaatgacca caaagatcat catgagcaca tcaatggcag tgctggtagt   3660
catgatcttg ggaggatttt caatgagtga cctggccaag cttgtgatcc tgatgggtgc   3720
tactttcgca gaaatgaaca ctggaggaga tgtagctcac ttggcattgg tagcggcatt   3780
taaagtcaga ccagccttgc tggtctcctt cattttcaga gccaattgga caccccgtga   3840
gagcatgctg ctagccctgg cttcgtgtct tctgcaaact gcgatctctg ctcttgaagg   3900
tgacttgatg gtcctcatta atggatttgc tttggcctgg ttggcaattc gagcaatggc   3960
cgtgccacgc actgacaaca tcgctctacc aatcttggct gctctaacac cactagctcg   4020
aggcacactg ctcgtggcat ggagagcggg cctggctact tgtggaggga tcatgctcct   4080
ctccctgaaa gggaaaggta gtgtgaagaa gaacctgcca tttgtcatgg ccctgggatt   4140
gacagctgtg agggtagtag accctattaa tgtggtagga ctactgttac tcacaaggag   4200
tgggaagcgg agctggcccc ctagtgaagt tctcacagcc gttggcctga tatgtgcact   4260
ggccggaggg tttgccaagg cagacattga gatggctgga cccatggctg cagtaggctt   4320
gctaattgtc agctatgtgg tctcgggaaa gagtgtggac atgtacattg aaagagcagg   4380
tgacatcaca tgggaaaagg acgcggaagt cactggaaac agtcctcggc ttgacgtggc   4440
actggatgag agtggtgact tctccttggt agaggaagat ggtccaccca tgagagagat   4500
catactcaag gtggtcctga tggccatctg tggcatgaac ccaatagcta taccttttgc   4560
tgcaggagcg tggtatgtgt atgtgaagac tgggaaaagg agtggcgccc tctgggacgt   4620
gcctgctccc aaagaagtga agaaaggaga gaccacagat ggagtgtaca gagtgatgac   4680
tcgcagactg ctaggttcaa cacaggttgg agtgggagtc atgcaagagg gagtcttcca   4740
caccatgtgg cacgttacaa aaggagccgc actgaggagc ggtgagggaa gacttgatcc   4800
atactggggg gatgtcaagc aggacttggt gtcatactgt gggccttgga agttggatgc   4860
agcttgggat ggactcagcg aggtacagct tttggccgta cctcccggag agagggccag   4920
aaacattcag accctgcctg gaatattcaa gacaaaggac ggggacatcg gagcagttgc   4980
tctggactac cctgcaggga cctcaggatc tccgatccta gacaaatgtg gaagagtgat   5040
aggactctat ggcaatgggg ttgtgatcaa gaatggaagc tatgttagtg ctataaccca   5100
gggaaagagg gaggaggaga ctccggttga atgtttcgaa ccctcgatgc tgaagaagaa   5160
```

-continued

```
gcagctaact gtcttggatc tgcatccagg agccggaaaa accaggagag ttcttcctga   5220
aatagtccgt gaagccataa aaaagagact ccggacagtg atcttggcac caactagggt   5280
tgtcgctgct gagatggagg aggccttgag aggacttccg gtgcgttaca tgacaacagc   5340
agtcaacgtc acccattctg ggacagaaat cgttgatttg atgtgccatg ccactttcac   5400
ttcacgctta ctacaaccca tcagagtccc taattacaat ctcaacatca tggatgaagc   5460
ccacttcaca gacccctcaa gtatagctgc aagaggatac atatcaacaa gggttgaaat   5520
gggcgaggcg gctgccattt ttatgactgc cacaccacca ggaacccgtg atgcgtttcc   5580
tgactctaac tcaccaatca tggacacaga agtggaagtc ccagagagag cctggagctc   5640
aggctttgat tgggtgacag accattctgg gaaaacagtt tggttcgttc caagcgtgag   5700
aaacggaaat gaaatcgcag cctgtctgac aaaggctgga aagcgggtca tacagctcag   5760
caggaagact tttgagacag aatttcagaa aacaaaaaat caagagtggg actttgtcat   5820
aacaactgac atctcagaga tgggcgccaa cttcaaggct gaccgggtca tagactctag   5880
gagatgccta aaaccagtca tacttgatgg tgagagagtc atcttggctg ggcccatgcc   5940
tgtcacgcat gctagtgctg ctcagaggag aggacgtata ggcaggaacc ctaacaaacc   6000
tggagatgag tacatgtatg gaggtgggtg tgcagagact gatgaaggcc atgcacactg   6060
gcttgaagca agaatgcttc ttgacaacat ctacctccag gatggcctca tagcctcgct   6120
ctatcggcct gaggccgata aggtagccgc cattgaggga gagtttaagc tgaggacaga   6180
gcaaaggaag accttcgtgg aactcatgaa gagaggagac cttcccgtct ggctagccta   6240
tcaggttgca tctgccggaa taacttacac agacagaaga tggtgctttg atggcacaac   6300
caacaacacc ataatggaag acagtgtacc agcagaggtt tggacaaagt atggagagaa   6360
gagagtgctc aaaccgagat ggatggatgc tagggtctgt tcagaccatg cggccctgaa   6420
gtcgttcaaa gaattcgccg ctggaaaaag aggagcggct ttgggagtaa tggaggccct   6480
gggaacactg ccaggacaca tgacagagag gtttcaggaa gccattgaca acctcgccgt   6540
gctcatgcga gcagagactg gaagcaggcc ttataaggca gcggcagccc aactgccgga   6600
gaccctagag accattatgc tcttaggttt gctgggaaca gtttcactgg ggatcttctt   6660
cgtcttgatg cggaataagg gcatcgggaa gatgggcttt ggaatggtaa cccttggggc   6720
cagtgcatgg ctcatgtggc tttcggaaat tgaaccagcc agaattgcat gtgtcctcat   6780
tgttgtgttt ttattactgg tggtgctcat acccgagcca gagaagcaaa gatctcccca   6840
agataaccag atggcaatta tcatcatggt ggcagtgggc cttctaggtt tgataactgc   6900
aaacgaactt ggatggctgg aaagaacaaa aaatgacata gctcatctaa tgggaaggag   6960
agaagaagga gcaaccatgg gattctcaat ggacattgat ctgcggccag cctccgcctg   7020
ggctatctat gccgcattga caactctcat caccccagct gtccaacatg cggtaaccac   7080
ttcatacaac aactactcct taatggcgat ggccacacaa gctggagtgc tgtttggcat   7140
gggcaaaggg atgccattta tgcatgggga ccttggagtc ccgctgctaa tgatgggttg   7200
ctattcacaa ttaacacccc tgactctgat agtagctatc attctgcttg tggcgcacta   7260
catgtacttg atcccaggcc tacaagcggc agcagcgcgt gctgcccaga aaaggacagc   7320
agctggcatc atgaagaatc ccgttgtgga tggaatagtg gtaactgaca ttgacacaat   7380
gacaatagac ccccaggtgg agaagaagat gggacaagtg ttactcatag cagtagccat   7440
ctccagtgct gtgctgctgc ggaccgcctg ggatgggggg gaggctggag ctctgatcac   7500
agcagcgacc tccaccttgt gggaaggctc tccaaacaaa tactggaact cctctacagc   7560
```

-continued

```
cacctcactg tgcaacatct tcagaggaag ctatctggca ggagcttccc ttatctatac   7620
agtgacgaga aacgctggcc tggttaagag acgtggaggt gggacgggag agactctggg   7680
agagaagtgg aaagctcgtc tgaatcagat gtcggccctg gagttctact cttataaaaa   7740
gtcaggtatc actgaagtgt gtagagagga ggctcgccgt gccctcaagg atggagtggc   7800
cacaggagga catgccgtat cccggggaag tgcaaagatc agatggttgg aggagagagg   7860
atatctgcag ccctatggga aggttgttga cctcggatgt ggcagagggg gctggagcta   7920
ttatgccgcc accatccgca aagtgcagga ggtgagagga tacacaaagg gaggtcccgg   7980
tcatgaagaa cccatgctgg tgcaaagcta tgggtggaac atagttcgtc tcaagagtgg   8040
agtggacgtc ttccacatgg cggctgagcc gtgtgacact ctgctgtgtg acataggtga   8100
gtcatcatct agtcctgaag tggaagagac acgaacactc agagtgctct ctatggtggg   8160
ggactggctt gaaaaaagac caggggcctt ctgtataaag gtgctgtgcc catacaccag   8220
cactatgatg gaaaccatgg agcgactgca acgtaggcat gggggaggat tagtcagagt   8280
gccattgtgt cgcaactcca cacatgagat gtactgggtc tctggggcaa agagcaacat   8340
cataaaaagt gtgtccacca caagtcagct cctcctggga cgcatggatg gccccaggag   8400
gccagtgaaa tatgaggagg atgtgaacct cggctcgggt acacgagctg tggcaagctg   8460
tgctgaggct cctaacatga aaatcatcgg caggcgcatt gagagaatcc gcaatgaaca   8520
tgcagaaaca tggtttcttg atgaaaacca cccatacagg acatgggcct accatgggag   8580
ctacgaagcc cccacgcaag gatcagcgtc ttccctcgtg aacggggttg ttagactcct   8640
gtcaaagcct tgggacgtgg tgactggagt tacaggaata gccatgactg acaccacacc   8700
atacggccaa caaagagtct tcaaagaaaa agtggacacc agggtgccag atccccaaga   8760
aggcactcgc caggtaatga acatagtctc ttcctggctg tggaaggagc tggggaaacg   8820
caagcggcca cgcgtctgca ccaaagaaga gtttatcaac aaggtgcgca gcaatgcagc   8880
actgggagca atatttgaag aggaaaaaga atggaagacg gctgtggaag ctgtgaatga   8940
tccaaggttt tgggccctag tggataggga gagagaacac cacctgagag gagagtgtca   9000
cagctgtgtg tacaacatga tgggaaaaag agaaaagaag caaggagagt tcgggaaagc   9060
aaaaggtagc cgcgccatct ggtacatgtg gttgggagcc agattcttgg agtttgaagc   9120
ccttggattc ttgaacgagg accattggat gggaagagaa aactcaggag gtggagtcga   9180
agggttagga ttgcaaagac ttggatacat tctagaagaa atgaatcggg caccaggagg   9240
aaagatgtac gcagatgaca ctgctggctg ggacacccgc attagtaagt ttgatctgga   9300
gaatgaagct ctgattacca accaaatgga ggaagggcac agaactctgg cgttggccgt   9360
gattaaatac acataccaaa acaaagtggt gaaggttctc agaccagctg aaggaggaaa   9420
aacagttatg gacatcattt caagacaaga ccagagaggg agtggacaag ttgtcactta   9480
tgctctcaac acattcacca acttggtggt gcagcttatc cggaacatgg aagctgagga   9540
agtgttagag atgcaagact tatggttgtt gaggaagcca gagaaagtga ccagatggtt   9600
gcagagcaat ggatgggata gactcaaacg aatggcggtc agtggagatg actgcgttgt   9660
gaagccaatc gatgataggt ttgcacatgc cctcaggttc ttgaatgaca tgggaaaagt   9720
taggaaagac acacaggagt ggaaaccctc gactggatgg agcaattggg aagaagtccc   9780
gttctgctcc caccacttca acaagctgta cctcaaggat gggagatcca ttgtggtccc   9840
ttgccgccac caagatgaac tgattggccg agctcgcgtc tcaccagggg caggatggag   9900
```

```
catccgggag actgcctgtc ttgcaaaatc atatgcgcag atgtggcagc tcctttattt   9960

ccacagaaga gaccttcgac tgatggctaa tgccatttgc tcggctgtgc cagttgactg  10020

ggtaccaact gggagaacca cctggtcaat ccatggaaag ggagaatgga tgaccactga  10080

ggacatgctc atggtgtgga atagagtgtg gattgaggag aacgaccata tggaggacaa  10140

gactcctgta acaaaatgga cagacattcc ctatctagga aaaagggagg acttatggtg  10200

tggatccctt atagggcaca gaccccgcac cacttgggct gaaaacatca aagacacagt  10260

caacatggtg cgcaggatca taggtgatga agaaaagtac atggactatc tatccaccca  10320

agtccgctac ttgggtgagg aagggtccac acccggagtg ttgtaagcac caattttagt  10380

gttgtcaggc ctgctagtca gccacagttt ggggaaagct gtgcagcctg taacccccc   10440

aggagaagct gggaaaccaa gctcatagtc aggccgagaa cgccatggca cggaagaagc  10500

catgctgcct gtgagcccct cagaggacac tgagtcaaaa aaccccacgc gcttggaagc  10560

gcaggatggg aaaagaaggt ggcgaccttc cccacccttc aatctggggc ctgaactgga  10620

gactagctgt gaatctccag cagagggact agtggttaga ggagaccccc cggaaaacgc  10680

aaaacagcat attgacgtgg gaaagaccag agactccatg agtttccacc acgctggccg  10740

ccaggcacag atcgccgaac ttcggcggcc ggtgtgggga aatccatggt ttct        10794


<210> SEQ ID NO 13
<211> LENGTH: 10617
<212> TYPE: DNA
<213> ORGANISM: Zika virus

<400> SEQUENCE: 13

agtatcaaca ggttttattt tggatttgga aacgagagtt tctggtcatg aaaaacccaa     60

aaaagaaatc cggaggattc cggattgtca atatgctaaa acgcggagta gcccgtgtga    120

gcccctttgg gggcttgaag aggctgccag ccggacttct gctgggtcat gggcccatca    180

ggatggtctt ggcgattcta gcctttttga gattcacggc aatcaagcca tcactgggtc    240

tcatcaatag atggggttca gtggggaaaa aagaggctat ggaaataata aagaagttca    300

agaaagatct ggctgccatg ctgagaataa tcaatgctag gaaggagaag aagagacgag    360

gcgcagatac tagtgtcgga attgttggcc tcctgctgac cacagctatg gcagcggagg    420

tcactagacg tgggagtgca tactatatgt acttggacag aaacgacgct ggggaggcca    480

tatcttttcc aaccacattg ggatgaata agtgttatat acagatcatg gatcttggac    540

acatgtgtga tgccaccatg agctatgaat gccctatgct ggatgagggg gtggaaccag    600

atgacgtcga ttgttggtgc aacacgacgt caacttgggt tgtgtacgga acctgccatc    660

acaaaaaagg tgaagcacgg agatctagaa gagctgtgac gctcccctcc cattccacta    720

ggaagctgca aacgcggtcg caaacctggt tggaatcaag agaatacaca aagcacttga    780

ttagagtcga aaattggata ttcaggaacc ctggcttcgc gttagcagca gctgccatcg    840

cttggctttt gggaagctca acgagccaaa aagtcatata cttggtcatg atactgctga    900

ttgccccggc atacagcatc aggtgcatag gagtcagcaa tagggacttt gtggaaggta    960

tgtcaggtgg gacttgggtt gatgttgtct tggaacatgg aggttgtgtc accgtaatgg   1020

cacaggacaa accgactgtc gacatagagc tggttacaac aacagtcagc aacatggcgg   1080

aggtaagatc ctactgctat gaggcatcaa tatcggacat ggcttcggac agccgctgcc   1140

caacacaagg tgaagcctac cttgacaagc aatcagacac tcaatatgtc tgcaaaagaa   1200

cgttagtgga cagaggctgg ggaaatggat gtggactttt tggcaaaggg agcctggtga   1260
```

```
catgcgctaa gtttgcatgc tccaagaaaa tgaccgggaa gagcatccag ccagagaatc   1320
tggagtaccg gataatgctg tcagttcatg gctcccagca cagtgggatg atcgttaatg   1380
acacaggaca tgaaactgat gagaatagag cgaaggttga gataacgccc aattcaccaa   1440
gagccgaagc caccctgggg ggttttggaa gcctaggact tgattgtgaa ccgaggacag   1500
gccttgactt ttcagatttg tattacttga ctatgaataa caagcactgg ttggttcaca   1560
aggagtggtt ccacgacatt ccattacctt ggcacgctgg ggcagacacc ggaactccac   1620
actggaacaa caaagaagca ctggtagagt tcaaggacgc acatgccaaa aggcaaactg   1680
tcgtggttct agggagtcaa gaaggagcag ttcacacggc ccttgctgga gctctggagg   1740
ctgagatgga tggtgcaaag ggaaggctgt cctctggcca cttgaaatgt cgcctgaaaa   1800
tggataaact tagattgaag ggcgtgtcat actccttgtg taccgcagcg ttcacattca   1860
ccaagatccc ggctgaaaca ctgcacggga cagtcacagt ggaggtacag tacgcaggga   1920
cagatggacc ttgcaaggtt ccagctcaga tggcggtgga catgcaaact ctgaccccag   1980
ttgggaggtt gataaccgct aaccccgtaa tcactgaaag cactgagaac tctaagatga   2040
tgctggaact tgatccacca tttggggact cttacattgt cataggagtc ggggagaaga   2100
agatcaccca ccactggcac aggagtggca gcaccattgg aaaagcattt gaagccactg   2160
tgagaggtgc caagagaatg gcagtcttgg gagacacagc ctgggacttt ggatcagttg   2220
gaggcgctct caactcattg ggcaagggca tccatcaaat ttttggagca gctttcaaat   2280
cattgtttgg aggaatgtcc tggttctcac aaattctcat tggaacgttg ctgatgtggt   2340
tgggtctgaa cacaaagaat ggatctattt cccttatgtg cttggcctta gggggagtgt   2400
tgatcttctt atccacagct gtctctgctg atgtggggtg ctcggtggac ttctcaaaga   2460
aggagacgag atgcggtaca ggggtgttcg tctataacga cgttgaagcc tggagggaca   2520
ggtacaagta ccatcctgac tccccccgta gattggcagc agcagtcaag caagcctggg   2580
aagatggtat ctgtgggatc tcctctgttt caagaatgga aaacatcatg tggagatcag   2640
tagaagggga gctcaacgca atcctggaag agaatggagt tcaactgacg gtcgttgtgg   2700
gatctgtaaa aaaccccatg tggagaggtc cacagagatt gcccgtgcct gtgaacgagc   2760
tgccccacgg ctggaaggct tgggggaaat cgtacttcgt cagagcagca aagacaaata   2820
acagctttgt cgtggatggt gacacactga aggaatgccc actcaaacat agagcatgga   2880
acagctttct tgtggaggat catgggttcg ggggtatttca cactagtgtc tggctcaagg   2940
ttagagaaga ttattcatta gagtgtgatc cagccgttat tggaacagct gttaagggaa   3000
aggaggctgt acacagtgat ctaggctact ggattgagag tgagaagaat gacacatgga   3060
ggctgaagag ggcccatctg atcgagatga aaacatgtga atggccaaag tcccacacat   3120
tgtggacaga tggaatagaa gagagtgatc tgatcatacc caagtcttta gctgggccac   3180
tcagccatca caataccaga gagggctaca ggacccaaat gaaagggcca tggcacagtg   3240
aagagcttga aattcggttt gaggaatgcc caggcactaa ggtccacgtg gaggaaacat   3300
gtggaacaag aggaccatct ctgagatcaa ccactgcaag cggaagggtg atcgaggaat   3360
ggtgctgcag ggagtgcaca atgcccccac tgtcgttccg ggctaaagat ggctgttggt   3420
atggaatgga gataaggccc aggaaagaac cagaaagtaa cttagtaagg tcaatggtga   3480
ctgcaggatc aactgatcac atggatcact tctcccttgg agtgcttgtg attctgctca   3540
tggtgcagga agggctgaag aagagaatga ccacaaagat catcataagc acatcgatgg   3600
```

```
cagtgctggt agctatgatc ctgggaggat tttcaatgag tgacctggct aagcttgcaa   3660
ttttgatggg tgccaccttc gcggaaatga acactggagg agatgtagct catctggcgc   3720
tgatagcggc attcaaagtc agaccagcgt tgctggtatc tttcatcttc agagctaatt   3780
ggacaccccg tgaaagcatg ctgctggcct tggcctcgtg tcttttgcaa actgcgatct   3840
ccgccttgga aggcgacctg atggttctca tcaatggttt tgctttggcc tggttggcaa   3900
tacgagcgat ggttgttcca cgcactgata acatcacctt ggcaatcctg gctgctctga   3960
caccactggc ccggggcaca ctgcttgtgg cgtggagagc aggccttgct acttgcgggg   4020
ggtttatgct cctctctctg aagggaaaag gcagtgtgaa gaagaactta ccatttgtca   4080
tggccctggg actaaccgct gtgaggctgg tcgaccccat caacgtggtg ggactgctgt   4140
tgctcacaag gagtgggaag cggagctggc cccctagcga agtactcaca gctgttggcc   4200
tgatatgcgc attggctgga gggttcgcca aggcagatat agagatggct gggcccatgg   4260
ccgcggtcgg tctgctaatt gtcagttacg tggtctcagg aaagagtgtg gacatgtaca   4320
ttgaaagagc aggtgacatc acatgggaaa aagatgcgga agtcactgga aacagtcccc   4380
ggctcgatgt ggcgctagat gagagtggtg atttctccct ggtggaggat gacggtcccc   4440
ccatgagaga gatcatactc aaggtggtcc tgatgaccat ctgtggcatg aacccaatag   4500
ccataccctt tgcagctgga gcgtggtacg tatacgtgaa gactggaaaa aggagtggtg   4560
ctctatggga tgtgcctgct cccaaggaag taaaaaaggg ggagaccaca gatggagtgt   4620
acagagtaat gactcgtaga ctgctaggtt caacacaagt tggagtggga gttatgcaag   4680
agggggtctt tcacactatg tggcacgtca caaaaggatc cgcgctgaga agcggtgaag   4740
ggagacttga tccatactgg ggagatgtca agcaggatct ggtgtcatac tgtggtccat   4800
ggaagctaga tgccgcctgg gacgggcaca gcgaggtgca gctcttggcc gtgccccccg   4860
gagagagagc gaggaacatc cagactctgc ccggaatatt taagacaaag gatggggaca   4920
ttggagcggt tgcgctggat tacccagcag gaacttcagg atctccaatc ctagacaagt   4980
gtgggagagt gataggactt tatggcaatg gggtcgtgat caaaaatggg agttatgtta   5040
gtgccatcac ccaagggagg agggaggaag agactcctgt tgagtgcttc gagccttcga   5100
tgctgaagaa gaagcagcta actgtcttag acttgcatcc tggagctggg aaaaccagga   5160
gagttcttcc tgaaatagtc cgtgaagcca taaaaacaag actccgtact gtgatcttag   5220
ctccaaccag ggttgtcgct gctgaaatgg aggaagccct tagagggctt ccagtgcgtt   5280
atatgacaac agcagtcaat gtcacccact ctggaacaga aatcgtcgac ttaatgtgcc   5340
atgccacctt cacttcacgt ctactacagc caatcagagt ccccaactat aatctgtata   5400
ttatggatga ggcccacttc acagatccct caagtatagc agcaagagga tacatttcaa   5460
caagggttga gatgggcgag gcggctgcca tcttcatgac cgccacgcca ccaggaaccc   5520
gtgacgcatt tccggactcc aactcaccaa ttatggacac cgaagtggaa gtcccagaga   5580
gagcctggag ctcaggcttt gattgggtga cggatcattc tggaaaaaca gtttggtttg   5640
ttccaagcgt gaggaacggc aatgagatcg cagcttgtct gacaaaggct ggaaaacggg   5700
tcatacagct cagcagaaag acttttgaga cagagttcca gaaaacaaaa catcaagagt   5760
gggactttgt cgtgacaact gacatttcag agatgggcgc caactttaaa gctgaccgtg   5820
tcatagattc caggagatgc ctaaagccgg tcatacttga tggcgagaga gtcattctgg   5880
ctggacccat gcctgtcaca catgccagcg ctgcccagag gagggggcgc ataggcagga   5940
atcccaacaa acctggagat gagtatctgt atggaggtgg gtgcgcagag actgacgaag   6000
```

-continued accatgcaca ctggcttgaa gcaagaatgc tccttgacaa tatttacctc caagatggcc 6060
tcatagcctc gctctatcga cctgaggccg acaaagtagc agccattgag ggagagttca 6120
agcttaggac ggagcaaagg aagacctttg tggaactcat gaaaagagga gatcttcctg 6180
tttggctggc ctatcaggtt gcatctgccg gaataaccta cacagataga agatggtgct 6240
ttgatggcac gaccaacaac accataatgg aagacagtgt gccggcagag gtgtggacca 6300
gacacggaga gaaaagagtg ctcaaaccga ggtggatgga cgccagagtt tgttcagatc 6360
atgcggccct gaagtcattc aaggagtttg ccgctgggaa aagaggagcg gcttttggag 6420
tgatggaagc cctgggaaca ctgccaggac acatgacaga gagattccag gaagccattg 6480
acaacctcgc tgtgctcatg cgggcagaga ctggaagcag gccttacaaa gccgcggcgg 6540
cccaattgcc ggagacccta gagaccatta tgcttttggg gttgctggga acagtctcgc 6600
tgggaatctt tttcgtcttg atgaggaaca agggcatagg gaagatgggc tttggaatgg 6660
tgactcttgg ggccagcgca tggctcatgt ggctctcgga aattgagcca gccagaattg 6720
catgtgtcct cattgttgtg ttcctattgc tggtggtgct catacctgag ccagaaaagc 6780
aaagatctcc ccaggacaac caaatggcaa tcatcatcat ggtagcagta ggtcttctgg 6840
gcttgattac cgccaatgaa ctcggatggt tggagagaac aaagagtgac ctaagccatc 6900
taatgggaag gagagaggag gggggcaacca taggattctc aatggacatt gacctgcggc 6960
cagcctcagc ttgggccatc tatgctgcct tgacaacttt cattacccca gccgtccaac 7020
atgcagtgac cacttcatac aacaactact ccttaatggc gatggccacg caagctggag 7080
tgttgtttgg tatgggcaaa gggatgccat tctacgcatg ggactttgga gtcccgctgc 7140
taatgatagg ttgctactca caattaacac ccctgaccct aatagtggcc atcattttgc 7200
tcgtggcgca ctacatgtac ttgatcccag ggctgcaggc agcagctgcg cgtgctgccc 7260
agaagagaac ggcagctggc atcatgaaga accctgttgt ggatggaata gtggtgactg 7320
acattgacac aatgacaatt gacccccaag tggagaaaaa gatgggacag gtgctactca 7380
tagcagtagc cgtctccagc gccatactgt cgcggaccgc ctgggggtgg ggggaggctg 7440
gggccctgat cacagcggca acttccactt tgtgggaagg ctctccgaac aagtactgga 7500
actcctctac agccacttca ctgtgtaaca tttttagggg aagttacttg gctggagctt 7560
ctctaatcta cacagtaaca agaaacgctg gcttggtcaa gagacgtggg ggtggaacag 7620
gagagaccct gggagagaaa tggaaggccc gcttgaacca gatgtcggcc ctggagttct 7680
actcctacaa aaagtcaggc atcaccgagg tgtgcagaga agaggcccgc cgcgccctca 7740
aggacggtgt ggcaacggga ggccatgctg tgtcccgagg aagtgcaaag ctgagatggt 7800
tggtggagcg gggatacctg cagccctatg gaaaggtcat tgatcttgga tgtggcagag 7860 gggctggag ttactacgcc gccaccatcc gcaaagttca agaagtgaaa ggatacacaa 7920
aaggaggccc tggtcatgaa gaacccatgt tggtgcaaag ctatgggtgg aacatagtcc 7980
gtcttaagag tggggtggac gtctttcata tggcggctga gccgtgtgac acgttgctgt 8040
gtgacatagg tgagtcatca tctagtcctg aagtggaaga agcacggacg ctcagagtcc 8100
tctccatggt gggggattgg cttgaaaaaa gaccaggagc cttttgtata aaagtgttgt 8160
gcccatacac cagcactatg atggaaaccc tggagcgact gcagcgtagg tatgggggag 8220
gactggtcag agtgccactc tcccgcaact ctacacatga gatgtactgg gtctctggag 8280
cgaaaagcaa caccataaaa agtgtgtcca ccacgagcca gctcctcttg ggcgcatgg 8340

-continued

```
acgggcccag gaggccagtg aaatatgagg aggatgtgaa tctcggctct ggcacgcggg   8400
ctgtggtaag ctgcgctgaa gctcccaaca tgaagatcat tggtaaccgc attgaaagga   8460
tccgcagtga gcacgcggaa acgtggttct ttgacgagaa ccacccatat aggacatggg   8520
cttaccatgg aagctatgag gcccccacac aagggtcagc gtcctctcta ataaacgggg   8580
ttgtcaggct cctgtcaaaa ccctgggatg tggtgactgg agtcacagga atagccatga   8640
ccgacaccac accgtatggt cagcaaagag ttttcaagga aaaagtggac actagggtgc   8700
cagaccccca agaaggcact cgtcaggtta tgagcatggt ctcttcctgg ttgtggaaag   8760
agctaggcaa acacaaacgg ccacgagtct gtaccaaaga agagttcatc aacaaggttc   8820
gtagcaatgc agcattaggg gcaatatttg aagaggaaaa agagtggaag actgcagtgg   8880
aagctgtgaa cgatccaagg ttctgggctc tagtggacaa ggaaagagag caccacctga   8940
gaggagagtg ccagagttgt gtgtacaaca tgatgggaaa aagagaaaag aaacaagggg   9000
aatttggaaa ggccaagggc agccgcgcca tctggtatat gtggctaggg gctagatttc   9060
tagagttcga agcccttgga ttcttgaacg aggatcactg gatggggaga gagaactcag   9120
gaggtggtgt tgaagggctg ggattacaaa gactcggata tgtcctagaa gagatgagtc   9180
gcataccagg aggaaggatg tatgcagatg acactgctgg ctgggacacc cgcatcagca   9240
ggtttgatct ggagaatgaa gctctaatca ccaaccaaat ggagaaaggg cacagggcct   9300
tggcattggc cataatcaag tacacatacc aaaacaaagt ggtaaaggtc cttagaccag   9360
ctgaaaaagg gaagacagtt atggacatta tttcgagaca agaccaaagg gggagcggac   9420
aagttgtcac ttacgctctt aacacattta ccaacctagt ggtgcaactc attcggaata   9480
tggaggctga ggaagttcta gagatgcaag acttgtggct gctgcggagg tcagagaaag   9540
tgaccaactg gttgcagagc aacggatggg ataggctcaa acgaatggca gtcagtggag   9600
atgattgcgt tgtgaagcca attgatgata ggtttgcaca tgccctcagg ttcttgaatg   9660
atatgggaaa agttaggaag gacacacaag agtggaaacc ctcaactgga tgggacaact   9720
gggaagaagt tccgttttgc tcccaccact tcaacaagct ccatctcaag gacgggaggt   9780
ccattgtggt tccctgccgc caccaagatg aactgattgg ccgggcccgc gtctctccag   9840
gggcgggatg gagcatccgg gagactgctt gcctagcaaa atcatatgcg caaatgtggc   9900
agctccttta tttccacaga agggacctcc gactgatggc caatgccatt tgttcatctg   9960
tgccagttga ctgggttcca actgggagaa ctacctggtc aatccatgga aagggagaat  10020
ggatgaccac tgaagacatg cttgtggtgt ggaacagagt gtggattgag gagaacgacc  10080
acatggaaga caagacccca gttacgaaat ggacagacat tccctatttg ggaaaaaggg  10140
aagacttgtg gtgtggatct ctcatagggc acagaccgcg caccacctgg gctgagaaca  10200
ttaaaaacac agtcaacatg gtgcgcagga tcataggtga tgaagaaaag tacatggact  10260
acctatccac ccaagttcgc tacttgggtg aagaagggtc tacacctgga gtgctgtaag  10320
caccaatctt agtgttgtca ggcctgctag tcagccacag cttggggaaa gctgtgcagc  10380
ctgtgacccc cccaggagaa gctgggaaac caagcctata gtcaggccga gaacgccatg  10440
gcacggaaga agccatgctg cctgtgagcc cctcagagga cactgagtca aaaaacccca  10500
cgcgcttgga ggcgcaggat gggaaaagaa ggtggcgacc ttccccaccc ttcaatctgg  10560
ggcctgaact ggagatcagc tgtggatctc cagaagaggg actagtggtt agaggag     10617
```

<210> SEQ ID NO 14
<211> LENGTH: 498

<212> TYPE: PRT
<213> ORGANISM: Zika virus

<400> SEQUENCE: 14

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ala Gly Ala Asp
    210                 215                 220

Thr Gly Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Phe Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300

Ala Phe Thr Phe Thr Lys Val Pro Ala Glu Thr Leu His Gly Thr Val
305                 310                 315                 320

Thr Val Glu Val Gln Tyr Ala Gly Thr Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
        355                 360                 365

Met Leu Glu Leu Asp Pro Pro Phe Gly Asp Ser Tyr Ile Val Ile Gly
    370                 375                 380

Val Gly Asp Lys Lys Ile Thr His His Trp His Arg Ser Gly Ser Thr
385                 390                 395                 400
```

-continued

```
Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
    450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala


<210> SEQ ID NO 15
<211> LENGTH: 498
<212> TYPE: PRT
<213> ORGANISM: Zika virus

<400> SEQUENCE: 15

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175

Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ser Gly Ala Asp
    210                 215                 220

Thr Glu Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270
```

Gly Ala Lys Gly Arg Leu Ser Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300

Ala Phe Thr Phe Thr Lys Val Pro Ala Glu Thr Leu His Gly Thr Val
305                 310                 315                 320

Thr Val Glu Val Gln Tyr Ala Gly Arg Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
        355                 360                 365

Met Leu Glu Leu Asp Pro Pro Phe Gly Asp Ser Tyr Ile Val Ile Gly
    370                 375                 380

Val Gly Asp Lys Lys Ile Thr His His Trp His Arg Ser Gly Ser Ile
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
    450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala

<210> SEQ ID NO 16
<211> LENGTH: 504
<212> TYPE: PRT
<213> ORGANISM: Zika virus
<220> FEATURE:
<221> NAME/KEY: misc_feature
<222> LOCATION: (156)..(162)
<223> OTHER INFORMATION: X=any amino acid

<400> SEQUENCE: 16

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys

-continued

```
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Xaa Xaa Xaa Xaa Xaa
145                 150                 155                 160

Xaa Xaa Asn Arg Ala Glu Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 17
<211> LENGTH: 504
<212> TYPE: PRT
<213> ORGANISM: Zika virus
```

<220> FEATURE:
<221> NAME/KEY: misc_feature
<222> LOCATION: (152)..(156)
<223> OTHER INFORMATION: X=any amino acid

<400> SEQUENCE: 17

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Xaa Xaa Xaa Xaa Xaa Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Arg Leu Val Arg Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380
```

-continued

```
Ser Tyr Ile Val Ile Gly Val Gly Asp Lys Lys Ile Thr His His Trp
385                 390                 395                 400

Leu Lys Lys Gly Ser Ser Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 18
<211> LENGTH: 504
<212> TYPE: PRT
<213> ORGANISM: Zika virus

<400> SEQUENCE: 18

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255
```

Val Leu Gly Ser Gln Glu Gly Ala Val His Thr Ala Leu Ala Gly Ala
260 265 270

Leu Glu Ala Glu Met Asp Gly Ala Lys Gly Arg Leu Phe Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Val Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Asp Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Val Phe Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Val Trp Leu Gly Leu Asn Thr Lys
465 470 475 480

Asn Gly Ser Ile Ser Leu Thr Cys Leu Ala Leu Gly Gly Val Met Ile
485 490 495

Phe Leu Ser Thr Ala Val Ser Ala
500

<210> SEQ ID NO 19
<211> LENGTH: 504
<212> TYPE: PRT
<213> ORGANISM: Zika virus

<400> SEQUENCE: 19

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Thr Cys Ser Lys Lys Met Thr Gly Lys

```
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500
```

<210> SEQ ID NO 20
<211> LENGTH: 504
<212> TYPE: PRT
<213> ORGANISM: Zika virus

<400> SEQUENCE: 20

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
```

```
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500
```

<210> SEQ ID NO 21
<211> LENGTH: 504
<212> TYPE: PRT
<213> ORGANISM: Zika virus

<400> SEQUENCE: 21

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270
```

-continued

```
Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Val His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 22
<211> LENGTH: 504
<212> TYPE: PRT
<213> ORGANISM: Zika virus

<400> SEQUENCE: 22

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140
```

Gly Ser Gln His Ser Gly Met Ile Val Asn Asp Thr Gly His Glu Thr
145 150 155 160

Asp Glu Asn Arg Ala Lys Val Glu Val Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Arg Leu Phe Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Val Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Asp Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Val Phe Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Val Trp Leu Gly Leu Asn Thr Lys
465 470 475 480

Asn Gly Ser Ile Ser Leu Thr Cys Leu Ala Leu Gly Gly Val Met Ile
485 490 495

Phe Leu Ser Thr Ala Val Ser Ala
500

<210> SEQ ID NO 23
<211> LENGTH: 504
<212> TYPE: PRT
<213> ORGANISM: Zika virus

<400> SEQUENCE: 23

Ile Arg Cys Ile Gly Val Ser Asn Arg Asp Phe Val Glu Gly Met Ser

-continued

```
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Thr Val Asn Asp Ile Gly Tyr Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430
```

Ser Val Gly Gly Val Phe Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Val Trp Leu Gly Leu Asn Thr Lys
465 470 475 480

Asn Gly Ser Ile Ser Leu Thr Cys Leu Ala Leu Gly Gly Val Met Ile
485 490 495

Phe Leu Ser Thr Ala Val Ser Ala
500

<210> SEQ ID NO 24
<211> LENGTH: 504
<212> TYPE: PRT
<213> ORGANISM: Zika virus

<400> SEQUENCE: 24

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Thr Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Thr Val Asn Asp Ile Gly Tyr Glu Thr
145 150 155 160

Asp Glu Asn Arg Ala Lys Val Glu Val Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Lys Leu Phe Ser Gly His
275 280 285

Leu Lys Cys Arg Leu Lys Met Asp Lys Leu Arg Leu Lys Gly Val Ser

```
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 25
<211> LENGTH: 504
<212> TYPE: PRT
<213> ORGANISM: Zika virus

<400> SEQUENCE: 25

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly Tyr Glu Thr
145                 150                 155                 160
```

-continued

```
Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Lys Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Ile Pro Val Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500
```

<210> SEQ ID NO 26
<211> LENGTH: 504
<212> TYPE: PRT
<213> ORGANISM: Zika virus

<400> SEQUENCE: 26

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30
```

-continued

```
Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Val Cys Thr Ala Ala Lys Val Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445
```

```
Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 27
<211> LENGTH: 500
<212> TYPE: PRT
<213> ORGANISM: Zika virus

<400> SEQUENCE: 27

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320
```

Thr Val Thr Val Glu Val Gln Tyr Ala Gly Thr Asp Gly Pro Cys Lys
325 330 335

Ile Pro Val Gln Met Ala Val Asp Met Gln Thr Leu Thr Pro Val Gly
340 345 350

Arg Leu Ile Thr Ala Asn Pro Val Ile Thr Glu Ser Thr Glu Asn Ser
355 360 365

Lys Met Met Leu Glu Leu Asp Pro Pro Phe Gly Asp Ser Tyr Ile Val
370 375 380

Ile Gly Val Gly Asp Lys Lys Ile Thr His His Trp His Arg Ser Gly
385 390 395 400

Ser Thr Ile Gly Lys Ala Phe Glu Ala Thr Val Arg Gly Ala Lys Arg
405 410 415

Met Ala Val Leu Gly Asp Thr Ala Trp Asp Phe Gly Ser Val Gly Gly
420 425 430

Val Phe Asn Ser Leu Gly Lys Gly Ile His Gln Ile Phe Gly Ala Ala
435 440 445

Phe Lys Ser Leu Phe Gly Gly Met Ser Trp Phe Ser Gln Ile Leu Ile
450 455 460

Gly Thr Leu Leu Val Trp Leu Gly Leu Asn Thr Lys Asn Gly Ser Ile
465 470 475 480

Ser Leu Thr Cys Leu Ala Leu Gly Gly Val Met Ile Phe Leu Ser Thr
485 490 495

Ala Val Ser Ala
500

<210> SEQ ID NO 28
<211> LENGTH: 500
<212> TYPE: PRT
<213> ORGANISM: Zika virus

<400> SEQUENCE: 28

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Thr Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Gly Tyr Glu Thr Asp Glu Asp Arg
145 150 155 160

Ala Lys Val Glu Val Thr Pro Asn Ser Pro Arg Ala Glu Ala Thr Leu
165 170 175

Gly Gly Phe Gly Ser Leu Gly Leu Asp Cys Glu Pro Arg Thr Gly Leu

```
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500


<210> SEQ ID NO 29
<211> LENGTH: 500
<212> TYPE: PRT
<213> ORGANISM: Zika virus

<400> SEQUENCE: 29

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45
```

```
Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
```

```
465                 470                 475                 480

Ser Leu Thr Cys Leu Ala Leu Gly Gly Val Met Ile Phe Leu Ser Thr
                485                 490                 495

Ala Val Ser Ala
            500


<210> SEQ ID NO 30
<211> LENGTH: 504
<212> TYPE: PRT
<213> ORGANISM: Zika virus

<400> SEQUENCE: 30

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Thr Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335
```

```
Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Gly
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 31
<211> LENGTH: 504
<212> TYPE: PRT
<213> ORGANISM: Zika virus

<400> SEQUENCE: 31

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205
```

```
Lys His Trp Leu Val His Lys Glu Trp Phe His Asp Ile Pro Leu Pro
    210                 215                 220

Trp His Thr Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Gly
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 32
<211> LENGTH: 504
<212> TYPE: PRT
<213> ORGANISM: Zika virus

<400> SEQUENCE: 32

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
```

-continued

```
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495
```

```
Phe Leu Ser Thr Ala Val Ser Ala
            500


<210> SEQ ID NO 33
<211> LENGTH: 504
<212> TYPE: PRT
<213> ORGANISM: Zika virus

<400> SEQUENCE: 33

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
```

-continued

```
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 34
<211> LENGTH: 504
<212> TYPE: PRT
<213> ORGANISM: Zika virus

<400> SEQUENCE: 34

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220
```

```
Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 35
<211> LENGTH: 504
<212> TYPE: PRT
<213> ORGANISM: Zika virus

<400> SEQUENCE: 35

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95
```

```
Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 36
<211> LENGTH: 504
<212> TYPE: PRT
<213> ORGANISM: Zika virus

<400> SEQUENCE: 36

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Thr Gly His Glu Thr
145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Val His Lys Glu Trp Phe His Asp Ile Pro Leu Pro
210 215 220

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Arg Leu Ser Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Ile Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

```
Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 37
<211> LENGTH: 504
<212> TYPE: PRT
<213> ORGANISM: Zika virus

<400> SEQUENCE: 37

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
```

```
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 38
<211> LENGTH: 504
<212> TYPE: PRT
<213> ORGANISM: Zika virus

<400> SEQUENCE: 38

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110
```

-continued

```
Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 39
<211> LENGTH: 504
<212> TYPE: PRT

<213> ORGANISM: Zika virus

<400> SEQUENCE: 39

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400
```

```
His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 40
<211> LENGTH: 504
<212> TYPE: PRT
<213> ORGANISM: Zika virus

<400> SEQUENCE: 40

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270
```

```
Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 41
<211> LENGTH: 504
<212> TYPE: PRT
<213> ORGANISM: Zika virus

<400> SEQUENCE: 41

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
```

-continued

```
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 42
<211> LENGTH: 504
<212> TYPE: PRT
<213> ORGANISM: Zika virus

<400> SEQUENCE: 42

-continued

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
```

```
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 43
<211> LENGTH: 504
<212> TYPE: PRT
<213> ORGANISM: Zika virus

<400> SEQUENCE: 43

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285
```

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 44
<211> LENGTH: 504
<212> TYPE: PRT
<213> ORGANISM: Zika virus

<400> SEQUENCE: 44

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

```
Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 45
<211> LENGTH: 504
<212> TYPE: PRT
<213> ORGANISM: Zika virus

<400> SEQUENCE: 45

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
```

-continued

```
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445
```

```
Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 46
<211> LENGTH: 504
<212> TYPE: PRT
<213> ORGANISM: Zika virus

<400> SEQUENCE: 46

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
```

```
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 47
<211> LENGTH: 504
<212> TYPE: PRT
<213> ORGANISM: Zika virus

<400> SEQUENCE: 47

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175
```

-continued

```
Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 48
<211> LENGTH: 504
<212> TYPE: PRT
<213> ORGANISM: Zika virus

<400> SEQUENCE: 48

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45
```

-continued

```
Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460
```

```
Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 49
<211> LENGTH: 504
<212> TYPE: PRT
<213> ORGANISM: Zika virus

<400> SEQUENCE: 49

Ile Arg Cys Ile Gly Val Ser Asn Arg Asp Phe Val Glu Gly Met Ser
1               5                   10                  15

Gly Gly Thr Trp Val Asp Ile Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335
```

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Thr Lys
465 470 475 480

Asn Gly Ser Ile Ser Leu Met Cys Leu Ala Leu Gly Gly Val Leu Ile
485 490 495

Phe Leu Ser Thr Ala Val Ser Ala
500

<210> SEQ ID NO 50
<211> LENGTH: 504
<212> TYPE: PRT
<213> ORGANISM: Zika virus

<400> SEQUENCE: 50

Ile Arg Cys Ile Gly Val Ser Asn Arg Asp Phe Val Glu Gly Met Ser
1 5 10 15

Gly Gly Thr Trp Val Asp Ile Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Thr Gly His Glu Thr
145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn

```
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 51
<211> LENGTH: 504
<212> TYPE: PRT
<213> ORGANISM: Zika virus

<400> SEQUENCE: 51

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Ile Arg Ser Tyr Cys Tyr Glu Ala Ser
    50                  55                  60
```

-continued

```
Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
```

-continued

```
                485                 490                 495

Phe Leu Ser Thr Ala Val Ser Ala
            500


<210> SEQ ID NO 52
<211> LENGTH: 504
<212> TYPE: PRT
<213> ORGANISM: Zika virus

<400> SEQUENCE: 52

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Thr Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350
```

```
Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 53
<211> LENGTH: 504
<212> TYPE: PRT
<213> ORGANISM: Zika virus

<400> SEQUENCE: 53

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220
```

Trp His Ala Gly Ala Asp Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Thr Gln Glu Gly Ala Val His Thr Ala Leu Ala Gly Ala
260 265 270

Leu Glu Ala Glu Met Asp Gly Ala Lys Gly Arg Leu Ser Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Ile Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Thr Lys
465 470 475 480

Asn Gly Ser Ile Ser Leu Met Cys Leu Ala Leu Gly Gly Val Leu Ile
485 490 495

Phe Leu Ser Thr Ala Val Ser Ala
500

<210> SEQ ID NO 54
<211> LENGTH: 504
<212> TYPE: PRT
<213> ORGANISM: Zika virus

<400> SEQUENCE: 54

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu

-continued

```
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Arg Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 55
<211> LENGTH: 504
<212> TYPE: PRT
<213> ORGANISM: Zika virus

<400> SEQUENCE: 55

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
```

```
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 56
<211> LENGTH: 504
<212> TYPE: PRT
<213> ORGANISM: Zika virus

<400> SEQUENCE: 56

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240
```

```
Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 57
<211> LENGTH: 504
<212> TYPE: PRT
<213> ORGANISM: Zika virus

<400> SEQUENCE: 57

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110
```

-continued

```
Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Ala Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 58
<211> LENGTH: 504

```
<212> TYPE: PRT
<213> ORGANISM: Zika virus

<400> SEQUENCE: 58

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Thr Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400
```

```
His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 59
<211> LENGTH: 504
<212> TYPE: PRT
<213> ORGANISM: Zika virus

<400> SEQUENCE: 59

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Gly Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
```

```
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500


<210> SEQ ID NO 60
<211> LENGTH: 504
<212> TYPE: PRT
<213> ORGANISM: Zika virus

<400> SEQUENCE: 60

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125
```

```
Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Leu Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500
```

<210> SEQ ID NO 61
<211> LENGTH: 504
<212> TYPE: PRT
<213> ORGANISM: Zika virus

<400> SEQUENCE: 61

-continued

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Ala Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415
```

```
Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500


<210> SEQ ID NO 62
<211> LENGTH: 504
<212> TYPE: PRT
<213> ORGANISM: Zika virus

<400> SEQUENCE: 62

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285
```

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Ile Pro Ala Glu
305 310 315 320

Thr Leu His Gly Thr Val Thr Val Glu Val Gln Tyr Ala Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Phe Gly Ala Ala Phe Lys Ser Leu Phe Gly Gly Met Ser Trp Phe Ser
450 455 460

Gln Ile Leu Ile Gly Thr Leu Leu Val Trp Leu Gly Leu Asn Thr Lys
465 470 475 480

Asn Gly Ser Ile Ser Leu Thr Cys Leu Ala Leu Gly Gly Val Leu Ile
485 490 495

Phe Leu Ser Thr Ala Val Ser Ala
500

<210> SEQ ID NO 63
<211> LENGTH: 504
<212> TYPE: PRT
<213> ORGANISM: Zika virus

<400> SEQUENCE: 63

Ile Arg Cys Ile Gly Val Ser Asn Arg Asp Phe Val Glu Gly Met Ser
1 5 10 15

Gly Gly Thr Trp Val Asp Val Val Leu Glu His Gly Gly Cys Val Thr
20 25 30

Val Met Ala Gln Asp Lys Pro Thr Val Asp Ile Glu Leu Val Thr Thr
35 40 45

Thr Val Ser Asn Met Ala Glu Val Arg Ser Tyr Cys Tyr Glu Ala Ser
50 55 60

Ile Ser Asp Met Ala Ser Asp Ser Arg Cys Pro Thr Gln Gly Glu Ala
65 70 75 80

Tyr Leu Asp Lys Gln Ser Asp Thr Gln Tyr Val Cys Lys Arg Thr Leu
85 90 95

Val Asp Arg Gly Trp Gly Asn Gly Cys Gly Leu Phe Gly Lys Gly Ser
100 105 110

Leu Val Thr Cys Ala Lys Phe Ala Cys Ser Lys Lys Met Thr Gly Lys
115 120 125

Ser Ile Gln Pro Glu Asn Leu Glu Tyr Arg Ile Met Leu Ser Val His
130 135 140

Gly Ser Gln His Ser Gly Met Ile Val Asn Asp Thr Gly His Glu Thr

```
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500
```

<210> SEQ ID NO 64
<211> LENGTH: 504
<212> TYPE: PRT
<213> ORGANISM: Zika virus

<400> SEQUENCE: 64

```
Ile Arg Cys Ile Gly Val Ser Asn Arg Asp Phe Val Glu Gly Met Ser
1               5                   10                  15
```

```
Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Ser Thr
        35                  40                  45

Thr Val Ser Asn Met Ala Glu Val Arg Ser Tyr Cys Tyr Glu Ala Thr
    50                  55                  60

Ile Ser Asp Ile Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Ala Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
```

435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Ala
            500

<210> SEQ ID NO 65
<211> LENGTH: 504
<212> TYPE: PRT
<213> ORGANISM: Zika virus
<220> FEATURE:
<221> NAME/KEY: misc_feature
<222> LOCATION: (1)..(504)
<223> OTHER INFORMATION: X=any amino acid

<400> SEQUENCE: 65

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Xaa Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

```
Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

Xaa Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Leu Ile
                485                 490                 495

Phe Leu Ser Thr Ala Val Ser Ala
            500


<210> SEQ ID NO 66
<211> LENGTH: 504
<212> TYPE: PRT
<213> ORGANISM: Zika virus

<400> SEQUENCE: 66

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Ala Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Leu Val Asn Asp Thr Gly His Glu Thr
```

145 150 155 160

Asp Glu Asn Arg Ala Lys Val Glu Ile Thr Pro Asn Ser Pro Arg Ala
165 170 175

Glu Ala Thr Leu Gly Gly Phe Gly Ser Leu Gly Leu Asp Cys Glu Pro
180 185 190

Arg Thr Gly Leu Asp Phe Ser Asp Leu Tyr Tyr Leu Thr Met Asn Asn
195 200 205

Lys His Trp Leu Ala His Lys Glu Trp Phe His Asp Ile Pro Leu Pro
210 215 220

Trp His Ala Gly Ala Ala Thr Gly Thr Pro His Trp Asn Asn Lys Glu
225 230 235 240

Ala Leu Val Glu Phe Lys Asp Ala His Ala Lys Arg Gln Thr Val Val
245 250 255

Val Leu Gly Ser Gln Glu Gly Ala Val His Thr Ala Leu Ala Gly Ala
260 265 270

Leu Glu Ala Glu Met Asp Gly Ala Lys Gly Arg Leu Ser Ser Gly His
275 280 285

Leu Lys Cys Arg Leu Lys Met Asp Lys Leu Arg Leu Lys Gly Val Ser
290 295 300

Tyr Ser Leu Cys Thr Ala Ala Phe Thr Phe Thr Lys Ile Pro Ala Glu
305 310 315 320

Thr Val Asp Gly Thr Val Thr Val Glu Gly Gln Tyr Gly Gly Thr Asp
325 330 335

Gly Pro Cys Lys Val Pro Ala Gln Met Ala Val Asp Met Gln Thr Leu
340 345 350

Thr Pro Val Gly Arg Leu Ile Thr Ala Asn Pro Val Ile Thr Glu Ser
355 360 365

Thr Glu Asn Ser Lys Met Met Leu Glu Leu Asp Pro Pro Phe Gly Asp
370 375 380

Ser Tyr Ile Val Ile Gly Val Gly Glu Lys Lys Ile Thr His His Trp
385 390 395 400

His Arg Ser Gly Ser Thr Ile Gly Lys Ala Phe Glu Ala Thr Val Arg
405 410 415

Gly Ala Lys Arg Met Ala Val Leu Gly Asp Thr Ala Trp Asp Phe Gly
420 425 430

Ser Val Gly Gly Ala Leu Asn Ser Leu Gly Lys Gly Ile His Gln Ile
435 440 445

Ile Gly Ala Ala Phe Lys Ser Leu Phe Gly Gly Met Ser Trp Phe Ser
450 455 460

Gln Ile Leu Ile Gly Thr Leu Leu Met Trp Leu Gly Leu Asn Thr Lys
465 470 475 480

Asn Gly Ser Ile Ser Leu Met Cys Leu Ala Leu Gly Gly Val Leu Ile
485 490 495

Phe Leu Ser Thr Ala Val Ser Gly
500

<210> SEQ ID NO 67
<211> LENGTH: 504
<212> TYPE: PRT
<213> ORGANISM: Zika virus

<400> SEQUENCE: 67

Ile Arg Cys Ile Gly Val Ser Asn Arg Asp Phe Val Glu Gly Met Ser
1 5 10 15

-continued

```
Gly Gly Thr Trp Val Asp Val Val Leu Glu His Gly Gly Cys Val Thr
            20                  25                  30

Ala Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Leu Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Ala His Lys Glu Trp Phe His Asp Ile Pro Leu Pro
    210                 215                 220

Trp His Ala Gly Ala Ala Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Val Asp Gly Thr Val Thr Val Glu Gly Gln Tyr Gly Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
```

```
        435                 440                 445

Ile Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495

Phe Leu Ser Thr Ala Val Ser Gly
            500


<210> SEQ ID NO 68
<211> LENGTH: 504
<212> TYPE: PRT
<213> ORGANISM: Zika virus

<400> SEQUENCE: 68

Ile Ser Cys Ile Gly Val Ser Asn Arg Asp Leu Val Glu Gly Met Ser
1               5                   10                  15

Gly Gly Thr Trp Val Asp Val Val Leu Glu His Gly Gly Cys Val Thr
            20                  25                  30

Glu Met Ala Gln Asp Lys Pro Thr Val Asp Ile Glu Leu Val Thr Met
        35                  40                  45

Thr Val Ser Asn Met Ala Glu Val Arg Ser Tyr Cys Tyr Glu Ala Ser
    50                  55                  60

Leu Ser Asp Met Ala Ser Ala Ser Arg Cys Pro Thr Gln Gly Glu Pro
65                  70                  75                  80

Ser Leu Asp Lys Gln Ser Asp Thr Gln Ser Val Cys Lys Arg Thr Leu
                85                  90                  95

Gly Asp Arg Gly Trp Gly Asn Gly Cys Gly Ile Phe Gly Lys Gly Ser
            100                 105                 110

Leu Val Thr Cys Ser Lys Phe Thr Cys Cys Lys Lys Met Pro Gly Lys
        115                 120                 125

Ser Ile Gln Pro Glu Asn Leu Glu Tyr Arg Ile Met Leu Pro Val His
    130                 135                 140

Gly Ser Gln His Ser Gly Met Ile Val Asn Asp Ile Gly His Glu Thr
145                 150                 155                 160

Asp Glu Asn Arg Ala Lys Val Glu Val Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Phe Ser Gly His
        275                 280                 285

Leu Lys Cys Arg Leu Lys Met Asp Lys Leu Arg Leu Lys Gly Val Ser
    290                 295                 300
```

```
Tyr Ser Leu Cys Thr Ala Ala Phe Thr Phe Thr Lys Val Pro Ala Glu
305                 310                 315                 320

Thr Leu His Gly Thr Val Thr Val Glu Val Gln Ser Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Asp Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Val Phe Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Val Trp Leu Gly Leu Asn Thr Lys
465                 470                 475                 480

Asn Gly Ser Ile Ser Leu Thr Cys Leu Ala Leu Gly Gly Val Met Ile
                485                 490                 495

Phe Leu Ser Thr Ala Val Ser Ala
            500


<210> SEQ ID NO 69
<211> LENGTH: 498
<212> TYPE: PRT
<213> ORGANISM: Zika virus

<400> SEQUENCE: 69

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Glu Asn Arg Ala Lys
145                 150                 155                 160

Val Glu Val Thr Pro Asn Ser Pro Arg Ala Glu Ala Thr Leu Gly Gly
                165                 170                 175
```

```
Phe Gly Ser Leu Gly Leu Asp Cys Glu Pro Arg Thr Gly Leu Asp Phe
            180                 185                 190

Ser Asp Leu Tyr Tyr Leu Thr Met Asn Asn Lys His Trp Leu Val His
        195                 200                 205

Lys Glu Trp Phe His Asp Ile Pro Leu Pro Trp His Ala Gly Ala Asp
    210                 215                 220

Thr Gly Thr Pro His Trp Asn Asn Lys Glu Ala Leu Val Glu Phe Lys
225                 230                 235                 240

Asp Ala His Ala Lys Arg Gln Thr Val Val Val Leu Gly Ser Gln Glu
                245                 250                 255

Gly Ala Val His Thr Ala Leu Ala Gly Ala Leu Glu Ala Glu Met Asp
            260                 265                 270

Gly Ala Lys Gly Arg Leu Phe Ser Gly His Leu Lys Cys Arg Leu Lys
        275                 280                 285

Met Asp Lys Leu Arg Leu Lys Gly Val Ser Tyr Ser Leu Cys Thr Ala
    290                 295                 300

Ala Phe Thr Phe Thr Lys Val Pro Ala Glu Thr Leu His Gly Thr Val
305                 310                 315                 320

Thr Val Glu Val Gln Tyr Ala Gly Thr Asp Gly Pro Cys Lys Val Pro
                325                 330                 335

Ala Gln Met Ala Val Asp Met Gln Thr Leu Thr Pro Val Gly Arg Leu
            340                 345                 350

Ile Thr Ala Asn Pro Val Ile Thr Glu Ser Thr Glu Asn Ser Lys Met
        355                 360                 365

Met Leu Glu Leu Asp Pro Pro Phe Gly Asp Ser Tyr Ile Val Ile Gly
    370                 375                 380

Val Gly Asp Lys Lys Ile Thr His His Trp His Arg Ser Gly Ser Thr
385                 390                 395                 400

Ile Gly Lys Ala Phe Glu Ala Thr Val Arg Gly Ala Lys Arg Met Ala
                405                 410                 415

Val Leu Gly Asp Thr Ala Trp Asp Phe Gly Ser Val Gly Gly Val Phe
            420                 425                 430

Asn Ser Leu Gly Lys Gly Ile His Gln Ile Phe Gly Ala Ala Phe Lys
        435                 440                 445

Ser Leu Phe Gly Gly Met Ser Trp Phe Ser Gln Ile Leu Ile Gly Thr
    450                 455                 460

Leu Leu Val Trp Leu Gly Leu Asn Thr Lys Asn Gly Ser Ile Ser Leu
465                 470                 475                 480

Thr Cys Leu Ala Leu Gly Gly Val Met Ile Phe Leu Ser Thr Ala Val
                485                 490                 495

Ser Ala
```

<210> SEQ ID NO 70
<211> LENGTH: 26
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(26)
<223> OTHER INFORMATION: n=inosine

<400> SEQUENCE: 70
ncncncncnc ncncncncnc ncncnc 26

<210> SEQ ID NO 71
<211> LENGTH: 11
<212> TYPE: PRT
<213> ORGANISM: Artificial Sequence
<220> FEATURE:
<223> OTHER INFORMATION: synthetic peptide

<400> SEQUENCE: 71

Lys Leu Lys Leu Leu Leu Leu Leu Lys Leu Lys
1 5 10

<210> SEQ ID NO 72
<211> LENGTH: 10773
<212> TYPE: DNA
<213> ORGANISM: Zika virus

<400> SEQUENCE: 72
cagactgcga cagttcgagt ttgaagcgaa agctagcaac agtatcaaca ggttttattt 60
tggatttgga aacgagagtt tctggtcatg aaaaacccaa aaaagaaatc cggaggattc 120
cggattgtca atatgctaaa acgcggagta gcccgtgtga gcccctttgg gggcttgaag 180
aggctgccag ccggacttct gctgggtcat gggcccatca ggatggtctt ggcgattcta 240
gcctttttga gattcacggc aatcaagcca tcactgggtc tcatcaatag atggggttca 300
gtggggaaaa aagaggctat ggaaataata aagaagttca agaaagatct ggctgccatg 360
ctgagaataa tcaatgctag gaaggagaag aagagacgag gcgcagatac tagtgtcgga 420
attgttggcc tcctgctgac cacagctatg gcagcggagg tcactagacg tgggagtgca 480
tactatatgt acttggacag aaacgacgct ggggaggcca tatcttttcc aaccacattg 540
gggatgaata agtgttatat acagatcatg gatcttggac acatgtgtga tgccaccatg 600
agctatgaat gccctatgct ggatgagggg gtggaaccag atgacgtcga ttgttggtgc 660
aacacgacgt caacttgggt tgtgtacgga acctgccatc acaaaaaagg tgaagcacgg 720
agatctagaa gagctgtgac gctcccctcc cattccacta ggaagctgca aacgcggtcg 780
caaacctggt tggaatcaag agaatacaca aagcacttga ttagagtcga aaattggata 840
ttcaggaacc ctggcttcgc gttagcagca gctgccatcg cttggctttt gggaagctca 900
acgagccaaa aagtcatata cttggtcatg atactgctga ttgccccggc atacagcatc 960
aggtgcatag gagtcagcaa tagggacttt gtggaaggta tgtcaggtgg gacttgggtt 1020
gatgttgtct tggaacatgg aggttgtgtc accgtaatgg cacaggacaa accgactgtc 1080
gacatagagc tggttacaac aacagtcagc aacatggcgg aggtaagatc ctactgctat 1140
gaggcatcaa tatcggacat ggcttcggac agccgctgcc caacacaagg tgaagcctac 1200
cttgacaagc aatcagacac tcaatatgtc tgcaaaagaa cgttagtgga cagaggctgg 1260
ggaaatggat gtggactttt tggcaaaggg agcctggtga catgcgctaa gtttgcatgc 1320
tccaagaaaa tgaccgggaa gagcatccag ccagagaatc tggagtaccg gataatgctg 1380
tcagttcatg gctcccagca cagtgggatg atcgttaatg acacaggaca tgaaactgat 1440
gagaatagag cgaaggttga gataacgccc aattcaccaa gagccgaagc caccctgggg 1500
ggttttggaa gcctaggact tgattgtgaa ccgaggacag gccttgactt ttcagatttg 1560
tattacttga ctatgaataa caagcactgg ttggttcaca aggagtggtt ccacgacatt 1620
ccattacctt ggcacgctgg ggcagacacc ggaactccac actggaacaa caaagaagca 1680
ctggtagagt tcaaggacgc acatgccaaa aggcaaactg tcgtggttct agggagtcaa 1740

-continued

```
gaaggagcag ttcacacggc ccttgctgga gctctggagg ctgagatgga tggtgcaaag   1800
ggaaggctgt cctctggcca cttgaaatgt cgcctgaaaa tggataaact tagattgaag   1860
ggcgtgtcat actccttgtg taccgcagcg ttcacattca ccaagatccc ggctgaaaca   1920
ctgcacggga cagtcacagt ggaggtacag tacgcaggga cagatggacc ttgcaaggtt   1980
ccagctcaga tggcggtgga catgcaaact ctgaccccag ttgggaggtt gataaccgct   2040
aaccccgtaa tcactgaaag cactgagaac tctaagatga tgctggaact tgatccacca   2100
tttggggact cttacattgt cataggagtc ggggagaaga agatcaccca ccactggcac   2160
aggagtggca gcaccattgg aaaagcattt gaagccactg tgagaggtgc caagagaatg   2220
gcagtcttgg gagacacagc ctgggacttt ggatcagttg gaggcgctct caactcattg   2280
ggcaagggca tccatcaaat ttttggagca gctttcaaat cattgtttgg aggaatgtcc   2340
tggttctcac aaattctcat tggaacgttg ctgatgtggt tgggtctgaa cacaaagaat   2400
ggatctattt cccttatgtg cttggcctta gggggagtgt tgatcttctt atccacagct   2460
gtctctgctg atgtggggtg ctcggtggac ttctcaaaga aggagacgag atgcggtaca   2520
ggggtgttcg tctataacga cgttgaagcc tggagggaca ggtacaagta ccatcctgac   2580
tccccccgta gattggcagc agcagtcaag caagcctggg aagatggtat ctgtgggatc   2640
tcctctgttt caagaatgga aaacatcatg tggagatcag tagaagggga gctcaacgca   2700
atcctggaag agaatggagt tcaactgacg gtcgttgtgg gatctgtaaa aaaccccatg   2760
tggagaggtc cacagagatt gcccgtgcct gtgaacgagc tgccccacgg ctggaaggct   2820
tgggggaaat cgtacttcgt cagagcagca aagacaaata acagctttgt cgtggatggt   2880
gacacactga aggaatgccc actcaaacat agagcatgga acagctttct tgtggaggat   2940
catgggttcg ggtatttca cactagtgtc tggctcaagg ttagagaaga ttattcatta   3000
gagtgtgatc cagccgttat tggaacagct gttaagggaa aggaggctgt acacagtgat   3060
ctaggctact ggattgagag tgagaagaat gacacatgga ggctgaagag ggcccatctg   3120
atcgagatga aaacatgtga atggccaaag tcccacacat tgtggacaga tggaatagaa   3180
gagagtgatc tgatcatacc caagtcttta gctgggccac tcagccatca caataccaga   3240
gagggctaca ggacccaaat gaaagggcca tggcacagtg aagagcttga aattcggttt   3300
gaggaatgcc caggcactaa ggtccacgtg gaggaaacat gtggaacaag aggaccatct   3360
ctgagatcaa ccactgcaag cggaagggtg atcgaggaat ggtgctgcag ggagtgcaca   3420
atgcccccac tgtcgttccg ggctaaagat ggctgttggt atggaatgga gataaggccc   3480
aggaaagaac cagaaagtaa cttagtaagg tcaatggtga ctgcaggatc aactgatcac   3540
atggatcact tctcccttgg agtgcttgtg attctgctca tggtgcagga agggctgaag   3600
aagagaatga ccacaaagat catcataagc acatcgatgg cagtgctggt agctatgatc   3660
ctgggaggat tttcaatgag tgacctggct aagcttgcaa ttttgatggg tgccaccttc   3720
gcggaaatga acactggagg agatgtagct catctggcgc tgatagcggc attcaaagtc   3780
agaccagcgt tgctggtatc tttcatcttc agagctaatt ggacaccccg tgaaagcatg   3840
ctgctggcct tggcctcgtg tcttttgcaa actgcgatct ccgccttgga aggcgacctg   3900
atggttctca tcaatggttt tgctttggcc tggttggcaa tacgagcgat ggttgttcca   3960
cgcactgata acatcacctt ggcaatcctg gctgctctga caccactggc ccggggcaca   4020
ctgcttgtgg cgtggagagc aggccttgct acttgcgggg ggtttatgct cctctctctg   4080
aagggaaaag gcagtgtgaa gaagaactta ccatttgtca tggccctggg actaaccgct   4140
```

gtgaggctgg tcgaccccat caacgtggtg ggactgctgt tgctcacaag gagtgggaag 4200
cggagctggc cccctagcga agtactcaca gctgttggcc tgatatgcgc attggctgga 4260
gggttcgcca aggcagatat agagatggct gggcccatgg ccgcggtcgg tctgctaatt 4320
gtcagttacg tggtctcagg aaagagtgtg gacatgtaca ttgaaagagc aggtgacatc 4380
acatgggaaa aagatgcgga agtcactgga aacagtcccc ggctcgatgt ggcgctagat 4440
gagagtggtg atttctccct ggtggaggat gacggtcccc ccatgagaga gatcatactc 4500
aaggtggtcc tgatgaccat ctgtggcatg aacccaatag ccataccctt tgcagctgga 4560
gcgtggtacg tatacgtgaa gactggaaaa aggagtggtg ctctatggga tgtgcctgct 4620
cccaaggaag taaaaaaggg ggagaccaca gatggagtgt acagagtaat gactcgtaga 4680
ctgctaggtt caacacaagt tggagtggga gttatgcaag agggggtctt tcacactatg 4740
tggcacgtca caaaaggatc cgcgctgaga agcggtgaag ggagacttga tccatactgg 4800
ggagatgtca agcaggatct ggtgtcatac tgtggtccat ggaagctaga tgccgcctgg 4860
gacgggcaca gcgaggtgca gctcttggcc gtgccccccg gagagagagc gaggaacatc 4920
cagactctgc ccggaatatt taagacaaag gatggggaca ttggagcggt tgcgctggat 4980
tacccagcag gaacttcagg atctccaatc ctagacaagt gtgggagagt gataggactt 5040
tatggcaatg ggggtcgtgat caaaaatggg agttatgtta gtgccatcac ccaagggagg 5100
agggaggaag agactcctgt tgagtgcttc gagccttcga tgctgaagaa gaagcagcta 5160
actgtcttag acttgcatcc tggagctggg aaaaccagga gagttcttcc tgaaatagtc 5220
cgtgaagcca taaaaacaag actccgtact gtgatcttag ctccaaccag ggttgtcgct 5280
gctgaaatgg aggaagccct tagagggctt ccagtgcgtt atatgacaac agcagtcaat 5340
gtcacccact ctggaacaga aatcgtcgac ttaatgtgcc atgccacctt cacttcacgt 5400
ctactacagc caatcagagt ccccaactat aatctgtata ttatggatga ggcccacttc 5460
acagatccct caagtatagc agcaagagga tacatttcaa caagggttga gatgggcgag 5520
gcggctgcca tcttcatgac cgccacgcca ccaggaaccc gtgacgcatt tccggactcc 5580
aactcaccaa ttatggacac cgaagtggaa gtcccagaga gagcctggag ctcaggcttt 5640
gattgggtga cggatcattc tggaaaaaca gtttggtttg ttccaagcgt gaggaacggc 5700
aatgagatcg cagcttgtct gacaaaggct ggaaaacggg tcatacagct cagcagaaag 5760
acttttgaga cagagttcca gaaaacaaaa catcaagagt gggactttgt cgtgacaact 5820
gacatttcag agatgggcgc caactttaaa gctgaccgtg tcatagattc caggagatgc 5880
ctaaagccgg tcatacttga tggcgagaga gtcattctgg ctggacccat gcctgtcaca 5940
catgccagcg ctgcccagag gagggggcgc ataggcagga atcccaacaa acctggagat 6000
gagtatctgt atggaggtgg gtgcgcagag actgacgaag accatgcaca ctggcttgaa 6060
gcaagaatgc tccttgacaa tatttacctc caagatggcc tcatagcctc gctctatcga 6120
cctgaggccg acaaagtagc agccattgag ggagagttca agcttaggac ggagcaaagg 6180
aagacctttg tggaactcat gaaaagagga gatcttcctg tttggctggc ctatcaggtt 6240
gcatctgccg gaataaccta cacagataga agatggtgct ttgatggcac gaccaacaac 6300
accataatgg aagacagtgt gccggcagag gtgtggacca gacacggaga gaaaagagtg 6360
ctcaaaccga ggtggatgga cgccagagtt tgttcagatc atgcggccct gaagtcattc 6420
aaggagtttg ccgctgggaa aagaggagcg gcttttggag tgatggaagc cctgggaaca 6480
ctgccaggac acatgacaga gagattccag gaagccattg acaacctcgc tgtgctcatg 6540
cgggcagaga ctggaagcag gccttacaaa gccgcggcgg cccaattgcc ggagacccta 6600
gagaccatta tgcttttggg gttgctggga acagtctcgc tgggaatctt tttcgtcttg 6660
atgaggaaca agggcatagg gaagatgggc tttggaatgg tgactcttgg ggccagcgca 6720
tggctcatgt ggctctcgga aattgagcca gccagaattg catgtgtcct cattgttgtg 6780
ttcctattgc tggtggtgct catacctgag ccagaaaagc aaagatctcc ccaggacaac 6840
caaatggcaa tcatcatcat ggtagcagta ggtcttctgg gcttgattac cgccaatgaa 6900
ctcggatggt tggagagaac aaagagtgac ctaagccatc taatgggaag gagagaggag 6960
ggggcaacca taggattctc aatggacatt gacctgcggc cagcctcagc ttgggccatc 7020
tatgctgcct tgacaacttt cattacccca gccgtccaac atgcagtgac cacttcatac 7080
aacaactact ccttaatggc gatggccacg caagctggag tgttgtttgg tatgggcaaa 7140
gggatgccat tctacgcatg ggactttgga gtcccgctgc taatgatagg ttgctactca 7200
caattaacac ccctgaccct aatagtggcc atcattttgc tcgtggcgca ctacatgtac 7260
ttgatcccag ggctgcaggc agcagctgcg cgtgctgccc agaagagaac ggcagctggc 7320
atcatgaaga accctgttgt ggatggaata gtggtgactg acattgacac aatgacaatt 7380
gacccccaag tggagaaaaa gatgggacag gtgctactca tagcagtagc cgtctccagc 7440
gccatactgt cgcggaccgc ctgggggtgg ggggaggctg gggccctgat cacagcggca 7500
acttccactt tgtgggaagg ctctccgaac aagtactgga actcctctac agccacttca 7560
ctgtgtaaca tttttagggg aagttacttg gctggagctt ctctaatcta cacagtaaca 7620
agaaacgctg gcttggtcaa gagacgtggg ggtggaacag gagagaccct gggagagaaa 7680
tggaaggccc gcttgaacca gatgtcggcc ctggagttct actcctacaa aaagtcaggc 7740
atcaccgagg tgtgcagaga agaggcccgc cgcgccctca aggacggtgt ggcaacggga 7800
ggccatgctg tgtcccgagg aagtgcaaag ctgagatggt tggtggagcg gggatacctg 7860
cagccctatg gaaaggtcat tgatcttgga tgtggcagag gggctggagg ttactacgcc 7920
gccaccatcc gcaaagttca agaagtgaaa ggatacacaa aaggaggccc tggtcatgaa 7980
gaacccatgt tggtgcaaag ctatgggtgg aacatagtcc gtcttaagag tggggtggac 8040
gtctttcata tggcggctga gccgtgtgac acgttgctgt gtgacatagg tgagtcatca 8100
tctagtcctg aagtggaaga agcacggacg ctcagagtcc tctccatggt gggggattgg 8160
cttgaaaaaa gaccaggagc cttttgtata aaagtgttgt gcccatacac cagcactatg 8220
atggaaaccc tggagcgact gcagcgtagg tatgggggag gactggtcag agtgccactc 8280
tcccgcaact ctacacatga gatgtactgg gtctctggag cgaaaagcaa caccataaaa 8340
agtgtgtcca ccacgagcca gctcctcttg ggcgcatgg acgggcccag gaggccagtg 8400
aaatatgagg aggatgtgaa tctcggctct ggcacgcggg ctgtggtaag ctgcgctgaa 8460
gctcccaaca tgaagatcat tggtaaccgc attgaaagga tccgcagtga gcacgcggaa 8520
acgtggttct ttgacgagaa ccacccatat aggacatggg cttaccatgg aagctatgag 8580
gcccccacac aagggtcagc gtcctctcta ataaacgggg ttgtcaggct cctgtcaaaa 8640
ccctgggatg tggtgactgg agtcacagga atagccatga ccgacaccac accgtatggt 8700
cagcaaagag ttttcaagga aaaagtggac actagggtgc cagaccccca agaaggcact 8760
cgtcaggtta tgagcatggt ctcttcctgg ttgtggaaag agctaggcaa acacaaacgg 8820
ccacgagtct gtaccaaaga agagttcatc aacaaggttc gtagcaatgc agcattaggg 8880

-continued

```
gcaatatttg aagaggaaaa agagtggaag actgcagtgg aagctgtgaa cgatccaagg   8940
ttctgggctc tagtggacaa ggaaagagag caccacctga gaggagagtg ccagagttgt   9000
gtgtacaaca tgatgggaaa aagagaaaag aaacaagggg aatttggaaa ggccaagggc   9060
agccgcgcca tctggtatat gtggctaggg gctagatttc tagagttcga agcccttgga   9120
ttcttgaacg aggatcactg gatggggaga gagaactcag gaggtggtgt tgaagggctg   9180
ggattacaaa gactcggata tgtcctagaa gagatgagtc gcataccagg aggaaggatg   9240
tatgcagatg acactgctgg ctgggacacc cgcatcagca ggtttgatct ggagaatgaa   9300
gctctaatca ccaaccaaat ggagaaaggg cacagggcct tggcattggc cataatcaag   9360
tacacatacc aaaacaaagt ggtaaaggtc cttagaccag ctgaaaaagg gaagacagtt   9420
atggacatta tttcgagaca agaccaaagg gggagcggac aagttgtcac ttacgctctt   9480
aacacattta ccaacctagt ggtgcaactc attcggaata tggaggctga ggaagttcta   9540
gagatgcaag acttgtggct gctgcggagg tcagagaaag tgaccaactg gttgcagagc   9600
aacggatggg ataggctcaa acgaatggca gtcagtggag atgattgcgt tgtgaagcca   9660
attgatgata ggtttgcaca tgccctcagg ttcttgaatg atatgggaaa agttaggaag   9720
gacacacaag agtggaaacc ctcaactgga tgggacaact gggaagaagt tccgttttgc   9780
tcccaccact tcaacaagct ccatctcaag gacgggaggt ccattgtggt tccctgccgc   9840
caccaagatg aactgattgg ccgggcccgc gtctctccag ggcgggatg gagcatccgg   9900
gagactgctt gcctagcaaa atcatatgcg caaatgtggc agctccttta tttccacaga   9960
agggacctcc gactgatggc caatgccatt tgttcatctg tgccagttga ctgggttcca  10020
actgggagaa ctacctggtc aatccatgga aagggagaat ggatgaccac tgaagacatg  10080
cttgtggtgt ggaacagagt gtggattgag gagaacgacc acatggaaga caagacccca  10140
gttacgaaat ggacagacat tccctatttg ggaaaaaggg aagacttgtg gtgtggatct  10200
ctcatagggc acagaccgcg caccacctgg gctgagaaca ttaaaaacac agtcaacatg  10260
gtgcgcagga tcataggtga tgaagaaaag tacatggact acctatccac ccaagttcgc  10320
tacttgggtg aagaagggtc tacacctgga gtgctgtaag caccaatctt agtgttgtca  10380
ggcctgctag tcagccacag cttggggaaa gctgtgcagc ctgtgacccc cccaggagaa  10440
gctgggaaac caagcctata gtcaggccga gaacgccatg gcacggaaga agccatgctg  10500
cctgtgagcc cctcagagga cactgagtca aaaaaacccca cgcgcttgga ggcgcaggat  10560
gggaaaagaa ggtggcgacc ttccccaccc ttcaatctgg ggcctgaact ggagatcagc  10620
tgtggatctc cagaagaggg actagtggtt agaggagacc ccccggaaaa cgcaaaacag  10680
catattgacg ctgggaaaga ccagagactc catgagtttc caccacgctg gccgccaggc  10740
acagatcgcc gaatagcggc ggccggtgtg ggg                                10773
```

<210> SEQ ID NO 73
<211> LENGTH: 3423
<212> TYPE: PRT
<213> ORGANISM: Zika virus

<400> SEQUENCE: 73

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30
```

-continued

```
Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
```

```
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
        835                 840                 845

Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880
```

```
Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
        915                 920                 925

Val Asp Gly Asp Thr Leu Lys Glu Cys Pro Leu Lys His Arg Ala Trp
    930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys  Asn Asp Thr Trp Arg  Leu Lys Arg
        995                 1000                1005

Ala His  Leu Ile Glu Met Lys  Thr Cys Glu Trp Pro  Lys Ser His
    1010                 1015                 1020

Thr Leu  Trp Thr Asp Gly Ile  Glu Glu Ser Asp Leu  Ile Ile Pro
    1025                 1030                 1035

Lys Ser  Leu Ala Gly Pro Leu  Ser His His Asn Thr  Arg Glu Gly
    1040                 1045                 1050

Tyr Arg  Thr Gln Met Lys Gly  Pro Trp His Ser Glu  Glu Leu Glu
    1055                 1060                 1065

Ile Arg  Phe Glu Glu Cys Pro  Gly Thr Lys Val His  Val Glu Glu
    1070                 1075                 1080

Thr Cys  Gly Thr Arg Gly Pro  Ser Leu Arg Ser Thr  Thr Ala Ser
    1085                 1090                 1095

Gly Arg  Val Ile Glu Glu Trp  Cys Cys Arg Glu Cys  Thr Met Pro
    1100                 1105                 1110

Pro Leu  Ser Phe Arg Ala Lys  Asp Gly Cys Trp Tyr  Gly Met Glu
    1115                 1120                 1125

Ile Arg  Pro Arg Lys Glu Pro  Glu Ser Asn Leu Val  Arg Ser Met
    1130                 1135                 1140

Val Thr  Ala Gly Ser Thr Asp  His Met Asp His Phe  Ser Leu Gly
    1145                 1150                 1155

Val Leu  Val Ile Leu Leu Met  Val Gln Glu Gly Leu  Lys Lys Arg
    1160                 1165                 1170

Met Thr  Thr Lys Ile Ile Ile  Ser Thr Ser Met Ala  Val Leu Val
    1175                 1180                 1185

Ala Met  Ile Leu Gly Gly Phe  Ser Met Ser Asp Leu  Ala Lys Leu
    1190                 1195                 1200

Ala Ile  Leu Met Gly Ala Thr  Phe Ala Glu Met Asn  Thr Gly Gly
    1205                 1210                 1215

Asp Val  Ala His Leu Ala Leu  Ile Ala Ala Phe Lys  Val Arg Pro
    1220                 1225                 1230

Ala Leu  Leu Val Ser Phe Ile  Phe Arg Ala Asn Trp  Thr Pro Arg
    1235                 1240                 1245

Glu Ser  Met Leu Leu Ala Leu  Ala Ser Cys Leu Leu  Gln Thr Ala
    1250                 1255                 1260

Ile Ser  Ala Leu Glu Gly Asp  Leu Met Val Leu Ile  Asn Gly Phe
    1265                 1270                 1275
```

-continued

```
Ala Leu Ala Trp Leu Ala Ile Arg Ala Met Val Val Pro Arg Thr
    1280                1285                1290

Asp Asn Ile Thr Leu Ala Ile Leu Ala Ala Leu Thr Pro Leu Ala
    1295                1300                1305

Arg Gly Thr Leu Leu Val Ala Trp Arg Ala Gly Leu Ala Thr Cys
    1310                1315                1320

Gly Gly Phe Met Leu Leu Ser Leu Lys Gly Lys Gly Ser Val Lys
    1325                1330                1335

Lys Asn Leu Pro Phe Val Met Ala Leu Gly Leu Thr Ala Val Arg
    1340                1345                1350

Leu Val Asp Pro Ile Asn Val Val Gly Leu Leu Leu Leu Thr Arg
    1355                1360                1365

Ser Gly Lys Arg Ser Trp Pro Pro Ser Glu Val Leu Thr Ala Val
    1370                1375                1380

Gly Leu Ile Cys Ala Leu Ala Gly Gly Phe Ala Lys Ala Asp Ile
    1385                1390                1395

Glu Met Ala Gly Pro Met Ala Ala Val Gly Leu Leu Ile Val Ser
    1400                1405                1410

Tyr Val Val Ser Gly Lys Ser Val Asp Met Tyr Ile Glu Arg Ala
    1415                1420                1425

Gly Asp Ile Thr Trp Glu Lys Asp Ala Glu Val Thr Gly Asn Ser
    1430                1435                1440

Pro Arg Leu Asp Val Ala Leu Asp Glu Ser Gly Asp Phe Ser Leu
    1445                1450                1455

Val Glu Asp Asp Gly Pro Pro Met Arg Glu Ile Ile Leu Lys Val
    1460                1465                1470

Val Leu Met Thr Ile Cys Gly Met Asn Pro Ile Ala Ile Pro Phe
    1475                1480                1485

Ala Ala Gly Ala Trp Tyr Val Tyr Val Lys Thr Gly Lys Arg Ser
    1490                1495                1500

Gly Ala Leu Trp Asp Val Pro Ala Pro Lys Glu Val Lys Lys Gly
    1505                1510                1515

Glu Thr Thr Asp Gly Val Tyr Arg Val Met Thr Arg Arg Leu Leu
    1520                1525                1530

Gly Ser Thr Gln Val Gly Val Gly Val Met Gln Glu Gly Val Phe
    1535                1540                1545

His Thr Met Trp His Val Thr Lys Gly Ser Ala Leu Arg Ser Gly
    1550                1555                1560

Glu Gly Arg Leu Asp Pro Tyr Trp Gly Asp Val Lys Gln Asp Leu
    1565                1570                1575

Val Ser Tyr Cys Gly Pro Trp Lys Leu Asp Ala Ala Trp Asp Gly
    1580                1585                1590

His Ser Glu Val Gln Leu Leu Ala Val Pro Pro Gly Glu Arg Ala
    1595                1600                1605

Arg Asn Ile Gln Thr Leu Pro Gly Ile Phe Lys Thr Lys Asp Gly
    1610                1615                1620

Asp Ile Gly Ala Val Ala Leu Asp Tyr Pro Ala Gly Thr Ser Gly
    1625                1630                1635

Ser Pro Ile Leu Asp Lys Cys Gly Arg Val Ile Gly Leu Tyr Gly
    1640                1645                1650

Asn Gly Val Val Ile Lys Asn Gly Ser Tyr Val Ser Ala Ile Thr
    1655                1660                1665

Gln Gly Arg Arg Glu Glu Glu Thr Pro Val Glu Cys Phe Glu Pro
```

```
    1670                1675                1680

Ser Met  Leu Lys Lys Lys Gln  Leu Thr Val Leu Asp  Leu His Pro
    1685                1690                1695

Gly Ala  Gly Lys Thr Arg Arg  Val Leu Pro Glu Ile  Val Arg Glu
    1700                1705                1710

Ala Ile  Lys Thr Arg Leu Arg  Thr Val Ile Leu Ala  Pro Thr Arg
    1715                1720                1725

Val Val  Ala Ala Glu Met Glu  Glu Ala Leu Arg Gly  Leu Pro Val
    1730                1735                1740

Arg Tyr  Met Thr Thr Ala Val  Asn Val Thr His Ser  Gly Thr Glu
    1745                1750                1755

Ile Val  Asp Leu Met Cys His  Ala Thr Phe Thr Ser  Arg Leu Leu
    1760                1765                1770

Gln Pro  Ile Arg Val Pro Asn  Tyr Asn Leu Tyr Ile  Met Asp Glu
    1775                1780                1785

Ala His  Phe Thr Asp Pro Ser  Ser Ile Ala Ala Arg  Gly Tyr Ile
    1790                1795                1800

Ser Thr  Arg Val Glu Met Gly  Glu Ala Ala Ala Ile  Phe Met Thr
    1805                1810                1815

Ala Thr  Pro Pro Gly Thr Arg  Asp Ala Phe Pro Asp  Ser Asn Ser
    1820                1825                1830

Pro Ile  Met Asp Thr Glu Val  Glu Val Pro Glu Arg  Ala Trp Ser
    1835                1840                1845

Ser Gly  Phe Asp Trp Val Thr  Asp His Ser Gly Lys  Thr Val Trp
    1850                1855                1860

Phe Val  Pro Ser Val Arg Asn  Gly Asn Glu Ile Ala  Ala Cys Leu
    1865                1870                1875

Thr Lys  Ala Gly Lys Arg Val  Ile Gln Leu Ser Arg  Lys Thr Phe
    1880                1885                1890

Glu Thr  Glu Phe Gln Lys Thr  Lys His Gln Glu Trp  Asp Phe Val
    1895                1900                1905

Val Thr  Thr Asp Ile Ser Glu  Met Gly Ala Asn Phe  Lys Ala Asp
    1910                1915                1920

Arg Val  Ile Asp Ser Arg Arg  Cys Leu Lys Pro Val  Ile Leu Asp
    1925                1930                1935

Gly Glu  Arg Val Ile Leu Ala  Gly Pro Met Pro Val  Thr His Ala
    1940                1945                1950

Ser Ala  Ala Gln Arg Arg Gly  Arg Ile Gly Arg Asn  Pro Asn Lys
    1955                1960                1965

Pro Gly  Asp Glu Tyr Leu Tyr  Gly Gly Gly Cys Ala  Glu Thr Asp
    1970                1975                1980

Glu Asp  His Ala His Trp Leu  Glu Ala Arg Met Leu  Leu Asp Asn
    1985                1990                1995

Ile Tyr  Leu Gln Asp Gly Leu  Ile Ala Ser Leu Tyr  Arg Pro Glu
    2000                2005                2010

Ala Asp  Lys Val Ala Ala Ile  Glu Gly Glu Phe Lys  Leu Arg Thr
    2015                2020                2025

Glu Gln  Arg Lys Thr Phe Val  Glu Leu Met Lys Arg  Gly Asp Leu
    2030                2035                2040

Pro Val  Trp Leu Ala Tyr Gln  Val Ala Ser Ala Gly  Ile Thr Tyr
    2045                2050                2055

Thr Asp  Arg Arg Trp Cys Phe  Asp Gly Thr Thr Asn  Asn Thr Ile
    2060                2065                2070
```

```
Met Glu  Asp Ser Val Pro Ala  Glu Val Trp Thr Arg  His Gly Glu
    2075                 2080                 2085

Lys Arg  Val Leu Lys Pro Arg  Trp Met Asp Ala Arg  Val Cys Ser
    2090                 2095                 2100

Asp His  Ala Ala Leu Lys Ser  Phe Lys Glu Phe Ala  Ala Gly Lys
    2105                 2110                 2115

Arg Gly  Ala Ala Phe Gly Val  Met Glu Ala Leu Gly  Thr Leu Pro
    2120                 2125                 2130

Gly His  Met Thr Glu Arg Phe  Gln Glu Ala Ile Asp  Asn Leu Ala
    2135                 2140                 2145

Val Leu  Met Arg Ala Glu Thr  Gly Ser Arg Pro Tyr  Lys Ala Ala
    2150                 2155                 2160

Ala Ala  Gln Leu Pro Glu Thr  Leu Glu Thr Ile Met  Leu Leu Gly
    2165                 2170                 2175

Leu Leu  Gly Thr Val Ser Leu  Gly Ile Phe Phe Val  Leu Met Arg
    2180                 2185                 2190

Asn Lys  Gly Ile Gly Lys Met  Gly Phe Gly Met Val  Thr Leu Gly
    2195                 2200                 2205

Ala Ser  Ala Trp Leu Met Trp  Leu Ser Glu Ile Glu  Pro Ala Arg
    2210                 2215                 2220

Ile Ala  Cys Val Leu Ile Val  Val Phe Leu Leu Leu  Val Val Leu
    2225                 2230                 2235

Ile Pro  Glu Pro Glu Lys Gln  Arg Ser Pro Gln Asp  Asn Gln Met
    2240                 2245                 2250

Ala Ile  Ile Ile Met Val Ala  Val Gly Leu Leu Gly  Leu Ile Thr
    2255                 2260                 2265

Ala Asn  Glu Leu Gly Trp Leu  Glu Arg Thr Lys Ser  Asp Leu Ser
    2270                 2275                 2280

His Leu  Met Gly Arg Arg Glu  Glu Gly Ala Thr Ile  Gly Phe Ser
    2285                 2290                 2295

Met Asp  Ile Asp Leu Arg Pro  Ala Ser Ala Trp Ala  Ile Tyr Ala
    2300                 2305                 2310

Ala Leu  Thr Thr Phe Ile Thr  Pro Ala Val Gln His  Ala Val Thr
    2315                 2320                 2325

Thr Ser  Tyr Asn Asn Tyr Ser  Leu Met Ala Met Ala  Thr Gln Ala
    2330                 2335                 2340

Gly Val  Leu Phe Gly Met Gly  Lys Gly Met Pro Phe  Tyr Ala Trp
    2345                 2350                 2355

Asp Phe  Gly Val Pro Leu Leu  Met Ile Gly Cys Tyr  Ser Gln Leu
    2360                 2365                 2370

Thr Pro  Leu Thr Leu Ile Val  Ala Ile Ile Leu Leu  Val Ala His
    2375                 2380                 2385

Tyr Met  Tyr Leu Ile Pro Gly  Leu Gln Ala Ala Ala  Ala Arg Ala
    2390                 2395                 2400

Ala Gln  Lys Arg Thr Ala Ala  Gly Ile Met Lys Asn  Pro Val Val
    2405                 2410                 2415

Asp Gly  Ile Val Val Thr Asp  Ile Asp Thr Met Thr  Ile Asp Pro
    2420                 2425                 2430

Gln Val  Glu Lys Lys Met Gly  Gln Val Leu Leu Ile  Ala Val Ala
    2435                 2440                 2445

Val Ser  Ser Ala Ile Leu Ser  Arg Thr Ala Trp Gly  Trp Gly Glu
    2450                 2455                 2460
```

-continued

Ala Gly Ala Leu Ile Thr Ala Ala Thr Ser Thr Leu Trp Glu Gly
2465 2470 2475

Ser Pro Asn Lys Tyr Trp Asn Ser Ser Thr Ala Thr Ser Leu Cys
2480 2485 2490

Asn Ile Phe Arg Gly Ser Tyr Leu Ala Gly Ala Ser Leu Ile Tyr
2495 2500 2505

Thr Val Thr Arg Asn Ala Gly Leu Val Lys Arg Arg Gly Gly Gly
2510 2515 2520

Thr Gly Glu Thr Leu Gly Glu Lys Trp Lys Ala Arg Leu Asn Gln
2525 2530 2535

Met Ser Ala Leu Glu Phe Tyr Ser Tyr Lys Lys Ser Gly Ile Thr
2540 2545 2550

Glu Val Cys Arg Glu Glu Ala Arg Arg Ala Leu Lys Asp Gly Val
2555 2560 2565

Ala Thr Gly Gly His Ala Val Ser Arg Gly Ser Ala Lys Leu Arg
2570 2575 2580

Trp Leu Val Glu Arg Gly Tyr Leu Gln Pro Tyr Gly Lys Val Ile
2585 2590 2595

Asp Leu Gly Cys Gly Arg Gly Gly Trp Ser Tyr Tyr Ala Ala Thr
2600 2605 2610

Ile Arg Lys Val Gln Glu Val Lys Gly Tyr Thr Lys Gly Gly Pro
2615 2620 2625

Gly His Glu Glu Pro Met Leu Val Gln Ser Tyr Gly Trp Asn Ile
2630 2635 2640

Val Arg Leu Lys Ser Gly Val Asp Val Phe His Met Ala Ala Glu
2645 2650 2655

Pro Cys Asp Thr Leu Leu Cys Asp Ile Gly Glu Ser Ser Ser Ser
2660 2665 2670

Pro Glu Val Glu Glu Ala Arg Thr Leu Arg Val Leu Ser Met Val
2675 2680 2685

Gly Asp Trp Leu Glu Lys Arg Pro Gly Ala Phe Cys Ile Lys Val
2690 2695 2700

Leu Cys Pro Tyr Thr Ser Thr Met Met Glu Thr Leu Glu Arg Leu
2705 2710 2715

Gln Arg Arg Tyr Gly Gly Gly Leu Val Arg Val Pro Leu Ser Arg
2720 2725 2730

Asn Ser Thr His Glu Met Tyr Trp Val Ser Gly Ala Lys Ser Asn
2735 2740 2745

Thr Ile Lys Ser Val Ser Thr Thr Ser Gln Leu Leu Leu Gly Arg
2750 2755 2760

Met Asp Gly Pro Arg Arg Pro Val Lys Tyr Glu Glu Asp Val Asn
2765 2770 2775

Leu Gly Ser Gly Thr Arg Ala Val Val Ser Cys Ala Glu Ala Pro
2780 2785 2790

Asn Met Lys Ile Ile Gly Asn Arg Ile Glu Arg Ile Arg Ser Glu
2795 2800 2805

His Ala Glu Thr Trp Phe Phe Asp Glu Asn His Pro Tyr Arg Thr
2810 2815 2820

Trp Ala Tyr His Gly Ser Tyr Glu Ala Pro Thr Gln Gly Ser Ala
2825 2830 2835

Ser Ser Leu Ile Asn Gly Val Val Arg Leu Leu Ser Lys Pro Trp
2840 2845 2850

Asp Val Val Thr Gly Val Thr Gly Ile Ala Met Thr Asp Thr Thr

-continued

```
    2855                2860                2865

Pro Tyr  Gly Gln Gln Arg Val  Phe Lys Glu Lys Val  Asp Thr Arg
    2870                2875                2880

Val Pro  Asp Pro Gln Glu Gly  Thr Arg Gln Val Met  Ser Met Val
    2885                2890                2895

Ser Ser  Trp Leu Trp Lys Glu  Leu Gly Lys His Lys  Arg Pro Arg
    2900                2905                2910

Val Cys  Thr Lys Glu Glu Phe  Ile Asn Lys Val Arg  Ser Asn Ala
    2915                2920                2925

Ala Leu  Gly Ala Ile Phe Glu  Glu Glu Lys Glu Trp  Lys Thr Ala
    2930                2935                2940

Val Glu  Ala Val Asn Asp Pro  Arg Phe Trp Ala Leu  Val Asp Lys
    2945                2950                2955

Glu Arg  Glu His His Leu Arg  Gly Glu Cys Gln Ser  Cys Val Tyr
    2960                2965                2970

Asn Met  Met Gly Lys Arg Glu  Lys Lys Gln Gly Glu  Phe Gly Lys
    2975                2980                2985

Ala Lys  Gly Ser Arg Ala Ile  Trp Tyr Met Trp Leu  Gly Ala Arg
    2990                2995                3000

Phe Leu  Glu Phe Glu Ala Leu  Gly Phe Leu Asn Glu  Asp His Trp
    3005                3010                3015

Met Gly  Arg Glu Asn Ser Gly  Gly Gly Val Glu Gly  Leu Gly Leu
    3020                3025                3030

Gln Arg  Leu Gly Tyr Val Leu  Glu Glu Met Ser Arg  Ile Pro Gly
    3035                3040                3045

Gly Arg  Met Tyr Ala Asp Asp  Thr Ala Gly Trp Asp  Thr Arg Ile
    3050                3055                3060

Ser Arg  Phe Asp Leu Glu Asn  Glu Ala Leu Ile Thr  Asn Gln Met
    3065                3070                3075

Glu Lys  Gly His Arg Ala Leu  Ala Leu Ala Ile Ile  Lys Tyr Thr
    3080                3085                3090

Tyr Gln  Asn Lys Val Val Lys  Val Leu Arg Pro Ala  Glu Lys Gly
    3095                3100                3105

Lys Thr  Val Met Asp Ile Ile  Ser Arg Gln Asp Gln  Arg Gly Ser
    3110                3115                3120

Gly Gln  Val Val Thr Tyr Ala  Leu Asn Thr Phe Thr  Asn Leu Val
    3125                3130                3135

Val Gln  Leu Ile Arg Asn Met  Glu Ala Glu Glu Val  Leu Glu Met
    3140                3145                3150

Gln Asp  Leu Trp Leu Leu Arg  Arg Ser Glu Lys Val  Thr Asn Trp
    3155                3160                3165

Leu Gln  Ser Asn Gly Trp Asp  Arg Leu Lys Arg Met  Ala Val Ser
    3170                3175                3180

Gly Asp  Asp Cys Val Val Lys  Pro Ile Asp Asp Arg  Phe Ala His
    3185                3190                3195

Ala Leu  Arg Phe Leu Asn Asp  Met Gly Lys Val Arg  Lys Asp Thr
    3200                3205                3210

Gln Glu  Trp Lys Pro Ser Thr  Gly Trp Asp Asn Trp  Glu Glu Val
    3215                3220                3225

Pro Phe  Cys Ser His His Phe  Asn Lys Leu His Leu  Lys Asp Gly
    3230                3235                3240

Arg Ser  Ile Val Val Pro Cys  Arg His Gln Asp Glu  Leu Ile Gly
    3245                3250                3255
```

```
Arg Ala Arg Val Ser Pro Gly Ala Gly Trp Ser Ile Arg Glu Thr
    3260                3265                3270

Ala Cys Leu Ala Lys Ser Tyr Ala Gln Met Trp Gln Leu Leu Tyr
    3275                3280                3285

Phe His Arg Arg Asp Leu Arg Leu Met Ala Asn Ala Ile Cys Ser
    3290                3295                3300

Ser Val Pro Val Asp Trp Val Pro Thr Gly Arg Thr Thr Trp Ser
    3305                3310                3315

Ile His Gly Lys Gly Glu Trp Met Thr Thr Glu Asp Met Leu Val
    3320                3325                3330

Val Trp Asn Arg Val Trp Ile Glu Glu Asn Asp His Met Glu Asp
    3335                3340                3345

Lys Thr Pro Val Thr Lys Trp Thr Asp Ile Pro Tyr Leu Gly Lys
    3350                3355                3360

Arg Glu Asp Leu Trp Cys Gly Ser Leu Ile Gly His Arg Pro Arg
    3365                3370                3375

Thr Thr Trp Ala Glu Asn Ile Lys Asn Thr Val Asn Met Val Arg
    3380                3385                3390

Arg Ile Ile Gly Asp Glu Glu Lys Tyr Met Asp Tyr Leu Ser Thr
    3395                3400                3405

Gln Val Arg Tyr Leu Gly Glu Glu Gly Ser Thr Pro Gly Val Leu
    3410                3415                3420
```

<210> SEQ ID NO 74
<211> LENGTH: 28
<212> TYPE: DNA
<213> ORGANISM: Artificial Sequence
<220> FEATURE:
<223> OTHER INFORMATION: primer

<400> SEQUENCE: 74
ttaggatccg ttgttgatct gtgtgaat 28

<210> SEQ ID NO 75
<211> LENGTH: 26
<212> TYPE: DNA
<213> ORGANISM: Artificial Sequence
<220> FEATURE:
<223> OTHER INFORMATION: primer

<400> SEQUENCE: 75
taactcgagc gtacacaacc caagtt 26

<210> SEQ ID NO 76
<211> LENGTH: 27
<212> TYPE: DNA
<213> ORGANISM: Artificial Sequence
<220> FEATURE:
<223> OTHER INFORMATION: primer

<400> SEQUENCE: 76
ttaggatcct cactagacgt gggagtg 27

<210> SEQ ID NO 77
<211> LENGTH: 29
<212> TYPE: DNA
<213> ORGANISM: Artificial Sequence
<220> FEATURE:
<223> OTHER INFORMATION: primer

<400> SEQUENCE: 77
taactcgaga agccatgtcy gatattgat 29

<210> SEQ ID NO 78
<211> LENGTH: 26
<212> TYPE: DNA
<213> ORGANISM: Artificial Sequence
<220> FEATURE:
<223> OTHER INFORMATION: primer

<400> SEQUENCE: 78
ttaggatccg catacagcat caggtg 26

<210> SEQ ID NO 79
<211> LENGTH: 27
<212> TYPE: DNA
<213> ORGANISM: Artificial Sequence
<220> FEATURE:
<223> OTHER INFORMATION: primer

<400> SEQUENCE: 79
taactcgagt gtggagttcc ggtgtct 27

<210> SEQ ID NO 80
<211> LENGTH: 31
<212> TYPE: DNA
<213> ORGANISM: Artificial Sequence
<220> FEATURE:
<223> OTHER INFORMATION: primer

<400> SEQUENCE: 80
ttaggatccg aatagagcga argttgagat a 31

<210> SEQ ID NO 81
<211> LENGTH: 28
<212> TYPE: DNA
<213> ORGANISM: Artificial Sequence
<220> FEATURE:
<223> OTHER INFORMATION: primer

<400> SEQUENCE: 81
taactcgagt ggtgggtgat cttcttct 28

<210> SEQ ID NO 82
<211> LENGTH: 31
<212> TYPE: DNA
<213> ORGANISM: Artificial Sequence
<220> FEATURE:
<223> OTHER INFORMATION: primer

<400> SEQUENCE: 82
ttaggatcca gtcacagtgg aggtacagta c 31

<210> SEQ ID NO 83
<211> LENGTH: 27
<212> TYPE: DNA
<213> ORGANISM: Artificial Sequence
<220> FEATURE:
<223> OTHER INFORMATION: primer

<400> SEQUENCE: 83
taactcgagc rcagatacca tcttccc 27

<210> SEQ ID NO 84
<211> LENGTH: 28
<212> TYPE: DNA

<213> ORGANISM: Artificial Sequence
<220> FEATURE:
<223> OTHER INFORMATION: primer

<400> SEQUENCE: 84
ttaggatccc ttatgtgctt ggccttag 28

<210> SEQ ID NO 85
<211> LENGTH: 26
<212> TYPE: DNA
<213> ORGANISM: Artificial Sequence
<220> FEATURE:
<223> OTHER INFORMATION: primer

<400> SEQUENCE: 85
taactcgagt cttcagcctc catgtg 26

<210> SEQ ID NO 86
<211> LENGTH: 29
<212> TYPE: DNA
<213> ORGANISM: Artificial Sequence
<220> FEATURE:
<223> OTHER INFORMATION: primer

<400> SEQUENCE: 86
ttaggatcca atgcccactc aaacataga 29

<210> SEQ ID NO 87
<211> LENGTH: 30
<212> TYPE: DNA
<213> ORGANISM: Artificial Sequence
<220> FEATURE:
<223> OTHER INFORMATION: primer

<400> SEQUENCE: 87
taactcgagt cattctcttc ttcagccctt 30

<210> SEQ ID NO 88
<211> LENGTH: 26
<212> TYPE: DNA
<213> ORGANISM: Artificial Sequence
<220> FEATURE:
<223> OTHER INFORMATION: primer

<400> SEQUENCE: 88
ttaggatcca agggtgatcg aggaat 26

<210> SEQ ID NO 89
<211> LENGTH: 29
<212> TYPE: DNA
<213> ORGANISM: Artificial Sequence
<220> FEATURE:
<223> OTHER INFORMATION: primer

<400> SEQUENCE: 89
taactcgagt tcccttcaga gagaggagc 29

<210> SEQ ID NO 90
<211> LENGTH: 28
<212> TYPE: DNA
<213> ORGANISM: Artificial Sequence
<220> FEATURE:
<223> OTHER INFORMATION: primer

<400> SEQUENCE: 90
ttaggatcct cttttgcaaa ctgcgatc 28

<210> SEQ ID NO 91
<211> LENGTH: 27
<212> TYPE: DNA
<213> ORGANISM: Artificial Sequence
<220> FEATURE:
<223> OTHER INFORMATION: primer

<400> SEQUENCE: 91
taactcgagt ccagctgcaa agggtat 27

<210> SEQ ID NO 92
<211> LENGTH: 28
<212> TYPE: DNA
<213> ORGANISM: Artificial Sequence
<220> FEATURE:
<223> OTHER INFORMATION: primer

<400> SEQUENCE: 92
ttaggatccg tgtggacatg tacattga 28

<210> SEQ ID NO 93
<211> LENGTH: 26
<212> TYPE: DNA
<213> ORGANISM: Artificial Sequence
<220> FEATURE:
<223> OTHER INFORMATION: primer

<400> SEQUENCE: 93
taactcgagc ccattgccat aaagtc 26

<210> SEQ ID NO 94
<211> LENGTH: 28
<212> TYPE: DNA
<213> ORGANISM: Artificial Sequence
<220> FEATURE:
<223> OTHER INFORMATION: primer

<400> SEQUENCE: 94
ttaggatcct catactgtgg tccatgga 28

<210> SEQ ID NO 95
<211> LENGTH: 26
<212> TYPE: DNA
<213> ORGANISM: Artificial Sequence
<220> FEATURE:
<223> OTHER INFORMATION: primer

<400> SEQUENCE: 95
taactcgagg cccatctcaa cccttg 26

<210> SEQ ID NO 96
<211> LENGTH: 26
<212> TYPE: DNA
<213> ORGANISM: Artificial Sequence
<220> FEATURE:
<223> OTHER INFORMATION: primer

<400> SEQUENCE: 96
ttaggatcct agagggcttc cagtgc 26

<210> SEQ ID NO 97
<211> LENGTH: 31
<212> TYPE: DNA
<213> ORGANISM: Artificial Sequence
<220> FEATURE:

<223> OTHER INFORMATION: primer

<400> SEQUENCE: 97
taactcgaga tactcatctc caggtttgtt g 31

<210> SEQ ID NO 98
<211> LENGTH: 30
<212> TYPE: DNA
<213> ORGANISM: Artificial Sequence
<220> FEATURE:
<223> OTHER INFORMATION: primer

<400> SEQUENCE: 98
ttaggatccg aaaacaaaac atcaagagtg 30

<210> SEQ ID NO 99
<211> LENGTH: 31
<212> TYPE: DNA
<213> ORGANISM: Artificial Sequence
<220> FEATURE:
<223> OTHER INFORMATION: primer

<400> SEQUENCE: 99
taactcgagg aatctctctg tcatgtgtcc t 31

<210> SEQ ID NO 100
<211> LENGTH: 26
<212> TYPE: DNA
<213> ORGANISM: Artificial Sequence
<220> FEATURE:
<223> OTHER INFORMATION: primer

<400> SEQUENCE: 100
ttaggatcct tgatggcacg accaac 26

<210> SEQ ID NO 101
<211> LENGTH: 28
<212> TYPE: DNA
<213> ORGANISM: Artificial Sequence
<220> FEATURE:
<223> OTHER INFORMATION: primer

<400> SEQUENCE: 101
ttaggatccg ttgttgatct gtgtgaat 28

<210> SEQ ID NO 102
<211> LENGTH: 26
<212> TYPE: DNA
<213> ORGANISM: Artificial Sequence
<220> FEATURE:
<223> OTHER INFORMATION: primer

<400> SEQUENCE: 102
taactcgagc aggtcaatgt ccattg 26

<210> SEQ ID NO 103
<211> LENGTH: 30
<212> TYPE: DNA
<213> ORGANISM: Artificial Sequence
<220> FEATURE:
<223> OTHER INFORMATION: primer

<400> SEQUENCE: 103
ttaggatcct gttgtgttcc tattgctggt 30

<210> SEQ ID NO 104
<211> LENGTH: 25
<212> TYPE: DNA
<213> ORGANISM: Artificial Sequence
<220> FEATURE:
<223> OTHER INFORMATION: primer

<400> SEQUENCE: 104
taactcgagt gatcagrgcc ccagc 25

<210> SEQ ID NO 105
<211> LENGTH: 26
<212> TYPE: DNA
<213> ORGANISM: Artificial Sequence
<220> FEATURE:
<223> OTHER INFORMATION: primer

<400> SEQUENCE: 105
ttaggatcct gctgcccaga agagaa 26

<210> SEQ ID NO 106
<211> LENGTH: 26
<212> TYPE: DNA
<213> ORGANISM: Artificial Sequence
<220> FEATURE:
<223> OTHER INFORMATION: primer

<400> SEQUENCE: 106
taactcgagc accaacaygg gttctt 26

<210> SEQ ID NO 107
<211> LENGTH: 25
<212> TYPE: DNA
<213> ORGANISM: Artificial Sequence
<220> FEATURE:
<223> OTHER INFORMATION: primer

<400> SEQUENCE: 107
ttaggatcct caaggacggt gtggc 25

<210> SEQ ID NO 108
<211> LENGTH: 28
<212> TYPE: DNA
<213> ORGANISM: Artificial Sequence
<220> FEATURE:
<223> OTHER INFORMATION: primer

<400> SEQUENCE: 108
taactcgagc aatgatcttc atgttggg 28

<210> SEQ ID NO 109
<211> LENGTH: 26
<212> TYPE: DNA
<213> ORGANISM: Artificial Sequence
<220> FEATURE:
<223> OTHER INFORMATION: primer

<400> SEQUENCE: 109
ttaggatcct atgggggagg actggt 26

<210> SEQ ID NO 110
<211> LENGTH: 25
<212> TYPE: DNA
<213> ORGANISM: Artificial Sequence
<220> FEATURE:
<223> OTHER INFORMATION: primer

<400> SEQUENCE: 110
taactcgagc ccagaacctt ggatc 25

<210> SEQ ID NO 111
<211> LENGTH: 25
<212> TYPE: DNA
<213> ORGANISM: Artificial Sequence
<220> FEATURE:
<223> OTHER INFORMATION: primer

<400> SEQUENCE: 111
ttaggatcca gacccccaag aaggc 25

<210> SEQ ID NO 112
<211> LENGTH: 26
<212> TYPE: DNA
<213> ORGANISM: Artificial Sequence
<220> FEATURE:
<223> OTHER INFORMATION: primer

<400> SEQUENCE: 112
taactcgagc ccctttggtc ttgtct 26

<210> SEQ ID NO 113
<211> LENGTH: 29
<212> TYPE: DNA
<213> ORGANISM: Artificial Sequence
<220> FEATURE:
<223> OTHER INFORMATION: primer

<400> SEQUENCE: 113
ttaggatcca ggaaggatgt atgcagatg 29

<210> SEQ ID NO 114
<211> LENGTH: 30
<212> TYPE: DNA
<213> ORGANISM: Artificial Sequence
<220> FEATURE:
<223> OTHER INFORMATION: primer

<400> SEQUENCE: 114
taactcgaga catttgcgca tatgattttg 30

<210> SEQ ID NO 115
<211> LENGTH: 28
<212> TYPE: DNA
<213> ORGANISM: Artificial Sequence
<220> FEATURE:
<223> OTHER INFORMATION: primer

<400> SEQUENCE: 115
ttaggatcca ggaaggacac acaagagt 28

<210> SEQ ID NO 116
<211> LENGTH: 26
<212> TYPE: DNA
<213> ORGANISM: Artificial Sequence
<220> FEATURE:
<223> OTHER INFORMATION: primer

<400> SEQUENCE: 116
taactcgaga caggctgcac agcttt 26

<210> SEQ ID NO 117
<211> LENGTH: 28

-continued

```
<212> TYPE: DNA
<213> ORGANISM: Artificial Sequence
<220> FEATURE:
<223> OTHER INFORMATION: primer

<400> SEQUENCE: 117

ttaggatcct ctctcatagg gcacagac                                28
```